(12) United States Patent
Lu

(10) Patent No.: US 9,428,542 B2
(45) Date of Patent: Aug. 30, 2016

(54) LUPANE TRITERPENOID DERIVATIVES AND PHARMACEUTICAL USE THEREOF

(71) Applicants: JIANGXI QINGFENG PHARMACEUTICAL INC., Jiangxi (CN); Feng Lu, Shanghai (CN); Qiaodi Feng, Shanghai (CN)

(72) Inventor: Feng Lu, Shanghai (CN)

(73) Assignees: JIANGXI QINGFENG PHARMACEUTICAL INC. (CN); Qiaodi Feng (CN); Feng Lu (CN)

(*) Notice: Subject to any disclaimer, the term of this patent is extended or adjusted under 35 U.S.C. 154(b) by 123 days.

(21) Appl. No.: 14/374,832

(22) PCT Filed: Jan. 30, 2013

(86) PCT No.: PCT/CN2013/071100
§ 371 (c)(1),
(2) Date: Jul. 25, 2014

(87) PCT Pub. No.: WO2013/117137
PCT Pub. Date: Aug. 15, 2013

(65) Prior Publication Data
US 2015/0011517 A1    Jan. 8, 2015

(30) Foreign Application Priority Data

Feb. 8, 2012 (CN) .......................... 2012 1 0027090
Jan. 15, 2013 (CN) .......................... 2013 1 0014849

(51) Int. Cl.
| | | |
|---|---|---|
| *A61K 31/58* | (2006.01) |
| *C07J 53/00* | (2006.01) |
| *C07J 63/00* | (2006.01) |
| *A61K 45/06* | (2006.01) |
| *A61K 31/4152* | (2006.01) |
| *A61K 31/4196* | (2006.01) |
| *A61K 31/421* | (2006.01) |
| *A61K 31/4245* | (2006.01) |
| *A61K 31/433* | (2006.01) |
| *A61K 31/4439* | (2006.01) |
| *A61K 31/506* | (2006.01) |

(52) U.S. Cl.
CPC ........... *C07J 63/008* (2013.01); *A61K 31/4152* (2013.01); *A61K 31/4196* (2013.01); *A61K 31/421* (2013.01); *A61K 31/4245* (2013.01); *A61K 31/433* (2013.01); *A61K 31/4439* (2013.01); *A61K 31/506* (2013.01); *A61K 45/06* (2013.01)

(58) Field of Classification Search
CPC ............................. C07J 63/008; A61K 31/565
USPC .......................................... 552/510; 514/176
See application file for complete search history.

(56) References Cited

FOREIGN PATENT DOCUMENTS

| | | | |
|---|---|---|---|
| WO | 2009082818 A1 | 7/2009 |
| WO | 2009082819 A1 | 7/2009 |
| WO | 2011100308 A1 | 8/2011 |

OTHER PUBLICATIONS

International Search Report dated Apr. 25, 2013 in related PCT Application No. PCT/CN2013/071100, 4 pages.

*Primary Examiner* — Barbara P Badio
(74) *Attorney, Agent, or Firm* — Hauptman Ham, LLP

(57) ABSTRACT

The present invention relates to a lupane triterpenoid derivatives and pharmaceutical use thereof, specifically relates to a lupane triterpenoid derivatives of formula (I)~(III), a pharmaceutical composition and a combination preparation comprising a lupane triterpenoid derivatives or a pharmaceutically acceptable salt thereof in a therapeutically-effective dose, particularly relates to the use in preparation of a medicament for the treatment of HIV-1/AIDS.

19 Claims, No Drawings

LUPANE TRITERPENOID DERIVATIVES AND PHARMACEUTICAL USE THEREOF

RELATED APPLICATIONS

This application is national phase of International Application No. PCT/CN2013/071100 (WO2013/117137), filed on Jan. 30, 2013, entitled "LUPANE TRITERPENOID DERIVATIVES AND PHARMACEUTICAL USE THEREOF", which claims the benefit of Chinese Application No. 201210027090.4, filed Feb. 8, 2012, and Chinese Application No. 201310014849.X, filed Jan. 15, 2013.

FIELD OF THE INVENTION

The present invention relates to a novel lupane triterpenoid derivatives and pharmaceutical use thereof, specifically relates to a lupane triterpenoid derivatives of formula (I)~(III) and pharmaceutical use thereof, and further relates to a pharmaceutical composition and a combination preparation comprising a lupane triterpenoid derivatives or a pharmaceutically acceptable salt thereof in a therapeutically-effective dose, and the pharmaceutical use thereof, particularly relates to the uses in treatment of viral infection such as HIV-1/AIDS.

BACKGROUND OF THE INVENTION

Currently no an effective vaccine or cure for HIV/AIDS, the only treatment option is to suppress viral replication with antiretroviral therapy on a lifelong basis.

Although lots of drugs have been invented and used effectively to fight against HIV virus by employing a combinational use of nucleoside/nucleotide reverse transcriptase inhibitor, non-nucleoside reverse transcriptase inhibitors, and/or protease inhibitors, which are targeted at different stage of HIV virus life cycle, it has also brought out the side effects at same time. Among them, the most serious one is the multidrug-resistant viral strains evolved. Even with the new therapies available like fusion, entry, and integrase in recent years, the new resistant viral strains have also been reported both in vitro and in vivo. Therefore there is an urgent need to have a drug with a novel mechanism which may help to address increasing problems of current therapies.

Maturation is an essential step in the life-cycle of HIV-1. It is the transition of the immature, non-infectious virus particle to the mature and infectious virion which represents as an excellent target for development of new class of anti-HIV-1 drugs.

Some derivatives of lupane triterpenoid have been reported to have anti-HIV-1 activity, they bind to the preproteins (Gag) that specifically block HIV-1 protease to cleave p25 (CA-SPI) protein into their functional active form p24 (CA), resulting in the accumulation of the p25 (CA-SPI), immature and noninfectious HIV-1 virions that may prevent the subsequent cycles of HIV infection. These pharmacologically active lupane triterpenoid derivatives are called maturation inhibitors (MI), which represent a novel mechanism in fighting against HIV virus and may provide a new treatment for HIV with resistance to current therapies. Currently there is no such approval drug on the market based on this mechanism.

Bevirimat (PA-457) is a new experimental agent to inhibit this last step of p25 (CA-SPI) protein being converted into the functional form p24 (CA). It has been reported that Bevirimat can reduce ART-resistant strains and wide type HIV viral load in patients, and has demonstrated synergy with antiretrovirals from all classes, but patients with Gag polymorphisms at Q369, V370, or T371 are resistant to this agent's therapy.

BRIEF SUMMARY OF THE INVENTION

The present invention provides a novel lupane triterpenoid derivatives, or a pharmaceutically acceptable salt thereof, and pharmaceutical use thereof, particularly in their pharmaceutical use as a HIV maturation inhibitor; further to the use in preparing a medicament for the treatment of HIV infection and AIDS.

In the first aspect of the present invention, it provides a compound of the formula (I), or a pharmaceutically acceptable salt thereof,

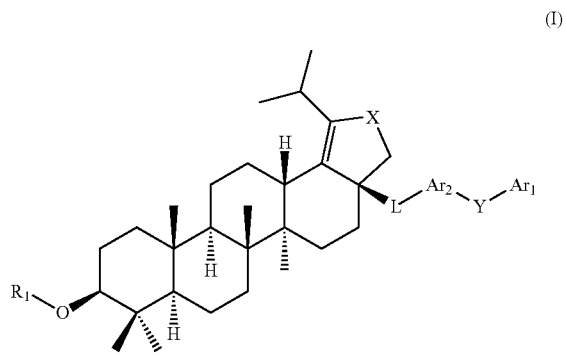

(I)

wherein:

$R_1$ is independently H,

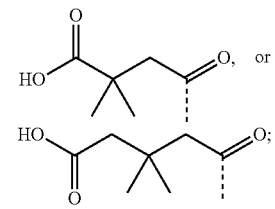

X is independently methylene, carbonyl, thiocarbonyl, CHF, or $CF_2$;

L is independently a direct bond, —$NR_4$—, -ethenyl-, -ethynyl-, —$(CH_2)r$—, —CHOH—,

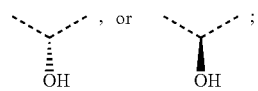

Y is independently a direct bond, —$NR_4$—, —$NR_4$—$CH_2$—, —CHOH—,

—$(CH_2)$—, —C(=O)—, —CH($CH_3$)—, —C($CH_3$)$_2$—, 1,1-cyclopropyldiyl, 1,1-cyclobutyldiyl, or 1,1-cyclopentyldiyl;

Ar₁ is independently optionally substituted or unsubstituted alkyl, optionally substituted or unsubstituted aryl, optionally substituted or unsubstituted heterocycloalkyl, optionally substituted or unsubstituted heteroaryl, or optionally substituted or unsubstituted aminoalkyl; when substituted, the substituents could be one, two or three groups independently selected from the group consisting of: halo, alkyl, alkoxy, haloalkyl, haloalkoxy, amino, aminoalkyl, hydroxyalkyl, thioalkyl, —NHC(O)NH₂, —NHC(O)NH(R₃), —N(R₃)C(O)NH(R₃), —NHC(O)N(R₃)₂, —N(R₃)C(O)N(R₃)₂, —NHC(O)NH(aryl), —NHC(O)NH(heteroaryl), —NHSO₂(R₃), —N(R₃)SO₂(R₃), —OH, —NO₂, —SH, —S(O)₀₋₃H, —S(O)₀₋₃(R₃), —SO₂NH₂, —SO₂NH(R₃), —SO₂N(R₃)₂, —(CH₂)rS(=O)CH₃, —(CH₂)rS(=O)₂CH₃, —P(O)(OH)₂, —P(O)(O—R₃)OH, —P(O)(O—R₃)₂, —CN, —C(O)OH, —R₃C(O)OH, HOOC—R₃—C(O)—, —C(O)O—R₃, —C(O)NH₂, —C(O)NH(R₃), —C(O)N(R₃)₂, —(CH₂)rCONH₂, —(CH₂)rCONHR₃, or —(CH₂)rCON(R₃)₂;

Ar₂ is independently optionally substituted or unsubstituted aryl, optionally substituted or unsubstituted heterocycloalkyl, or optionally substituted or unsubstituted heteroaryl; when substituted, the substituents could be one, two or three groups independently selected from the group consisting of: halo, haloalkyl, haloalkoxy, amino, —NHC(O)NH₂, —NHC(O)NH(R₃), —N(R₃)C(O)NH(R₃), —NHC(O)N(R₃)₂, —N(R₃)C(O)N(R₃)₂, —NHC(O)NH(aryl), —NHC(O)NH(heteroaryl), —NHSO₂(R₃), —N(R₃)SO₂(R₃), —OH, —NO₂, —SH, —S(O)₀₋₃H, —S(O)₀₋₃(R₃), —SO₂NH₂, —SO₂NH(R₃), —SO₂N(R₃)₂, —(CH₂)rS(=O)CH₃, —(CH₂)rS(=O)₂CH₃, —P(O)(OH)₂, —P(O)(O—R₃)OH, —P(O)(O—R₃)₂, —CN, —C(O)OH, —R₃C(O)OH, HOOC—R₃—C(O)—, HOOCC(CH₃)₂CH₂C(O)—, —C(O)O—R₃, —C(O)—R₃—NH₂, —C(O)—R₃—OH, —C(O)NH₂, —C(O)NH(R₃), —C(O)N(R₃)₂, —(CH₂)rCONH₂, —(CH₂)rCONHR₃, —(CH₂)rCON(R₃)₂, optionally substituted or unsubstituted aminoalkyl, optionally substituted or unsubstituted hydroxyalkyl, optionally substituted or unsubstituted alkyl, optionally substituted or unsubstituted alkenyl, optionally substituted or unsubstituted alkynyl, optionally substituted or unsubstituted alkoxy, optionally substituted or unsubstituted aryloxy, optionally substituted or unsubstituted cycloalkyl, optionally substituted or unsubstituted cycloalkylalkyl, optionally substituted or unsubstituted heterocycloalkyl, optionally substituted or unsubstituted heterocycloalkylalkyl, optionally substituted or unsubstituted aryl, optionally substituted or unsubstituted arylalkyl, optionally substituted or unsubstituted heteroaryl, or optionally substituted or unsubstituted heteroarylalkyl;

R₃ is independently alkyl, or two R₃ together with the nitrogen atom to which they are attached, form a 3- to 7-membered heterocycloalkyl ring which could be optionally substituted with methylsulfonyl group or alkyl group;

R₄ is independently H, alkyl, cycloalkyl, cycloalkylalkyl, aryl, arylalkyl, heterocycloalkyl, heterocycloalkylalkyl, heteroaryl, heteroarylalkyl, aminoalkyl, hydroxyalkyl, —S(O)₀₋₃(R₃), —SO₂NH₂, —SO₂NH(R₃), —(CH₂)rS(=O)CH₃, —(CH₂)rS(=O)₂CH₃, —P(O)(O—R₃)₂, —R₃C(O)OH, HOOC—R₃—C(O)—, HOOCC(CH₃)₂CH₂C(O)—, —C(O)O—R₃, —C(O)—R₃—NH₂, —C(O)—R₃—OH, —C(O)NH₂, —C(O)NH(R₃), —C(O)N(R₃)₂, —(CH₂)rCONH₂, —(CH₂)rCONHR₃, or —(CH₂)rCON(R₃)₂;

r is an integer from 1 to 8.

Said Aryl is a optionally substituted or unsubstituted phenyl group; said heterocycloalkyl is a 3-7-membered heterocycloalkyl group, and the heteroatom can be one, or more atoms independently selected from N, O, or S; said Heteroaryl is a 5-6-membered heteroaryl group. All of the representative example of them as describe below.

One subset of compounds of the present invention, or a pharmaceutically acceptable salt thereof, preferably the below formula (II), (II)

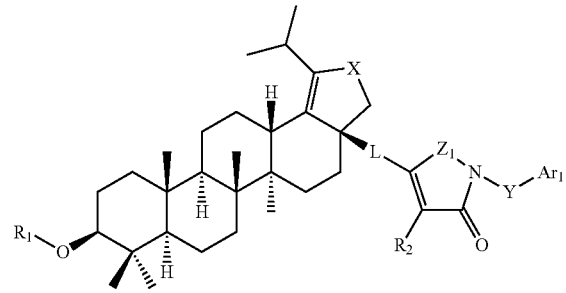

wherein:
R₁ is independently H,

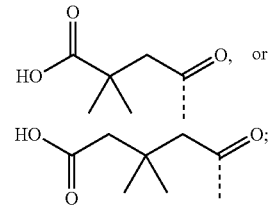

X is independently methylene, carbonyl, thiocarbonyl, CHF, or CF₂;
L is independently a direct bond, —(CH₂)r-, —CHOH—,

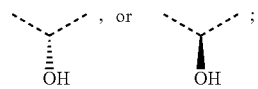

Y is independently a direct bond, —(CH₂)—, —C(=O)—, —CH(CH₃)—, —C(CH₃)₂—, 1,1-cyclopropyldiyl, 1,1-cyclobutyldiyl, or 1,1-cyclopentyldiyl;

R₂ is independently hydrogen, halo, —OH, —NO₂, amino, alkyl, haloalkyl, hydroxyalkyl, aminoalkyl, —C(O)OH, —C(O)O—R₃, —C(O)NH₂, —C(O)NH(R₃), or —C(O)N(R₃)₂;

Ar₁ is independently optionally substituted or unsubstituted alkyl, optionally substituted or unsubstituted aryl, optionally substituted or unsubstituted heterocycloalkyl, optionally substituted or unsubstituted heteroaryl, or optionally substituted or unsubstituted aminoalkyl; when substituted, the substituents could be one, two or three groups independently selected from the group consisting of: halo, alkyl, alkoxy, haloalkyl, haloalkoxy, amino, aminoalkyl, hydroxyalkyl, thioalkyl, —NHC(O)NH₂, —NHC(O)NH(R₃), —N(R₃)C(O)NH(R₃), —NHC(O)N(R₃)₂, —N(R₃)C(O)N(R₃)₂, —NHC(O)NH(aryl), —NHC(O)NH(heteroaryl), —NHSO₂(R₃), —N(R₃)SO₂(R₃), —OH, —NO₂, —SH, —S(O)₀₋₃H, —S(O)₀₋₃(R₃), —SO₂NH₂, —SO₂NH(R₃), —SO₂N(R₃)₂, —(CH₂)rS(=O)CH₃, —(CH₂)rS(=O)₂CH₃, —P(O)(OH)₂, —P(O)(O—R₃)OH, —P(O)(O—R₃)₂, —CN, —C(O)OH, —R₃C(O)OH, HOOC—R₃—C(O)—, —C(O)O—R₃, —C(O)NH₂, —C(O)NH(R₃), —C(O)N(R₃)₂, —(CH₂)rCONH₂, —(CH₂)rCONHR₃, or —(CH₂)rCON(R₃)₂;

$R_3$ is independently alkyl, or two $R_3$ groups together with the nitrogen atom to which they are attached, form a 3- to 7-membered heterocycloalkyl ring which could be optionally substituted with methylsulfonyl group or alkyl group;

$Z_1$ is independently O, S, or $NR_4$;

$R_4$ is independently hydrogen, alkyl, cycloalkyl, cycloalkylalkyl, aryl, arylalkyl, heterocycloalkyl, heterocycloalkylalkyl, heteroaryl, heteroarylalkyl, aminoalkyl, hydroxyalkyl, —$S(O)_{0-3}(R_3)$, —$SO_2NH_2$, —$SO_2NH(R_3)$, —$(CH_2)rS(=O)CH_3$, —$(CH_2)rS(=O)_2CH_3$, —$P(O)(O—R_3)_2$, —$R_3C(O)OH$, HOOC—$R_3$—C(O)—, HOOCC$(CH_3)_2CH_2C(O)$—, —C(O)O—$R_3$, —C(O)—$R_3$—$NH_2$, —C(O)—$R_3$—OH, —C(O)$NH_2$, —C(O)NH($R_3$), —C(O)N$(R_3)_2$, —$(CH_2)rCONH_2$, —$(CH_2)rCONHR_3$, or —$(CH_2)rCON(R_3)_2$;

r is an integer from 1 to 8.

Preferably a compound of formula (II), or a pharmaceutically acceptable salt thereof, wherein:

$R_1$ is independently

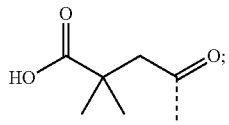

$R_2$ is independently H, Cl, or $CH_3$;

X is independently methylene, or carbonyl;

L is independently a direct bond, or —$(CH_2)$—;

$Z_1$ is independently $NR_4$;

$R_4$ is independently —$CH_3$, —$C_2H_5$, —$CH_2CH_2NH_2$, or —$CH_2CH_2N(CH_3)_2$;

Y is independently a direct bond, or —$CH_2$—;

$Ar_1$ is independently $(R_5)$n-phenyl-, $(R_5)$n-phenyl-$CH_2$—, $(R_5)$n-pyridyl-, $(R_5)$n-pyridyl-$CH_2$—, $(R_5)$n-pyrimidyl-, $(R_5)$n-pyrimidyl-$CH_2$—, —$CH_2CH_2N(CH_3)_2$, —$CH_2COOH$, —$CH_2CONH_2$, —$CH_2CONHCH_3$, or —$CH_2CON(CH_3)_2$;

$R_5$ is independently methyl, methoxy, F, Cl, CN, or $CF_3$;

n is independently 0, 1, or 2.

One subset of compounds of the present invention, or a pharmaceutically acceptable salt thereof, preferably the below formula (III),

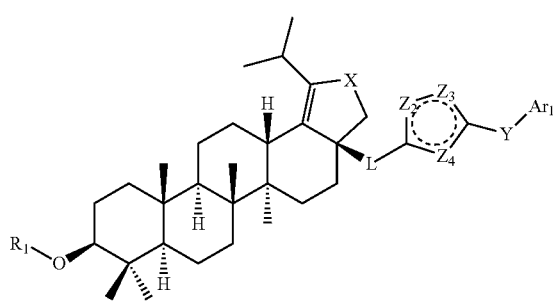

(III)

wherein:

$R_1$ is independently H,

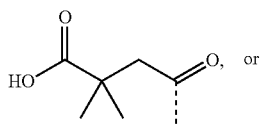

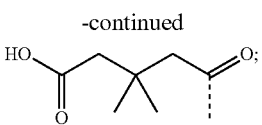

X is independently methylene, carbonyl, thiocarbonyl, CHF, or $CF_2$;

L is independently a direct bond, —$NR_4$—, -ethenyl-, -ethynyl-, —$(CH_2)r$-, —CHOH—,

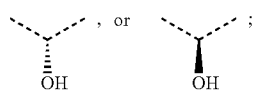

Y is independently a direct bond, —$NR_4$—, —$NR_4$—$CH_2$—, —CHOH—,

—$CH_2$—, —C(=O)—, —$CH(CH_3)$—, —$C(CH_3)_2$—, 1,1-cyclopropyldiyl, 1,1-cyclobutyldiyl, or 1,1-cyclopentyldiyl;

$Z_2$, and $Z_3$ are independently O, N, or CH; $Z_4$ is independently O, S, N, or $NR_4$;

$Ar_1$ is independently optionally substituted or unsubstituted aryl, optionally substituted or unsubstituted heterocycloalkyl, or optionally substituted or unsubstituted heteroaryl; when substituted, the substituents could be one, two or three groups independently selected from the group consisting of: halo, alkyl, alkoxy, haloalkyl, haloalkoxy, amino, aminoalkyl, hydroxyalkyl, thioalkyl, —NHC(O)$NH_2$, —NHC(O)NH($R_3$), —N($R_3$)C(O)NH($R_3$), —NHC(O)N($R_3)_2$, —N($R_3$)C(O)N($R_3)_2$, —NHC(O)NH(aryl), —NHC(O)NH(heteroaryl), —$NHSO_2(R_3)$, —N($R_3$)$SO_2$($R_3$), —OH, —$NO_2$, —SH, —$S(O)_{0-3}H$, —$S(O)_{0-3}(R_3)$, —$SO_2NH_2$, —$SO_2NH(R_3)$, —$SO_2N(R_3)_2$, —$(CH_2)rS(=O)CH_3$, —$(CH_2)rS(=O)_2CH_3$, —$P(O)(OH)_2$, —$P(O)(O—R_3)OH$, —$P(O)(O—R_3)_2$, —CN, —C(O)OH, —$R_3C(O)OH$, HOOC—$R_3$—C(O)—, —C(O)O—$R_3$, —C(O)$NH_2$, —C(O)NH($R_3$), —C(O)N($R_3)_2$, —$(CH_2)rCONH_2$, —$(CH_2)rCONHR_3$, or —$(CH_2)rCON(R_3)_2$;

$R_3$ is independently alkyl, or two $R_3$ groups together with the nitrogen atom to which they are attached, form a 3- to 7-membered heterocycloalkyl ring which optionally substituted with methylsulfonyl group or alkyl group;

$R_4$ is independently hydrogen, alkyl, cycloalkyl, cycloalkylalkyl, aryl, arylalkyl, heterocycloalkyl, heterocycloalkylalkyl, heteroaryl, heteroarylalkyl, aminoalkyl, hydroxyalkyl, —$S(O)_{0-3}(R_3)$, —$SO_2NH_2$, —$SO_2NH(R_3)$, —$(CH_2)rS(=O)CH_3$, —$(CH_2)rS(=O)_2CH_3$, —$P(O)(O—R_3)_2$, —$R_3C(O)OH$, HOOC—$R_3$—C(O)—, HOOCC$(CH_3)_2CH_2C(O)$—, —C(O)O—$R_3$, —C(O)—$R_3$—$NH_2$, —C(O)—$R_3$—OH, —C(O)$NH_2$, —C(O)NH($R_3$), —C(O)N$(R_3)_2$, —$(CH_2)rCONH_2$, —$(CH_2)rCONHR_3$, or —$(CH_2)rCON(R_3)_2$;

r is an integer from 1 to 8.

Preferably a compound of formula (III), or a pharmaceutically acceptable salt thereof, wherein:
R₁ is independently

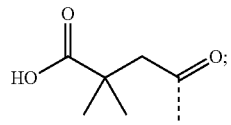

X is independently methylene or carbonyl;
L is independently a direct bond, —NR₄—, —CHOH—,

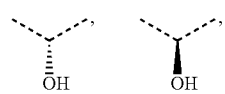

—CH₂CHOH—, or —(CH₂)r—;
Y is independently a direct bond, —NR₄—, —NR₄—CH₂—, —CHOH—,

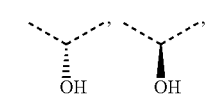

—CH₂—, —C(=O)—, —CH(CH₃)—, —C(CH₃)₂—, 1,1-cyclopropyldiyl, 1,1-cyclobutyldiyl, or 1,1-cyclopentyldiyl;
R₄ is independently H, or —CH₂CH₂N(CH₃)₂;
Z₂, and Z₃ are independently N; Z₄ is O or S, that means

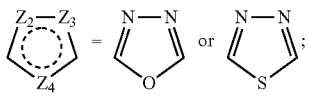

Ar₁ is independently (R₅)n-phenyl-, (R₅)n-phenyl-CH₂—, (R₅)n-pyridyl-, (R₅)n-pyridyl-CH₂—, (R₅)n-pyrimidyl-, or (R₅)n-pyrimidyl-CH₂—;
R₅ is independently methyl, methoxy, F, Cl, Br, CN, or CF₃;
n is independently 0, 1, or 2.
Preferably a compound of formula (III), or a pharmaceutically acceptable salt thereof, wherein:
R₁ is

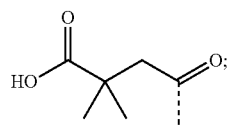

X is independently methylene, or carbonyl;
L is independently a direct bond, —CHOH—,

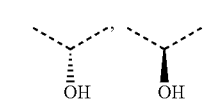

or —CH₂—;

Y is independently a direct bond;
Z₂, and Z₃ are independently N; Z₄ is NR₄, that means

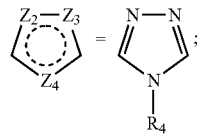

R₄ is independently methyl, —CH₂CH₂NH₂, —CH₂CH₂NHCH₃, or —CH₂CH₂N(CH₃)₂;
Ar₁ is independently (R₅)n-phenyl-;
R₅ is independently Cl;
n=1.
Preferably a compound of formula (III), or a pharmaceutically acceptable salt thereof, wherein:
R₁ is

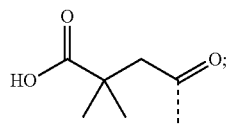

X is independently methylene, or carbonyl;
L is independently a direct bond;
Y is independently a direct bond;
Z₂ is N, Z₃ is CH, and Z₄ is O; or Z₂ is CH, Z₃ is N, and Z₄ is O, that means

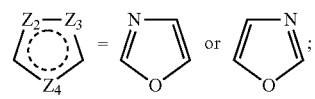

Ar₁ is independently (R₅)n-phenyl-;
R₅ is independently Cl;
n=1.
Preferably a compound of formula (III), or a pharmaceutically acceptable salt thereof, wherein:
R₁ is

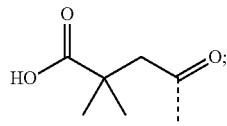

X is independently methylene, or carbonyl;
L is independently a direct bond or —CH₂—;
Y is independently a direct bond;
Z₂ is O, Z₃, and Z₄ are independently N; or Z₃ is O, Z₂, and Z₄ are independently N, that means

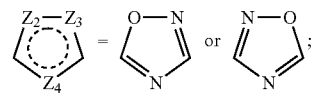

Ar₁ is independently (R₅)n-phenyl-;
R₅ is independently Cl;
n=1.

The compounds of formula (I)~(III) in present invention as described above, or a pharmaceutically acceptable salt thereof, wherein the compound is selected from the below compounds, but not limited to:
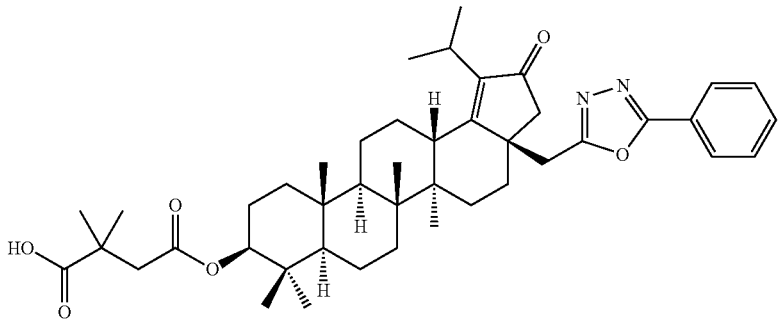
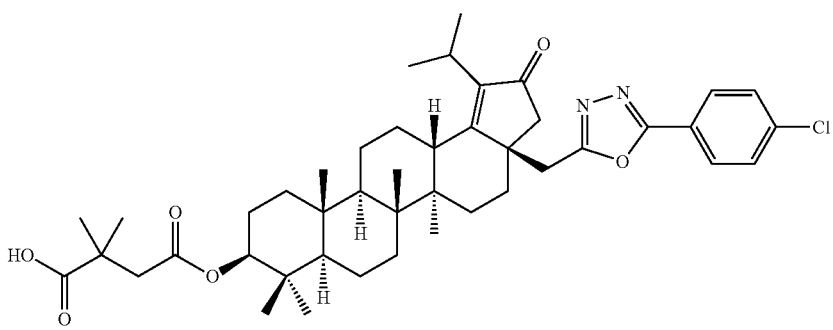
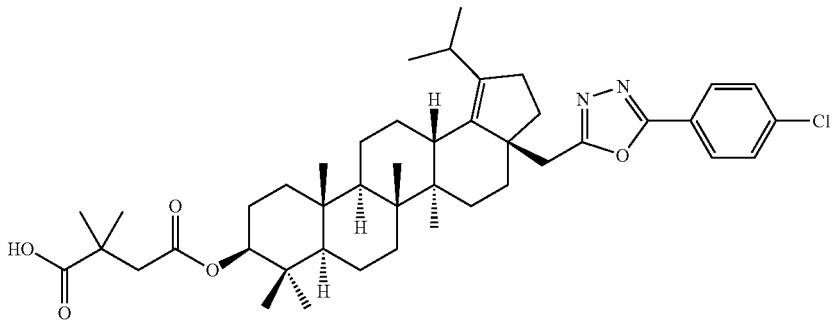
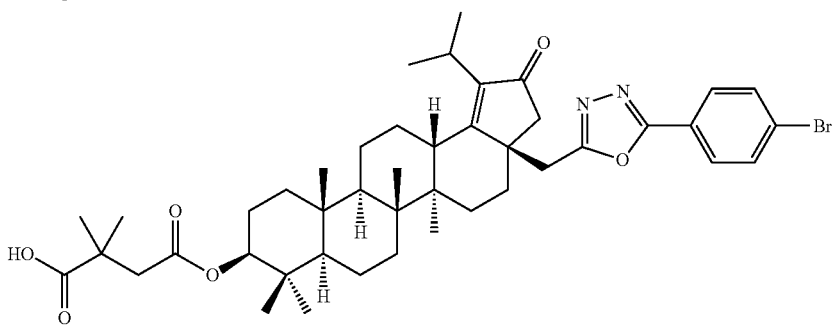
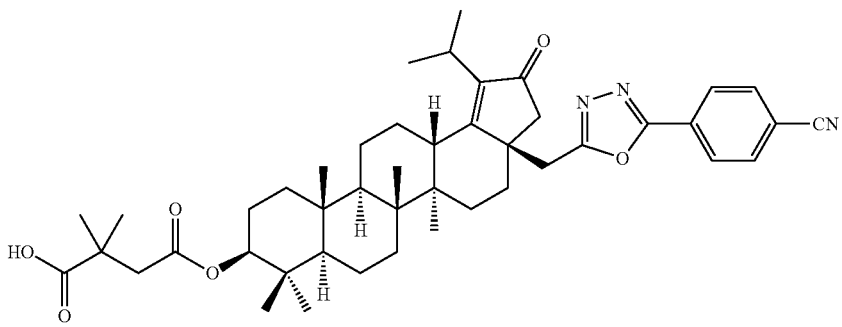

-continued
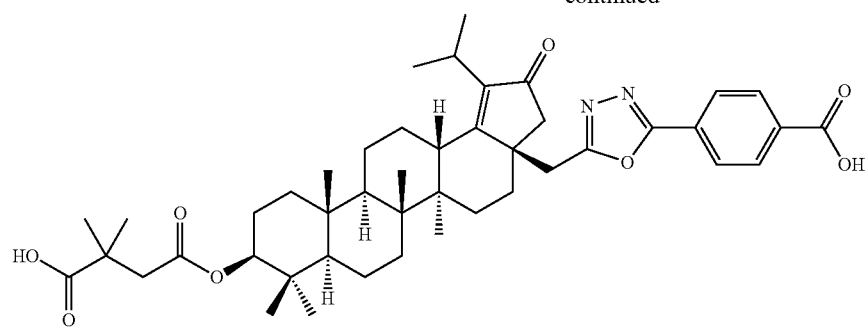
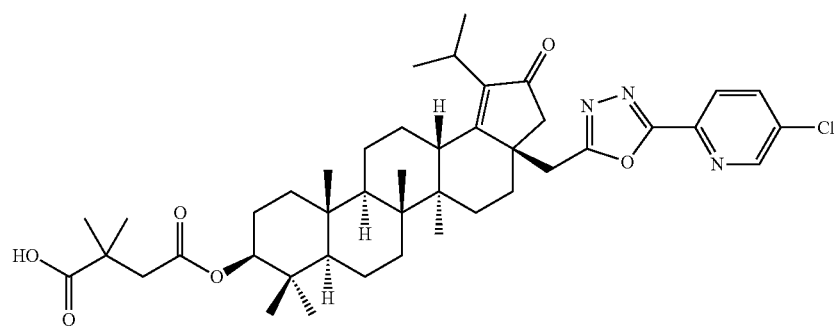
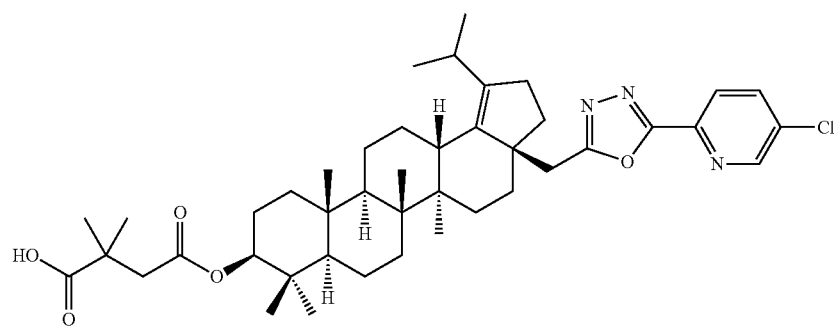
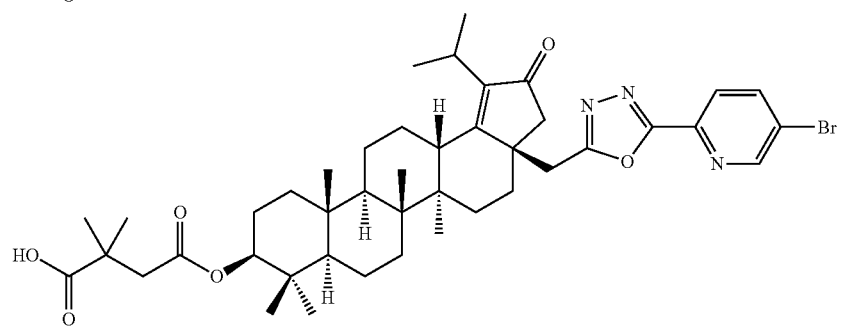
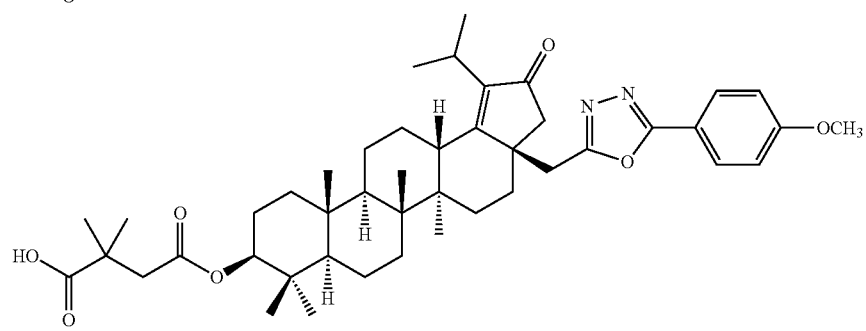

-continued
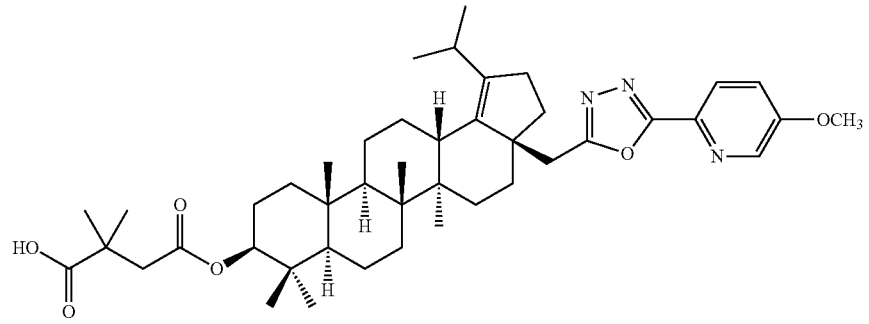
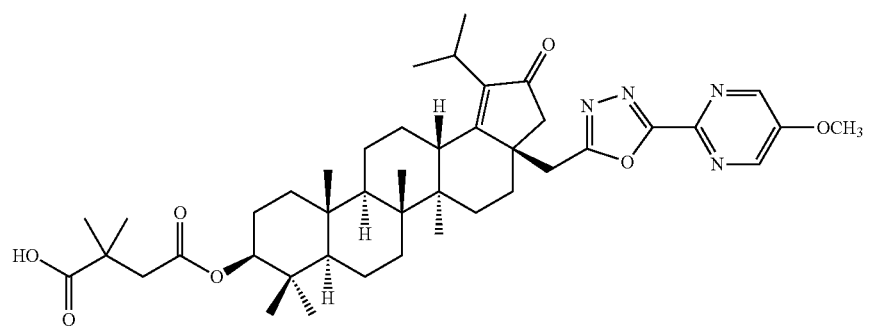
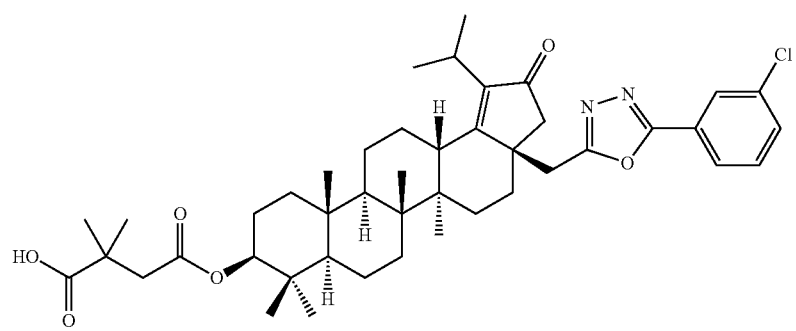
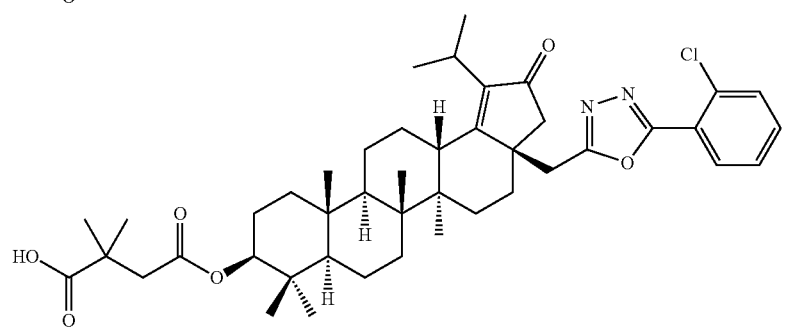
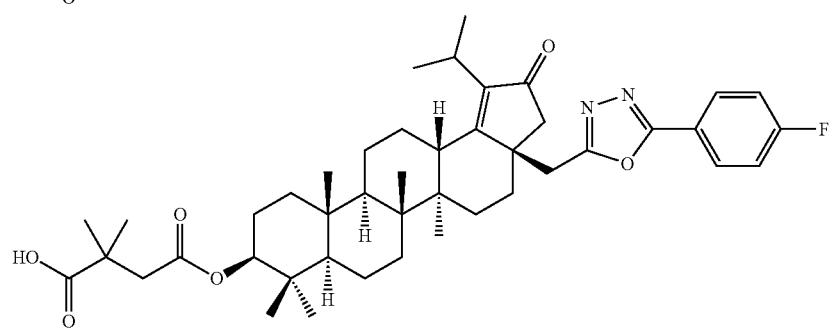

-continued
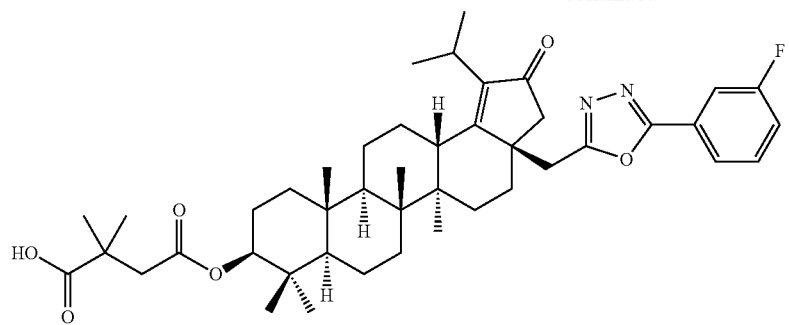
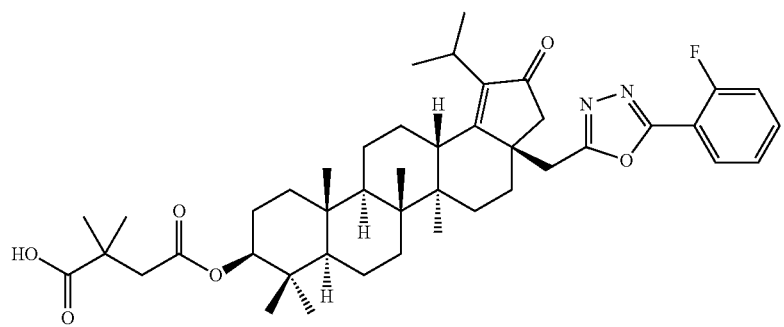
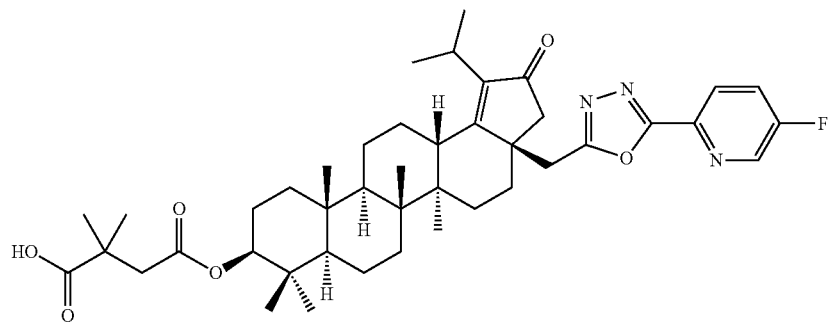
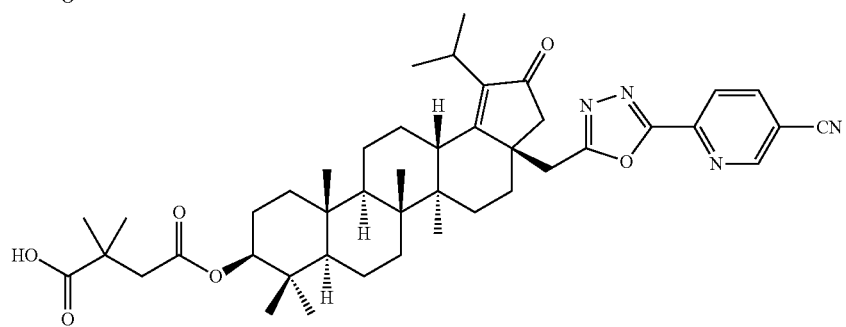
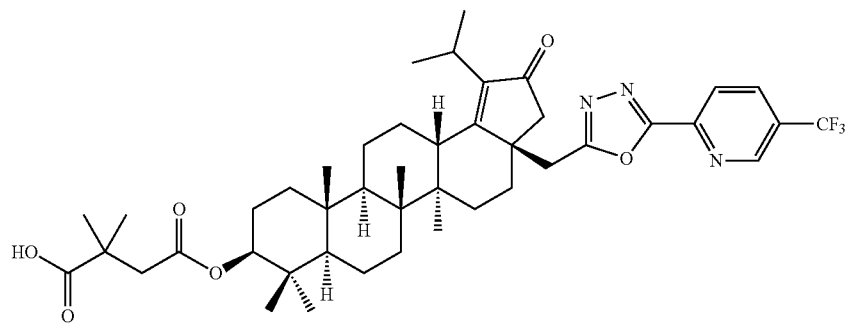

-continued
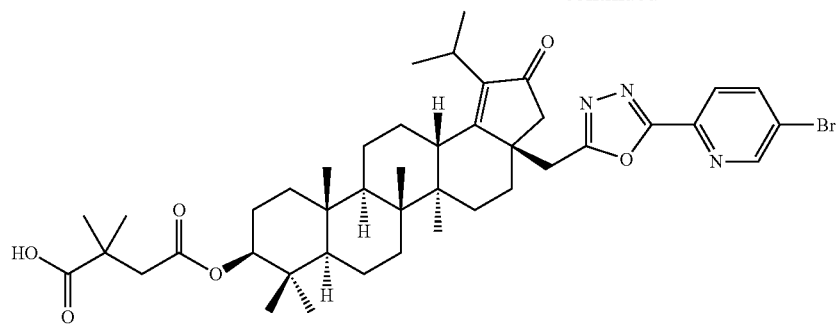
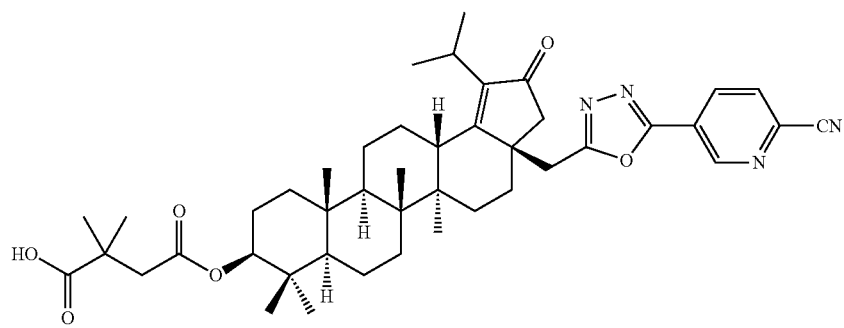
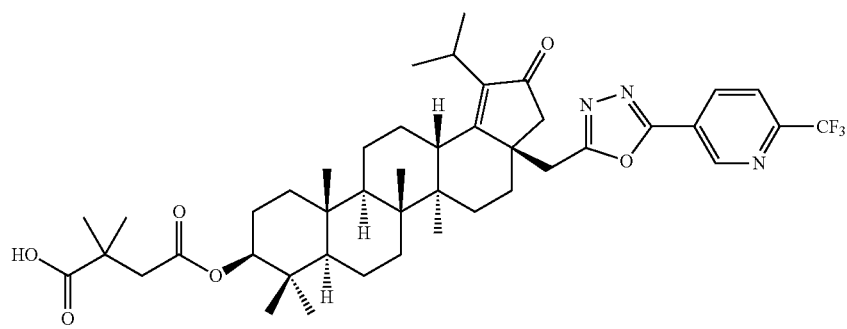
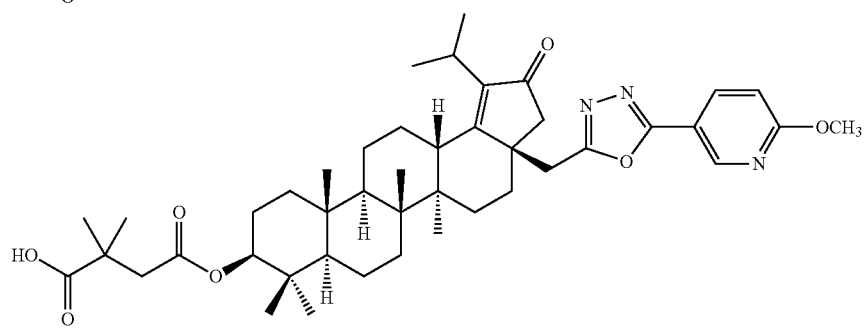
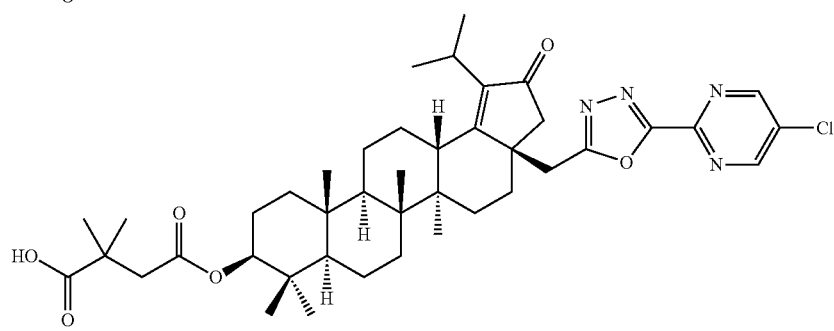

-continued
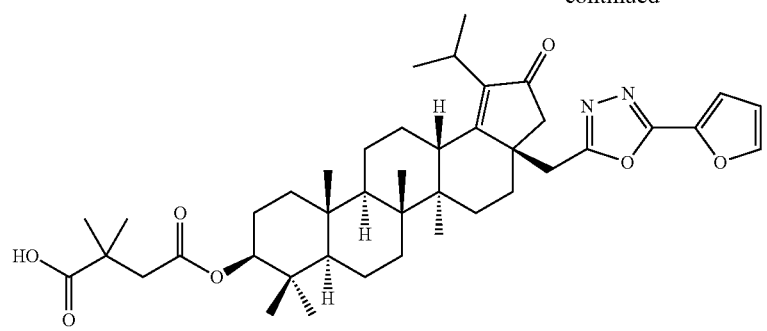
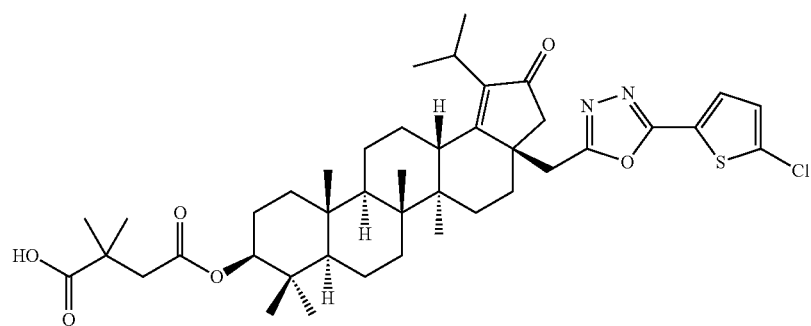
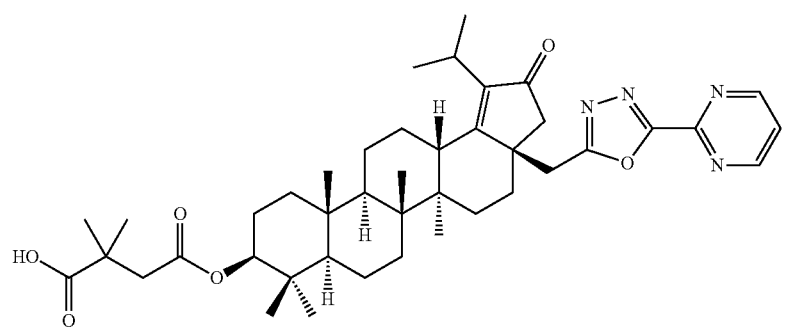
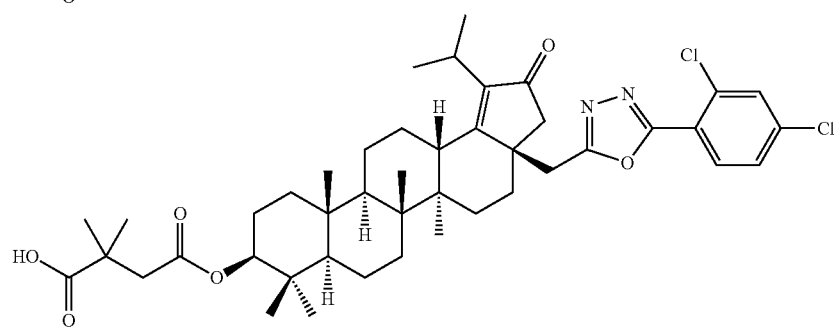
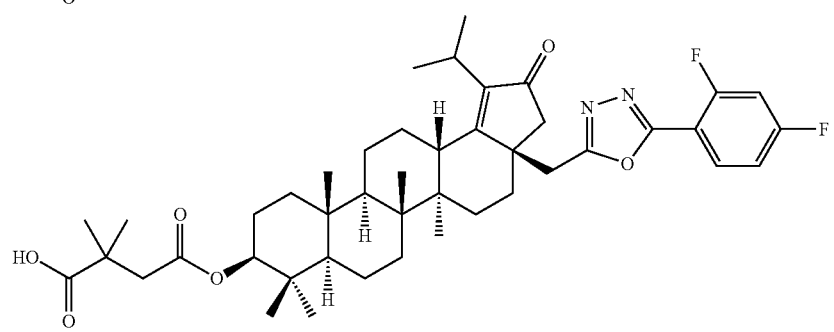

-continued
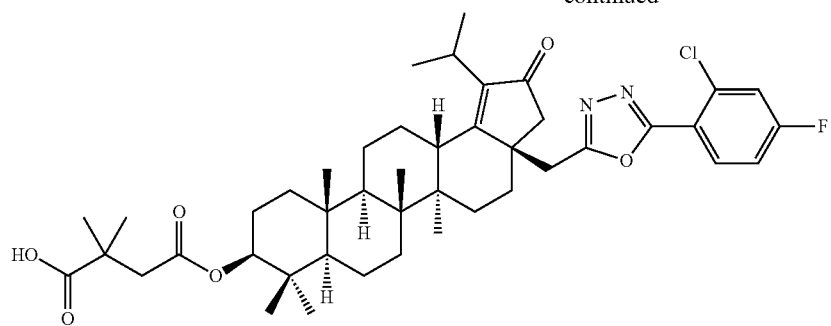
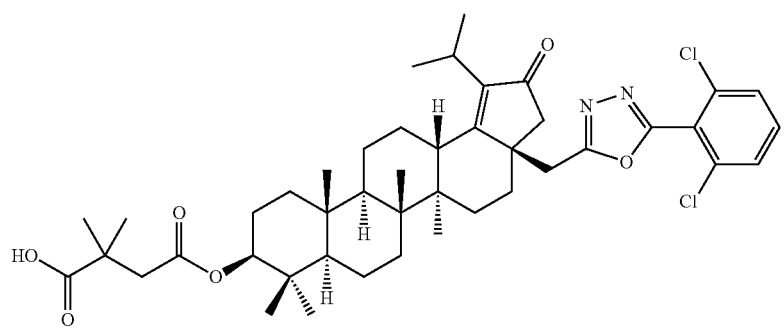
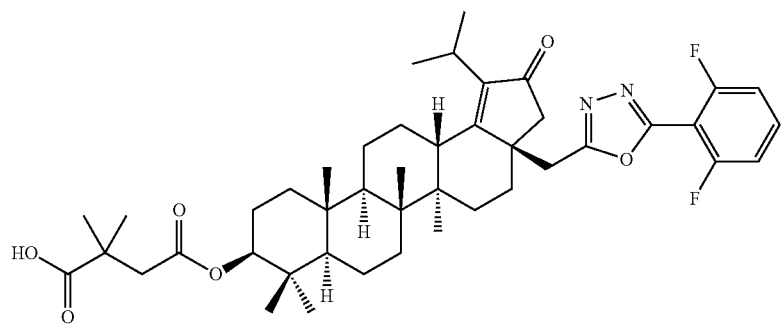
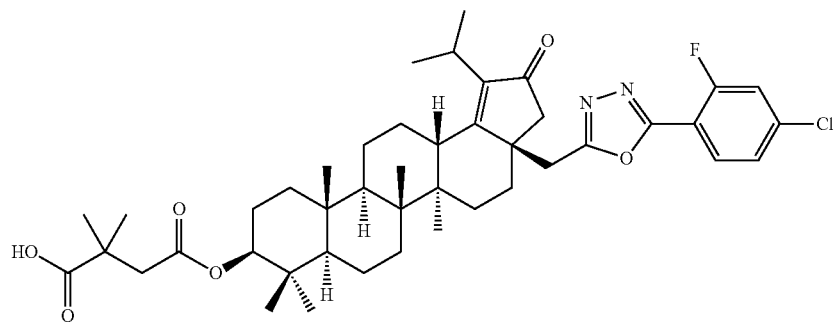
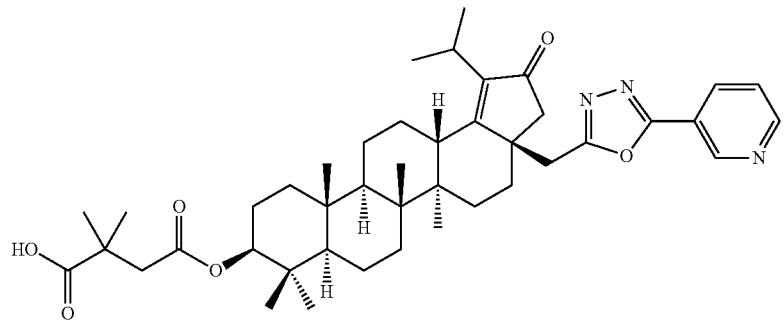

-continued
23 24
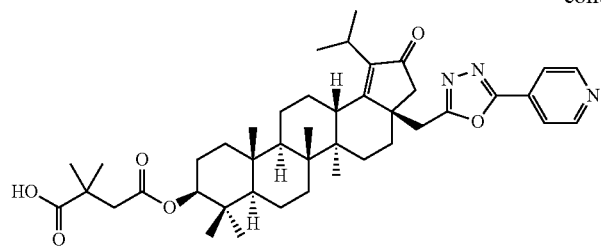
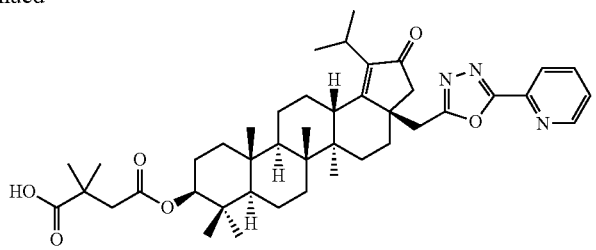
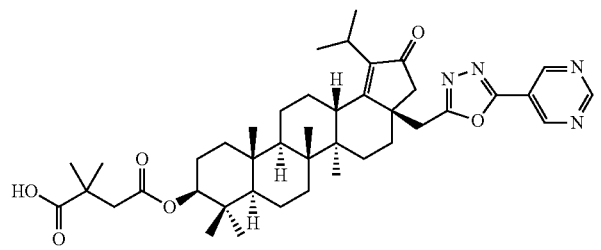
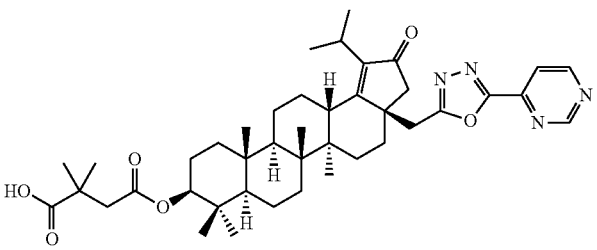
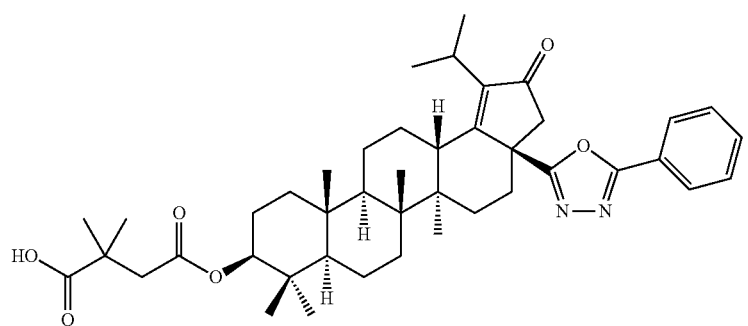
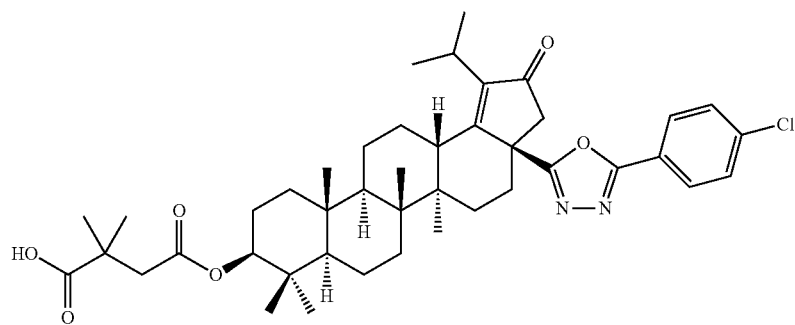
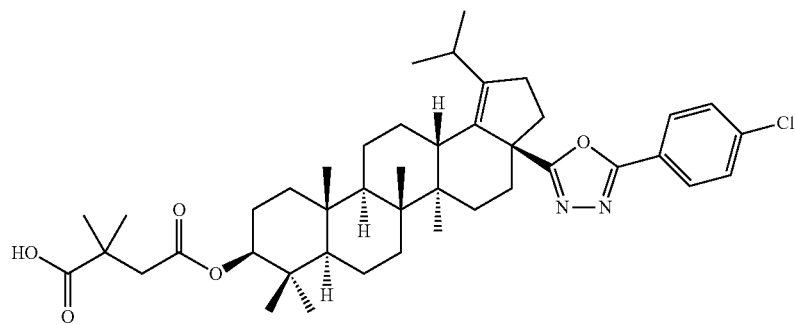

-continued
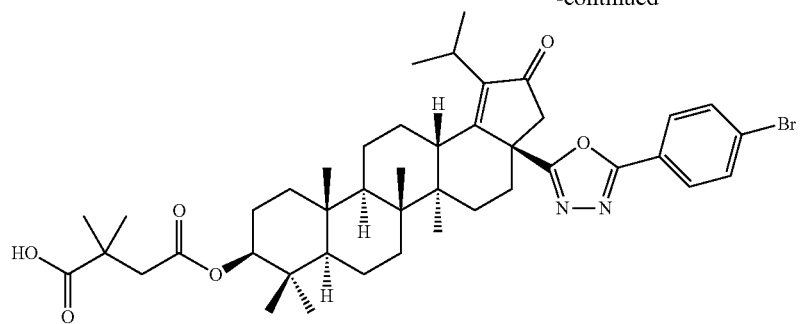
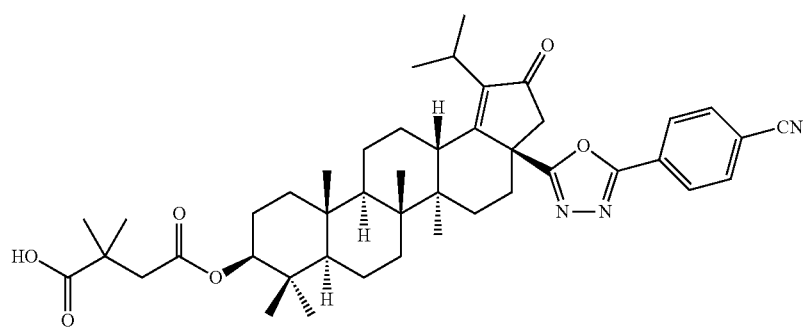
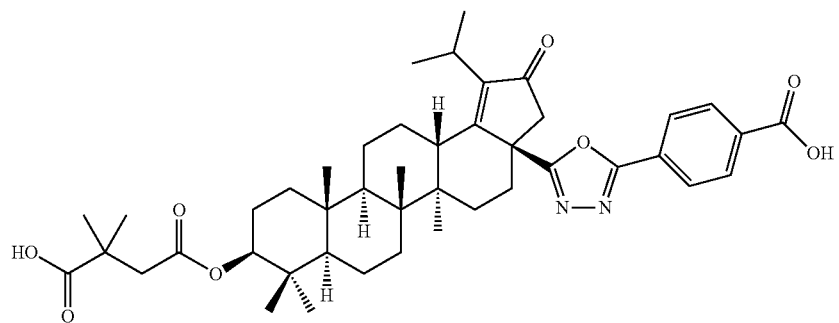
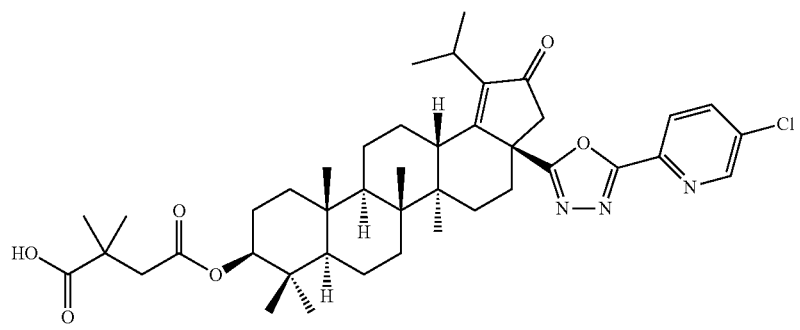
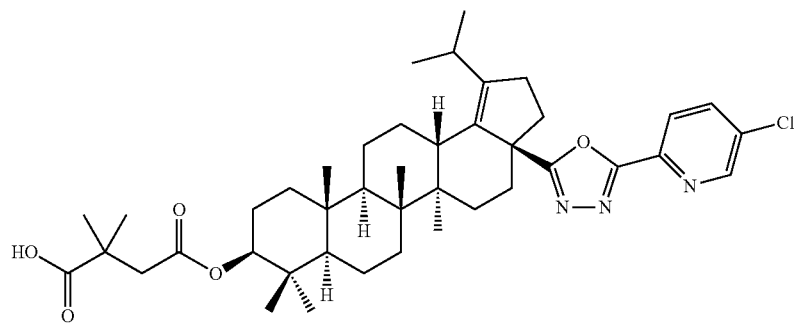

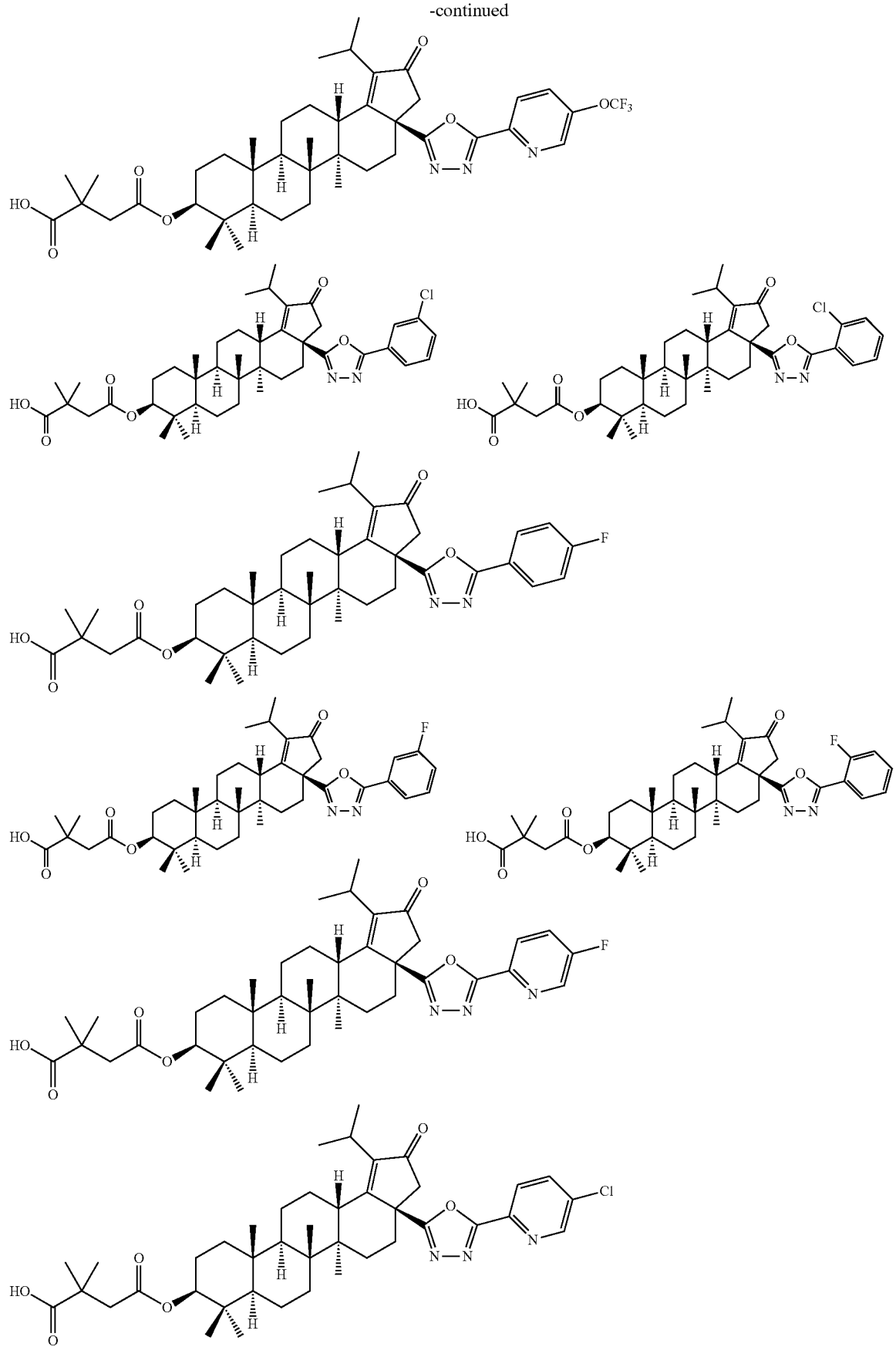

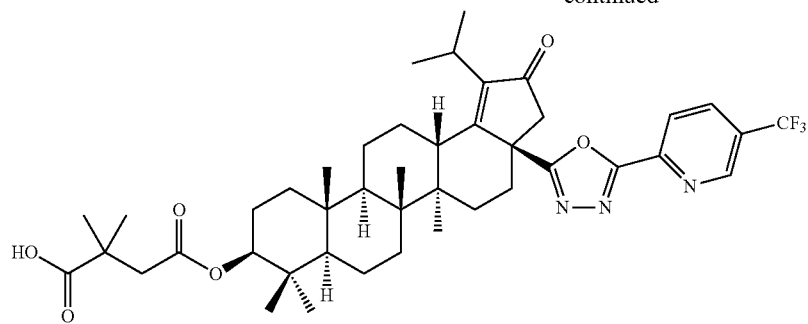
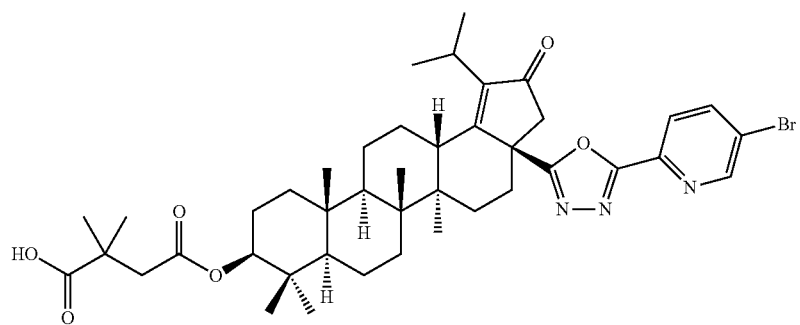
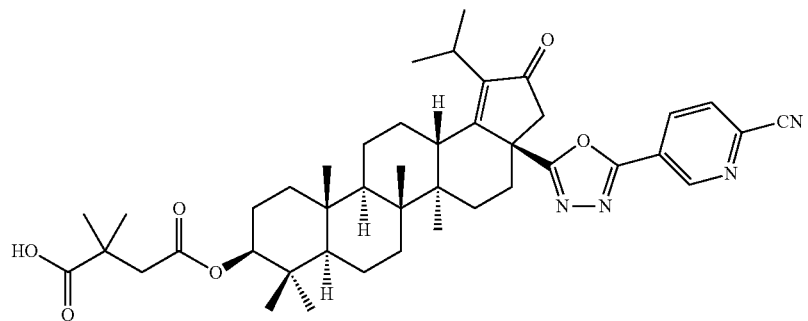
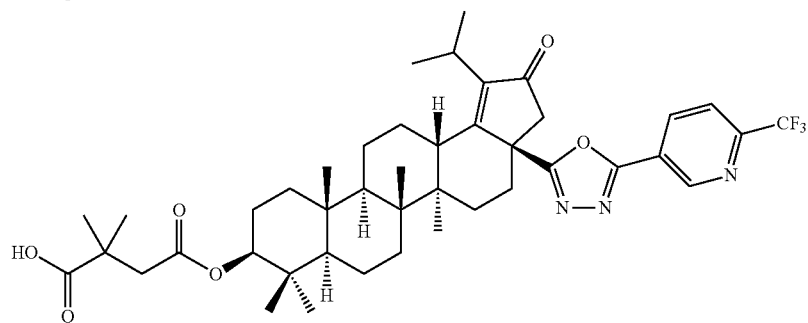
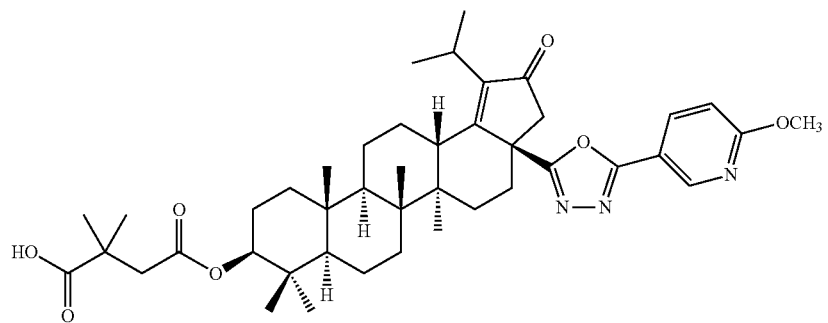

-continued
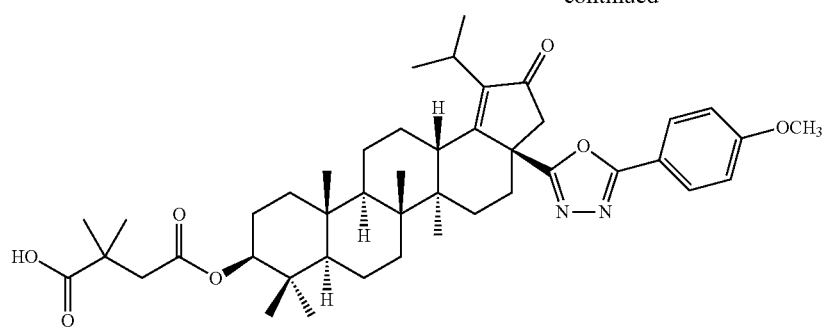
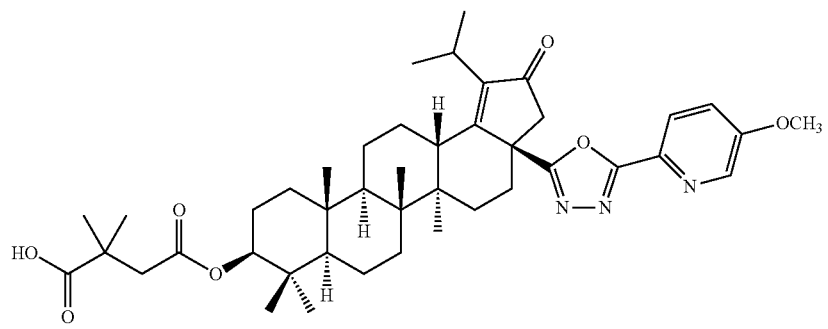
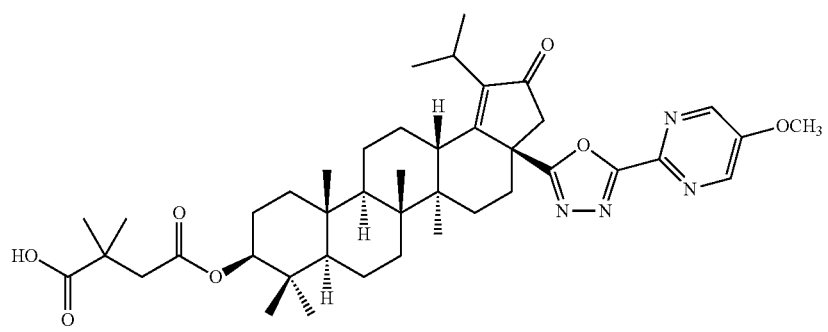
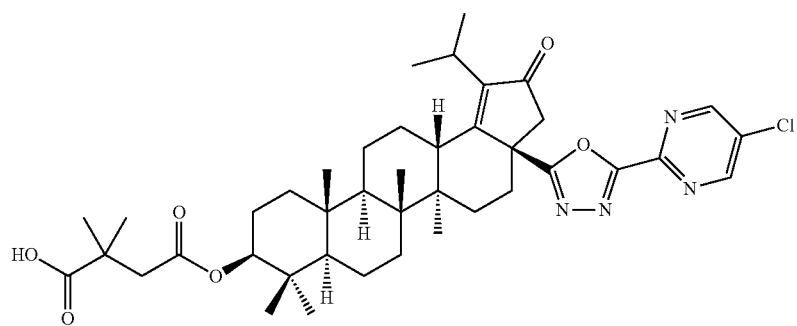
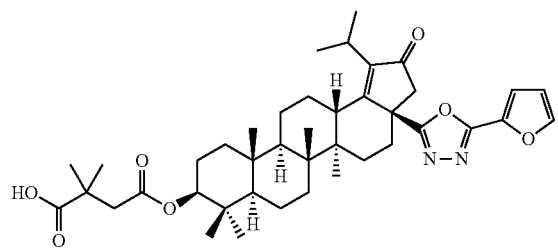
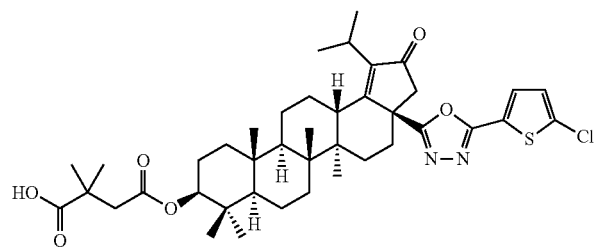

-continued
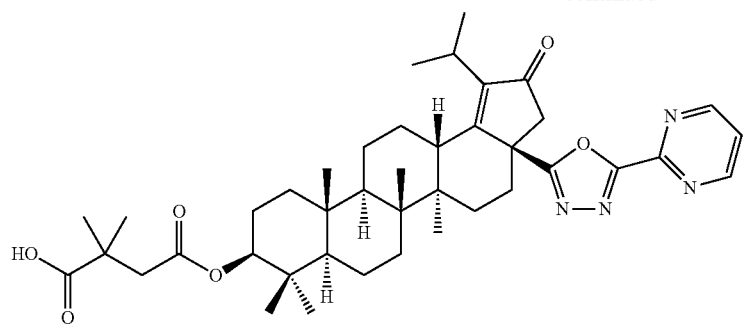
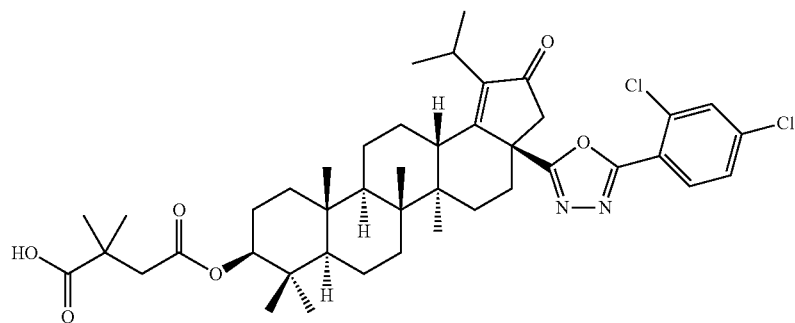
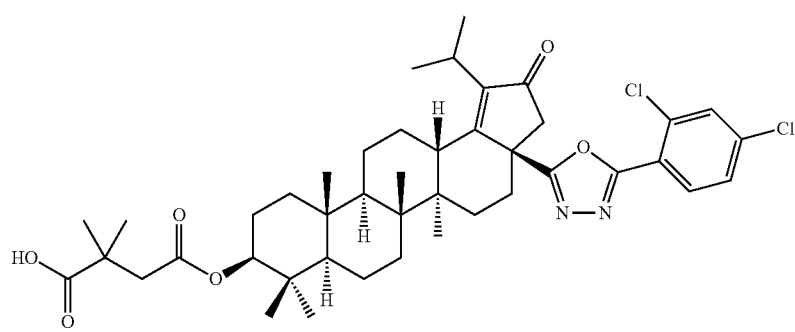
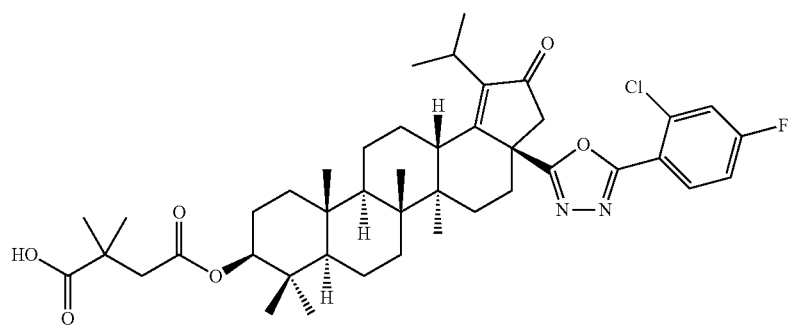
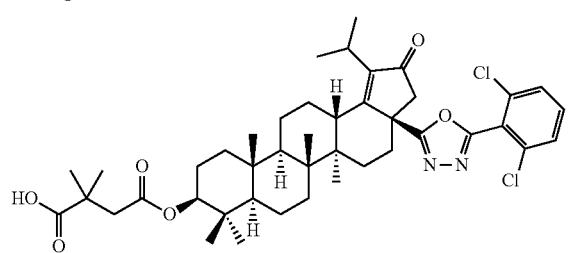
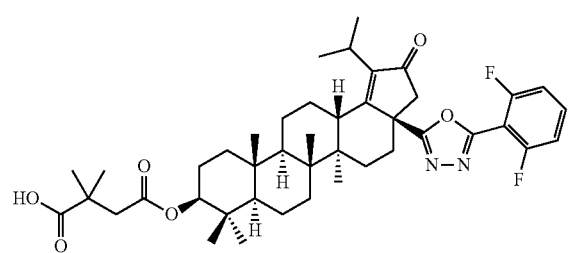

-continued
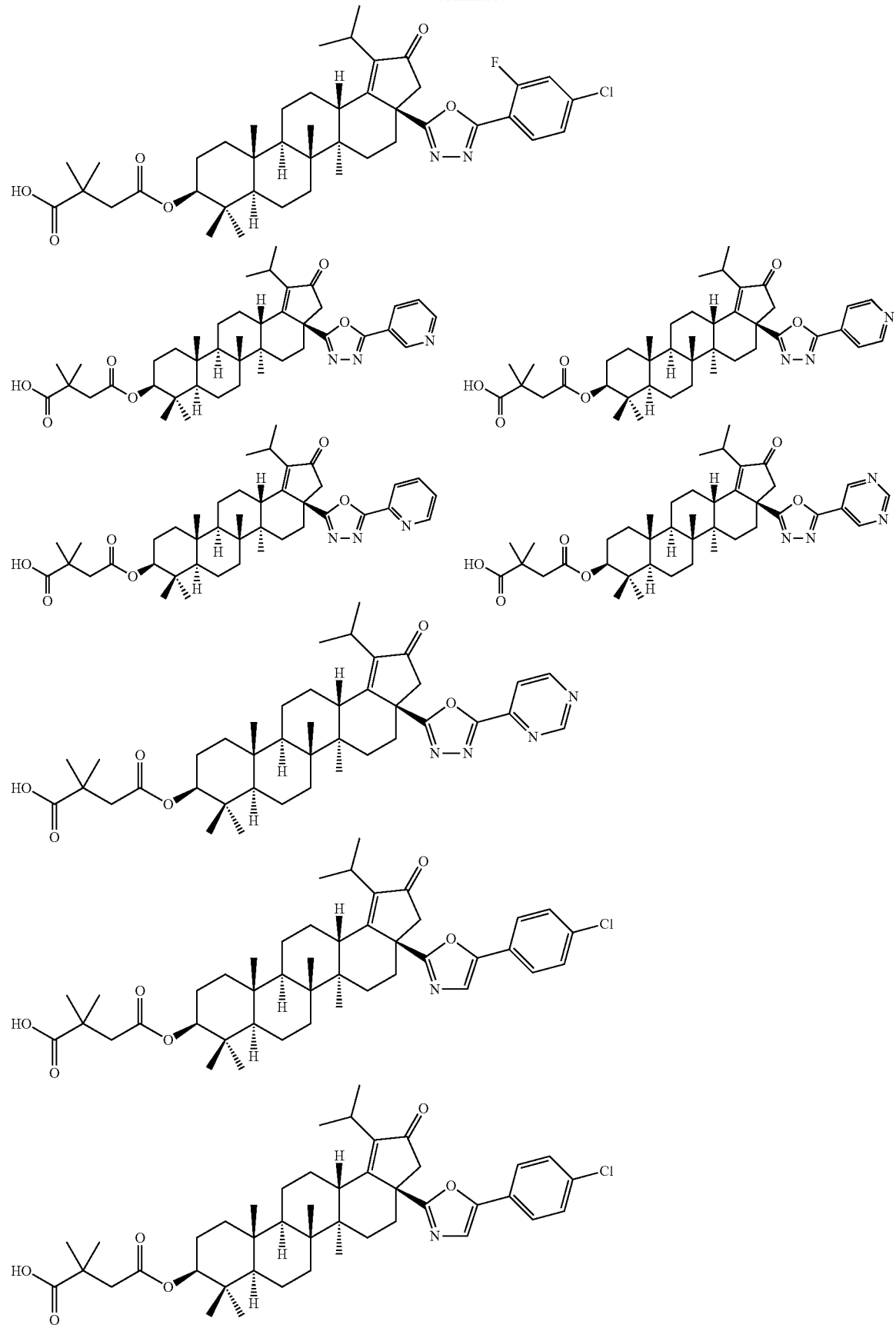

-continued
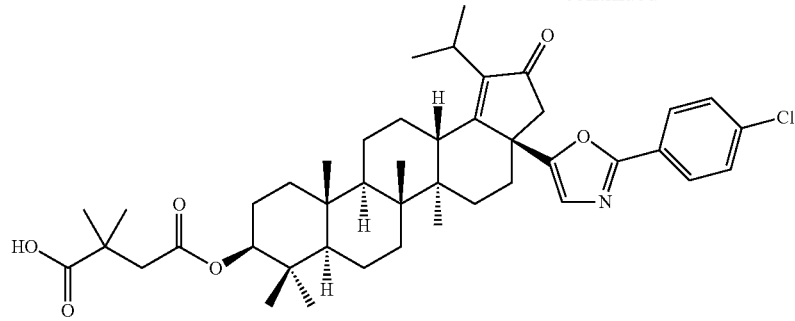
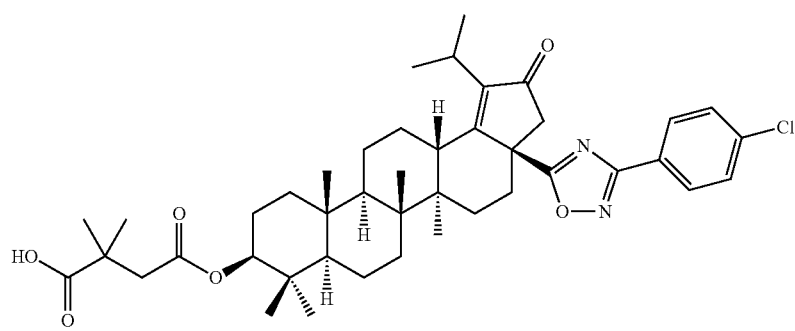
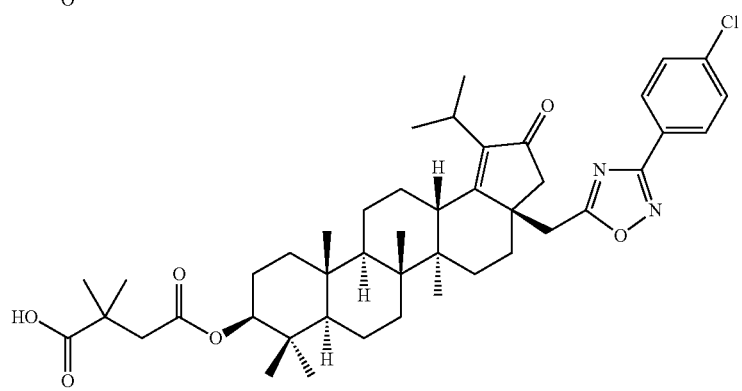
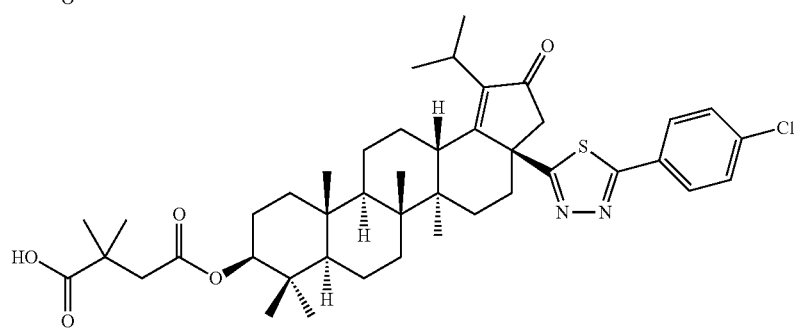
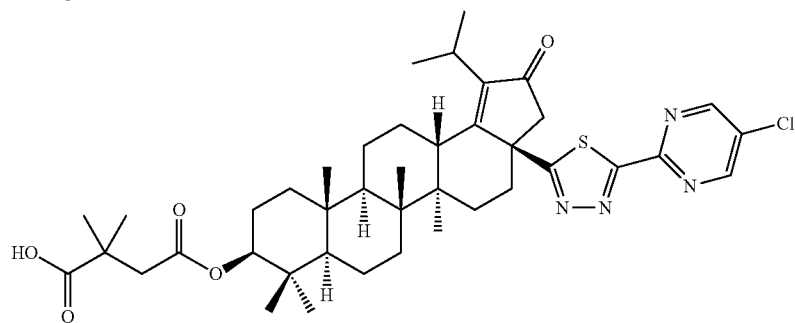

-continued
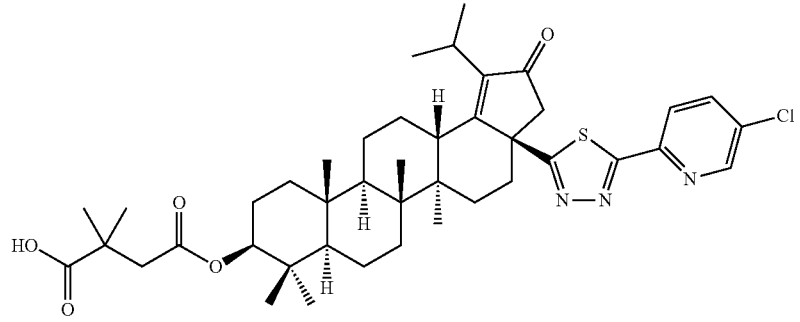
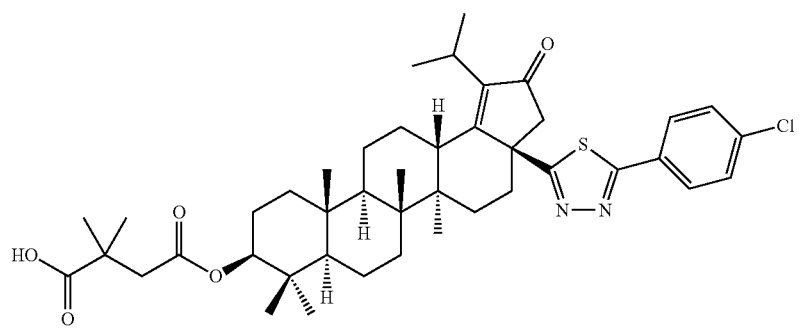
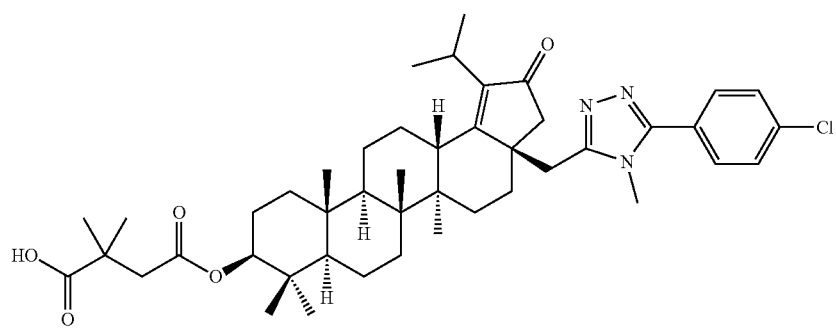
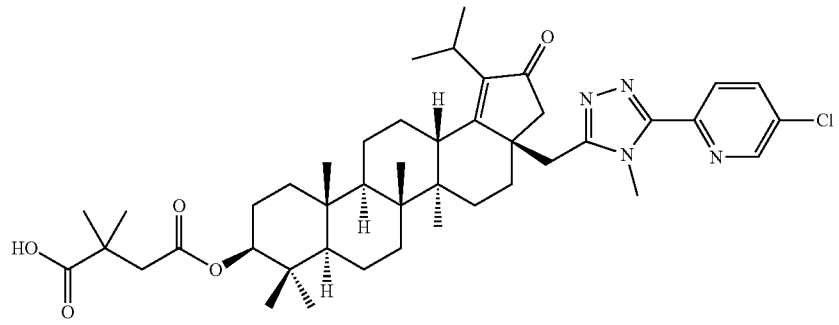
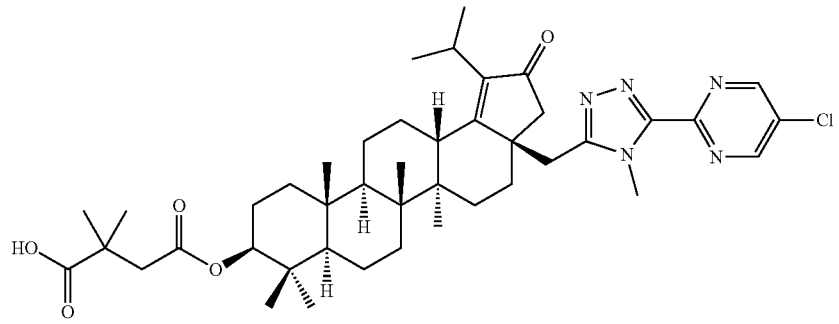

-continued
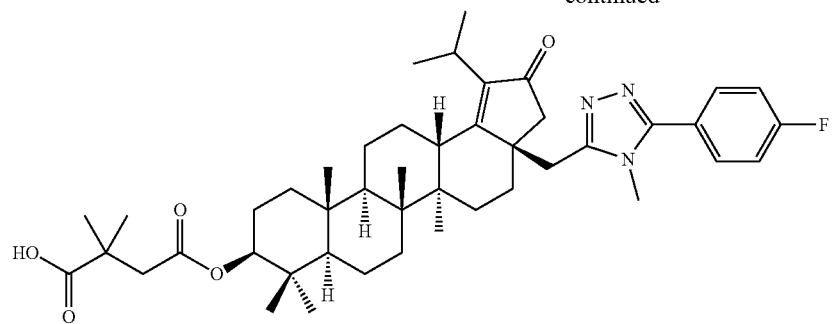
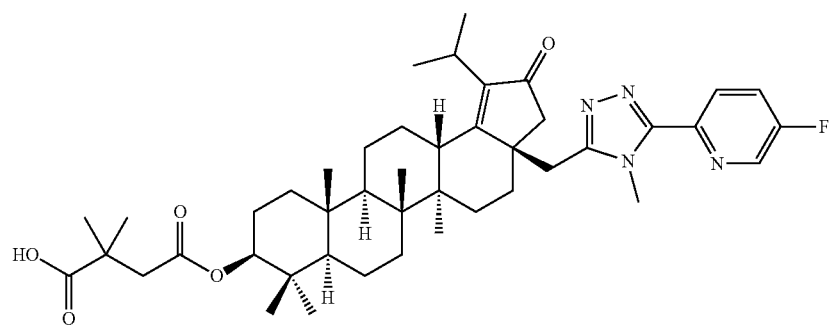
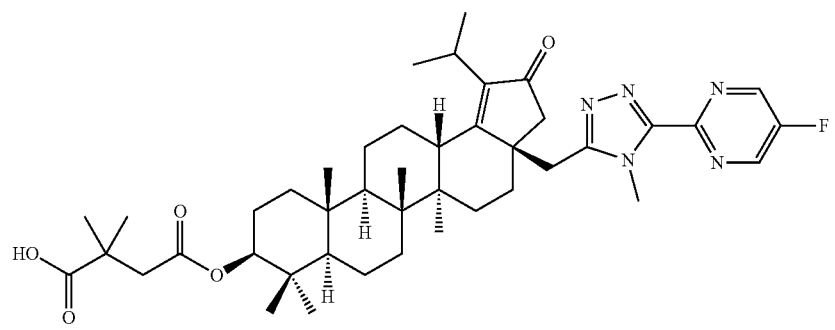
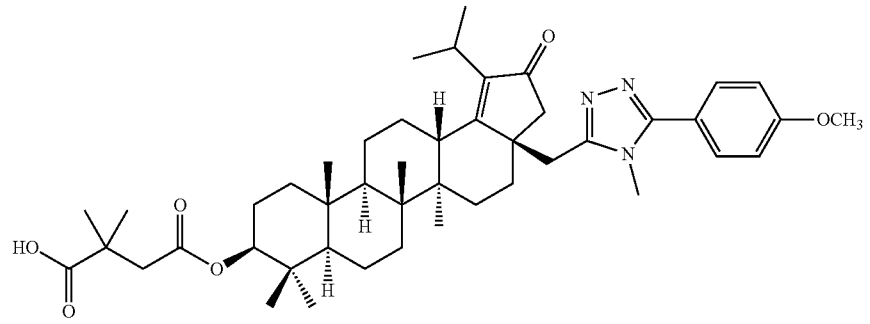
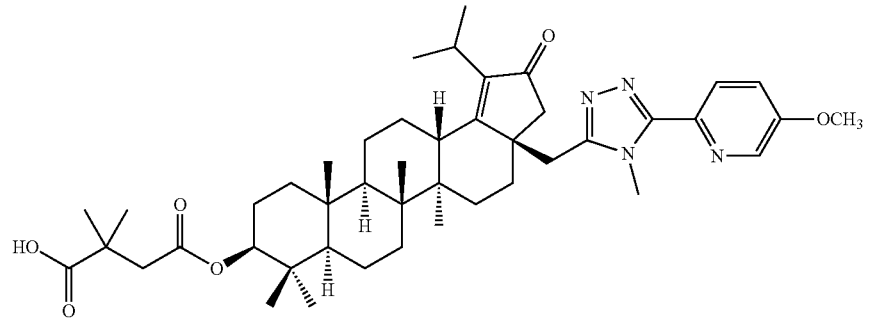

-continued
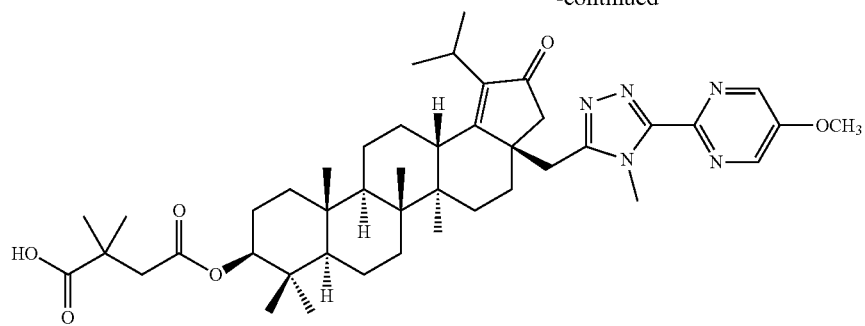
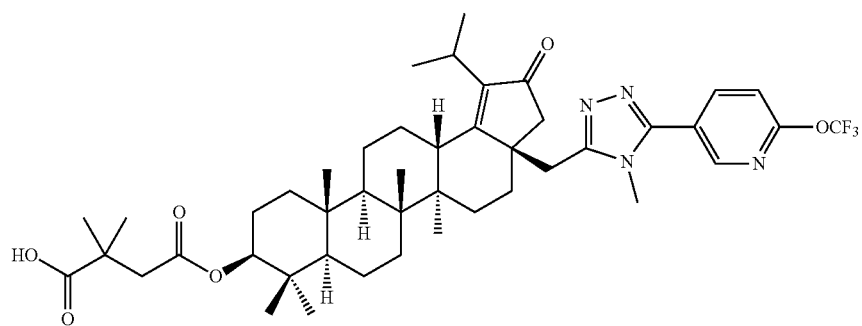
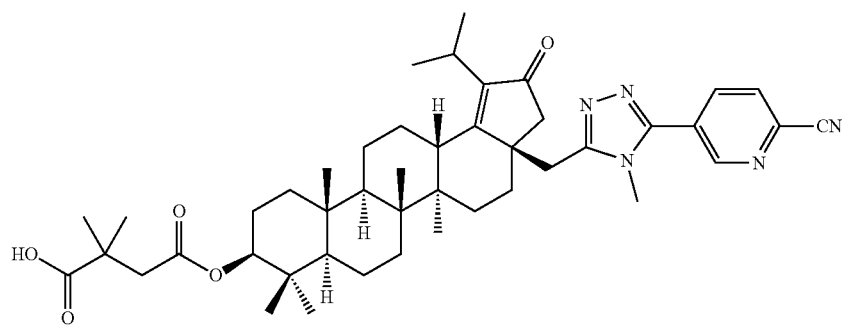
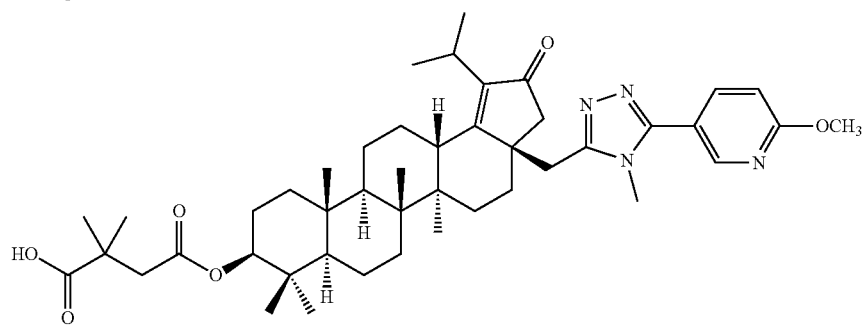
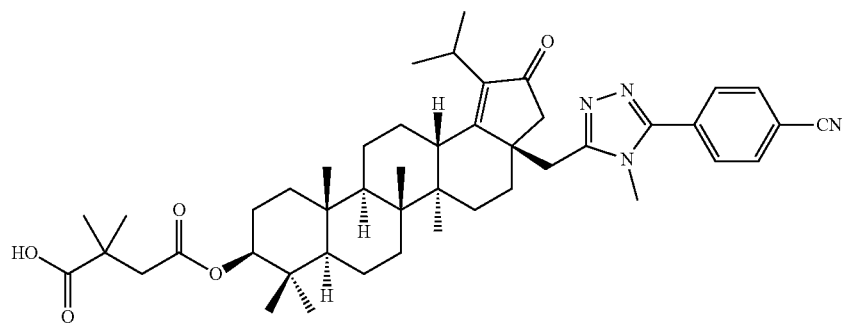

-continued
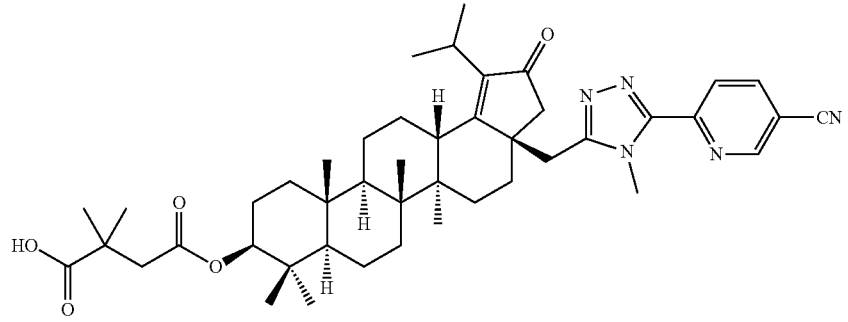
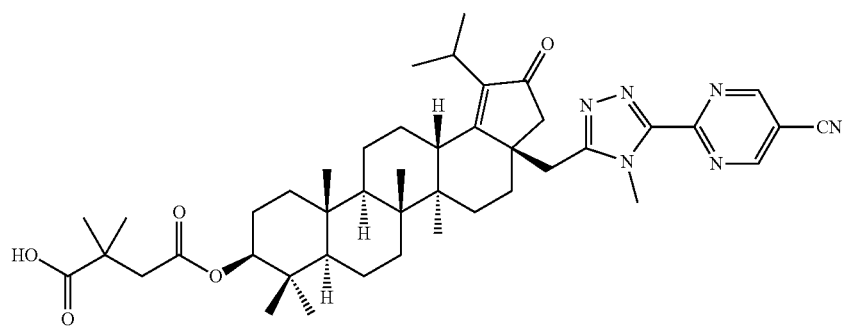
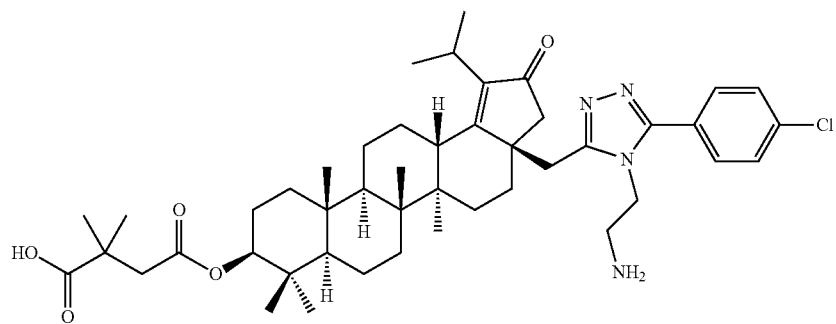
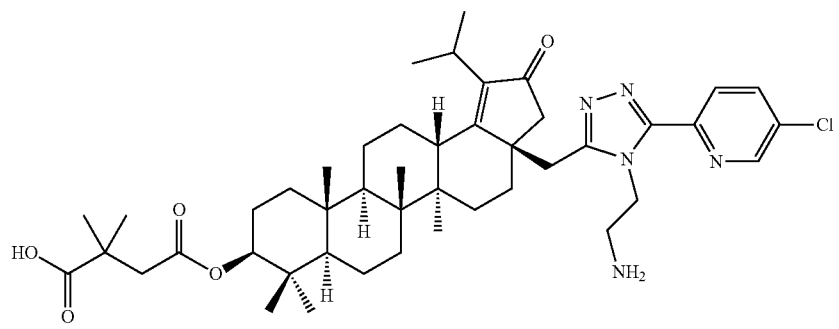
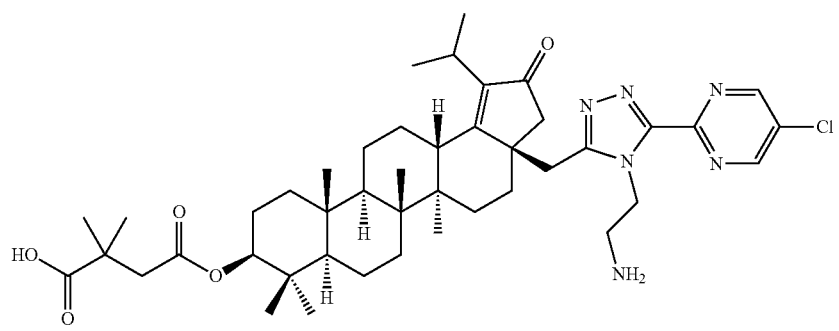

-continued
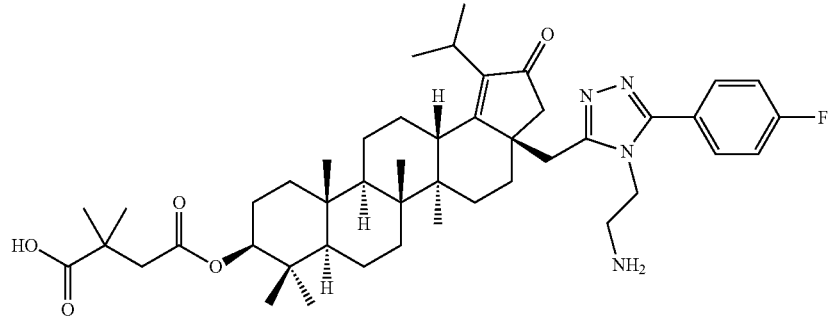
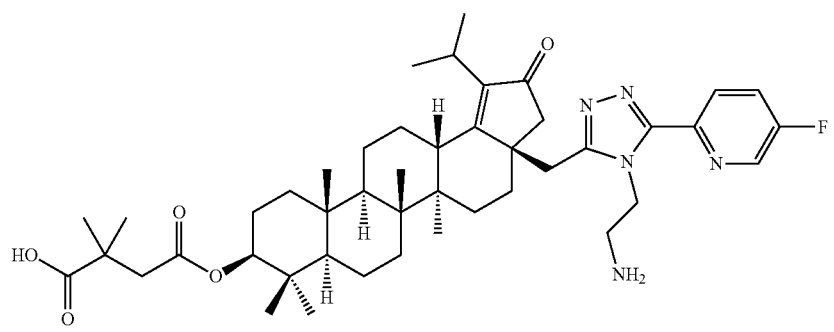
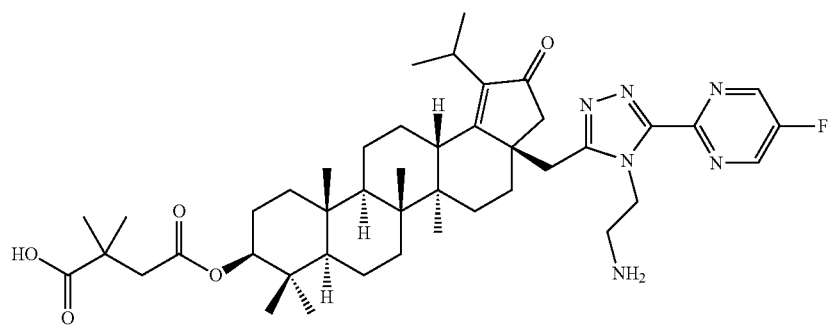
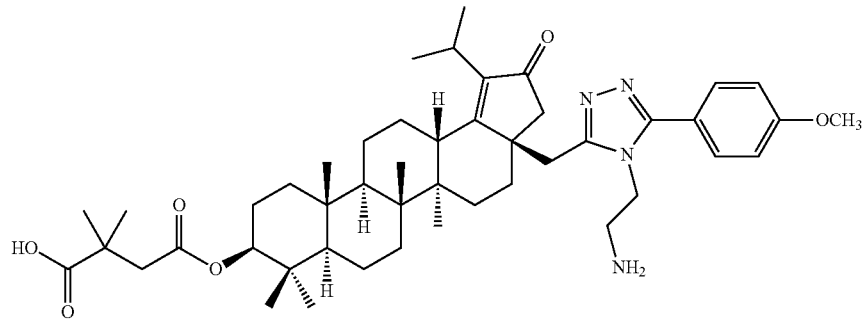
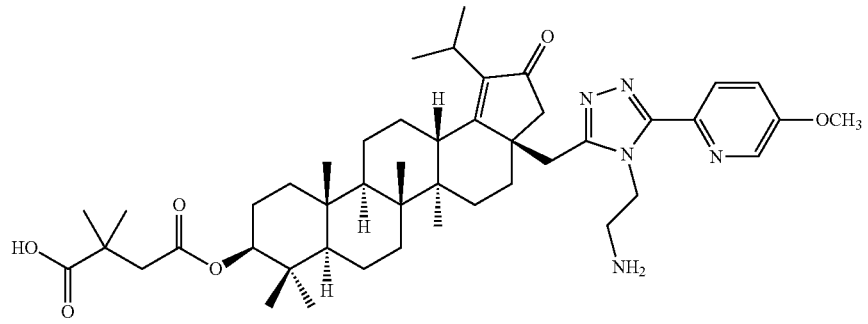

-continued
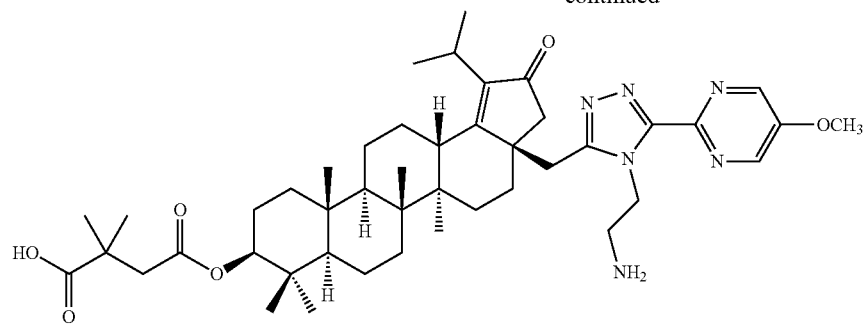
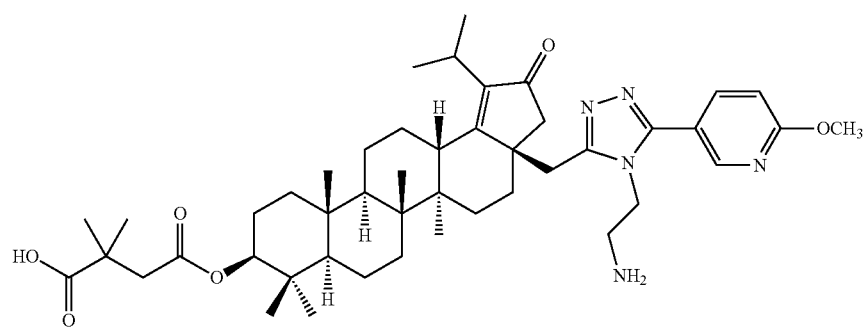
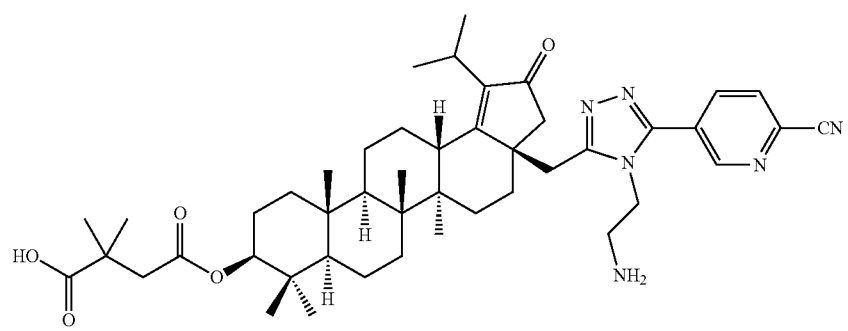
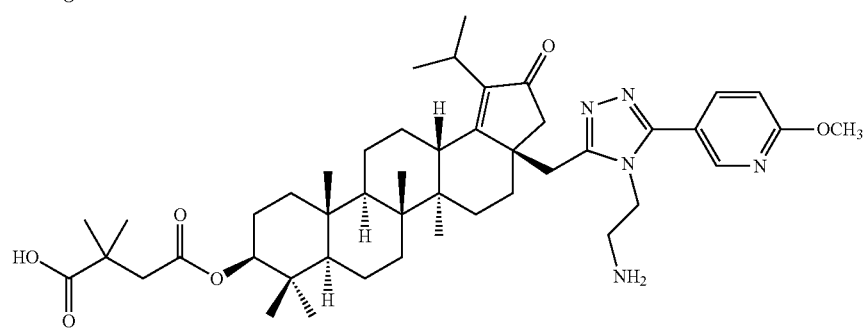
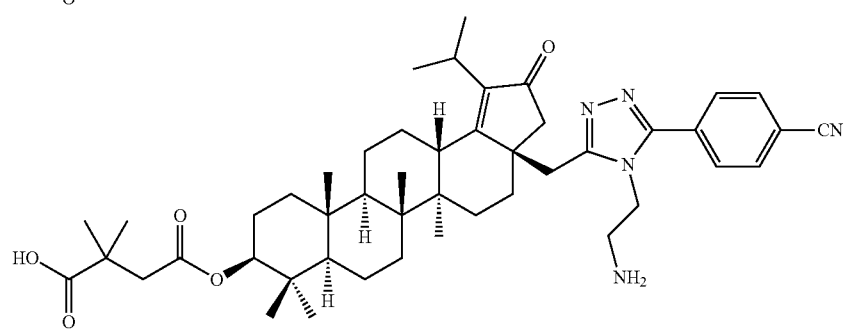

-continued
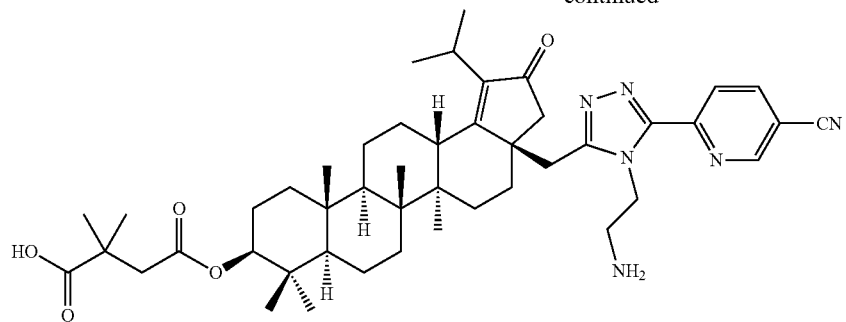
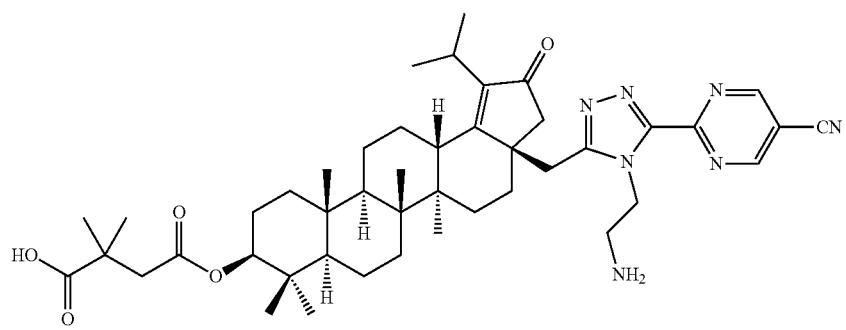
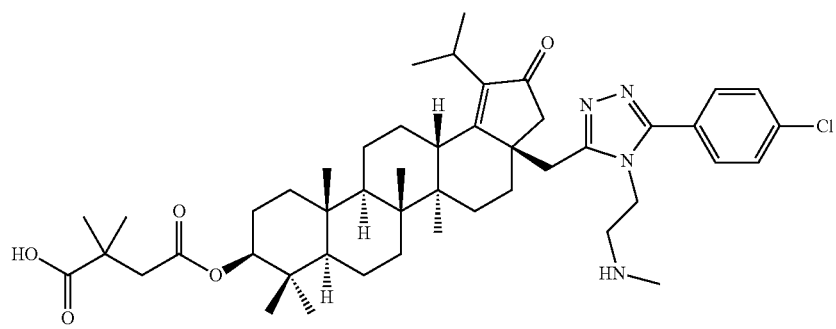
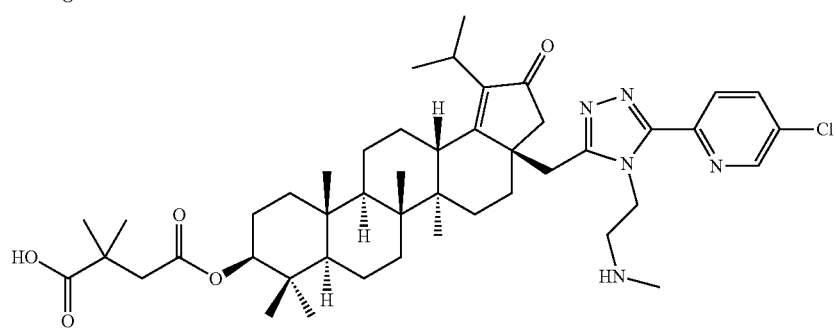
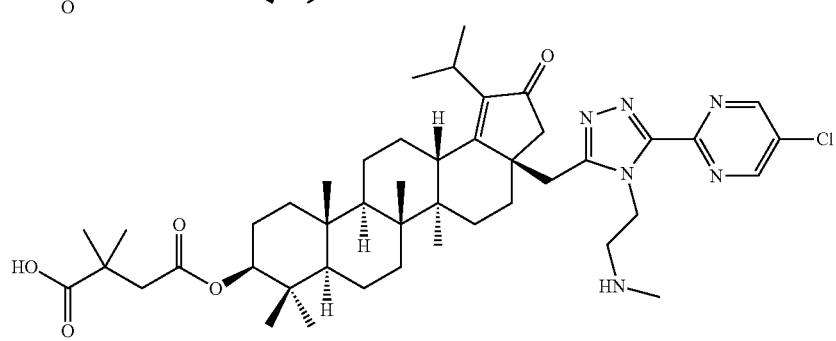

-continued
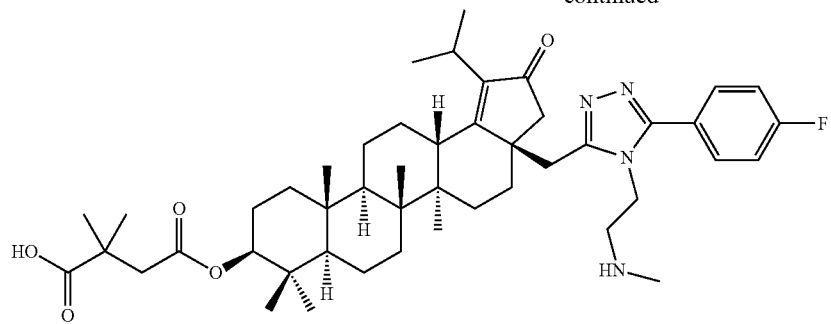
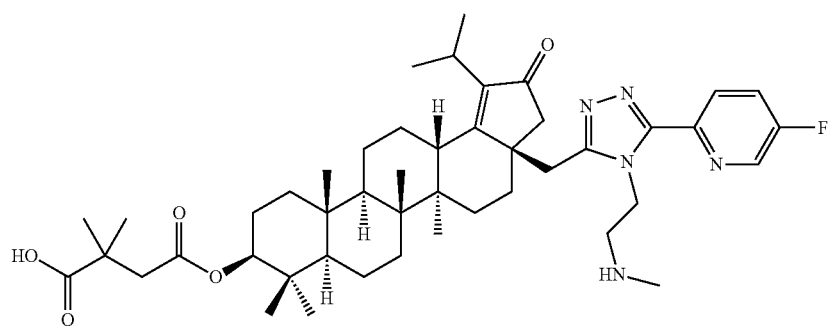
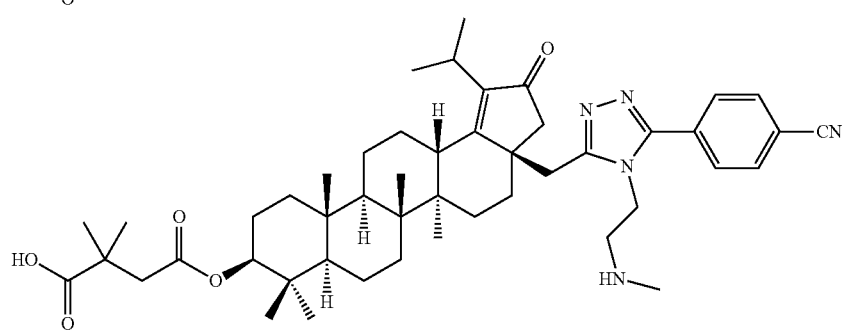

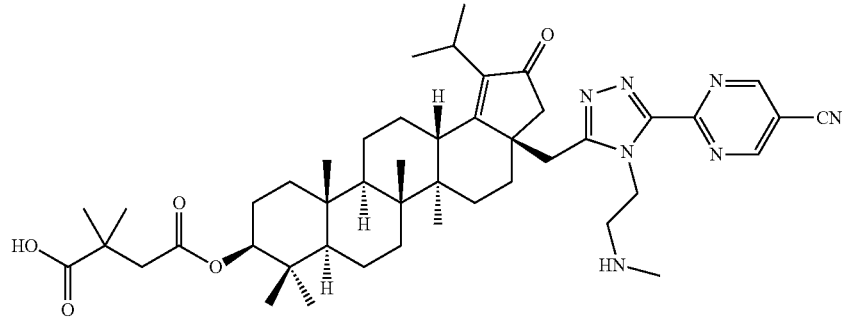
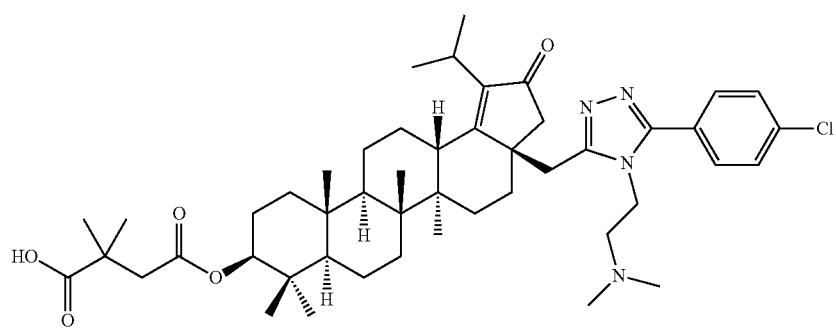
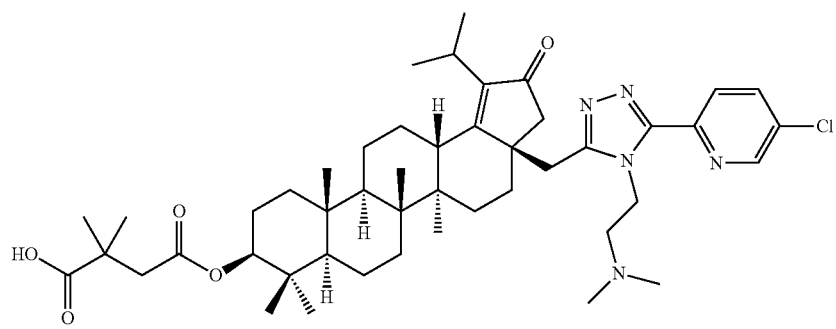
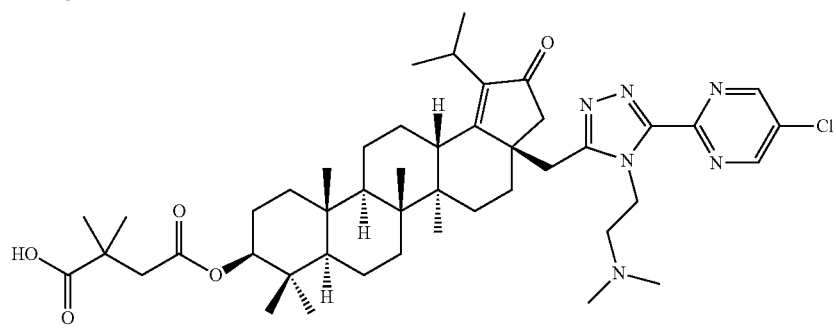
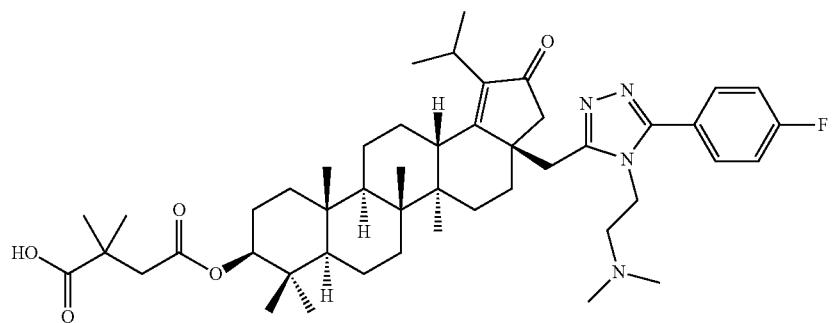

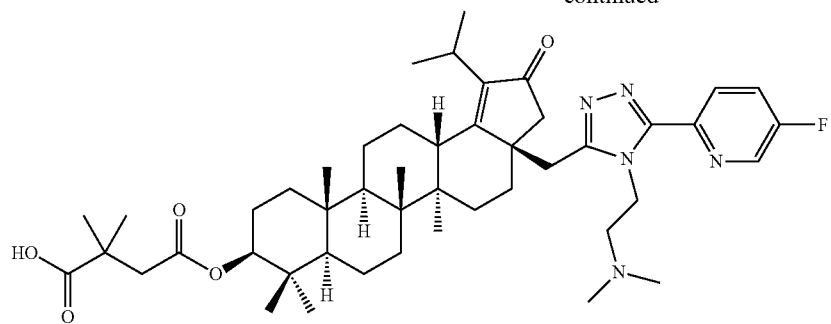
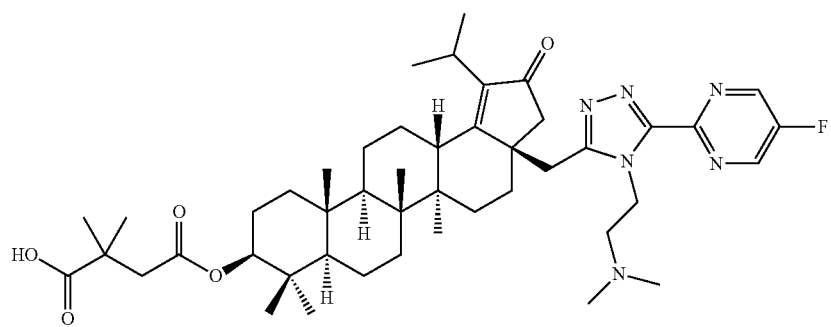
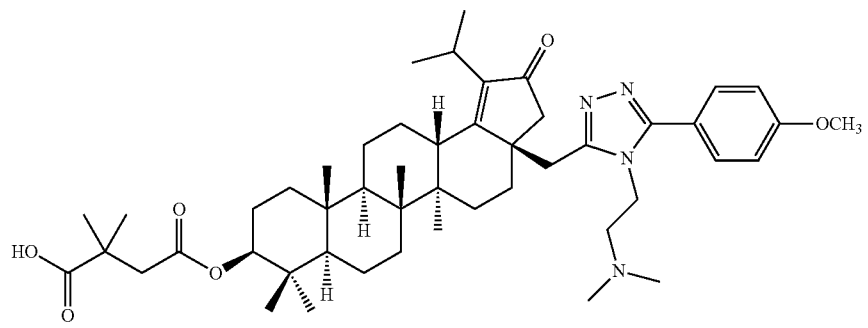
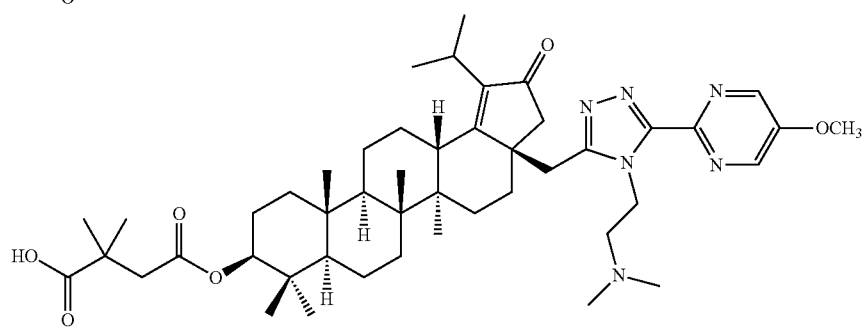

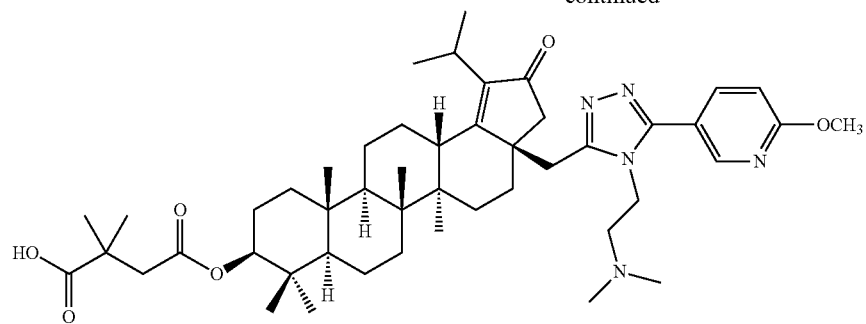
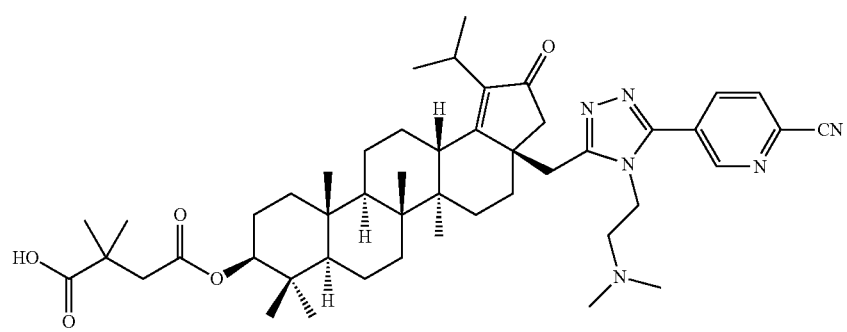
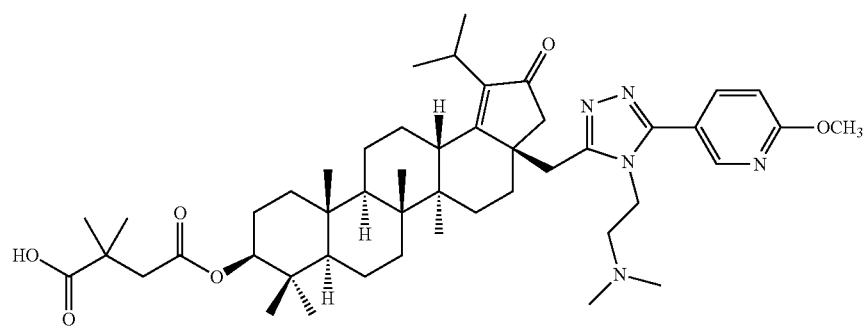
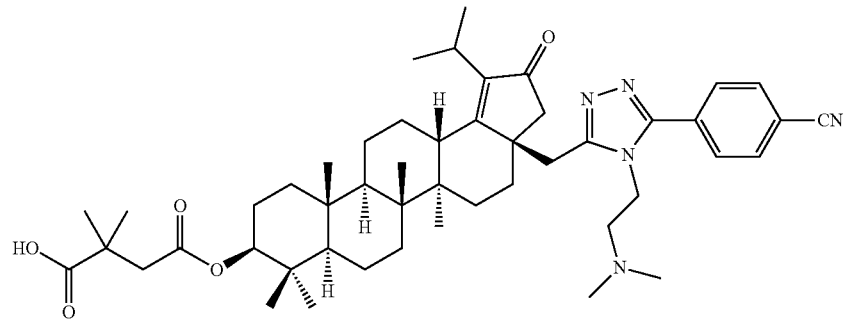
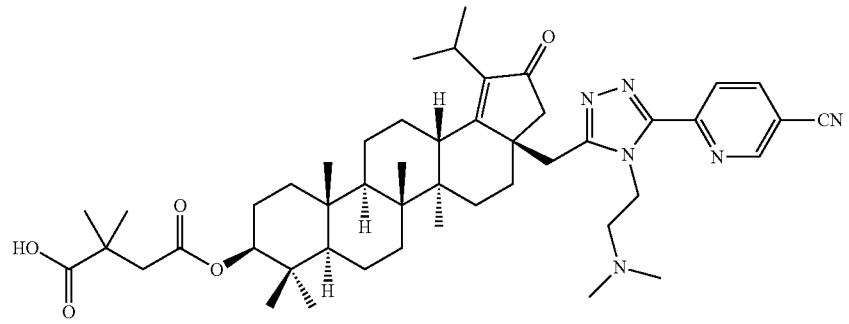

-continued
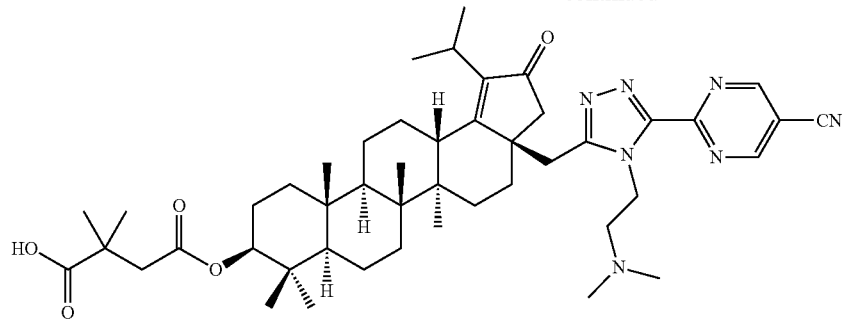
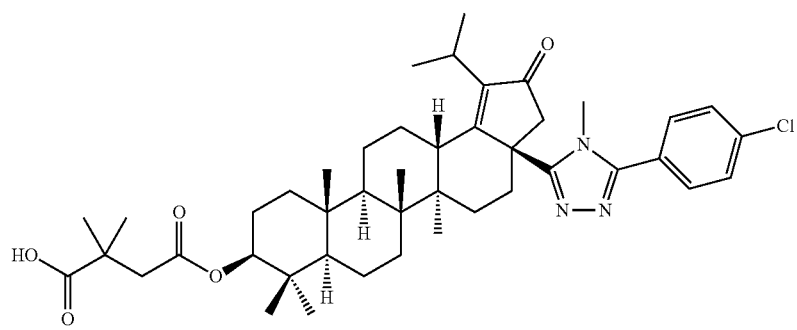
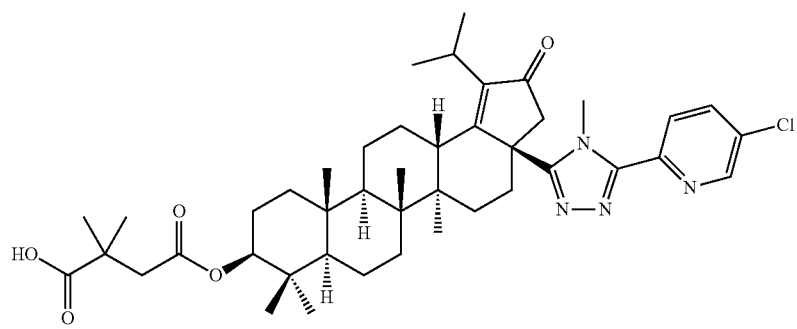
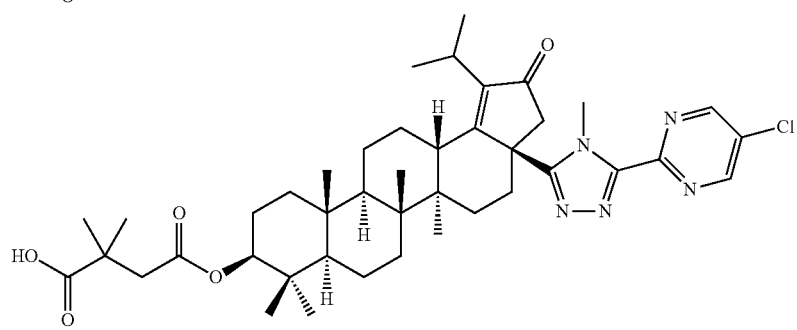
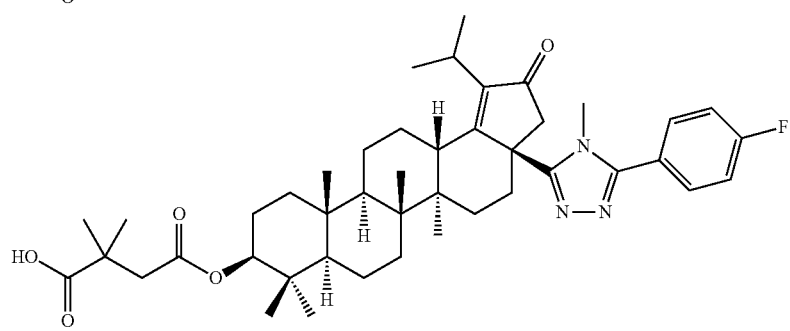

-continued
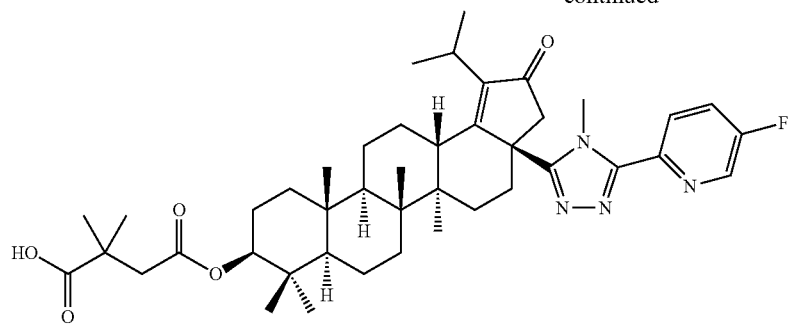
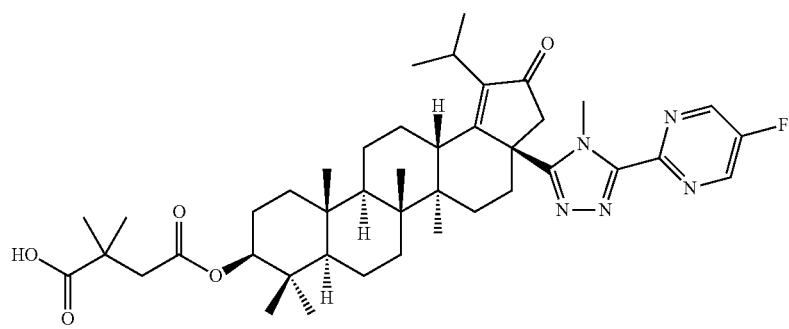
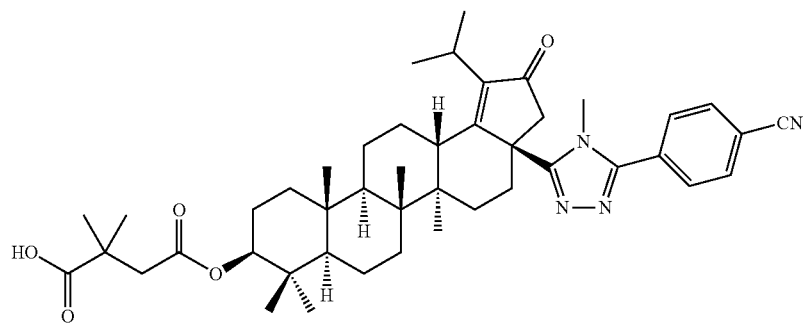
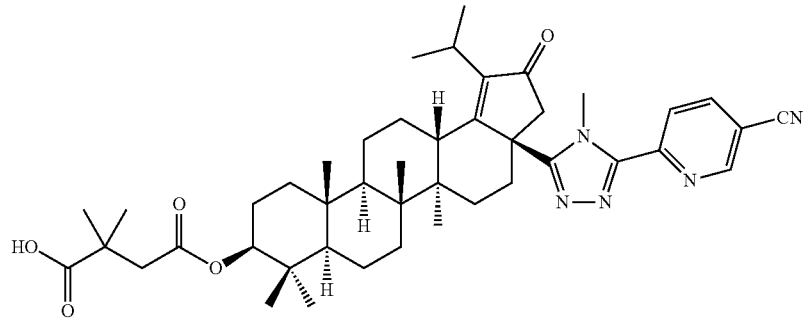
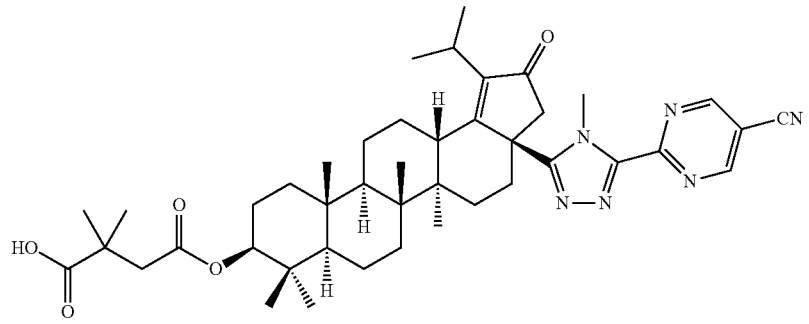

-continued
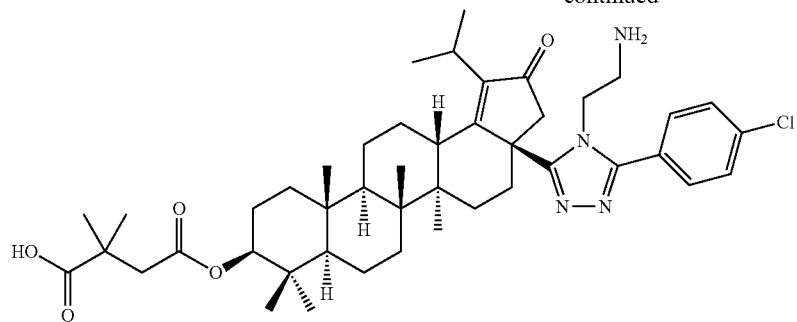
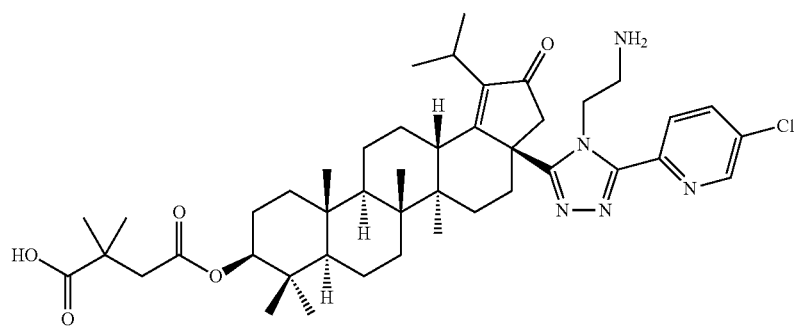
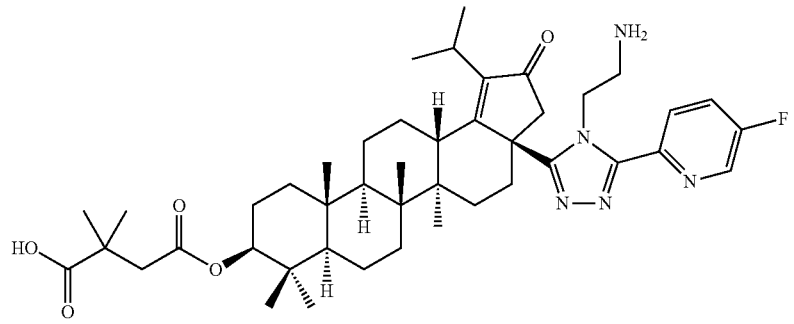

-continued
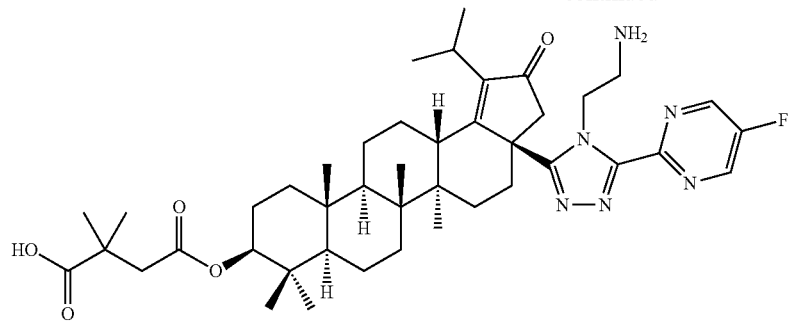
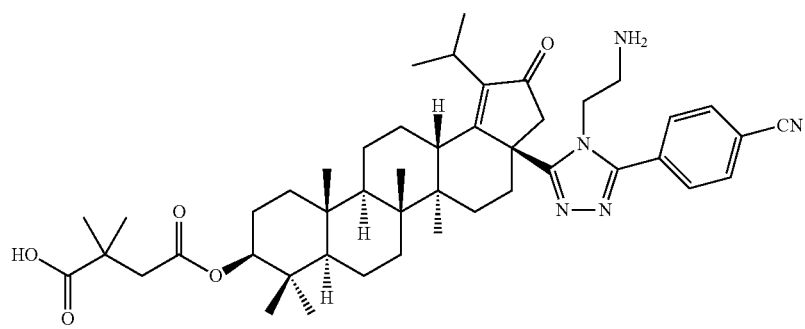
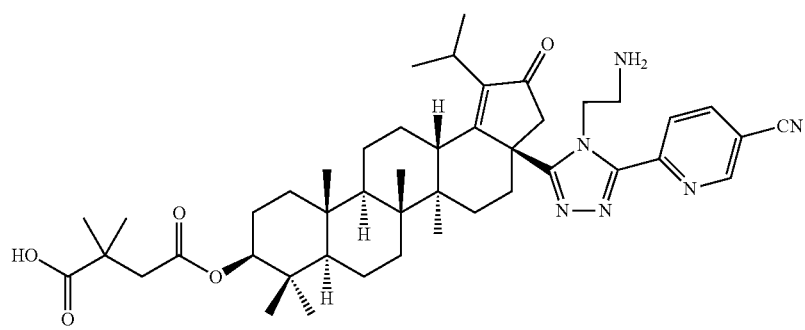
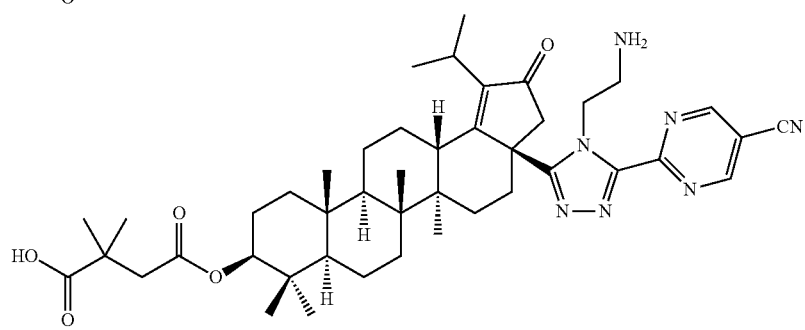
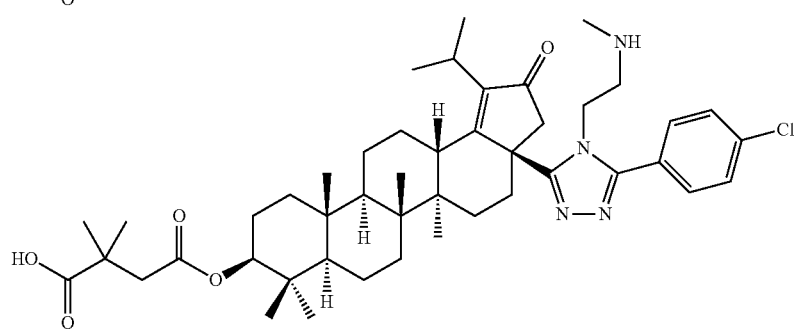

-continued
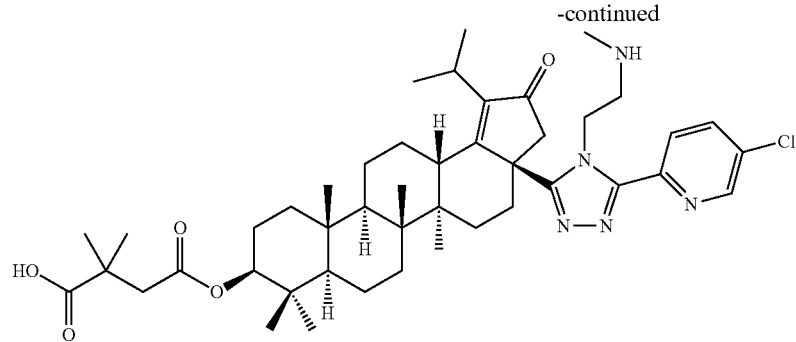
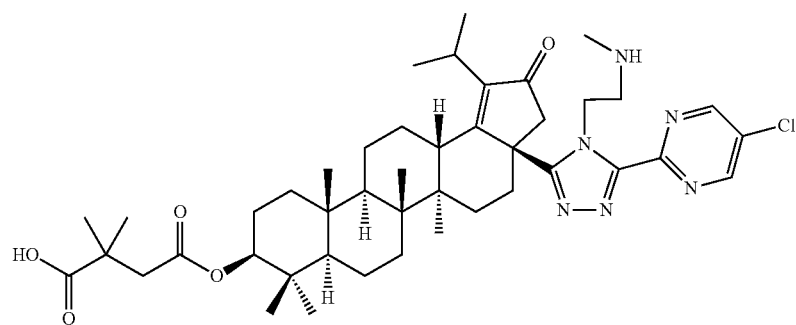
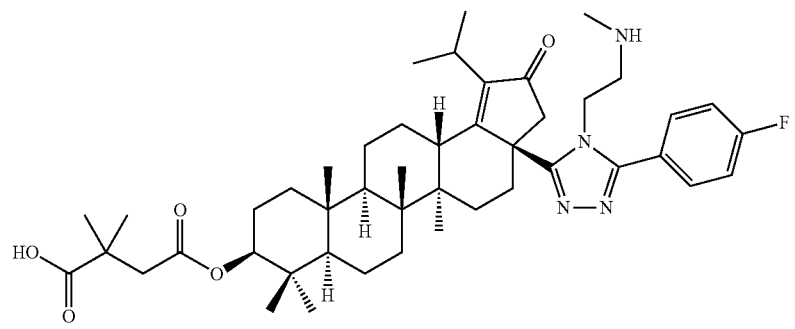
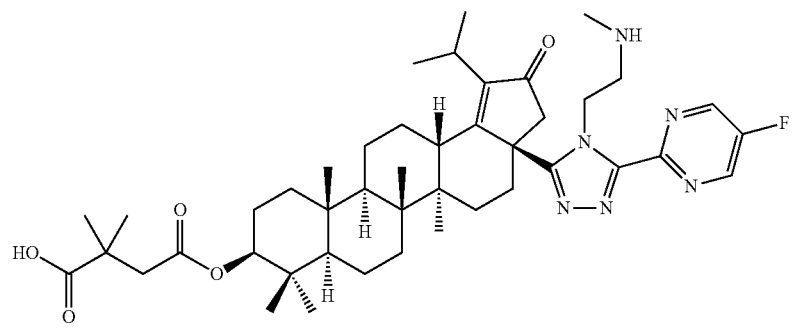

-continued
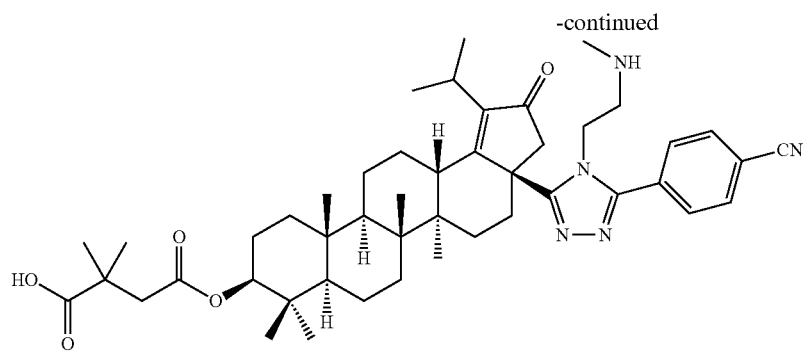
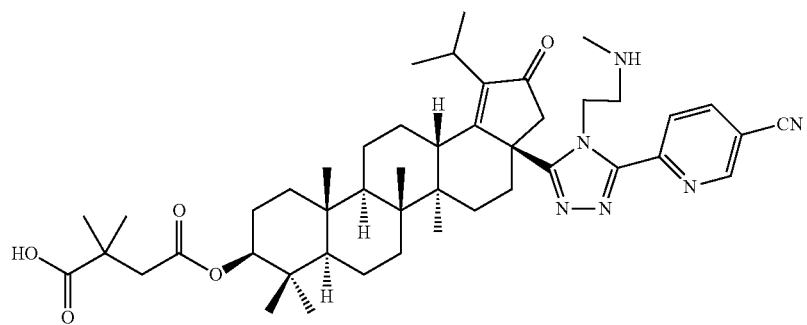
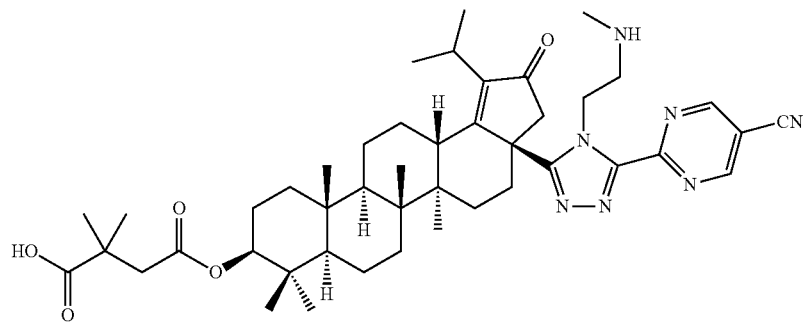
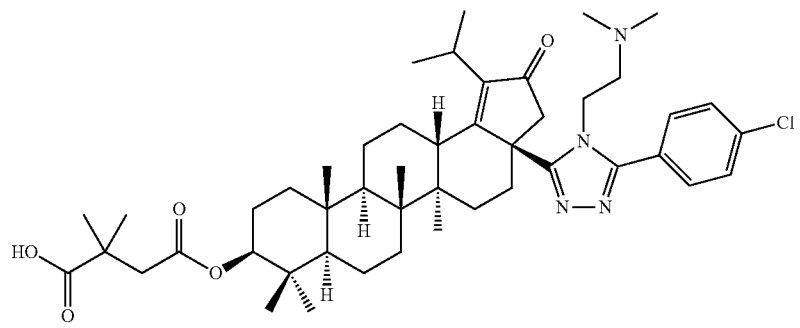
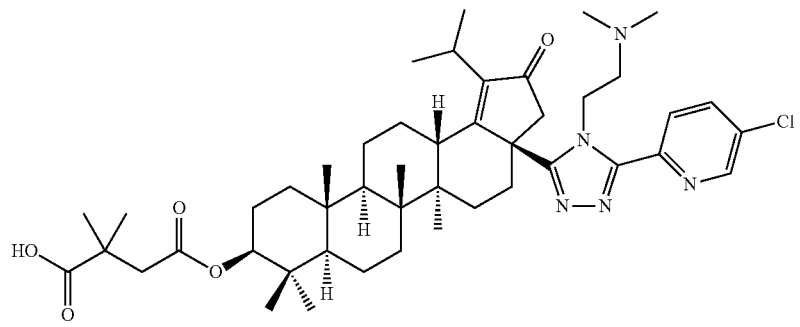

-continued
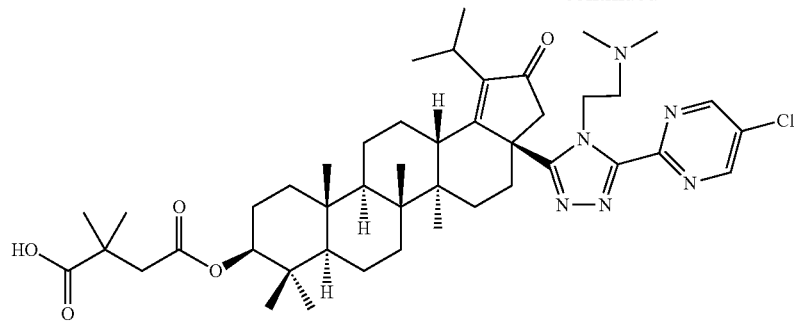
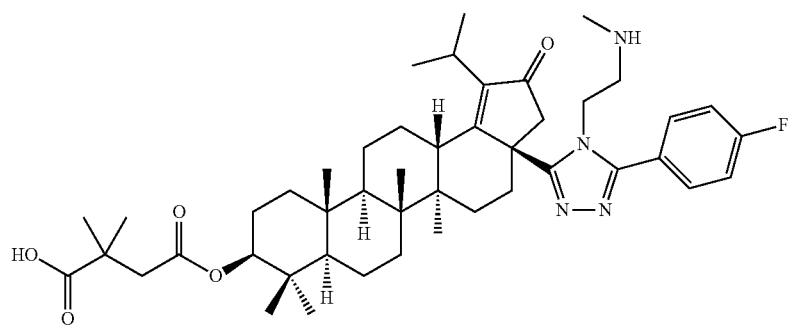
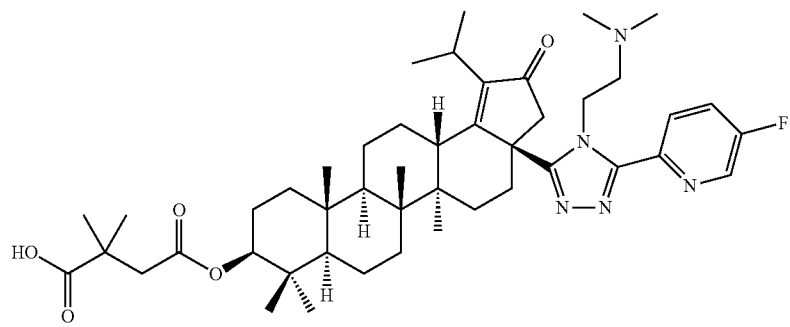
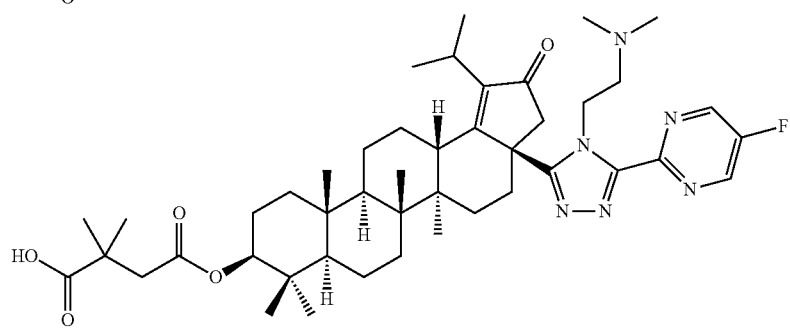
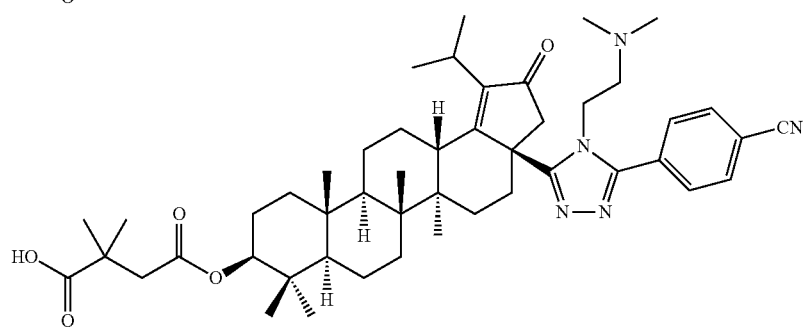

-continued
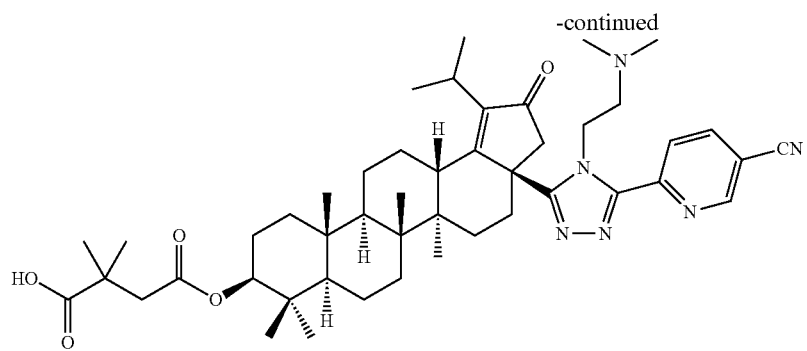
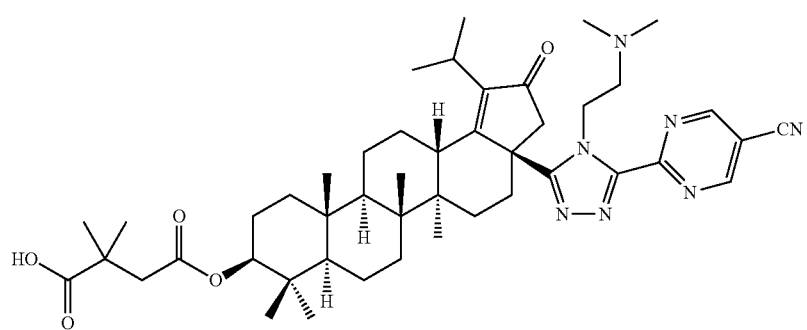
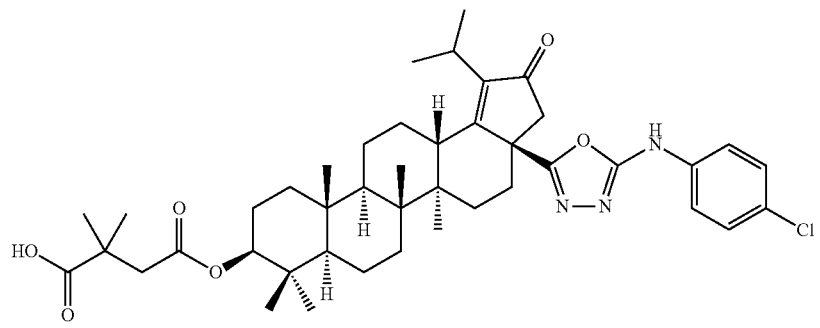
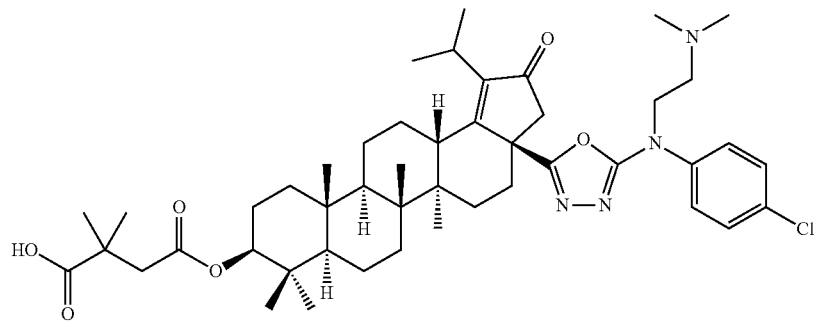
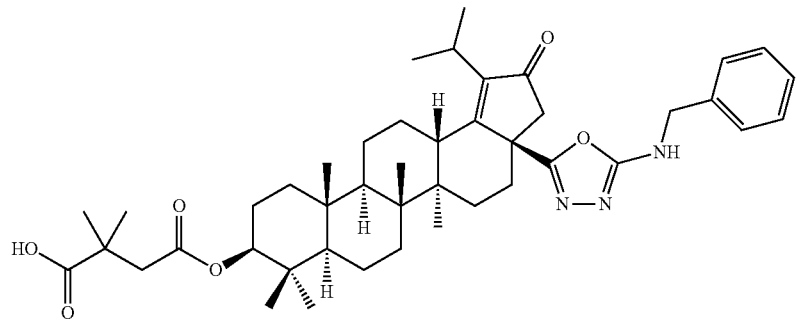

-continued
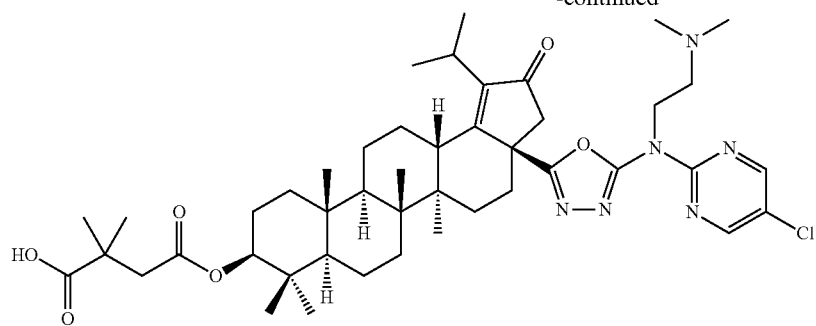
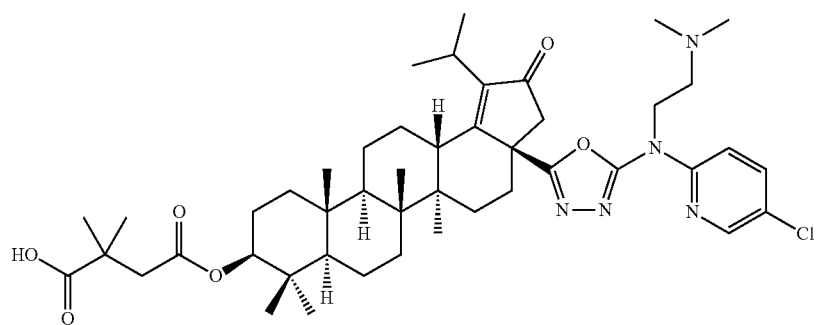
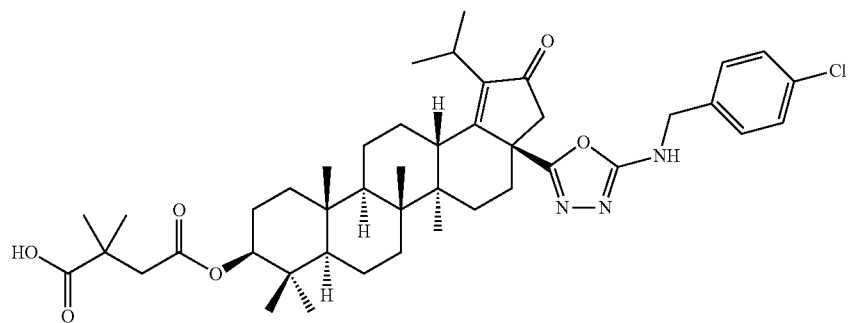
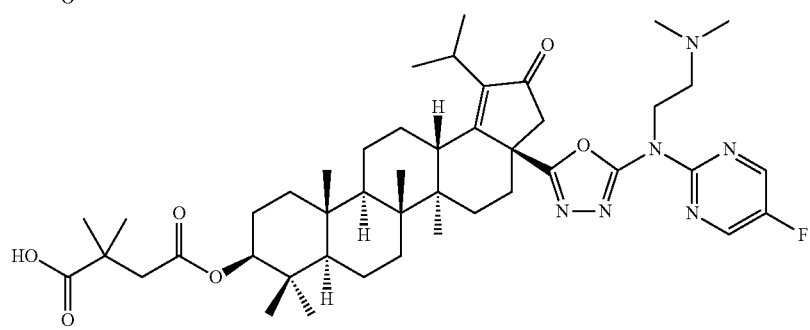
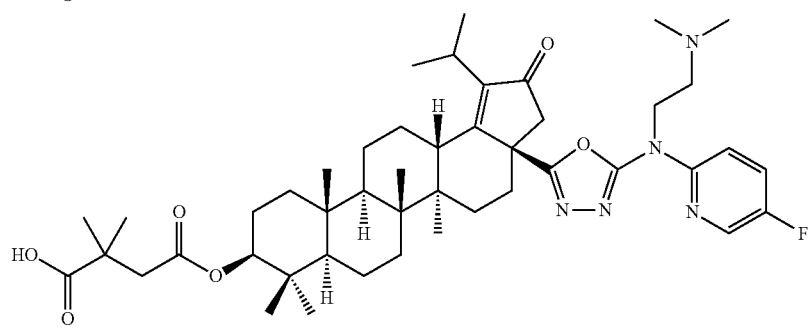

-continued
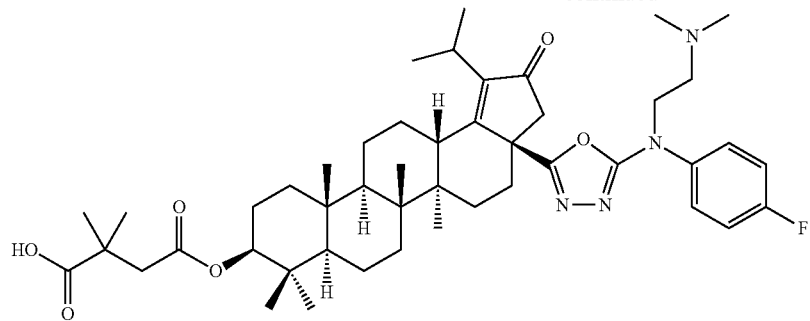
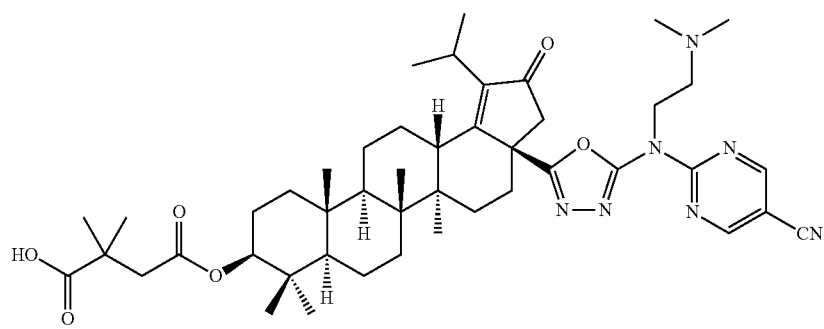
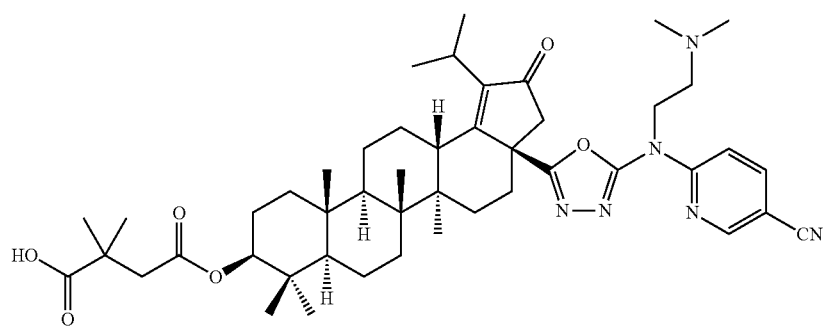
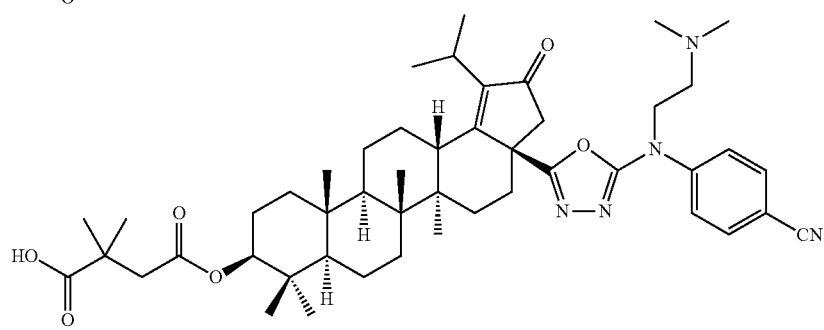
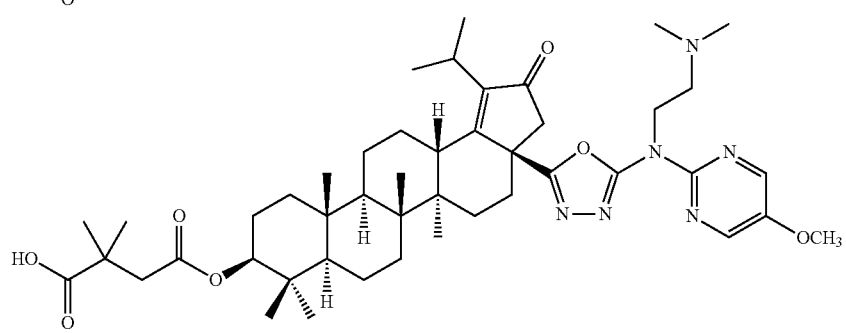

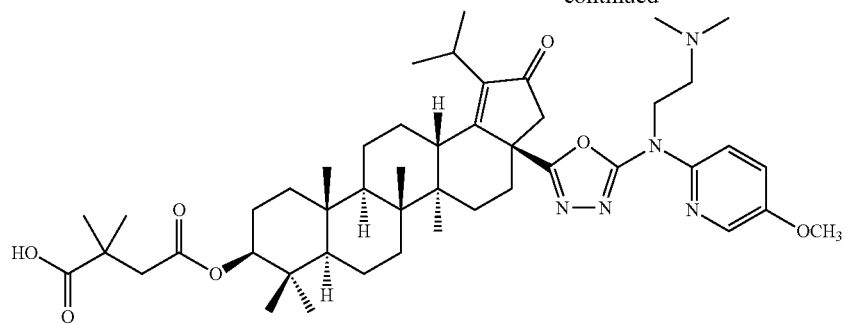
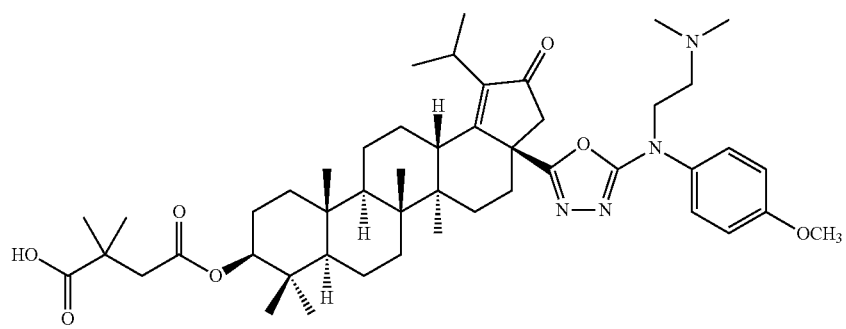
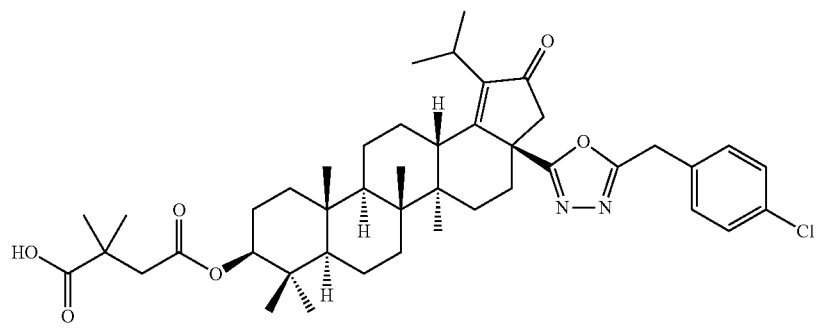

-continued
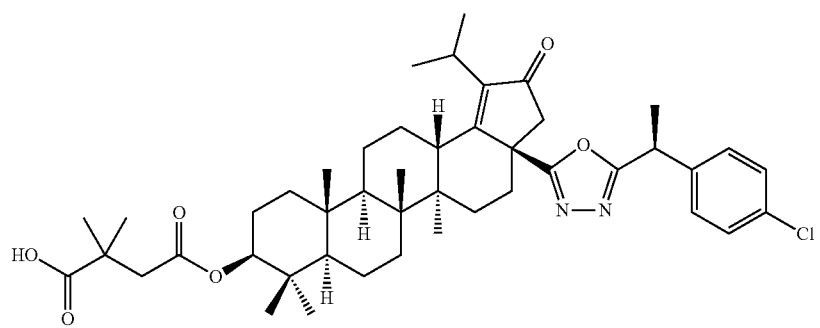
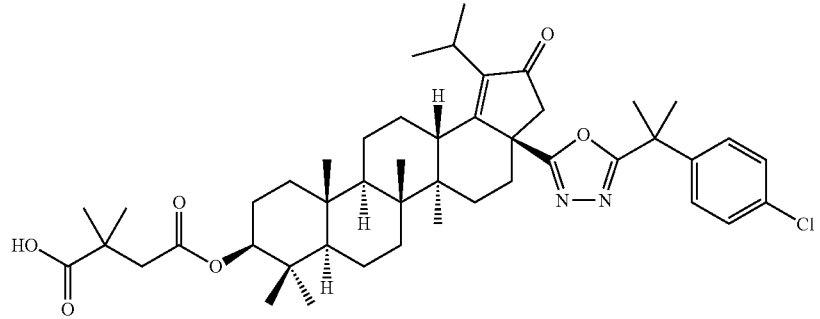
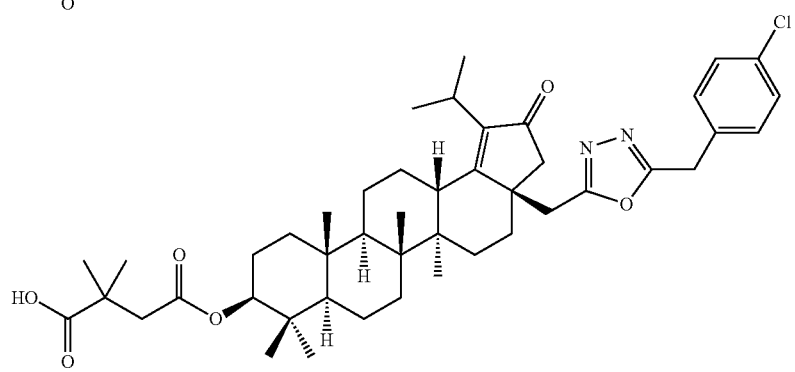
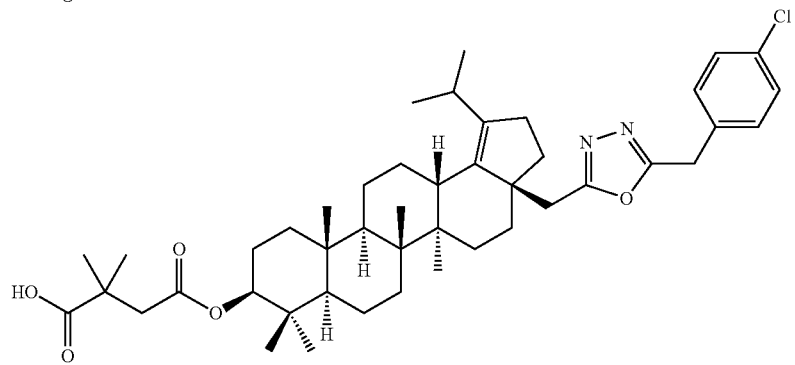

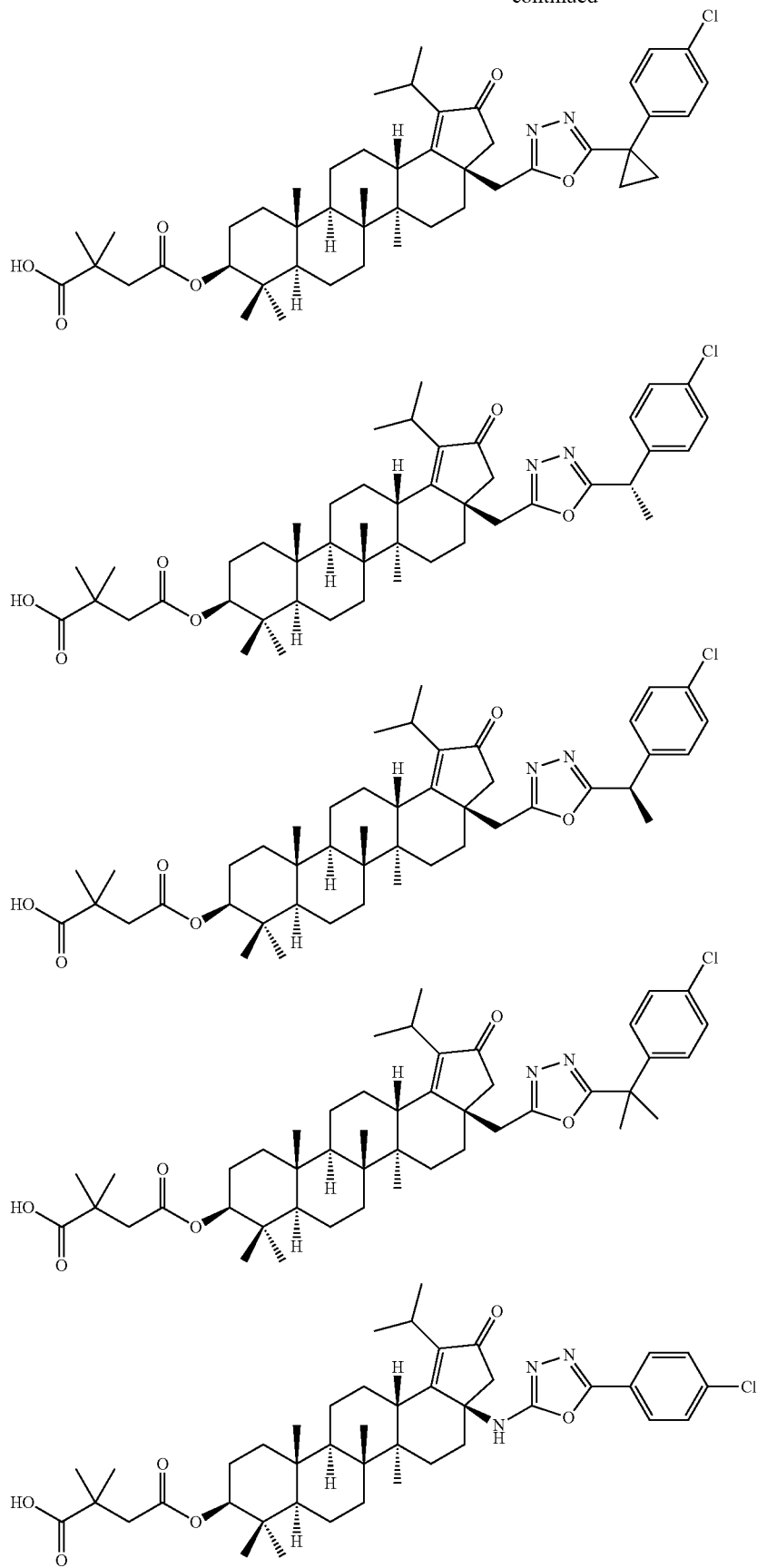

-continued
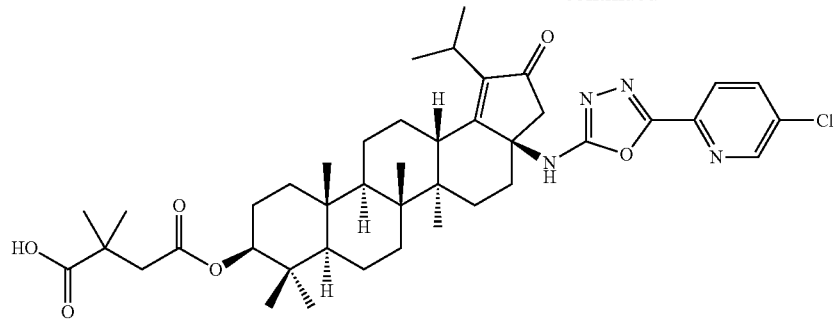
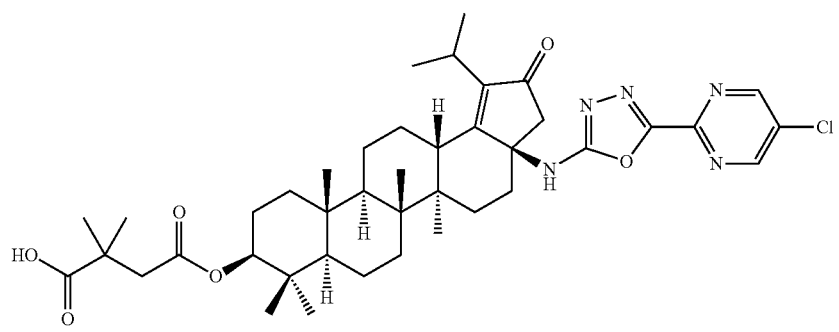
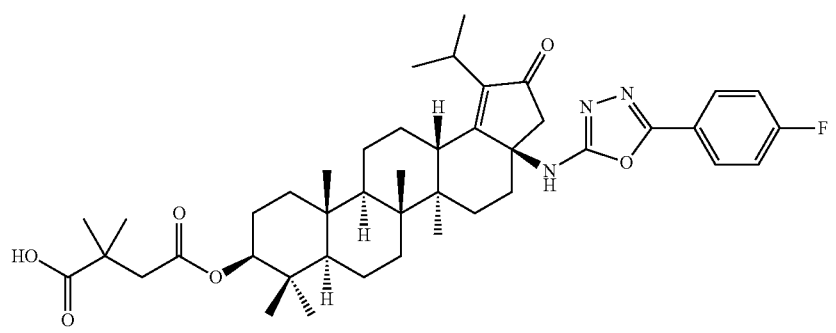
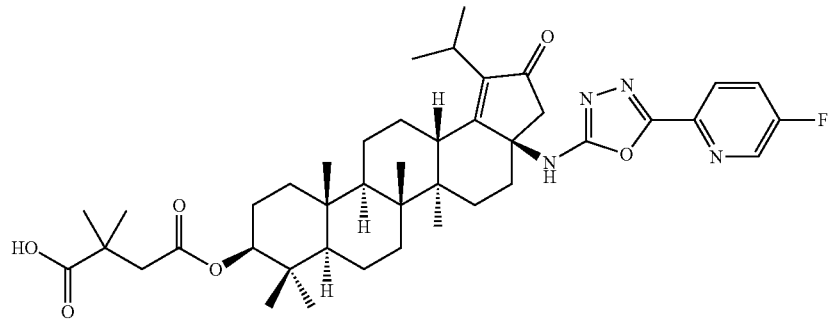
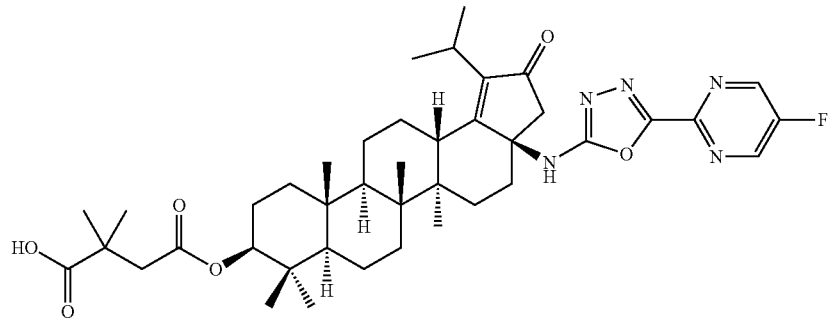

-continued
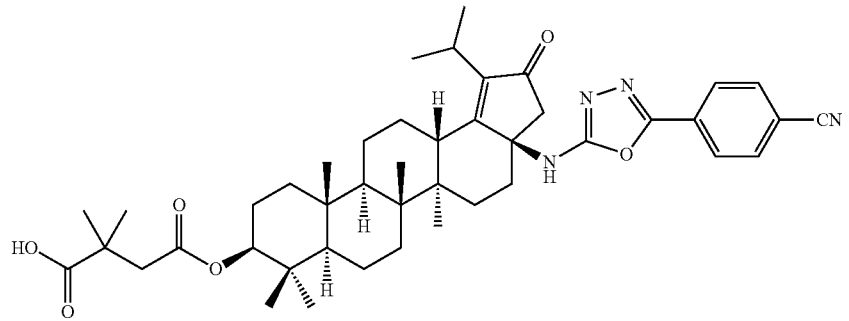
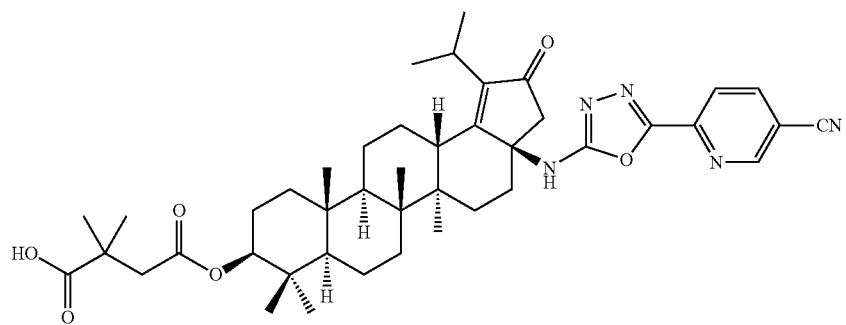
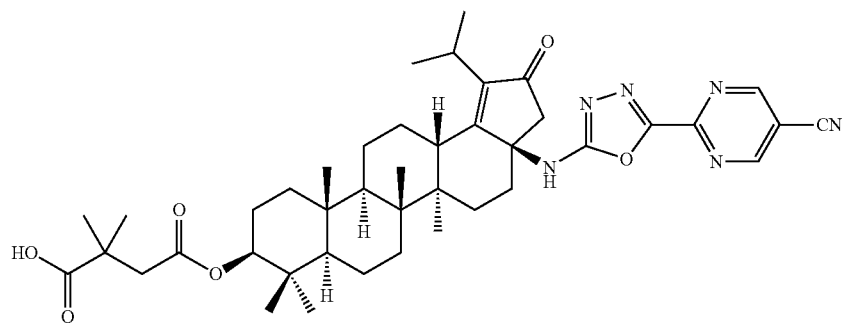
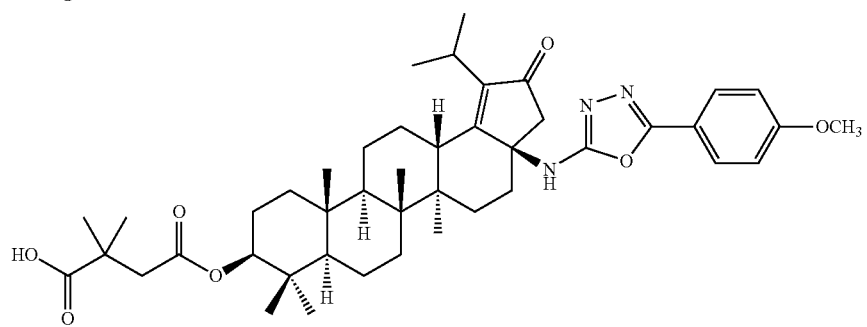
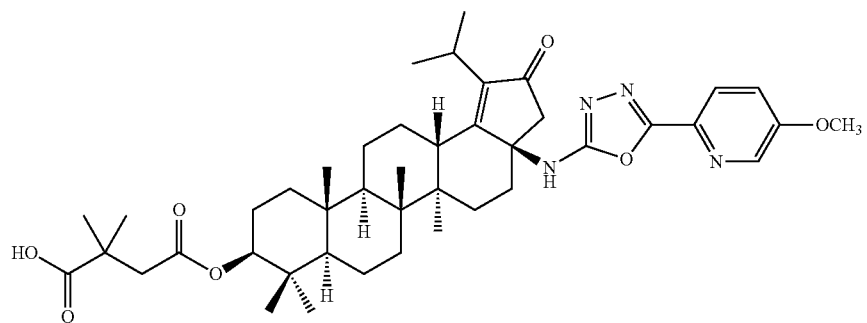

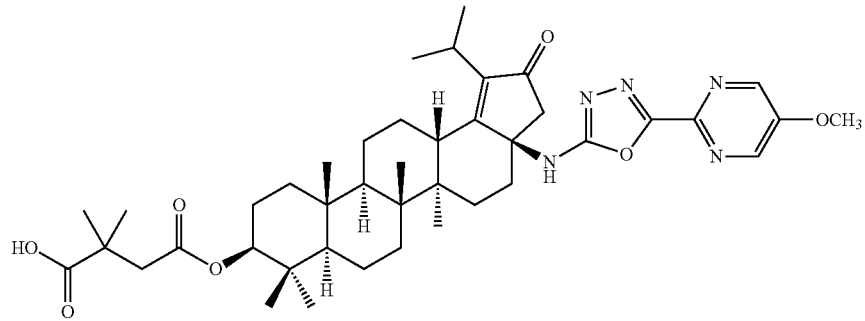
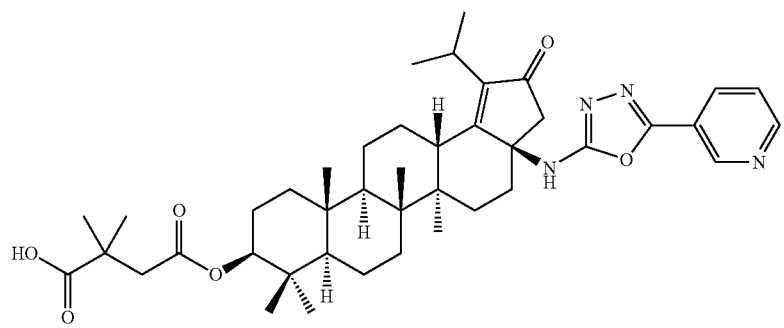
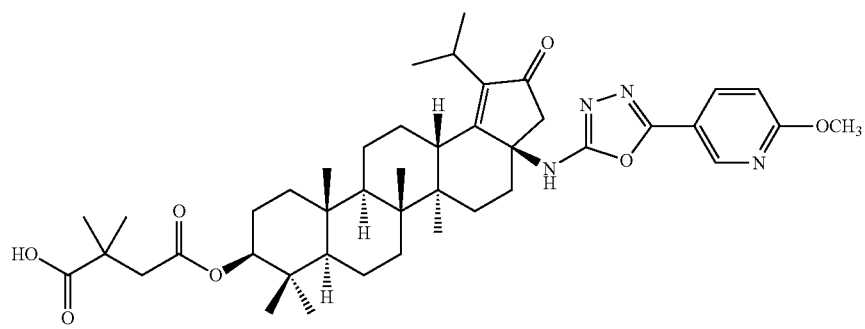
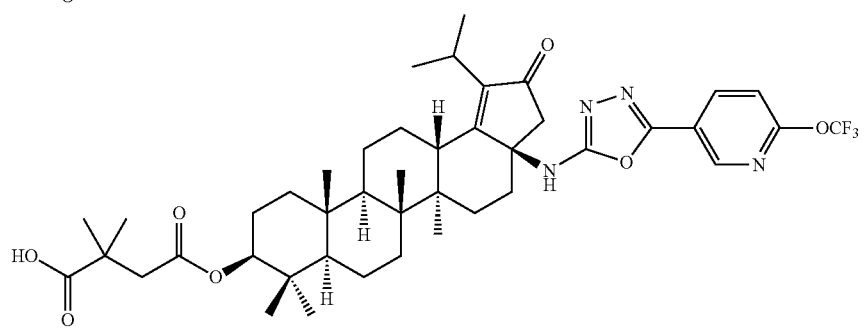
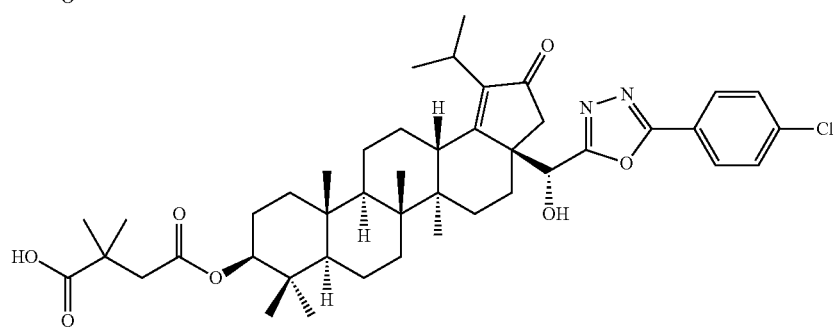

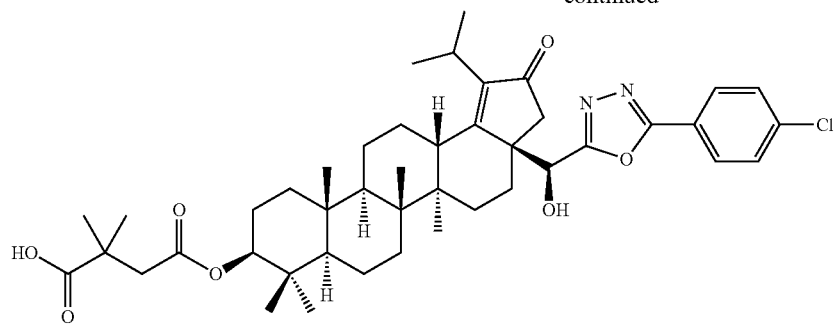
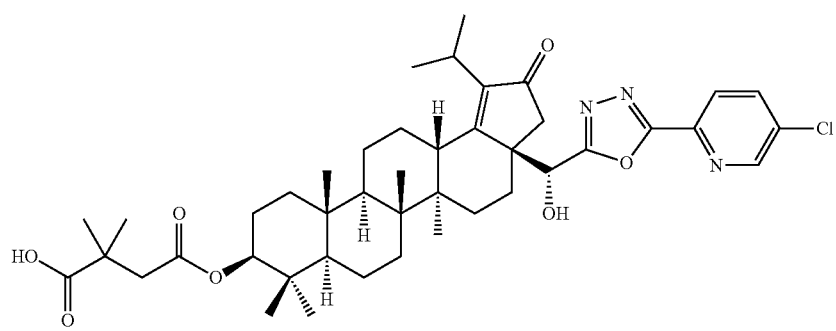
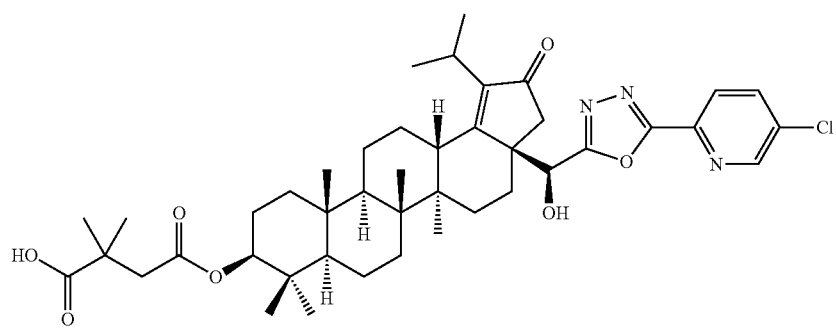
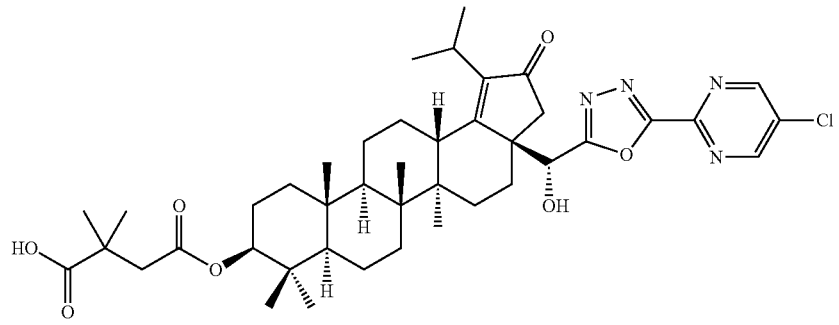
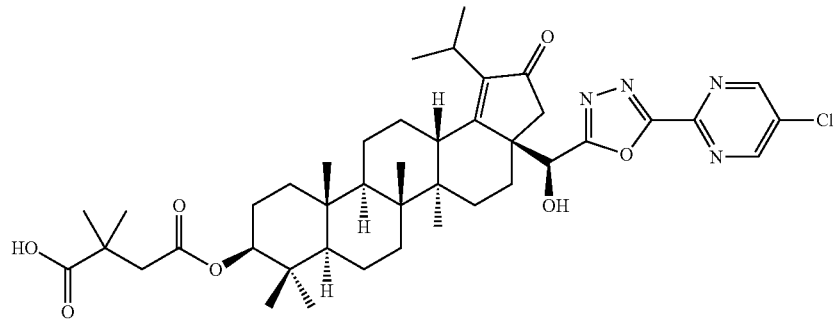

-continued
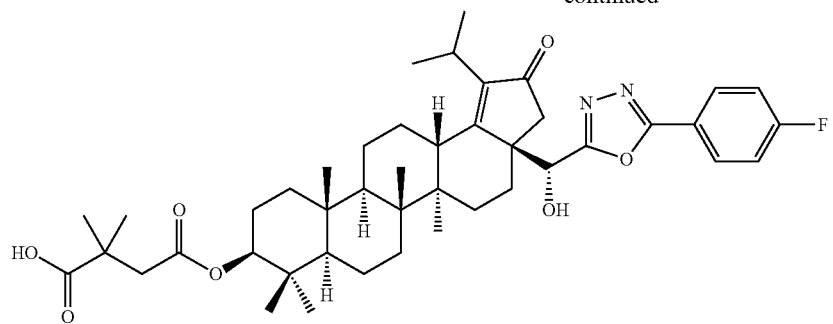
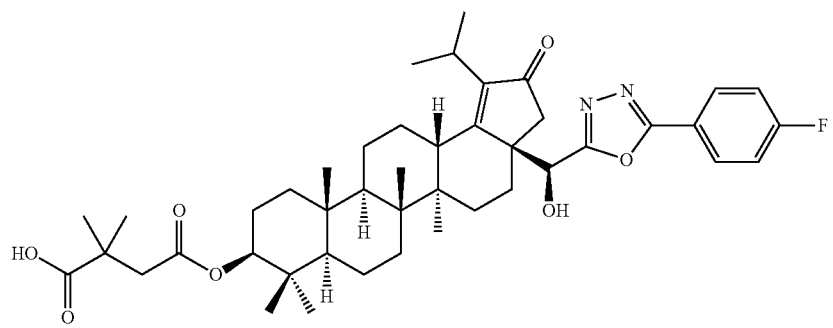
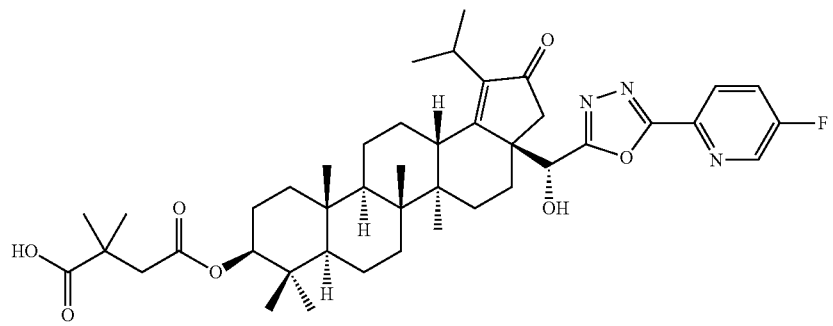
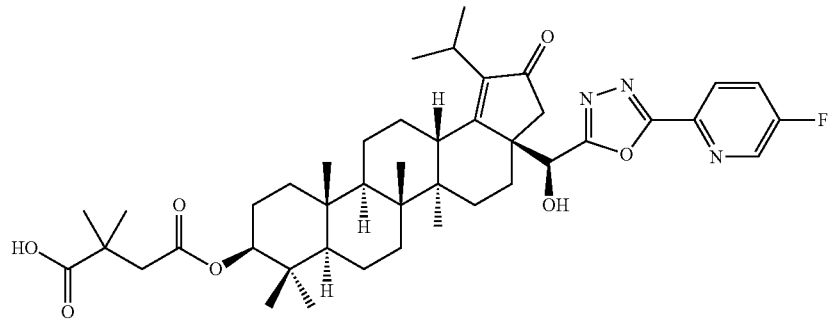
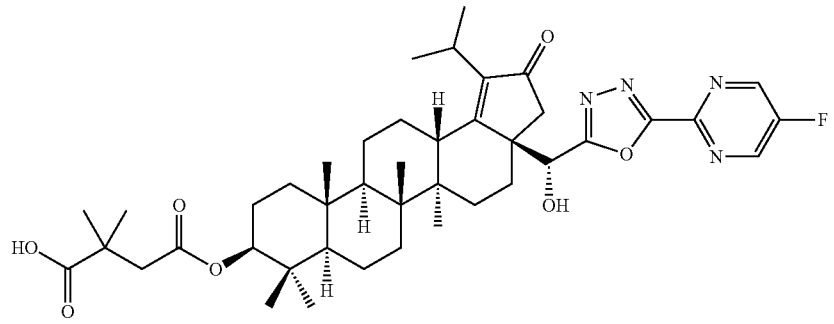

-continued
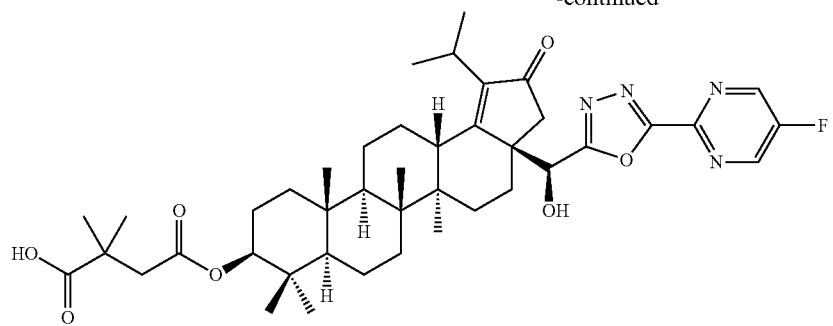
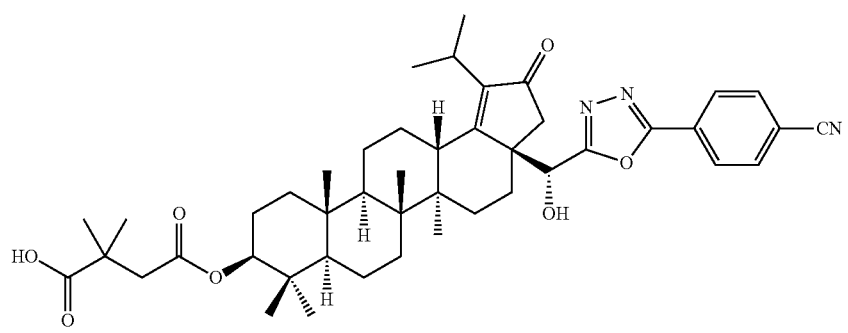
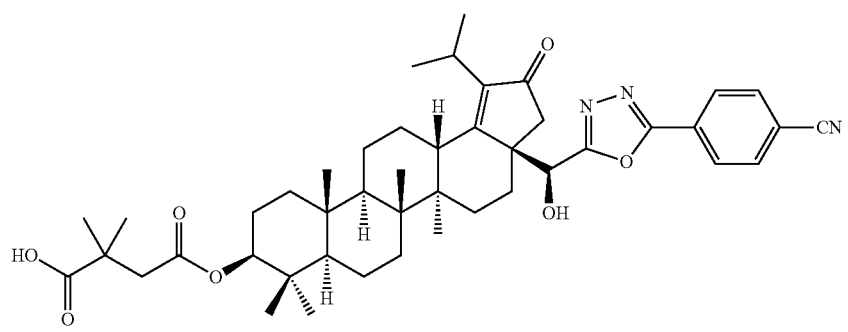
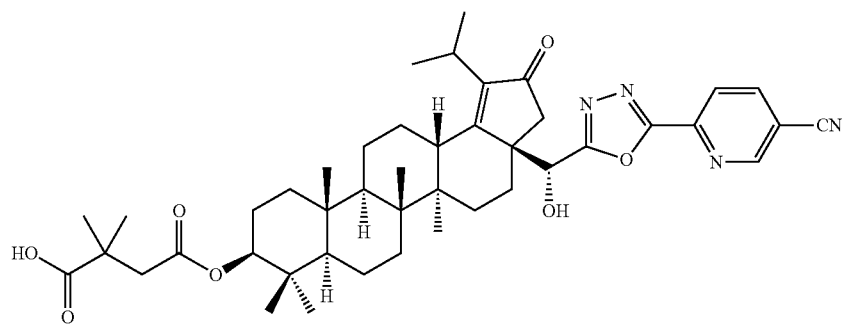
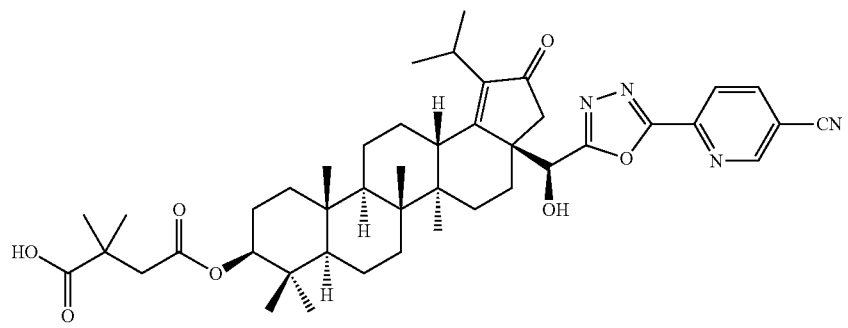

-continued
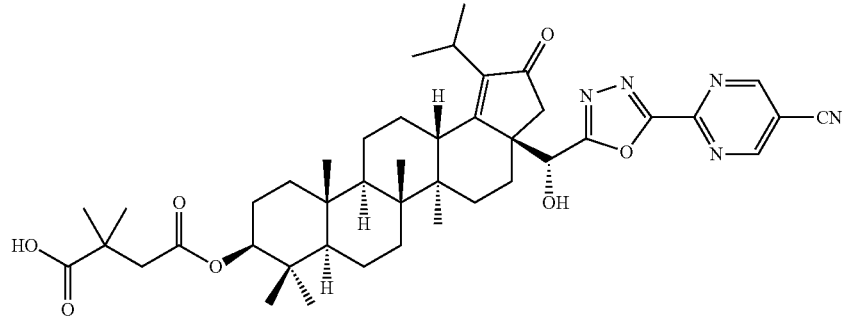
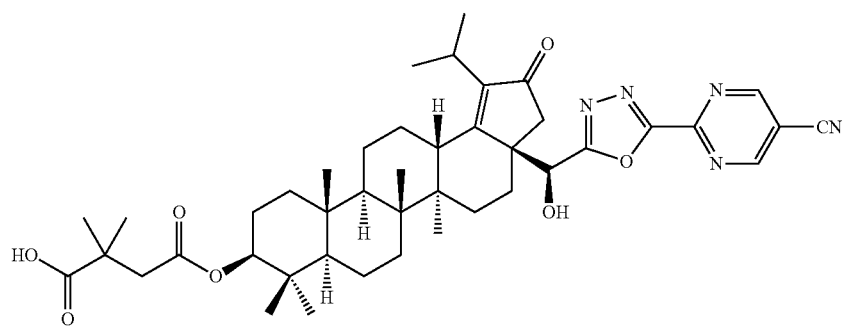
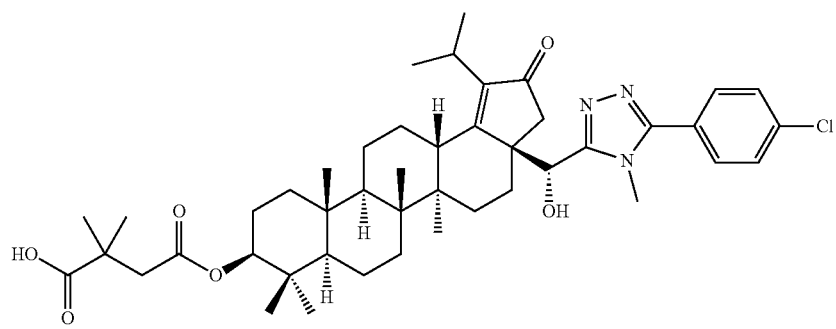
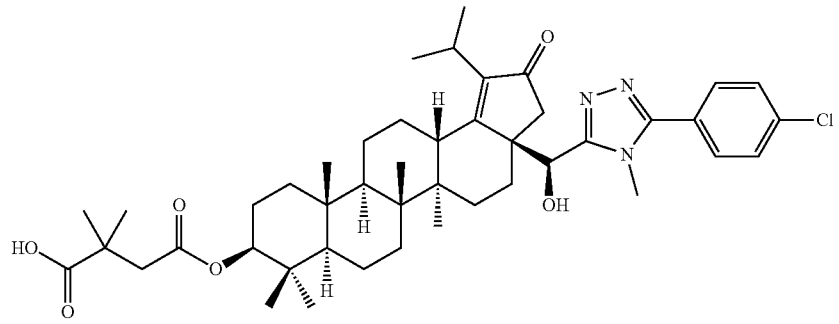
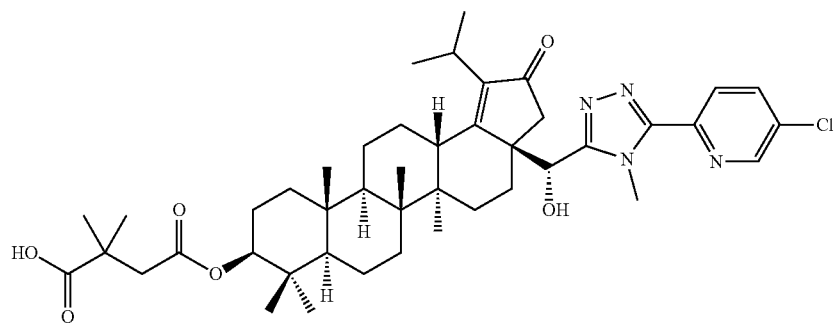

-continued
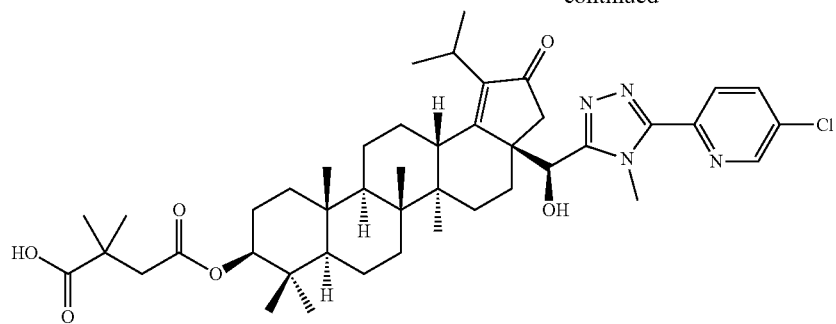
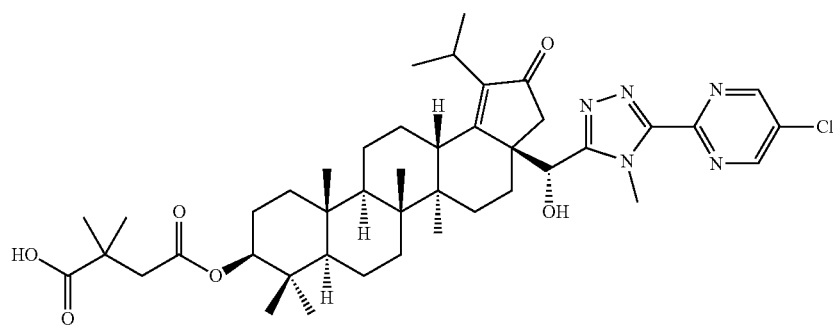
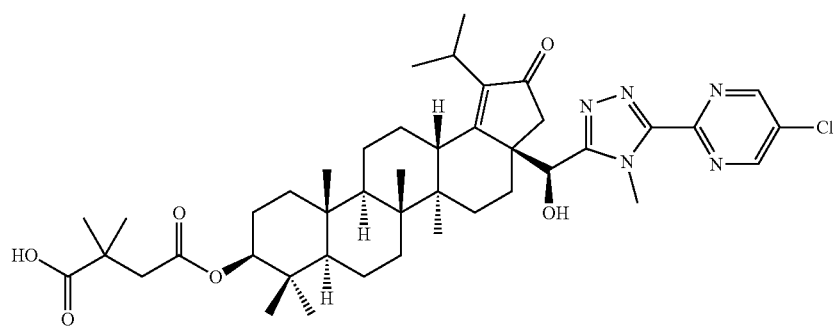
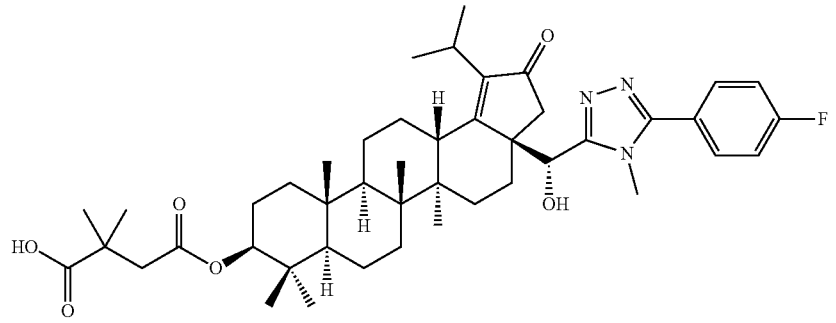
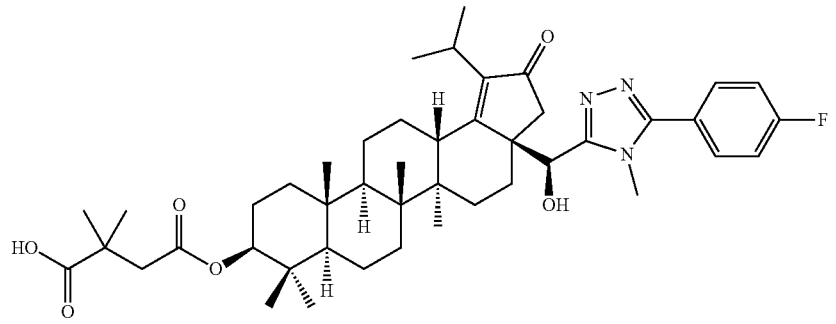

-continued
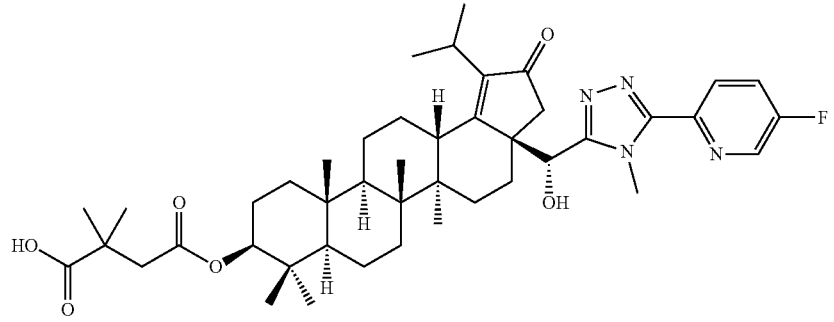
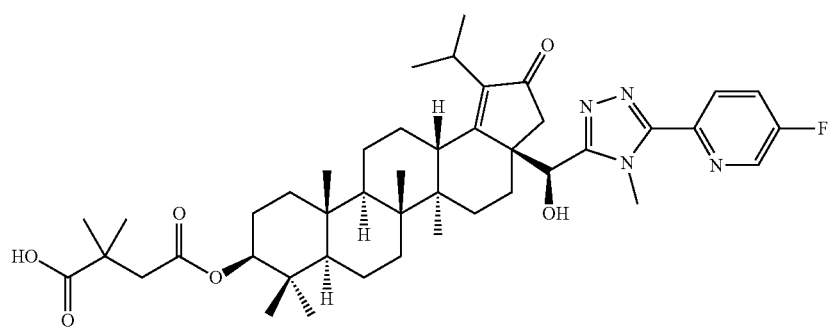
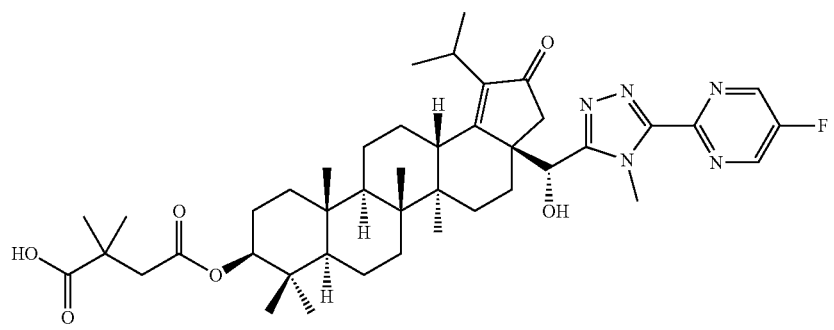
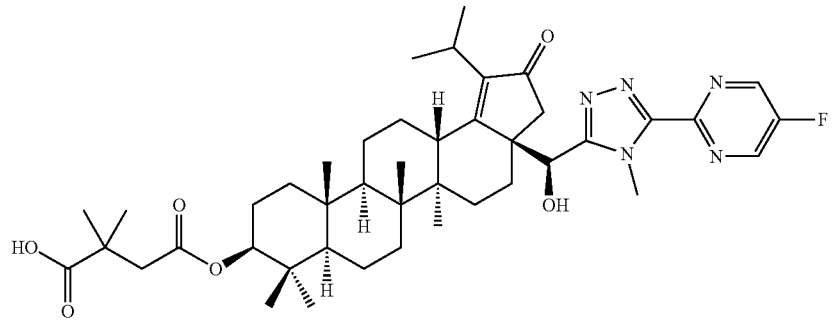
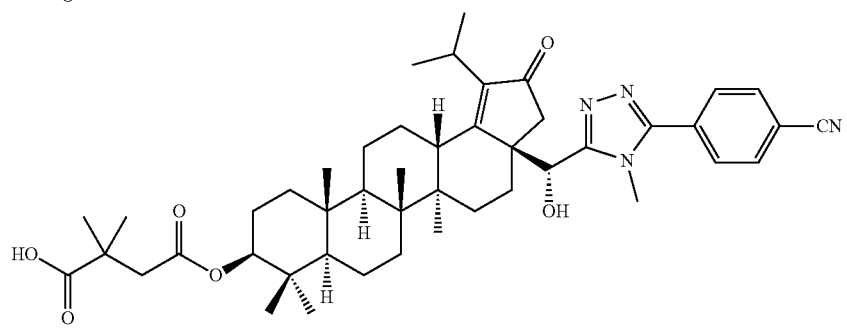

-continued
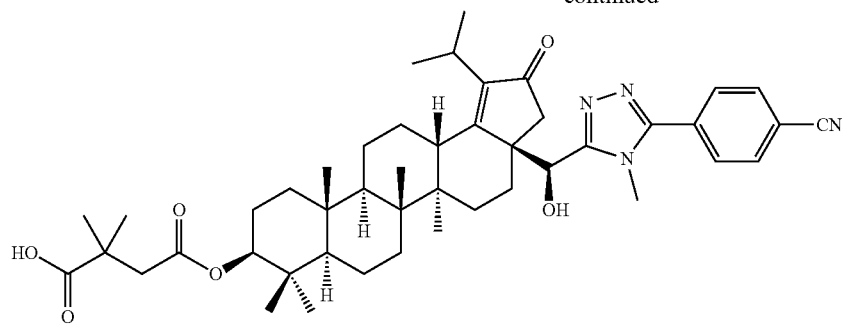
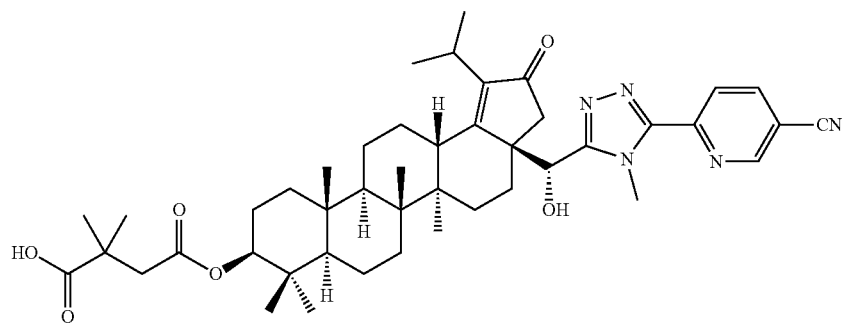
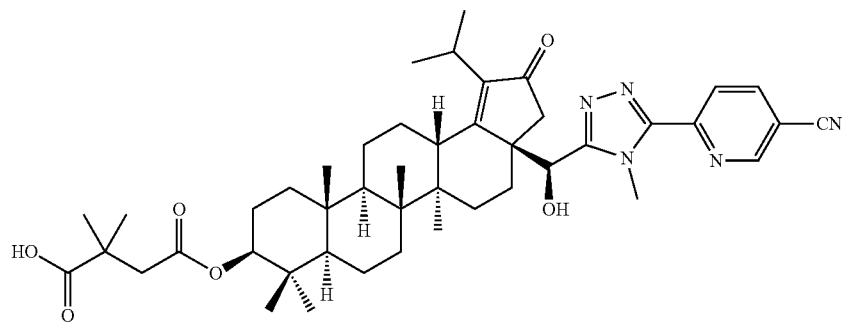
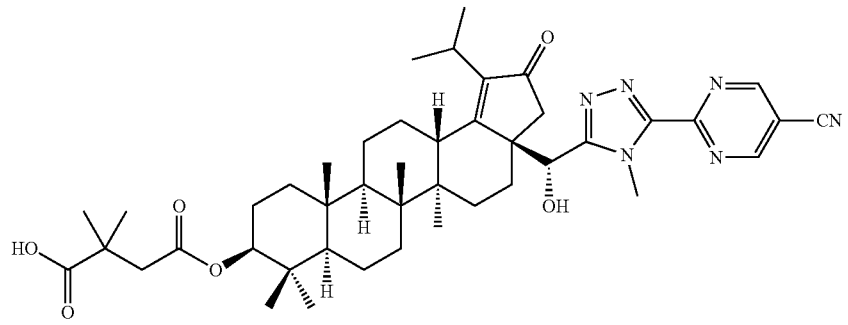
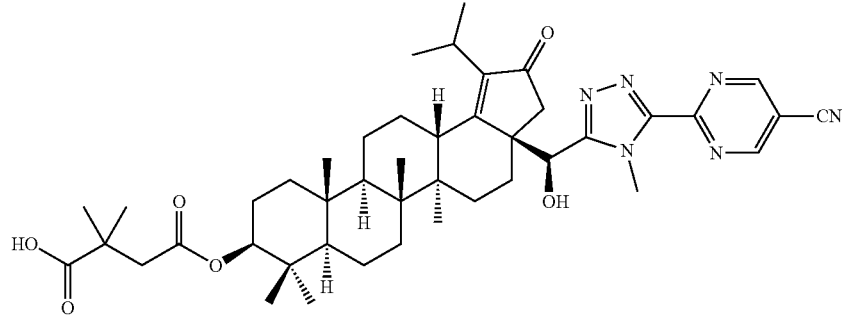

-continued
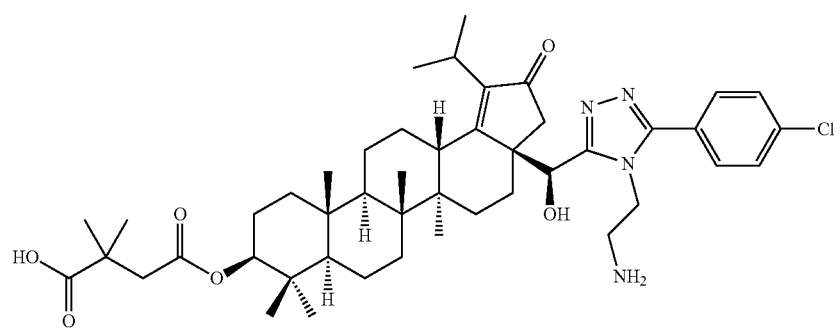
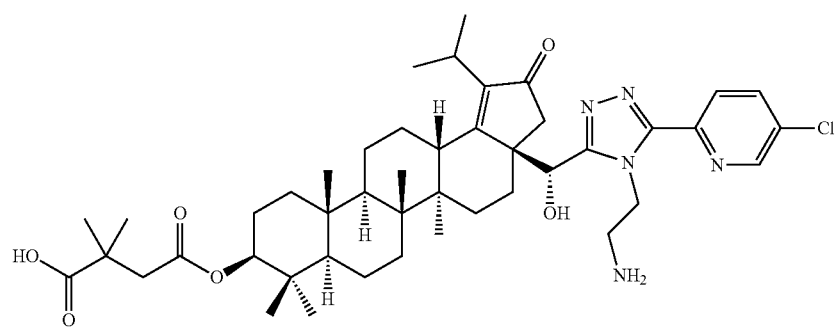
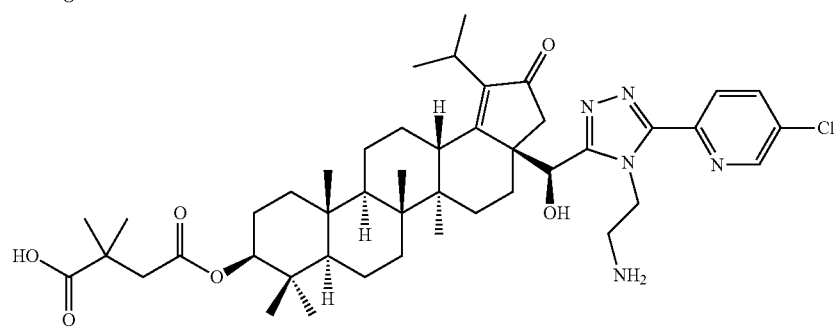
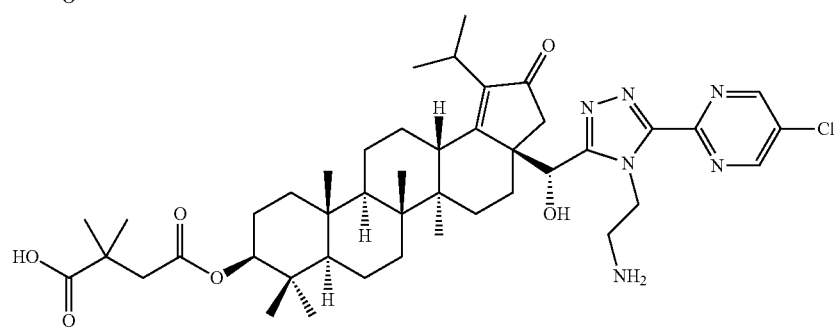

-continued
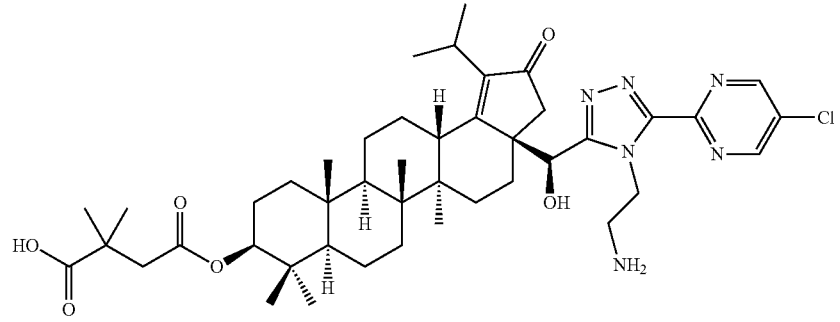
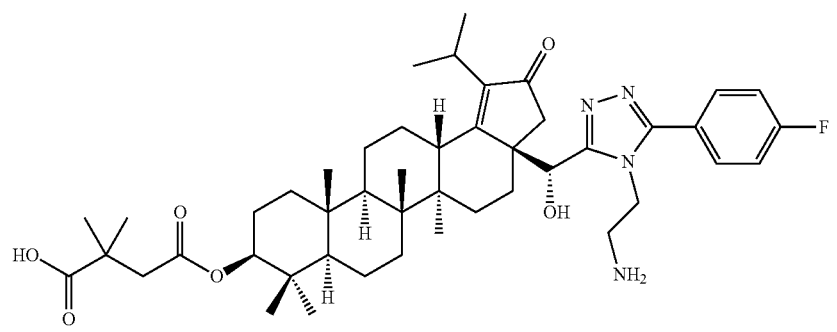
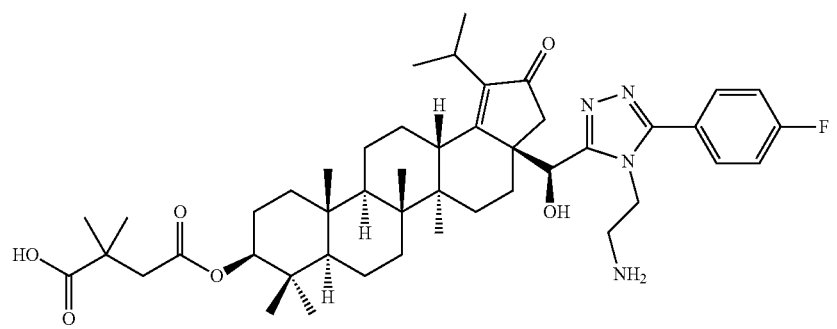
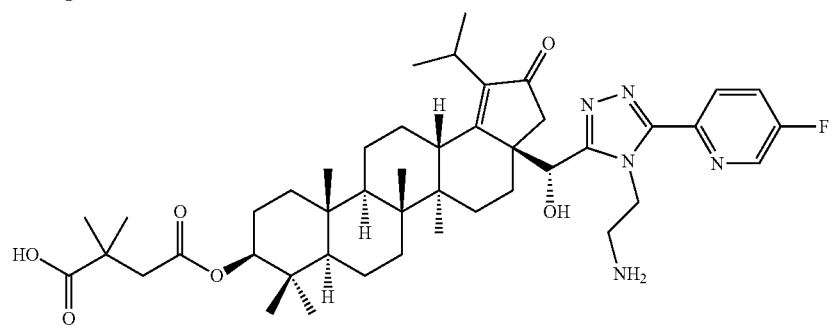
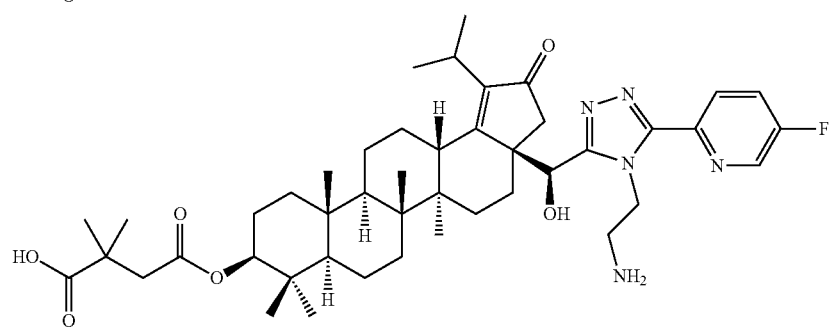

-continued
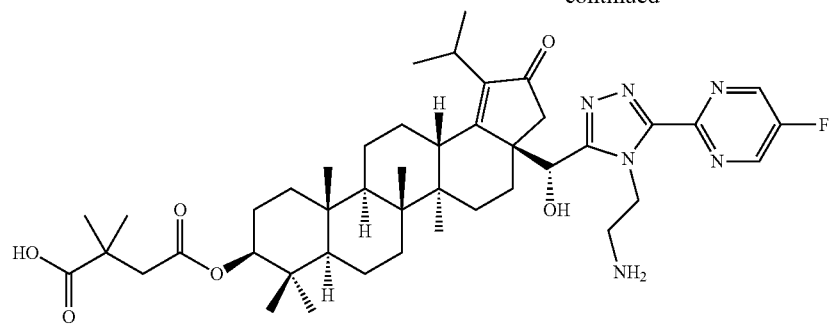
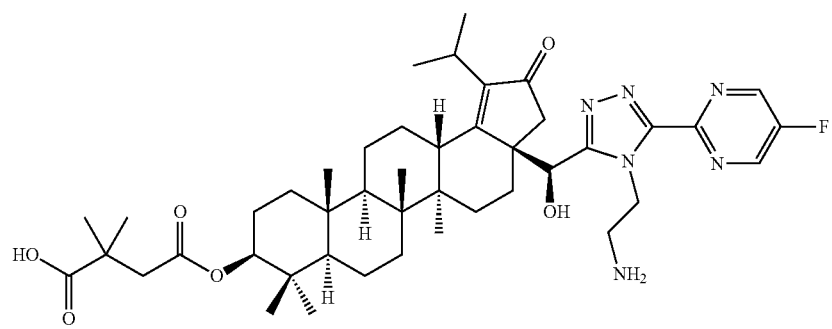
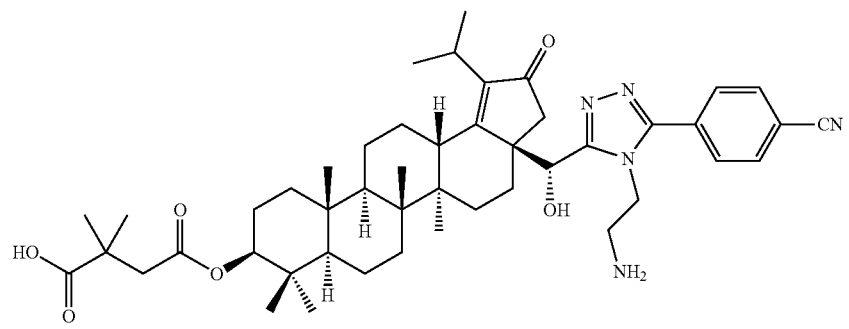
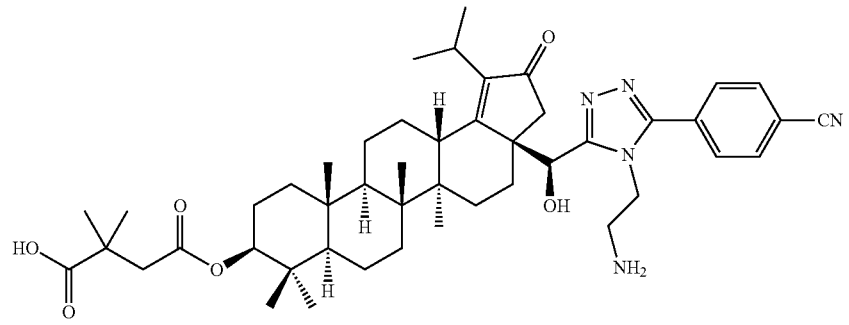
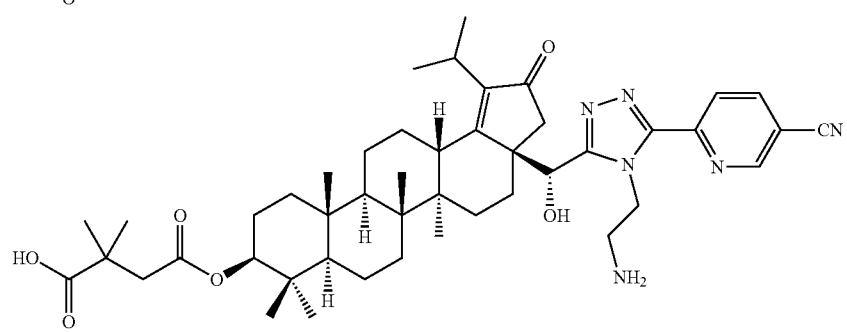

-continued
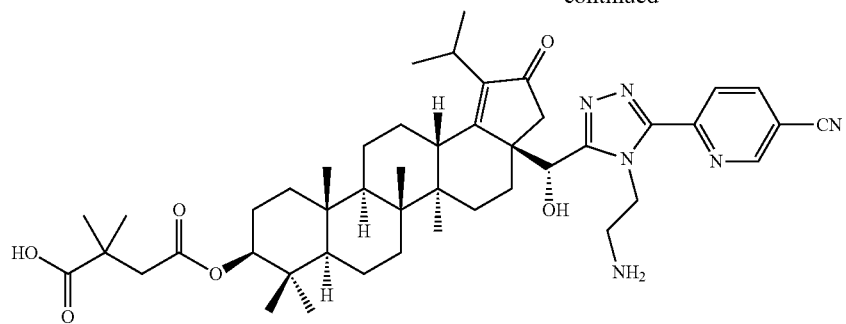
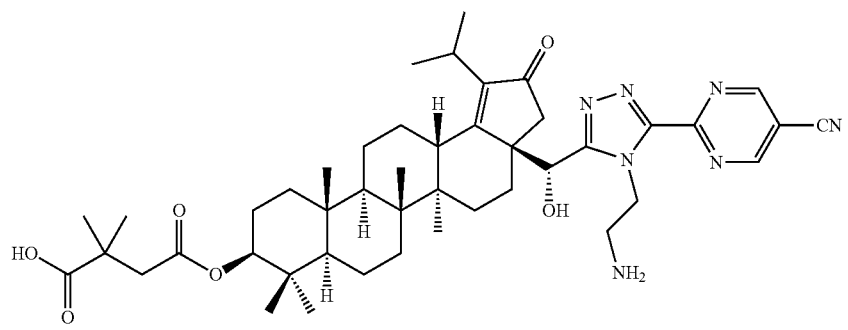
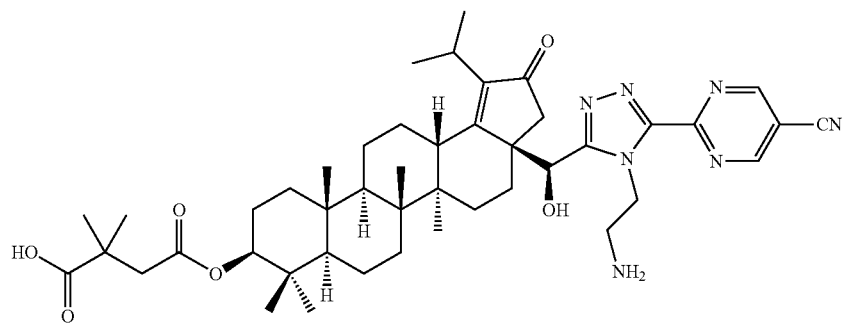
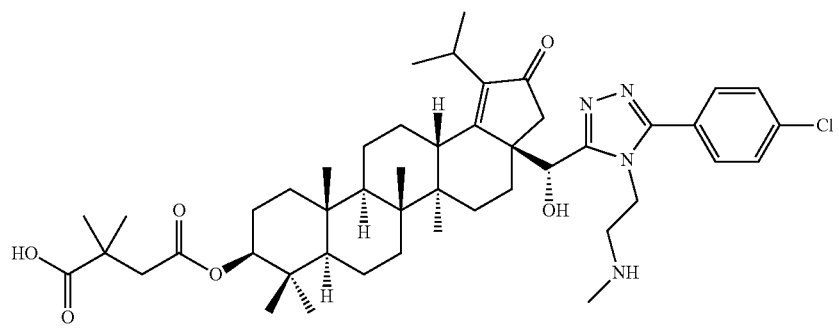
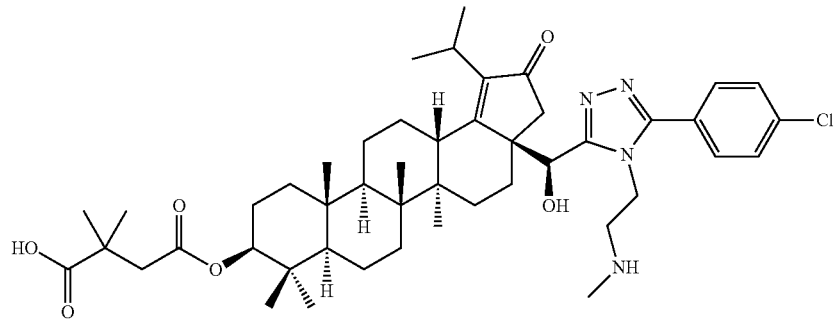

-continued
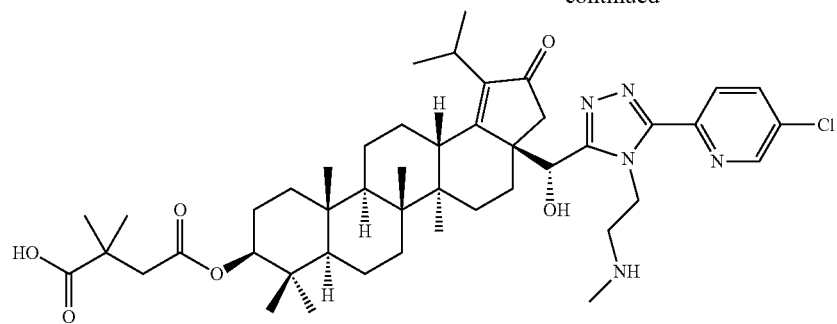
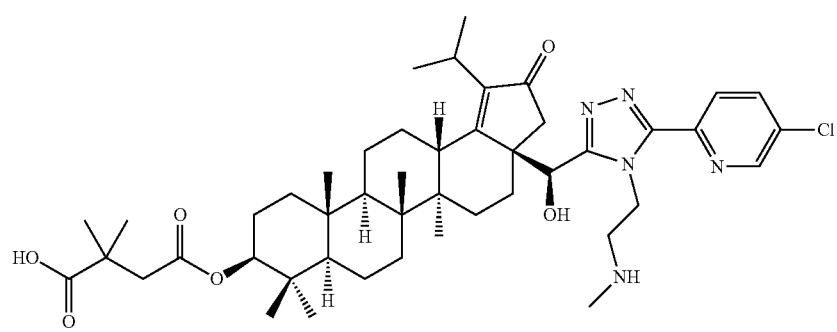
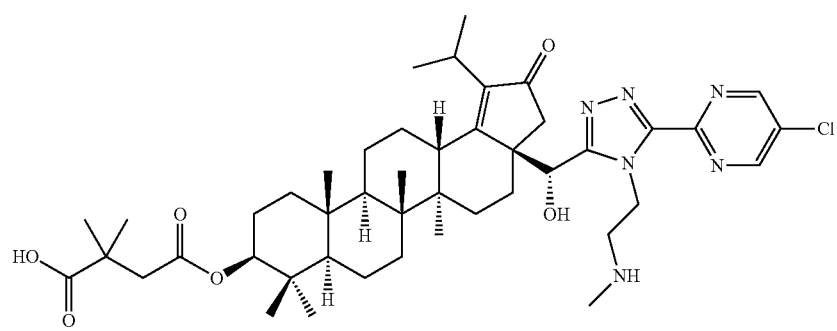
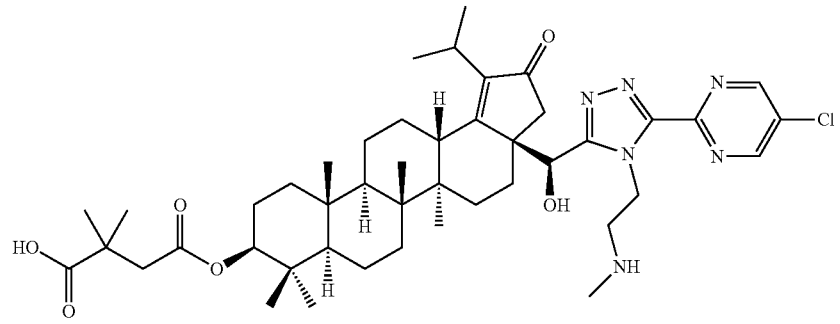
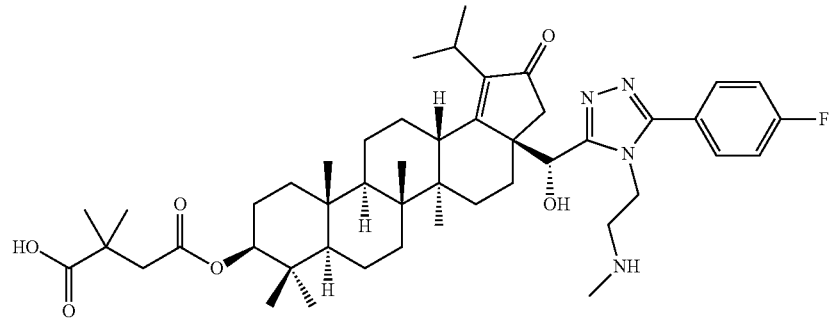

-continued
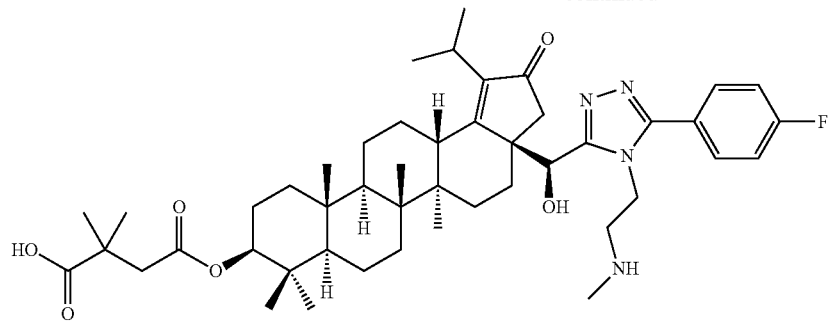
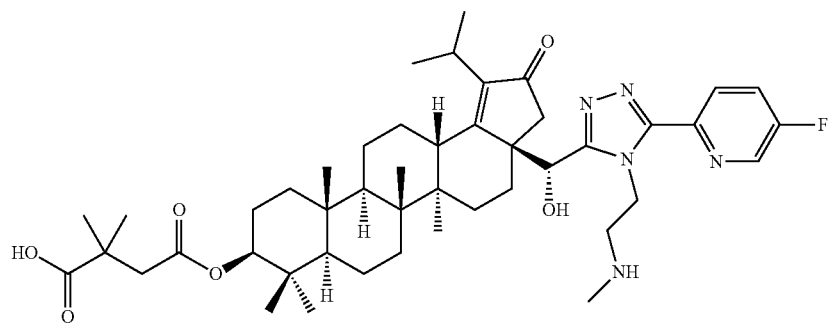
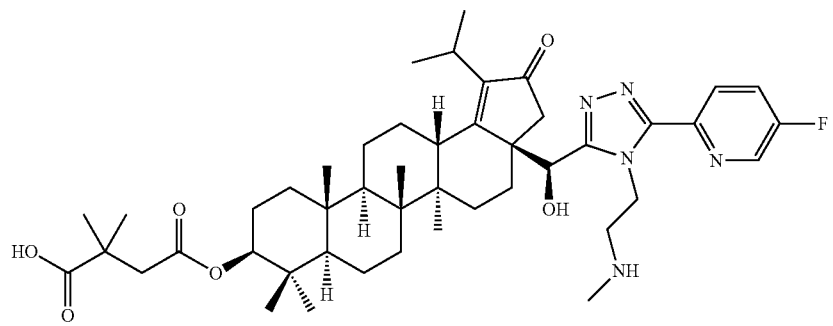
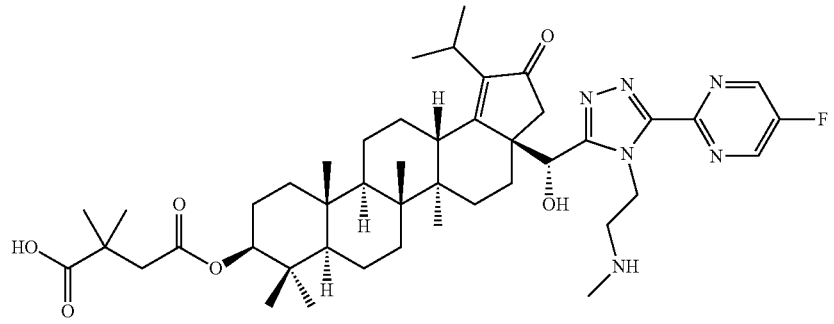
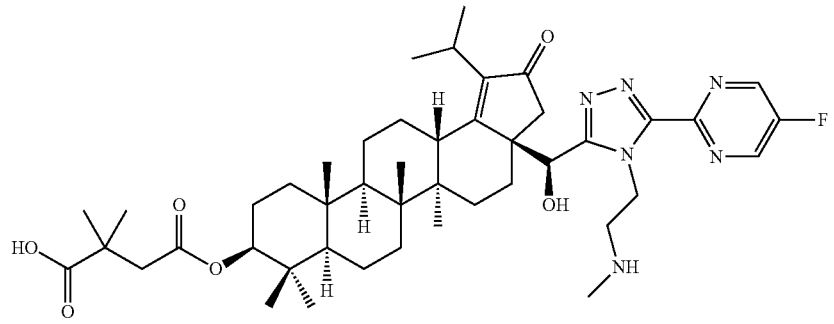

-continued
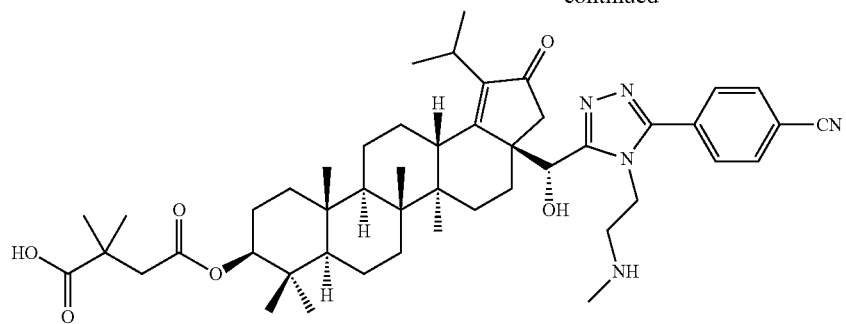
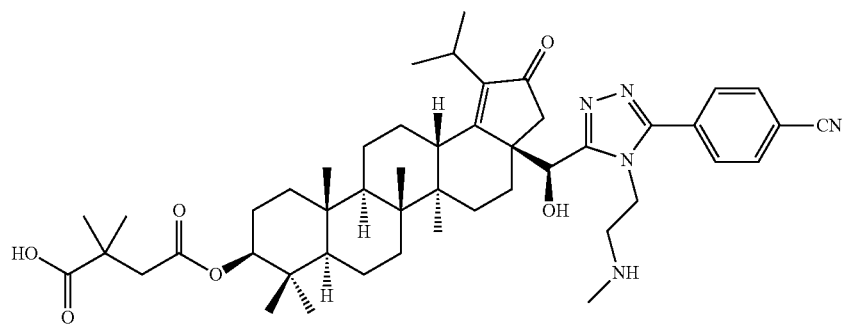
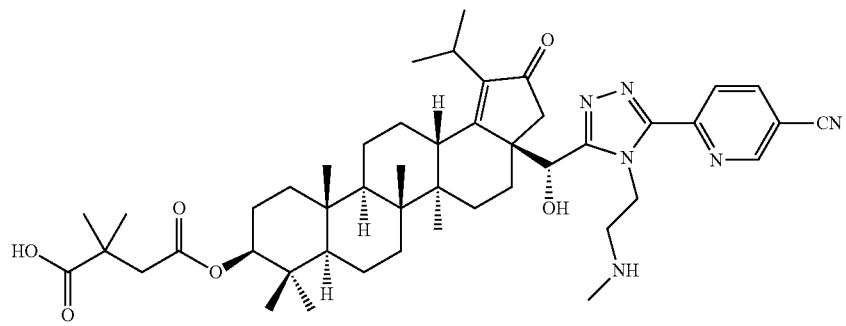
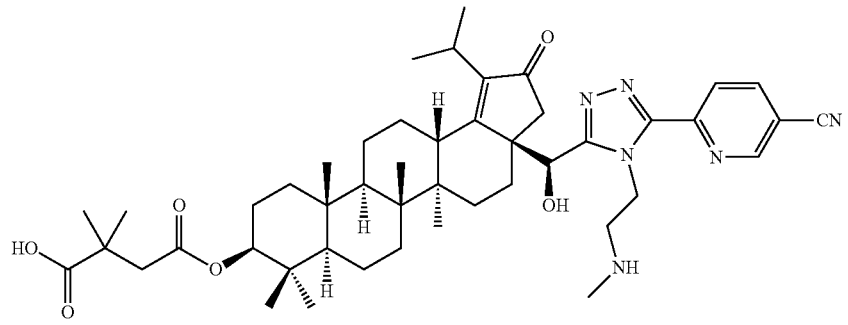
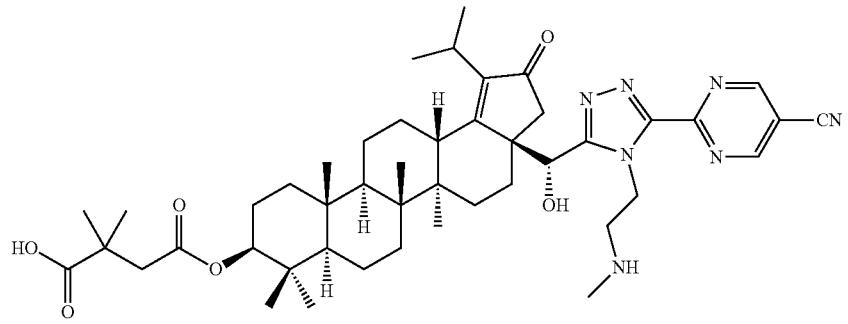

-continued
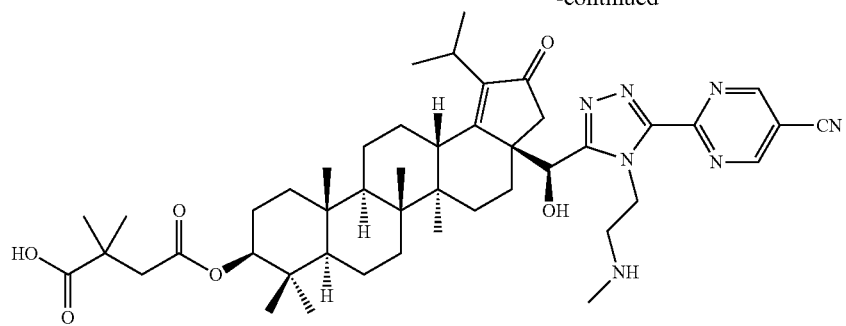
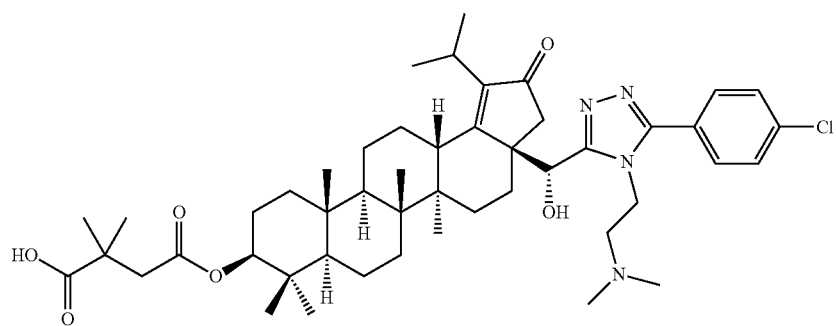
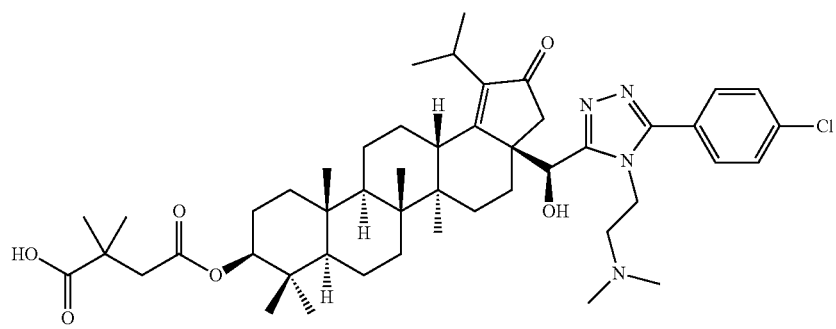
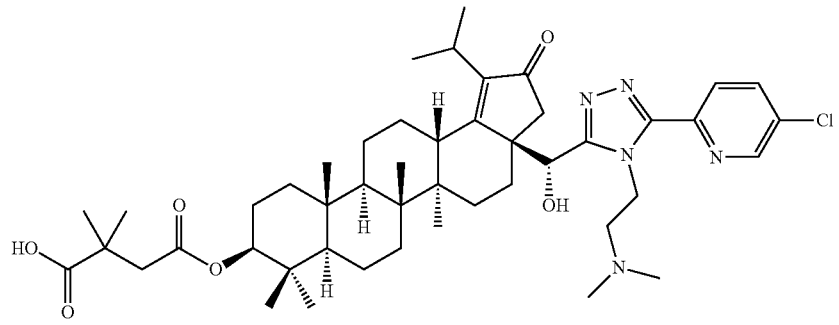

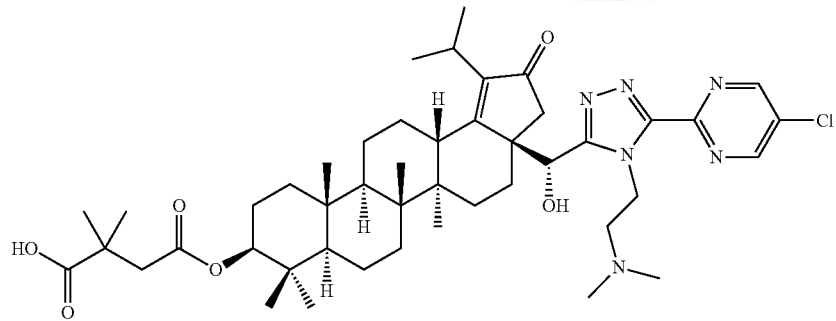
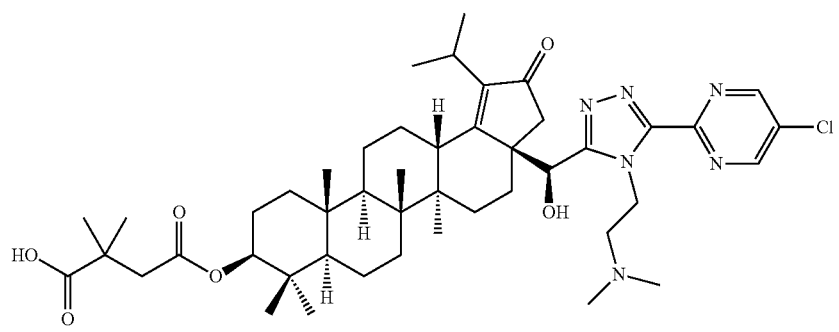
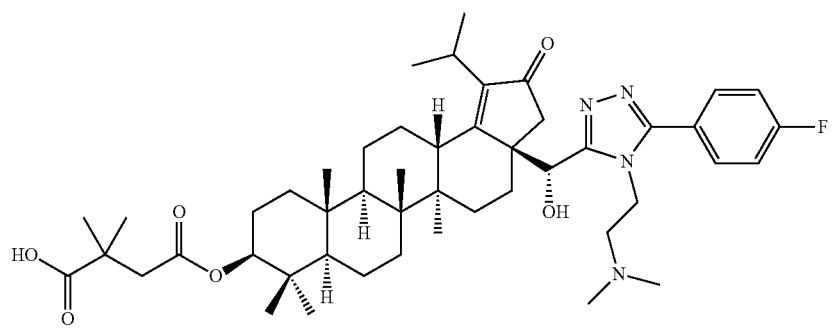
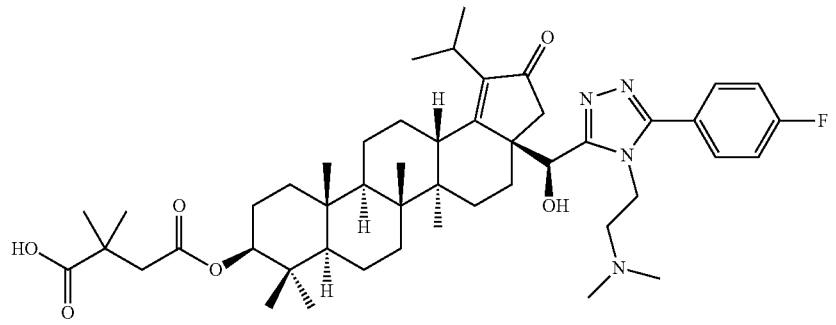
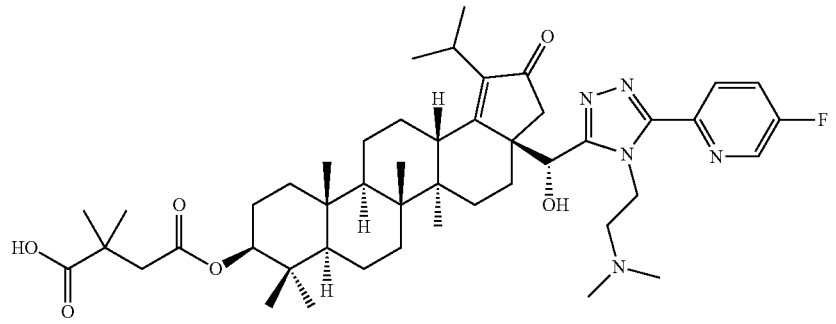

-continued
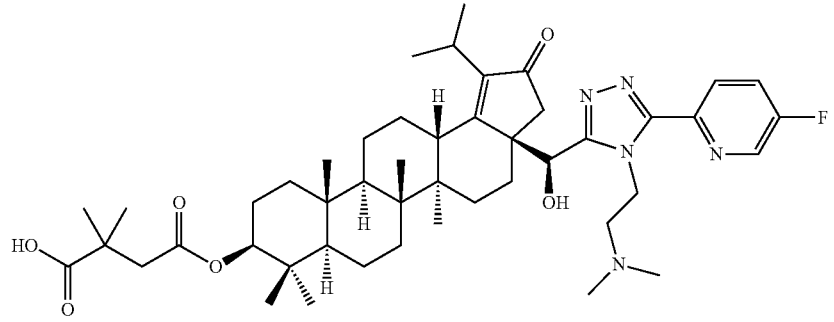
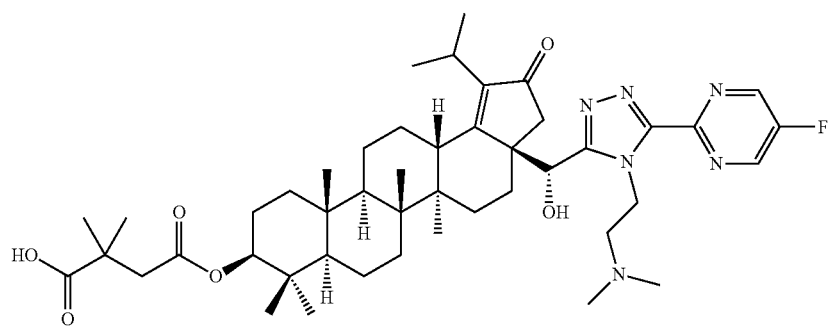
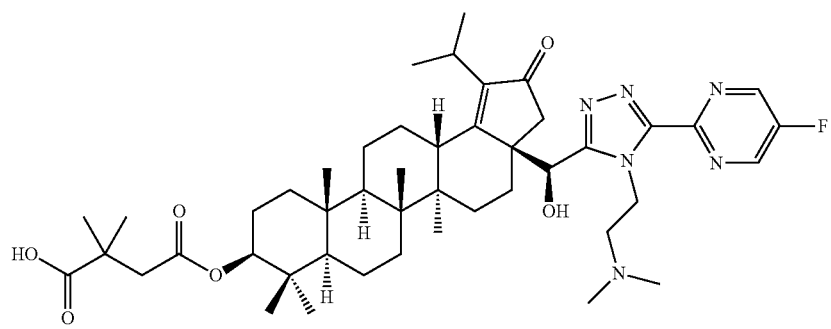
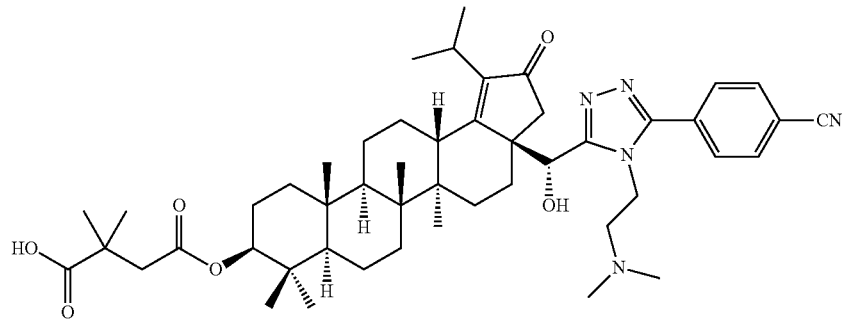
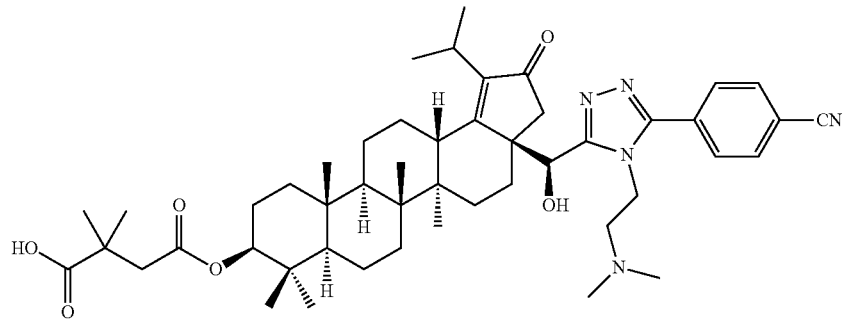

-continued
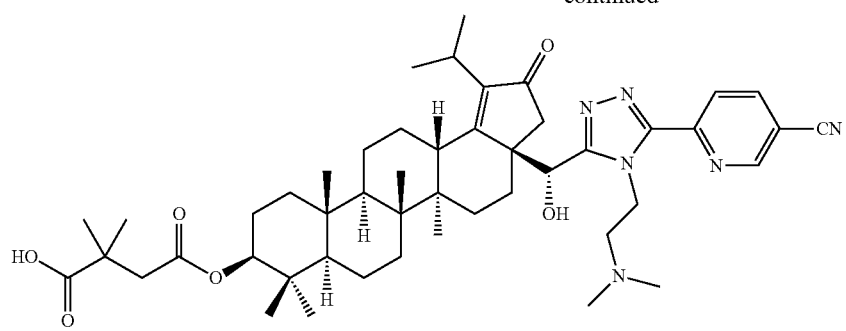
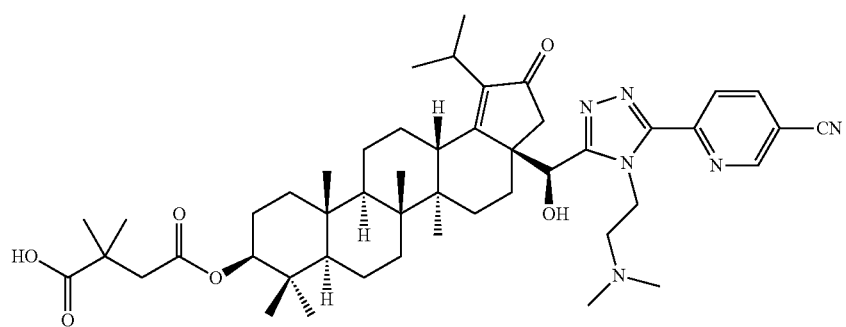
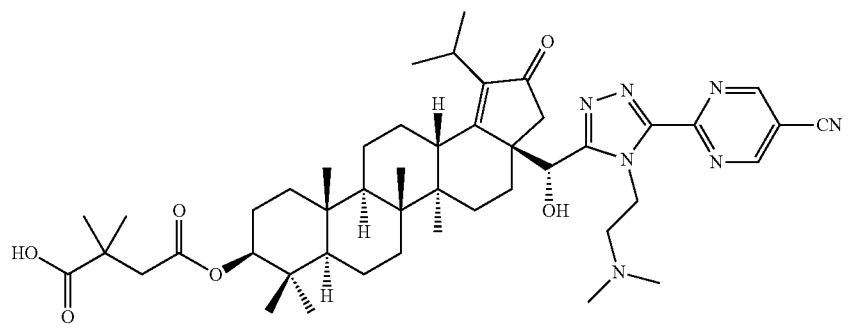
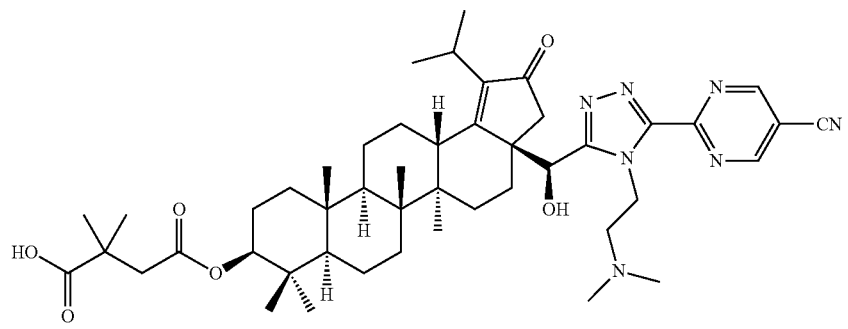
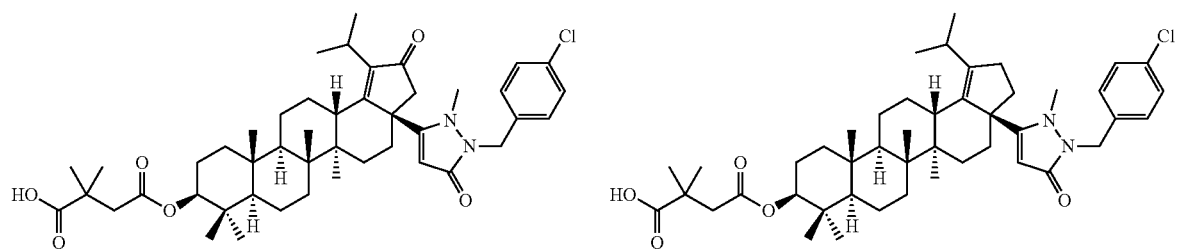

-continued
129
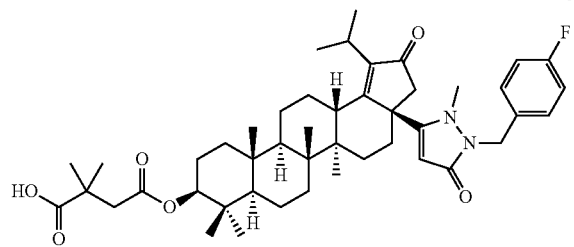
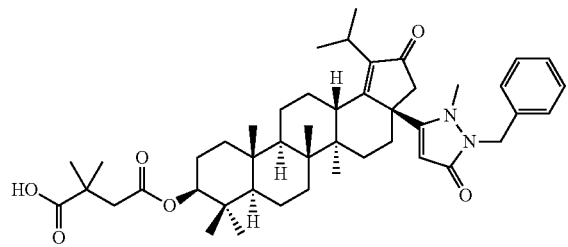
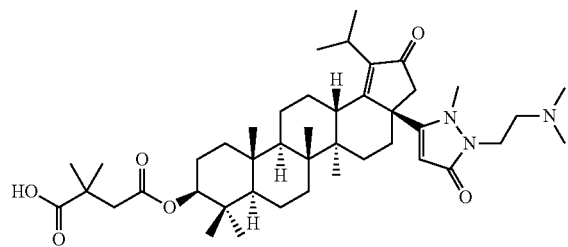
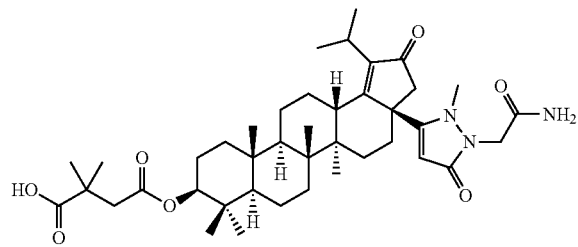
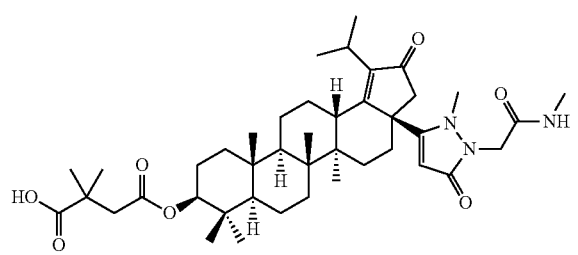
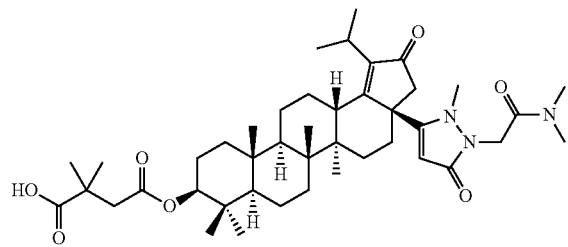
130
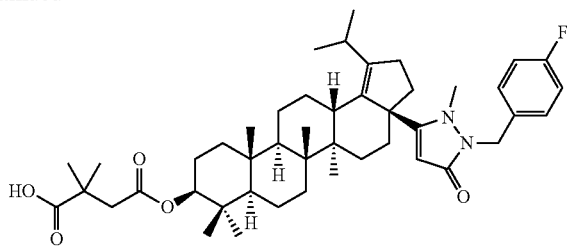
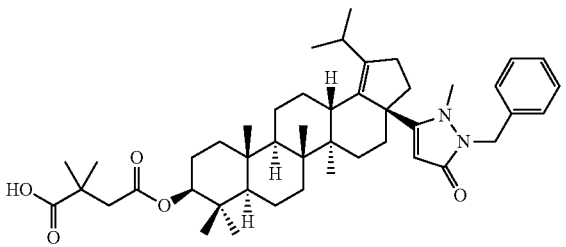
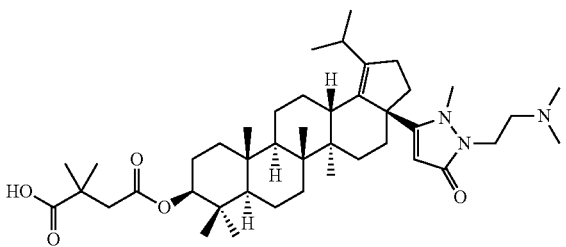
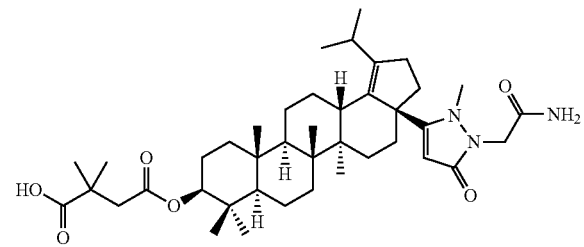
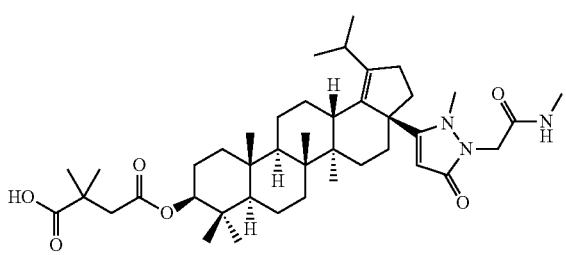
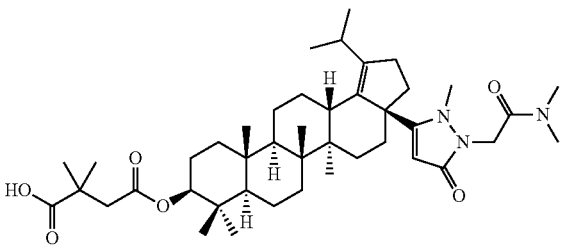

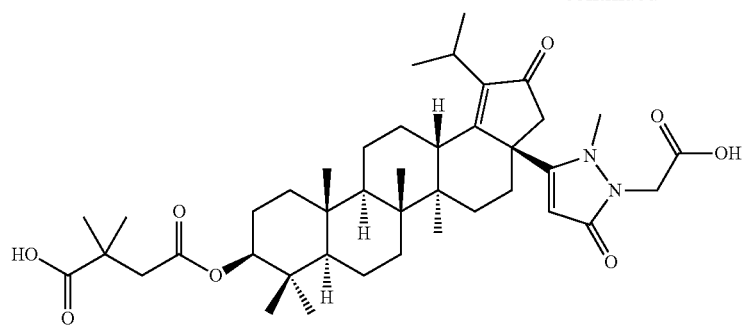
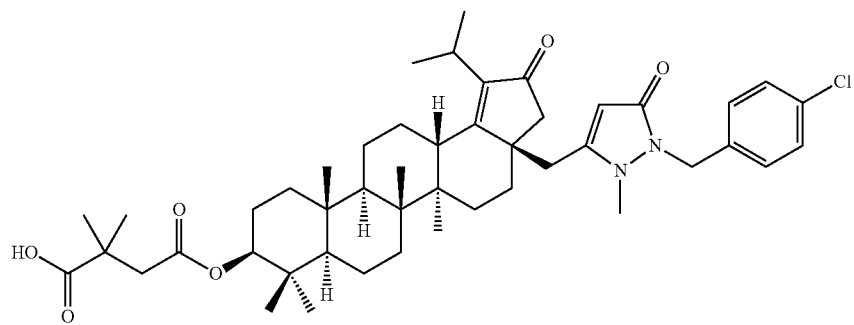
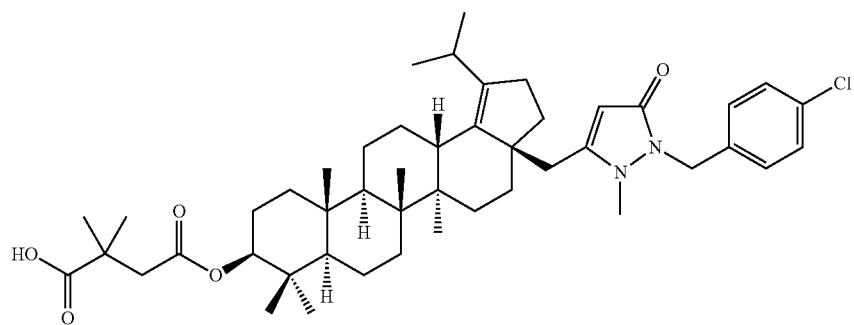
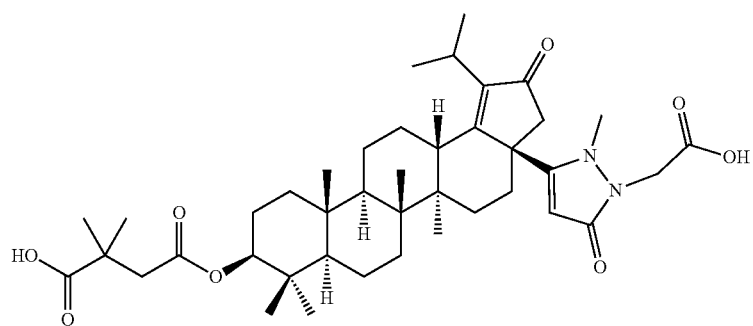
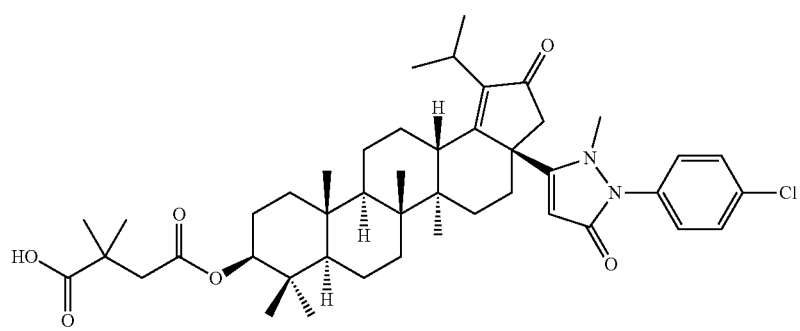

-continued
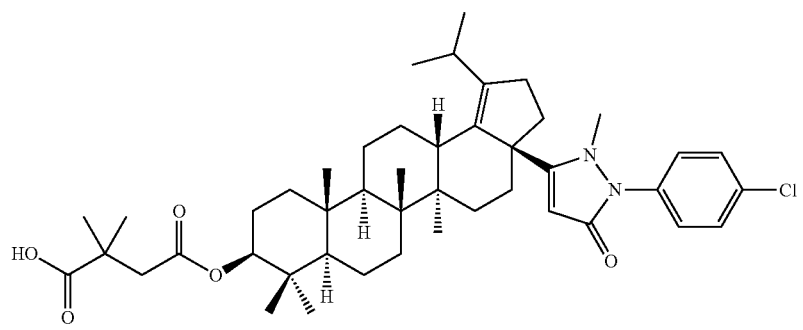
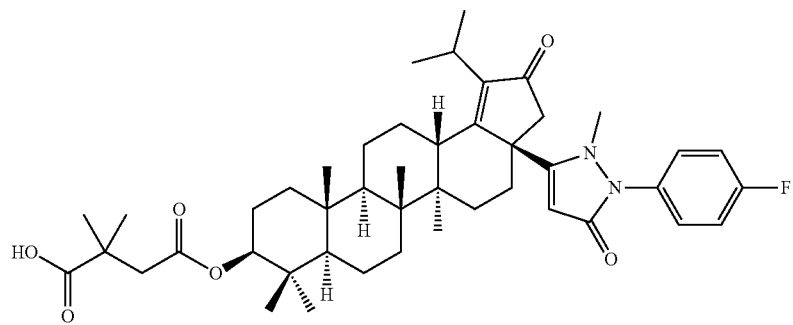
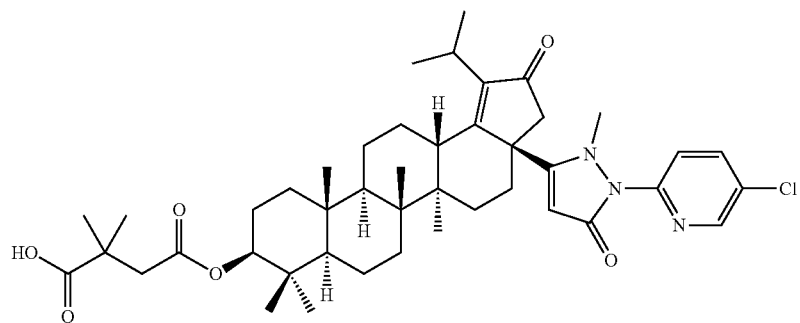
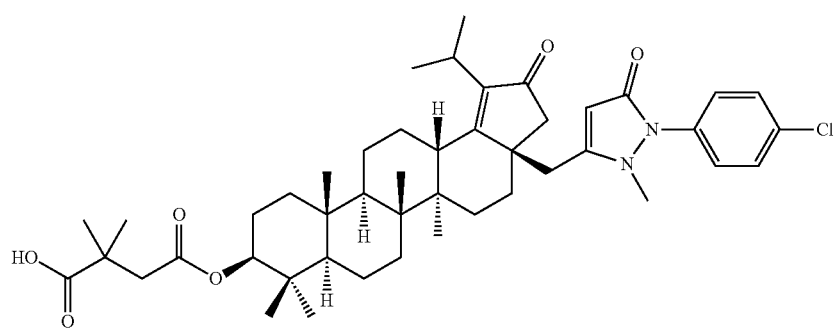
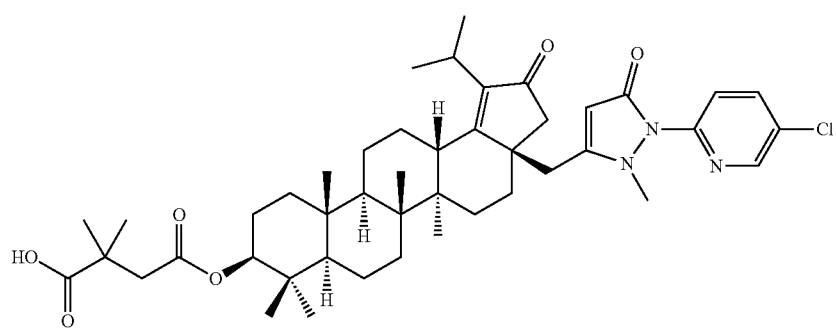

-continued
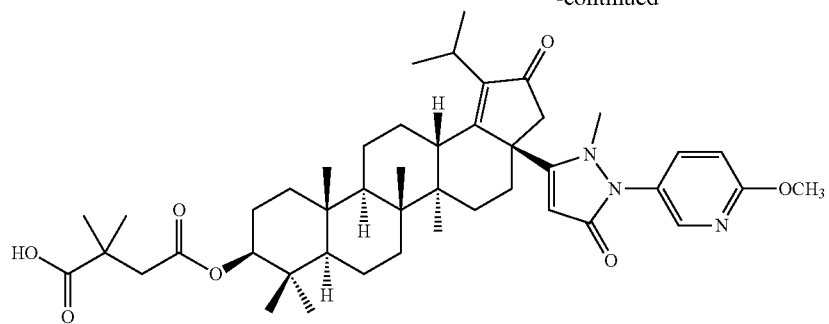
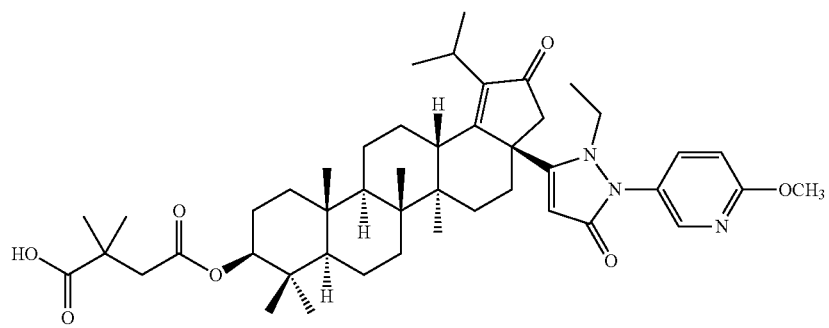
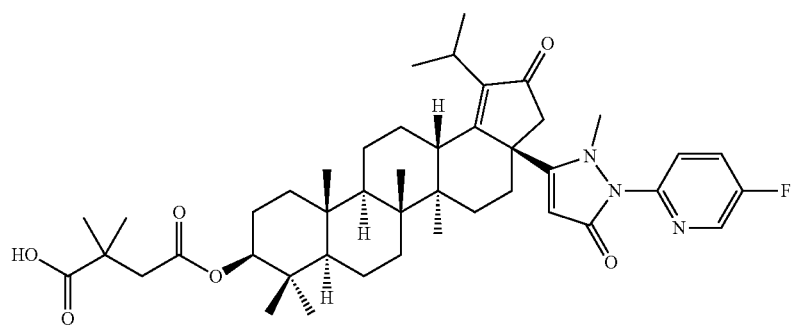
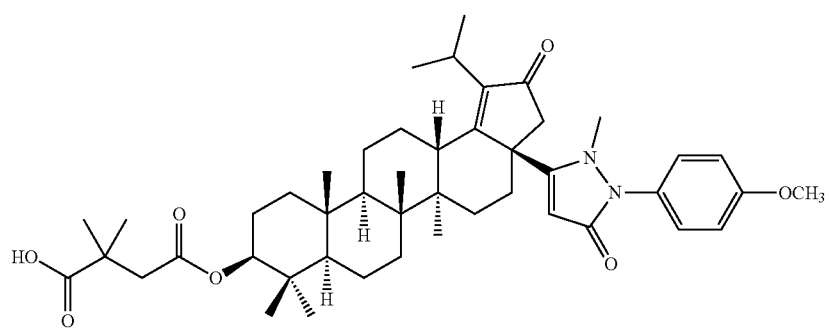
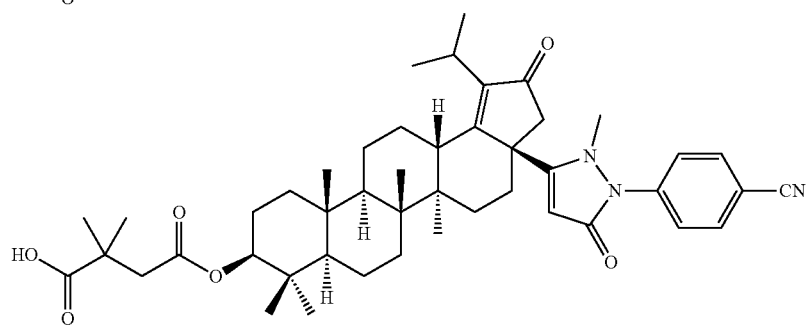

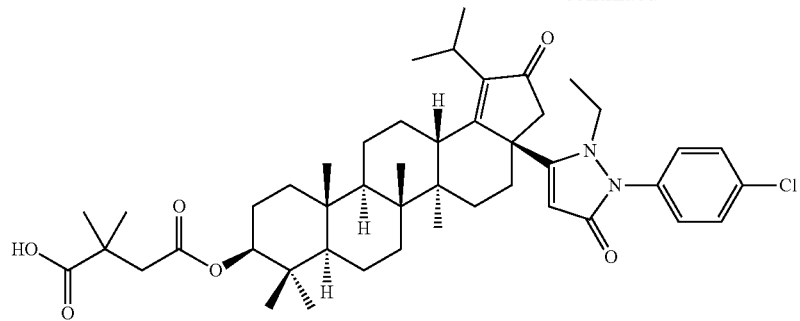
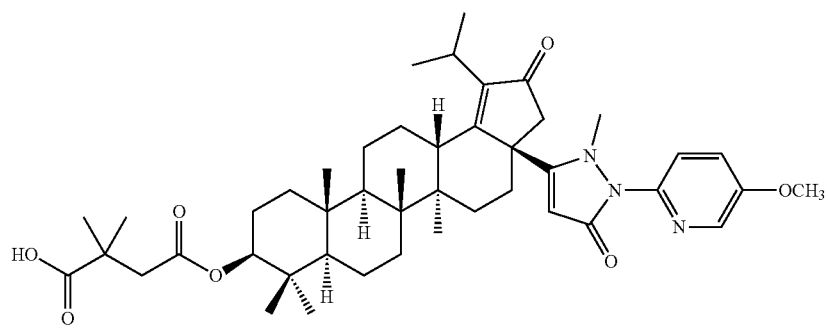
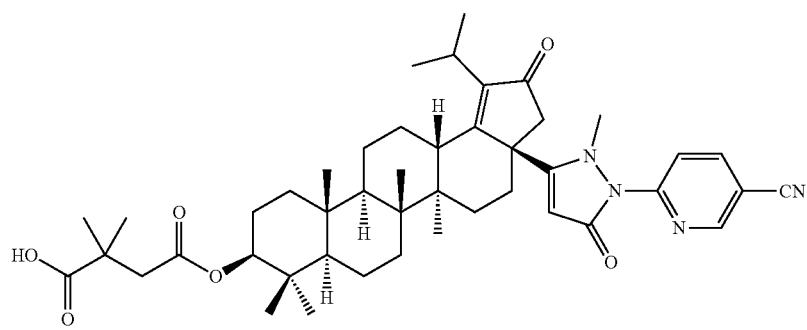
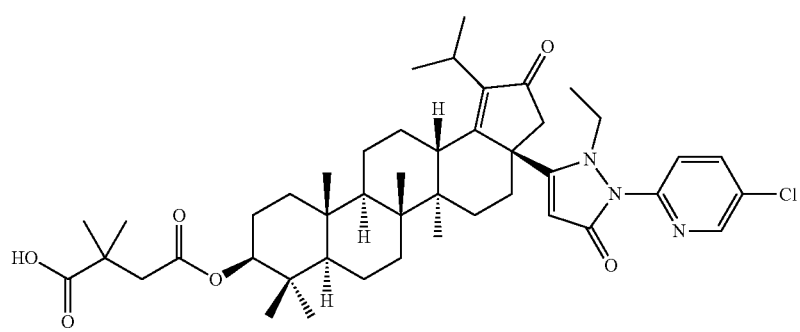
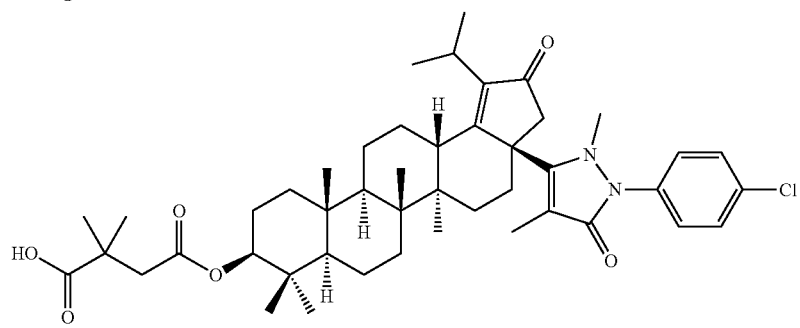

-continued
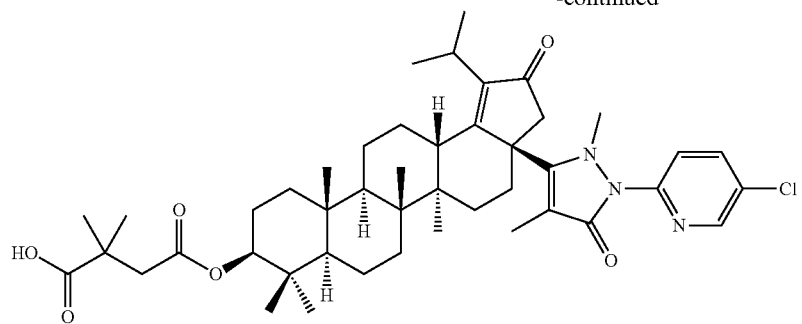
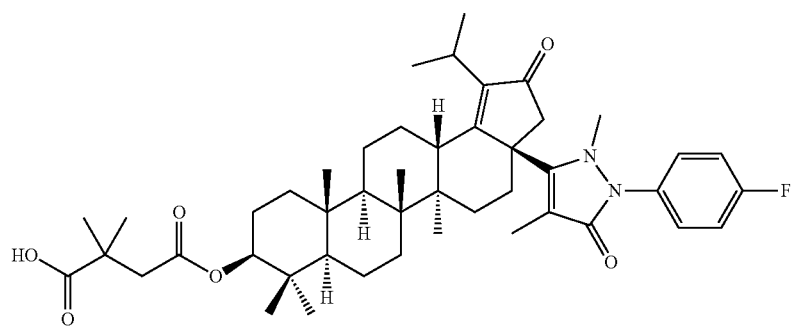
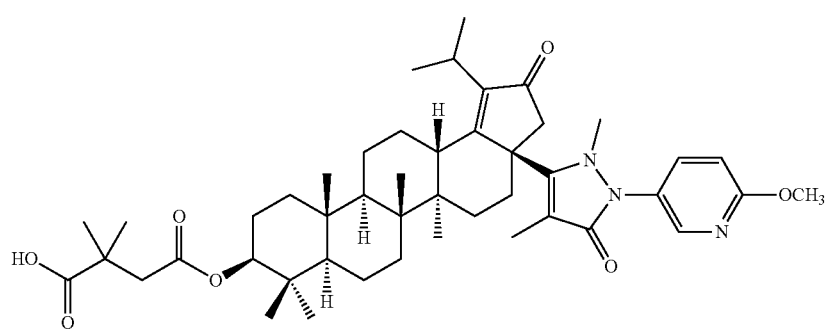
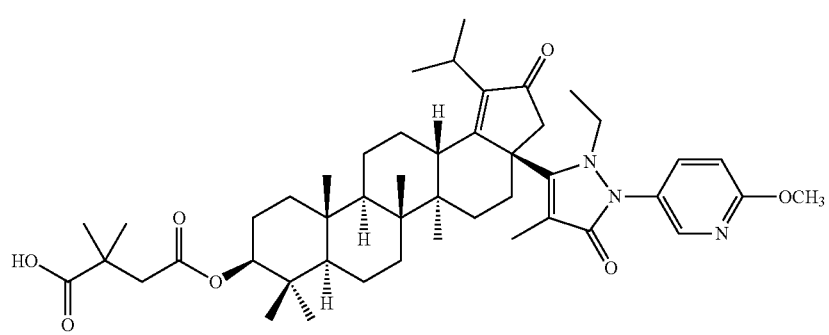
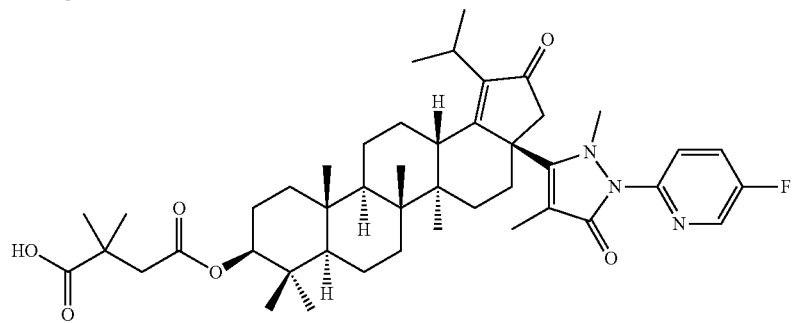

-continued
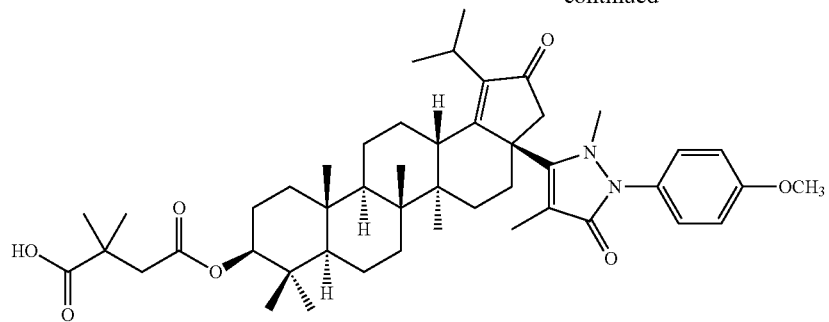
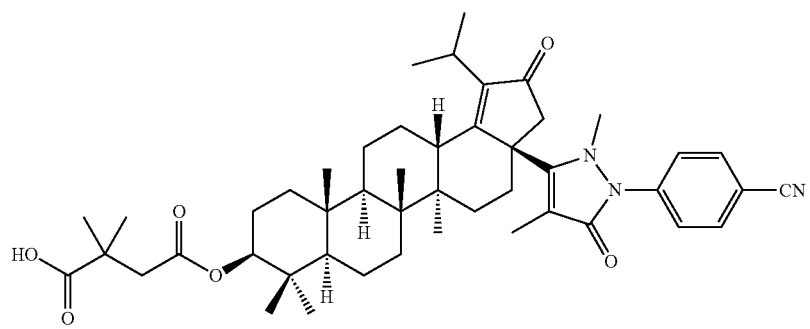
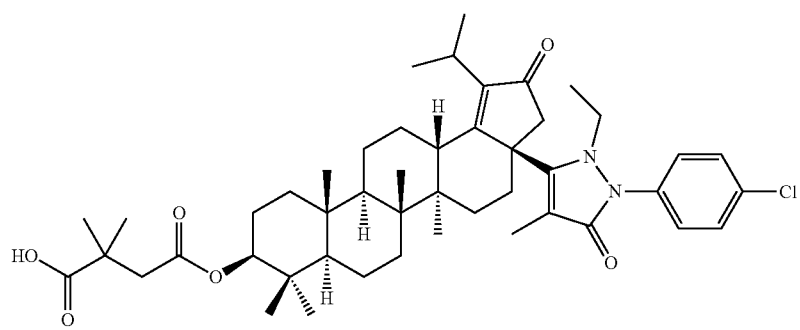
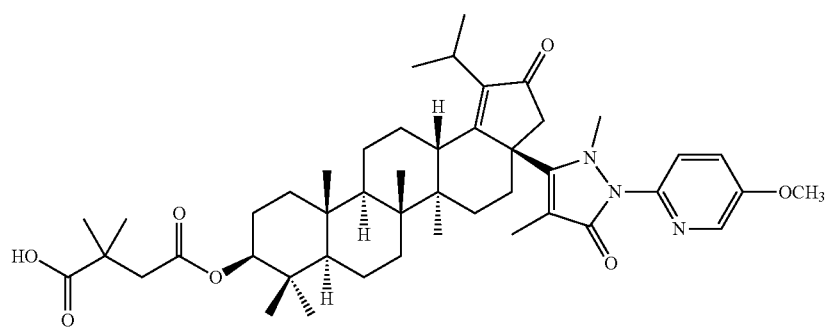
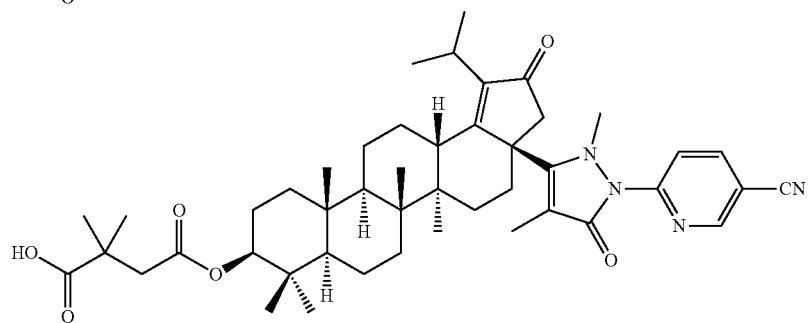

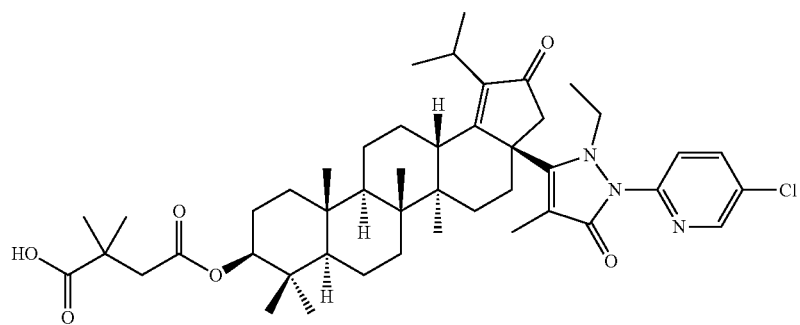
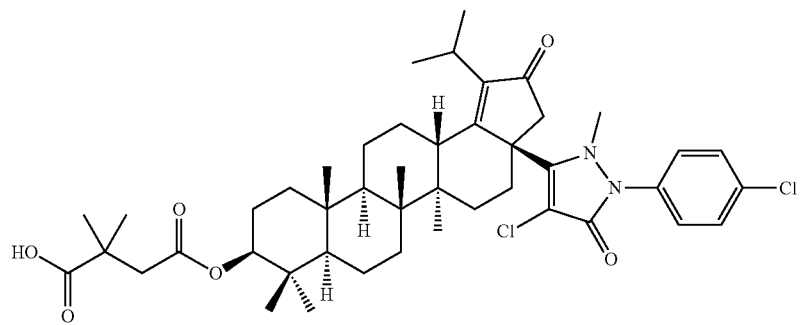
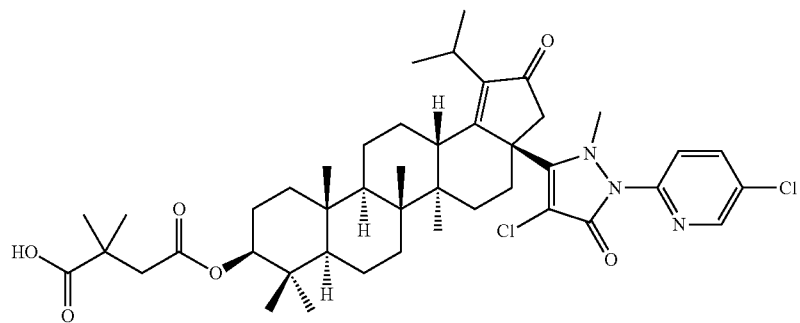
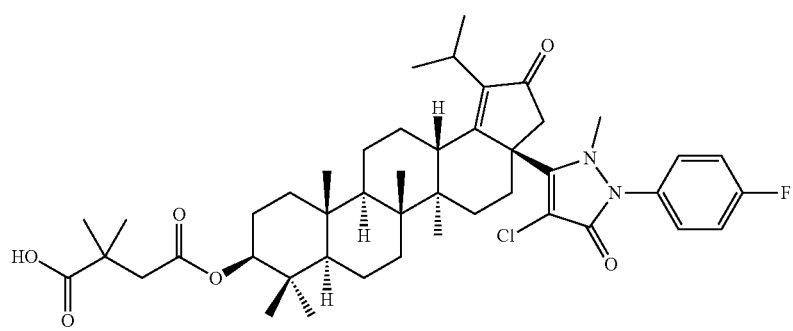
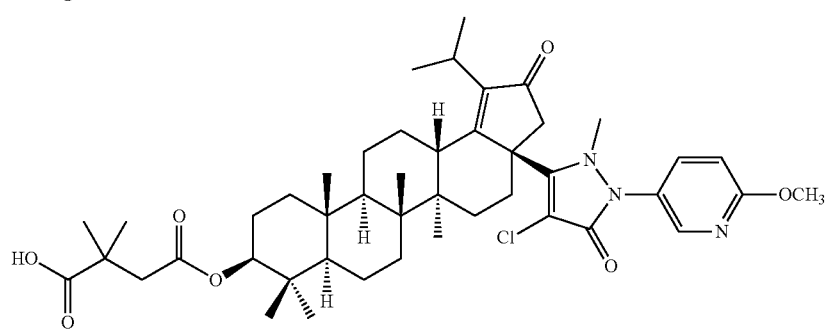

-continued
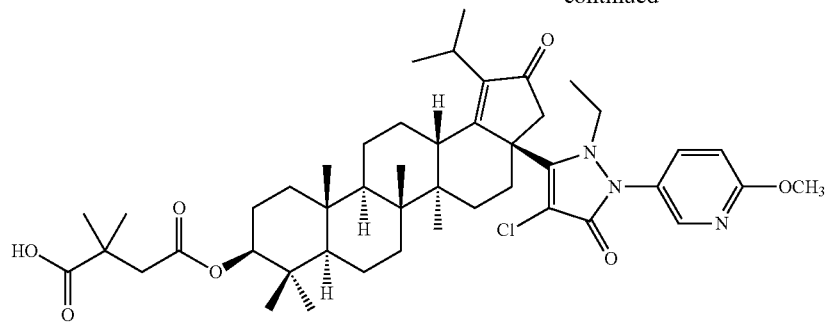
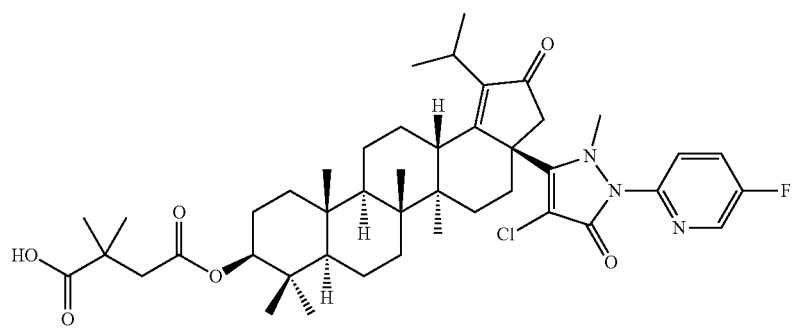
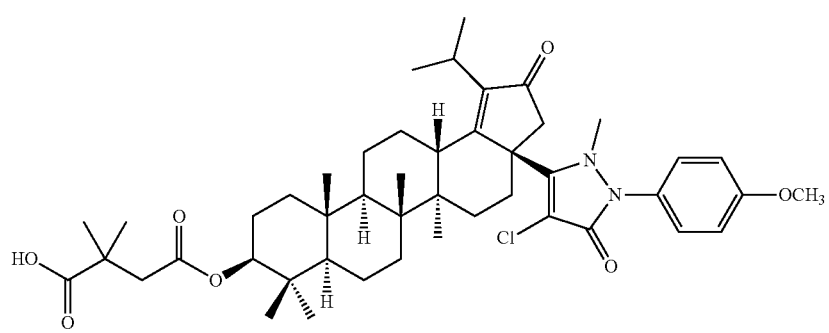
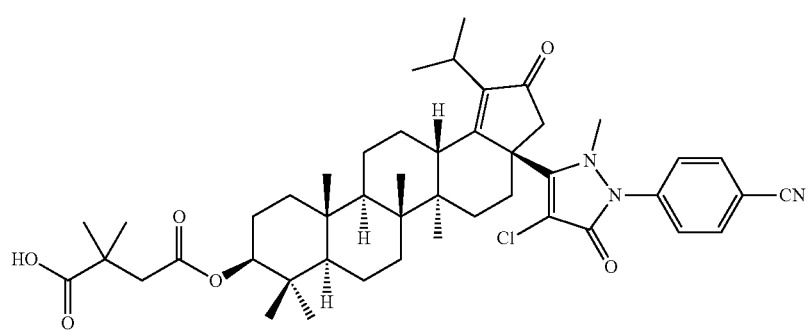
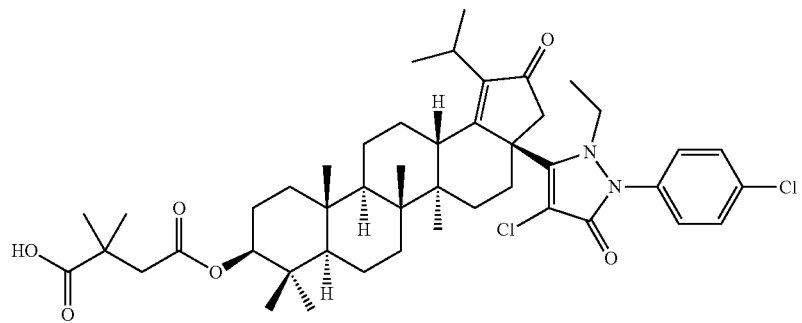

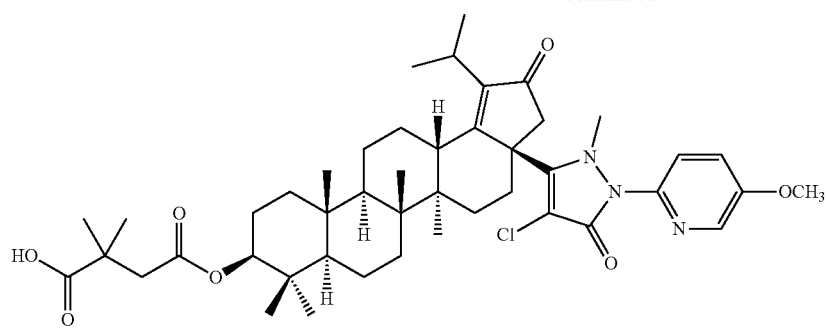
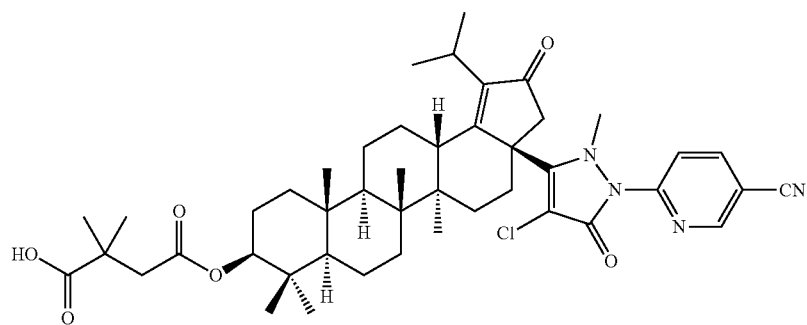
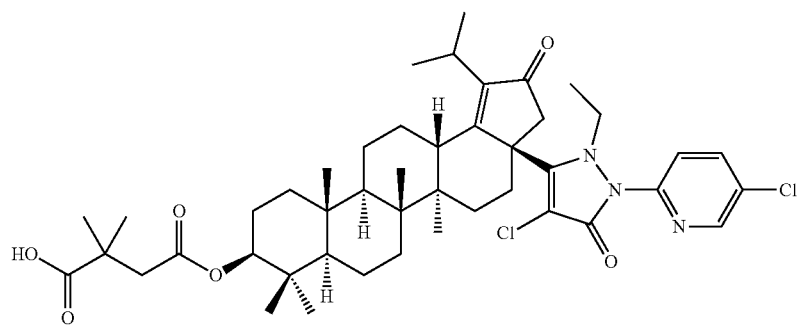
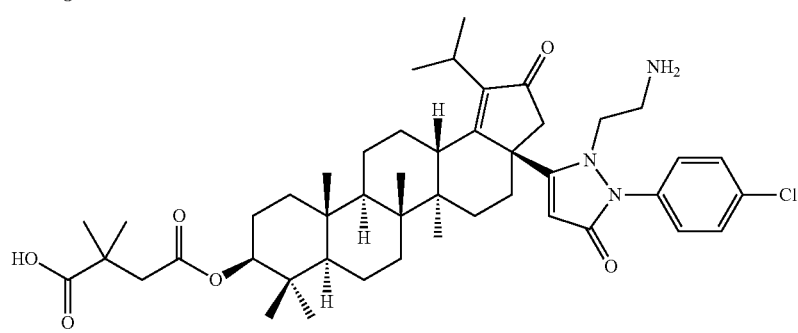
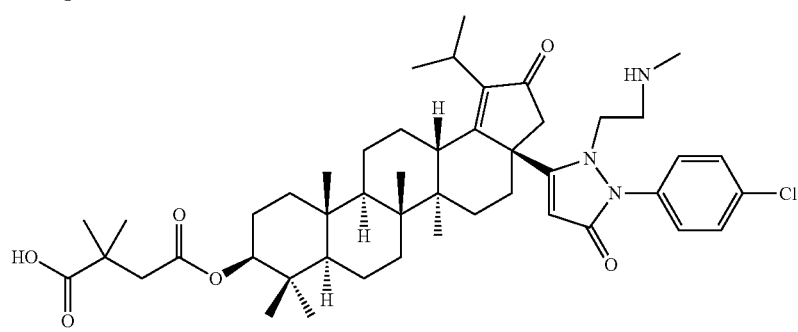

-continued
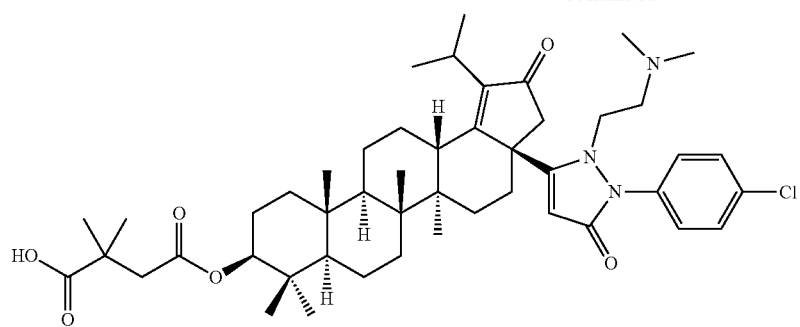
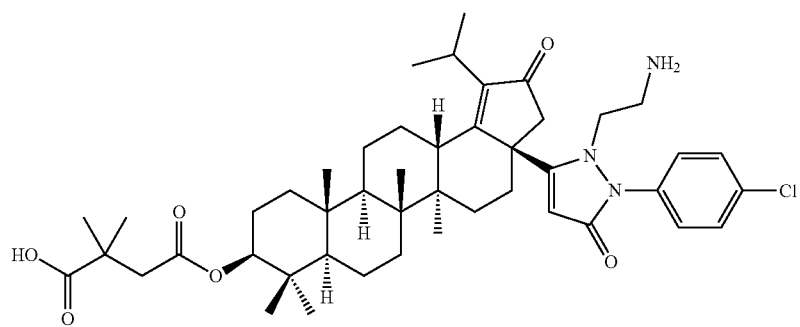
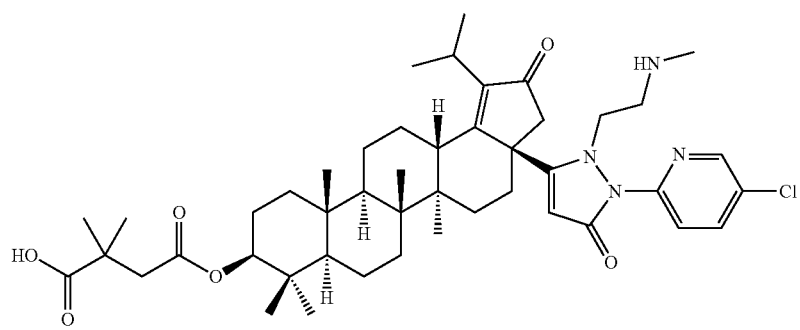
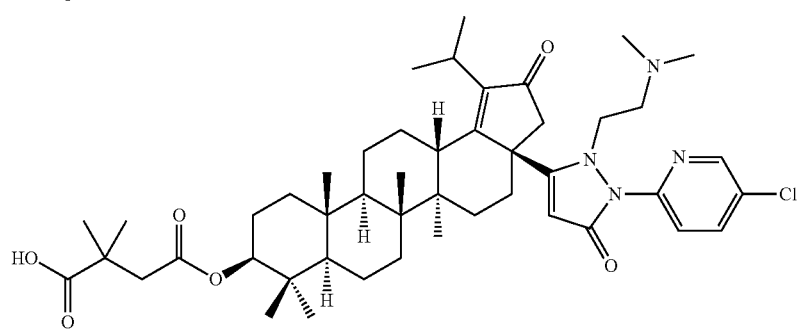
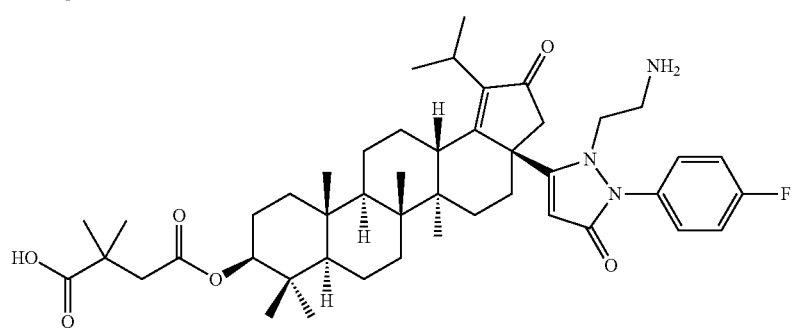

-continued
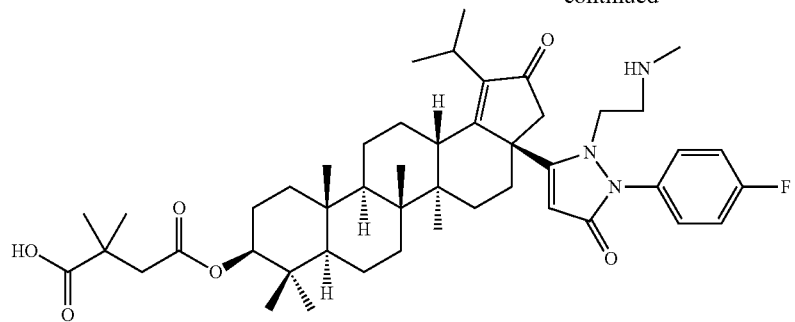
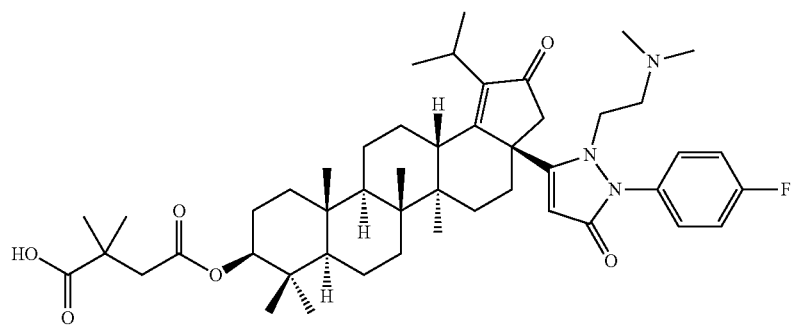
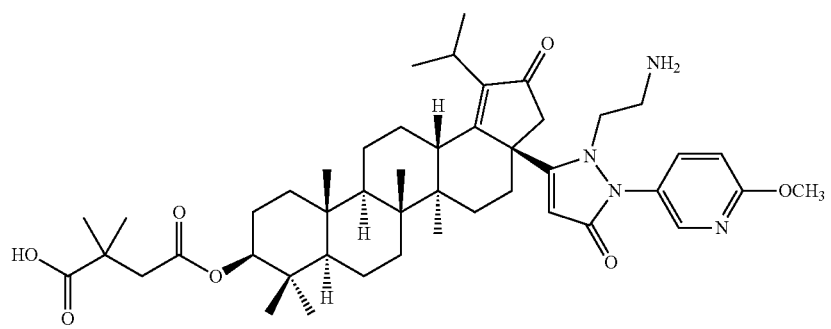
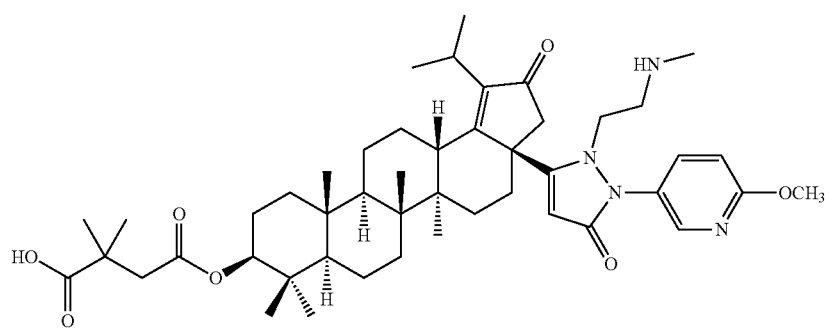
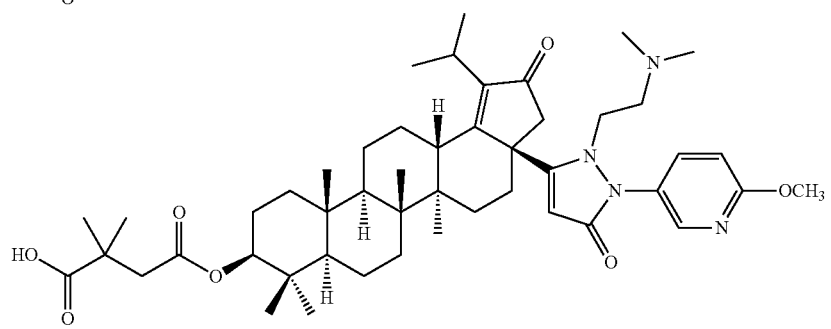

-continued
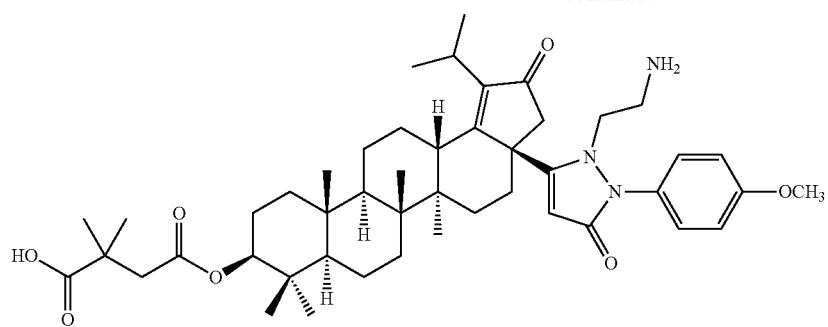
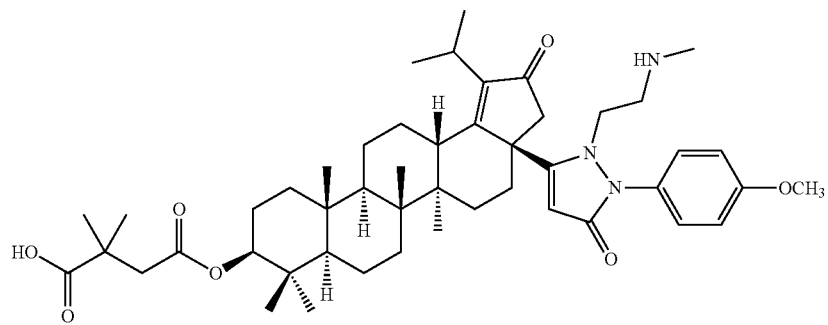
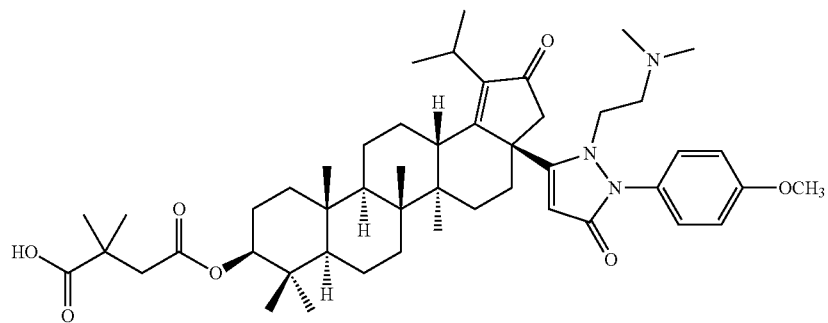
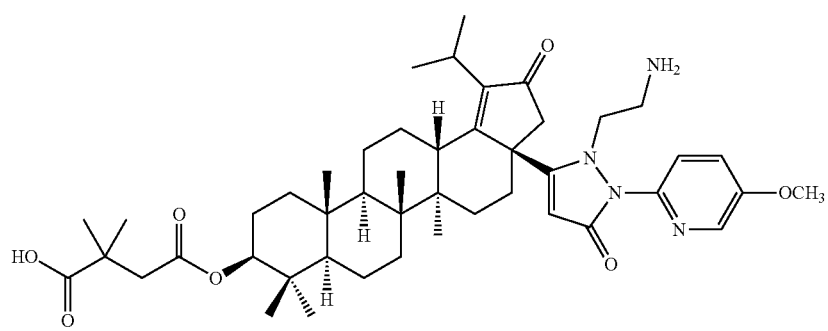
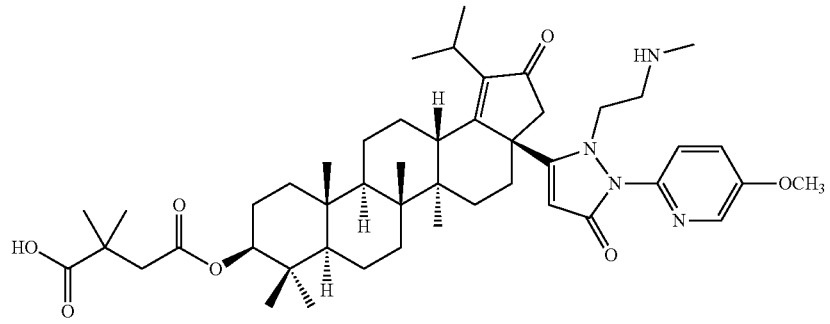

-continued
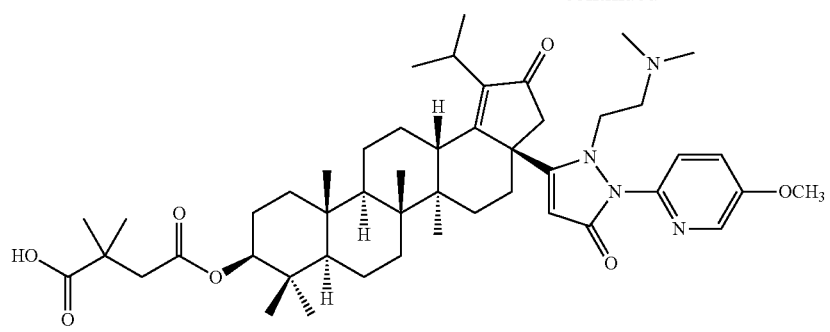
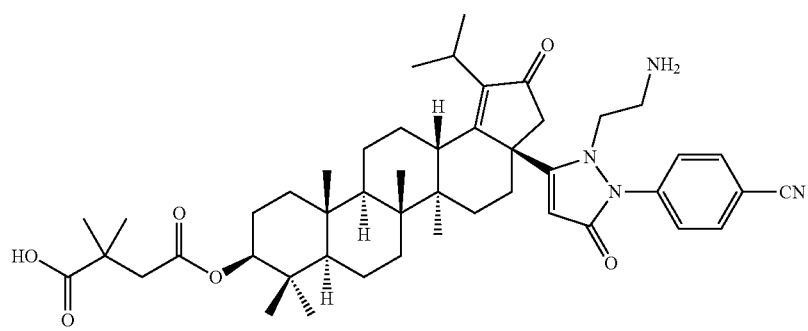
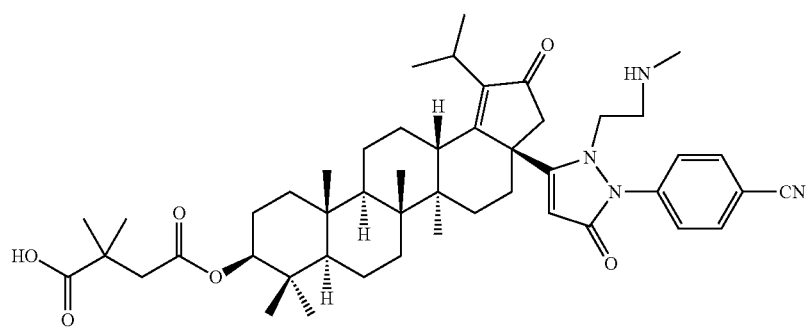
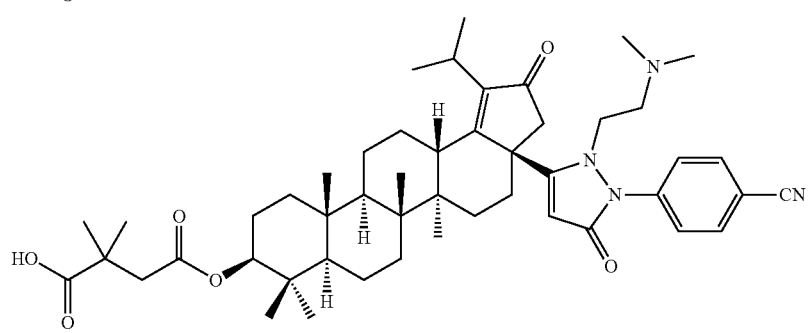
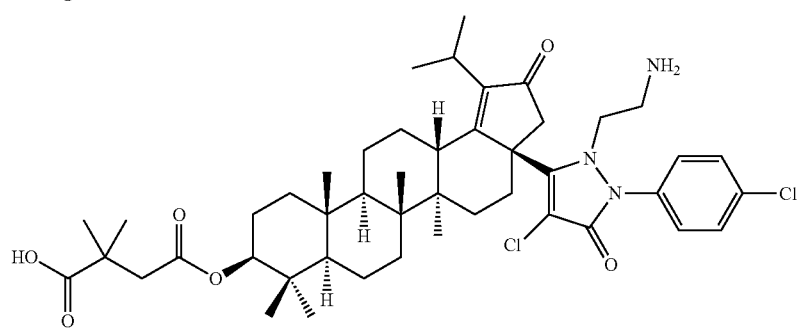

-continued
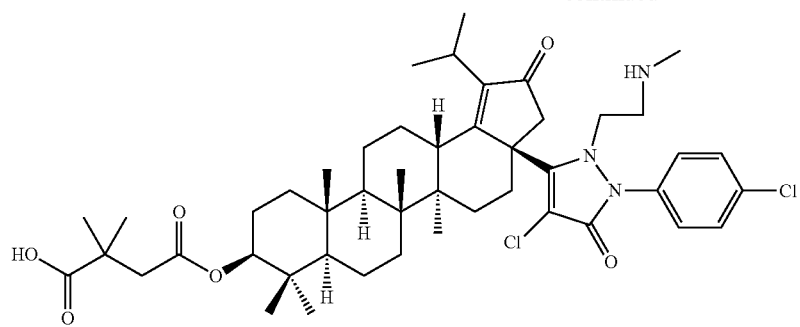
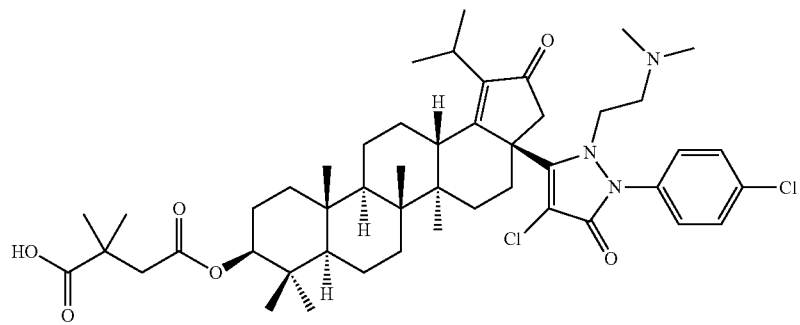
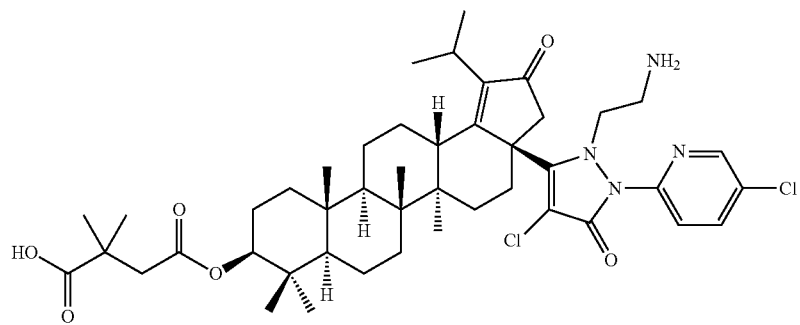
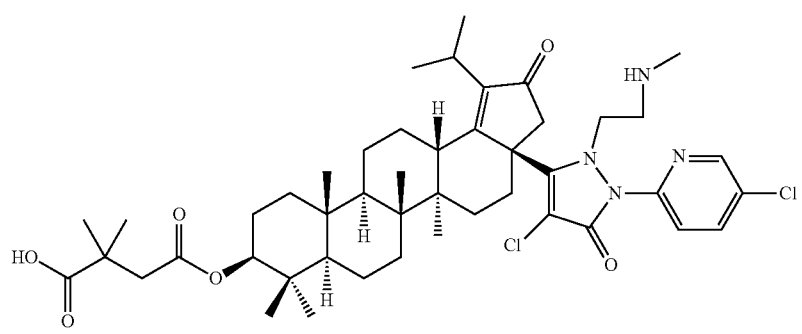
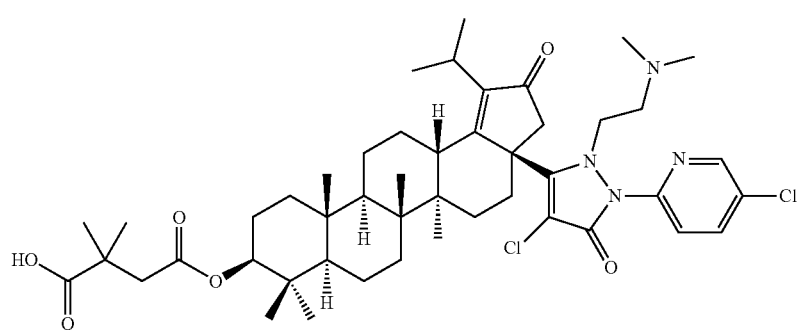

-continued
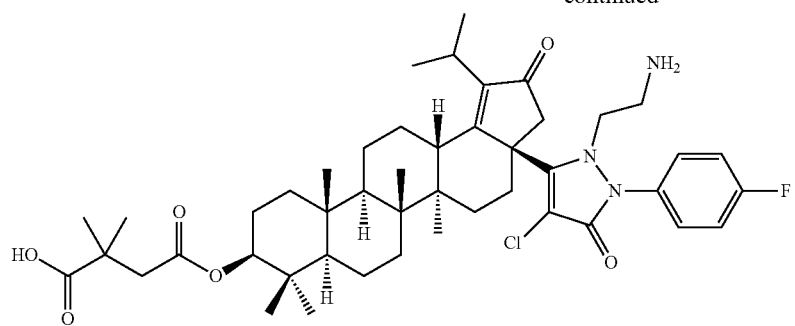
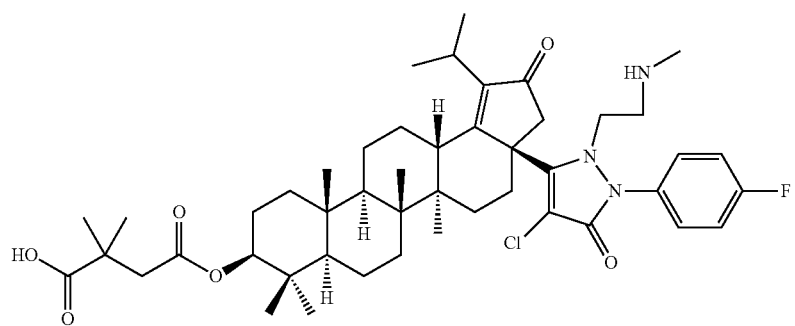
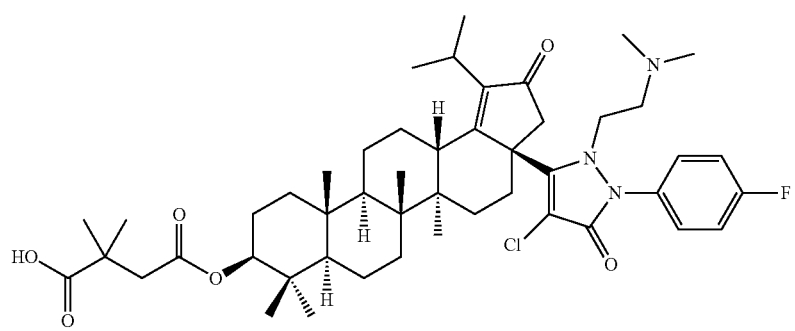
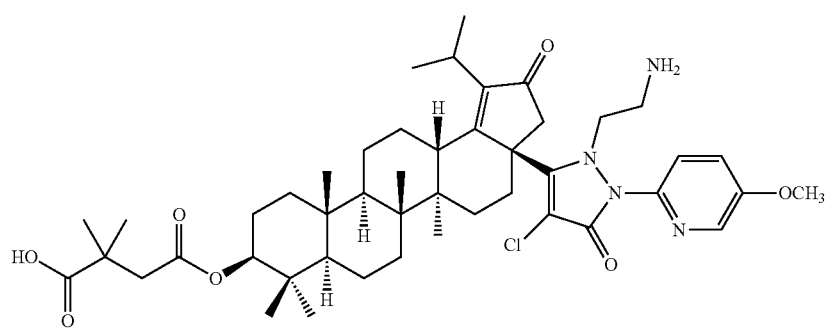
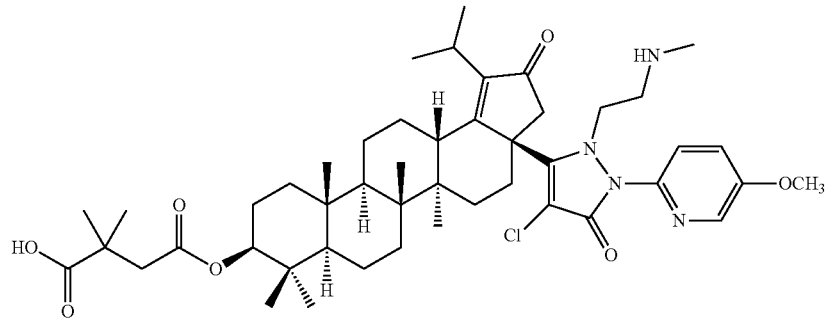

-continued
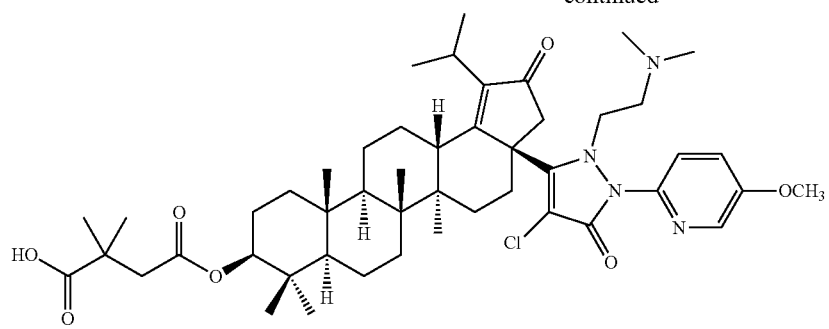
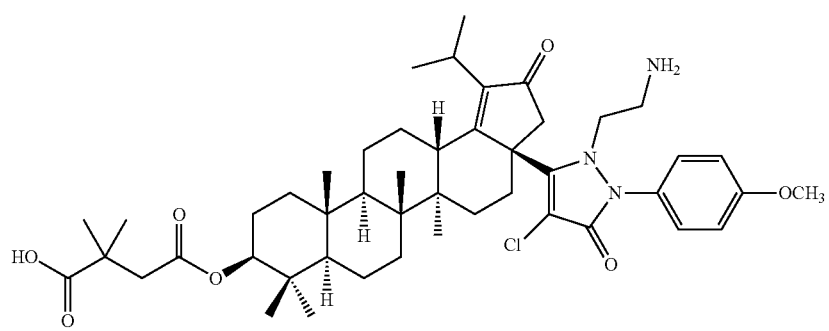
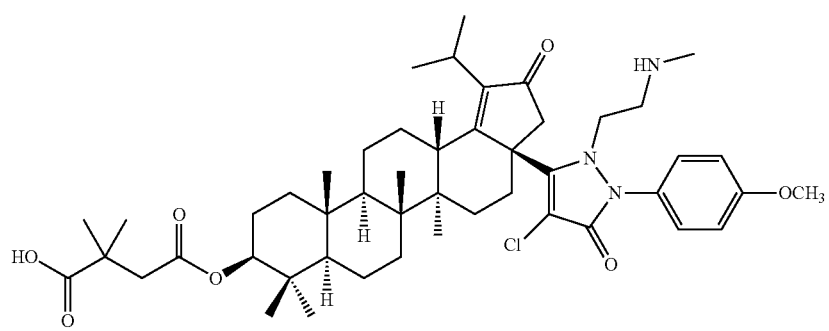
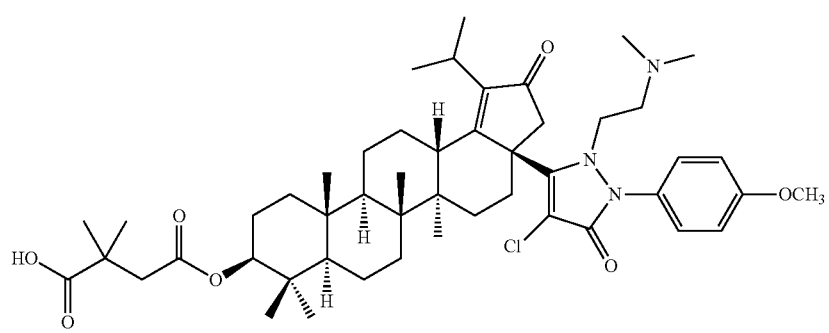
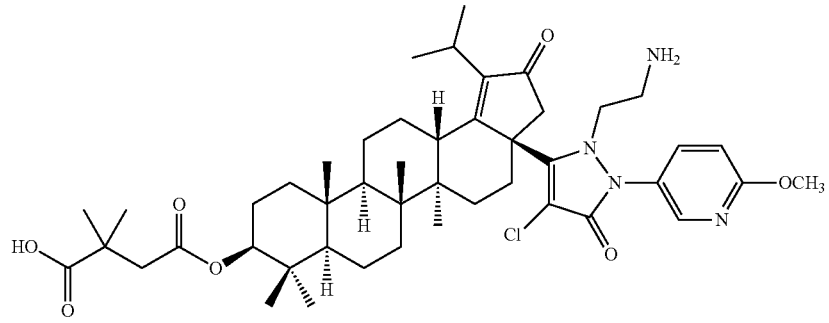

-continued
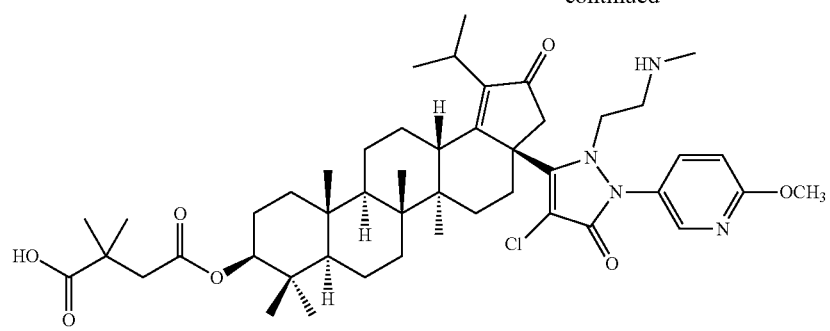
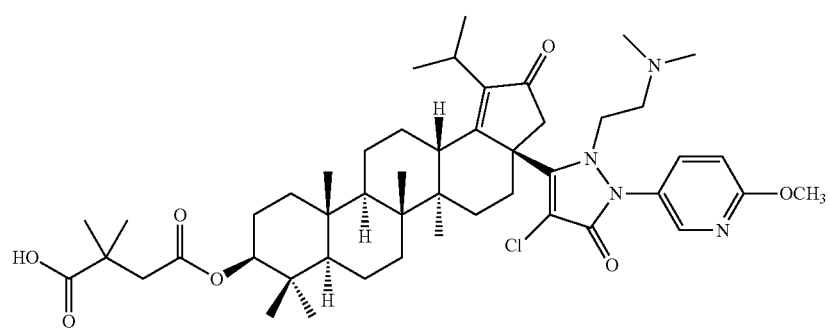
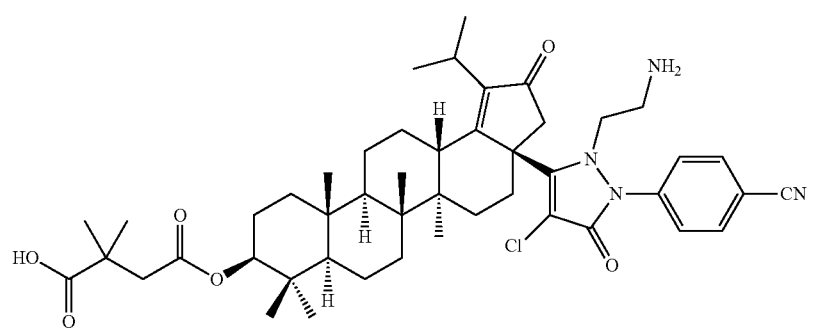
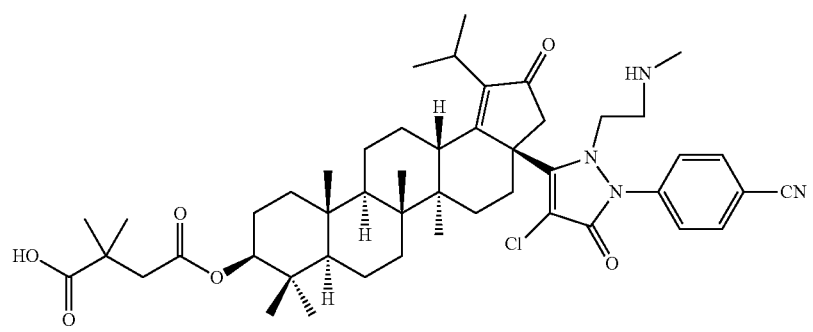
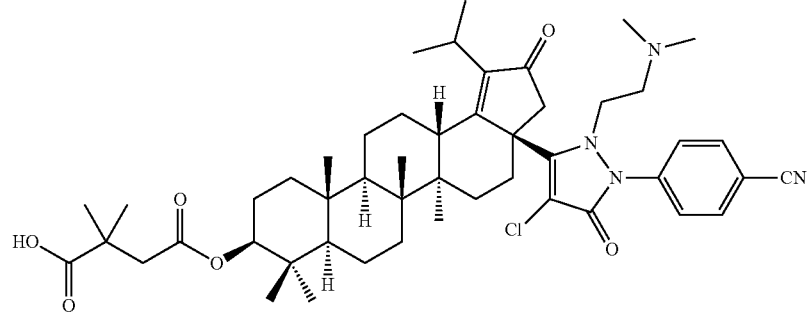

-continued
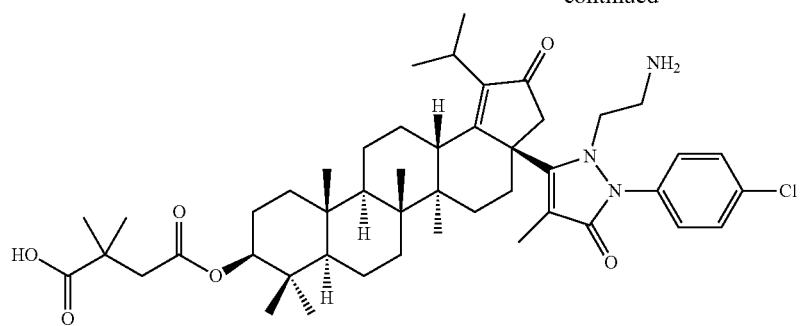
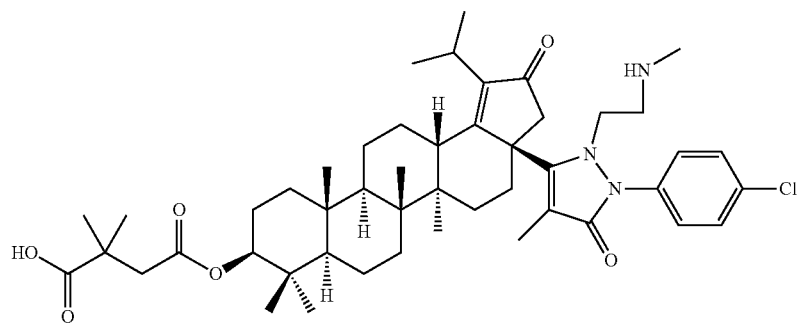
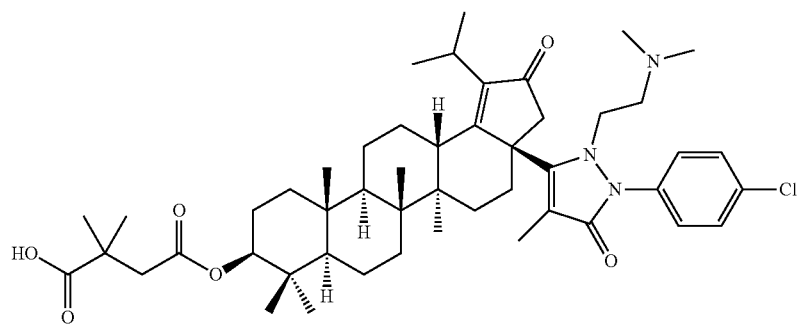
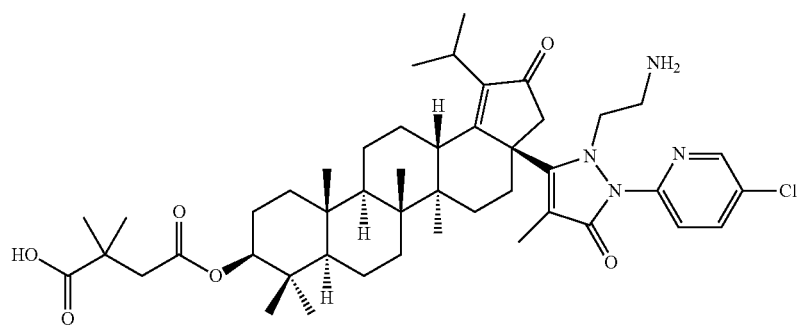
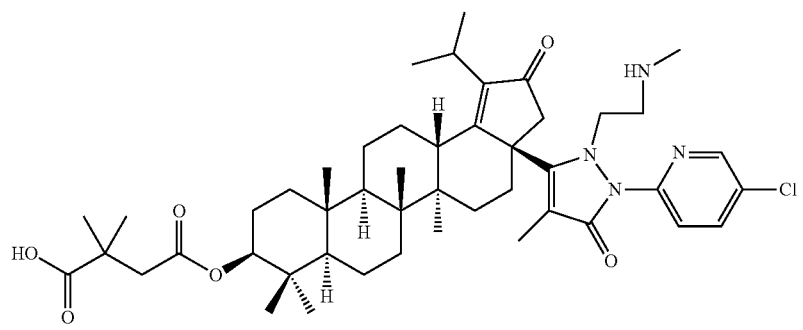

-continued
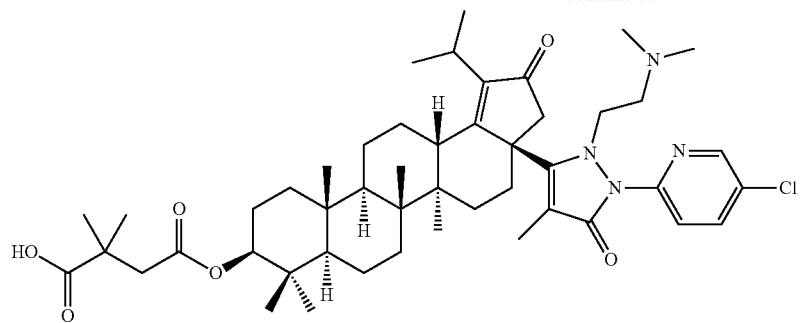
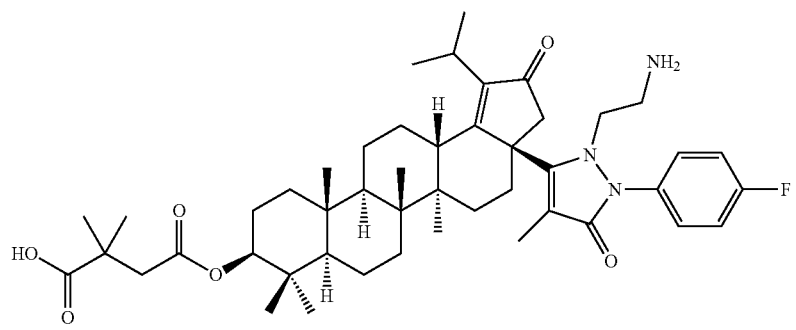
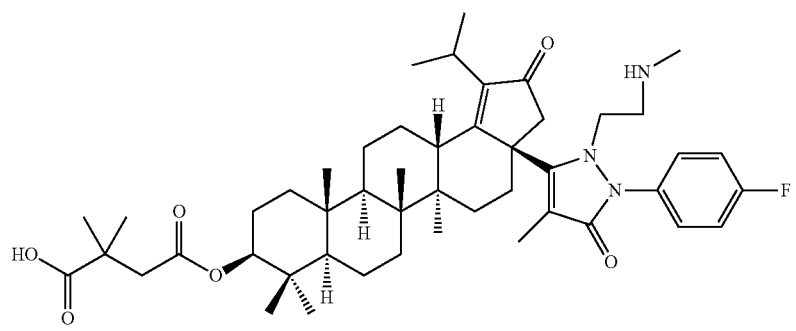
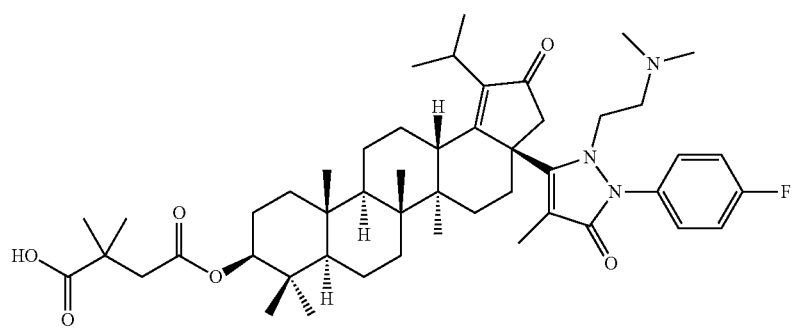
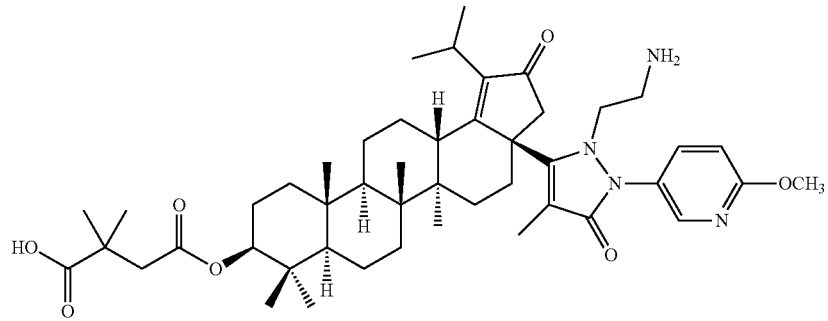

-continued
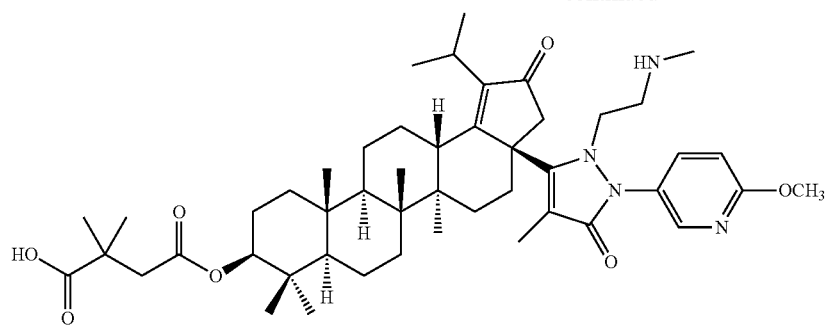
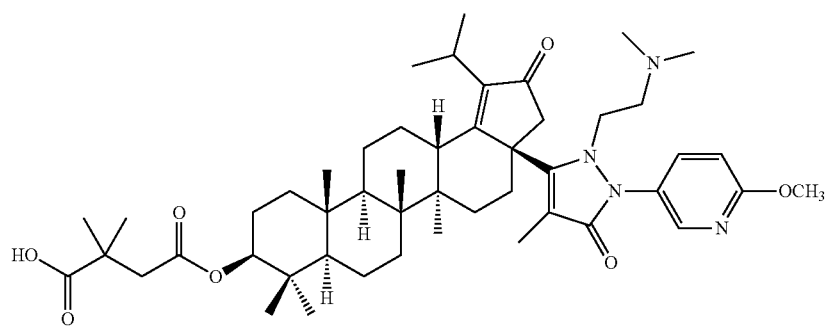
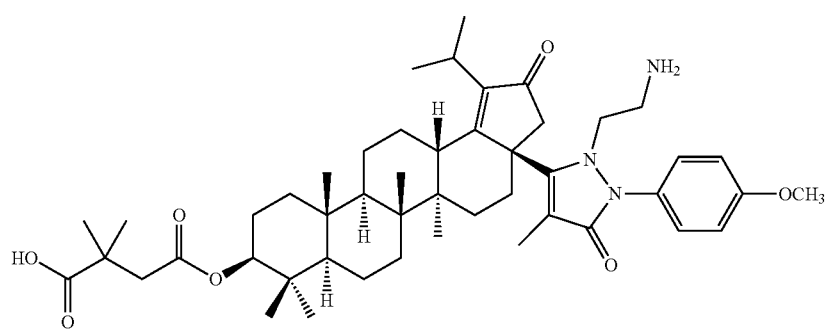
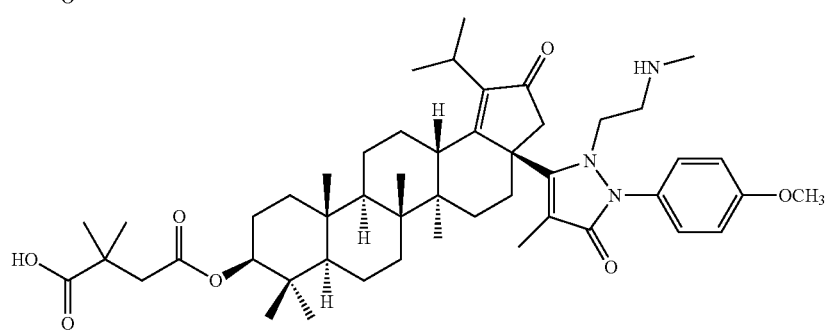
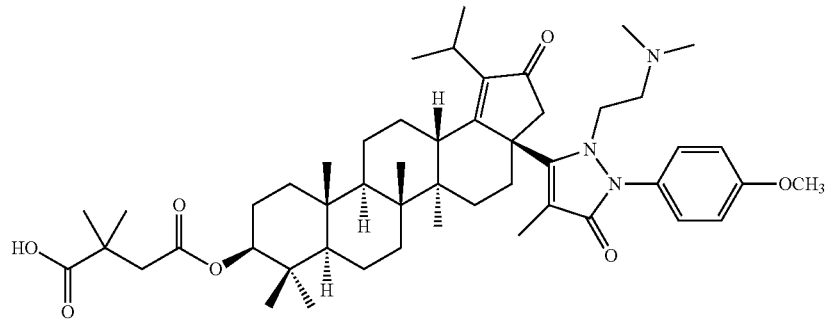

-continued
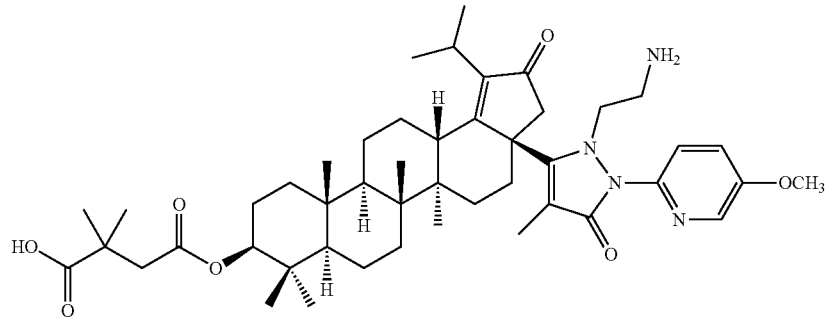
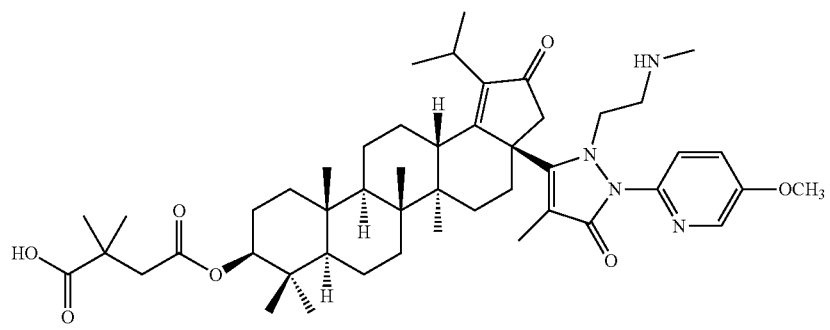
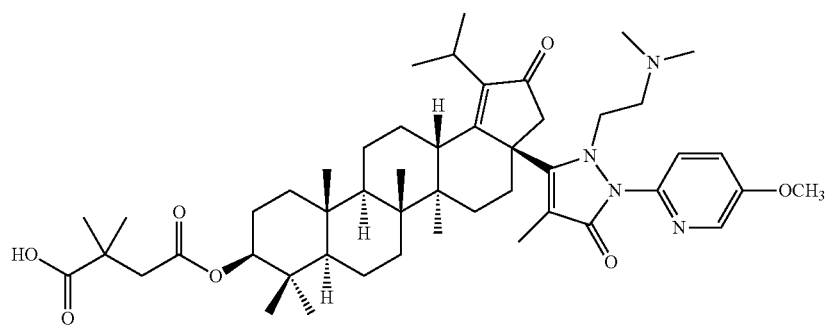
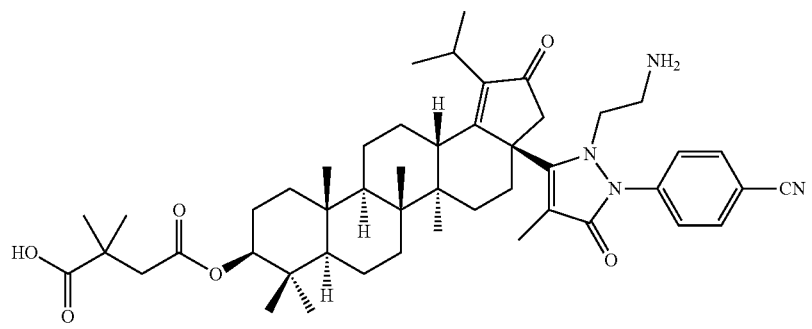
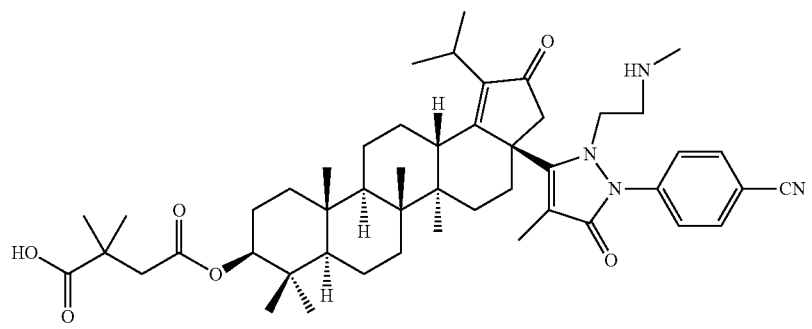

-continued
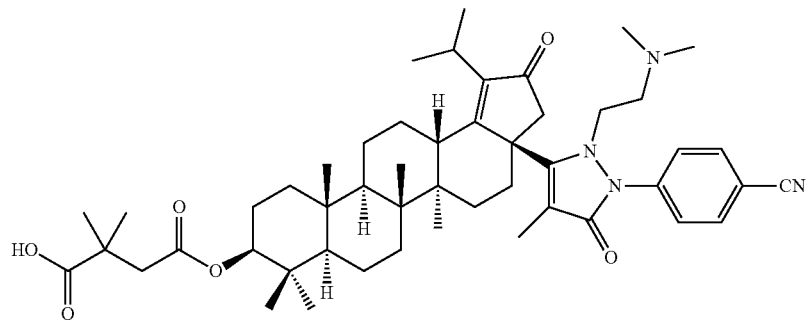
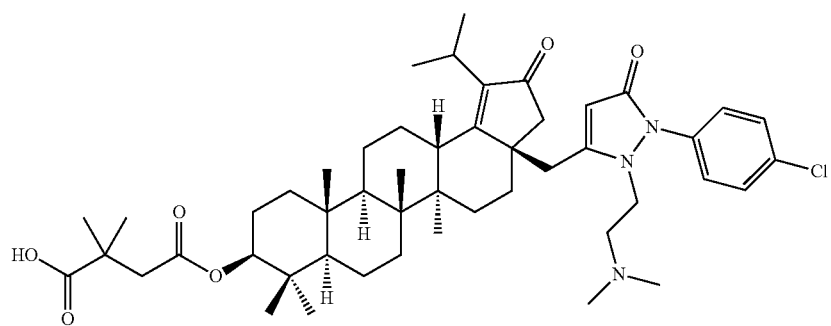
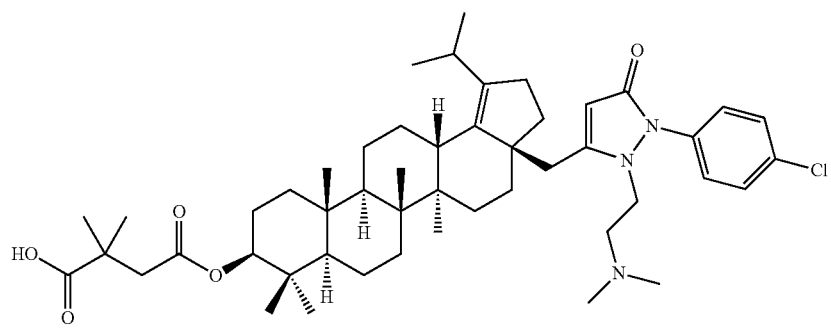
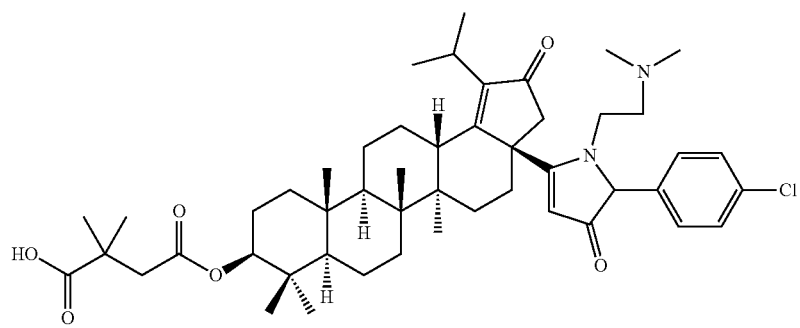
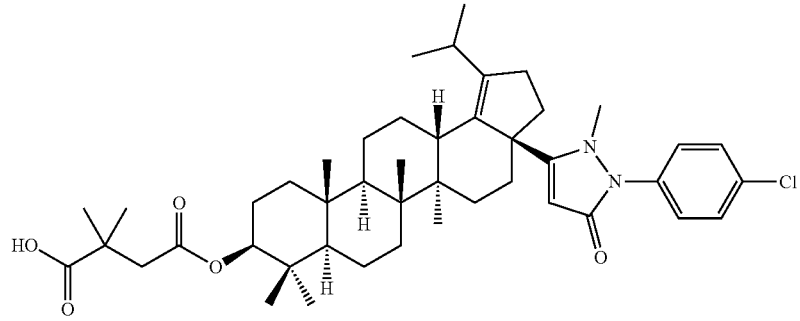

-continued
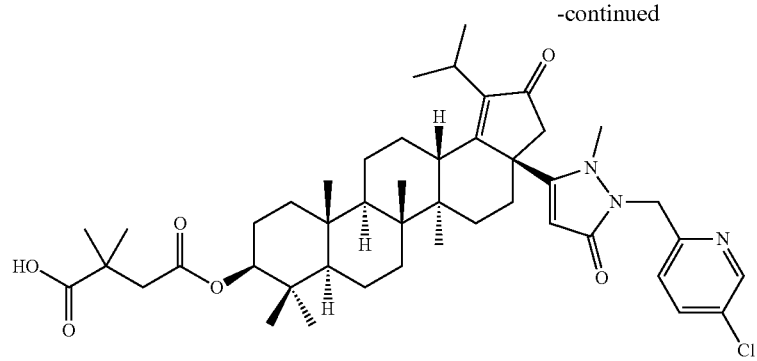
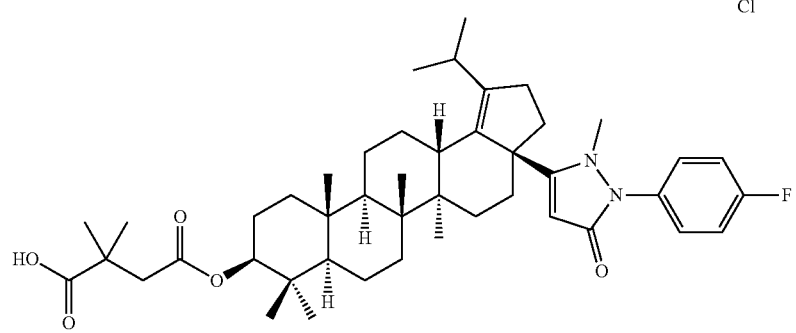
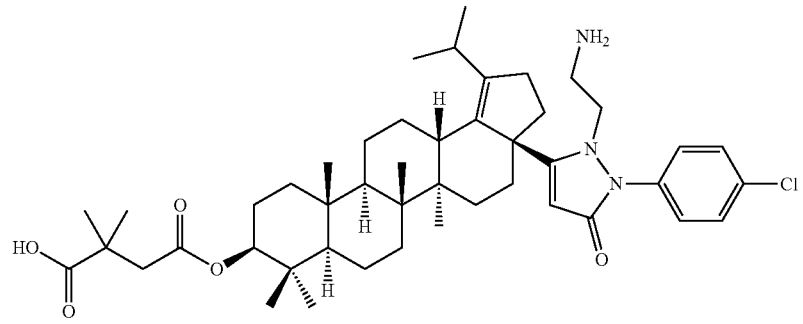
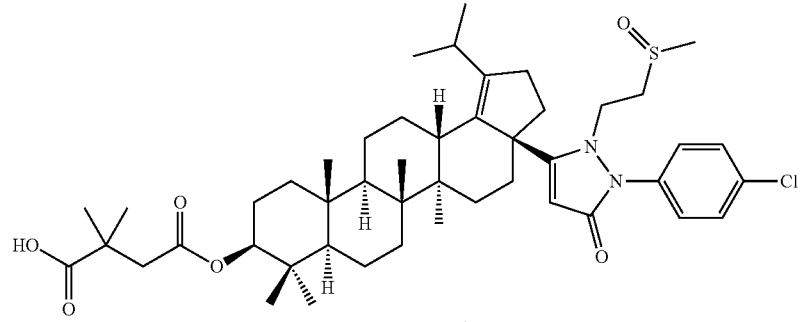
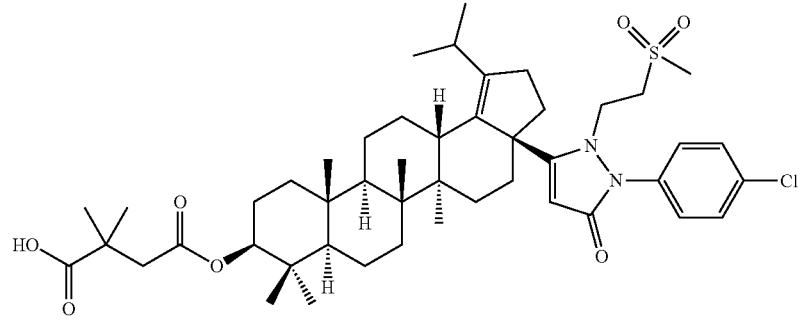
In the second respect, the present invention provides a pharmaceutical composition comprising any one of compounds of the formula (I)~(III) as defined above, or a pharmaceutically acceptable salt thereof in a therapeutically-effective dose, as well as a pharmaceutical acceptable carrier, adjuvant, excipient, or vehicle.

In the third respect, the present invention provides any one of compounds of the formula (I)~(III) as defined above, or a pharmaceutically acceptable salt thereof for the use in preparation of a medicament for preventing or treating HIV-1 infections in a subject in need of a therapeutically-effective amount.

In the fourth respect, the present invention provides a combination preparation, which comprising any one of compounds of formula (I)~(III) as defined above, or a pharmaceutically acceptable salt thereof, the combination preparation can be used in anti-HIV combination therapies along with at least one further therapeutic drug, such as nucleoside/nucleotide reverse transcriptase inhibitor, non-nucleoside reverse transcriptase inhibitors, protease inhibitors, fusion inhibitor, entry inhibitor, and/or integrase inhibitors.

The pharmaceutical use of the compound of formula (I)~(III) of the present invention refers to anti-virus, especially in preparation of a medicament for preventing or treating HIV and AIDS.

DETAILED DESCRIPTION OF THE INVENTION

Unless otherwise stated, the following terms used in the specification and claims have the meanings discussed below.

The term "alkyl" refers to a saturated aliphatic hydrocarbon group including $C_1$-$C_{20}$ straight chain and branched chain groups. Preferably an alkyl group is a moderate size alkyl having 1 to 10 carbon atoms, e.g., methyl, ethyl, propyl, 2-propyl, n-butyl, iso-butyl, tert-butyl, pentyl, n-hexyl, and the like. More preferably, it is a lower alkyl having 1 to 6 carbon atoms, e.g., methyl, ethyl, propyl, 2-propyl, n-butyl, iso-butyl, or tert-butyl, pentyl, n-hexyl, and the like.

The term "alkyl" could be optionally substituted, that means the alkyl group which may be independently substituted by one to four substituents selected from the group consisting of halo, cycloalkyl, hydroxyl, mercapto, lower alkloxy, lower haloalkloxy, amino, amido, ureido, sulfonamido, methylsulfonyl, methylsulfinyl, aminocarbonyl, cyano, alkenyl, alkynyl, carboxylic acid, and carboxylic ester, aryl (optionally substituted with one or more groups which each independently is halo, cyano, hydroxy, carboxylic acid, lower alkyl, lower haloalkoxy, or lower alkoxy groups), aryloxy(optionally substituted with one or more groups which each independently is halo, cyano, hydroxy, carboxylic acid, lower alkyl, lower haloalkoxy, or lower alkoxy groups), heteroaryl(optionally substituted with one or more groups which each independently is halo, cyano, hydroxy, carboxylic acid, lower alkyl, lower haloalkoxy, or lower alkoxy groups), heterocycloalkyl(optionally substituted with one or more groups which each independently is halo, cyano, hydroxy, carboxylic acid, lower alkyl, lower haloalkoxy, or lower alkoxy groups).

The term "alkenyl" refers to an alkyl group as defined above having at least 2 carbon atoms and at least one carbon-carbon double bond. Representative examples include, but are not limited to ethenyl, 1-propenyl, 2-propenyl, 1-, 2-, 3-butynyl, and the like. The optionally substituted alkenyl means the alkenyl which may be substituted with one or more groups which each independently is halo, cyano, lower alkyl or lower alkoxy groups.

The term "alkynyl" refers to an alkyl group as defined above having at least 2 carbon atoms and at least one carbon-carbon triple bond. Representative examples include, but are not limited to ethynyl, 1-propynyl, 2-propynyl, 1-, 2-, 3-butynyl, and the like. The optionally substituted alkenyl means the alkynyl which may be substituted with one or more groups which each independently is halo, cyano, lower alkyl or lower alkoxy groups.

The term "cycloalkyl" refers to a 3 to 8 membered all-carbon monocyclic ring. Examples of cycloalkyl groups include but not limit to cyclopropyl, cyclobutyl, cyclopentyl, cyclopentenyl, chcyclohexyl, cyclohexadienyl, cycloheptyl, cycloheptatrienyl, and the like. The cycloalkyl group may be substituted or unsubstituted. When substituted, the substituent group(s) is preferably one or more independently selected from the group consisting of lower alkyl, haloalkyl, halo, hydroxy, hydroxyalkyl, aminoalkyl, carboxylic acid, lower alkoxy, lower haloalkoxy, amino, aminocarbonyl, sulfonamido, ureido, amido, methylsulfonyl, methylsulfinyl, cyano, amido, thioacyl, O-carbamyl, N-carbamyl, O-thiocarbamyl, N-thiocarbamyl, mercapto, or nitro; aryl(optionally substituted with one or more groups which each independently is halo, cyano, hydroxy, carboxylic acid, lower alkyl, lower haloalkoxy, or lower alkoxy groups); aryloxy (optionally substituted with one or more groups which each independently is halo, cyano, hydroxy, carboxylic acid, lower alkyl, lower haloalkoxy, or lower alkoxy groups); 6-membered heteroaryl (having 1 to 3 nitrogen atoms on the ring, the carbons on the ring being optionally substituted with one or more groups which each independently is halo, cyano, hydroxy, carboxylic acid, lower alkyl, lower haloalkoxy, or lower alkoxy groups); 5-membered heteroaryl (having 1 to 3 heteroatoms selected from the group consisting of nitrogen, oxygen and sulfur, the carbon and nitrogen atoms of the group being optionally substituted with one or more groups which each independently is halo, cyano, hydroxy, carboxylic acid, lower alkyl, lower haloalkoxy, or lower alkoxy groups); 5- or 6-membered heterocyclic alkyl [having 1 to 3 heteroatoms selected from the group consisting of nitrogen, oxygen and sulfur, the carbon and nitrogen (if present) atoms of the group being optionally substituted with one or more groups which each independently is halo, cyano, hydroxy, carboxylic acid, lower alkyl, lower haloalkoxy, or lower alkoxy groups]; or arylthio (optionally substituted with one or more groups which each independently is halo, cyano, hydroxy, carboxylic acid, lower alkyl, lower haloalkoxy, or lower alkoxy groups).

The term "halo" refers to fluoro, chloro, bromo, or iodo, preferably fluoro or chloro.

The term "cyano" refers to a —C≡N group.

The term "hydroxy" refers to an —OH group.

The term "carboxylic acid" refers to —COOH group.

The term "thioalkyl" refers to a -(alkyl)-SH and a -(unsubstituted cycloalkyl)-SH group. Representative examples include, but are not limited to, methylthio, ethylthio, propylthio, butylthio, cyclopropylthio, cyclobutylthio, cyclopentylthio, cyclohexylthio, and the like.

The term "heterocycloalkyl" refers to a mono-heterocycloalkyl with 4 to 7 ring atoms, wherein one, or two ring heteroatoms are selected from the group consisting of N, O, and S(O)n (n is integer from 0 to 2), the remaining ring atoms are C, in addition, the ring may also have one or more double bonds, but not have a completely conjugated pi-electron system. Examples of heterocycloalkyl include but not limit to azetidyl, pyrrolidyl, piperidyl, piperazinyl, N-methyl-piperazinyl, 4-methyl-piperazinyl, morpholinyl, thiomorpholinyl, homopiperazinyl, and the like. The heterocycloalkyl may be substituted or unsubstituted. When substituted, the substituent group is preferably one or more, more preferably one, two, or three, further more preferably one or two groups, each independently selected from the group consisting of lower alkyl, cycloalkyl, lower hydroxyalkyl, haloalkyl, halo, hydroxy, aminoalkyl, carboxylic acid, lower alkoxy, lower haloalkoxy, cyano, amino, sulfonamido, methylsulfonyl, methylsulfinyl, ureido, and amido.

The term "aryl" refers to an optionally substituted phenyl. When substituted, the substituted group could be one or more groups and each independently selected from the group consisting of -alkylCOOH, carboxylic acid, halo, alkyl, haloalkyl, hydroxy, hydroxyalkyl, alkylthio, mercapto, nitro, amino, aminoalkyl, cyano, alkoxy and haloalkoxy, alkyl is defined as above. Representative examples of substituted aryl include, but are not limited to, $(R_5)$n-phenyl-, $(R_5)$n-phenyl-$CH_2$— etc., wherein $R_5$ is independently $CH_3$, $CH_3O$, F, Cl, CN, or $CF_3$; n is independently 0, 1, or 2.

The term "heteroaryl" refers to an optionally substituted heteroaryl having 1 to 4 heteroatoms selected from the group consisting of N, O, and S as ring atoms, the remaining ring atoms being C. Said heteroaryl is 5- or 6-membered ring. When substituted, the substituted group could be one or more groups and each independently selected from the group consisting of —$(CH_2)_2S(O)CH_3$, —$(CH_2)_2S(O)_2CH_3$, -alkyl-C(O)OH, —COOH, acylamino, —$CH_2$-amido, halo, alkyl, haloalkyl, hydroxy, hydroxyalkyl, alkylthio, mercapto, nitro, amino, aminoalkyl, cyano, alkoxy and haloalkoxy. The examples of heteroaryl groups include but not limit to furyl, thienyl, pyrazolyl, pyridyl, pyrrolyl, N-alkyl pyrrolyl, 1,2,4-oxadiazolyl, 1,3,4-oxadiazolyl, 1,3,4-thiadiazolyl, oxazolyl, isoxazolyl, thiazolyl, isothiazole, pyrimidinyl, pyrazinyl, imidazolyl, triazolyl, tetrazolyl, oxatriazolyl, pyridazinyl, triazinyl,

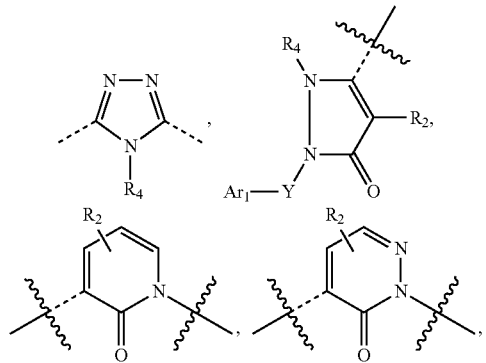

$(R_5)$n-pyridyl-, $(R_5)$n-pyridyl-$CH_2$—, $(R_5)$n-pyrimidyl-, $(R_5)$n-pyrimidyl-$CH_2$— and the like. Wherein Y, $Ar_1$, $R_2$, $R_4$, $R_5$, n are as defined above, (preferably $R_4$ is independently selected from the group consisting of methyl, ethyl, or

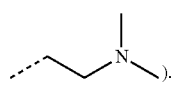

The term "cycloalkylalkyl" refers to a radical of the formula -RaRb, where Ra is an alkyl radical as defined above and Rb is a cycloalkyl radical as defined above. The alkyl radical and the cycloalkyl radical may be optionally substituted as defined above.

The term "Arylalkyl" refers to a radical of the formula -RaRc where Ra is an alkyl radical as defined above and Rc is aryl radicals as defined above, e.g., benzyl, diphenylmethyl and the like. The aryl radical(s) may be optionally substituted as described above.

The term "Heterocycloalkylalkyl" refers to a radical of the formula -RaRd where Ra is an alkyl radical as defined above and Rd is a heterocycloalkyl radical as defined above, and if the heterocycloalkyl is a nitrogen-containing heterocycloalkyl, the heterocycloalkyl may be attached to the alkyl radical at the nitrogen atom or at carbon atom. The alkyl part of the heterocycloalkylalkyl radical may be optionally substituted as defined above for an alkyl group. The heterocycloalkyl part of the heterocycloalkylalkyl radical may be optionally substituted as defined above for a heterocycloalkyl group.

The term "heteroarylalkyl" refers to a radical of the formula -RaRe where Ra is an alkyl radical as defined above and Re is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

The term "methylene" refers to $CH_2$.

The term "carbonyl" refers to C(=O).

The term "thiocarbonyl" refers to C(=S).

The term "amino" refers to a —$NH_2$, —$NHCH_3$, —$N(CH_3)_2$, —NH-cyclopropyl, —NH-Ph, —NH-pyridyl, pyrrolidinyl, piperazinyl, N-methyl-morpholino, 4-methyl-piperazinyl, morpholino, piperidino, and the like.

The term "amido" refers to a —C(=O)$NR_fR_f'$, which $R_f$ and $R_f'$ refer to amino substituents, $R_f$ and $R_f'$ may be the same or may not be same, which independently are hydrogen or alkyl, aryl, or heteroaryl (alkyl, aryl, and heteroaryl are as defined above) Representative amido groups include, —C(=O)$NH_2$, —C(=O)$NHCH_3$, —C(=O)$N(CH_3)_2$, —C(=O)$NCH_3CH_2CH_3$, as well as the groups in which $R_f$ and $R_f'$ together with the nitrogen atom to which they are attached, form a heterocyclic ring, like morpholino, piperazinyl, piperidino, and the like.

The term "aminocarbonyl" including but are not limited to: —NHC(=O)$CH_3$, —$NCH_3$C(=O)$CH_3$, —NHC(=O)$CH_2CH_3$, —$NCH_3$C(=O)$CH_2CH_3$, —NHC(=O)-cyclopropyl, —$NCH_3$C(=O)-cyclopropyl, —NHC(=O)Ph, —$NCH_3$C(=O)Ph, and the like.

The term "sulfonamido" refers to —$NR_gS(=O)_2R_g'$, wherein $R_g$ is independently hydrogen or alkyl, and $R_g'$ is independently alkyl, aryl, or heteroaryl, alkyl, aryl, and heteroaryl are as defined above.

The term "ureido" refers to —$NR_hC(O)NR_h'R_h''$, wherein $R_h$, $R_h'$, and $R_h''$ are independently hydrogen or alkyl, and the alkyl as defined above, or $R_h'$ and $R_h''$ together with the nitrogen atom to which they are attached, form a heterocyclic ring, like morpholino, piperazinyl, piperidino, and the like.

The term "aminoalkyl" refers to -alkyl-amino group, wherein alkyl and amino are as defined above, and may be optionally substituted. The representative aminoalkyl group include but are not limited to

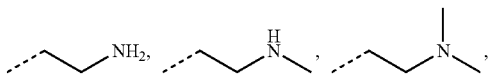

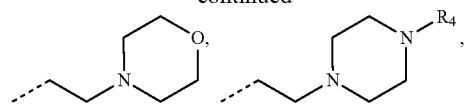

and the like, and $R_4$ as defined above.

The term "hydroxyalkyl" refers to -alkyl-hydroxy group, wherein the alkyl could be optional substituted or unsubstituted as defined above. The representative hydroxyalkyl group include but are not limited to —CH$_2$CH$_2$OH, —CH$_2$C(CH$_3$)$_2$OH.

The term "haloalkyl" refers to halo-alkyl group, wherein the halo and alkyl as defined above. The representative haloalkyl group include but are not limited to —CF$_3$, —CH$_2$F, or —CHF$_2$, and the like.

The term "alkoxy (lower alkoxy)" refers to both an —O—[alkyl (lower alky)] and an —O-(unsubstituted cycloalkyl) group, alkyl, lower alkyl, and cycloalkyl groups are as defined above. Representative examples include, but are not limited to, methoxy, ethoxy, propoxy, butoxy, cyclopropyloxy, cyclobutyloxy, cyclopentyloxy, cyclohexyloxy, and the like.

The term "arylkoxy" refers to —O-(aryl). Aryl as defined above.

The term "haloalkoxy (lower haloalkoxy)" refers to an —O—[haloalkyl (lower haloalky)], halo, alkyl, and lower alkyl groups are as defined above. Representative examples include, but are not limited to, fluoromethoxy, difluoromethoxy, trifluoromethoxy, trichloromethoxy, or tribromomethoxy, and the like. Halo and alkyl (lower alkyl) in haloalkyl (lower haloalkyl) are as defined above.

Two $R_3$ groups together with the nitrogen atom to which they are attached, may form a 3- to 7-membered heterocycloalkyl ring. The examples include but not limit to pyrrolidyl, piperidyl, piperazinyl, N-methyl-piperazinyl, 4-methyl-piperazinyl, morpholinyl, thiomorpholinyl, homopiperazinyl, and the like;

The representative examples of "Ar$_2$" include but are not limited to the structures as following:

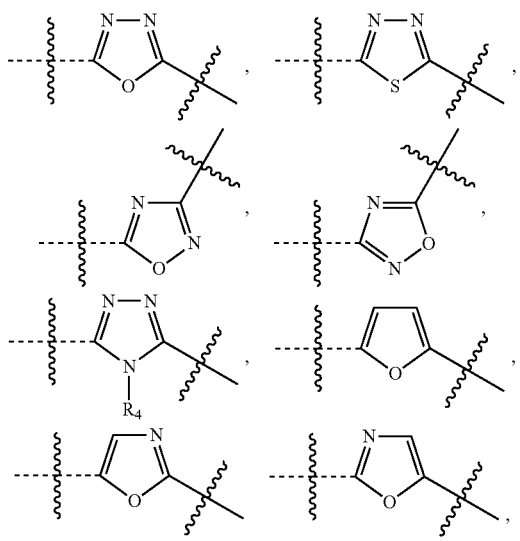

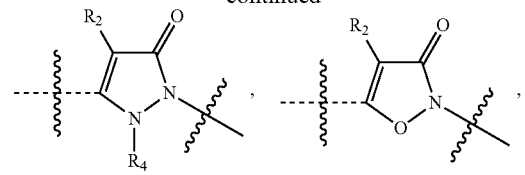

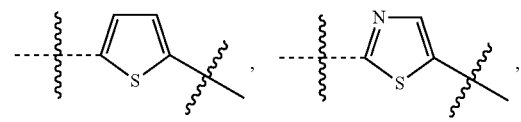

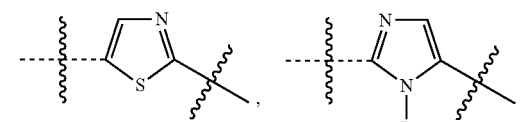

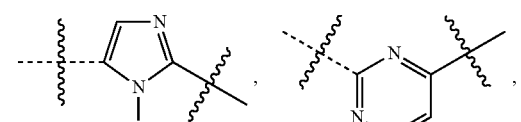

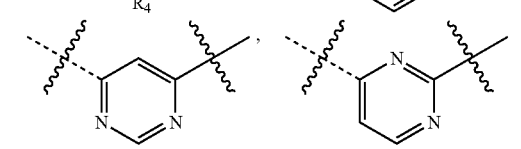

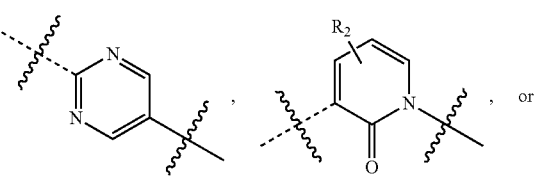

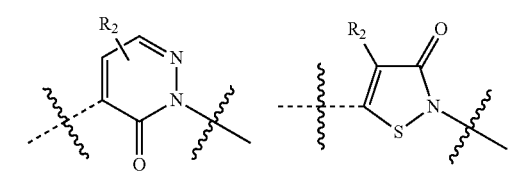

Wherein, $R_2$ is H, Cl or methyl; $R_4$ is H, methyl, ethyl,

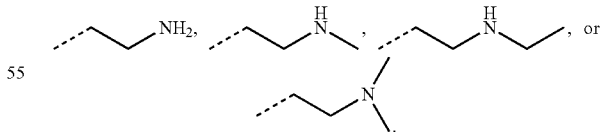

The term "r" means an integer from 1 to 8, preferable 1~3, more preferable 1 or 2.

The term "n" means 0, 1 or 2.

The term "Lupane triterpenoid derivatives" means the derivatives of Betulin.

The term "optional" or "optionally" means that the subsequently described event or circumstance may or may not occur, and that the description includes instances wherein the event or circumstance may or may not occur. For example, "aryl group optionally substituted with an alkyl group" means that the alkyl may or may not be present, that is, the description includes situations wherein the aryl group is substituted with an alkyl group and situations wherein the aryl group is not substituted with an alkyl group.

The term "hydrates" refers to a compound provided herein or salts thereof, that further includes a stoichiometric or non-stoichiometric amount of water bound by non-covalent intermolecular forces.

The term "solvates" refers to a corresponding solvate of the present invention compound or salts thereof, formed from the combination of solvent molecules with the present invention compound or a salt thereof (or ions of the solute). If the solvent is water, the solvate may be simply referred to as a hydrate, for example, a mono-hydrate, a di-hydrate, a tri-hydrate, etc.

The term "isomers" refer to the stereoisomers like enantiomers, diastereomers, racemates, and the mixtures thereof. The stereo chiral C of the present invention compounds of formula (I)~(III) is corresponding to the Betulin's, specific as follows:

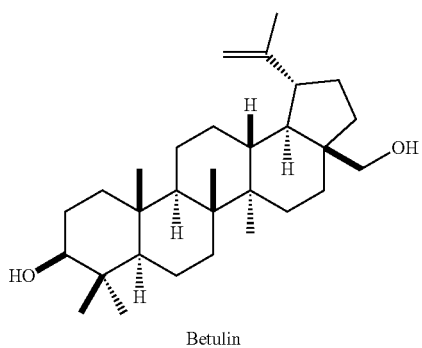
Betulin
(I)

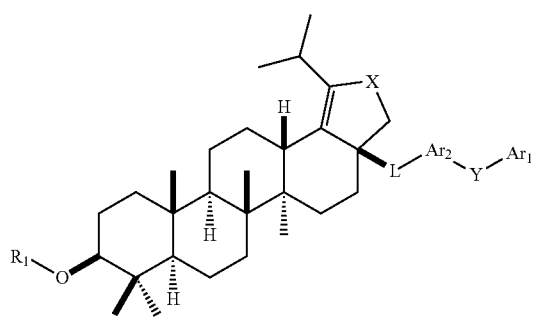
(II)

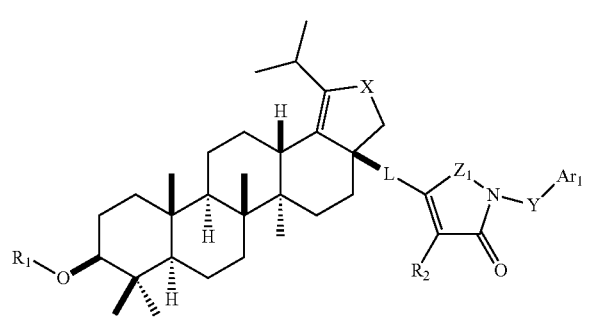

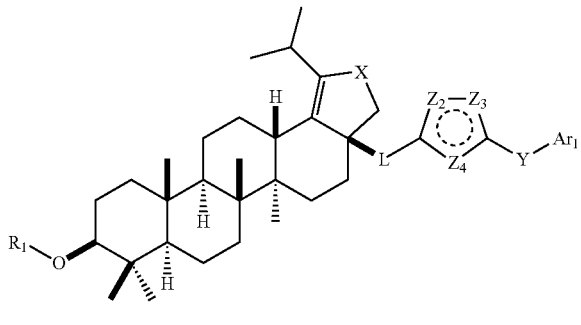
(III)

The term "prodrugs" refers to a compound which, when metabolized in vivo, converts back to the original active compound. Typically, the prodrug is inactive, or less active than the active compound, but may provide advantageous handling, administration, or metabolic properties.

The term "pharmaceutically acceptable salts" was discussed in Berge, et al., "pharmaceutically acceptable salts", J. Pharm. Sci., 66, 1-19 (1977) and would be apparent to the pharmaceutical chemist and, i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug.

The term "pharmaceutical composition" refers to a mixture of one or more of the compounds of formula (I) as described in present invention herein, or hydrates, or solvates, or isomers, or physiologically/pharmaceutically acceptable salts or prodrugs thereof, with other chemical components, such as physiologically/pharmaceutically acceptable carriers and recipients. The purpose of a pharmaceutical composition is to facilitate administration of a compound to warm blood animals and human.

SYNTHESIS OF THE COMPOUND OF THE INVENTION

The compounds of the present invention were synthesized from the commercially available natural occurring compound Betulin 1 as a key intermediate. Wherein the synthesis of key intermediates 6, 12, and 15 from Betulin, see the following steps:

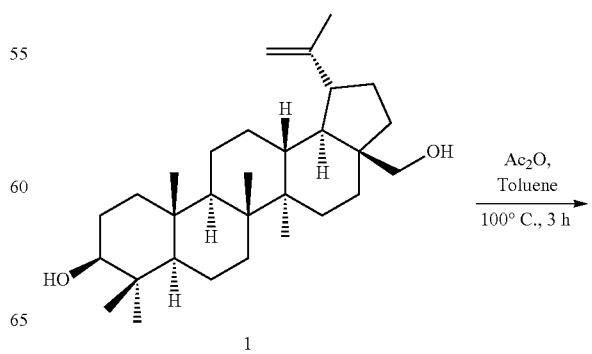
1

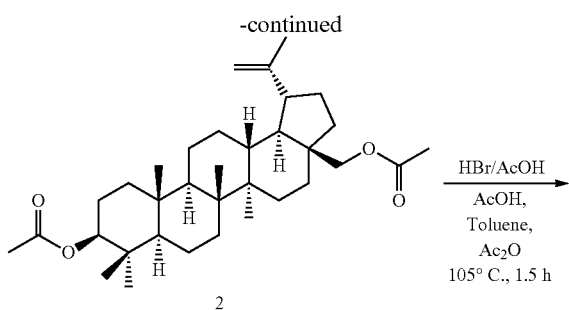

2

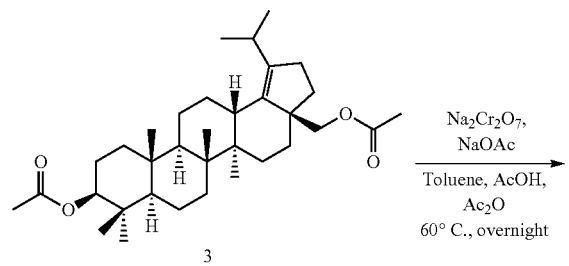

3

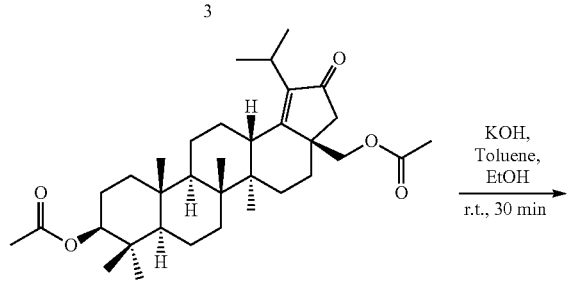

4

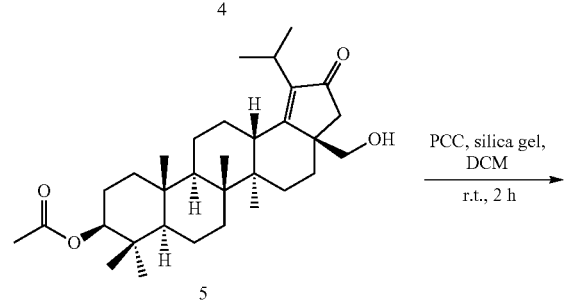

5

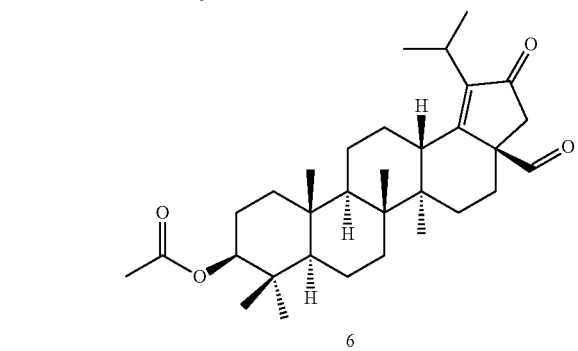

6

Synthesis of Compound 2

To a stirring solution of betulin 1 (20 g, 45.18 mmol) in toluene (30 ml) was added acetic anhydride (42.4 ml, 451.5 mmol) in one portion. The reaction mixture was stirred at 100 for 3 h, then the resulting mixture contained compound 2 was used directly in next step without the further purification.

Synthesis of Compound 3

The resulting mixture contained compound 2 (23.8 g, 45.18 mmol) from above was heated to 105° C., then sequentially added a solution of HBr in acetic acid (33%) (40 ml), toluene (40 ml), acetic anhydride (40 ml) and acetic acid (40 ml). The reaction mixture was stirred at this temperature for 1.5 h. After cooling down to room temperature, sodium acetate (8 g) was added and the mixture was evaporated to dryness. The brown residue was triturated with water (80 ml), filtered off and washed sequentially with water (15 ml×2), ethanol (95%) (15 ml×2) and petroleum ether (15 ml×2) to afford compound 3 (17.8 g, 75%), as an off-white solid, used in next step without the further purification.

m/z: [M+Na]$^+$ 549.3

Synthesis of Compound 4

A mixture of compound 3 (17 g, 32.3 mmol), sodium acetate (18.5 g, 225.9 mmol) and sodium dichromate dehydrate (9.3 g, 35.5 mmol) in a mixed solvent of toluene (50 ml), acetic anhydride (24.2 ml, 258.4 mmol) and acetic acid (50 ml) was stirred overnight at 60° C. After cooling down to room temperature, water (150 ml) and ethyl acetate (100 ml) were added. The organic layer was washed sequentially with water (100 ml×2), saturated solution of sodium bicarbonate (100 ml×3) and brine (100 ml×3), dried over sodium sulfate and concentrated to give the crude yellow solid which was triturated with methanol, and filtered to afford compound 4 (14.65 g, 84%), as a white solid, used in next step without the further purification.

m/z: [M+Na]$^+$ 563.4

Synthesis of Compound 5

To a solution of compound 4 (14 g, 25.89 mmol) in a mixed solvent of ethanol (80 ml) and toluene (80 ml) was added potassium hydroxide (1.6 g, 28.48 mmol). The resulted mixture was stirred at room temperature for 30 min, then neutralized with aqueous HCl (2N) and evaporated to dryness, The solid was taken up with water and minimum amount of acetone, and then filtered, The collected solid was dried to afford the compound 5 (10.6 g, 82%), as an off white solid, used in next step without the further purification.

m/z: [M+H]$^+$ 499.5

Synthesis of Compound 6

To a solution of compound 5 (10 g, 20.0 mmol) in dichloromethane (200 ml) was added pyridinium chlorochromate (8.64 g, 40.1 mmol) and silica gel (10 g). The resulting mixture was stirred at room temperature for 2 h, then water (100 ml) was added, the organic layer was washed with saturated solution of sodium bicarbonate (120 ml) and brine, dried over sodium sulfate and concentrated, the residue was purified by chromatography on silica gel (ethyl acetate/petroleum ether from 1:8 to 1:4) to afford compound 6 (7.2 g, 72%), as a white solid.

m/z: [M+H]$^+$ 497.4

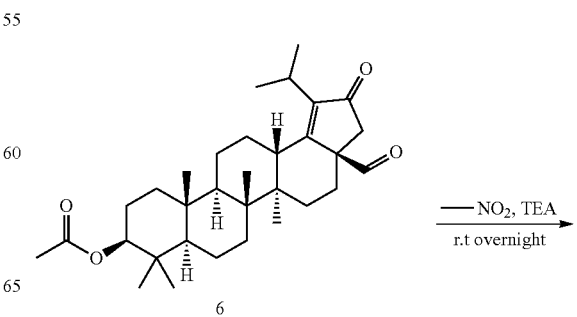

6

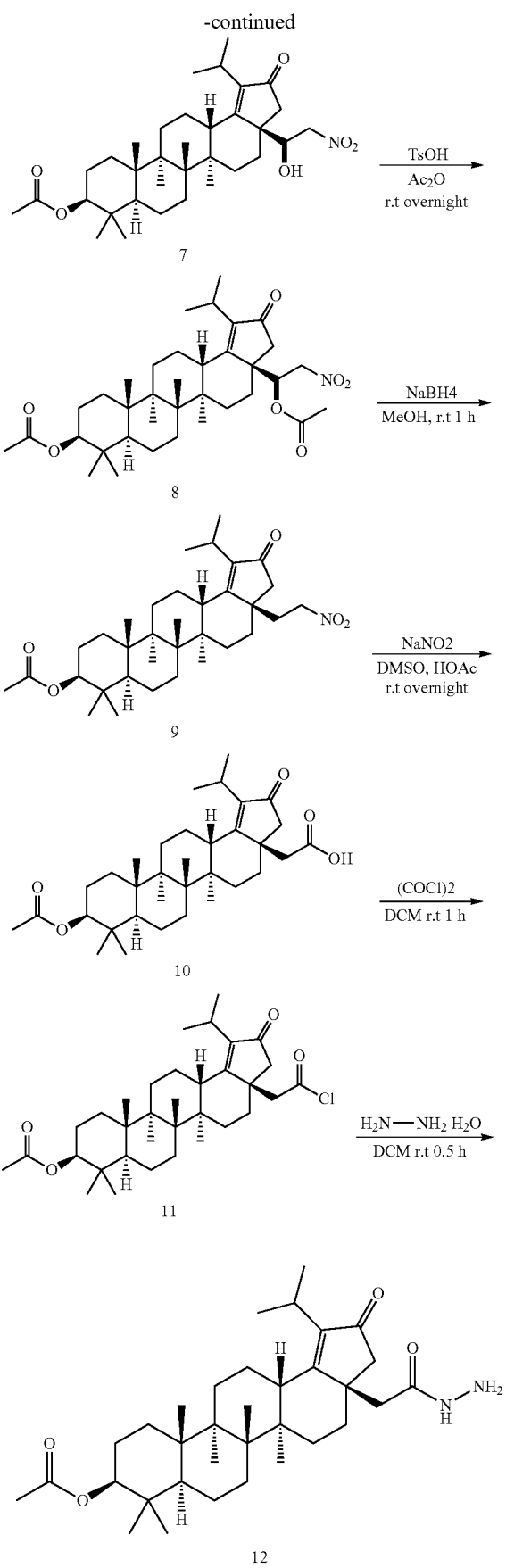

Synthesis of Compound 7

To a solution of compound 6 (20 g, 40.26 mmol) in nitromethane (60 ml) was added triethylamine (20 ml, 144 mmol), the mixture was stirred overnight at room temperature and concentrated to dryness. The residue was triturated with petroleum ether, and filtered to afford compound 7 (19.6 g, 87%), as a white solid, used in next step without the further purification.

m/z: [M+H]$^+$ 558.4

Synthesis of Compound 8

To a stirring suspension of compound 7 (19 g, 34.1 mmol) in acetic anhydride (100 ml) was added p-toluenesulfonic acid (1.47 g, 8.5 mmol). The resulting mixture was stirred overnight at room temperature, then diluted with ethyl acetate (200 ml), the organic layer was washed successively with saturated solution of sodium carbonate (100 ml×3) and brine, dried over sodium sulfate and concentrated to afford compound 8 (20.5 g, 100%), as a light yellow solid, used in next step without the further purification.

m/z: [M+H]$^+$ 600.4

Synthesis of Compound 9

To an ice-cooling solution of compound 8 (20 g, 33.3 mmol) in methanol (200 ml) was added sodium borohydride (5.05 g, 133.4 mmol) in small portions. After the reaction mixture was stirred at room temperature for 1 h, the reaction was quenched by the addition of water (100 ml). The reaction mixture was extracted with ethyl acetate (200 ml×3), and the combined organic phase was washed with brine, dried over sodium sulfate, filtered and the filtrate was concentrated. The residue was purified by chromatography on silica gel (ethyl acetate/petroleum ether from 1:8 to 1:5) to afford compound 9 (12.8 g, 71%) as a white solid.

m/z: [M+H]$^+$ 542.5

Synthesis of Compound 10

To a solution of compound 9 (12 g, 22.1 mmol) in dimethyl sulfoxide (60 ml) was added sodium nitrite (7.6 g, 0.11 mol) and acetic acid (6.77 ml, 0.36 mol). The reaction mixture was stirred overnight at room temperature, adjust the reaction mixture to pH=3.0 with aqueous HCl (2N), then diluted with water (150 ml). The mixture was extracted with ethyl acetate (200 ml×3). The combined organic phase was washed with water (100 ml×2) and brine, dried over sodium sulfate, filtered and concentrated. The residue was triturated with petroleum ether, and filtered to afford compound 10 (7.6 g, 65%) as a light yellow solid, used in next step without the further purification.

m/z: [M+H]$^+$ 527.3

Synthesis of Compound 11

To a solution of compound 10 (100 mg, 0.19 mmol) in dichloromethane (5 ml) was added oxalyl chloride (72 mg, 0.57 mmol) and one drop of N,N-dimethylformamide. The reaction mixture was stirred at room temperature for 1 h and concentrated to afford compound 11 (103 mg, 100%) as a yellow solid, used in next step without the further purification.

Synthesis of Compound 12

To the solution of compound 11 (103 mg, 0.19 mmol) in dichloromethane (1 ml) was added dropwise a solution of hydrazine hydrate (9 mg, 0.38 mmol) in dichloromethane (5 ml), the mixture was stirred at 0° C. for 30 min and concentrated to dryness, the residue was triturated with petroleum ether, filtered to afford compound 12 (60 mg, 59%) as a yellow solid, used in next step without the further purification.

m/z: [M+H]$^+$ 541.4

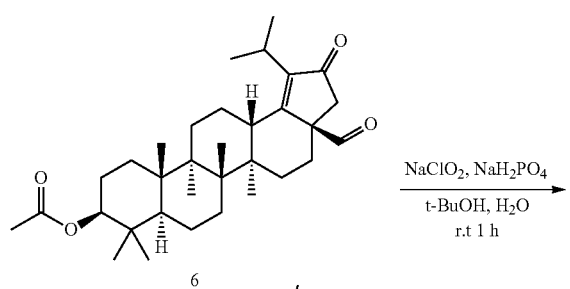

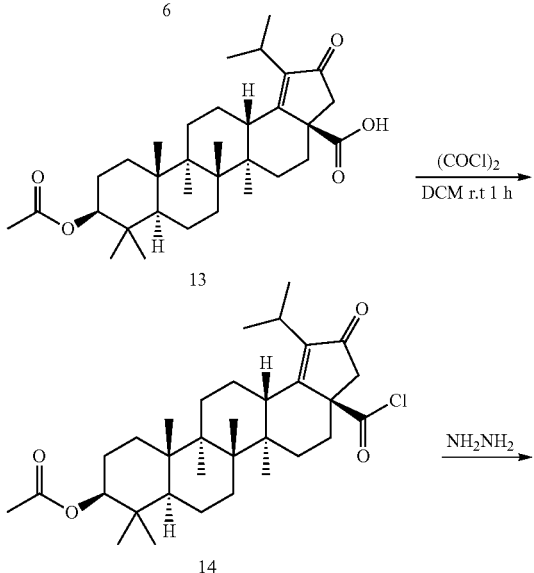

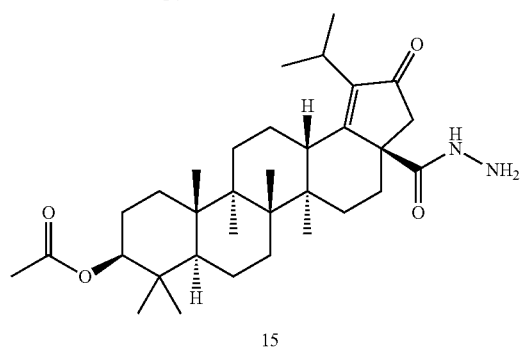

Synthesis of Compound 13

To a solution of compound 6 (1.0 g, 2.0 mmol) and 2-methyl-2-butane (0.5 ml, 6 mmol) in t-butanol (10 ml) was added a solution of sodium dihydrogen phosphate (1.2 g, 10 mmol) and sodium chlorite (546 mg, 6.0 mmol) in water (3 ml). The resulting mixture was stirred at room temperature for 1 h, then diluted with water (20 ml). The mixture was extracted with ethyl acetate (20 ml×3). The combined organic phase was washed with brine, dried over sodium sulfate, filtered and concentrated. The residue was triturated with petroleum ether, and filtered to afford compound 13 (0.68 g, 66%) as a yellow solid, used in next step without the further purification.

m/z: [M+H]$^+$ 513.4

Synthesis of Compound 14

To a solution of compound 13 (300 mg, 0.59 mmol) in dichloromethane (10 ml) was added oxalyl chloride (220 mg, 1.76 mmol) and a drop of N,N-dimethylformamide. The reaction mixture was stirred at room temperature for 30 min and concentrated to afford compound 14 (319 mg, 100%) as a light yellow solid, ued in next step without the further purification.

Synthesis of Compound 15

To this solution of compound 14 (319 mg, 0.59 mmol) in dichloromethane (2 ml) was added dropwise a solution of hydrazine hydrate (68 mg, 1.16 mmol) in dichlormethane (10 ml), the mixture was stirred at 0 for 1 h and concentrated to dryness, the residue was triturated with petroleum ether, and filtered to afford compound 15 (300 mg, 98%) as a yellow solid, used in next step without the further purification.

m/z: [M+H]$^+$ 527.3

Method 1: Compound 22-1~22-18 were prepared according to scheme 1.

Scheme 1

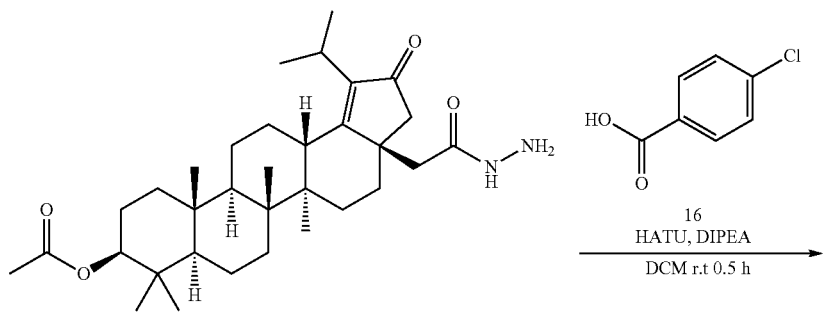

-continued
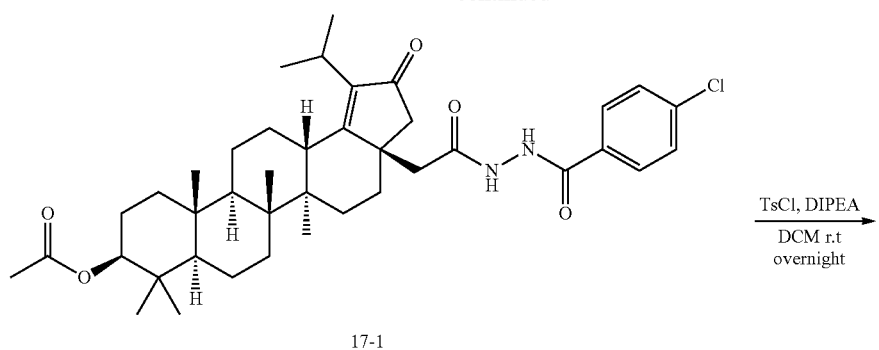
17-1
TsCl, DIPEA
DCM r.t
overnight
→
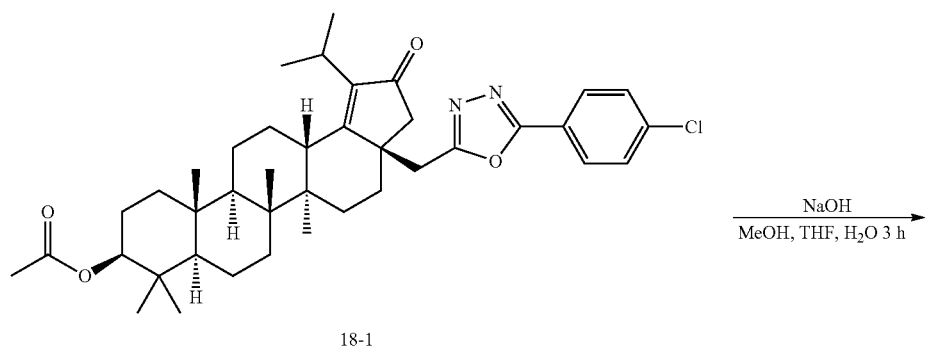
18-1
NaOH
MeOH, THF, H₂O 3 h
→
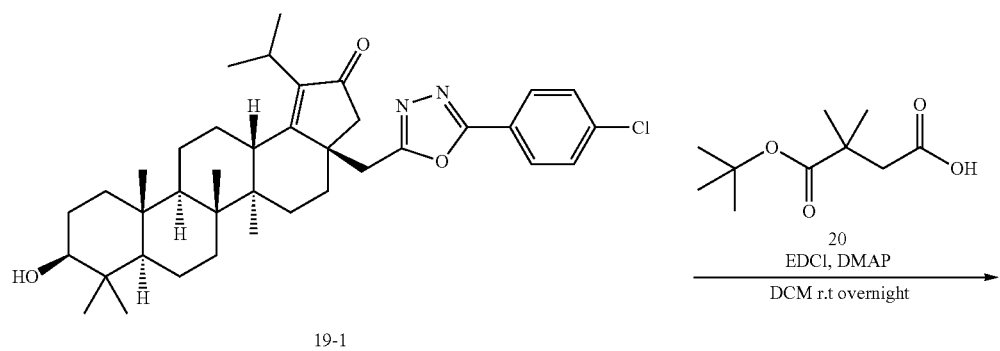
19-1
20
EDCl, DMAP
DCM r.t overnight
→
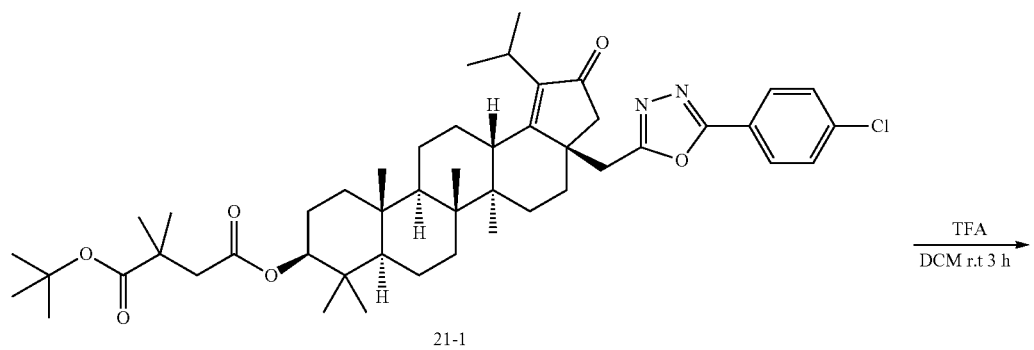
21-1
TFA
DCM r.t 3 h
→

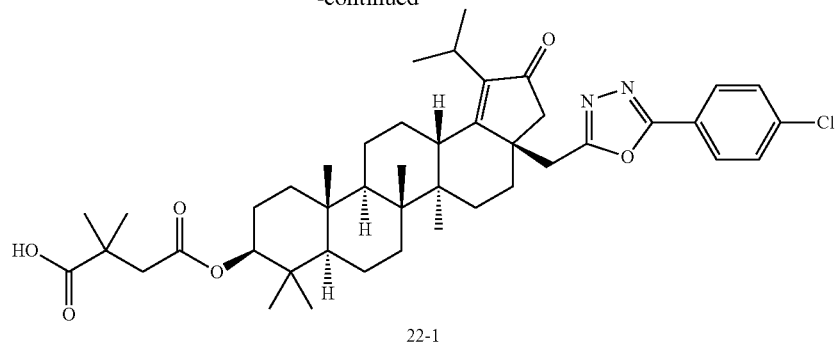
22-1
Method 2: Compound 27-1~27-14 were prepared according to scheme 2.
Scheme 2
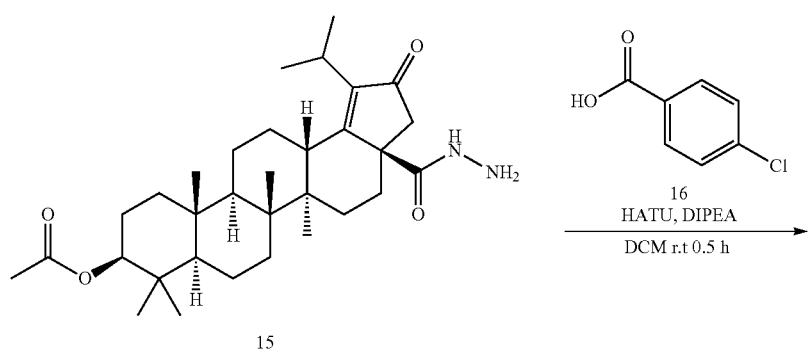
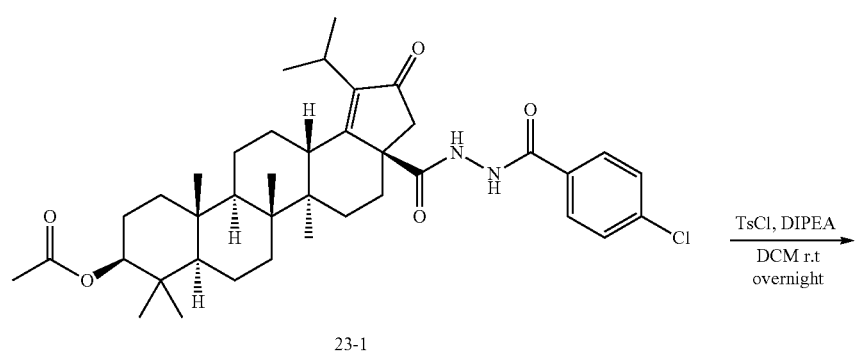
23-1
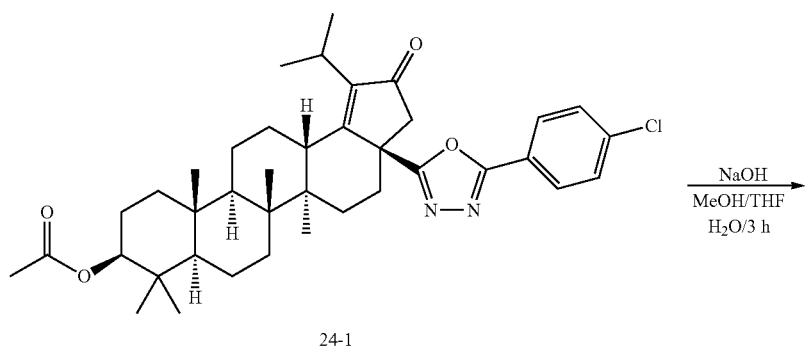
24-1

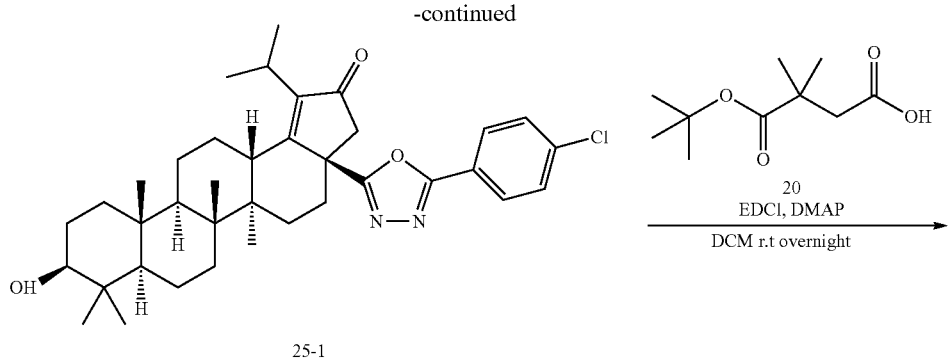
25-1
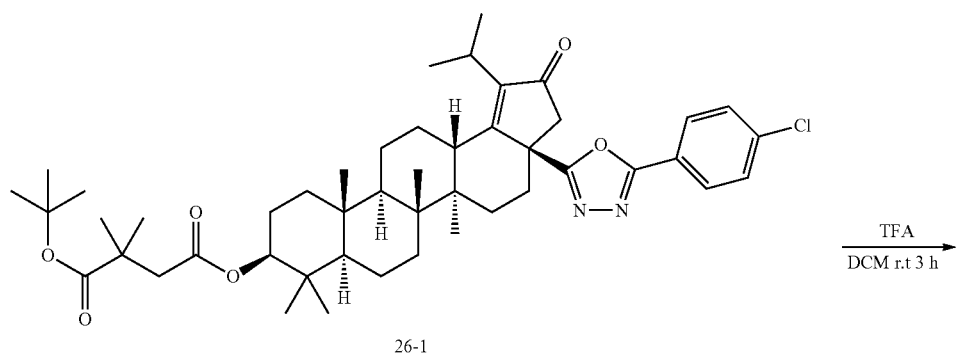
26-1
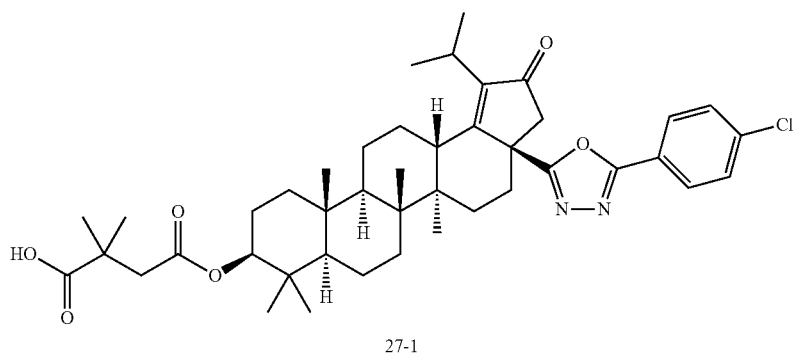
27-1
Method 3: Compound 33 was prepared according to scheme 3.
Scheme 3
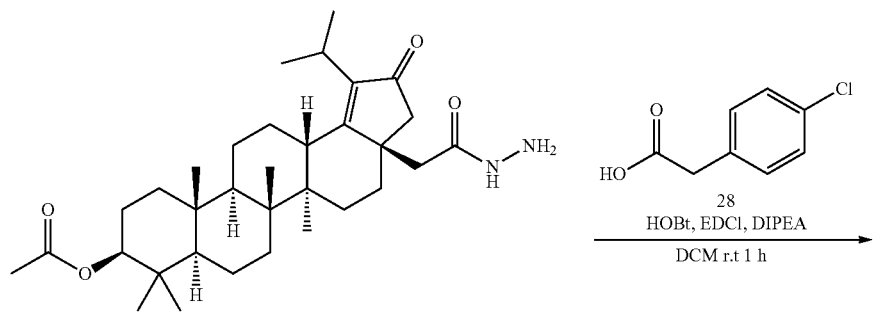
12

-continued
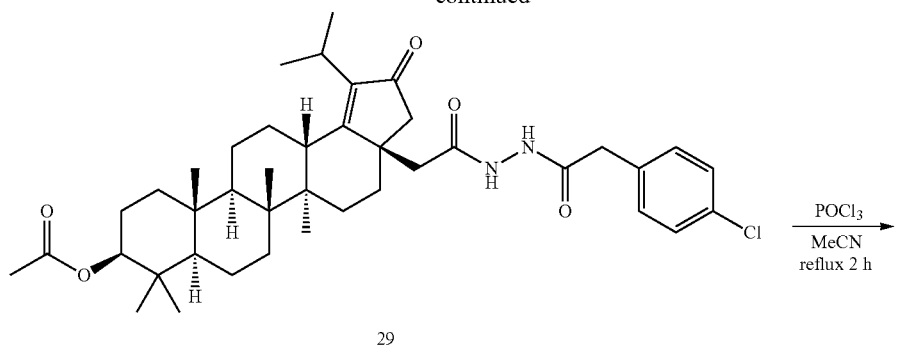
29
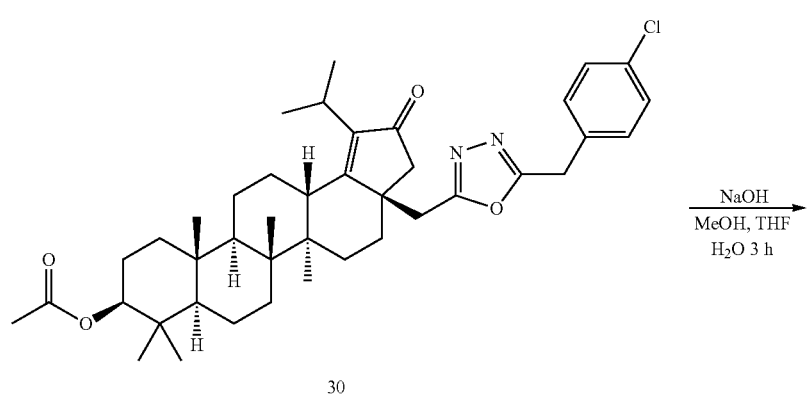
30
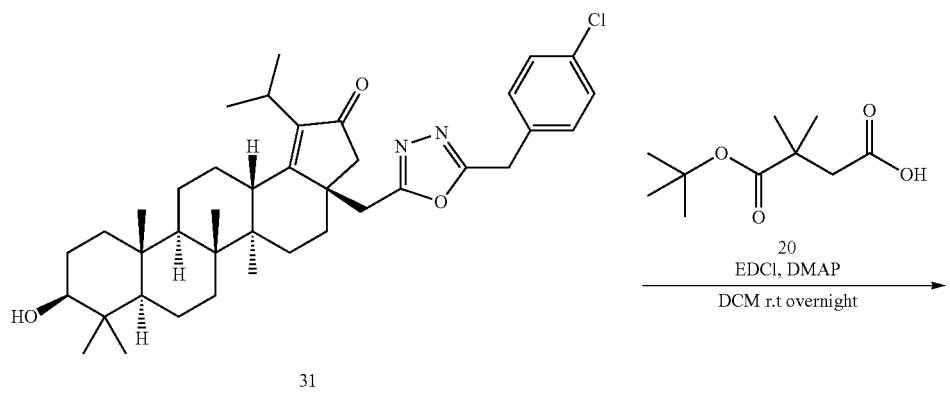
31
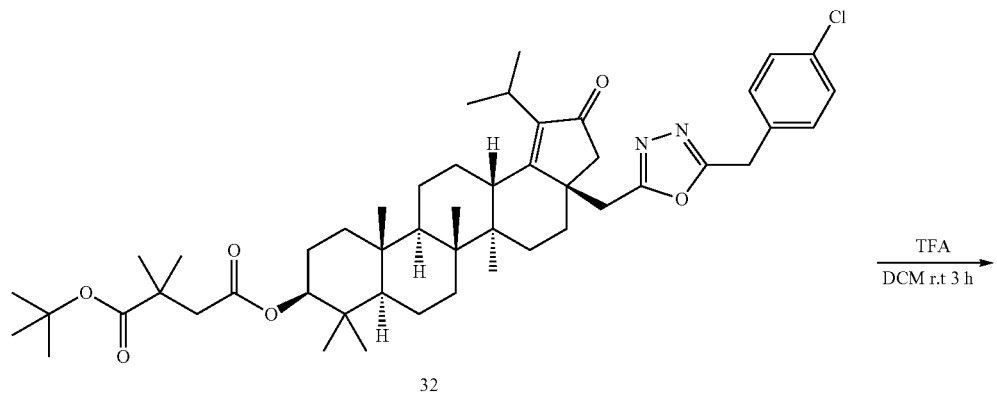
32

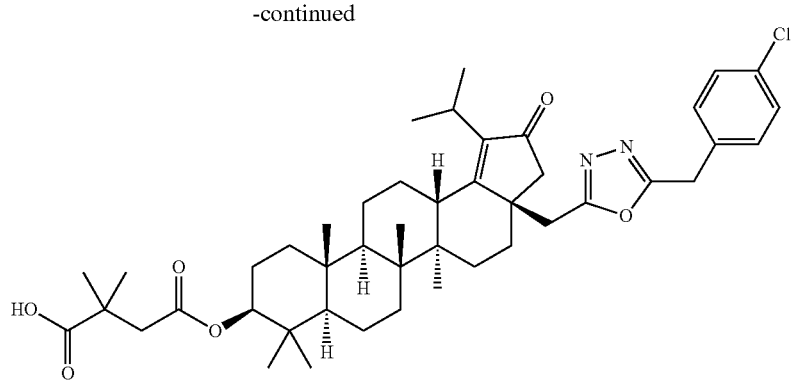
Method 4: Compound 38 was prepared according to scheme 4.
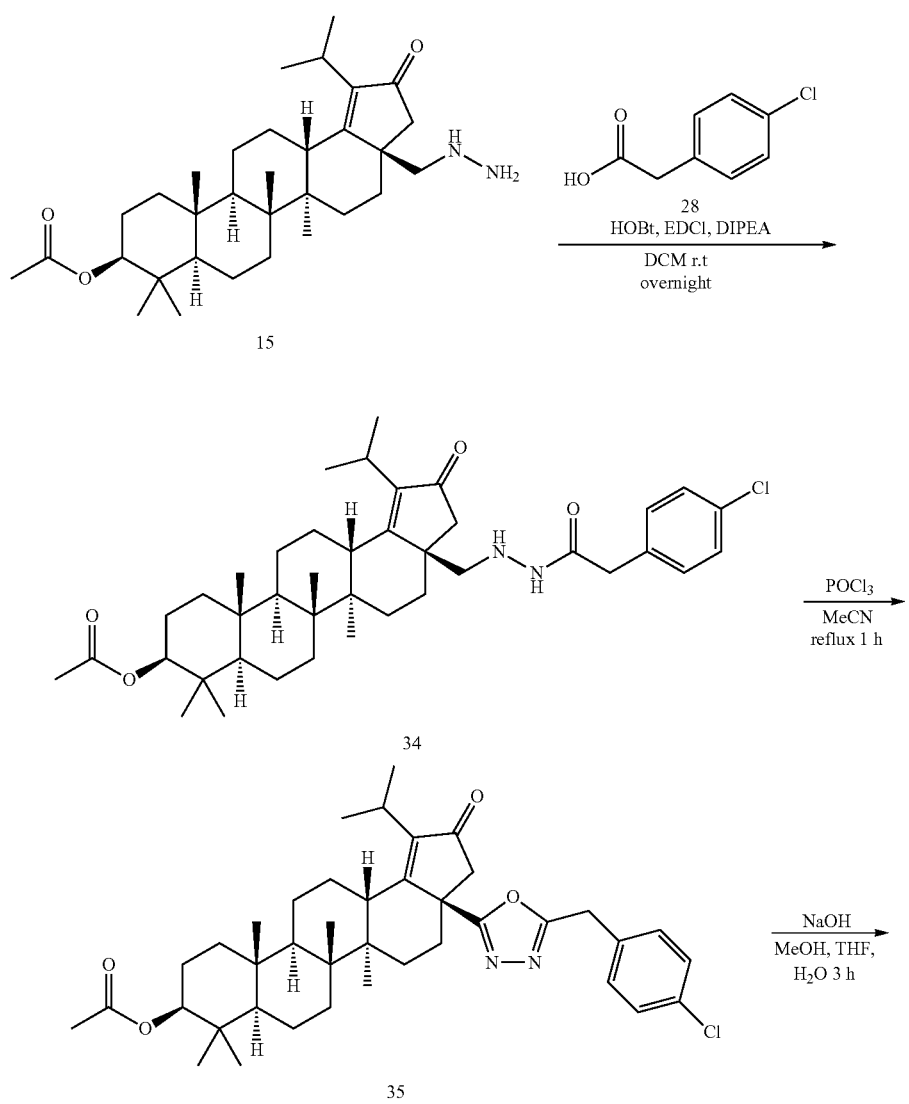

-continued
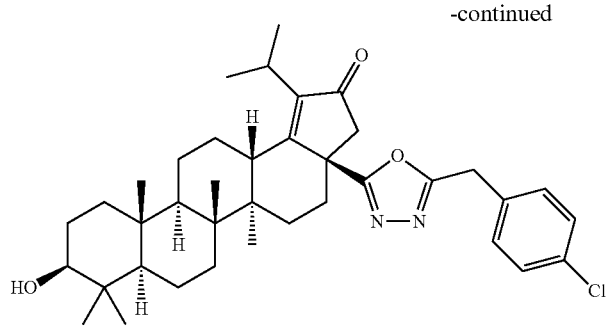 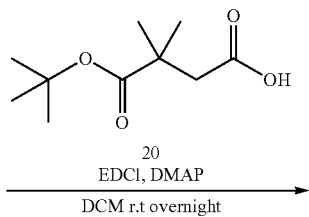
36
20
EDCl, DMAP
DCM r.t overnight
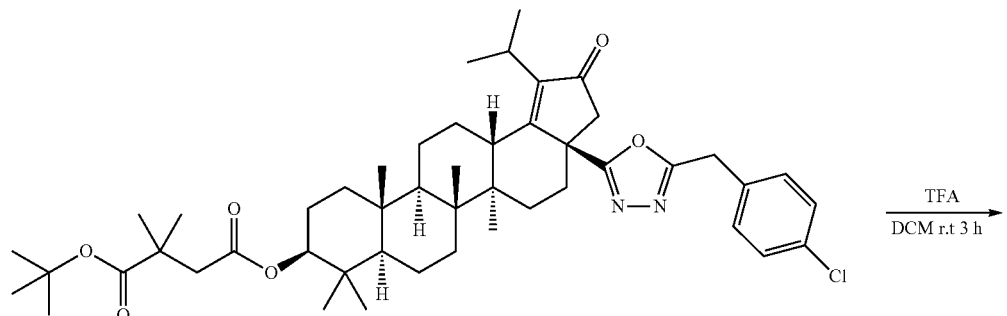
37
TFA
DCM r.t 3 h
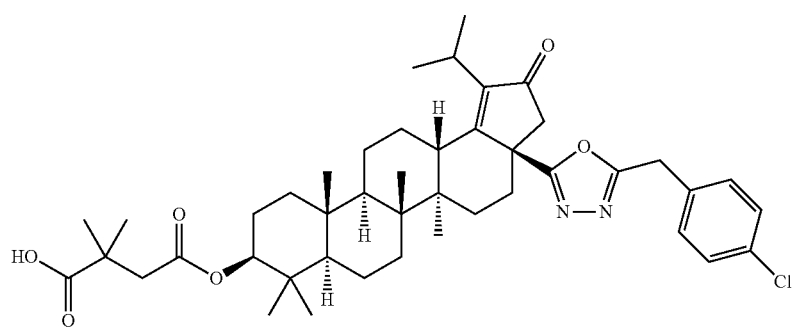
38
Method 5: Compound 54-1~54-2 were prepared according to scheme 5.
Scheme 5
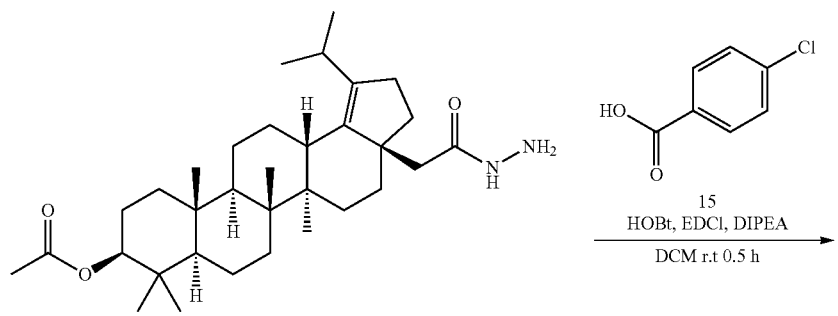
46
15
HOBt, EDCl, DIPEA
DCM r.t 0.5 h -continued
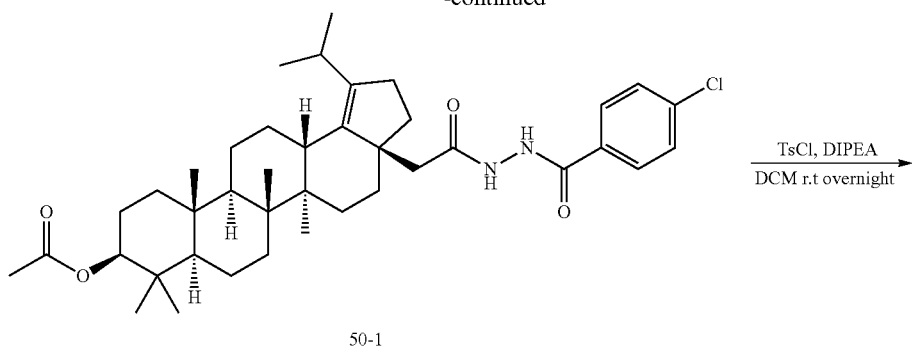
50-1
TsCl, DIPEA
DCM r.t overnight
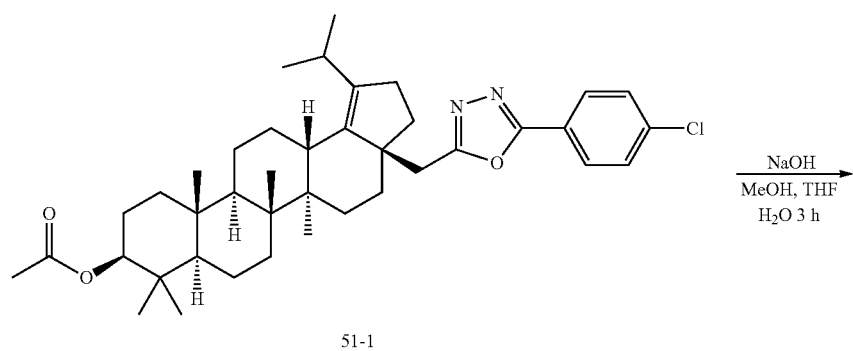
51-1
NaOH
MeOH, THF
H₂O 3 h
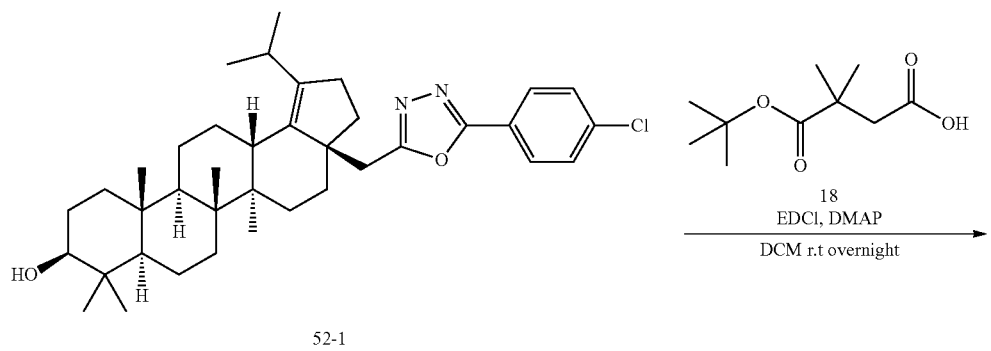
52-1
18
EDCl, DMAP
DCM r.t overnight
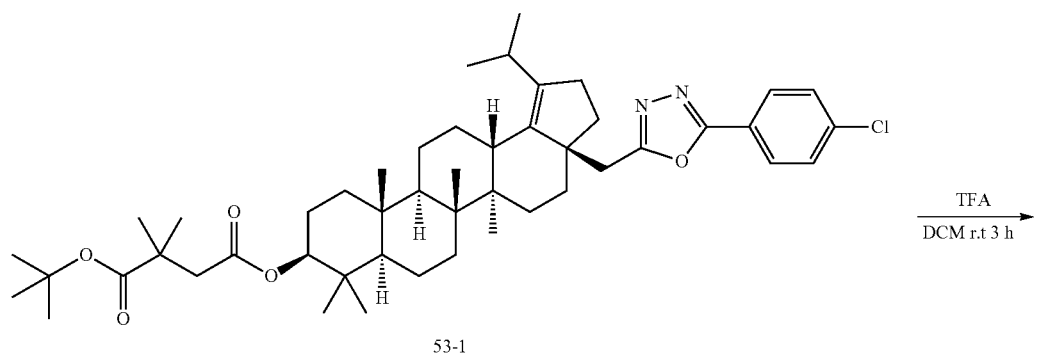
53-1
TFA
DCM r.t 3 h

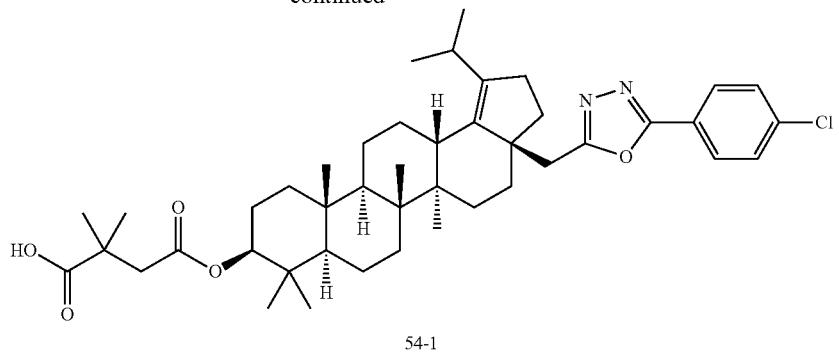
54-1
Method 6: Compound 59-1~59-3 were prepared according to scheme 6.
Scheme 6
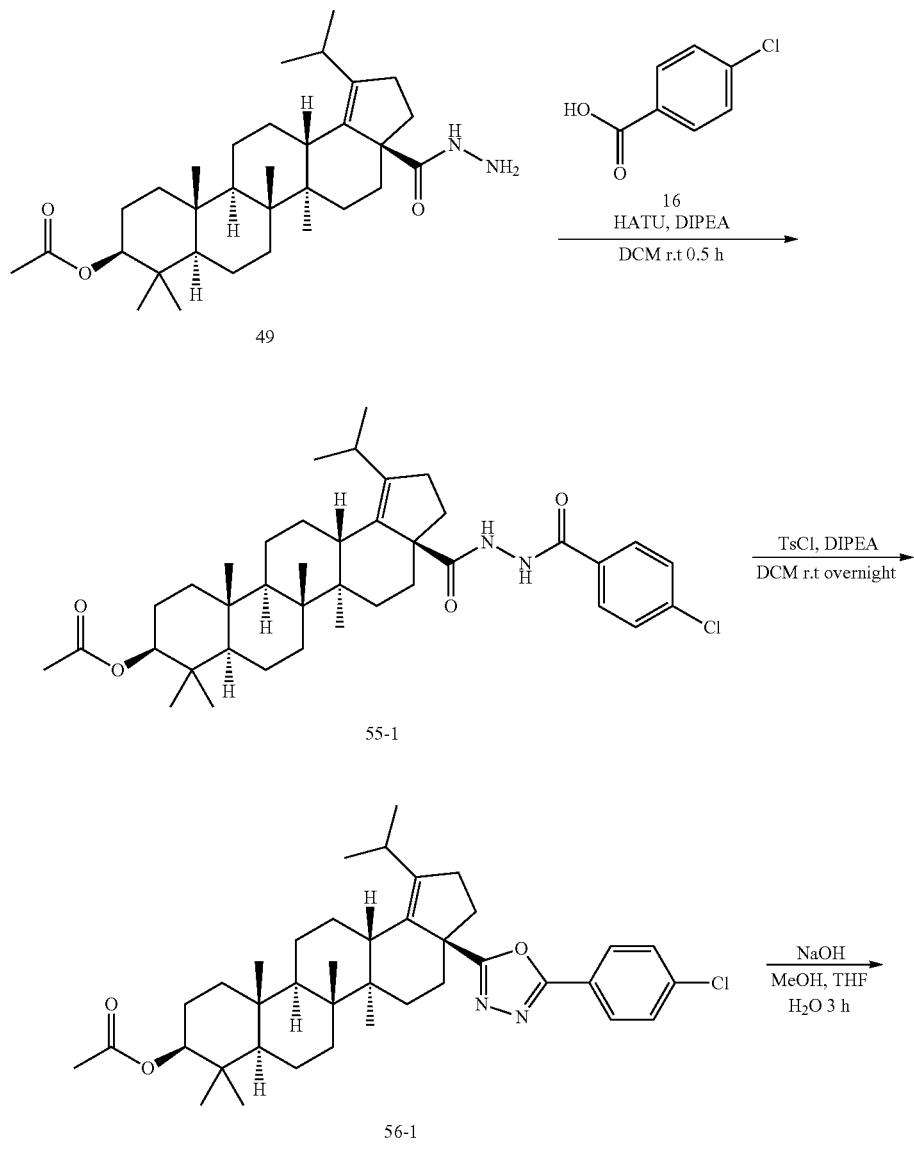

-continued
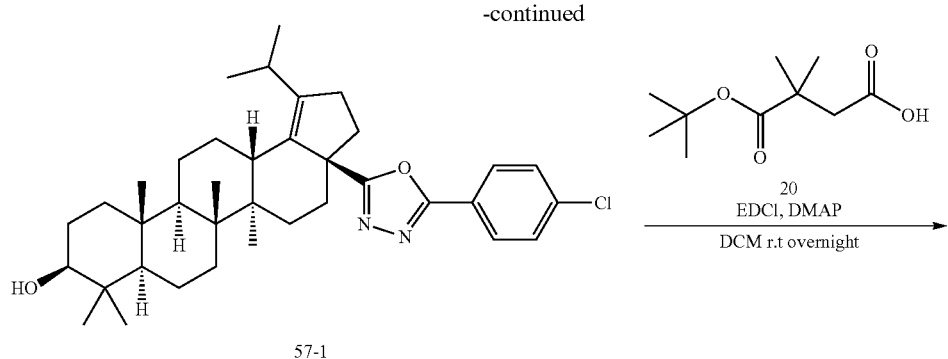
57-1
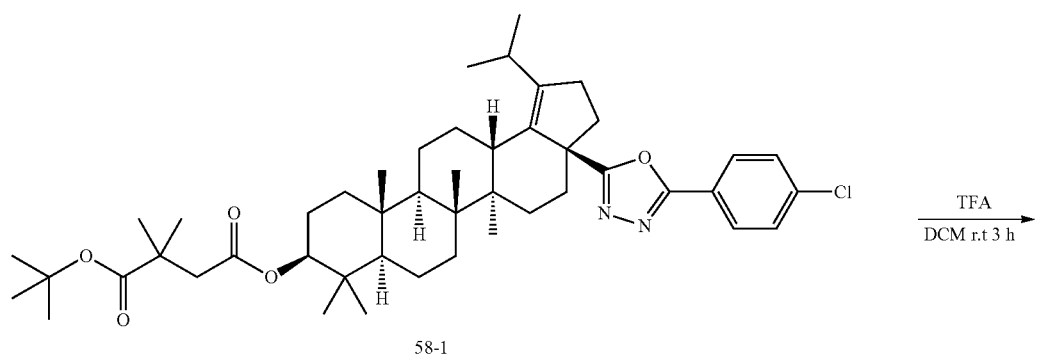
58-1
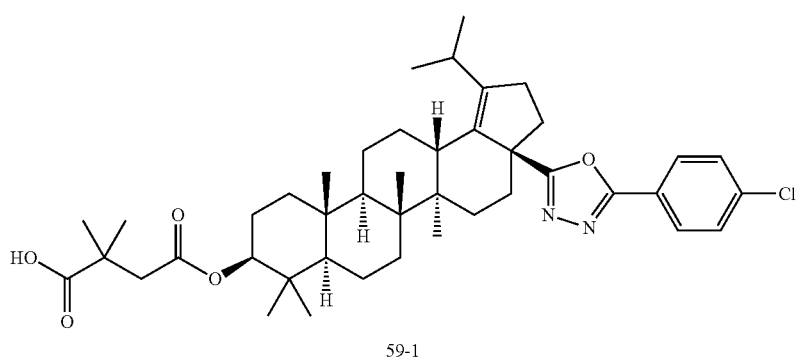
59-1
Method 7: Compound 65 was prepared according to scheme 7.
Scheme 7
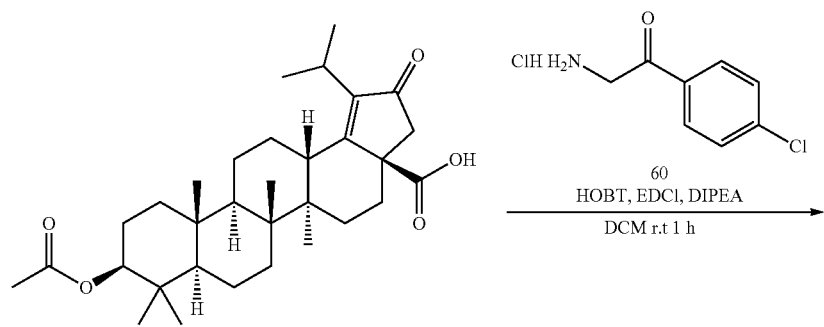
13

-continued
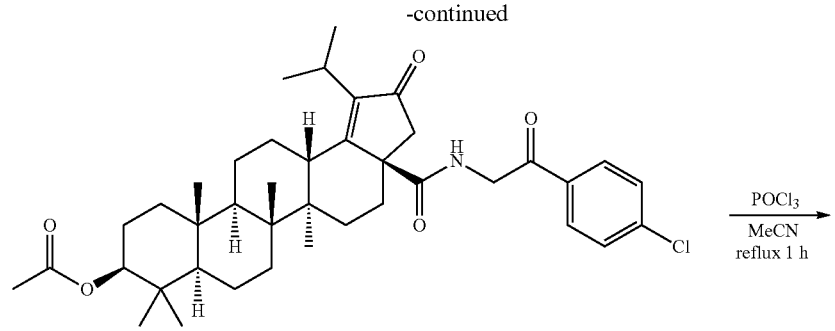
POCl₃
MeCN
reflux 1 h
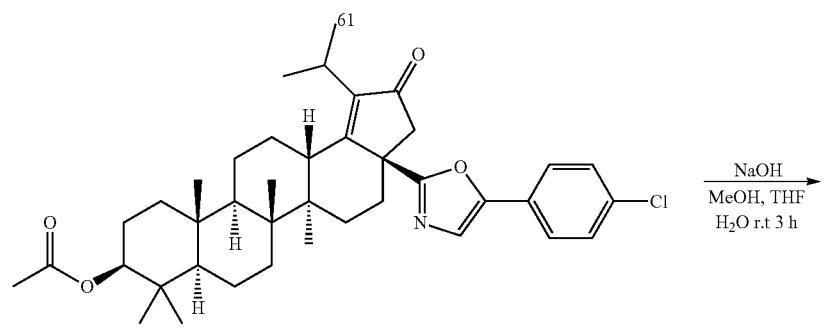
61
NaOH
MeOH, THF
H₂O r.t 3 h
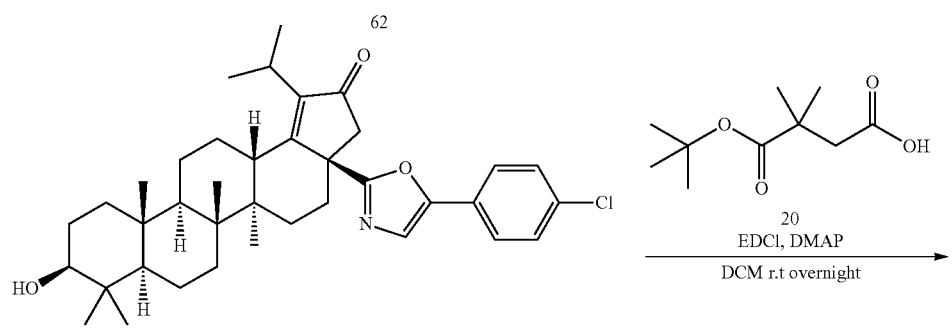
62
20
EDCl, DMAP
DCM r.t overnight
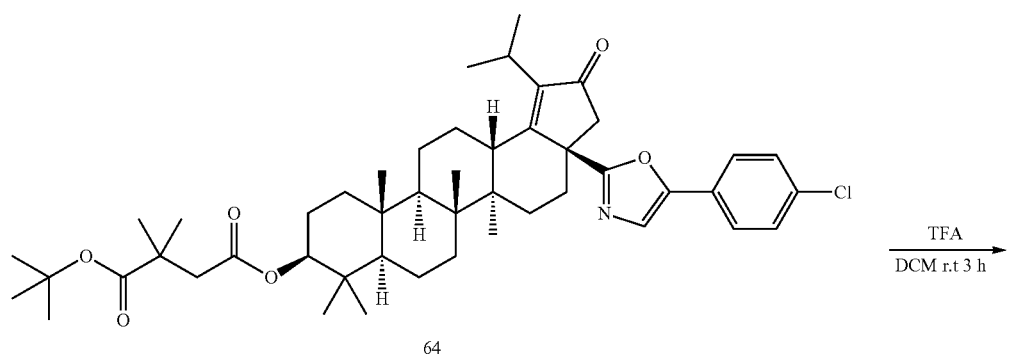
63
TFA
DCM r.t 3 h
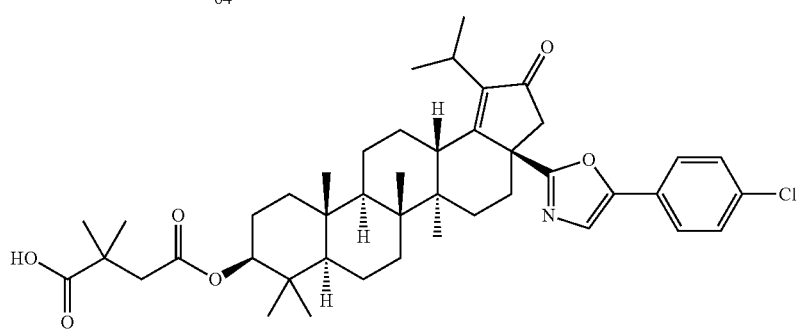
64
65

Method 8: Compound 70 was prepared according to scheme 8.
Scheme 8
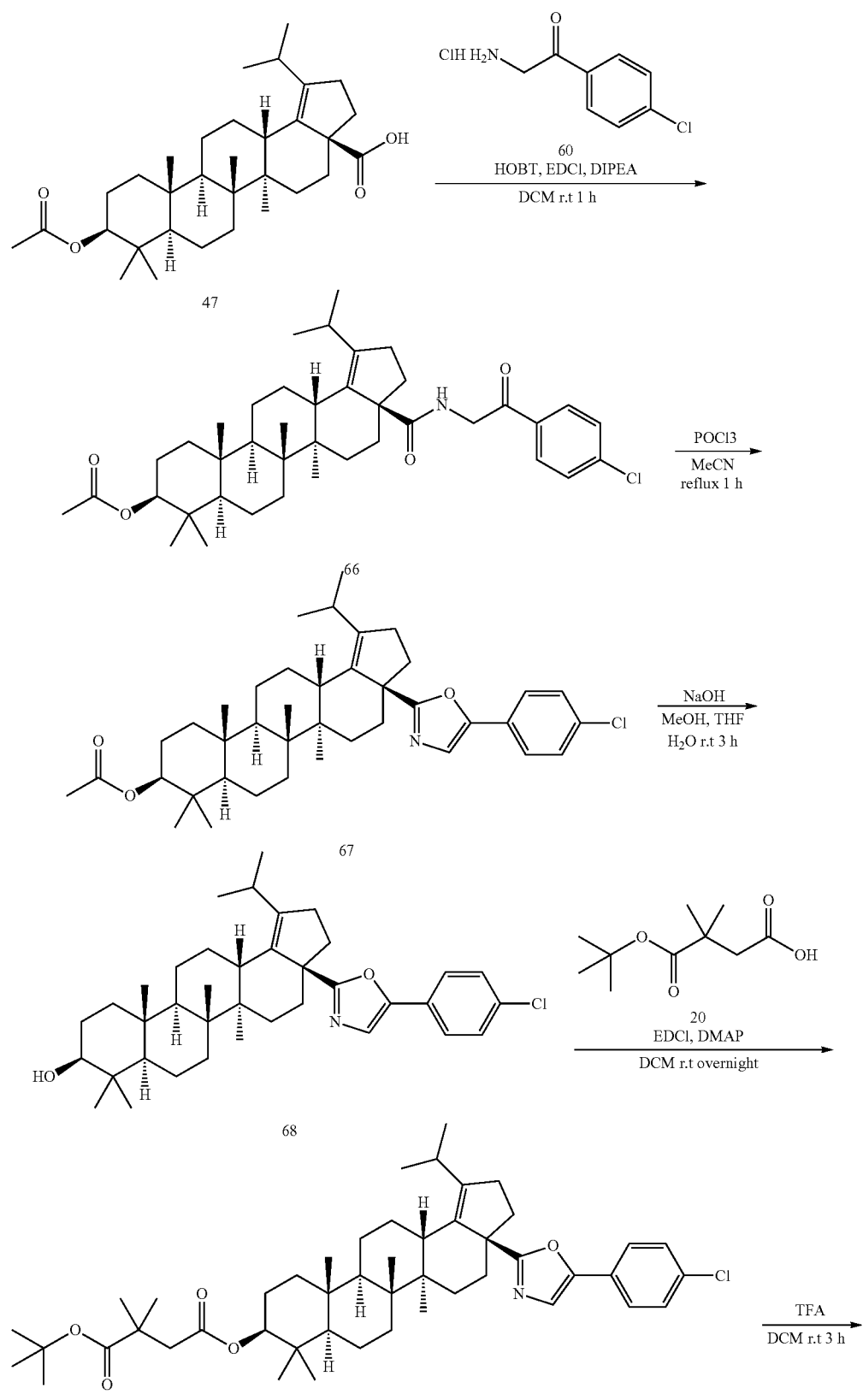

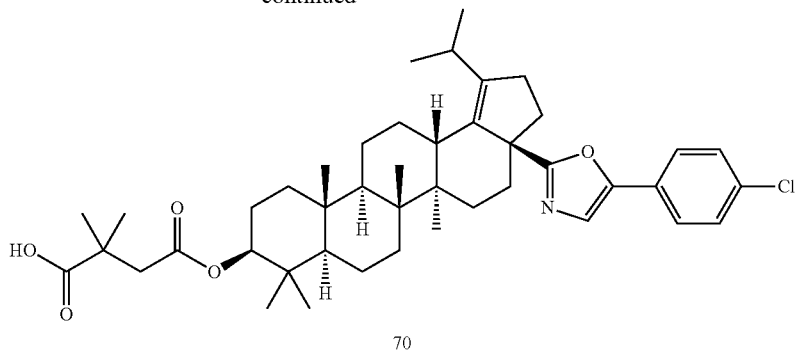
70
Method 9: Compound 77 was prepared according to scheme 9.
Scheme 9
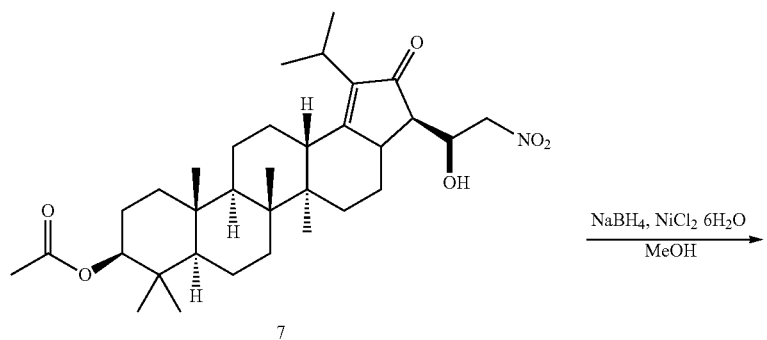
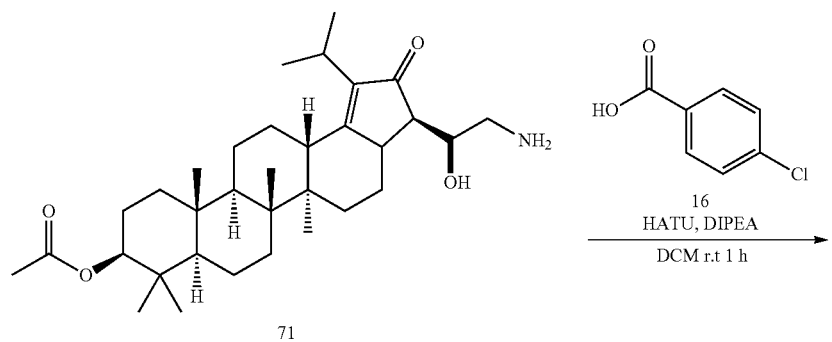
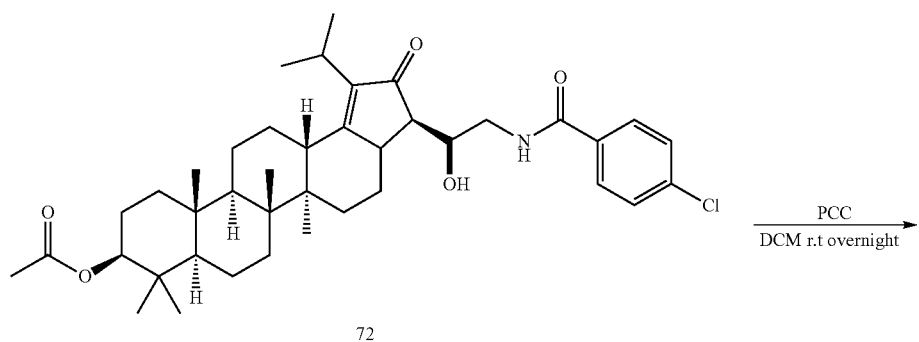

-continued
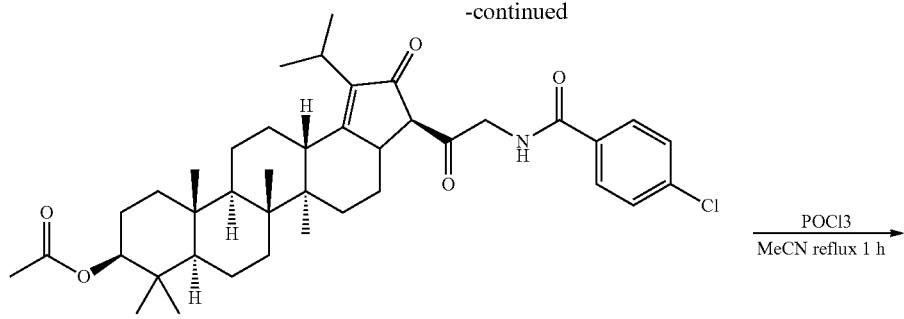
73
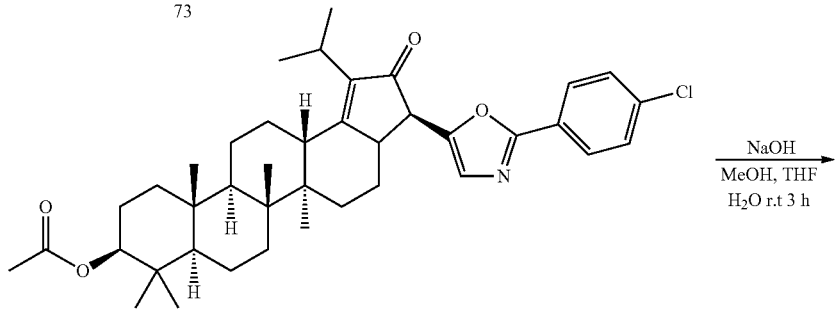
74
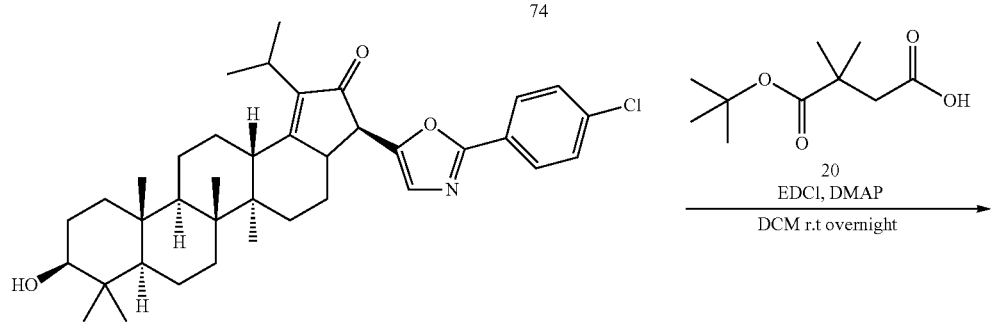
75
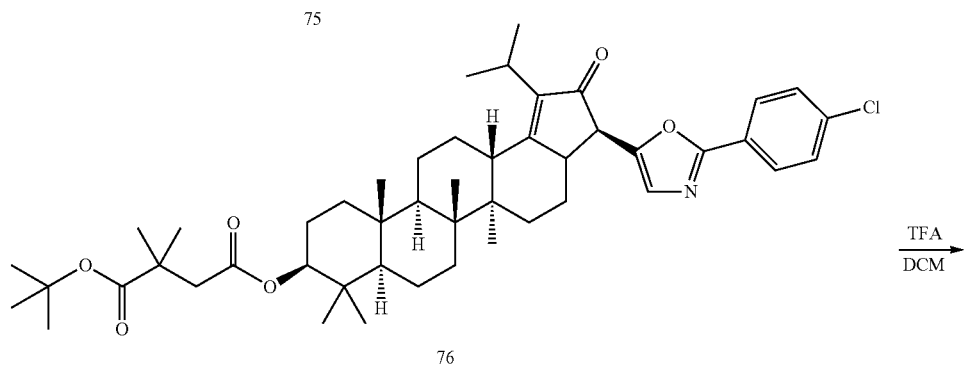
76
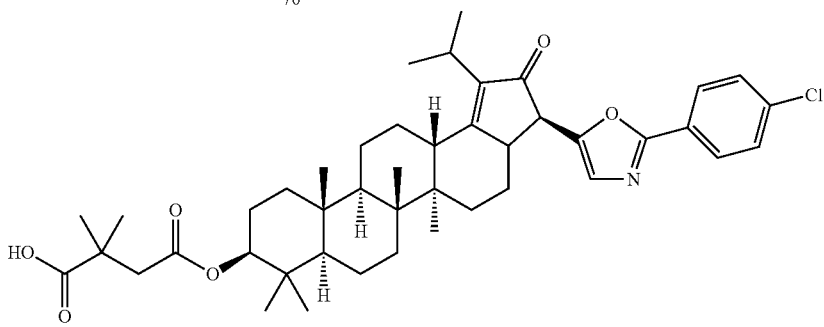
77
Method 10: Compound 89-1~89-7, 89'-1, 91-1~91-9 and 91'-1 were prepared according to scheme 10.

Scheme 10
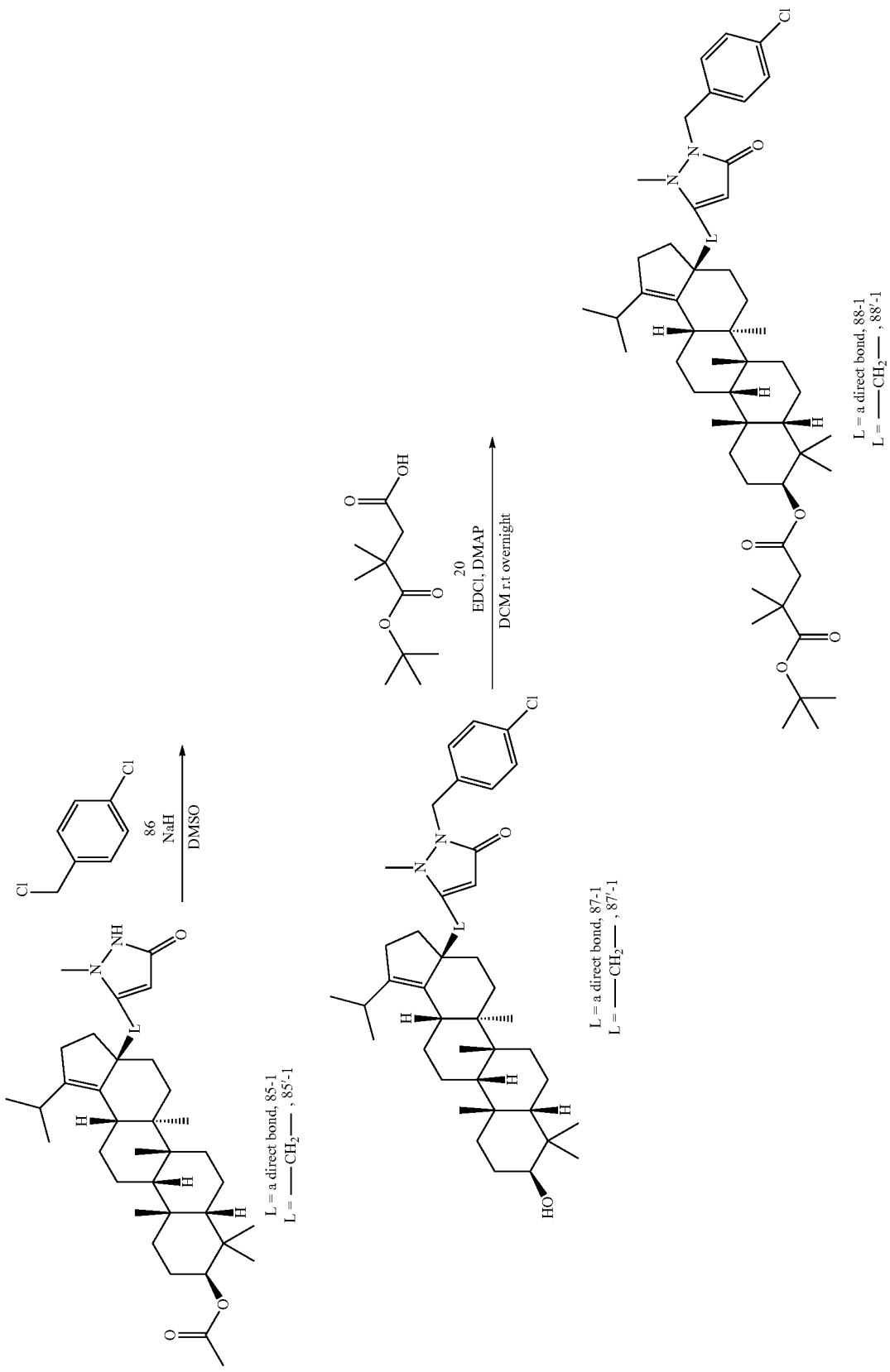

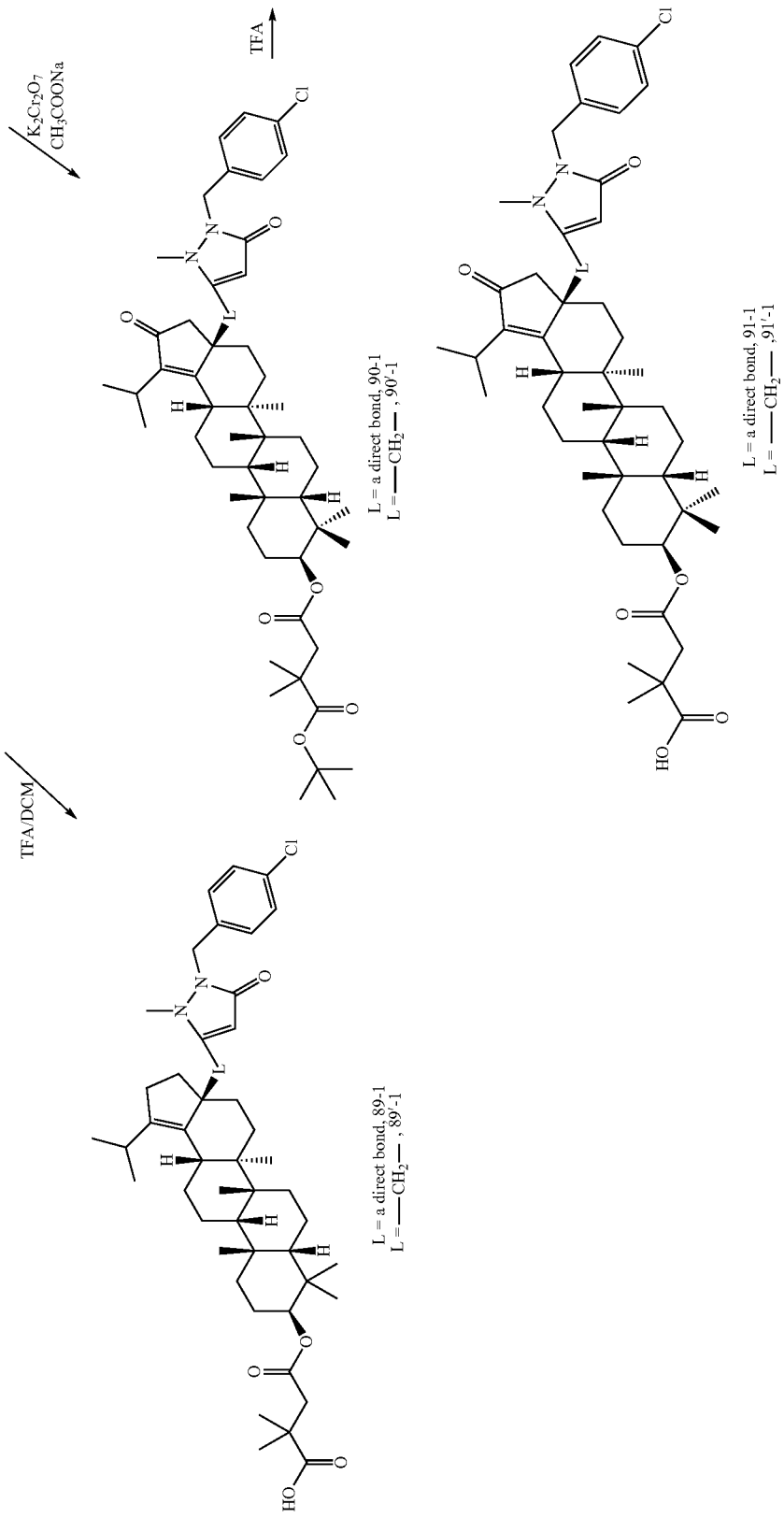

Method 11: Compound 96-1~96-2, 96'-1, 98-1~98-8 and 98'-1~98'-2 were prepared according to scheme 11.

Scheme 11
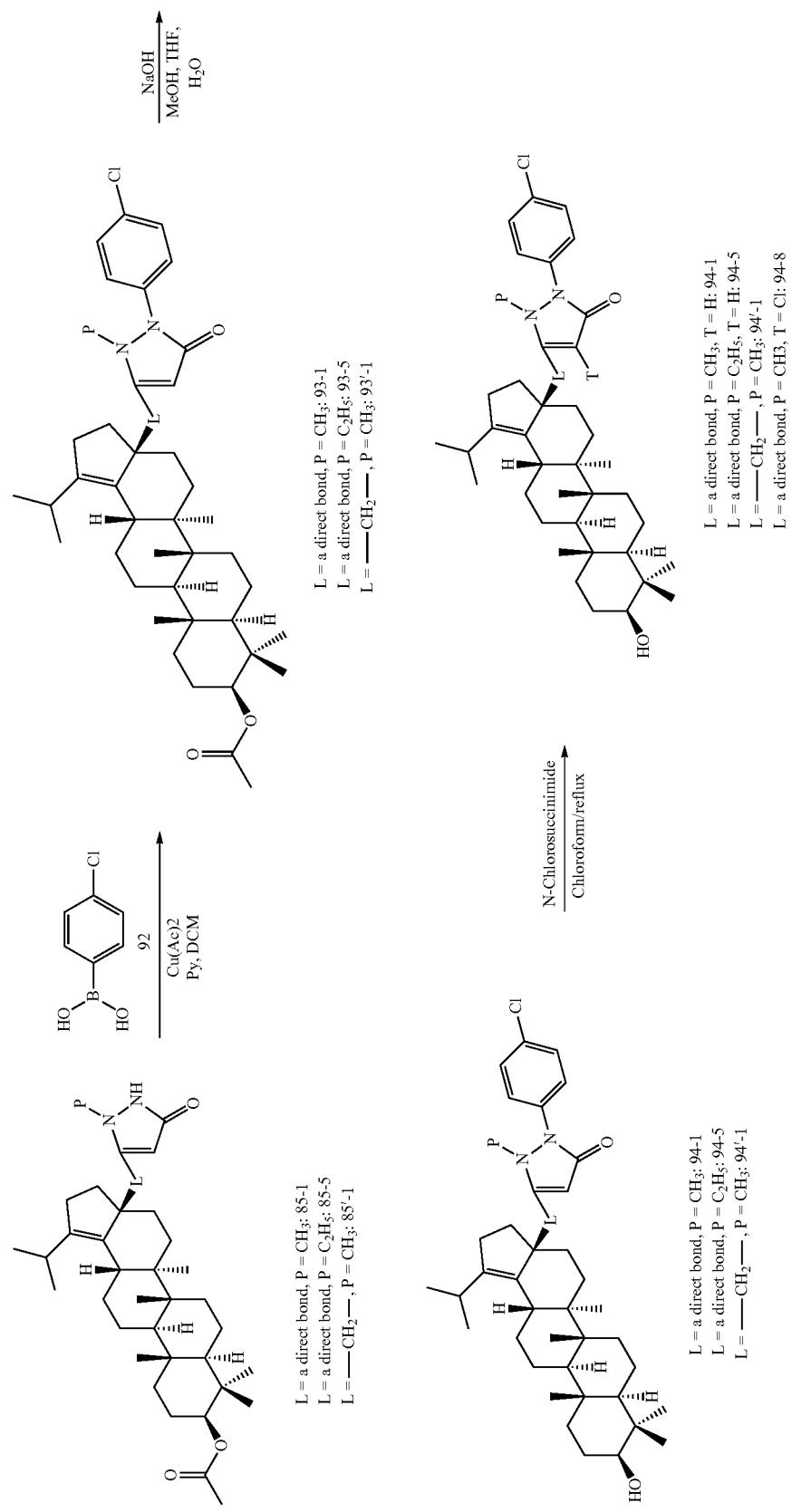

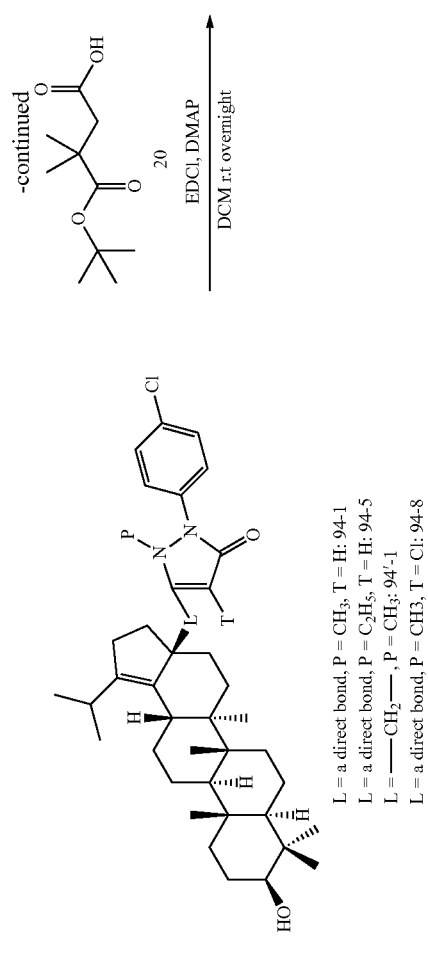
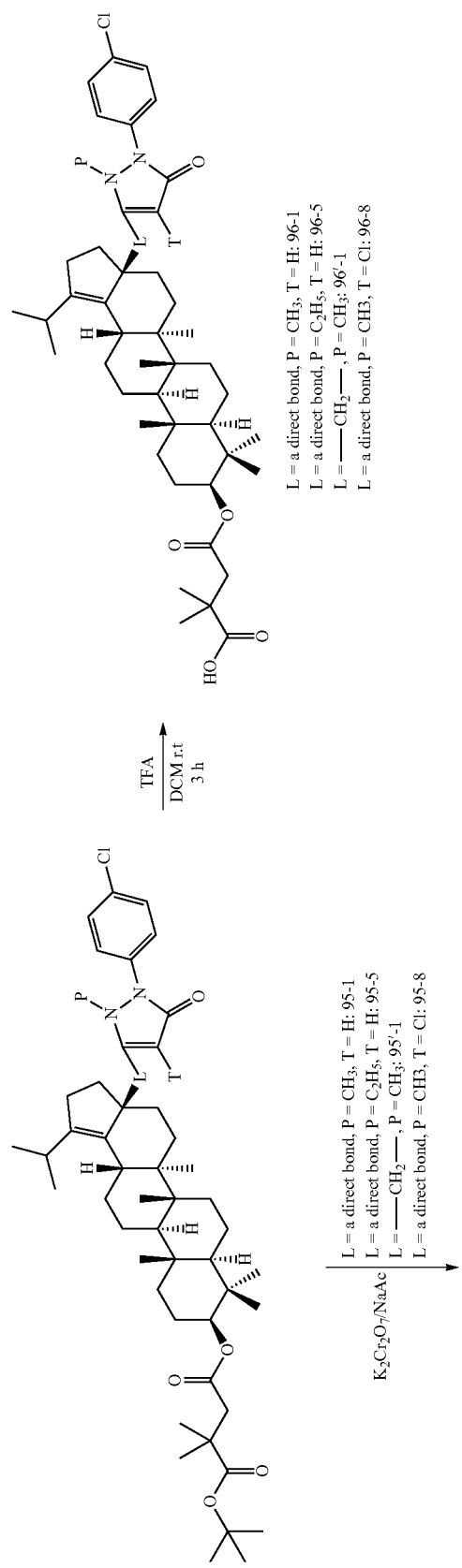

-continued
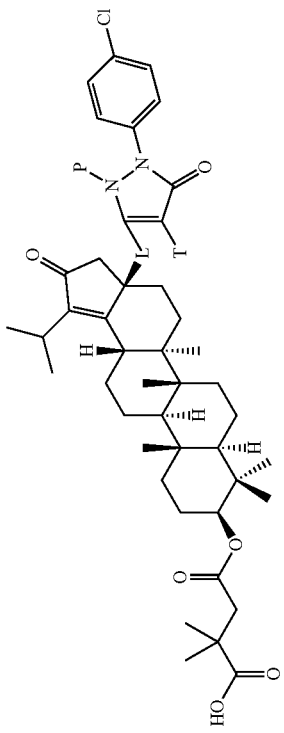
L = a direct bond, P = CH₃, T = H: 97-1
L = a direct bond, P = C₂H₅, T = H: 97-5
L = —CH₂—, P = CH₃; T = H 97'-1
L = a direct bond, P = CH3, T = Cl: 97-8
$\xrightarrow{\text{TFA}}{\text{DCM}}$
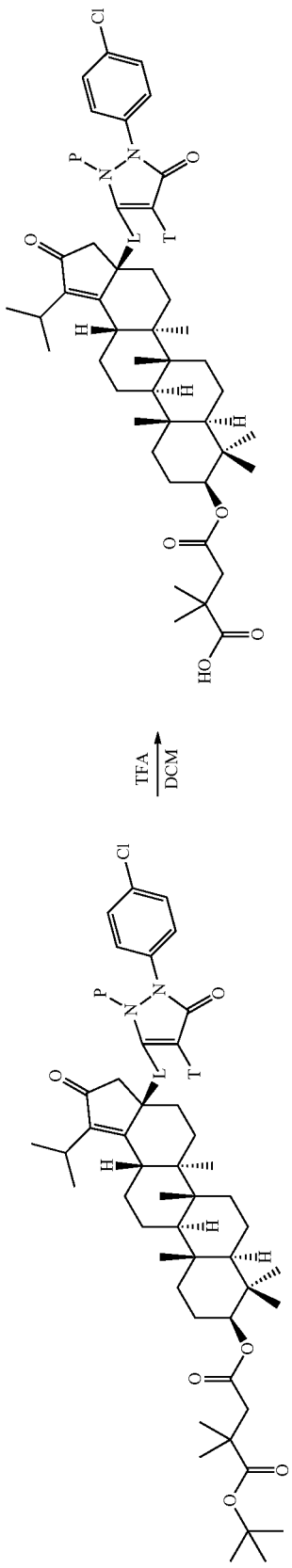
L = a direct bond, P = CH₃, T = H: 98-1
L = a direct bond, P = C₂H₅, T = H: 98-5
L = —CH₂—, P = CH₃; T = H 98'-1
L = a direct bond, P = CH3, T = Cl: 98-8

Method 12: Compound 102 was prepared according to scheme 12.
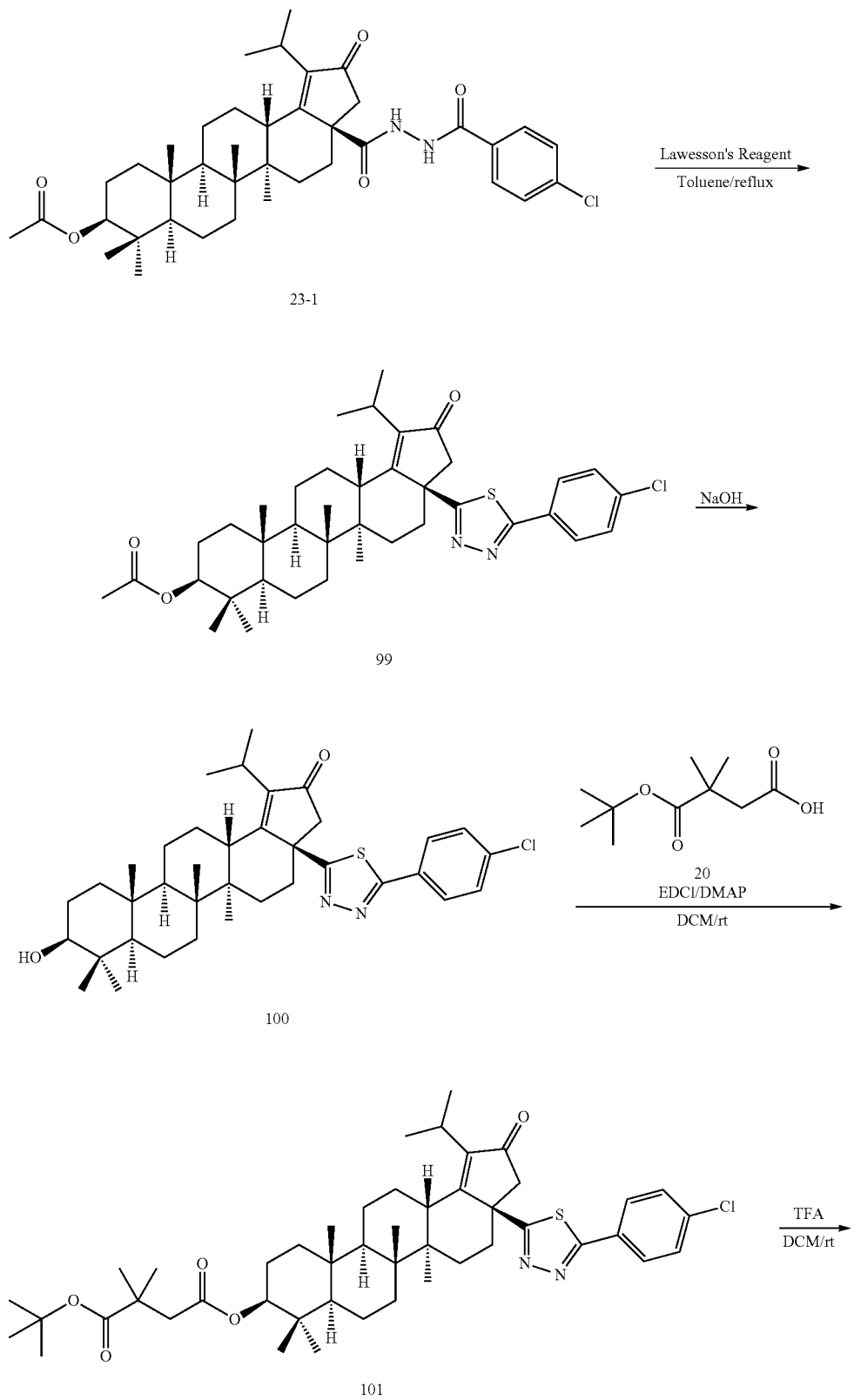

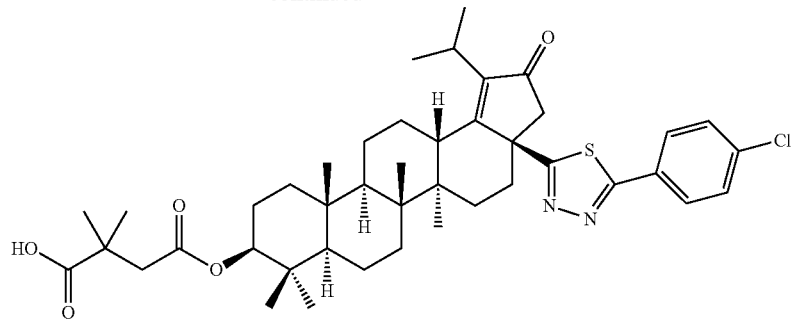
102
Method 13: Compound 108-1~108-2 were prepared according to scheme 13.
Scheme 13
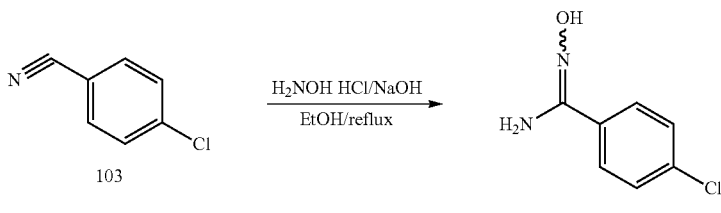
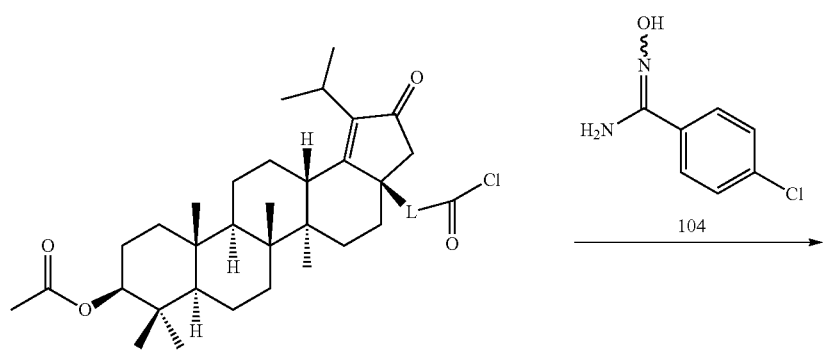
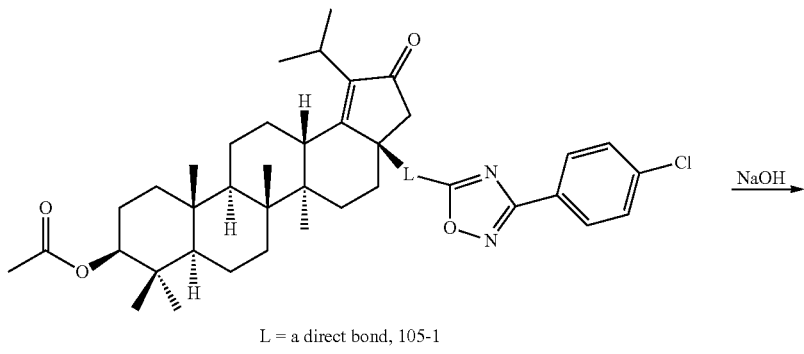

-continued
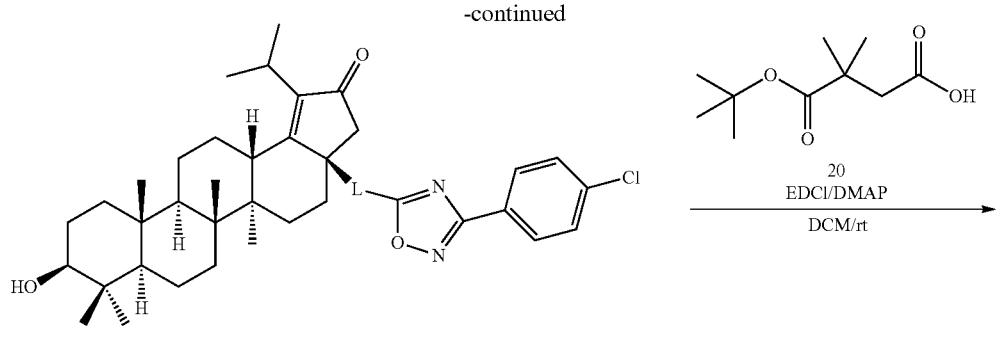
L = a direct bond, 106-1
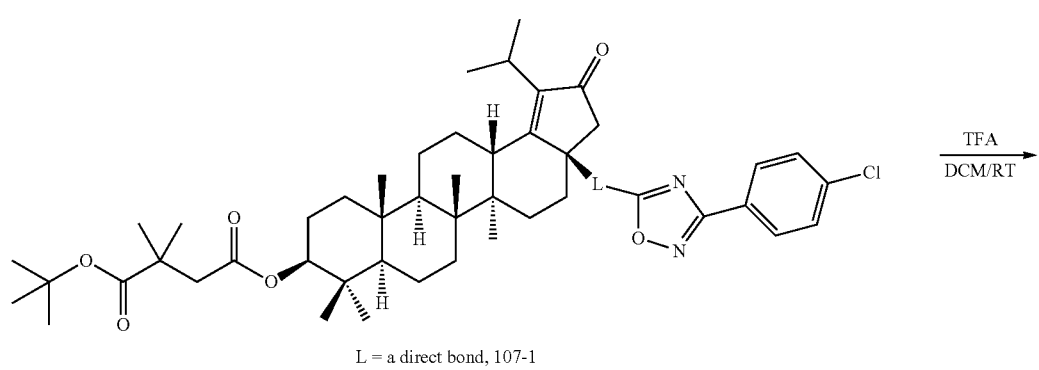
L = a direct bond, 107-1
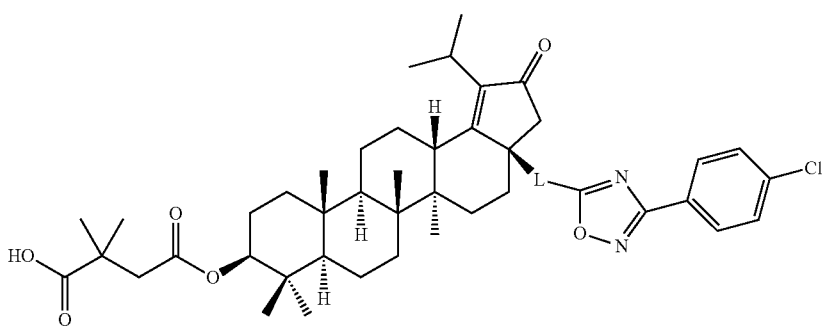
108-1 L = a direct bond
108-2 L = —CH$_2$—
Method 14: Compound 116-1~116-4 were prepared according to scheme 14.
Scheme 14
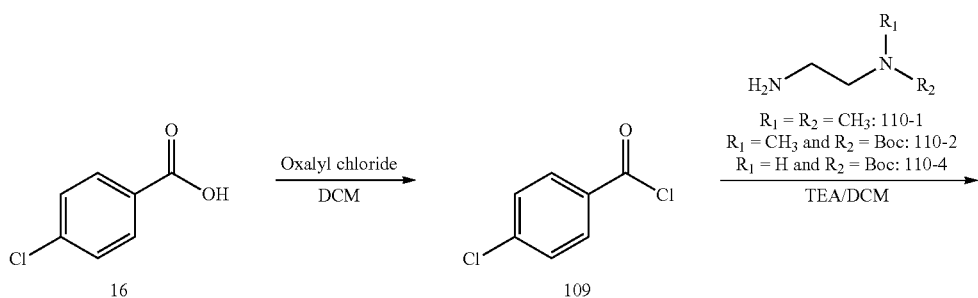
$R_1 = R_2 = CH_3$: 110-1
$R_1 = CH_3$ and $R_2 = $ Boc: 110-2
$R_1 = H$ and $R_2 = $ Boc: 110-4

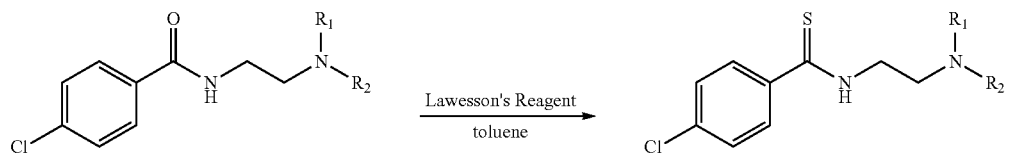

R₁ = R₂ = CH₃: 111-1
R₁ = CH₃ and R₂ = Boc: 111-2
R₁ = H and R₂ = Boc: 111-4

R₁ = R₂ = CH₃: 112-1
R₁ = CH₃ and R₂ = Boc: 112-2
R₁ = H and R₂ = Boc: 112-4

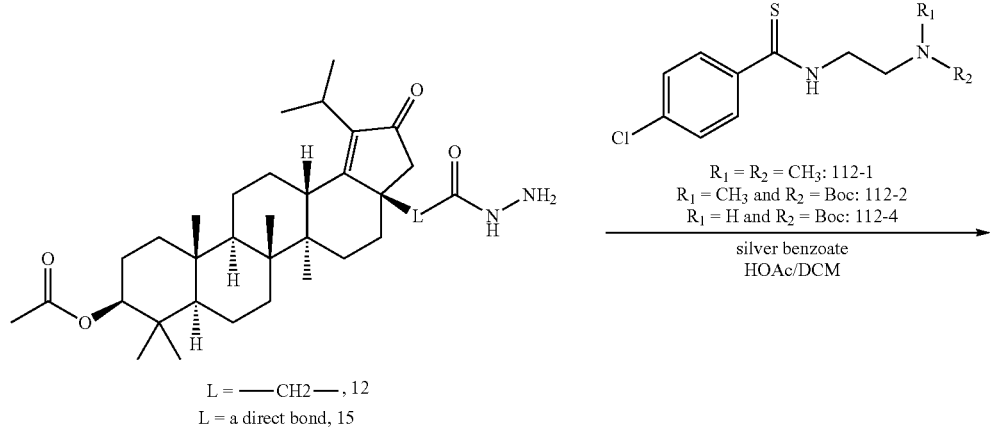

L = —CH2—, 12
L = a direct bond, 15

R₁ = R₂ = CH₃: 112-1
R₁ = CH₃ and R₂ = Boc: 112-2
R₁ = H and R₂ = Boc: 112-4 silver benzoate
HOAc/DCM

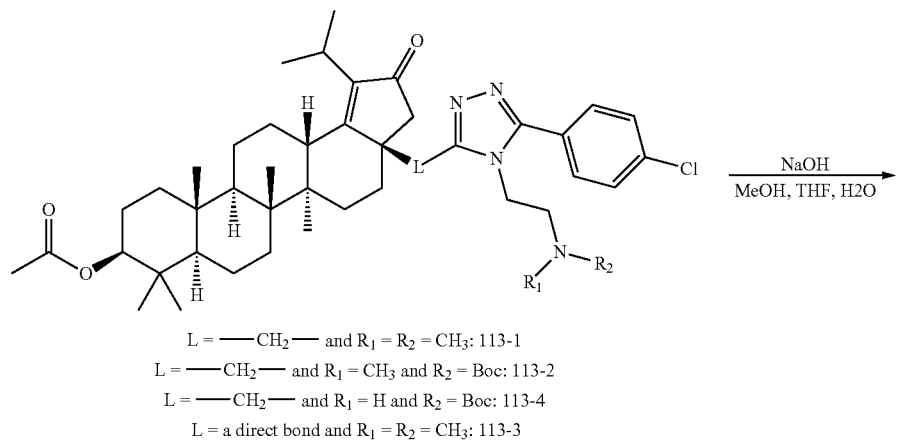

L = —CH₂— and R₁ = R₂ = CH₃: 113-1
L = —CH₂— and R₁ = CH₃ and R₂ = Boc: 113-2
L = —CH₂— and R₁ = H and R₂ = Boc: 113-4
L = a direct bond and R₁ = R₂ = CH₃: 113-3

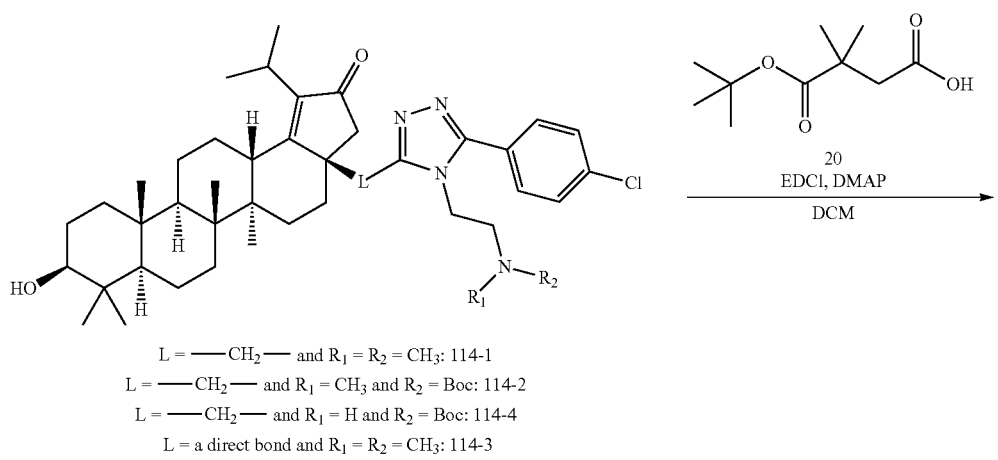

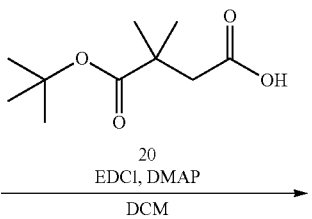

20
EDCl, DMAP
DCM

L = —CH₂— and R₁ = R₂ = CH₃: 114-1
L = —CH₂— and R₁ = CH₃ and R₂ = Boc: 114-2
L = —CH₂— and R₁ = H and R₂ = Boc: 114-4
L = a direct bond and R₁ = R₂ = CH₃: 114-3

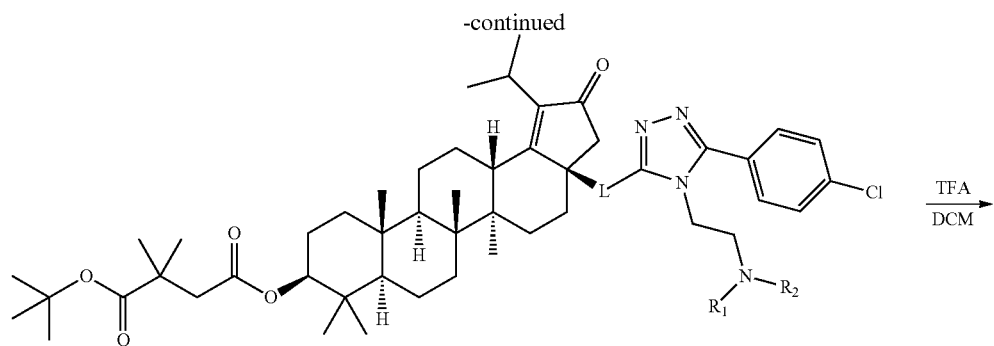
115-1, L = —CH₂—, R₁ = R₂ = CH₃
115-2, L = —CH₂—, R₁ = CH₃, R₂ = Boc
115-3, L = a direct bond, R₁ = R₂ = CH₃
115-4, L = —CH₂—, R₁ = H, R₂ = Boc
116
116-1, L = —CH₂—, R₁ = R₂ = CH₃
116-2, L = —CH₂—, R₁ = CH₃, R₂ = H
116-3, L = a direct bond, R₁ = R₂ = CH₃
116-4, L = —CH₂—, R₁ = R₂ = H
Method 15: Compound 127-1~127-5 were prepared according to scheme 15.
Scheme 15

-continued
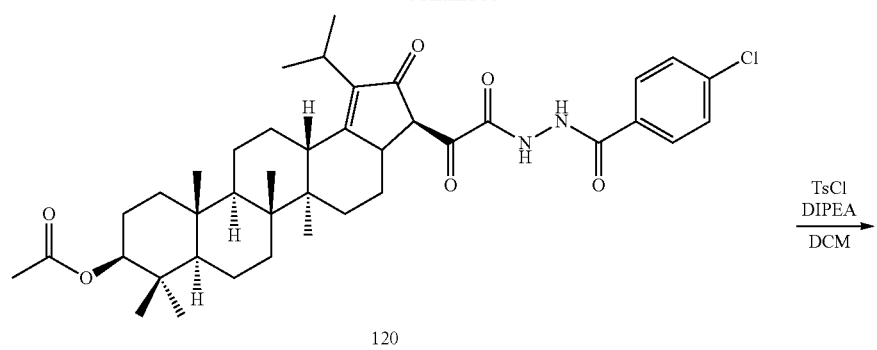
120
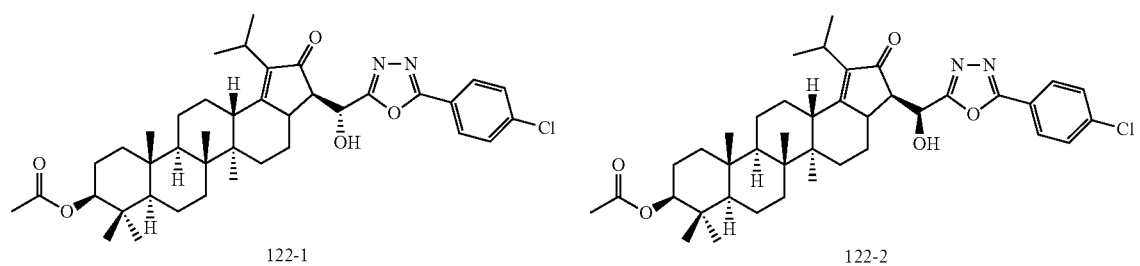
121
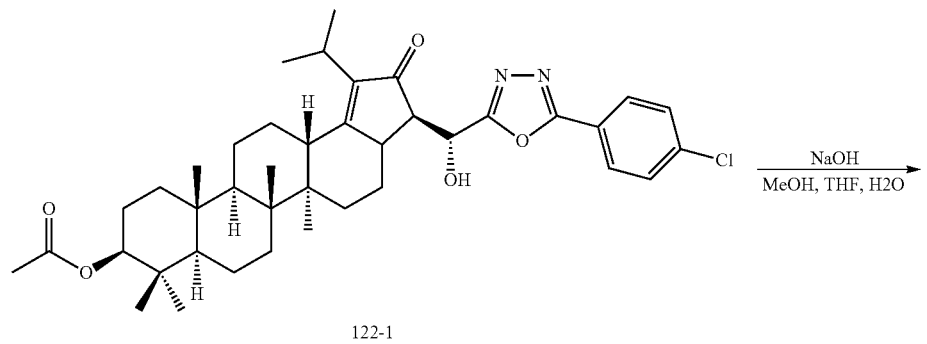
122-1        122-2

-continued
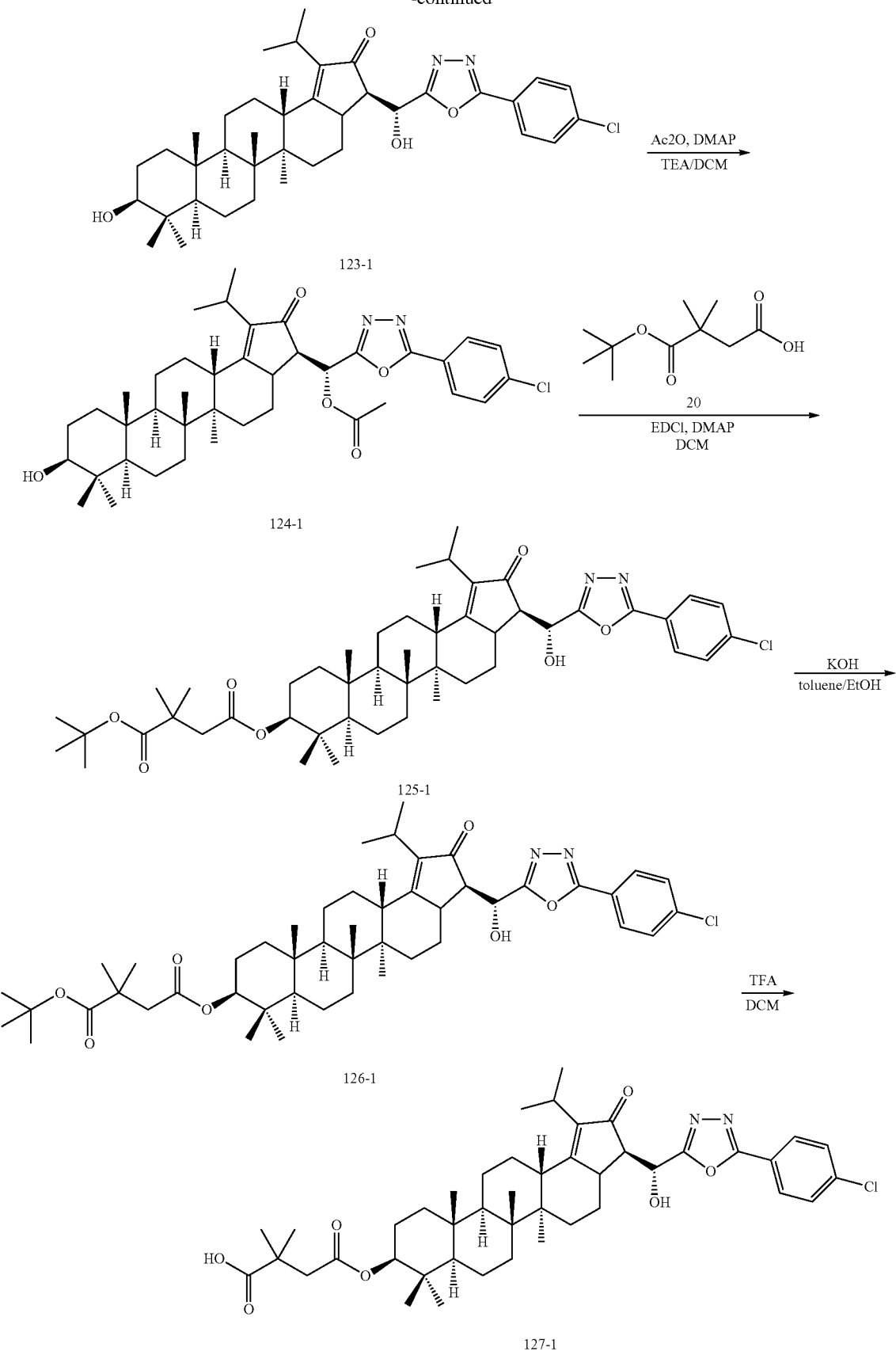

Method 16: Compound 133-1~133-3 were prepared according to scheme 16.
Scheme 16
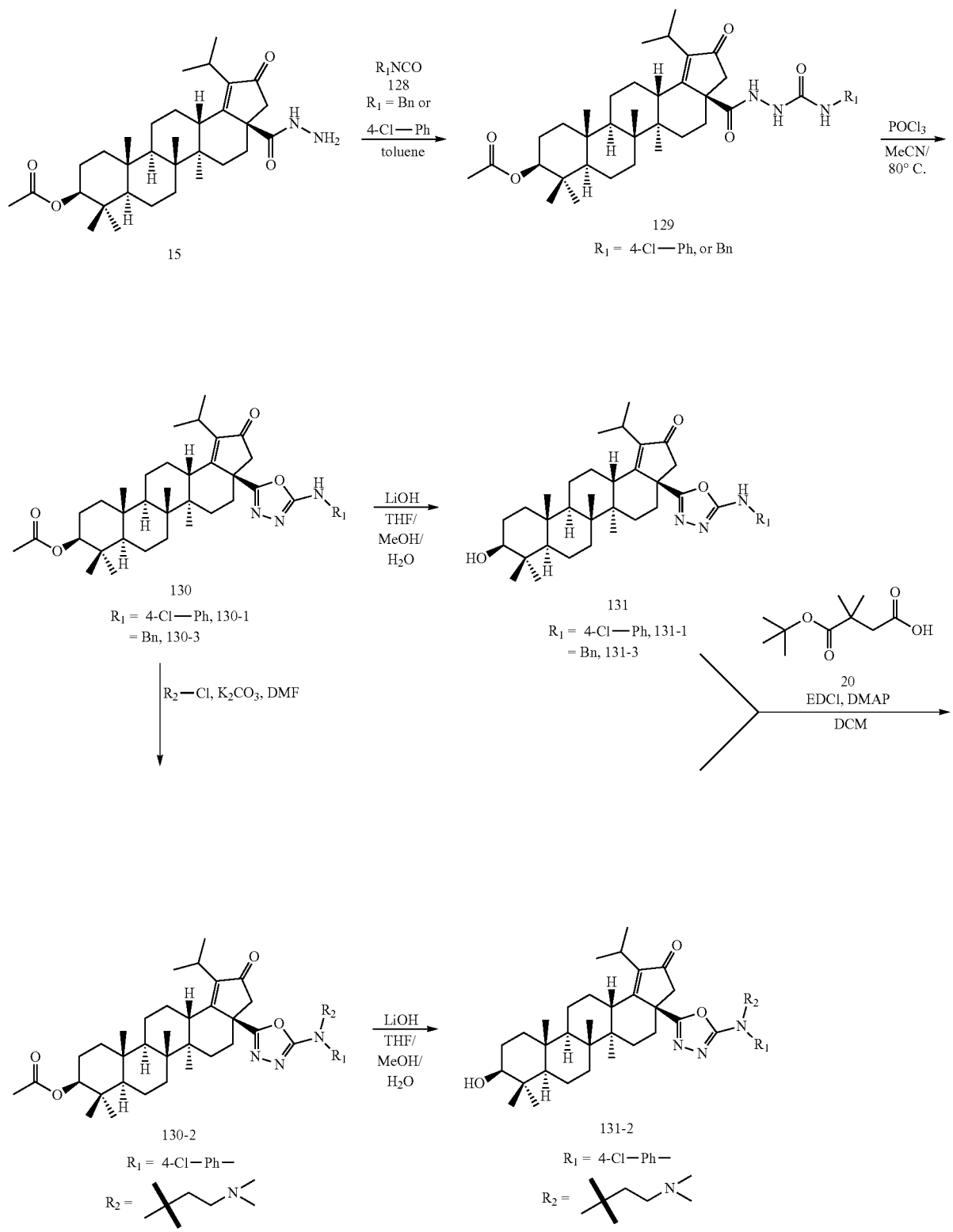

-continued
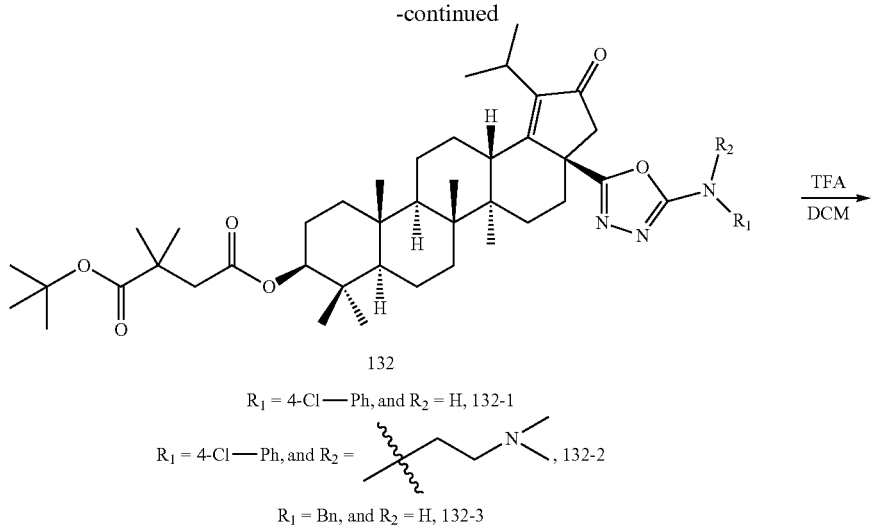
132
R₁ = 4-Cl—Ph, and R₂ = H, 132-1
R₁ = 4-Cl—Ph, and R₂ = [structure], 132-2
R₁ = Bn, and R₂ = H, 132-3
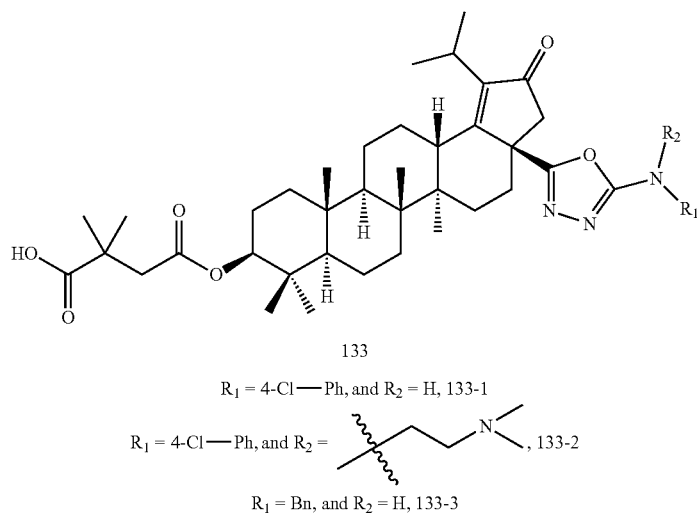
133
R₁ = 4-Cl—Ph, and R₂ = H, 133-1
R₁ = 4-Cl—Ph, and R₂ = [structure], 133-2
R₁ = Bn, and R₂ = H, 133-3
Method 17: Compound 141-1~141-2 were prepared according to scheme 17.
Scheme 17
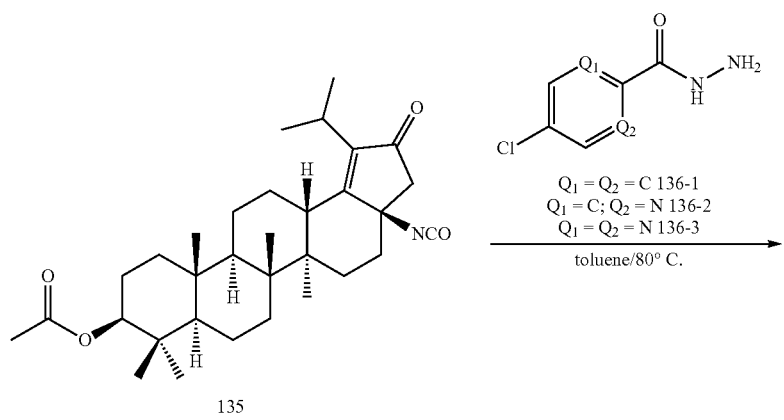
$Q_1 = Q_2 = C$ 136-1
$Q_1 = C; Q_2 = N$ 136-2
$Q_1 = Q_2 = N$ 136-3
toluene/80° C.
135

-continued
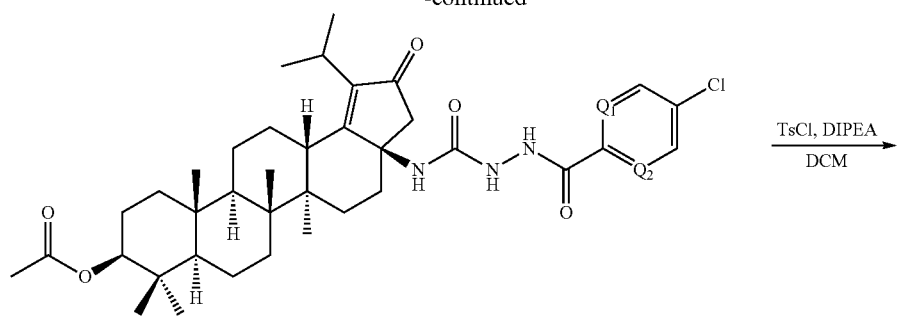
Q₁ = Q₂ = C 137-1
Q₁ = C; Q₂ = N 137-2
Q₁ = Q₂ = N 137-3
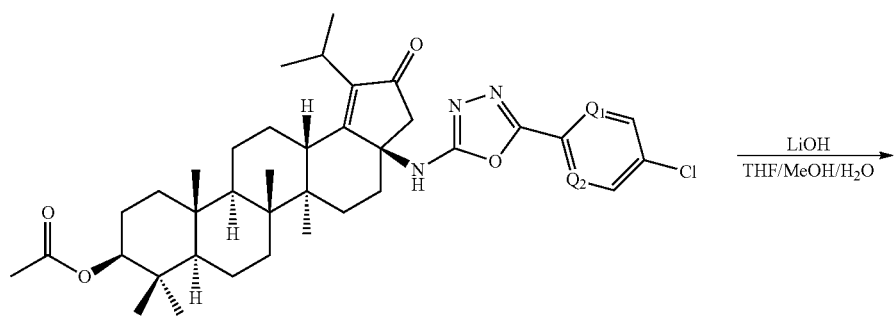
Q₁ = Q₂ = C 138-1
Q₁ = C; Q₂ = N 138-2
Q₁ = Q₂ = N 138-3
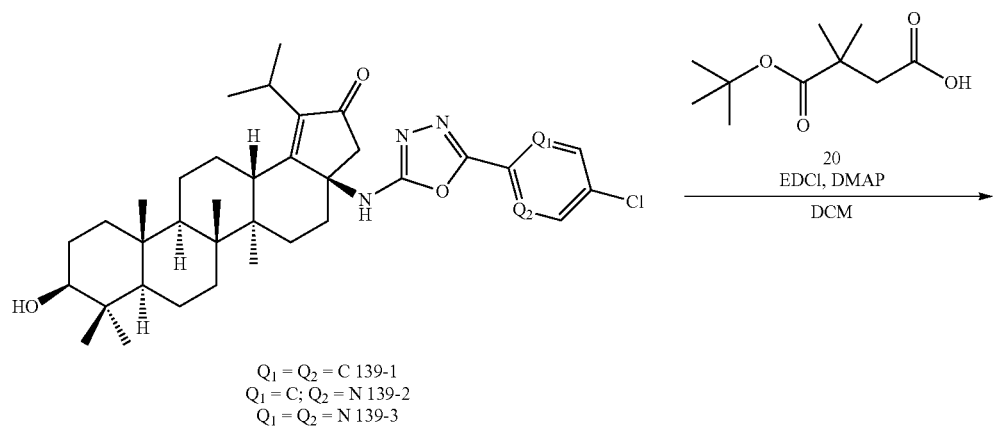
Q₁ = Q₂ = C 139-1
Q₁ = C; Q₂ = N 139-2
Q₁ = Q₂ = N 139-3
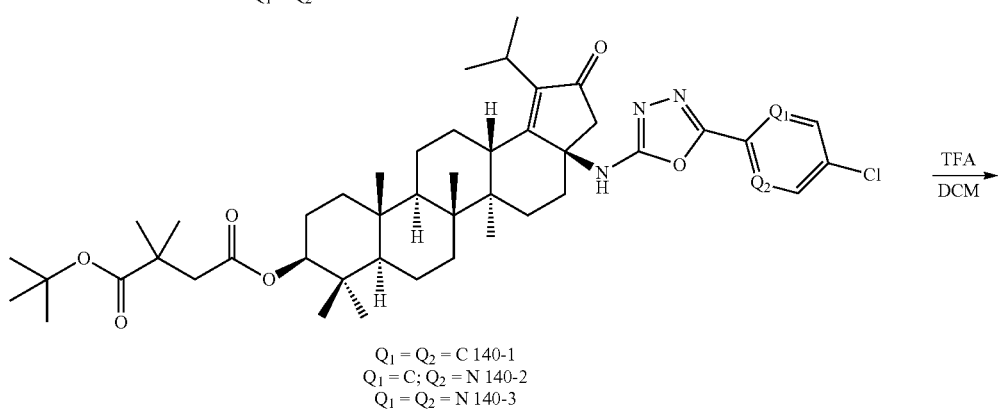
Q₁ = Q₂ = C 140-1
Q₁ = C; Q₂ = N 140-2
Q₁ = Q₂ = N 140-3

-continued
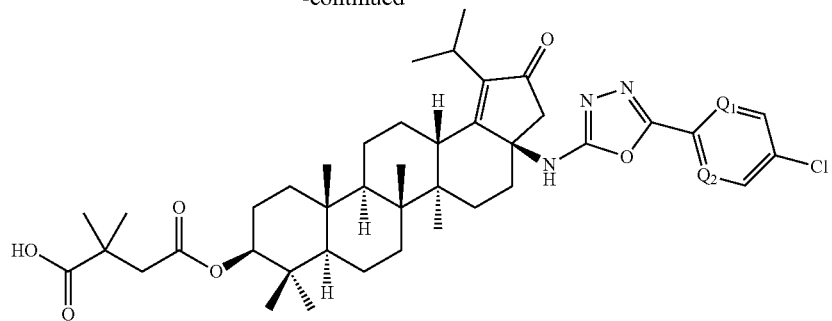
Q₁ = Q₂ = C 141-1
Q₁ = C; Q₂ = N 141-2
Q₁ = Q₂ = N 141-3
Method 18: Compound 153-1, 153'-1, 155-1~155-2, 155'-1, 156-1~156-2, and 156'-1 were prepared according to scheme 18.

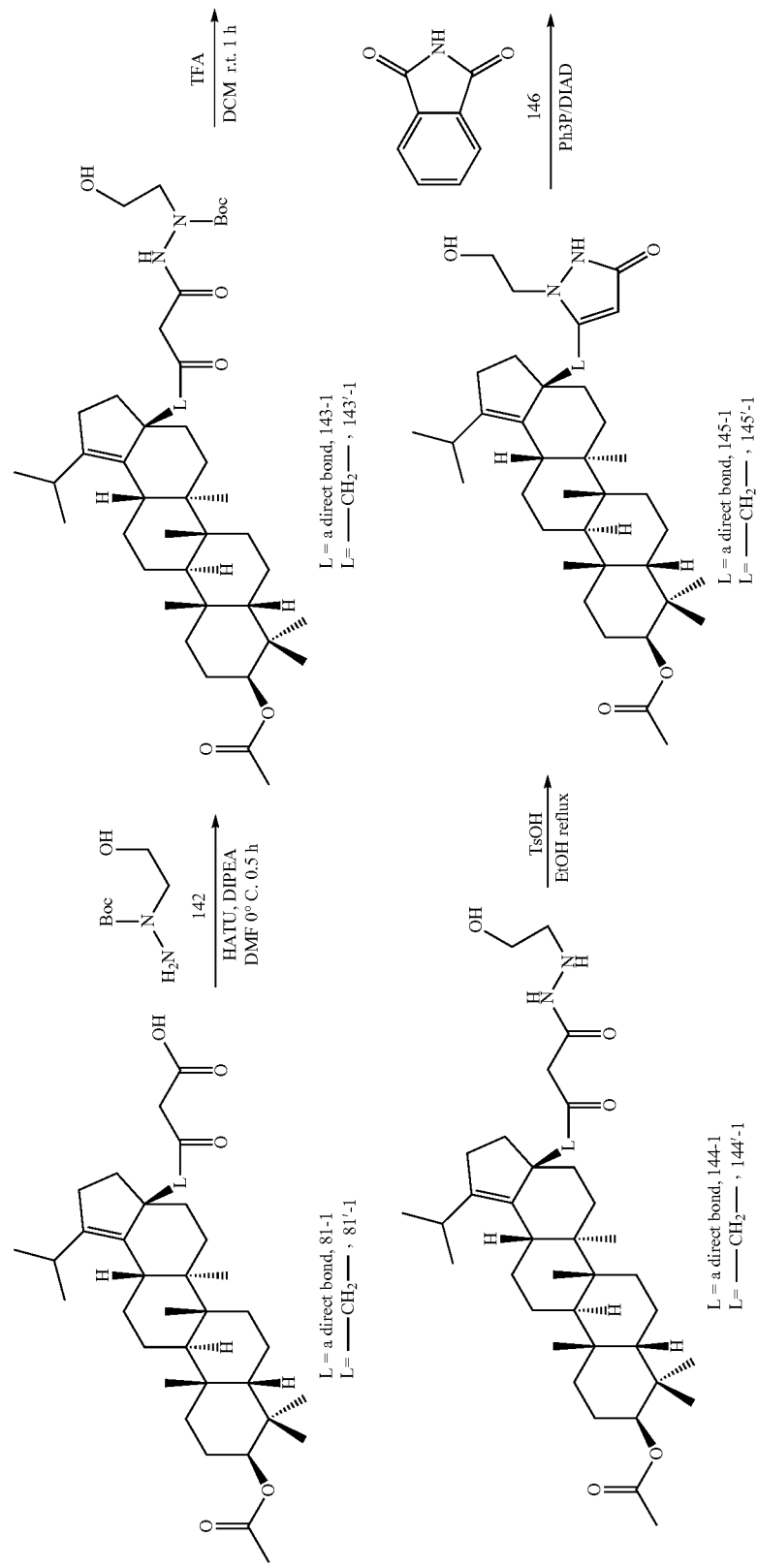

-continued
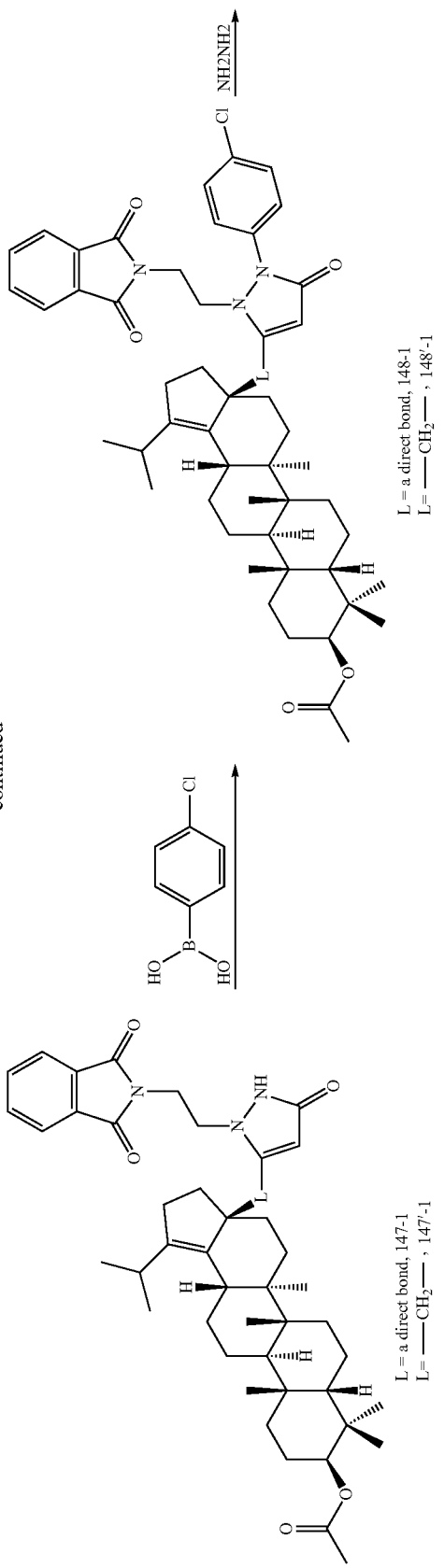
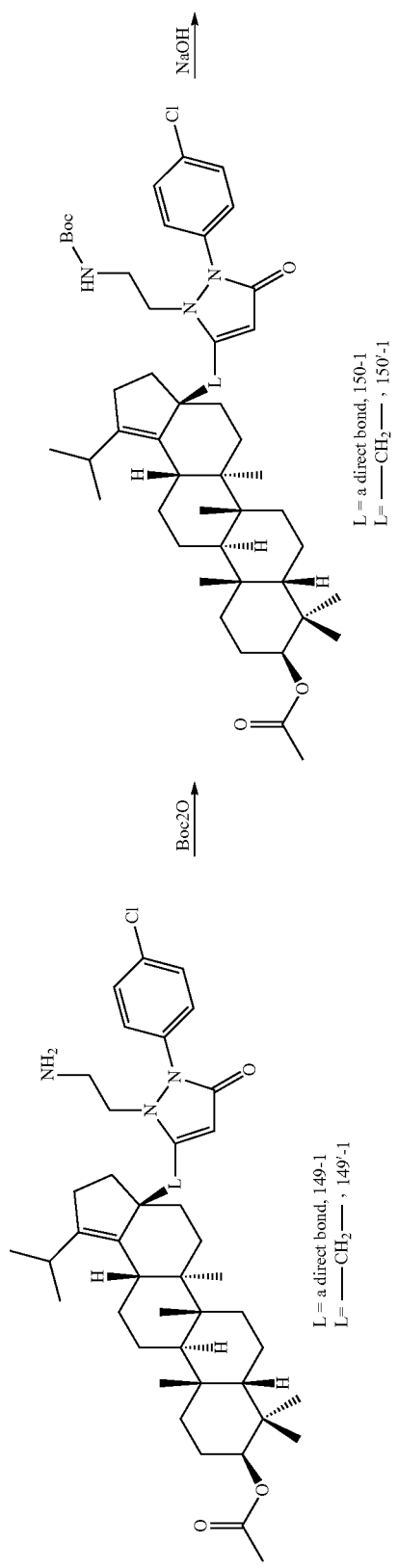

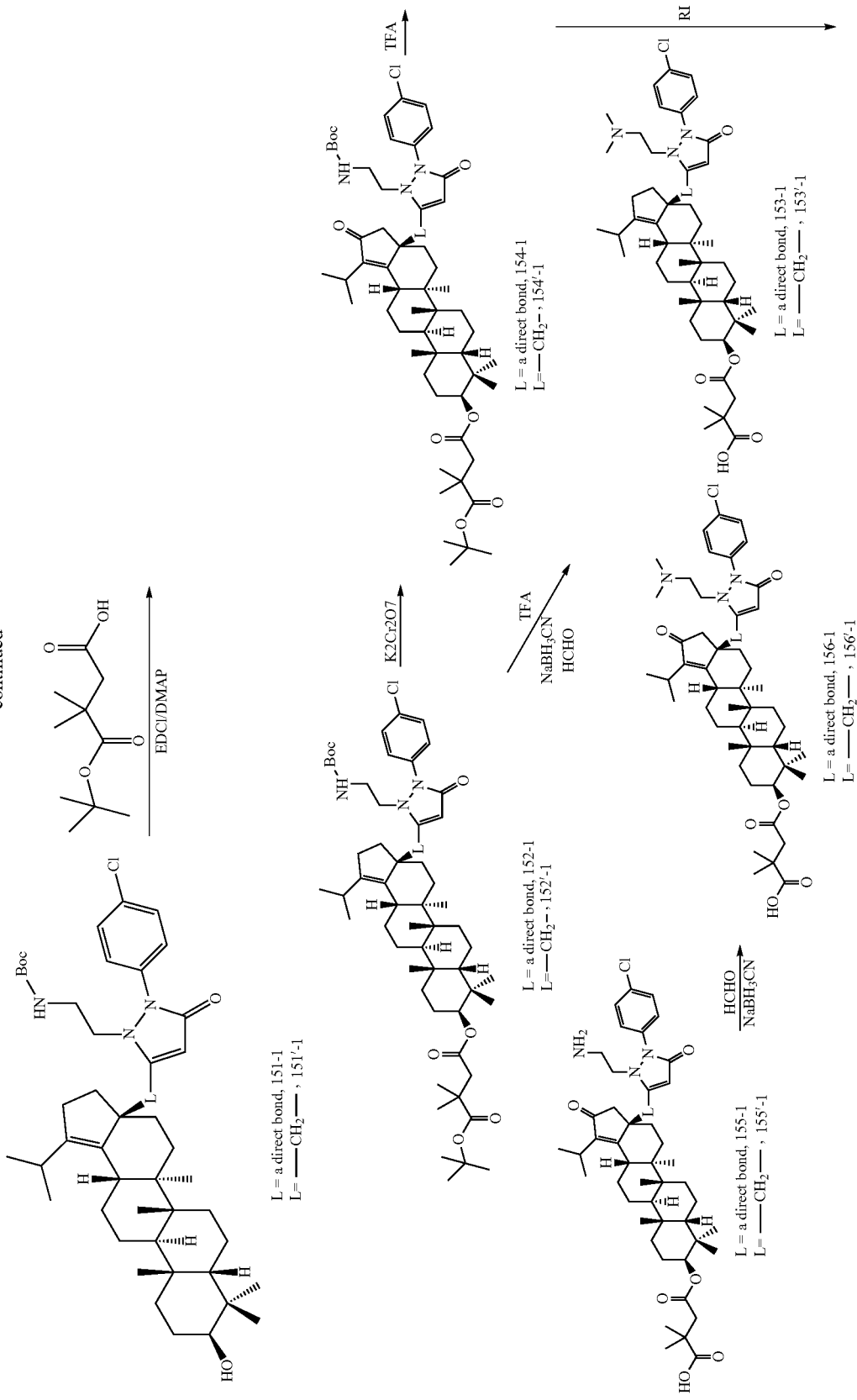

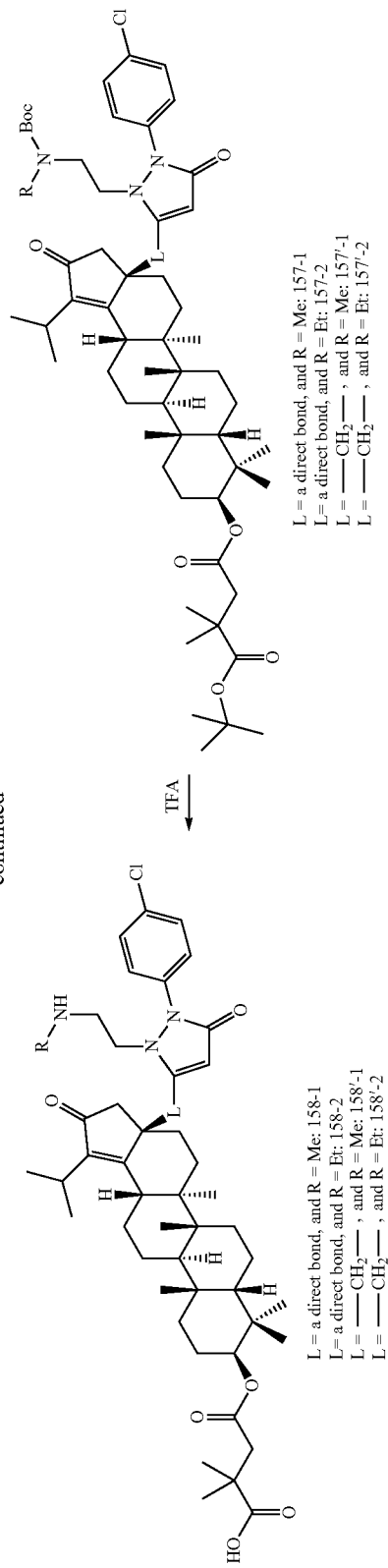

Method 19: Compound 164-1~164-2, and 165-1~165-2 were prepared according to scheme 19.
Scheme 19
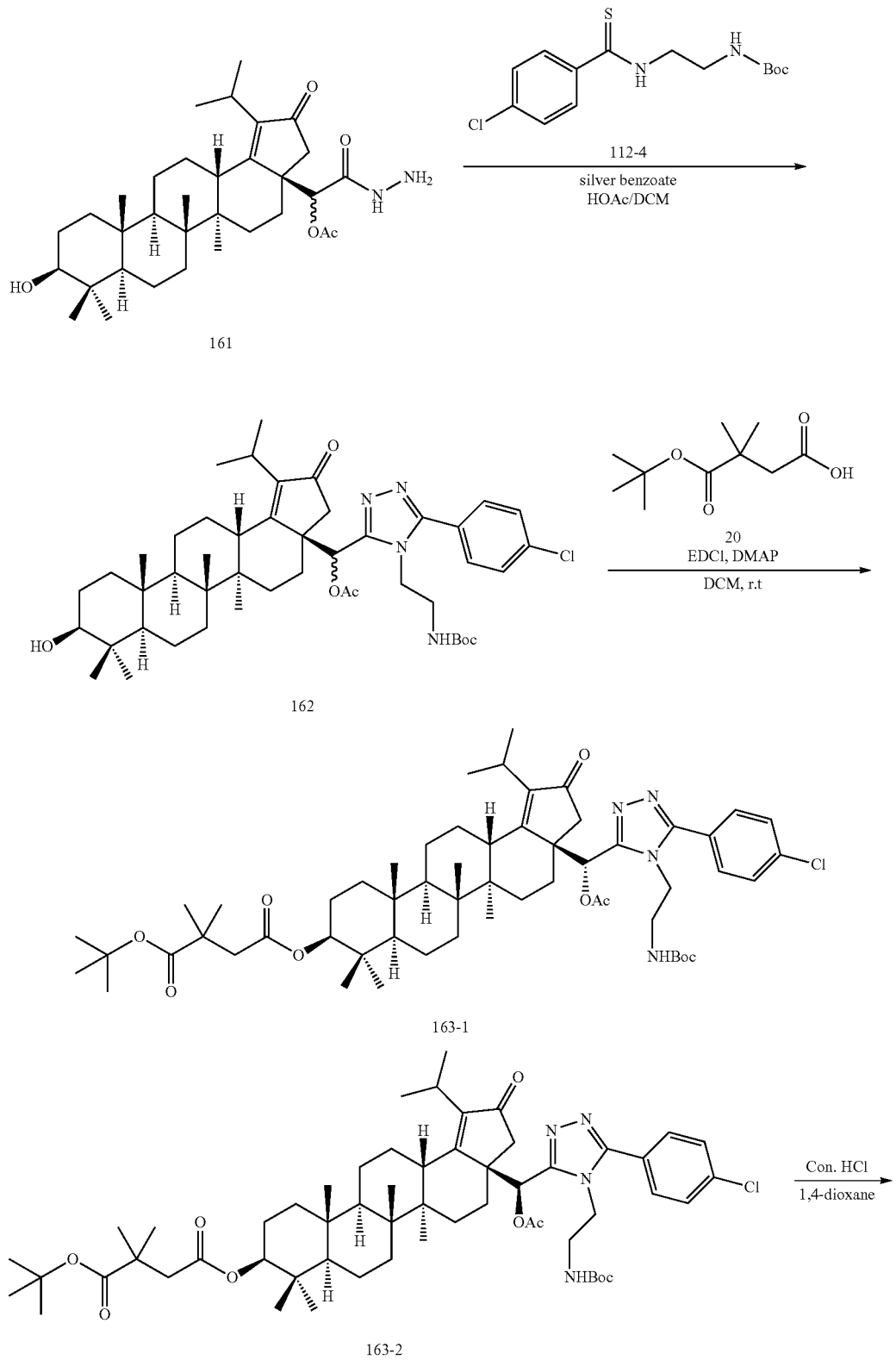

-continued

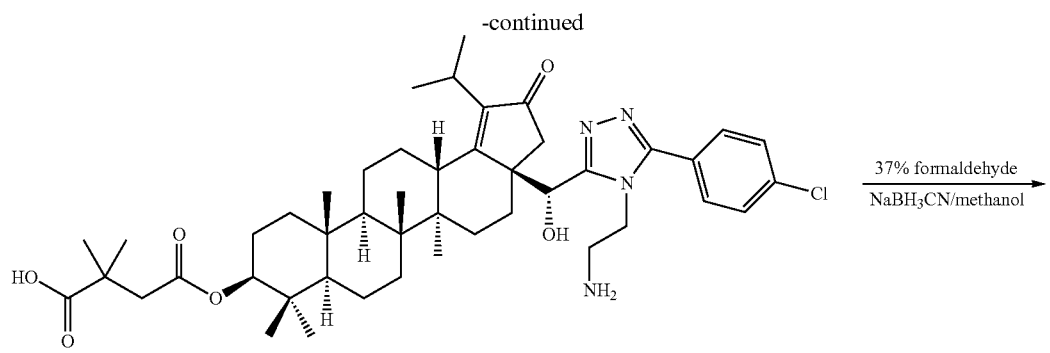

164-1

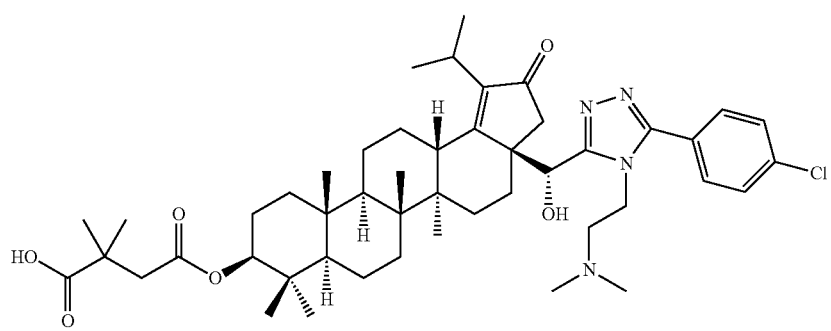

165-1

The compounds of the present invention may be in crystalline or non-crystalline form, it may exist in a number of different polymorphic forms, and may optionally be hydrated or solvated. This invention includes within its scope stoichiometric hydrates as well as compounds containing variable amount of water.

The pharmaceutically acceptable salts of the compounds of the present invention include conventional non-toxic salts, e.g. from non-toxic inorganic or organic acids or inorganic bases. For example, non-toxic salts include those derived from inorganic acids such as hydrochloric, hydrobromic, sulfuric, sulfamic, phosphoric, nitric and the like; and the salts prepared from organic acids such as acetic, propionic, benzoic, succinic, glycolic, gluconic, stearic, lactic, maleic, tartaric, citric, succinic, salicylic, ascorbic, pamoic, sulfanilic, 2-acetoxybenzoic, fumaric, formic, naphthalene-2-sulphonic, p-toluenesulfonic, benzenesulfonic, methanesulfonic, ethanesulfonic, ethane disulfonic, oxalic, isethionic, trifluoroacetic acids, and the like; and the salts prepared from inorganic bases such as NaOH, $Na_2CO_3$, $NaHCO_3$, $K_2CO_3$, KOH, and the like.

Generally, pharmaceutically acceptable salts can be prepared by reacting the free base or acid with stoichiometric amounts or with an excess of the desired salt-forming inorganic or organic acid or base, in a suitable solvent or solvent combination.

EXAMPLES

The following examples serve to illustrate the compounds in this invention and the preparation process, but the examples should not be considered as limiting the scope of the invention.

All the structures of the compounds in the present invention were confirmed by $^1$HNMR and MS. NMR Spectra: Bruker AVANCE-400 spectrometer in proper solvent: DMSO-$d_6$, $CDCl_3$, $CD_3OD$, δ in ppm rel. to $Me_4Si$ as internal standard.

The analytical low-resolution mass spectra (MS) were recorded on Agilent 1200 HPLC/6110 using a SunFire C18, 4.6×50 mm, 3.5 μm using a gradient elution method. The gradient elution method is: 80-5% solvent A and 20-95% solvent B for 1.8 mins, then solvent B and 5% solvent A 3 mins or more.

Solvent A: 0.01% trifluoroacetic acid (TFA) in water.
Solvent B: 0.01% TFA in acetonitrile
TLC: HSG-254 plates and GF254 plates.
Column chromatography (CC): silica gel (200-300 mesh).
The following abbreviations may be used in the below examples or in the process section hereinbefore:
DMSO-$D_6$: dimethyl sulfoxide-$d_6$
$CDCl_3$: chloroform-d
$CD_3OD$: methanol-$d_4$
THF: tetrahydrofuran
DMF: N,N-dimethylformamide
EtOAc: ethyl acetate
MeOH: methanol
EtOH: ethanol
MeCN: acetonitrile
DMSO: Dimethyl sulfoxide
DIPEA: ethyldiisopropylamine
TEA: triethylmaine
DCM: dichloromethane MeI: iodomethane
NaH: sodium hydride
Ac$_2$O: acetic anhydride
AcOH: acetic acid
HBr: hydrobromic acid
NaOAc: sodium acetate
K$_2$CO$_3$: potassium carbonate
NaOH: sodium hydroxide
KOH: potassium hydroxide
LiOH: lithium hydroxide
NaNO$_2$: sodium nitrite
TsCl: 4-methylbenzene-1-sulfonyl chloride
TsOH: 4-methylbenzenesulfonic acid
Na$_2$Cr$_2$O$_7$: sodium dichromate
K$_2$Cr$_2$O$_7$: potassium dichromate
NaClO$_2$: sodium chlorite
NaH$_2$PO$_4$: sodium dihydrogenorthophosphate
DMAP: 4-(dimethylamino)-pyridine
POCl$_3$: phosphoryl trichloride
NaBH$_4$: sodium borohydride
NaBH$_3$CN: sodium cyanogroupborohydride
HATU: 2-(7-aza-1H-benzotriazole-1-yl)-1,1,3,3-tetramethyluronium hexafluorophosphate
HBTU: 2-(1H-Benzotriazole-1-yl)-1,1,3,3-tetramethyluronium hexafluorophosphate
EDCl: N-(3-dimethylaminopropyl)-N'-ethylcarbodimide hydrochloride
HOBT: 1-hydroxybenzotriazole
PCC: pyridinium chlorochromate
Ph$_3$P: triphenylphosphine
DIAD: diisopropyl azodicarboxylate Example 1-18 (Compounds 22-1~22-18 were prepared according to method 1 and scheme 1 by using different acid intermediates like 16 and the like)

Synthesis of Compound 22-1

Synthesis of Compound 17-1

To a solution of compound 12 (100 mg, 0.18 mmol) in dichloromethane (5 ml) was added 4-chlorobenzoic acid 18 (43 mg, 0.28 mmol), HATU (102 mg, 0.27 mmol) and ethyldiisopropylamine (46 mg, 0.36 mmol) under nitrogen. The reaction mixture was stirred at room temperature for 1 h, concentrated and the resulted mixture (compound 17-1) was used directly in next step without the further purification.

m/z: [M+Na]$^+$ 701.3

Synthesis of Compound 18-1

Added tosyl chloride (102 mg, 0.54 mmol) and ethyldiisopropylamine (116 mg, 0.9 mmol) to the solution that contained compound 17-1 prepared above. The reaction mixture was stirred over night at room temperature, then directly purified by preparative TLC (ethyl acetate/petroleum ether=1:3) to afford compound 18-1 (39 mg, 32%) as an off-white solid.

m/z: [M+H]+661.4

Synthesis of Compound 19-1

To a solution of 18-1 (39 mg, 0.058 mmol) in a mixed solvent of methanol (2 ml), tetrahydrofuran (3 ml), and water (1 ml) was added sodium hydroxide (7 mg, 0.17 mmol). The resulted mixture was stirred at room temperature for 3 h, and diluted with water (10 ml). The mixture was extracted with dichloromethane (100 ml×3). The combined organic phase was washed with brine, dried over sodium sulfate, filtered and concentrated to afford crude compound 19-1 (33 mg, 90%) as a white solid, used directly in next step without the further purification.

m/z: [M+H]$^+$ 619.3

Synthesis of Compound 21-1

A solution of compound 19-1 (33 mg, 0.053 mmol), 4-tert-butoxy-3,3-dimethyl-4-oxobutanoic acid 20 (32 mg, 0.16 mmol), 4-dimethylaminopyridine (19 mg, 0.16 mmol) and EDCl (50 mg, 0.26 mmol) in dichloromethane (5 ml) was stirred overnight at room temperature, the resulted mixture (compound 21-1) was used directly in next step without the further purification.

Synthesis of Compound 22-1

To the solution of compound 21-1 prepared above in dichloromethane (5 ml) was added trifluoroacetic acid (0.5 ml), the reaction mixture was stirred at room temperature for 3 h, then diluted with water (10 ml). The mixture was extracted with dichloromethane (10 ml×3). The combined organic phase was washed with saturated solution of sodium bicarbonate (10 ml) and brine, dried over sodium sulfate, filtered and concentrated, the residue was purified by preparative TLC (methanol/dichloromethane=1:20) to afford compound 22-1 (28 mg, 71%) as an off-white solid.

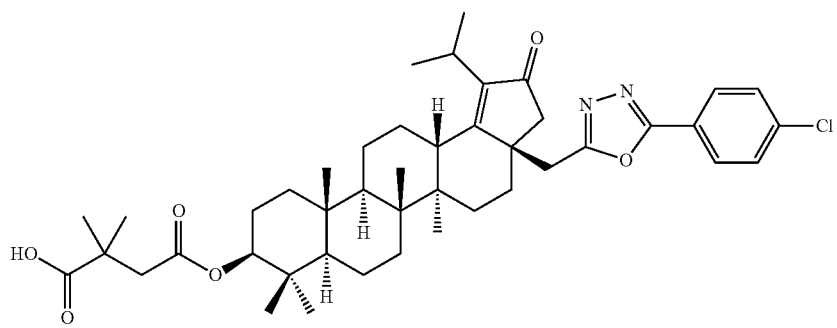

22-1 m/z: [M+H]$^+$ 747.4

$^1$HNMR (CDCl$_3$) δ 7.91-7.88 (2H, m), 7.48-7.45 (2H, m), 4.53-4.49 (1H, m), 3.38 (1H, d, J=14.4 Hz), 3.11 (1H, d, J=14.4 Hz), 3.07-2.97 (2H, m), 2.74-2.56 (4H, m). 2.10-0.79 (45H, m)

Compound 22-2 was prepared according to scheme 1 and method 1, as an off-white solid.

22-2
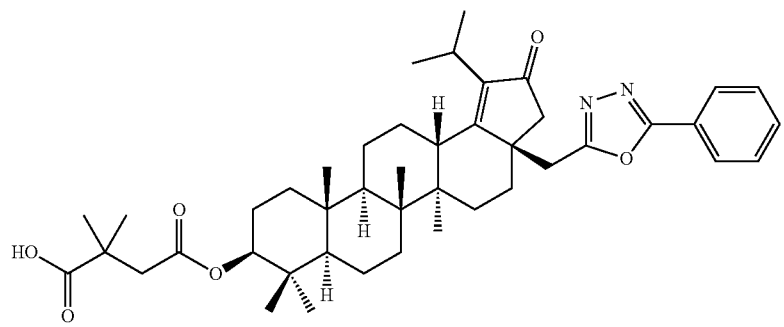
m/z: [M+H]⁺ 713.4
Compound 22-3 was prepared according to method 1 and scheme 1, as an off-white solid.
22-3
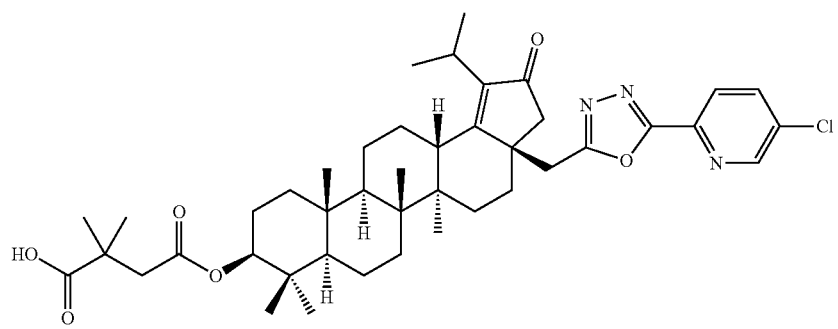
m/z: [M+H]⁺ 748.4
Compound 22-4 was prepared according to method 1 and scheme 1, as an off-white solid.
22-4
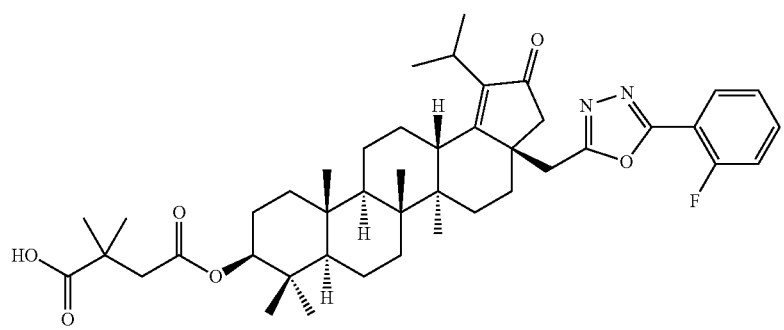
m/z: [M+H]⁺ 731.2
Compound 22-5 was prepared according to method 1 and scheme 1, as an off-white solid.

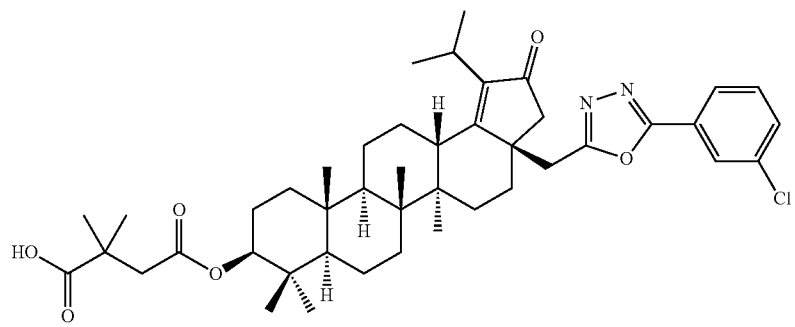
22-5
m/z: [M+H]+ 747.2
Compound 22-6 was prepared according to method 1 and scheme 1, as an off-white solid.
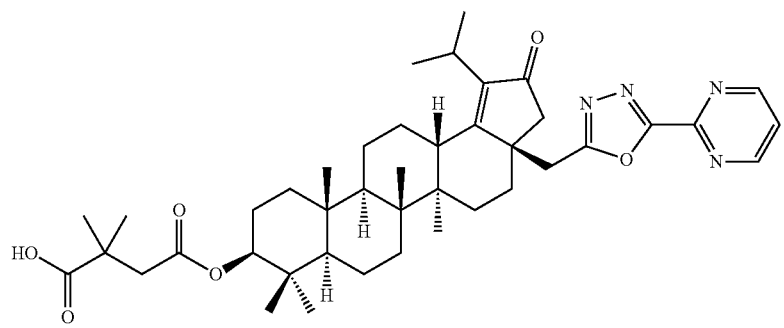
22-6
m/z: [M+H]+ 715.5
Compound 22-7 was prepared according to method 1 and scheme 1, as an off-white solid.
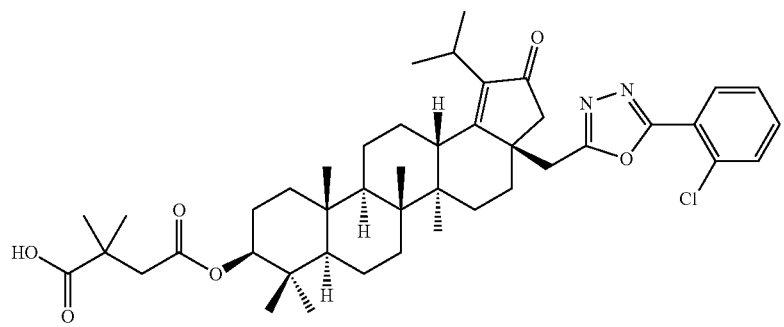
22-7
m/z: [M+H]+ 747.5
Compound 22-8 was prepared according to method 1 and scheme 1, as an off-white solid.

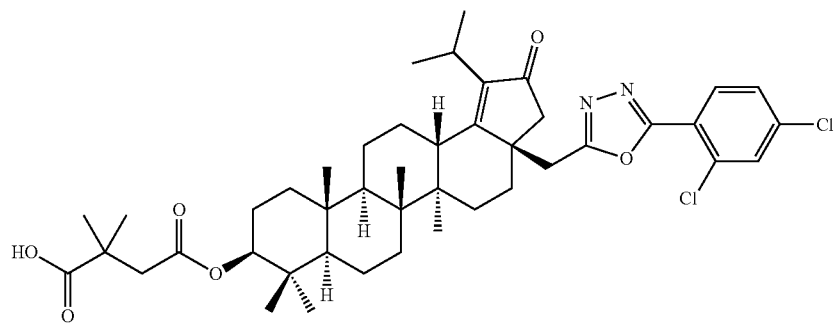
22-8
m/z: [M+H]⁺ 781.5
Compound 22-9 was prepared according to method 1 and scheme 1, as an off-white solid.
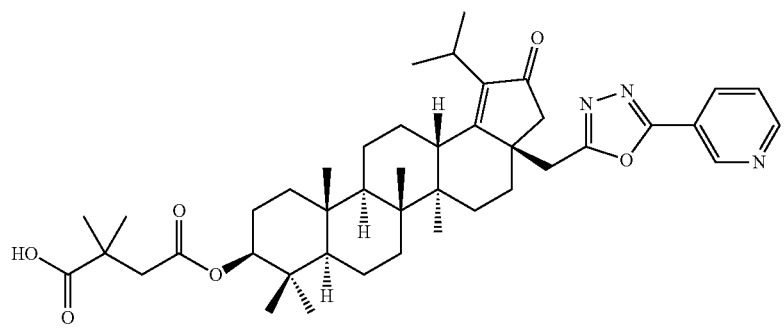
22-9
m/z: [M+H]⁺ 714.5
Compound 22-10 was prepared according to method 1 and scheme 1, as an off-white solid.
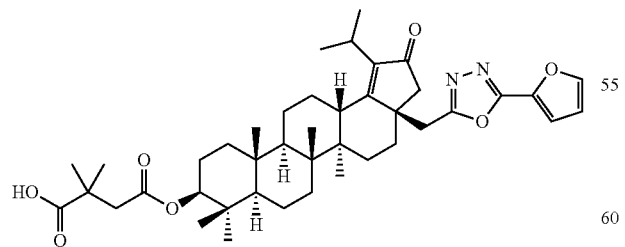
22-10
m/z: [M+H]⁺ 703.5
Compound 22-11 was prepared according to method 1 and scheme 1, as an off-white solid.

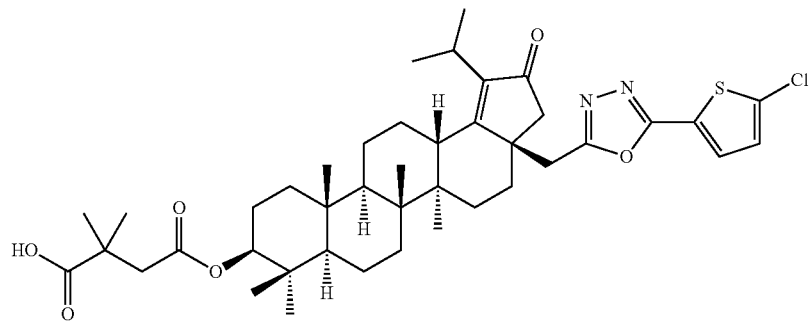
22-11
m/z: [M+H]$^+$ 753.4
Compound 22-12 was prepared according to scheme 1 and method 1, as an off-white solid.
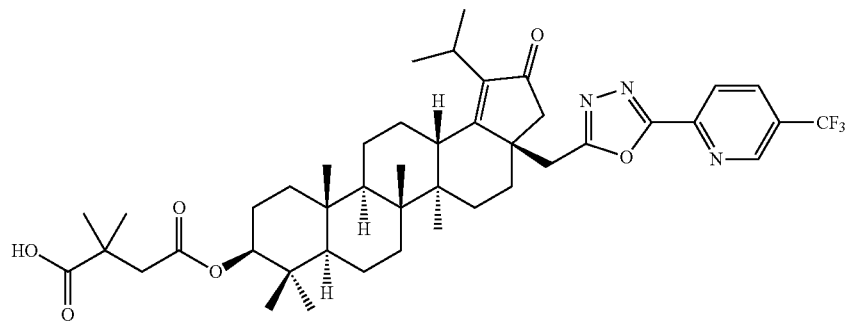
22-12
m/z: [M+H]$^+$ 782.4
Compound 22-13 was prepared according to scheme 1 and method 1, as an off-white solid.
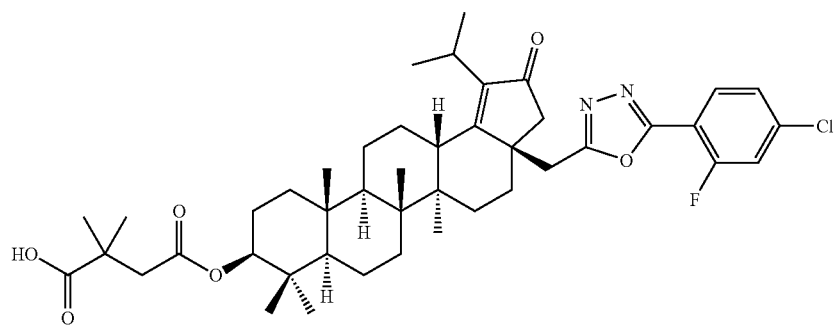
22-13
m/z: [M+H]$^+$ 765.3
Compound 22-14 was prepared according to method 1 and scheme 1, as an off-white solid.

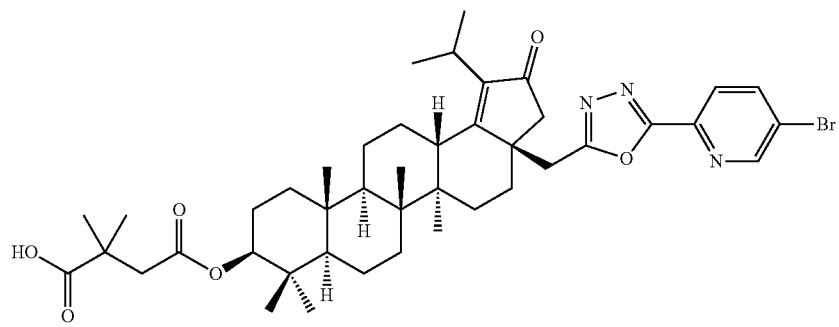
22-14
m/z: [M+H]⁺ 792.4
Compound 22-15 was prepared according to method 1 and scheme 1, as a white solid.
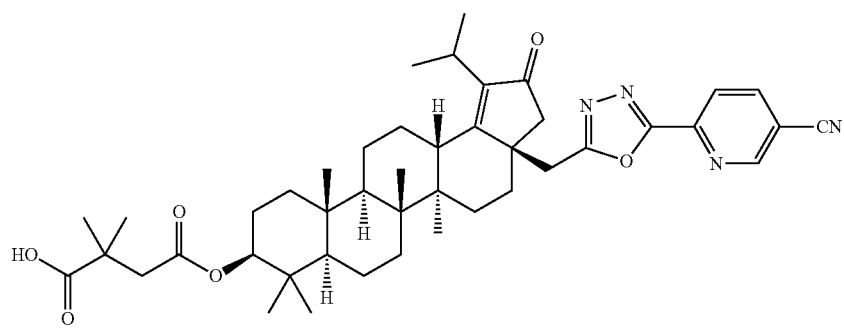
22-15
m/z: [M+H]⁺ 739.5
Compound 22-16 was prepared according to method 1 and scheme 1, as a white solid (5-chloropyrimidine-2-carboxylic acid was prepared according to US2007270438A1 and WO200528452A1).
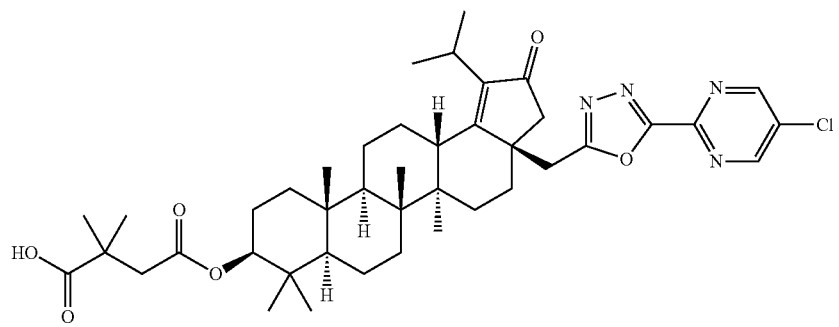
22-16
m/z: [M+H]⁺ 749.4
H¹NMR (CDCl₃) δ 8.88 (2H, s), 4.53-4.51 (1H, m), 3.30 (2H, s), 3.10-2.89 (3H, m), 2.71-2.56 (3H, m), 2.13-0.80 (45H, m)

Compound 22-17 was prepared according to method 1 and scheme 1, as an off white solid.

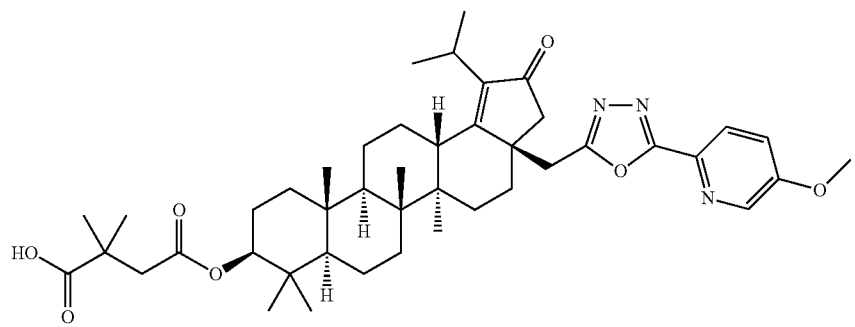

22-17 m/z: [M+H]+ 744.5

Compound 22-18 was prepared according to method 1 and scheme 1, as an off white solid.

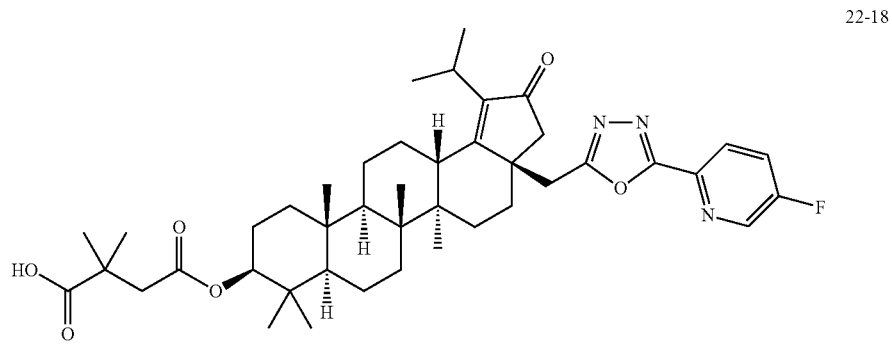

22-18 m/z: [M+H]+ 732.4

Example 19-32 (Compound 27-1~27-14 were prepared according to method 1 and scheme 2 by using different acid intermediates like 16 and the like)

Synthesis of Compound 23-1

To a solution of compound 15 (150 mg, 0.28 mmol) in dichloromethane (5 ml) was added 4-chlorobenzoic acid 18 (68 mg, 0.43 mmol), HATU (159 mg, 0.43 mmol) and ethyldiisopropylamine (72 mg, 0.56 mmol) under nitrogen. The reaction mixture was stirred at room temperature for 1 h, and the resulted mixture (compound 23-1) was used directly in next step without the further purification.

m/z: [M+Na]+ 687.3

Synthesis of Compound 24-1

To the solution of compound 23-1 prepared above in dichloromethane (5 ml) was added tosyl chloride (159 mg, 0.84 mmol) and ethyldiisopropylamine (180 mg, 1.4 mmol). The resulted mixture was stirred over night at room temperature, then directly purified by preparative TLC (ethyl acetate/petroleum ether=1:3) to afford compound 24-1 (61 mg, 34%) as an off-white solid.

m/z: [M+H]+ 669.2

Synthesis of Compound 25-1

To a solution of 24-1 (61 mg, 0.094 mmol) in a mixed solvent of methanol (2 ml), tetrahydrofuran (1 ml), and water (0.5 ml) was added sodium hydroxide (11 mg, 0.28 mmol). The resulted mixture was stirred at room temperature for 3 h. The mixture was diluted with water (10 ml), extracted with dichloromethane (100 ml×3). The combined organic phase was washed with brine, dried over sodium sulfate, filtered and concentrated to afford compound 25-1 (55 mg, 96%) as a white solid, used directly in next step without the further purification.

m/z: [M+H]+ 605.4

Synthesis of Compound 26-1

A solution of compound 25-1 (55 mg, 0.090 mmol), 4-tert-butoxy-3,3-dimethyl-4-oxobutanoic acid 20 (55 mg, 0.27 mmol), 4-dimethylaminopyridine (33 mg, 0.27 mmol) and EDCl (85 mg, 0.45 mmol) in dichloromethane (5 ml) was stirred overnight at room temperature, the resulted mixture (compound 26-1) was used directly in next step without the further purification.

Synthesis of Compound 27-1

To the solution of compound 26-1 prepared above in dichloromethane (5 ml) was added trifluoroacetic acid (0.5 ml). After the reaction mixture was stirred at room temperature for 3 hr, then diluted with water (10 ml). The mixture was extracted with dichloromethane (10 ml×3). The combined organic phase was washed with saturated solution of sodium bicarbonate (10 ml), aqueous HCl (1N, 10 ml) and brine, dried over sodium sulfate, filtered and concentrated, the residue was purified by preparative TLC (methanol/dichloromethane=1:20) to afford compound 27-1 (54 mg, 71%) as an off-white solid.

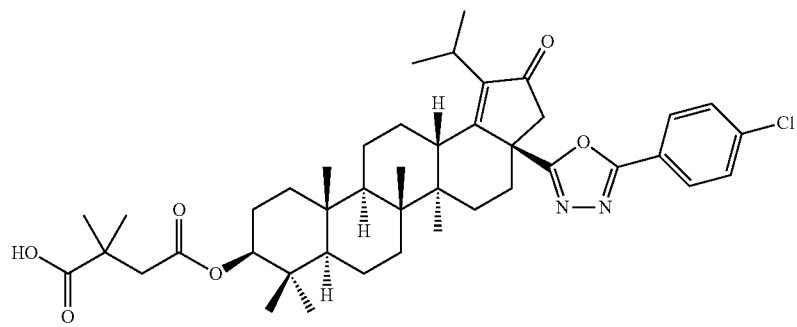
27-1
m/z: [M+H]⁺ 733.3
¹HNMR (CDCl₃) δ 7.94-7.90 (2H, m), 7.50-7.47 (2H, m), 4.51-4.47 (1H, m), 3.30-3.26 (1H, m), 2.81-2.38 (6H, m), 2.16-0.76 (44H, m)
Compound 27-2 was prepared according to method 2 and scheme 2, as an off-white solid.
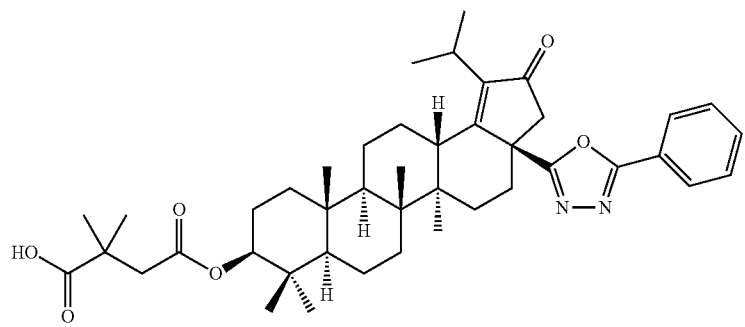
27-2
m/z: [M+H]⁺ 699.4
Compound 27-3 was prepared according to method 2 and scheme 2, as an off-white solid.
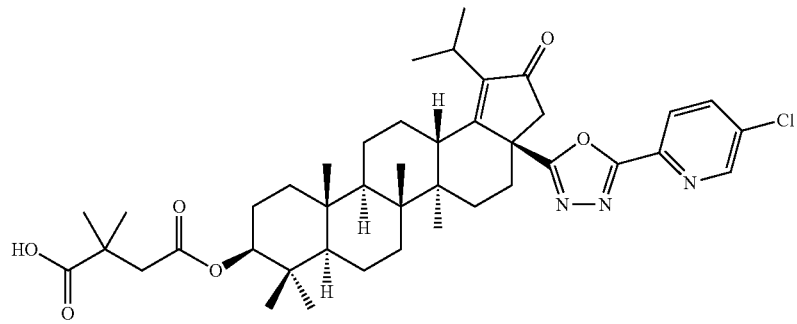
27-3
m/z: [M+H]⁺ 734.4
Compound 27-4 was prepared according to method 2 and scheme 2, as an off-white solid.

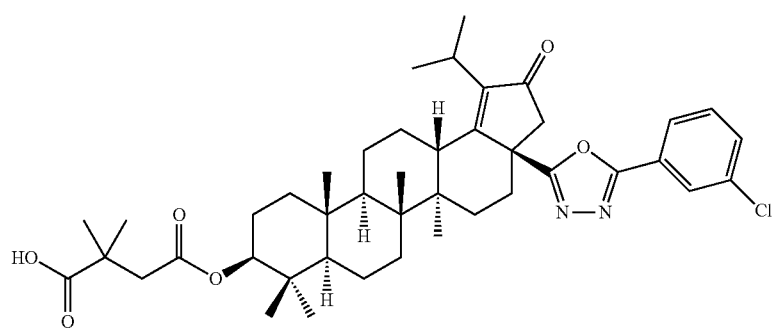

27-4 m/z: [M+H]+ 733.2

Compound 27-5 was prepared according to method 2 and scheme 2, as an off-white solid.

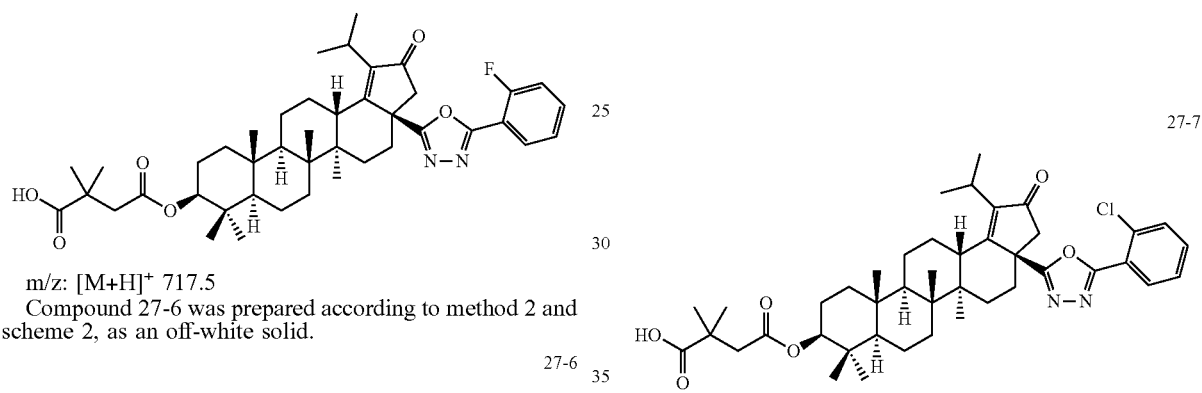

27-5 m/z: [M+H]+ 717.5

Compound 27-6 was prepared according to method 2 and scheme 2, as an off-white solid.

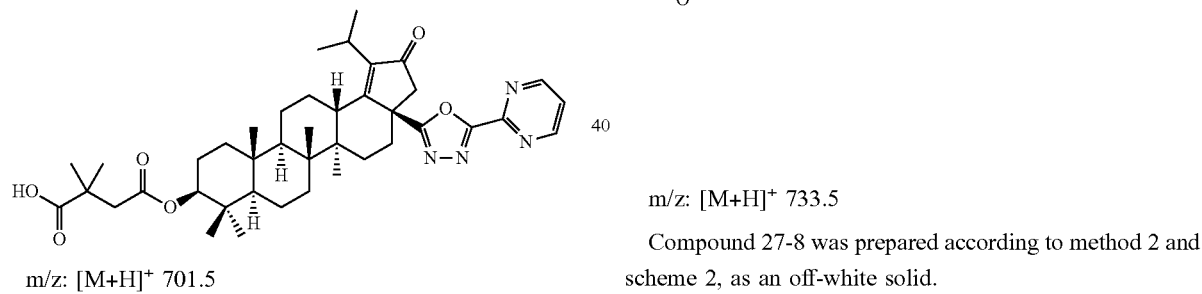

27-6 m/z: [M+H]+ 701.5

Compound 27-7 was prepared according to method 2 and scheme 2, as an off-white solid.

27-7 m/z: [M+H]+ 733.5

Compound 27-8 was prepared according to method 2 and scheme 2, as an off-white solid.

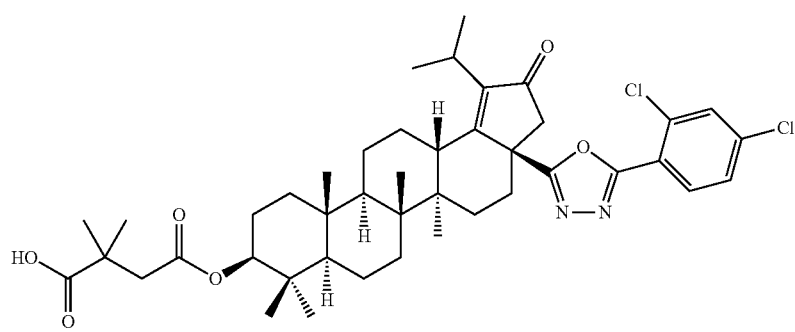

27-8 m/z: [M+H]+ 767.5

Compound 27-9 was prepared according to method 2 and scheme 2, as an off-white solid.

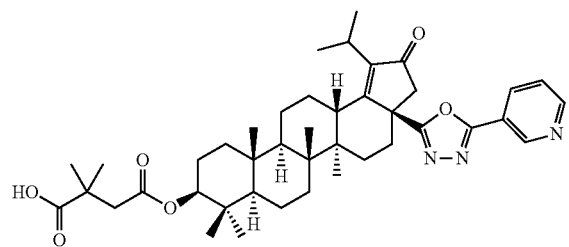
m/z: [M+H]+ 700.5
Compound 27-10 was prepared according to method 2 and scheme 2, as an off-white solid.
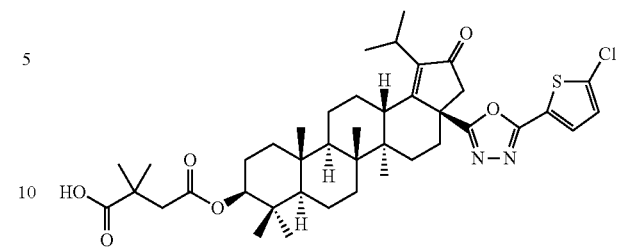
m/z: [M+H]+ 739.2
Compound 27-11 was prepared according to method 2 and scheme 2, as an off-white solid.
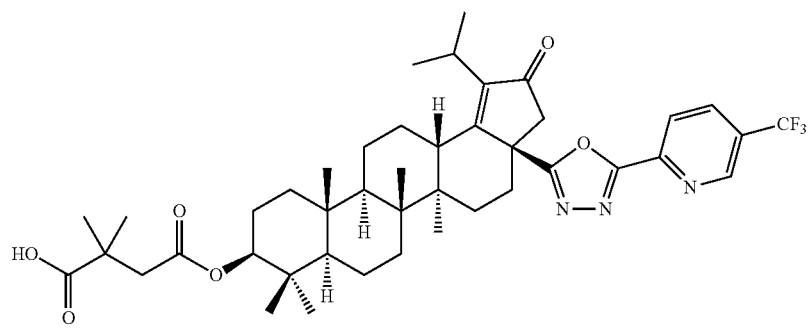
m/z: [M+H]+ 768.2
Compound 27-12 was prepared according to method 2 and scheme 2, as an off-white solid.
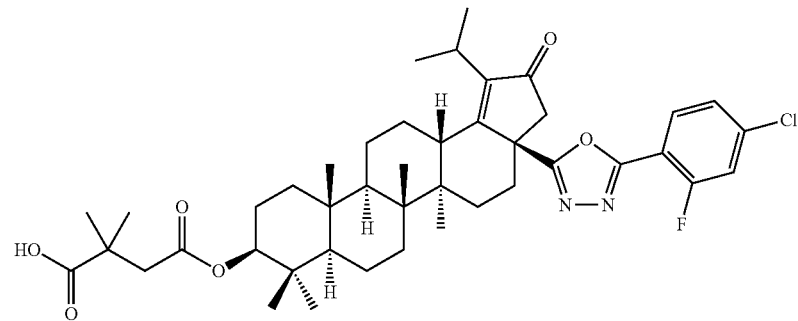
m/z: [M+H]+ 751.3
Compound 27-13 was prepared according to method 2 and scheme 2, as an off-white solid.
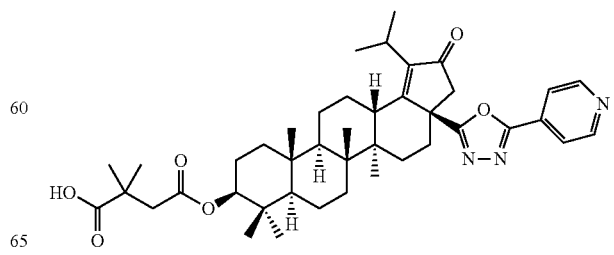
m/z: [M+H]+ 700.5

Compound 27-14 was prepared according to method 2 and scheme 2, as an off white solid.

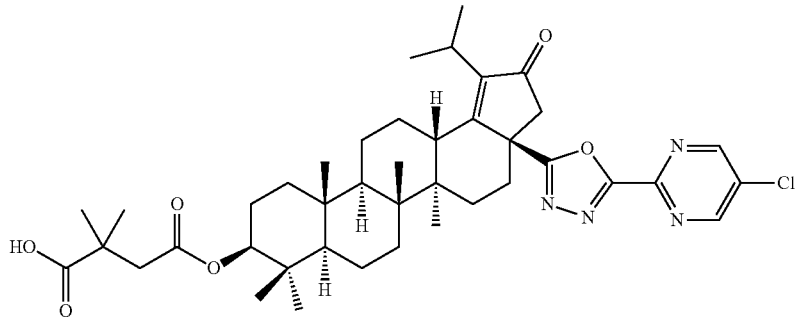

27-14 m/z: [M+H]+ 735.3

Example 33 (Compound 33 was prepared according to method 3 and scheme 3)

Synthesis of Compound 29

A mixture of compound 12 (100 mg, 0.18 mmol), 4-chlorophenylacetic acid 28 (45 mg, 0.27 mmol), 1-hydroxybenzotriazole (36 mg, 0.27 mmol), EDCl (69 mg, 0.36 mmol) and ethyldiisopropylamine (46 mg, 0.36 mmol) in dichloromethane (5 ml) was stirred at room temperature for 1 h, then directly purified by preparative TLC (methanol/dichloromethane=1:20) to afford compound 29 (100 mg, 78%) as a white solid.

m/z: [M+Na]+ 715.4

Synthesis of Compound 30

To a solution of compound 29 (100 mg, 0.14 mmol) in acetonitrile (5 ml) was added phosphorus oxychloride (221 mg, 1.4 mmol). The reaction mixture was stirred at reflux for 2 h, then cooling down to room temperature, the reaction mixture was added crushed ice, and extracted with ethyl acetate (20 ml×3). The combined organic phase was washed with brine, dried over sodium sulfate, filtered and concentrated, the residue was purified by preparative TLC (ethyl acetate/petroleum ether=1:3) to afford compound 30 (30 mg, 31%) as a white solid.

extracted with dichloromethane (10 ml×3). The combined organic phase was washed with brine, dried over sodium sulfate, filtered and concentrated to afford compound 31 (29 mg, 100%) as a white solid, used directly in next step without the further purification.

m/z: [M+H]+ 633.3

Synthesis of Compound 32

A solution of compound 31 (29 mg, 0.046 mmol), 4-tert-butoxy-3,3-dimethyl-4-oxobutanoic acid 20 (28 mg, 0.13 mmol), 4-dimethylaminopyridine (17 mg, 0.13 mmol) and EDCl (44 mg, 0.23 mmol) in dichloromethane (5 ml) was stirred overnight at room temperature, the resulted mixture (compound 32) was used directly in next step without the further purification.

Synthesis of Compound 33

To the solution of compound 32 prepared above in dichloromethane (5 ml) was added trifluoroacetic acid (0.5 ml). After the reaction mixture was stirred at room temperature for 3 h, then water (10 ml) was added, and the aqueous phase was extracted with dichloromethane (10 ml×3). The combined organic phase was washed with saturated solution of sodium carbonate (10 ml) and brine, dried over sodium sulfate, filtered and concentrated. The residue was purified preparative TLC (ethyl acetate/petroleum ether=1:1) to afford compound 33 (13 mg, 37%) as a white foam.

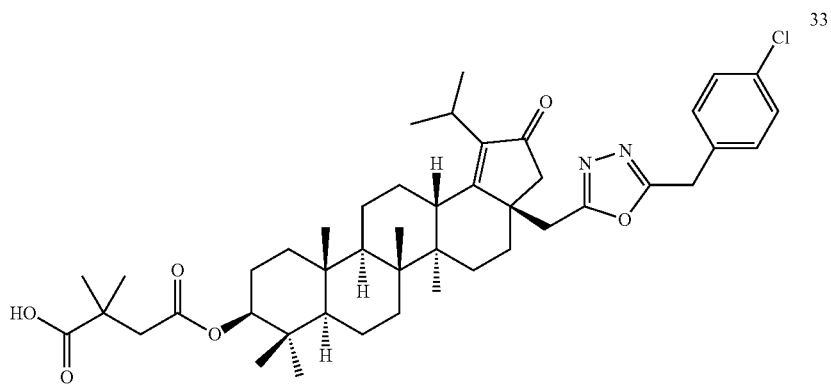

33 m/z: [M+H]+ 675.3

Synthesis of Compound 31

To a solution of compound 30 (30 mg, 0.044 mmol) in a mixed solvent of methanol (2 ml), tetrahydrofuran (1 ml), and water (0.5 ml) was added sodium hydroxide (5 mg, 0.13 mmol). The resulted mixture was stirred at room temperature for 3 h. The reaction was diluted with water (10 ml), m/z: [M+Na]+ 783.4

Example 34 (Compound 38 was prepared according to method 4 and scheme 4)

Synthesis of Compound 34

A mixture of compound 15 (100 mg, 0.19 mmol), 4-chlorophenylacetic acid 28 (48 mg, 0.28 mmol), 1-hydroxybenzotriazole (38 mg, 0.28 mmol), EDCl (72 mg, 0.38 mmol) and ethyldiisopropylamine (44 mg, 0.38 mmol) in dichloromethane (5 ml) was stirred at room temperature for 1 h, then directly purified by preparative TLC (ethyl acetate/petroleum ether=1:1) to afford compound 34 (80 mg, 62%) as a white solid.

m/z: [M+Na]$^+$ 701.3

Synthesis of Compound 35

To a solution of compound 34 (80 mg, 0.12 mmol) in acetonitrile (5 ml) was added phosphorus oxychloride (180 mg, 1.1 mmol). The reaction mixture was refluxed for 1 h and concentrated to dryness. The residue was purified by preparative TLC (ethyl acetate/petroleum ether=1:1) to afford compound 35 (50 mg, 64%) as a white solid, used directly in next step without the further purification.

m/z: [M+H]$^+$ 661.4

Synthesis of Compound 36

To a solution of compound 35 (50 mg, 0.075 mmol) in a mixed solvent of methanol (2 ml), tetrahydrofuran (1 ml), and water (0.5 ml) was added sodium hydroxide (9 mg, 0.23 mmol). The resulted mixture was stirred at room temperature for 3 h. The reaction was diluted with water (10 ml), extracted with dichloromethane (10 ml×3). The combined organic phase was washed with brine, dried over sodium sulfate, filtered and concentrated to afford compound 36 (46 mg, 98%) as a white solid, used directly in next step without the further purification.

m/z: [M+H]$^+$ 619.4

Synthesis of Compound 37

A solution of compound 36 (46 mg, 0.074 mmol), 4-tert-butoxy-3,3-dimethyl-4-oxobutanoic acid 20 (45 mg, 0.22 mmol), 4-dimethylaminopyridine (27 mg, 0.22 mmol) and EDCl (71 mg, 0.37 mmol) in dichloromethane (5 ml) was stirred overnight at room temperature, the resulted mixture (compound 37) was used directly in next step without the further purification.

Synthesis of Compound 38

To the solution of compound 37 prepared above in dichloromethane (5 ml) was added trifluoroacetic acid (0.5 ml). After the reaction mixture was stirred at room temperature for 3 hr, the reaction mixture was diluted with water (10 ml), extracted with dichloromethane (10 ml×3). The combined organic phase was washed with saturated solution of sodium carbonate (10 ml) and brine, dried over sodium sulfate, filtered and concentrated. The residue was purified by preparative TLC (ethyl acetate/petroleum ether=1:1) to afford compound 33 (20 mg, 36%) as a white foam.

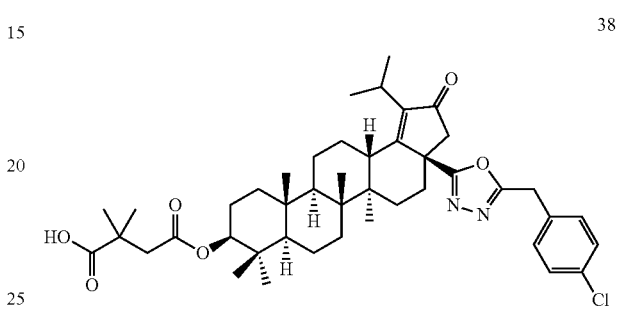

38 m/z: [M+Na]$^+$ 747.4

$^1$ HNMR (CDCl3) δ 7.31-7.29 (2H, m), 7.20-7.18 (2H, m), 4.51-4.47 (1H, m), 4.15 (2H, dd, J=16 Hz, J=36 Hz), 3.24-3.17 (1H, m), 2.70-0.73 (50H, m)

Example 35-36 (Compound 54-1~54-2 was prepared according to method 5 and scheme 5)

Synthesis of Key Intermediates 40-1, 40-2, 46 and 49

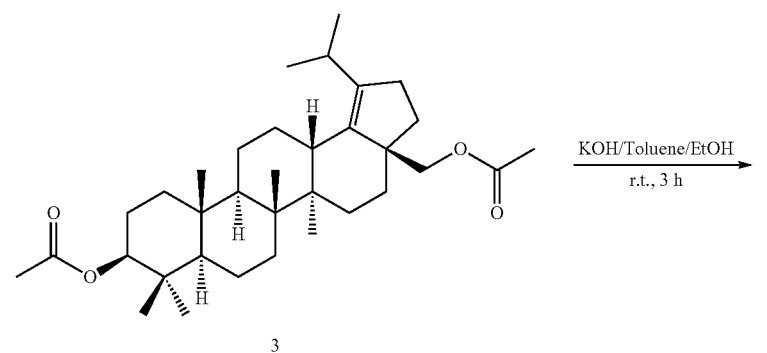

3

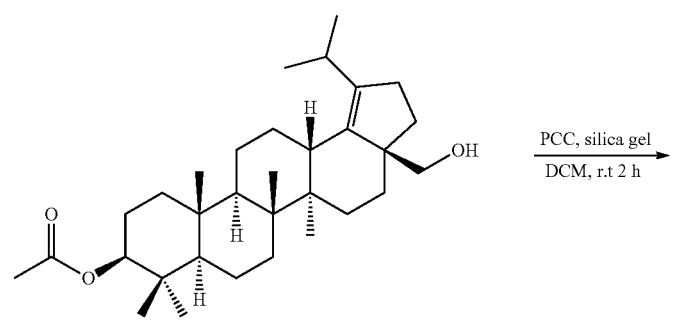

39

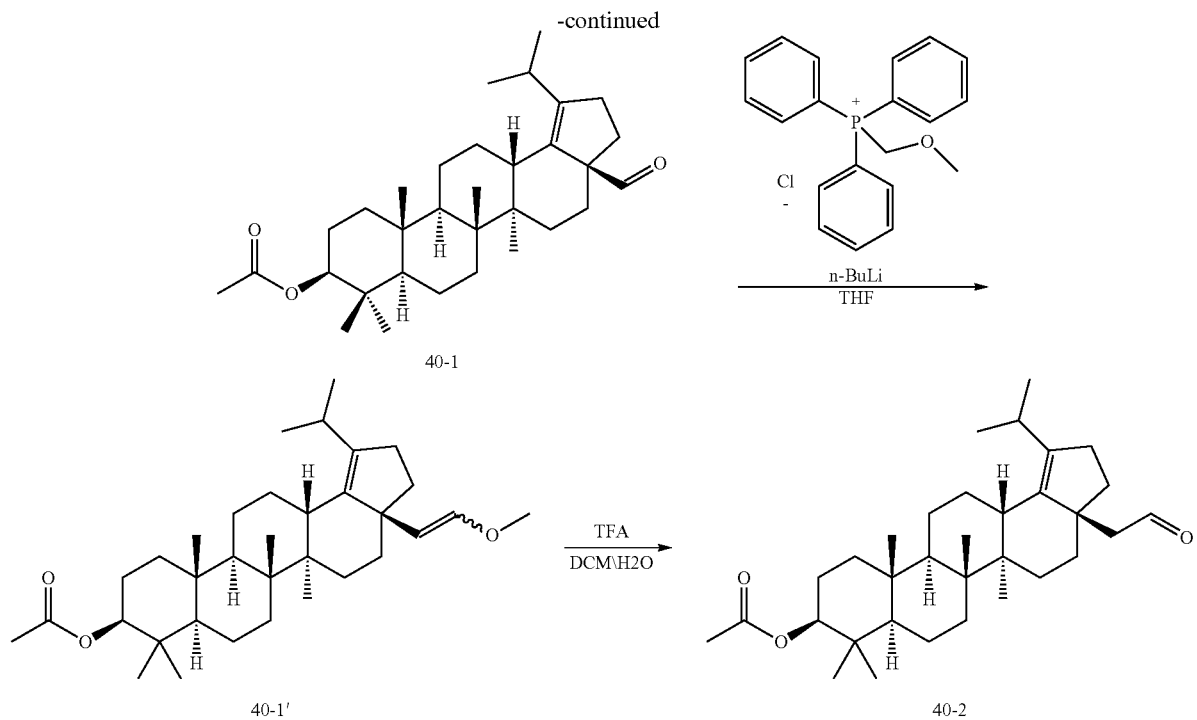

Synthesis of Compound 39

To a solution of compound 3 (18 g, 34.1 mmol) in a mixed solvent of ethanol (100 ml) and toluene (100 ml) was added potassium hydroxide (2.1 g, 37.5 mmol). The resulted mixture was stirred at room temperature for 3 hr, neutralized with aqueous HCl (2N) and then evaporated to dryness. The solid was triturated with water and minimum of acetone, and solid was collected by filtration, and dried to afford compound 39 (15 g, 91%) as a white solid, used directly in next step without the further purification.

m/z: [M+Na]$^+$ 507.4

Synthesis of Compound 40-1

To a solution of compound 39 (10 g, 20.6 mmol) in dichloromethane (200 ml) was added pyridinium chlorochromate (8.8 g, 40.1 mmol) and silica gel (10 g). The resulted mixture was stirred at room temperature for 2 hr, then water (100 ml) was added, the organic layer was washed with saturated solution of sodium bicarbonate (120 ml) and brine (100 ml), dried over sodium sulfate and concentrated. The residue was purified by chromatography on silica gel (ethyl acetate/petroleum ether=1:10) to afford compound 40-1 (5.8 g, 58%) as a white solid.

m/z: [M+Na]$^+$ 505.4

Synthesis of Compound 40-1'

To an ice-cooling suspension of (methoxymethy)triphenylphosphonium (4.69 g, 13.67 mmol) in anhydrous tetrahydrofuran (40 ml) was added dropwise a 2.5 M n-butyllithium solution in hexanes (13.67 ml, 34.18 mmol). The solution was stirred at room temperature for 15 minutes to provide a deep red solution. Then added compound 40-1 (5.5 g, 11.39 mmol) in one portion at 0° C., the reaction mixture was stirred for 30 min. The solution was dry loaded directly onto silica gel and purified by chromatography on silica gel (PE/EA=100:1) to afford compound 40-1' (1.95 g, 34%) as a white solid.

Synthesis of Compound 40-2

To a solution of compound 40-1' (1.90 g, 3.72 mmol) in dichloromethane (20 ml) was added TFA (0.2 ml) and H2O (0.2 ml). The resulting solution was stirred at room temperature for overnight. The solution was dried over sodium sulfate and concentrated, the residue was purified by chromatography on silica gel (PE/EA=100:1~10:1) to afford compound 40-2 (0.8 g, 43%) as a white solid.

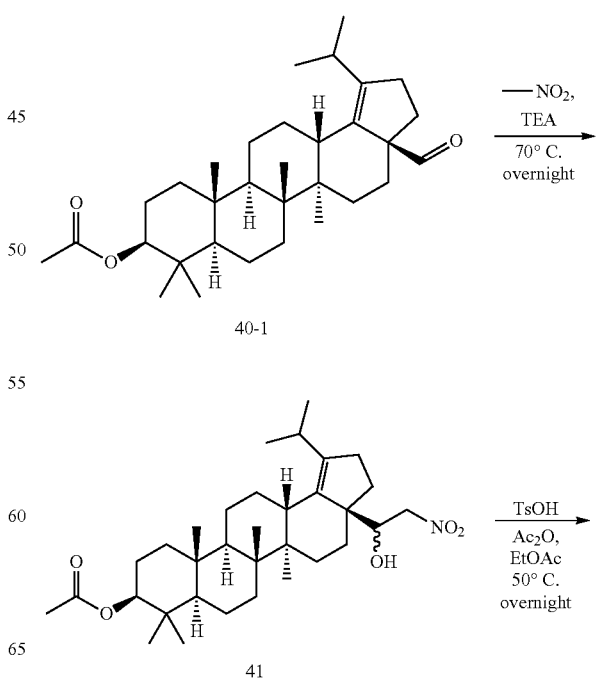

-continued

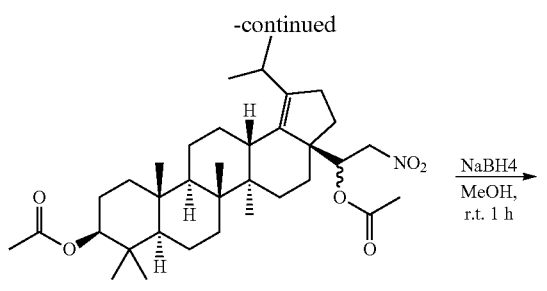

42

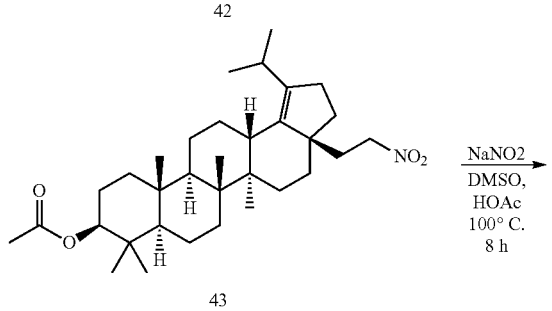

43

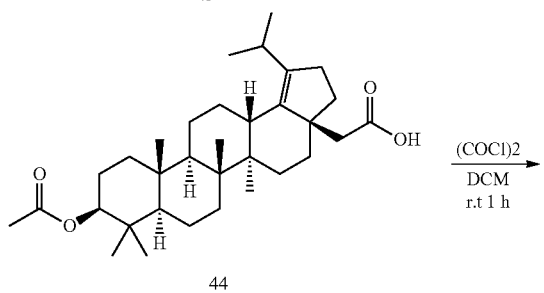

44

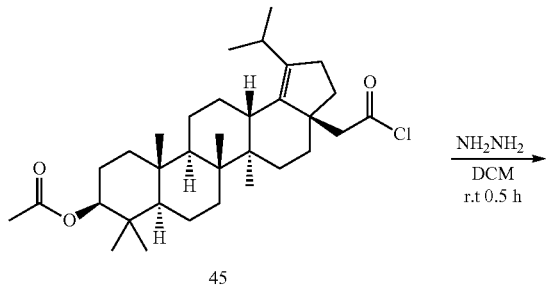

45

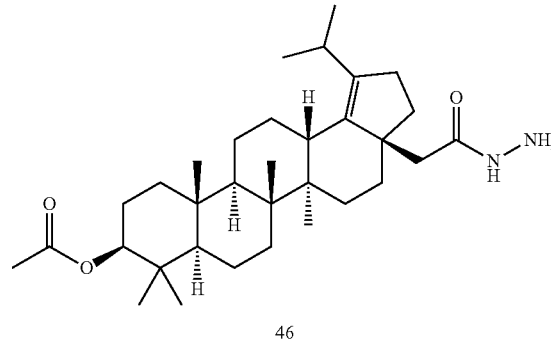

46

Synthesis of Compound 41

A solution of compound 40-1 (5 g, 10.36 mmol) in nitromethane (20 ml) and triethylamine (20 ml, 144 mmol) was stirred overnight at 70° C., and concentrated to dryness. The residue was purified by chromatography on silica gel (ethyl acetate/petroleum ether=1:10~1:7) to afford compound 41 (2.5 g, 44%) as a white solid.

m/z: [M+Na]$^+$ 566.8

Synthesis of Compound 42

To a solution of compound 41 (19 g, 34.1 mmol) in a mixed solvent of acetic anhydride (10 ml) and ethyl acetate (10 ml) was added p-toluenesulfonic acid (0.21 g, 1.15 mmol). The resulted mixture was stirred overnight at 50° C., then the solvent was evaporated, the residue was dissolved in dichloromethane (100 ml), the organic layer was washed with brine, dried over sodium sulfate and concentrated to afford compound 42 (2.65 g, 100%) as a yellow oil, used directly in next step without the further purification.

m/z: [M+Na]$^+$ 608.5

Synthesis of Compound 43

To an ice-cooling solution of compound 42 (2.65 g, 4.52 mmol) in methanol (25 ml) was added sodium borohydride (0.68 g, 18.09 mmol) in small portions. The reaction mixture was stirred at room temperature for 2 h, then the solvent was evaporated to dryness, the residue was dissolved in dichloromethane, the organic layer was washed with water and brine, dried over sodium sulfate and concentrated. The residue was purified by chromatography on silica gel (ethyl acetate/petroleum ether=1:20~1:3) to afford compound 43 (1 g, 42%) as a white solid.

Synthesis of Compound 44

To a solution of compound 43 (1 g, 22.1 mmol) in dimethyl sulfoxide (10 ml) was added sodium nitrite (0.65 g, 9.47 mmol) and acetic acid (1.88 g, 31.2 mmol). The reaction mixture was stirred overnight at 100° C., then diluted with water (30 ml), extracted with dichloromethane (30 ml×3). The combined organic phase was washed with brine, dried over sodium sulfate, filtered and concentrated. The residue was purified by chromatography on silica gel (ethyl acetate/petroleum ether=1:10~1:5) to afford compound 44 (220 mg, 23%) as a yellow solid.

m/z: [M+Na]$^+$ 535.5

Synthesis of Compound 45

To a solution of compound 44 (220 mg, 0.43 mmol) in dichloromethane (5 ml) was added oxalyl chloride (463 mg, 1.29 mmol) and a drop of N,N- dimethylformamide. The reaction mixture was stirred at room temperature for 1 h and concentrated to afford compound 45 (227 mg, 100%) as a yellow solid, used directly in next step without the further purification.

Synthesis of Compound 46

To this solution of Compound 45 (227 mg, 0.43 mmol) in dichloromethane (1 ml) was added dropwise a solution of hydrazine hydrate (75 mg, 1.28 mmol) in dichlormethane (5 ml), the mixture was stirred at 0 for 30 min and then concentrated to dryness. The residue was triturated with petroleum ether, and the solid was collected by filtration, and dried to afford compound 46 (200 mg, 89%) as a yellow solid, used directly in next step without the further purification.

m/z: [M+H]$^+$ 527.5

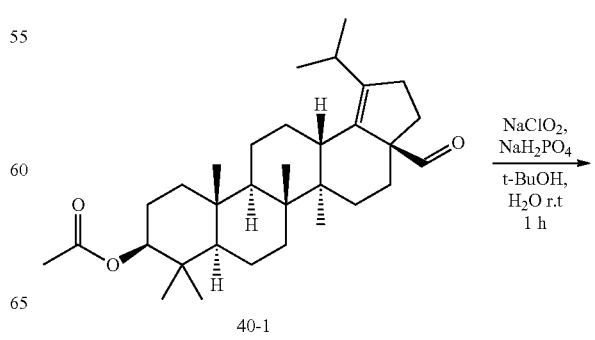

40-1

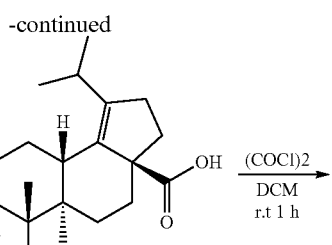

47

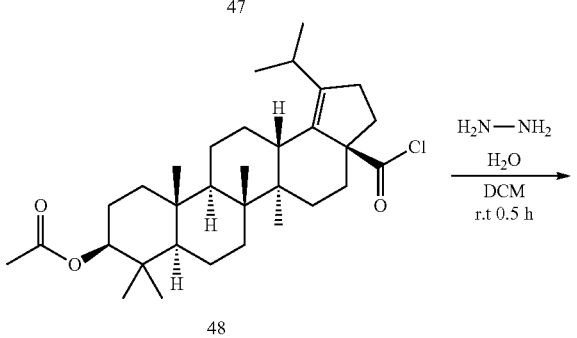

48

49

Synthesis of Compound 47

To a solution of compound 40-1 (2.0 g, 2.0 mmol) and 2-methyl-2-butene (1.2 ml, 12.4 mmol) in t-butanol (20 ml) was added a solution of sodium dihydrogen phosphate (1.49 g, 12.4 mmol) and sodium chlorite (1.12 g, 12.4 mmol) in water (5 ml). The resulted mixture was stirred at room temperature for 1 h, then water (20 ml) was added. The mixture was extracted with ethyl acetate (30 ml×3). The combined organic phase was washed with brine, dried over sodium sulfate, filtered and concentrated. The residue was triturated with petroleum ether, and the solid was collected by filtration, and dried to afford compound 47 (1.8 g, 87%) as a yellow solid, used directly in next step without the further purification.

m/z: [M+Na]$^+$ 521.3

Synthesis of Compound 48

To a solution of compound 47 (300 mg, 0.59 mmol) in dichloromethane (10 ml) was added oxalyl chloride (0.25 ml, 3.0 mmol) and a drop of N,N-dimethylformamide. The reaction mixture was stirred at room temperature for 1 h and concentrated to afford compound 48 (518 mg, 100%) as a light yellow solid, used directly in next step without the further purification.

Synthesis of Compound 49

To the solution of compound 49 (518 mg, 1.0 mmol) in dichloromethane (5 ml) was added dropwise a solution of hydrazine hydrate (177 mg, 3.0 mmol) in dichloromethane (10 ml), the mixture was stirred at 0 for 1 h and concentrated to dryness. The residue was triturated with petroleum ether, and the solid was collected by filtration and dried to afford compound 12 (500 mg, 97%) as a yellow solid, used directly in next step without the further purification.

m/z: [M+H]$^+$ 513.4

Synthesis of Compound 50-1

A mixture of compound 46 (100 mg, 0.19 mmol), 4-chlorobenzoic acid 16 (45 mg, 0.28 mmol), 1-hydroxybenzotriazole (38 mg, 0.28 mmol), EDCl (68 mg, 0.36 mmol) and ethyldiisopropylamine (49 mg, 0.36 mmol) in dichloromethane (5 ml) was stirred at room temperature for 3 hr. The mixture was then diluted with dichloromethane (50 ml), washed successively with water and brine, dried over sodium sulfate and concentrated to afford compound 50-1 (126 mg, 100%) as a yellow solid, used directly in next step without the further purification.

m/z: [M+Na]$^+$ 687.5

Synthesis of Compound 51-1

A mixture of compound 50-1 (126 mg, 0.19 mmol), tosyl chloride (108 mg, 0.57 mmol) and ethyldiisopropylamine (122 mg, 0.95 mmol) in dichloromethane (5 ml) was stirred overnight at room temperature. The mixture was directly purified by preparative TLC (ethyl acetate/petroleum ether=1:5) to afford compound 51-1 (25 mg, 20%) as an off-white solid.

m/z: [M+H]$^+$ 647.3

Synthesis of Compound 52-1

To a solution of compound 51-1 (25 mg, 0.038 mmol) in a mixed solvent of methanol (2 ml), tetrahydrofuran (1 ml), and water (0.5 ml) was added sodium hydroxide (5 mg, 0.20 mmol). The resulted mixture was stirred at room temperature for 3 h. The reaction was diluted with water (10 ml), extracted with dichloromethane (10 ml×3). The combined organic phase was washed with brine, dried over sodium sulfate, filtered and concentrated to afford compound 52-1 (25 mg, 100%) as a white solid, used directly in next step without the further purification.

m/z: [M+H]$^+$ 605.3

Synthesis of Compound 53-1

A solution of compound 52-1 (25 mg, 0.043 mmol), 4-tert-butoxy-3,3-dimethyl-4-oxobutanoic acid 20 (25 mg, 0.12 mmol), 4-dimethylaminopyridine (15 mg, 0.12 mmol) and EDCl (39 mg, 0.2 mmol) in dichloromethane (5 ml) was stirred overnight at room temperature, the resulted mixture (compound 53-1) was used directly in next step without the further purification.

Synthesis of Compound 54-1

To the solution of compound 53-1 prepared above in dichloromethane (5 ml) was added trifluoroacetic acid (0.5 ml). After the reaction mixture was stirred at room temperature for 3 h, water was added (10 ml), and extracted with dichloromethane (10 ml×3). The combined organic phase was washed with saturated solution of sodium carbonate (10 ml) and brine, dried over sodium sulfate, filtered and concentrated. The residue was purified by preparative TLC (ethyl acetate/petroleum ether=1:3) to afford compound 54-1 (21 mg, 68%) as an off-white solid.

54-1

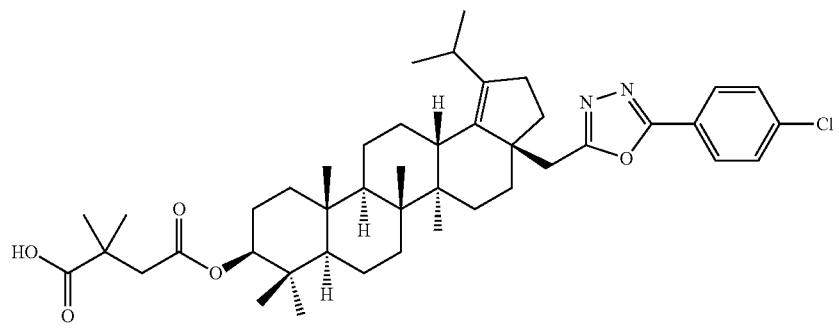

m/z: [M+H]$^+$ 733.5

1HNMR (CDCl$_3$) δ: 7.95-7.92 (2H, m), 7.49-7.46 (2H, m), 4.54-4.50 (1H, m), 3.13-2.91 (3H, m), 2.71-2.53 (4H, m), 2.21-0.64 (48H, m).

Compound 54-2 was prepared according to method 5 and scheme 5, as an off-white solid.

54-2

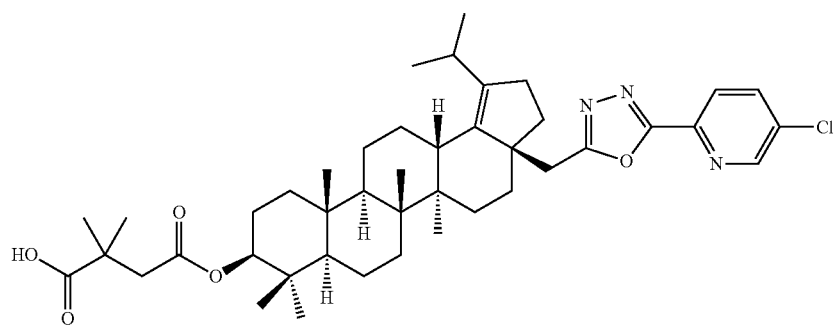

m/z: [M+H]$^+$ 734.5

Example 37-39 (Compound 59-1~59-3 was prepared according to method 6 and scheme 6)

Synthesis of Compound 55-1

A mixture of compound 49 (100 mg, 0.19 mmol), 4-chlorobenzoic acid 16 (46 mg, 0.29 mmol), 1-hydroxybenzotriazole (40 mg, 0.29 mmol), EDCl (75 mg, 0.39 mmol) and ethyldiisopropylamine (50 mg, 0.39 mmol) in dichloromethane (5 ml) was stirred at room temperature for 3 h. The mixture was diluted with dichloromethane (50 ml), washed successively with water and brine, dried over sodium sulfate and concentrated to afford compound 55-1 (127 mg, 100%) as a light yellow solid, used directly in next step without the further purification.

m/z: [M+Na]$^+$ 651.2

Synthesis of Compound 56-1

A mixture of compound 55-1 (127 mg, 0.15 mmol), tosyl chloride (111 mg, 0.58 mmol) and ethyldiisopropylamine (126 mg, 0.97 mmol) in dichloromethane (5 ml) was stirred overnight at room temperature. The mixture was directly purified by preparative TLC (ethyl acetate/petroleum ether=1:5) to afford compound 56-1 (43 mg, 35%) as an off-white solid.

m/z: [M+H]$^+$ 633.5

Synthesis of Compound 57-1

To a solution of compound 56-1 (43 mg, 0.068 mmol) in a mixed solvent of methanol (2 ml), tetrahydrofuran (1 ml), and water (0.5 ml) was added sodium hydroxide (8 mg, 0.20 mmol). The resulted mixture was stirred at room temperature for 4 h. The reaction was diluted with water (10 ml), extracted with dichloromethane (10 ml×3). The combined organic phase was washed with brine, dried over sodium sulfate, filtered and concentrated to afford compound 57-1 (40 mg, 99%) as a white solid, used directly in next step without the further purification.

m/z: [M+H]$^+$ 591.3

Synthesis of Compound 58-1

A solution of compound 57-1 (40 mg, 0.069 mmol), 4-tert-butoxy-3,3-dimethyl-4-oxobutanoic acid 20 (42 mg, 0.21 mmol), 4-dimethylaminopyridine (25 mg, 0.21 mmol) and EDCl (66 mg, 0.352 mmol) in dichloromethane (5 ml) was stirred overnight at room temperature, the resulted mixture (compound 58-1) was used directly in next step without the further purification.

Synthesis of Compound 59-1

To the solution of compound 58-1 prepared above in dichloromethane (5 ml) was added trifluoroacetic acid (0.5 ml). After the reaction mixture was stirred at room temperature for 3 h, water (10 ml) was added, and extracted with dichloromethane (10 ml×3). The combined organic phase was washed with saturated solution of sodium carbonate (10 ml) and brine, dried over sodium sulfate, filtered and concentrated. The residue was purified by preparative TLC (ethyl acetate/petroleum ether=1:5) to afford compound 59-1 (26 mg, 60%) as an off-white solid.

59-1

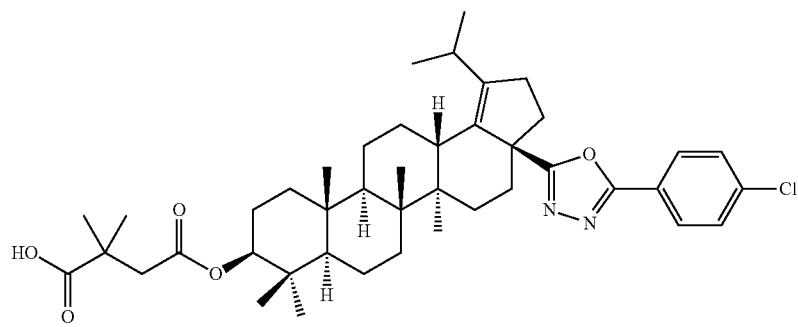

m/z: [M+H]⁺ 719.5
¹HNMR (CDCl₃) δ 7.95-7.92 (2H, m), 7.49-7.45 (2H, m), 4.54-4.48 (1H, m), 3.28-3.21 (1H, m), 2.69-0.76 (52H, m).

Compound 59-2 was prepared according to method 6 and scheme 6, as an off-white solid.

59-2

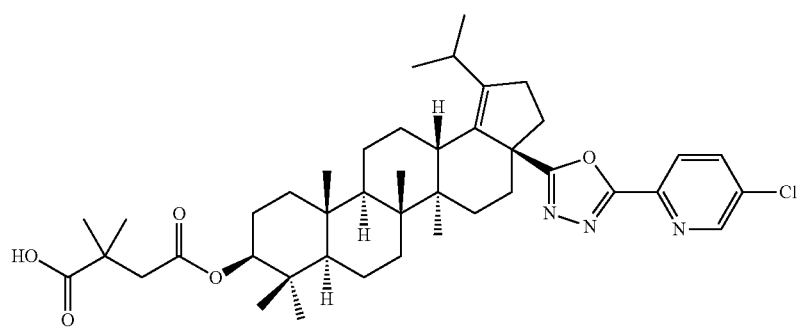

m/z: [M+H]⁺ 720.5

Compound 59-3 was prepared according to method 6 and scheme 6, as an off-white solid.

59-3

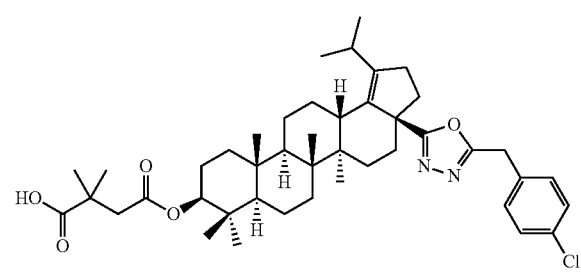

m/z: [M+H]⁺ 733.5

Example 40 (Compound 65 was prepared according to method 7 and scheme 7)

Synthesis of Compound 61

A mixture of compound 13 (100 mg, 0.19 mmol), 2-amino-4'-chloroacetophenone hydrochloride 60 (44 mg, 0.21 mmol), 1-hydroxybenzotriazole (40 mg, 0.29 mmol), EDCl (75 mg, 0.39 mmol) and ethyldiisopropylamine (50 mg, 0.39 mmol) in dichloromethane (5 ml) was stirred at room temperature for 1 h, then directly purified by preparative TLC (ethyl acetate/petroleum ether=1:3) to afford compound 61 (100 mg, 77%) as a white solid.

m/z: [M+Na]⁺ 664.5

Synthesis of Compound 62

To a solution of compound 61 (100 mg, 0.15 mmol) in acetonitrile (5 ml) was added phosphorus oxychloride (230 mg, 1.5 mmol). The reaction mixture was stirred at reflux for 1 h, then cooling down to room temperature. The mixture was neutralized with saturated solution of sodium bicarbonate, and extracted with ethyl acetate (20 ml×3). The combined organic phase was washed with saturated solution of sodium bicarbonate, dried over sodium sulfate, filtered and concentrated, the residue was purified by chromatography on silica gel (ethyl acetate/petroleum ether=1:10~1:5) to afford compound 62 (25 mg, 26%) as a white solid.

m/z: [M+H]⁺ 646.5

Synthesis of Compound 63

To a solution of compound 62 (25 mg, 0.039 mmol) in a mixed solvent of methanol (2 ml), tetrahydrofuran (1 ml), and water (0.5 ml) was added sodium hydroxide (5 mg, 0.12 mmol). The resulted mixture was stirred at room temperature for 3 h. The reaction was diluted with ethyl acetate (30 ml), washed with water (10 ml×3) and brine, dried over sodium sulfate, filtered and concentrated to afford crude compound 63 (23 mg, 98%) as a white solid, used directly in next step without the further purification.

m/z: [M+H] ⁺604.4

Synthesis of Compound 64

A solution of compound 63 (23 mg, 0.038 mmol), 4-tert-butoxy-3,3-dimethyl-4-oxobutanoic acid 20 (23 mg, 0.11 mmol), 4-dimethylaminopyridine (14 mg, 0.11 mmol) and EDCl (36 mg, 0.19 mmol) in dichloromethane (5 ml) was stirred overnight at room temperature, the resulted mixture (compound 64) was used directly in next step without the further purification.

Synthesis of Compound 65

To the solution of compound 64 prepared above in dichloromethane (5 ml) was added trifluoroacetic acid (0.5 ml), the reaction mixture was stirred at room temperature for 3 h, then diluted with water (10 ml), extracted with dichloromethane (10 ml×3). The combined organic phase was washed with saturated solution of sodium carbonate (10 ml) and brine, dried over sodium sulfate, filtered and concentrated. The residue was purified by preparative TLC (ethyl acetate/petroleum ether=1:3) to afford compound 65 (14 mg, 50%) as a white foam.

Synthesis of Compound 68

To a solution of compound 67 (90 mg, 0.14 mmol) in a mixed solvent of methanol (2 ml), tetrahydrofuran (1 ml), and water (0.5 ml) was added sodium hydroxide (17 mg, 0.42 mmol). The resulted mixture was stirred at room temperature for 3 h. The reaction was diluted with dichlo-

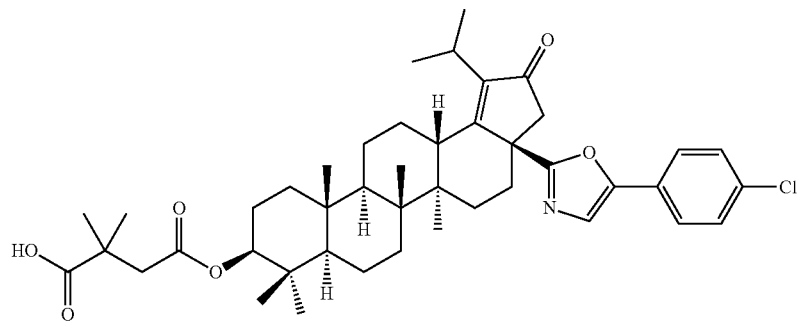

65 m/z: [M+H]+ 732.5

Example 41 (Compound 70 was prepared according to method 8 and scheme 8)

Synthesis of Compound 66

A mixture of compound 47 (400 mg, 0.8 mmol), 2-amino-4'-chloroacetophenone hydrochloride 60 (247 mg, 1.2 mmol), 1-hydroxybenzotriazole (162 mg, 1.2 mmol), EDCl (307 mg, 1.6 mmol) and ethyldiisopropylamine (204 mg, 1.6 mmol) in dichloromethane (20 ml) was stirred at room temperature for 1 h. The solvent was evaporated, and the residue was purified by chromatography on silica gel (ethyl acetate/petroleum ether=1:5) to afford compound 66 (500 mg, 96%) as a white solid.

$^1$HNMR (CDCl$_3$) δ 7.94-7.91 (2H, m), 7.49-7.46 (2H, m), 6.90-6.88 (1H, m), 4.72 (2H, d, J=4.8 Hz), 4.50-4.46 (1H, m), 3.34-3.29 (1H, m), 2.54-2.35 (4H, m). 2.09-1.94 (4H, m), 1.75-0.78 (39H, m).

Synthesis of Compound 67

To a solution of compound 66 (140 mg, 0.22 mmol) in acetonitrile (10 ml) was added phosphorus oxychloride (330 mg, 2.2 mmol). The reaction mixture was stirred at reflux for 2 h, then cooling down to room temperature. The mixture was neutralized with saturated solution of sodium carbonate (10 ml), diluted with water (20 ml), extracted with ethyl acetate (20 ml×3). The combined organic phase was washed with brine, dried over sodium sulfate, filtered and concentrated. The residue was purified by preparative TLC (ethyl acetate/petroleum ether=1:20) to afford compound 67 (22 mg, 16%) as a light yellow solid.

$^1$HNMR (CDCl$_3$) δ 7.51-7.48 (2H, m), 7.38-7.35 (2H, m), 7.23 (1H, s), 4.49-4.45 (1H, m), 3.29-3.19 (1H, m), 2.57-0.77 (47H, m).

romethane (30 ml), washed with water (10 ml×2) and brine, dried over sodium sulfate, filtered and concentrated to afford crude compound 68 (75 mg, 89%) as a white solid, used directly in next step without the further purification.

m/z: [M+H]+ 590.3

Synthesis of Compound 69

A solution of compound 68 (75 mg, 0.13 mmol), 4-tert-butoxy-3,3-dimethyl-4-oxobutanoic acid 20 (77 mg, 0.38 mmol), 4-dimethylaminopyridine (46 mg, 0.38 mmol) and EDCl (121 mg, 0.64 mmol) in dichloromethane (5 ml) was stirred overnight at room temperature, the resulted mixture was directly purified by chromatography on silica gel (ethyl acetate/petroleum ether=1:20~1:10) to afford compound 69 (63 mg, 64%) as a white solid.

Synthesis of Compound 70

A solution of compound 69 (20 mg, 0.0026 mmol) in dichloromethane (5 ml) and trifluoroacetic acid (0.5 ml) was stirred at room temperature for 1 h. The reaction mixture was diluted with dichloromethane (30 ml), washed with water (10 ml), saturated solution of sodium bicarbonate (10 ml) and brine, dried over sodium sulfate, filtered and concentrated. The residue was purified by preparative TLC (ethyl acetate/petroleum ether=1:4) to afford compound 70 (14 mg,) as an off-white solid.

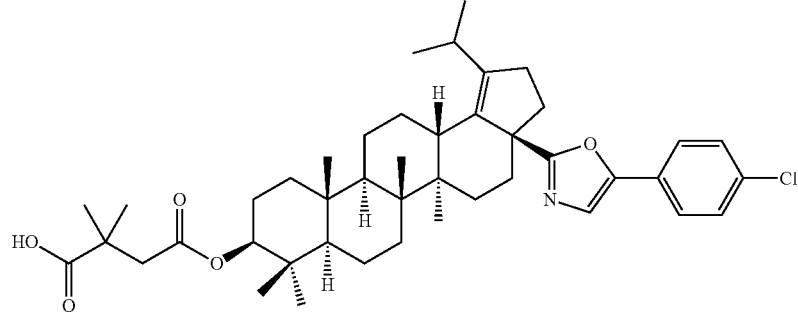

70 m/z: [M+H]+ 718.2

Example 42 (Compound 77 was prepared according to method 9 and scheme 9)

Synthesis of Compound 70

To an ice-cooling suspension of compound 7 (6 g, 10.76 mmol) and nickel(II) chloride hexahydrate (3.05 g, 12.91 mmol) in methanol (30 ml) was added sodium borohydride (2.03 g, 53.79 mmol) in small portions. The resulted mixture was stirred at 0 for 1 h, and ethyl acetate (200 ml) and saturated solution of ammonium chloride (50 ml) were added. The mixture was stirred until the aqueous layer was turned to blue, then the organic layer was separated and washed with water (50×3) and brine, dried over sodium sulfate, filtered and concentrated. The residue was triturated with petroleum ether, filtered to afford crude compound 71 (5.1 mg, 90%) as a white solid, used directly in next step without the further purification.

m/z: [M+H]$^+$ 528.5

Synthesis of Compound 72

To a solution of compound 71 (130 mg, 0.24 mmol) in dichloromethane (10 ml) was added 4-fluorobenzoic acid 16 (42 mg, 0.27 mmol), HATU (140 mg, 0.37 mmol) and ethyldiisopropylamine (64 mg, 0.49 mmol) under nitrogen. The reaction mixture was stirred at room temperature for 1 h, and the resulted mixture (compound 72) was used directly in next step without the further purification.

Synthesis of Compound 73

To the solution of compound 72 prepared above was added pyridinium chlorochromate (161 mg, 0.75 mmol) and silica gel (200 mg). The reaction mixture was stirred over night at room temperature and concentrated, the residue was purified by chromatography on silica gel (petroleum ether/ethyl acetate=10:1~5:1) to afford compound 73 (105 mg, 65%) as a white solid.

m/z: [M+H]$^+$ 661.4

Synthesis of Compound 74

To a solution of compound 73 (105 mg, 0.16 mmol) in acetonitrile (5 ml) was added phosphorus oxychloride (242 mg, 1.6 mmol). The reaction mixture was stirred at reflux for 1 h, then cooling down to room temperature. The mixture was neutralized with saturated solution of sodium carbonate (10 ml), and diluted with water (20 ml). The aqueous phase was extracted with ethyl acetate (20 ml×3). The combined organic phase was washed with brine, dried over sodium sulfate, filtered and concentrated. The residue was purified by preparative TLC (ethyl acetate/petroleum ether=1:10) to afford compound 74 (16 mg, 16%) as a light yellow solid.

m/z: [M+H]$^+$ 646.5

Synthesis of Compound 75

To a solution of compound 74 (16 mg, 0.24 mmol) in a mixed solvent of methanol (2 ml), tetrahydrofuran (1 ml), and water (0.5 ml) was added sodium hydroxide (3 mg, 0.74 mmol). The resulted mixture was stirred at room temperature for 3 hr. The reaction was diluted with dichloromethane (30 ml), washed with water (10 ml×2) and brine, dried over sodium sulfate, filtered and concentrated to afford crude compound 75 (15 mg, 100%) as a white solid, used directly in next step without the further purification.

m/z: [M+H]$^+$ 604.3

Synthesis of Compound 76

A solution of compound 75 (15 mg, 0.025 mmol), 4-tert-butoxy-3,3-dimethyl-4-oxobutanoic acid 20 (15 mg, 0.075 mmol), 4-dimethylaminopyridine (9 mg, 0.075 mmol) and EDCl (24 mg, 0.125 mmol) in dichloromethane (5 ml) was stirred overnight at room temperature, the resulted mixture (compound 76) was used directly in next step without the further purification.

Synthesis of Compound 77

To the solution of compound 76 prepared above in dichlorometane (5 ml) was added trifluoroacetic acid (0.5 ml), the reaction mixture was stirred at room temperature for 3 h, then diluted with dichloromethane (30 ml). The organic phase was washed with saturated solution of sodium bicarbonate (10 ml) and brine, dried over sodium sulfate, filtered and concentrated. The residue was purified by preparative TLC (ethyl acetate/petroleum ether=1:3) to afford compound 77 (5 mg, 28%) as a white solid.

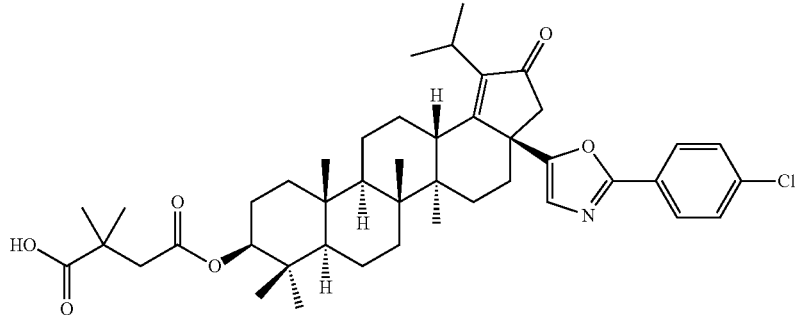

77 m/z: [M+H]$^+$ 732.5

Example 43-60 (Compound 89-1~89-7, 89'-1, 91-1~91-9 and 91'-1 were prepared according to method 10 and scheme 10, by using different alkylating intermediates like 86 and the like.)

Synthesis of Key Intermediates 81-1 and 85-1

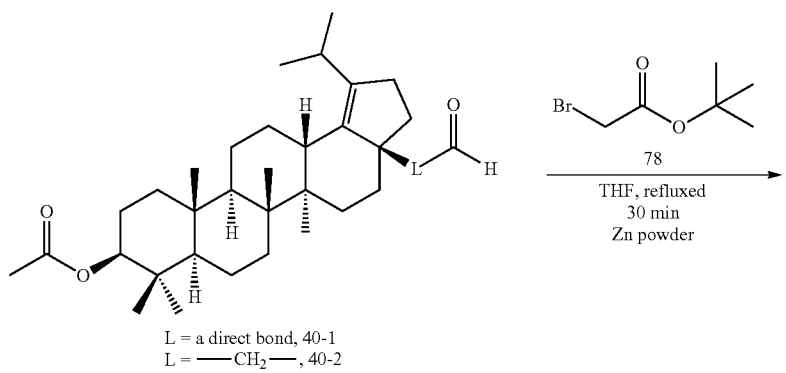

L = a direct bond, 40-1
L = ——CH$_2$——, 40-2

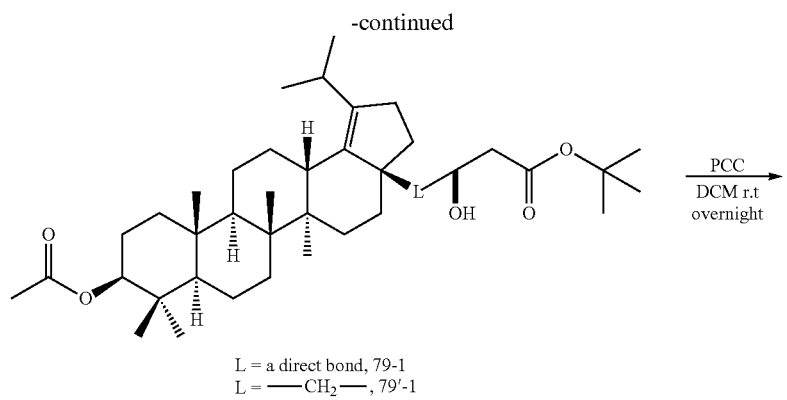

L = a direct bond, 79-1
L = ——CH₂——, 79'-1

PCC
DCM r.t
overnight

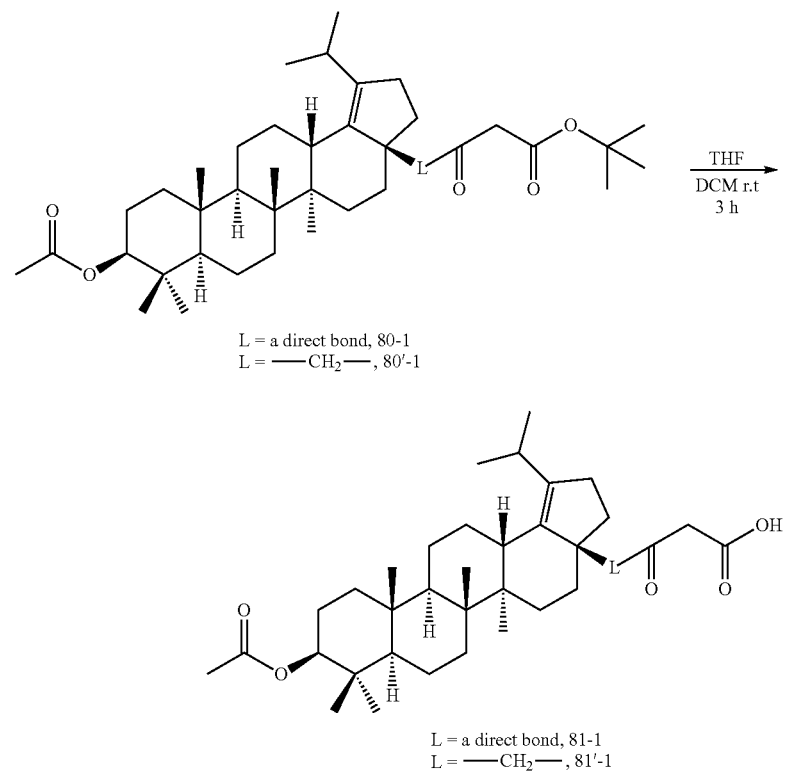

L = a direct bond, 80-1
L = ——CH₂——, 80'-1

TFA
DCM r.t
3 h

L = a direct bond, 81-1
L = ——CH₂——, 81'-1

Synthesis of Compound 79-1

To an refluxing suspension of active zinc powder (1.02 g, 15.5 mmol) in tetrahydrofuran (20 ml) was successively added t-butyl bromoacetate (1.69 ml, 10.36 mmol) and compound 40-1 (2.0 g, 4.14 mmol) during one min. The resulted mixture was stirred at reflux for 30 min, then cooling down to room temperature. The reaction was quenched by the addition of water (20 ml) and aqueous HCl (2 N) (10 ml), and the mixture was extracted with ethyl acetate (20 ml×3). The combined organic phase was washed with brine, dried over sodium sulfate, filtered and concentrated to afford crude compound 79-1 (2.1 g, 85%) as an off-white solid, used directly in next step without the further purification.

m/z: [M+Na]⁺ 621.5

Synthesis of Compound 80-1

A mixture of compound 79-1 (2.1 g, 23.51 mmol), pyridinium chlorochromate (2.27 g, 10.5 mmol) and silica gel (3 g) in dichloromethane (20 ml) was stirred overnight at room temperature. The reaction mixture was concentrated and the residue was purified by chromatography on silica gel (ethyl acetate/petroleum ether=1:10) to afford compound 80-1 (1.2 g, 57%) as a white solid.

m/z: [M+Na]⁺ 619.5

Synthesis of Compound 81-1

A solution of compound 80-1 (500 mg, 0.84 mmol) and trifluoroacetic acid (1 ml) in dichloromethane (10 ml) was stirred at room temperature for 3 h, then diluted with water (20 ml). The mixture was extracted with dichloromethane (20 ml×3), and the organic phase was successively washed with saturated solution of sodium bicarbonate (5 ml), aqueous HCl (2 N) (15 ml) and brine, dried over sodium sulfate, filtered and concentrated. The residue was triturated with petroleum ether to afford crude compound 81-1 (317 mg, 70%) as a white solid, used directly in next step without the further purification.

m/z: [M+Na]⁺ 563.5

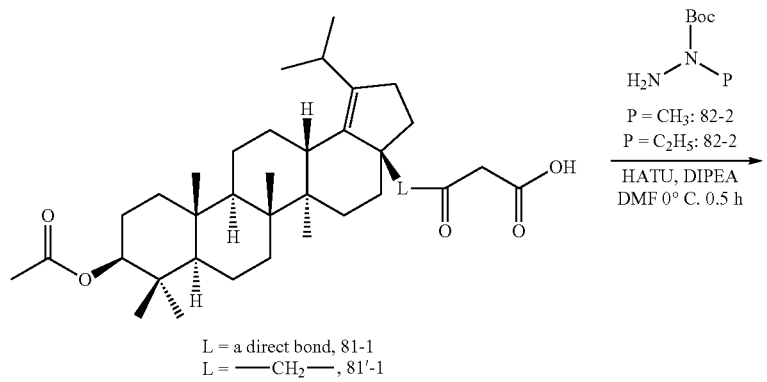
L = a direct bond, 81-1
L = —CH₂—, 81'-1
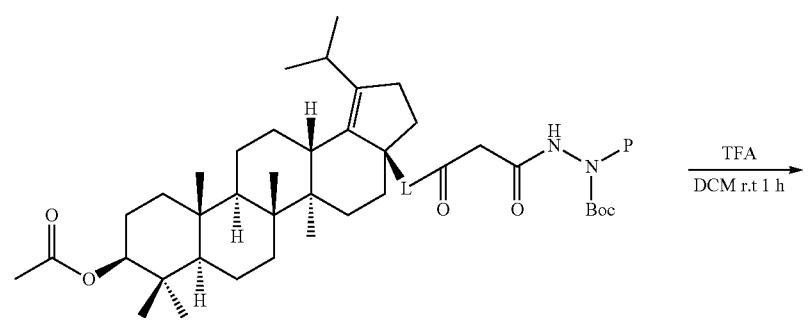
L = a direct bond, P = CH₃: 83-1
L = a direct bond, P = C₂H₅: 83-2
L = —CH₂—, P = CH₃: 83'-1

L = a direct bond, P = CH₃: 84-1
L = a direct bond, P = C₂H₅: 84-2
L = —CH₂—, P = CH₃: 84'-1
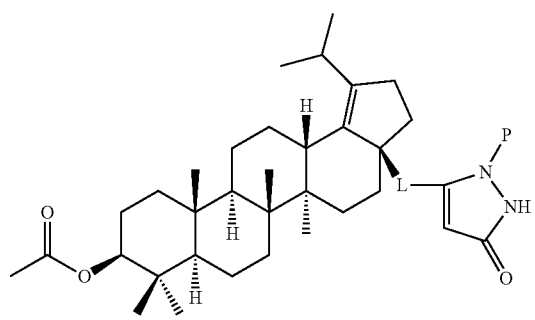
L = a direct bond, P = CH₃: 85-1
L = a direct bond, P = C₂H₅: 85-5
L = —CH₂—, P = CH₃: 85'-1

Synthesis of Compound 83-1

To an ice-cooling solution of compound 81-1 (300 mg, 0.55 mmol) in N,N-dimethylformamide (5 ml) was added tert-butyl 1-methylhydrazinecarboxylate 82 (121 mg, 0.83 mmol), ethyldiisopropylamine (143 mg, 1.11 mmol) and HATU (316 mg, 0.83 mmol). The resulted mixture was stirred at 0° C. for 30 min, then diluted with ethyl acetate (50 ml). The organic phase was washed with water (20 ml×3), brine, dried over sodium sulfate, filtered and concentrated. The residue was purified by chromatography on silica gel (ethyl acetate/petroleum ether=1:10~1:5) to afford compound 83-1 (208 mg, 56%) as an off-white foam.

m/z: [M+Na]$^+$ 691.5

Synthesis of Compound 84-1

A mixture of compound 83-1 (208 mg, 0.31 mmol) and trifluoroacetic acid (1 ml) in dichloromethane (5 ml) was stirred at room temperature for 1 h. The solvent was evaporated to dryness to afford crude compound 84-1 which was directly used in next step without the further purification.

m/z: [M+H]$^+$ 569.5

Synthesis of Compound 85-1

To a solution of crude compound 84-1 in ethanol (5 ml) was added a catalytic amount of p-toluenesulfonic acid. The reaction mixture was stirred at reflux for 2 h, then cooling down to room temperature. The mixture was diluted with dichloromethane (50 ml), washed with water (20 ml×2), brine, dried over sodium sulfate, filtered and concentrated to afford the crude compound 85-1 (170 mg, 100%) as a yellow foam, used directly in next step without the further purification.

m/z: [M+H]$^+$ 551.4

$^1$HNMR (DMSO-d6) δ 9.22 (1H, s), 5.26 (1H, s), 4.38-4.34 (1H, m), 3.47 (3H, s) 3.19-3.13 (1H, m), 2.57-0.77 (47H, m).

Synthesis of Compound 87-1

To a solution of compound 85 (100 mg, 0.18 mmol) in dimethyl sulfoxide (5 ml) was added sodium hydride (36 mg 60% in mineral oil, 0.91 mmol) and 4-chlorobenzyl chloride (44 mg, 0.27 mmol). The resulted mixture was stirred at 50° C. for 8 h, then cooling down to room temperature. The reaction was quenched by the addition of saturated solution of sodium bicarbonate, and the reaction mixture was extracted with ethyl acetate (20 ml×3). The combined organic phase was washed with water (20 ml×2) and brine, dried over sodium sulfate, filtered and concentrated to afford crude compound 87-1 (115 mg, 100%) as a yellow solid, used directly in next step without the further purification.

m/z: [M+H]$^+$ 633.5

Synthesis of Compound 88-1

A solution of compound 87-1 (110 mg, 0.17 mmol), 4-tert-butoxy-3,3-dimethyl-4-oxobutanoic acid 20 (105 mg, 0.52 mmol), 4-dimethylaminopyridine (64 mg, 0.52 mmol) and EDCl (166 mg, 0.87 mmol) in dichloromethane (10 ml) was stirred overnight at room temperature, the resulted mixture was concentrated and the residue was purified by chromatography on silica gel (ethyl acetate/petroleum ether=1:8~1:5) to afford compound 88-1 (63 mg, 45%) as an off-white solid.

Synthesis of Compound 89-1

A solution of compound 88-1 (20 mg, 0.024 mmol) and trifluoroacetic acid (0.5 ml) in dichloromethane (5 ml) was stirred at room temperature for 3 hr. The reaction mixture was diluted with dichloromethane (20 ml), washed with water (10 ml×2), saturated solution of sodium bicarbonate (10 ml), brine, dried over sodium sulfate, filtered and concentrated. The residue was purified by preparative TLC (ethyl acetate/petroleum ether=1:3) to afford compound 89-1 (12 mg, 64) as an off-white foam.

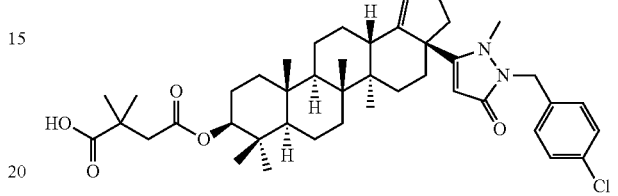

89-1 m/z: [M+H]$^+$ 761.5

Compound 89-2 was prepared according to method 10 and scheme 10, as an off-white solid.

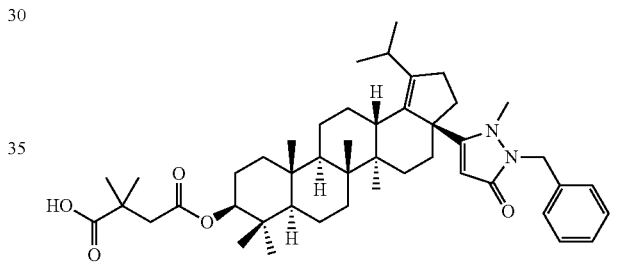

89-2 m/z: [M+H]$^+$ 727.5

$^1$HNMR (CDCl$_3$) δ: 7.45-7.30 (5H, m), 5.50 (1H, s), 5.15 (2H, dd, J1=12 Hz, J2=14 Hz), 4.50-4.47 (1H, m), 3.65 (3H, s), 3.20-3.17 (1H, m), 2.67 (1H, d, J=15.6 Hz), 2.56 (1H, d, J=16.0 Hz), 2.47-0.73 (50H, m).

Compound 89-3 was prepared according to method 10 and scheme 10, as an off-white solid.

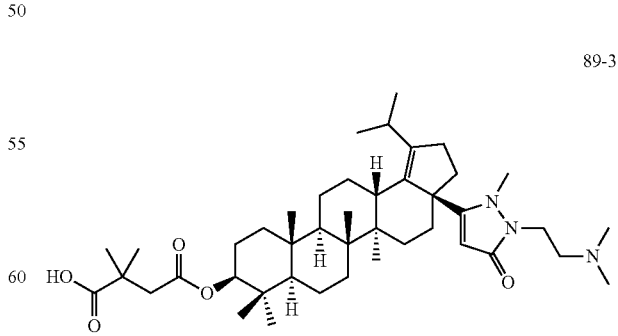

89-3 m/z: [M+H]$^+$ 708.5

Compound 89-4 was prepared according to method 10 and scheme 10, as an pink solid.

89-4

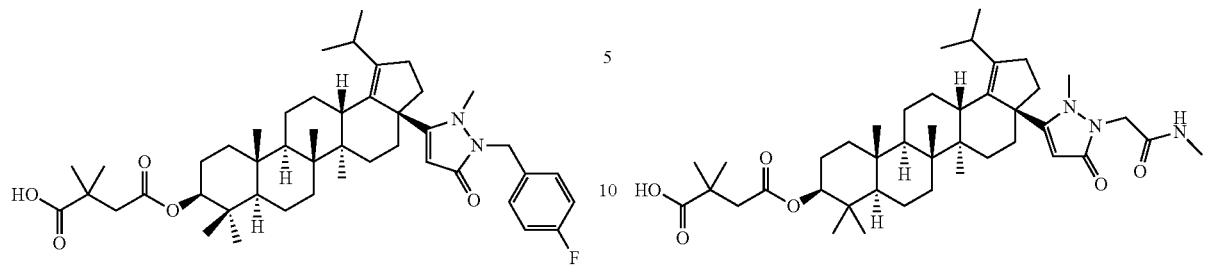

m/z: [M+H]$^+$ 745.5
Compound 89-5 was prepared according to method 10 and scheme 10, as an off-white solid.

89-5

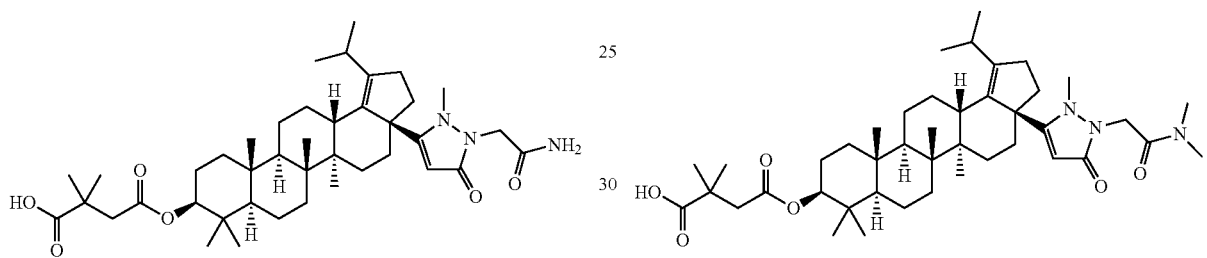

m/z: [M+H]$^+$ 694.5
Compound 89-6 was prepared according to method 10 and scheme 10, as an off-white solid.

89-6 m/z: [M+H]$^+$ 708.5
Compound 89-7 was prepared according to method 10 and scheme 10, as an off-white solid.

89-7 m/z: [M+H]$^+$ 722.5
Compound 89'-1 was prepared according to method 10 and scheme 10, as an off-white solid.

89'-1

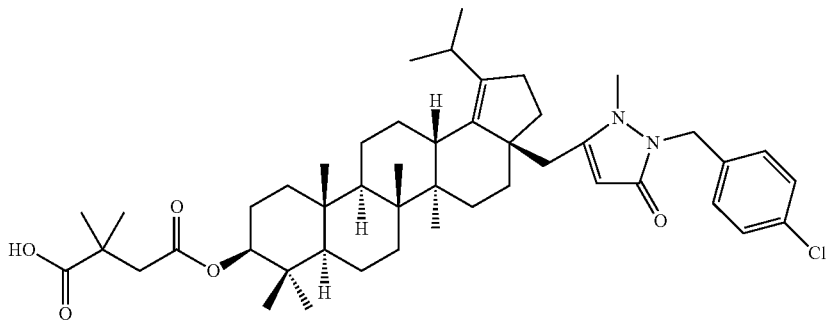

m/z: [M+H]$^+$ 775.5

Synthesis of Compound 90-1

A mixture of compound 88-1 (40 mg, 0.049 mmol), sodium acetate (40 mg, 0.49 mmol) and sodium dichromate dehydrate (14 mg, 0.058 mmol) in a mixed solvent of toluene (0.5 ml), acetic anhydride (0.5 ml) and acetic acid (0.5 ml) was stirred overnight at 60° C. After cooling down to room temperature, water (20 ml) and ethyl acetate (50 ml) were added. The aqueous layer was extracted with ethyl acetate (10 ml×3), and the combined organic layer was washed with saturated solution of sodium bicarbonate (20 ml×3) and brine, dried over sodium sulfate and concentrated to afford crude compound 90-1 (50 mg, 100%) as a light yellow solid, used in directly in next step without the further purification.

Synthesis of Compound 91-1

A solution of compound 90-1 (50 mg, 0.06 mmol) and trifluoroacetic acid (0.5 ml) in dichloromethane (5 ml) was stirred at room temperature for 3 h. The reaction mixture was added water (10 ml) and ethyl acetic (30 ml) and the aqueous layer was extracted with ethyl acetic (10 ml×2), the combined organic layer was washed with saturated solution of sodium bicarbonate (10 ml), brine, dried over sodium sulfate and concentrated. The residue was purified by preparative TLC (methanol/dichloromethane=1:20) to afford compound 91-1 (12 mg, 26%) as an off-white solid.

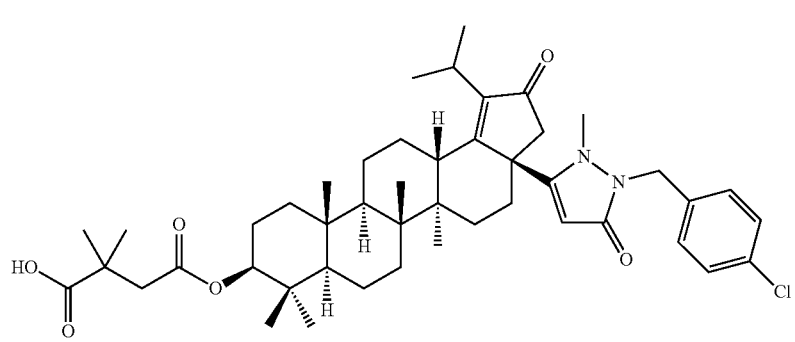

91-1 m/z: [M+H]$^+$ 775.5

$^1$HNMR (CDCl$_3$) δ 7.38-7.32 (4H, m), 5.62 (1H, s), 5.12 (2H, dd, J=12 Hz, J=17.2 Hz), 4.51-4.47 (1H, m), 3.47 (3H, s), 3.25-3.22 (1H, m), 2.70-0.73 (50H, m).

Compound 91-2 was prepared according to method 10 and scheme 10, as an off-white solid.

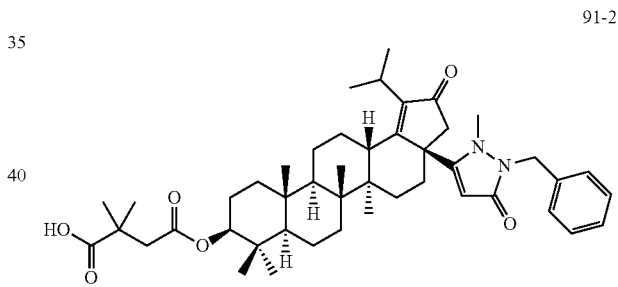

91-2 m/z: [M+H]$^+$ 741.5

Compound 91-3 was prepared according to method 10 and scheme 10, as an off-white solid.

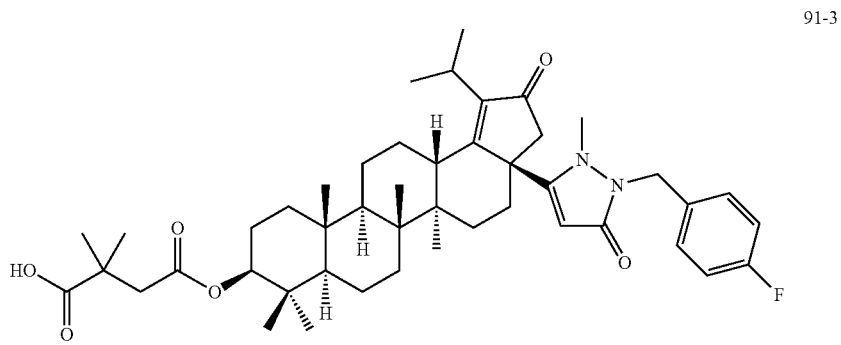

91-3 m/z: [M+H]$^+$ 759.5

Compound 91-4 was prepared according to method 10 and scheme 10, as an off-white solid.

91-4

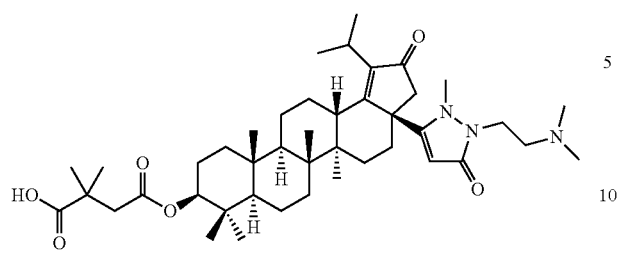

m/z: [M+H]+ 722.5

Compound 91-5 was prepared according to method 10 and scheme 10, as a pink solid.

91-5

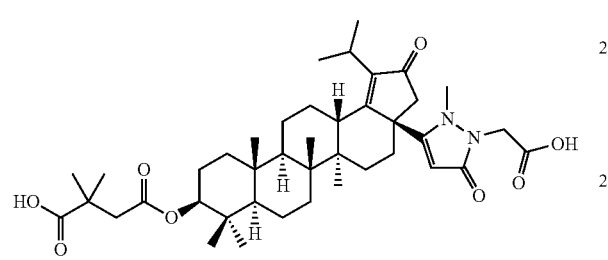

m/z: [M+H]+ 709.4

Compound 91-6 was prepared according to method 10 and scheme 10 as a white solid.

91-6

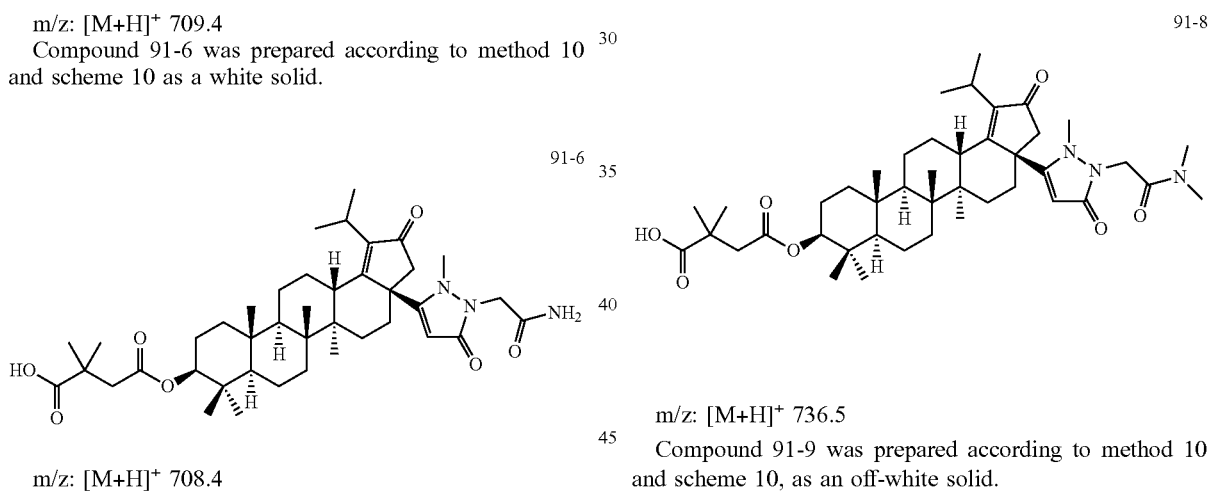

m/z: [M+H]+ 708.4

Compound 91-7 was prepared according to method 10 and scheme 10, as a white solid.

91-7

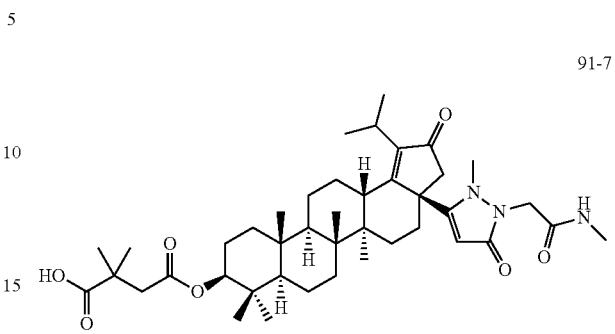

m/z: [M+H]+ 722.5

Compound 91-8 was prepared according to method 10 and scheme 10, as an off-white solid.

91-8

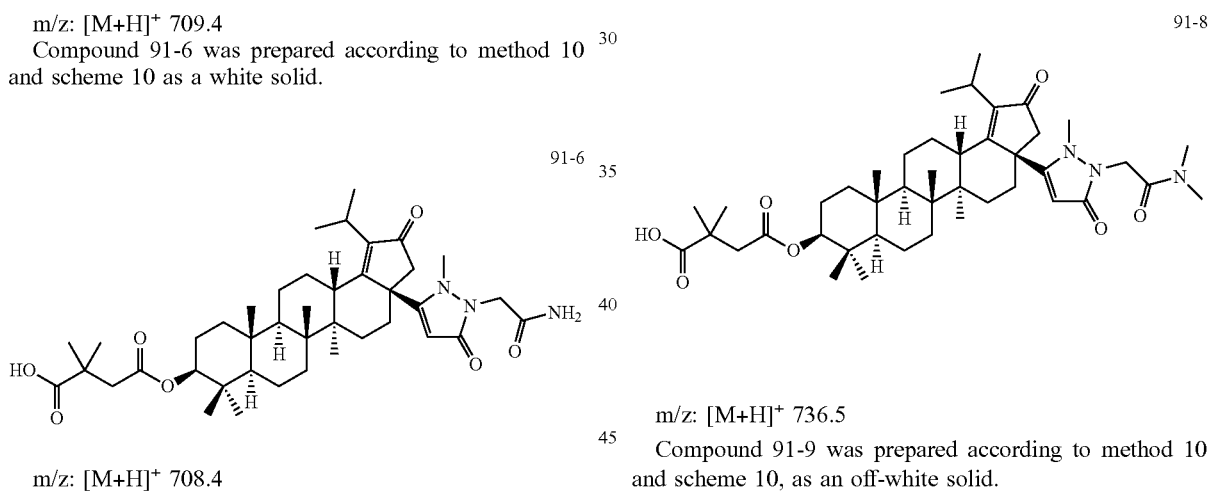

m/z: [M+H]+ 736.5

Compound 91-9 was prepared according to method 10 and scheme 10, as an off-white solid.

91-9

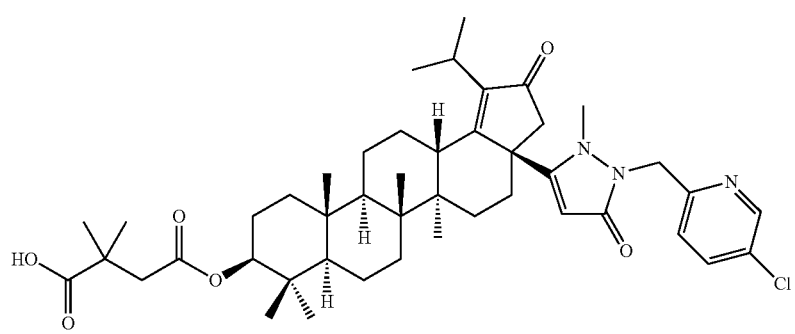

m/z: [M+H]+ 776.5

Compound 91'-1 was prepared according to method 10 and scheme 10, as a white solid.

91'-1

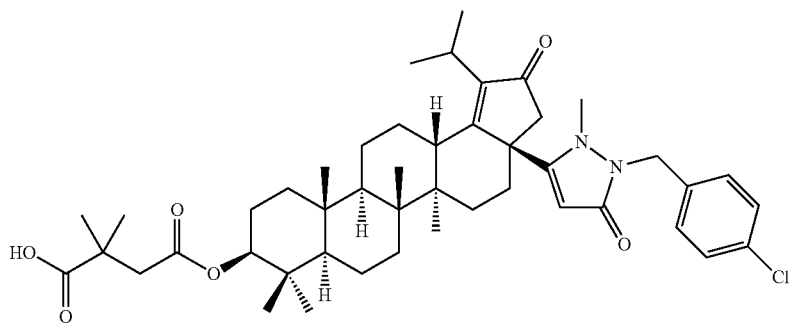

m/z: [M+H]⁺ 789.5

Example 61-73 (Compound 96-1~96-2, 96'-1, 98-1~98-8, and 98'-1~98'-2 were prepared according to method 11 and scheme 11 by using different boronic acid intermediates like 92 and the like.)

Synthesis of Compound 93-1

A mixture of compound 85-1 (75 mg, 0.14 mmol), 4-chlorophenylboronic acid 92 (42 mg, 0.27 mol), pyridine (21 mg, 0.27 mmol) and cupric acetate (30 mg, 0.20 mmol) in dichloromethane (5 ml) was reflux for 2 hr. The reaction mixture was cooling down to room temperature, water (20 ml) and dichloromethane (30 ml) were added and the layers were separated. The aqueous layer was extracted with dichloromethane (10 ml×2), and the combined organic layer was washed with water (10 ml×3), brine, dried over sodium sulfate and concentrated to afford crude compound 93-1 (90 mg, 100%) as an off-white solid, used directly in next step without the further purification.

m/z: [M+H]⁺ 661.5

Synthesis of Compound 94-1

To a solution of compound 93-1 (150 mg, 0.23 mmol) in a mixed solvent of methanol (2 ml), tetrahydrofuran (2 ml), and water (0.5 ml) was added sodium hydroxide (27 mg, 0.68 mmol). The resulted mixture was stirred at room temperature for 3 hr. The reaction was diluted with dichloromethane (50 ml), washed with water (10 ml×2) and brine, dried over sodium sulfate, filtered and concentrated to afford crude compound 95-1 (140 mg, 100%) as a white solid, used directly in next step without the further purification.

m/z: [M+H]⁺ 619.5

Synthesis of Compound 94-8

To a solution of compound 94-1 (60 mg, 0.099 mmol) in chloroform (5 ml) was added N-chlorosuccinimide (14 mg, 0.107 mmol), and stirred at reflux for overnight. The reaction was diluted with dichloromethane (50 ml), and washed with water (10 ml×2), brine, dried over sodium sulfate, filtered and concentrated to afford crude compound 94-8 (60 mg, yield 95%), as a light yellow solid, carried to next step reaction without further purification.

m/z: [M+H]⁺ 653.4

Synthesis of Compound 95-1

A solution of compound 94-1 (110 mg, 0.17 mmol), 4-tert-butoxy-3,3-dimethyl-4-oxobutanoic acid 20 (137 mg, 0.67 mmol), 4-dimethylaminopyridine (82 mg, 0.67 mmol) and EDCl (217 mg, 1.13 mmol) in dichloromethane (10 ml) was stirred overnight at room temperature, and the resulted mixture was directly purified by chromatography on silica gel (ethyl acetate/petroleum ether=1:8~1:5) to afford compound 95-1 (116 mg, 80%) as an off-white solid.

Synthesis of Compound 96-1

A solution of compound 95-1 (25 mg, 0.031 mmol) in a mixed solvent of dichloromethane (5 ml) and trifluoroacetic acid (0.5 ml) was stirred at room temperature for 3 h. The reaction mixture was diluted with dichloromethane (30 ml), washed with water (10 ml), saturated solution of sodium bicarbonate (10 ml) and brine, dried over sodium sulfate, filtered and concentrated. The residue was purified by preparative TLC (ethyl acetate/petroleum ether=1:20) to afford compound 96-1 (20 mg, 86%) as an off-white solid.

96-1

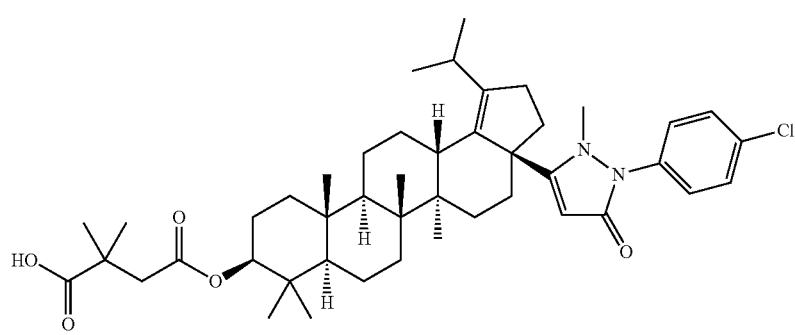

m/z: [M+H]⁺ 747.2

Compound 96-2 was prepared according to method 11 and scheme 11, as an off-white solid.

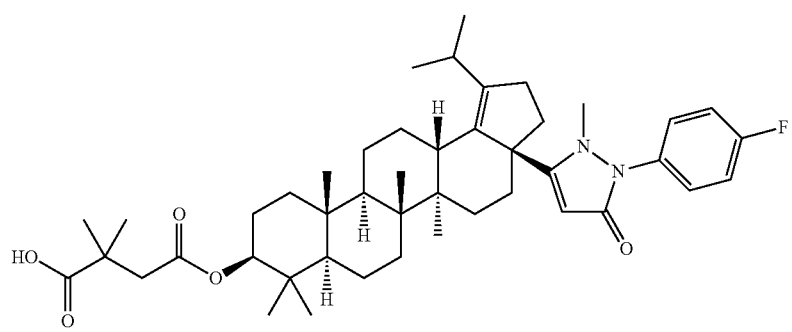

96-2 m/z: [M+H]⁺ 731.5

Compound 96'-1 was prepared according to method 11 and scheme 11, as a white solid.

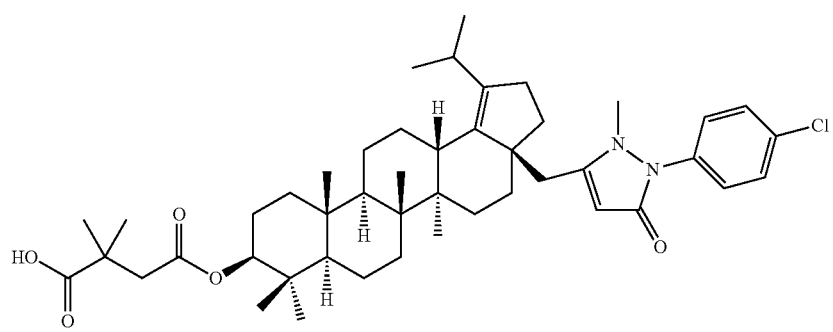

96'-1 m/z: [M+H]⁺ 761.5

Synthesis of Compound 97-1

A mixture of compound 95-1 (90 mg, 0.11 mmol), sodium acetate (92 mg, 1.1 mmol) and sodium dichromate dehydrate (32 mg, 0.13 mmol) in a mixed solvent of toluene (1.0 ml), acetic anhydride (1.0 ml) and acetic acid (1.0 ml) was stirred overnight at 60° C. After cooling down to room temperature, water (20 ml) was added. The mixture was extracted with dichloromethane (20 ml×3), and the combined organic layer was washed with saturated solution of sodium bicarbonate (10 ml×3), brine, dried over sodium sulfate and concentrated to afford crude compound 97-1 (83 mg, 91%) as a light yellow solid, used directly in next step without the further purification.

Synthesis of Compound 98-1

A solution of compound 97-1 (83 mg, 0.1 mmol) and trifluoroacetic acid (0.5 ml) in dichloromethane (5 ml) was stirred at room temperature for 3 h. The reaction mixture was diluted with dichloromethane (10 ml), and the reaction solution was washed with saturated solution of sodium bicarbonate (10 ml), brine, dried over sodium sulfate and concentrated. The residue was purified by preparative TLC (methanol/dichloromethane=1:12.5) to afford compound 98-1 (40 mg, 52%) as a white solid.

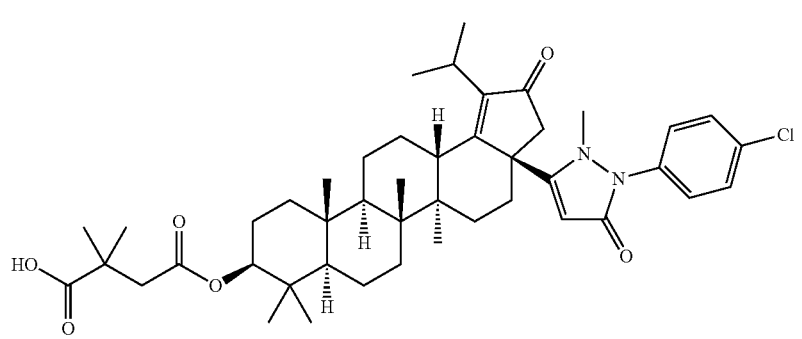

98-1 m/z: [M+H]⁺ 761.4

¹HNMR (CDCl₃) δ 7.46-7.44 (2H, m), 7.28-7.26 (2H, m), 5.75 (1H, br), 4.51-4.47 (1H, m), 3.30-3.23 (1H, m), 2.96 (3H, s), 2.72-0.76 (50H, m).

Compound 98-2 was prepared according to method 11 and scheme 11, as an off-white solid.
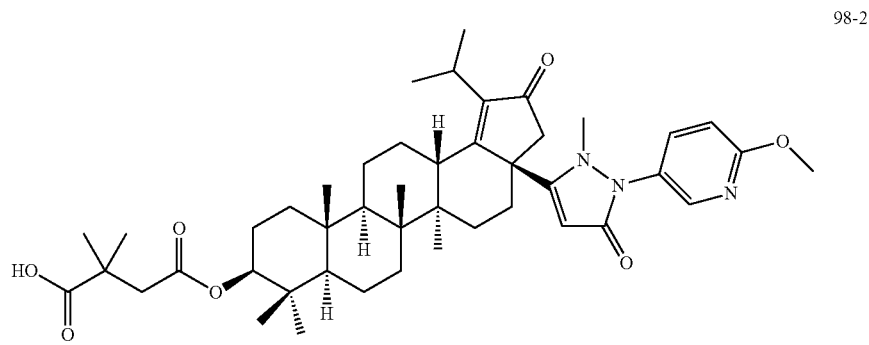
98-2
m/z: [M+H]⁺ 758.6
Compound 98-3 was prepared according to method 11 and scheme 11, as an off-white solid.
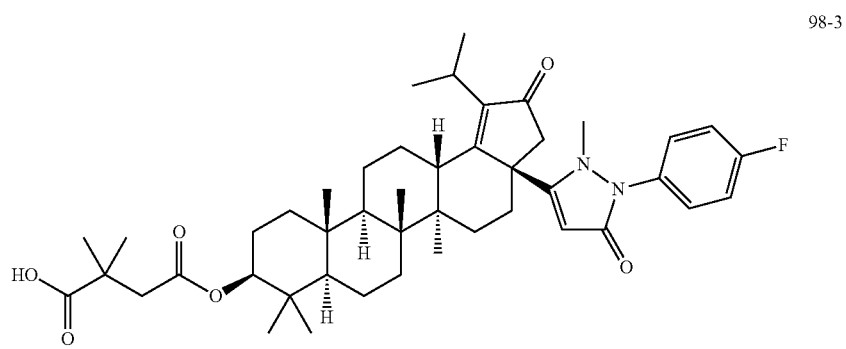
98-3
m/z: [M+H]⁺ 745.5
Compound 98-4 was prepared according to method 11 and scheme 11, as a light yellow solid.
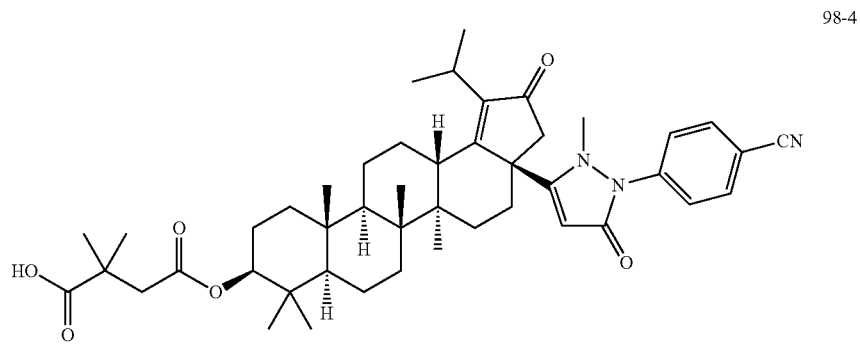
98-4
m/z: [M+H]⁺ 752.5

Compound 98-5 was prepared according to method 11 and scheme 11, an off-white solid.
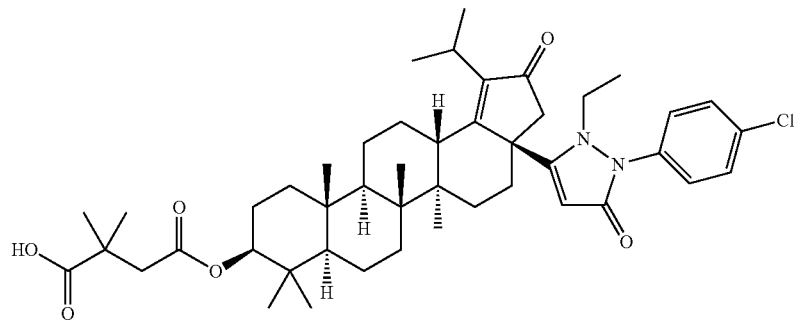
98-5
m/z: [M+H]⁺ 775.4
Compound 98-6 was prepared according to method 11 and scheme 11, as an off-white solid.
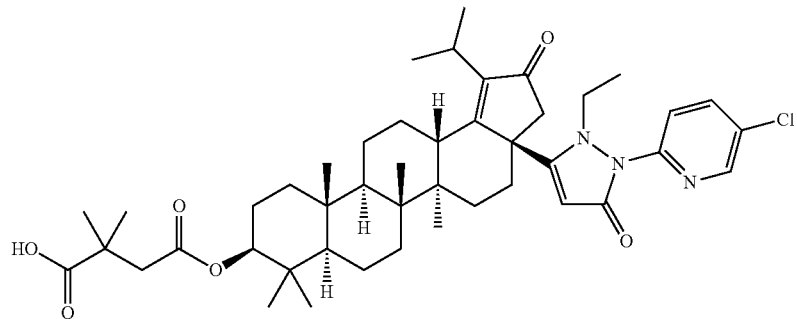
98-6
m/z: [M+H]⁺ 776.5
Compound 98-7 was prepared according to method 11 and scheme 11, as a white solid.
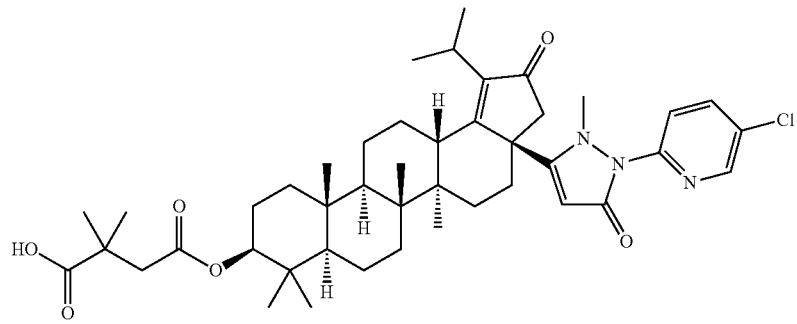
98-7
m/z: [M+H]⁺ 762.5

Compound 98-8 was prepared according to method 11 and scheme 11 by substituting 94-1 with 94-8, as an orange solid.

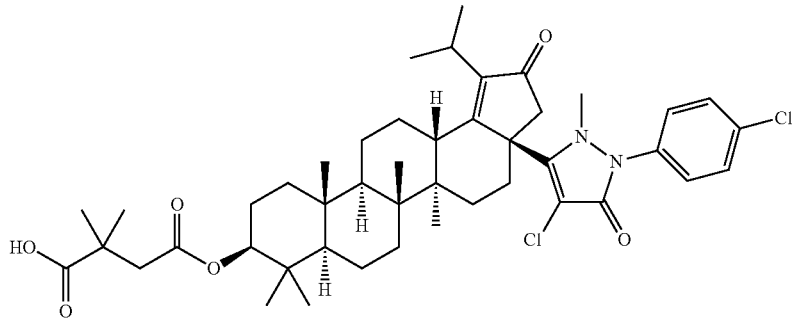

98-8 m/z: [M+H]+ 795.4

Compound 98'-1 was prepared according to method 11 and scheme 11, as an off-white solid.

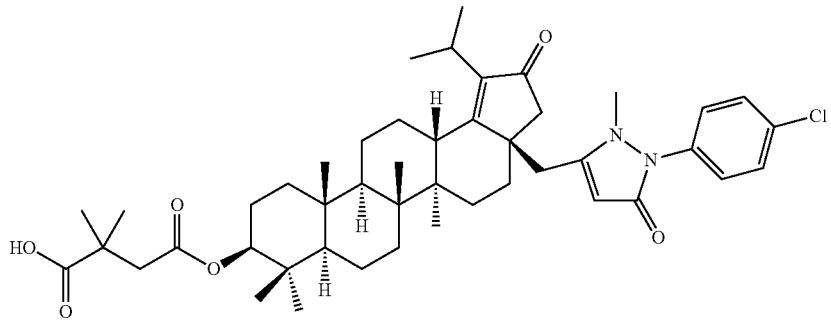

98'-1 m/z: [M+H]+ 775.4

Compound 98'-2 was prepared according to method 11 and scheme 11, as a light yellow solid.

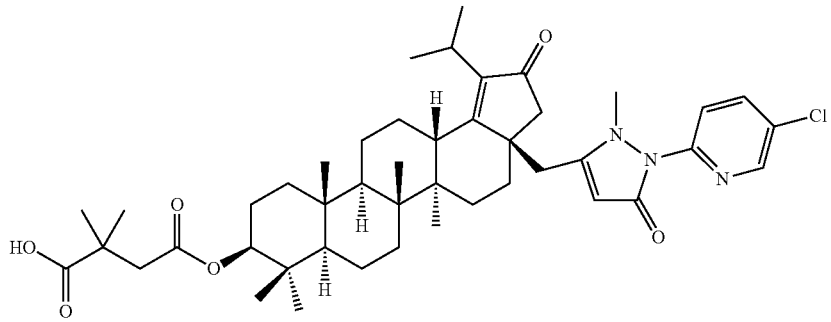

98'-2 m/z: [M+H]+ 776.4

Example 74 (Compound 102 was prepared according to method 12 and scheme 12)

Synthesis of Compound 99

A mixture of compound 23-1 (38 mg, 0.057 mmol) and Lawesson's Reagent (69 mg, 0.17 mmol) in toluene (3 ml) was reflux for 2 days. The solvent was evaporated to dryness, and the residue was purified by preparative TLC (ethyl acetate/petroleum ether=1:5) to afford compound 99 (6 mg, 16%) as an off-white solid.

m/z: [M+H]+ 663.3

Synthesis of Compound 100

To a solution of compound 99 (6 mg, 0.009 mmol) in a mixed solvent of methanol (2 ml), tetrahydrofuran (1 ml), and water (0.5 ml) was added sodium hydroxide (1 mg, 0.027 mmol). The resulted mixture was stirred at room temperature for 3 h. The reaction was diluted with dichloromethane (30 ml), washed with water (10 ml×2), brine, dried over sodium sulfate, filtered and concentrated to afford crude compound 100 (6 mg, 100%) as a white solid, used directly in next step without the further purification.

m/z: [M+H]$^+$ 621.3

Synthesis of Compound 101

A solution of compound 100 (6 mg, 0.010 mmol), 4-tert-butoxy-3,3-dimethyl-4-oxobutanoic acid 20 (6 mg, 0.030 mmol), 4-dimethylaminopyridine (3 mg, 0.030 mmol) and EDCl (9 mg, 0.050 mmol) in dichloromethane (5 ml) was stirred overnight at room temperature, and the resulted mixture (compound 100) was used directly in next step without the further purification.

Synthesis of Compound 102

To the solution of compound 101 prepared above in dichloromethane (5 ml) was added trifluoroacetic acid (0.5 ml), the reaction mixture was stirred at room temperature for 3 h, and diluted with dichloromethane (30 ml). The organic phase was washed with saturated solution of sodium bicarbonate (10 ml), brine, dried over sodium sulfate, filtered and concentrated. The residue was purified by preparative TLC (methanol/dichloromethane=1:20) to afford compound 102 (5 mg, 67%) as an off-white solid.

filtered and concentrated to afford crude compound 104 (380 mg, 68%), used directly in next step without the further purification.

Synthesis of Compound 105-1

To an ice-cooling solution of compound 104 (20 mg, 0.11 mmol) and ethyldiisopropylamine (25 mg, 0.19 mmol) in dioxane (3 ml) was added dropwise a solution of compound 14 (51 mg, 0.096 mmol) in dioxane (2 ml). The resulted mixture was stirred at room temperature for 30 min, and stirred at reflux overnight. The solvent was evaporated to dryness, and the residue was purified by preparative TLC (ethyl acetate/petroleum ether=1:5) to afford compound 105-1 (30 mg, 48%) as an off-white foam.

$^1$HNMR (CDCl$_3$) δ 8.05-8.01 (2H, m), 7.49-7.45 (2H, m), 4.49-4.45 (1H, m), 3.29-3.25 (1H, m), 2.77-2.62 (3H, m), 2.42-2.37 (1H, m), 2.08-0.78 (41H, m)

Synthesis of Compound 106-1

To a solution of compound 105-1 (30 mg, 0.046 mmol) in a mixed solvent of methanol (2 ml), tetrahydrofuran (1 ml), and water (0.5 ml) was added sodium hydroxide (18 mg, 0.46 mmol). The resulted mixture was stirred overnight at room temperature. The reaction was diluted with dichloromethane (20 ml), washed with water (10 ml×3), brine, dried over sodium sulfate, filtered and concentrated to afford crude compound 106-1 (24 mg, 85%) as a white solid, used directly in next step without the further purification.

Synthesis of Compound 107-1

A solution of compound 106-1 (24 mg, 0.04 mmol), 4-tert-butoxy-3,3-dimethyl-4-oxobutanoic acid 20 (24 mg, 0.12 mmol), 4-dimethylaminopyridine (14 mg, 0.12 mmol) and EDCl (38 mg, 0.20 mmol) in dichloromethane (5 ml) was stirred overnight at room temperature, and the resulted

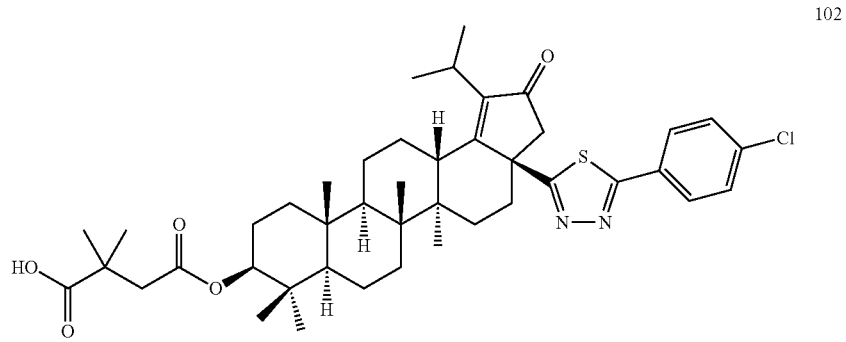

102 m/z: [M+H]$^+$ 749.5

Example 75-76 (Compound 108-1~108-2 were prepared according to method 13 and scheme 13)

Synthesis of Compound 104

To a solution of compound 103 (430 mg, 3.27 mmol) in ethanol (5 ml) was added aqueous solution of hydroxylamine hydrochloride (5 M) (0.74 ml, 3.7 mmol) and aqueous sodium hydroxide (10 M) (0.37 ml, 3.75 mmol). The resulted mixture was stirred at reflux for 3 h, then diluted with ethyl acetic (50 ml). The organic phase was washed with water (10 ml×3), brine, dried over sodium sulfate, mixture (compound 107-1) was used directly in next step without the further purification.

Synthesis of Compound 108-1

To the solution of compound 107-1 prepared above in dichloromethane (5 ml) was added trifluoroacetic acid (0.5 ml), and the reaction mixture was stirred at room temperature for 3 hr, then diluted with dichloromethane (30 ml), washed with water (10 ml×3) and brine, dried over sodium sulfate, filtered and concentrated. The residue was purified by preparative TLC (methanol/dichloromethane=1:20) to afford compound 108-1 (20 mg, 68%) as an off-white solid.

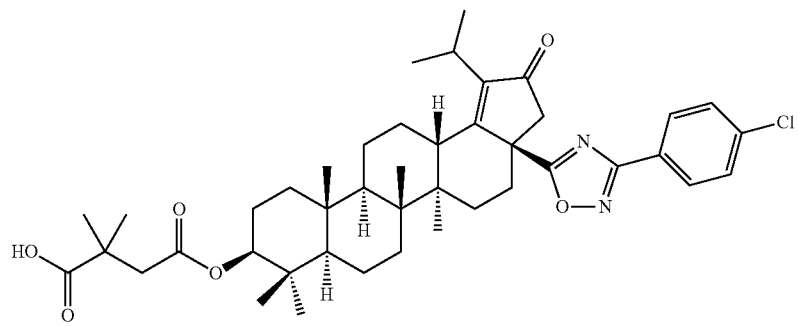

108-1 m/z: [M+H]+ 733.5

$^1$HNMR (CDCl$_3$) δ 8.06-8.04 (2H, m), 7.50-7.48 (2H, m), 4.54-4.50 (1H, m), 3.30-3.23 (1H, m), 2.77-0.76 (50H, m).

Compound 108-2 was prepared according to method 13 and scheme 13, as off white solid.

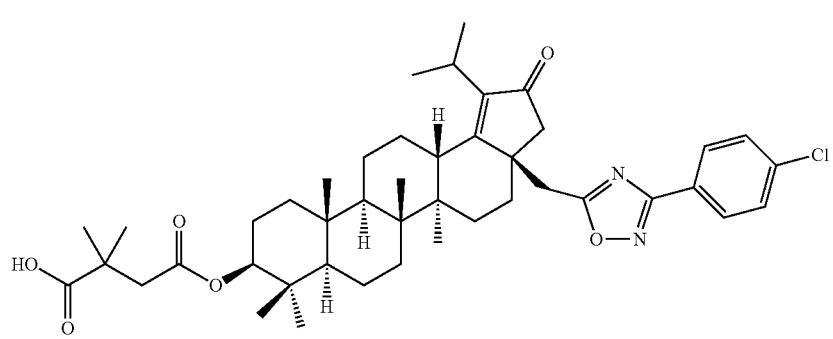

108-2 m/z: [M+H]+ 747.4

Example 77-80 (Compound 116-1~116-4 were prepared according to method 14 and scheme 14)

Synthesis of Compound 109

To a solution of compound 16 (1 g, 6.39 mmol) in dichloromethane (10 ml) was added oxalyl chloride (2.4 g, 19.1 mmol) and one drop of N,N-dimethylformamide. The reaction mixture was stirred overnight at room temperature and concentrated to afford crude compound 109 (1.12 g, 100%) as a colorless liquid, used directly in next step without the further purification.

Synthesis of compound 111-1

To an ice-cooling solution of 2-dimethylaminoethylamine (110-1) (0.62 g, 7.04 mmol) and triethylamine (0.97 g, 9.6 mmol) in dichloromethane (10 ml) was added dropwise a solution of compound 109 (1.12 g, 6.4 mmol) in dichloromethane (5 ml). The resulted mixture was stirred at 0° C. for 30 min, then water (50 ml) was added. The mixture was extracted with dichloromethane (20 ml×3), and the combined organic layer was washed with brine, dried over sodium sulfate, filtered and concentrated to afford crude compound 111-1 (1.25 g, 86%) as a white solid, used directly in next step without the further purification.

Synthesis of Compound 112-1

A mixture of compound 111-1 (300 mg, 1.32 mmol) and Lawesson's Reagent (267 mg, 0.66 mmol) in toluene (5 ml) was refluxed for 3 h. The solvent was evaporated to dryness, and the residue was purified by preparative TLC (methanol/dichloromethane=1:50~1:20) to afford compound 112-1 (180 mg, 56%) as a yellow oil.

m/z: [M+H]+ 243.3

Synthesis of Compound 113-1

To a solution of compound 12 (150 mg, 0.28 mmol) and compound 112-1 (101 mg, 0.42 mmol) in dichloromethane (10 ml) was added silver benzoate (190 mg, 0.83 mmol) and acetic acid (50 mg, 0.83 mmol). The resulted mixture was stirred at room temperature for 48 h, and concentrated. The residues was purified by chromatography on silica gel (methanol/dichloromethane=1:50~1:20) to afford compound 113-1 (57 mg, 28%) as a white solid.

m/z: [M+H]+ 731.5

Synthesis of Compound 114-1

To a solution of compound 113-1 (57 mg, 0.078 mmol) in a mixed solvent of methanol (2 ml), tetrahydrofuran (1 ml), and water (0.5 ml) was added sodium hydroxide (31 mg, 0.77 mmol). The resulted mixture was stirred at room temperature for 3 h. The reaction was diluted with dichloromethane (20 ml), washed with water (10 ml×3), brine, dried over sodium sulfate, filtered and concentrated to afford crude compound 114-1 (34 mg, 63%) as a white solid, used directly in next step without the further purification.

m/z: [M+H]+ 689.5

Synthesis of Compound 115-1

A solution of compound 114-1 (34 mg, 0.049 mmol), 4-tert-butoxy-3,3-dimethyl-4-oxobutanoic acid 20 (29 mg, 0.14 mmol), 4-dimethylaminopyridine (17 mg, 0.14 mmol) and EDCl (47 mg, 0.25 mmol) in dichloromethane (5 ml)

was stirred overnight at room temperature, and the resulted mixture (compound 115-1) was used directly in next step without the further purification.

Synthesis of Compound 116-1

To the solution of compound 115-1 prepared above in dichloromethane (5 ml) was added trifluoroacetic acid (0.5 ml), and the reaction mixture was stirred overnight at room temperature, then diluted with dichloromethane (20 ml), washed with water (10 ml×3), brine, dried over sodium sulfate, filtered and concentrated. The residue was purified by preparative TLC (methanol/dichloromethane=1:20) to afford compound 116-1 (2.3 mg, 6%) as an off-white solid.

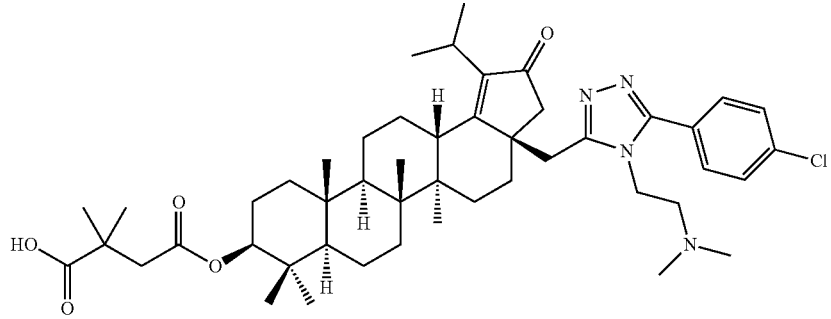
116-1 m/z: [M+H]$^+$ 817.5

Compound 116-2 was prepared according to method 14 and scheme 14, as a white solid.

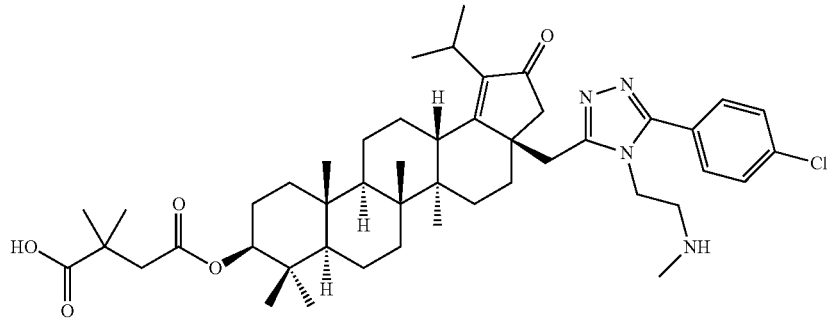
116-2 m/z: [M+H]$^+$ 803.5

Compound 116-3 was prepared according to method 14 and scheme 14, as a white solid.

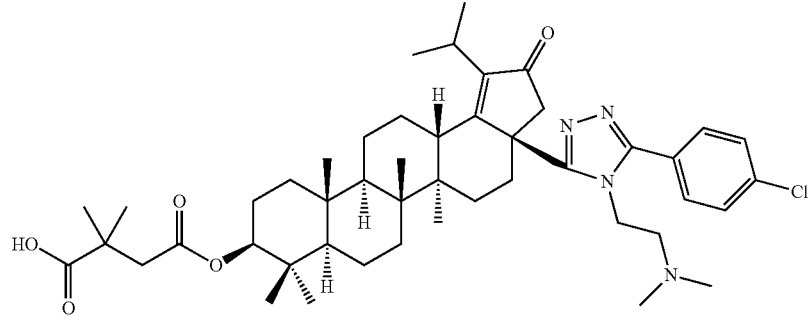
116-3 m/z: [M+H]+803.5

Compound 116-4 was prepared according to method 14 and scheme 14, as a white solid.

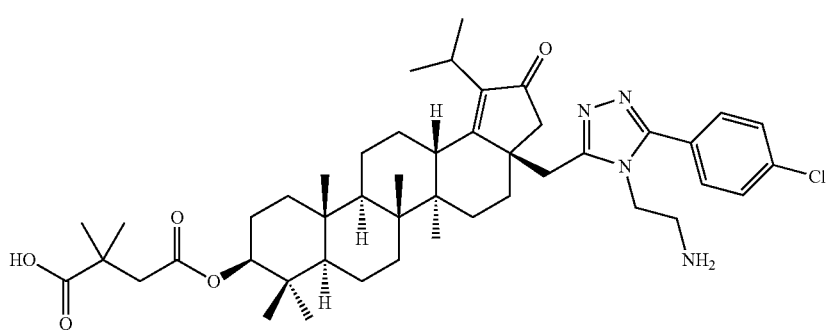

116-4 m/z: [M+H]$^+$ 789.5

Example 81-85 (Compound 127-1~127-5 were prepared according to method 15 and scheme 15 by using different hydrazide intermediates like 119 and the like.)

Synthesis of Key Intermediate 118

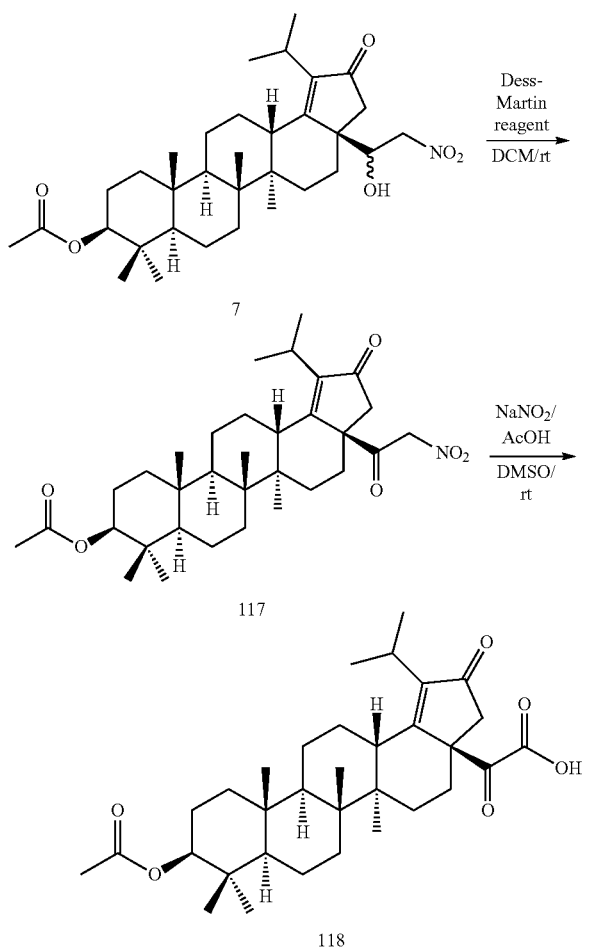

Synthesis of Compound 117

To a solution of compound 7 (6 g, 10.8 mmol) in dichloromethane (150 ml) was added Dess-martin reagent (6.8 g, 16.1 mmol). The resulted mixture was stirred at room temperature for 1 h, then the solid was filtered off, and the filtrate was evaporated to dryness. The residue was dissolved in ethyl acetate (500 ml), washed with water (300 ml×3), brine, dried over sodium sulfate, filtered and concentrated to afford crude compound 117 (4.8 g, 80%) as a light yellow solid, used directly in next step without the further purification.

m/z: [M+H]$^+$ 556.3

Synthesis of Compound 118

To a solution of compound 117 (2 g, 3.6 mmol) in dimethyl sulfoxide (20 ml) was added sodium nitrite (1 g, 14.4 mmol) and acetic acid (4 ml, 72.0 mmol). The resulted mixture was stirred overnight at room temperature, then adjusted reaction mixture pH=2-3 with aqueous HCl (2 N), and followed by adding water (100 ml) to introduce the precipitation. The precipitate was then collected by filtration and washed with water (200 ml). The solid was dissolved in dichloromethane (100 ml), washed with brine, dried over sodium sulfate, filtered and concentrate. The residue was added petroleum ether (100 ml) and a little dichloromethane, and a solid was formed by sonicate, and the solid was collected by filtration to afford crude compound 118 (1.4 g, 72%) as a light yellow solid, used directly in next step without the further purification.

m/z: [M+H]$^+$ 541.3

Synthesis of Compound 120

To a solution of compound 119 (92 mg, 0.44 mmol) and ethyldiisopropylamine (96 mg, 0.74 mmol) in N, N-dimethylformamide (5 ml) was added compound 118 (200 mg, 0.37 mmol) and HATU (250 mg, 0.66 mmol). The reaction mixture was stirred over night at room temperature, then diluted with dichloromethane (100 ml), washed with water (20 ml×3), brine, dried over sodium sulfate, filtered and concentrated to afford crude compound 120 (256 mg, 100%) as a light yellow solid, used directly in next step without the further purification.

m/z: [M+Na]$^+$ 693.4

Synthesis of Compound 121

To a solution of compound 120 (256 mg, 0.37 mmol) in dichloromethane (10 ml) was added tosyl chloride (211 mg, 1.11 mmol) and ethyldiisopropylamine (238 mg, 1.85 mmol). The reaction mixture was stirred at room temperature for 3 h, and purified directly by chromatography on silica gel (ethyl acetate/petroleum ether=1:15~1:10) to afford compound 121 (200 mg, 80%) as an off-white solid.

Synthesis of Compound 122-1 and Compound 122-2

To an ice-cooling solution of compound 8 (20 g, 33.3 mmol) in a mixed solvent of methanol (4 ml) and tetrahydrofuran (2 ml) was added sodium borohydride (34 mg, 0.88 mmol) in small portions. The reaction mixture was stirred at 0 for 30 min. The reaction was quenched by the addition of water (20 ml), and the mixture was extracted with dichloromethane (30 ml×3). The combined organic phase was washed with brine, dried over sodium sulfate, filtered and concentrated. The residue was purified by chromatography on silica gel (petroleum ether/ethyl acetate=5:1~3:1) to afford compound 122-1 (40 mg, 20%) and compound 122-2 (76 mg, 38%) as white solids.

Compound 122-1 ¹HNMR (CDCl₃) δ 7.91-7.88 (2H, m), 7.50-7.47 (2H, m), 5.60 (1H, d, J=5.2 Hz), 4.52-4.48 (1H, m), 3.51 (2H, d, J=5.2 Hz), 3.15-0.62 (44H, m).

Compound 122-2 ¹HNMR (CDCl₃) δ 8.01-7.95 (2H, m), 7.53-7.50 (2H, m), 5.61 (1H, d, J=4.4 Hz), 4.53-4.49 (1H, m), 3.51 (2H, d, J=5.2 Hz), 3.27-0.80 (46H, m).

Synthesis of Compound 123-1

To a solution of compound 122-1 (40 mg, 0.059 mmol) in a mixed solvent of methanol (2 ml), tetrahydrofuran (1 ml), and water (0.5 ml) was added sodium hydroxide (24 mg, 0.6 mmol). The resulted mixture was stirred overnight at room temperature. The reaction was diluted with dichloromethane (100 ml), washed with water (20 ml×3), brine, dried over sodium sulfate, filtered and concentrated to afford crude compound 123-1 (35 mg, 93%) as an off-white solid, used directly in next step without the further purification.

m/z: [M+H]⁺ 635.4

Synthesis of Compound 124-1

To an ice-cooling solution of compound 123-1 (35 mg, 0.055 mmol), triethylamine (7 mg, 0.066 mmol) and a catalytic amount of 4-dimethylaminopyridine in dichloromethane (10 ml) was added a solution of acetic anhydride in dichloromethane (10 mg/ml) (0.45 ml, 0.044 mmol). The reaction mixture was stirred at 0 for 1 h, then diluted with dichloromethane (100 ml), washed with water (10 ml×3), brine, dried over sodium sulfate, filtered and concentrated to afford crude compound 124-1 (40 mg, 100%) as an off-white solid, used directly in next step without the further purification.

m/z: [M+H]⁺ 677.3

Synthesis of Compound 125-1

A solution of compound 124-1 (40 mg, 0.059 mmol), 4-tert-butoxy-3,3-dimethyl-4-oxobutanoic acid 20 (36 mg, 0.17 mmol), 4-dimethylaminopyridine (22 mg, 0.17 mmol) and EDCl (56 mg, 0.29 mmol) in dichloromethane (5 ml) was stirred overnight at room temperature. The resulted mixture was directly purified by preparative TLC (ethyl acetate/petroleum ether=1:5) to afford compound 125-1 (36 mg, 69%) as a white solid.

Synthesis of Compound 126-1

To a solution of compound 125-1 (35 mg, 0.041 mmol) in a mixed solvent of ethanol (1 ml) and toluene (1 ml) was added a solution of potassium hydroxide in ethanol (10 mg/ml) (0.27 ml, 0.048 mmol). The reaction mixture was stirred at room temperature for 1 h, then one drop of trifluoroacetic acid was added and concentrated, and the residue (crude compound 126-1) was directly used in next step without the further purification.

Synthesis of Compound 127-1

To the solution of compound 126-1 prepared above in dichloromethane (5 ml) was added trifluoroacetic acid (0.5 ml), and the reaction mixture was stirred at room temperature for 3 h, then diluted with water (10 ml), extracted with dichloromethane (10 ml×3). The combined organic phase was washed with saturated solution of sodium bicarbonate (10 ml), brine, dried over sodium sulfate, filtered and concentrated. The residue was purified by preparative TLC (methanol/dichloromethane=1:20) to afford compound 127-1 (14 mg, 45%) as a pink solid.

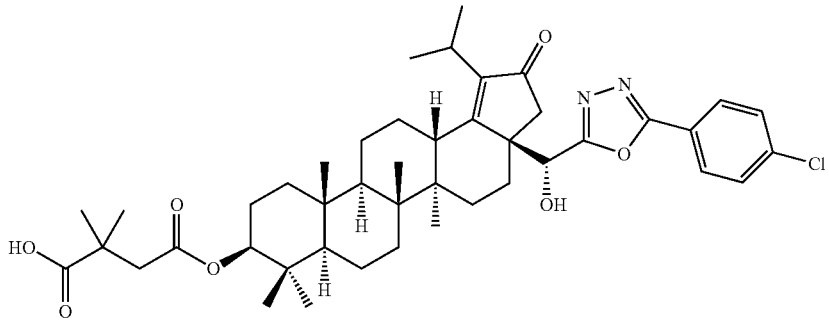

127-1 m/z: [M+H]⁺ 763.3

¹HNMR (CDCl₃) δ 7.89-7.87 (2H, m), 7.48-7.45 (2H, m), 5.60 (1H, s) 4.51-4.47 (1H, m), 3.49 (1H, s), 3.13 (1H, d, J=19.2 Hz), 2.97-2.87 (2H, m), 2.70 (1H, d, J=16.0 Hz), 2.57 (1H, d, J=16.0 Hz), 2.45-0.59 (45H, m).

Compound 127-2 was prepared according to method 15 and scheme 15, as an off-white solid.

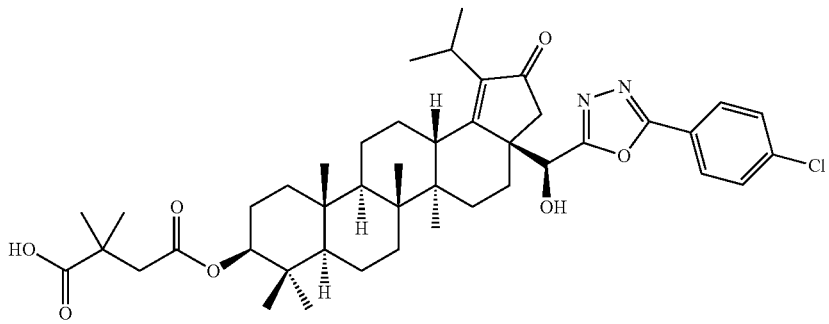

127-2 m/z: [M+H]⁺ 763.5

¹HNMR (CDCl₃) δ 7.95-7.93 (2H, m), 7.48-7.45 (2H, m), 5.61 (1H, s) 4.53-4.49 (1H, m), 3.49 (1H, s), 3.29-3.22 (1H, m), 3.01-3.94 (2H, m), 2.74 (1H, d, J=16.0 Hz), 2.56 (1H, d, J=16.0 Hz), 2.45-0.59 (45H, m).

Compound 127-3 was prepared according to method 15 and scheme 15, as an off-white solid.

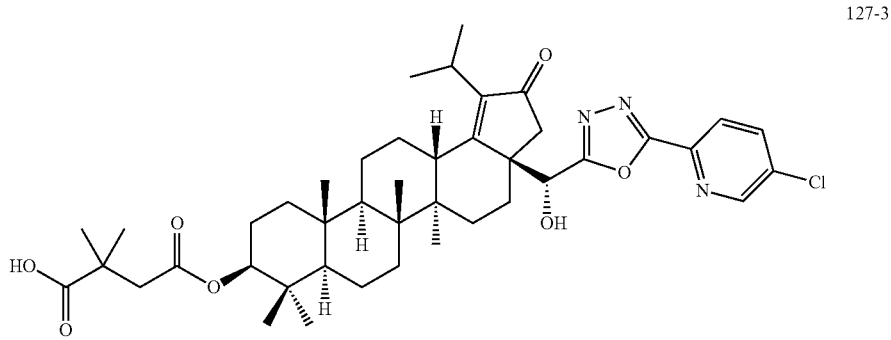

127-3 m/z: [M+H]+ 764.4

Compound 127-4 was prepared according to method 15 and scheme 15, as an off-white solid.

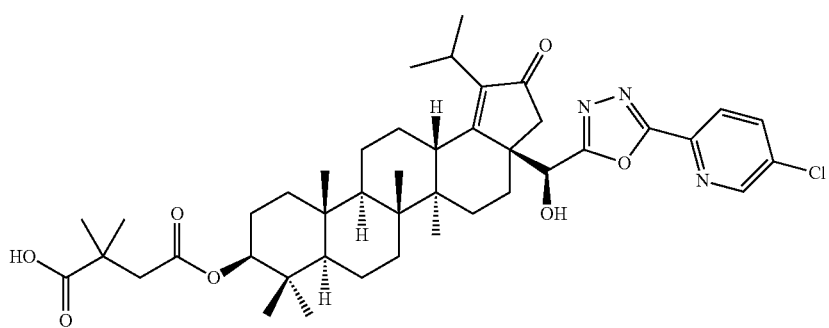

127-4 m/z: [M+H]+ 764.4

Compound 127-5 was prepared according to method 15 and scheme 15, as a yellow solid.

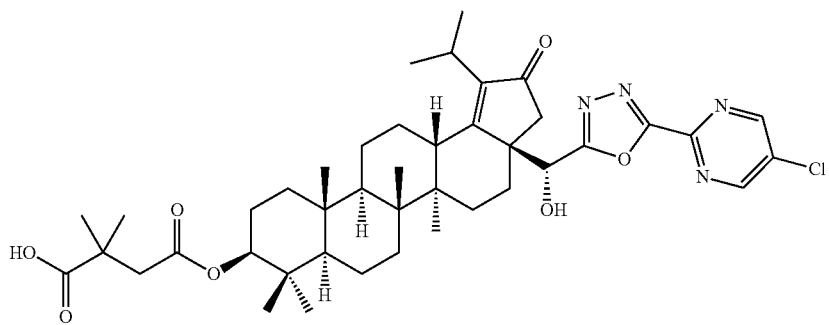

127-5 m/z: [M+H]+ 765.4

Example 86-88 (Compound 133-1~133-3 were prepared according to method 16 and scheme 16)

Synthesis of Compound 129

A mixture of compound 15 (150 mg, 0.29 mmol) and compound 128 (87 mg, 0.57 mmol) in toluene (5 ml) was stirred at room temperature for 1 h. The mixture was diluted with ethyl acetate (50 ml), washed with water (20 ml×3), brine, dried over sodium sulfate, filtered and concentrated. The residue was purified by preparative TLC (methanol/dichloromethane=1:40) to afford compound 129 (100 mg, 52%) as a white solid.

m/z: [M+H]+ 680.3

Synthesis of Compound 130-1

To a solution of compound 129 (90 mg, 0.12 mmol) in acetonitrile (5 ml) was added phosphorus oxychloride (140 mg, 1.18 mmol). The reaction mixture was stirred at 80° C. for 2 hr, then cooling down to room temperature. The mixture was neutralized with saturated solution of sodium bicarbonate, and extracted with ethyl acetate (20 ml×3). The combined organic phase was washed with saturated solution of sodium bicarbonate, dried over sodium sulfate, filtered and concentrated. The residue was purified by preparative TLC (methanol/dichloromethane=1:30) to afford compound 130-1 (30 mg, 39%) as a white solid.

m/z: [M+H]$^+$ 662.3

Synthesis of Compound 131-1

To a solution of compound 130-1 (30 mg, 0.04 mmol) in a mixed solvent of methanol (1 ml), tetrahydrofuran (0.5 ml), and water (0.5 ml) was added lithium hydroxide (9.5 mg, 0.39 mmol). The resulted mixture was stirred at room temperature for 3 h. The reaction was added water (10 ml), and extracted with dichloromethane (10 ml×3). The combined organic layer was washed with brine, dried over sodium sulfate, filtered and concentrated to afford crude compound 131-1 (25 mg, 88%) as a white solid.

m/z: [M+H]$^+$ 620.4

Synthesis of Compound 132-1

A solution of compound 131-1 (15 mg, 0.024 mmol), 4-tert-butoxy-3,3-dimethyl-4-oxobutanoic acid 20 (12.23 mg, 0.061 mmol), 4-dimethylaminopyridine (4.43 mg, 0.036 mmol) and EDCl (13.91 mg, 0.073 mmol) in dichloromethane (2 ml) was stirred overnight at room temperature, and the resulted mixture (crude compound 132-1) was used directly in next step without the further purification.

Synthesis of Compound 133-1

To the solution of compound 132-1 prepared above in dichloromethane (5 ml) was added trifluoroacetic acid (0.5 ml), and the reaction mixture was stirred at room temperature for 3 h, then diluted with water (10 ml), and extracted with dichloromethane (10 ml×3). The combined organic phase was washed with saturated solution of sodium carbonate (10 ml), brine, dried over sodium sulfate, filtered and concentrated. The residue was purified by preparative TLC (methanol/dichloromethane=1:30) to afford compound 133-1 (10 mg, 56%) as a white foam.

catalytic amount of sodium iodide in N,N-dimethylformamide (3 ml) was stirred overnight at room temperature. The reaction was added water (20 ml), and extracted with dichloromethane (20 ml×3). The combined organic phase was washed with brine, dried over sodium sulfate, filtered and concentrated to afford crude compound 130-2 (10 mg, 75%) as a yellow solid, used directly in next step without the further purification.

m/z: [M+H]$^+$ 733.4

Synthesis of Compound 131-2

To a solution of compound 130-2 (10 mg, 0.014 mmol) in a mixed solvent of methanol (1 ml), tetrahydrofuran (0.5 ml), and water (0.5 ml) was added lithium hydroxide (3 mg, 0.14 mmol). The resulted mixture was stirred at room temperature for 3 h. The reaction was added water (10 ml), and extracted with dichloromethane (10 ml×3). The combined organic layer was washed with brine, dried over sodium sulfate, filtered and concentrated to afford crude compound 131-2 (8 mg, 85%) as a white solid, used directly in next step without the further purification.

Synthesis of Compound 132-2

A solution of compound 131-2 (8 mg, 0.012 mmol), 4-tert-butoxy-3,3-dimethyl-4-oxobutanoic acid 20 (5.85 mg, 0.029 mmol), 4-dimethylaminopyridine (2.12 mg, 0.017 mmol) and EDCl (6.65 mg, 0.035 mmol) in dichloromethane (2 ml) was stirred overnight at room temperature, and the resulted mixture (crude compound 132-2) was used directly in next step without the further purification.

Synthesis of Compound 133-2

To a solution of compound 132-2 prepared above in dichloromethane (5 ml) was added trifluoroacetic acid (0.5 ml), and the reaction mixture was stirred at room temperature for 3 hr, then diluted with water (10 ml), extracted with dichloromethane (10 ml×3). The combined organic phase was washed with saturated solution of sodium bicarbonate

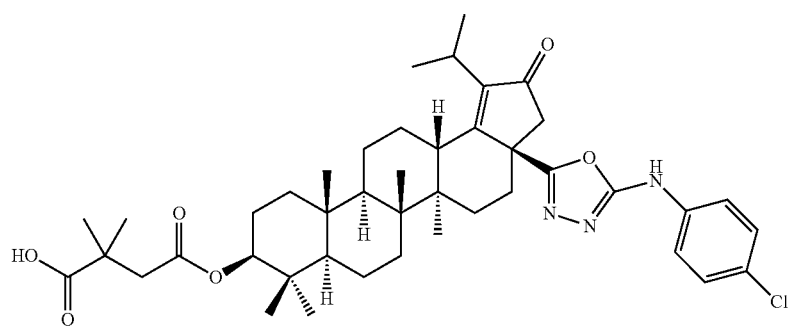

133-1 m/z: [M+H]$^+$ 748.4

Synthesis of Compound 130-2

A mixture of compound 130-1 (12 mg, 0.02 mmol), 2-chloro-N,N-dimethylethanamine (6 mg, 0.06 mmol) and a (10 ml), brine, dried over sodium sulfate, filtered and concentrated. The residue was purified by preparative TLC (methanol/dichloromethane=1:20) to afford compound 133-2 (3 mg, 32%) as a white solid.

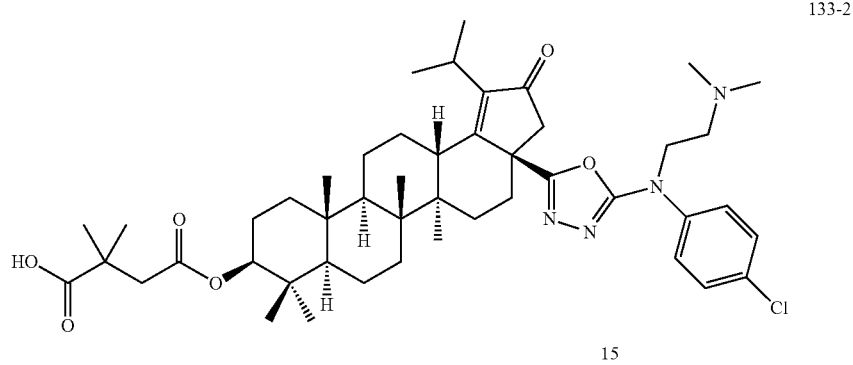

133-2 m/z: [M+H]+ 819.5

Compound 133-3 was prepared according to method 16 and scheme 16, as an off white solid.

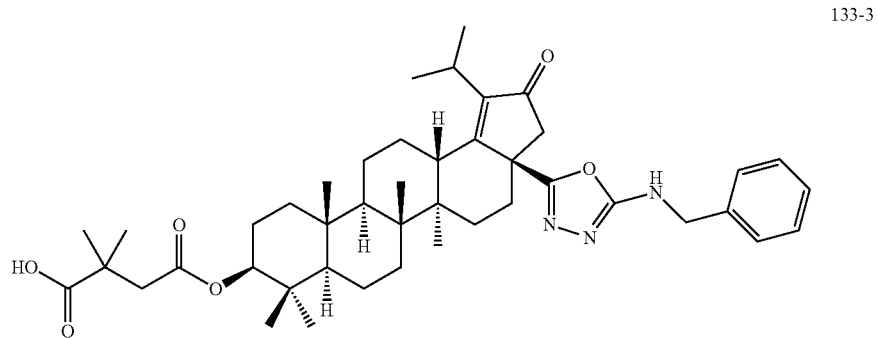

133-3 m/z: [M+H]+ 728.4

Example 89-91 (Compound 141-1~141-3 were prepared according to method 17 and scheme 17)

Synthesis of Key Intermediate 135

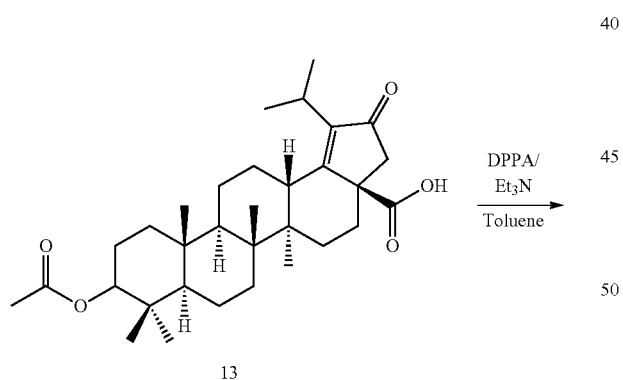

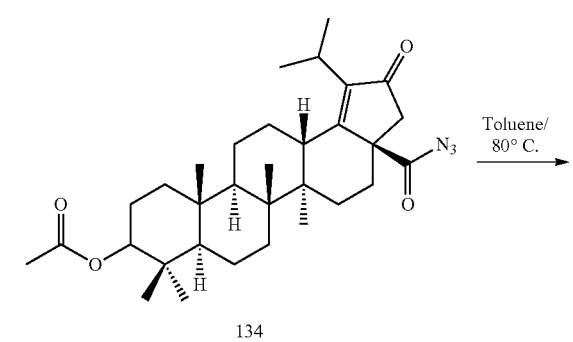

-continued

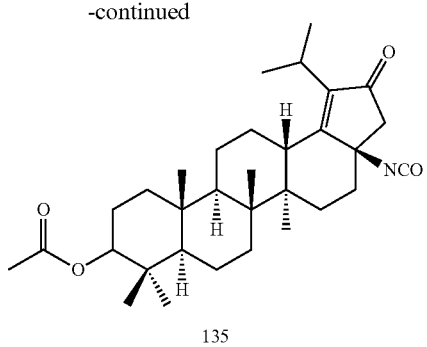

135

Synthesis of Compound 134

To a stirring suspension of compound 13 (500 mg, 0.98 mmol) in dry toluene (7.5 ml) was added triethylamine (0.16 ml, 1.17 mmol) and diphenylphosphoryl azide (0.25 ml, 1.17 mmol). The mixture was stirred at room temperature for 3 h and concentrated to dryness. The residue was purified by chromatography on silica gel (ethyl acetate/petroleum ether=1:15~1:10) to afford compound 134 (380 mg, 72%) as a white solid.

m/z: [M+H]+ 538.5

Synthesis of Compound 135

A solution of compound 134 (380 mg, 0.71 mmol) in toluene (8 ml) was stirred at 80 for 2 hr and the reaction mixture was concentrated to dryness to afford crude compound 135 (340 mg, 94%) as a white solid, used directly in next step without the further purification.

m/z: [M+H]+ 510.4

Synthesis of Compound 137-1

A solution of compound 135 (130 mg, 0.26 mmol) and compound 136-1 (45.6 mg, 0.27 mmol) in toluene (5 ml) was stirred at 80 for 20 min and the reaction mixture was concentrated to dryness to afford compound 137-1 (170 mg, 98%) as a white solid, used directly in next step without the further purification.

m/z: [M+Na]$^+$ 702.3

Synthesis of Compound 138-1

A solution of compound 137-1 (120 mg, 0.18 mmol), tosyl chloride (102 mg, 0.54 mmol) and ethyldiisopropylamine (116 mg, 0.9 mmol) in dichloromethane (5 ml) was stirred overnight at room temperature. The mixture was concentrated to dryness, and the residue was purified by chromatography on silica gel (methanol/dichloromethane=1:200~1:100) to afford compound 138-1 (100 mg, 86%) as a white foam.

m/z: [M+H]$^+$ 662.3

Synthesis of Compound 139-1

To a solution of compound 138-1 (100 mg, 0.15 mmol) in a mixed solvent of methanol (2 ml), tetrahydrofuran (4 ml), and water (2 ml) was added lithium hydroxide (36 mg, 1.15 mmol). The resulted mixture was stirred overnight at room temperature. The reaction was diluted with water (10 ml), and extracted with dichloromethane (10 ml×3). The combined organic phase was washed with brine, dried over sodium sulfate, filtered and concentrated to afford crude compound 139-1 (90 mg, 96%) as a white solid, used directly in next step without the further purification.

m/z: [M+H]$^+$ 620.3

Synthesis of Compound 140-1

A solution of compound 139-1 (90 mg, 0.15 mmol), 4-tert-butoxy-3,3-dimethyl-4-oxobutanoic acid 20 (73 mg, 0.36 mmol), 4-dimethylaminopyridine (27 mg, 0.22 mmol) and EDCl (84 mg, 0.44 mmol) in dichloromethane (5 ml) was stirred overnight at room temperature, and the resulted mixture (crude compound 140-1) was used directly in next step without the further purification.

Synthesis of Compound 141-1

To the solution of compound 140-1 prepared above in dichloromethane (5 ml) was added trifluoroacetic acid (0.5 ml), and the reaction mixture was stirred at room temperature for 3 hr, then diluted with water (10 ml), and extracted with dichloromethane (10 ml×3). The combined organic phase was washed with saturated solution of sodium bicarbonate (10 ml), brine, dried over sodium sulfate, filtered and concentrated. The residue was purified by preparative TLC (methanol/dichloromethane=1:40) to afford compound 141-1 (53 mg, 47%) as a white solid.

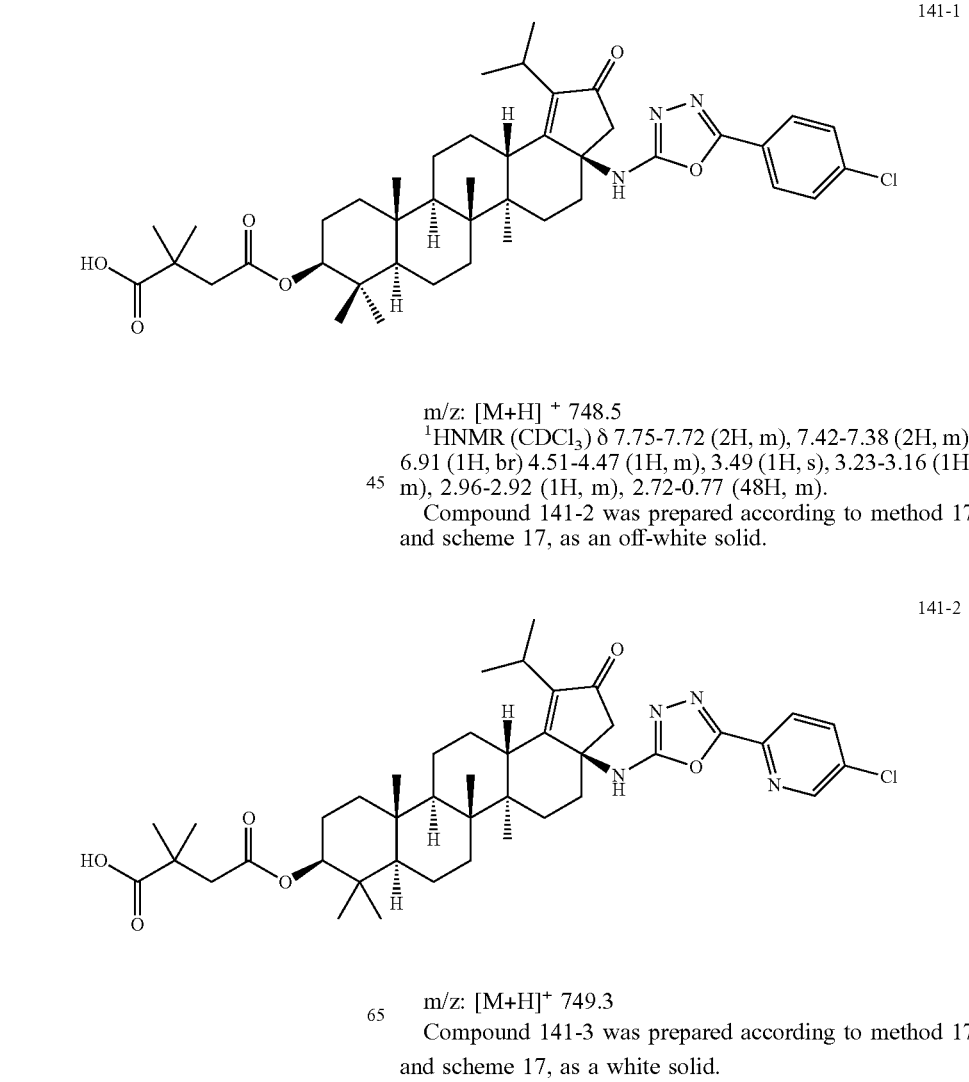

141-1 m/z: [M+H]$^+$ 748.5

$^1$HNMR (CDCl$_3$) δ 7.75-7.72 (2H, m), 7.42-7.38 (2H, m), 6.91 (1H, br) 4.51-4.47 (1H, m), 3.49 (1H, s), 3.23-3.16 (1H, m), 2.96-2.92 (1H, m), 2.72-0.77 (48H, m).

Compound 141-2 was prepared according to method 17 and scheme 17, as an off-white solid.

141-2 m/z: [M+H]$^+$ 749.3

Compound 141-3 was prepared according to method 17 and scheme 17, as a white solid.

141-3

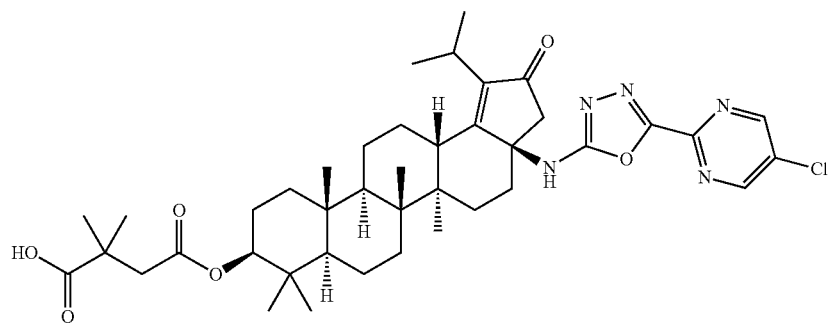

m/z: [M+H]⁺ 750.3

H¹NMR (CDCl₃) δ 8.77 (2H, s), 7.27 (1H, br), 4.52-4.48 (1H, m), 3.24-3.17 (1H, m), 2.93-2.90 (1H, m), 2.73-2.67 (2H, m), 2.57-2.41 (3H, m), 2.09-0.80 (44H, m).

Example 92-97 (Compound 153-1, 153'-1; 155-1; 155-2, 155'-1; 156-1, 156-2, and 156'-1 were prepared according to method 18 and scheme 18)

Synthesis of Compound 143-1

To an ice-cooling solution of compound 81-1 (2 g, 3.70 mmol) in N,N-dimethylformamide (10 ml) was added tert-butyl 1-(2-hydroxyethyl) hydrazinecarboxylate 142 (716 mg, 4.07 mmol), ethyldiisopropylamine (955 mg, 7.40 mmol) and HATU (1.69 g, 7.44 mmol). The resulted mixture was stirred at 0 for 30 min, then diluted with ethyl acetate (50 ml). The organic phase was washed with water (20 ml×3), brine, dried over sodium sulfate, filtered and concentrated to afford compound 143-1 (2.5 g, yield 97%) as an off-white foam.

m/z: [M+Na]⁺ 721.5

Synthesis of Compound 144-1

A mixture of compound 143-1 (2.5 g, 3.58 mmol) and trifluoroacetic acid (2 ml) in dichloromethane (20 ml) was stirred at room temperature for 1 h. The solvent was evaporated to dryness to afford crude compound 144-1 which was directly used for next step without the further purification.

Synthesis of Compound 145-1

To a solution of crude compound 144-1 in ethanol (20 ml) was added a catalytic amount of p-toluenesulfonic acid. The reaction mixture was stirred at reflux for overnight, then cooling down to room temperature. The mixture was diluted with dichloromethane (50 ml), washed with water (20 ml×2), brine, dried over sodium sulfate, filtered and concentrated. The residue was purified by chromatography on silica gel (methanol/dichloromethane=1:100-1:20) to afford compound 145-1 (1.4 g, yield 67%) as an off-white solid.

m/z: [M+H]⁺ 581.5

Synthesis of Compound 147-1

To an ice-cooling solution of compound 145-1 (1.4 g, 2.41 mmol), isoindoline-1,3-dione 146 (461 mg, 3.13 mmol) and triphenylphosphine (0.82 g, 3.13 mmol) in tetrahydrofuran (15 ml) was added diisopropyl azodicarboxylate (0.62 ml, 3.13 mmol). The reaction mixture was stirred at room temperature for 1 h, then diluted with ethyl acetate (50 ml), washed with water and brine, dried over sodium sulfate, filtered and concentrated. The residue was purified by chromatography on silica gel (ethyl acetate/petroleum ether=1:10~1:5) to afford compound 147-1 (1.6 g, yield 94%) as an off-white foam.

m/z: [M+H]+710.5

Synthesis of Compound 148-1

A mixture of compound 147-1 (1.6 g, 2.25 mmol), 4-chlorophenylboronic acid 92 (881 mg, 5.63 mol), pyridine (0.5 ml, 4.51 mmol) and cupric acetate (614 mg, 3.38 mmol) in 1,2-dichloroethane (15 ml) was stirred at 60 for overnight. The reaction mixture was cooling down to room temperature, water (20 ml) and dichloromethane (50 ml) were added and the layers were separated. The aqueous layer was extracted with dichloromethane (10 ml×2), and the combined organic layer was washed with water (10 ml×3), brine, dried over sodium sulfate and concentrated. The residue was purified by chromatography on silica gel (ethyl acetate/petroleum ether=1:6~1:3) to afford compound 148-1 (912 mg, yield 49%) as a yellow foam.

m/z: [M+H]⁺ 820.5

Synthesis of Compound 149-1

A solution of compound 148-1 (70 mg, 0.085 mmol) and hydrazine hydrate (25 mg, 85%, 0.43 mmol) in ethanol (5 ml) was reflux for 2 h. The reaction mixture was cooling down to room temperature, the insoluble solid was filtered off, and the filtrate was diluted with dichloromethane (50 ml), washed with water and brine, dried over sodium sulfate, filtered and concentrated to afford crude compound 149-1 (60 mg, yield 100%) as an off-white solid, used directly in next step without the further purification.

m/z: [M+H]⁺ 690.5

Synthesis of Compound 150-1

To a solution of compound 149-1 (168 mg, 0.24 mmol) in dichloromethane (5 ml) was added triethylamine (49 mg, 0.48 mmol) and di-tert-butyl dicarbonate (58 mg, 0.27 mmol). The reaction mixture was stirred at room temperature for about 3 h, then the mixture was diluted with dichloromethane (50 ml), washed with water and brine, dried over sodium sulfate, filtered and concentrated and purified by Prep-TLC (5% MeOH in DCM) to afford compound 150-1 (64 mg, yield 33%) as an off-white solid.

m/z: [M+H]⁺ 790.5

Synthesis of Compound 151-1

To a solution of compound 150-1 (64 mg, 0.081 mmol) in a mixed solvent of methanol (1 ml), tetrahydrofuran (1 ml), and water (0.5 ml) was added sodium hydroxide (32 mg, 0.81 mmol). The resulted mixture was stirred at room temperature for 3 h. The reaction was diluted with dichloromethane (50 ml), washed with water (10 ml×2) and brine, dried over sodium sulfate, filtered and concentrated to afford crude compound 151-1 (63 mg, yield 100%) as an off-white solid, used directly in next step without the further purification.

m/z: [M+H]⁺ 748.5

Synthesis Compound 151-2

To a solution of compound 151-1 (90 mg, 0.12 mmol) in chloroform (5 ml) was added N-chlorosuccinimide (24 mg, 0.18 mmol), and the mixture was stirred for overnight at 50° C. The reaction mixture was diluted with dichloromethane (50 ml) and washed with water (10 ml×2), and brine, dried over anhydrous sodium sulphate, filtered and concentrated to yield the crude compound 151-2 (73 mg, 81%) as an off white solid, carried to next step reaction without further purification.

m/z: [M+H]$^+$ 782.5

Synthesis of Compound 152-1

A solution of compound 151-1 (63 mg, 0.084 mmol), 4-tert-butoxy-3,3-dimethyl-4-oxobutanoic acid 20 (68 mg, 0.34 mmol), 4-dimethylaminopyridine (31 mg, 0.25 mmol) and EDCl (149 mg, 0.84 mmol) in dichloromethane (2 ml) was stirred at room temperature overnight, and the resulted mixture was directly purified by Prep-TLC (PE:EtOAc=3:1) to afford compound 152-1 (50 mg, yield 64%) as a white solid.

Synthesis of Compound 153-1

A solution of compound 152-1 (5 mg, 0.006 mmol) in dichloromethane (2 ml) was added trifluoroacetic acid (0.2 ml) and stirred at room temperature for 3 h. The reaction mixture was diluted with dichloromethane (20 ml), washed with water (10 ml), saturated solution of sodium bicarbonate (10 ml) and brine, dried over sodium sulfate, filtered and concentrated. The residue was dissolved in methanol (5 ml), added aqueous formaldehyde (3 mg, 37%, 0.038 mmol), the mixture was stirred at room temperature for 30 min, then added sodium cyanogroupborohydride (2 mg, 0.030 mmol). The reaction mixture was stirred for another 2 h, diluted with ethyl acetate (30 ml), washed with water and brine, dried over sodium sulfate, filtered and concentrated and purified by Prep-TLC (5% MeOH in DCM) to afford compound 153-1 (2 mg, yield 43%) as an off-white solid.

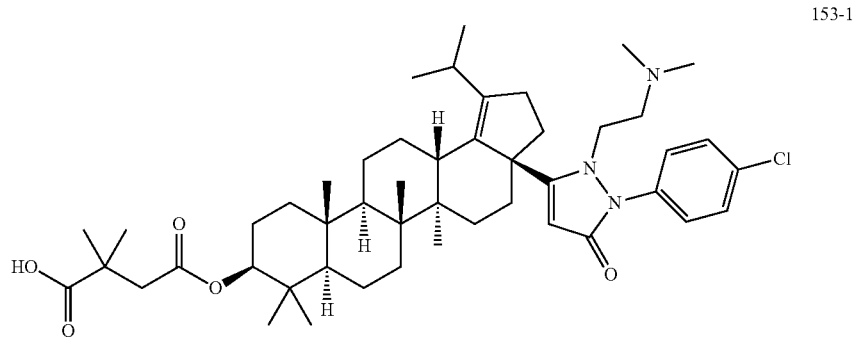

153-1 m/z: [M+H]$^+$ 804.5

Compound 153'-1 was prepared according to method 18 and scheme 18, as an off white solid.

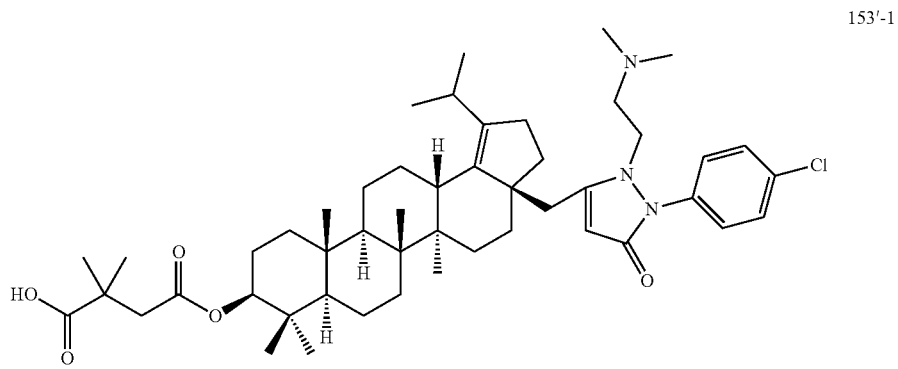

153'-1 m/z: [M+H]$^+$ 818.5

Synthesis of Compound 154-1

A mixture of compound 152-1 (40 mg, 0.043 mmol), sodium acetate (35 mg, 0.43 mmol) and potassium dichromate (15 mg, 0.051 mmol) in a mixed solvent of toluene (0.5 ml), acetic anhydride (0.5 ml) and acetic acid (0.5 ml) was stirred overnight at 60° C. After cooling down to room temperature, water (20 ml) was added. The mixture was extracted with dichloromethane (20 ml×3), and the combined organic layer was washed with saturated solution of sodium bicarbonate (10 ml×3), brine, dried over sodium sulfate and concentrated to afford crude compound 154-1 (40 mg, yield 98%) as a light yellow solid, used directly in next step without the further purification.

m/z: [M+H]⁺ 946.7

Synthesis of Compound 155-1

To a solution of compound 154-1 (30 mg, 0.032 mmol) in dichloromethane (5 ml) was added trifluoroacetic acid (0.5 ml), and stirred at room temperature for 3 h. The reaction mixture was diluted with dichloromethane (10 ml), and washed with saturated solution of sodium bicarbonate (10 ml), brine, dried over sodium sulfate and concentrated. The residue was purified by Prep-TLC (6% MeOH in DCM) to afford compound 155-1 (15 mg, yield 60%) as an off-white solid.

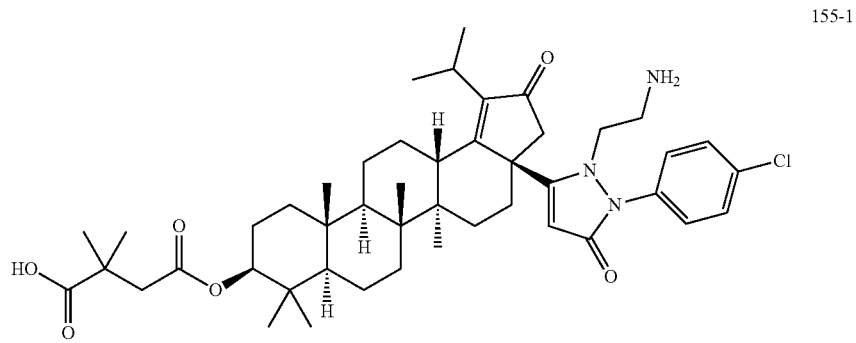

155-1 m/z: [M+H]⁺ 790.5

Compound 155-2 was prepared according to method 18 and scheme 18 by substituting 151-1 with 151-2, as an off white solid.

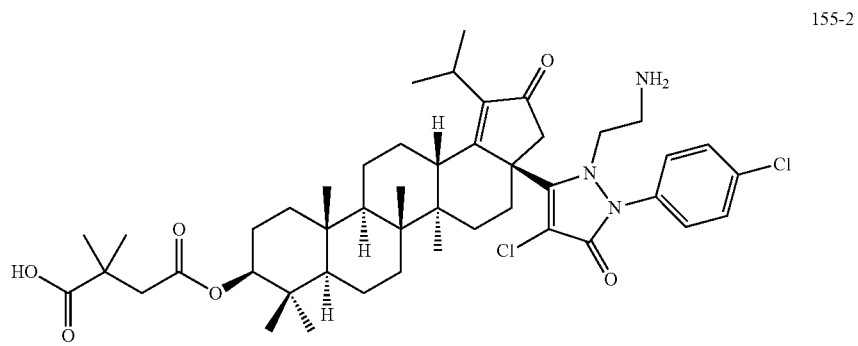

155-2 m/z: [M+H]⁺ 824.5

Compound 155'-1 was prepared according to method 18 and scheme 18, as an off white solid.

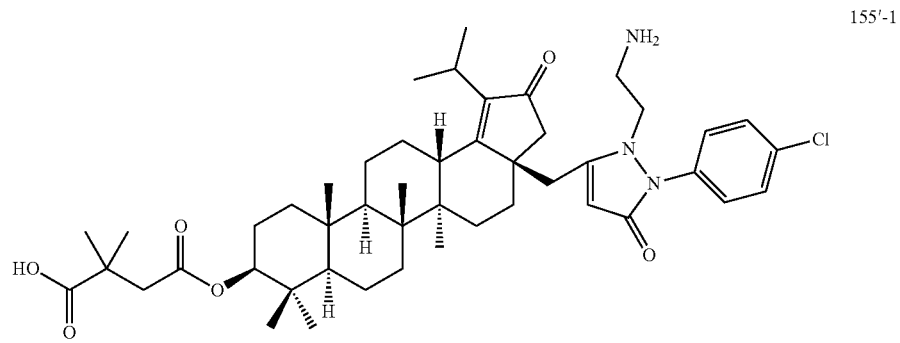

155'-1 m/z: [M+H]⁺ 804.5

Synthesis of Compound 156-1

To a solution of compound 155-1 (12 mg, 0.015 mmol) in methanol (2 ml) was added aqueous formaldehyde (6 mg, 37%, 0.076 mmol), the mixture was stirred at room temperature for 30 min, then added sodium cyanogroupborohydride (4 mg, 0.060 mmol). The reaction mixture was stirred for another 2 h, diluted with ethyl acetate (30 ml), washed with water and brine, dried over sodium sulfate, filtered and concentrated, the residue was purified by Prep-TLC (5% MeOH in DCM) to afford compound 156-1 (8 mg, yield 64%) as an-off white solid.

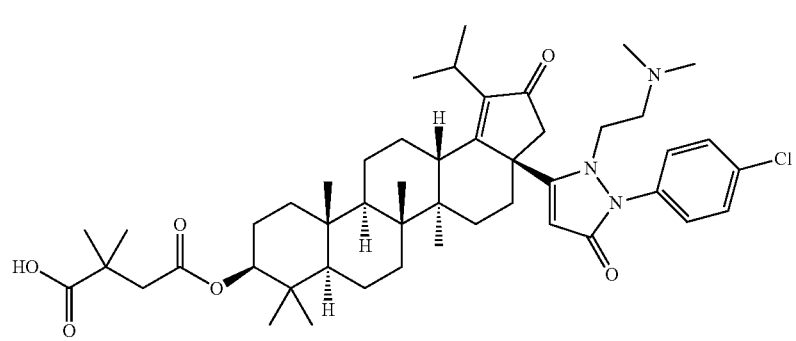

156-1 m/z: [M+H]$^+$ 818.5

Compound 156-2 was prepared according to method 18 and scheme 18 by substituting 151-1 with 151-2, as an off white solid.

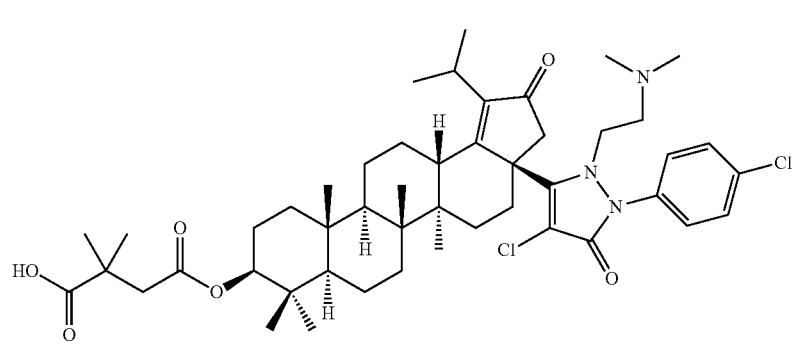

156-2 m/z: [M+H]$^+$ 852.5

Compound 156'-1 was prepared according to method 18 and scheme 18, as an off white solid.

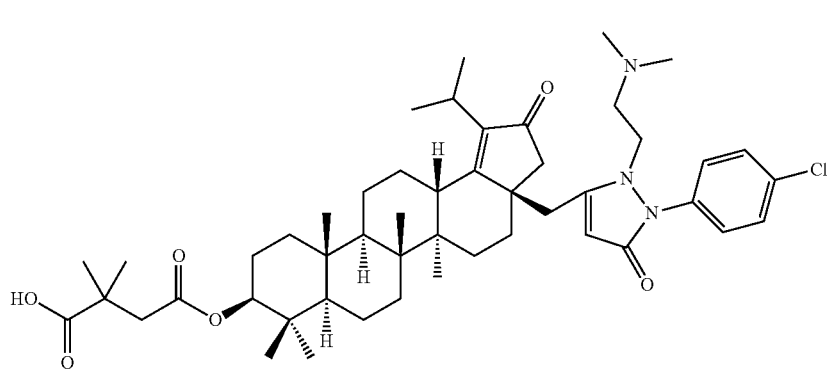

156'-1 m/z: [M+H]$^+$ 832.5

Example 100-103 (Compound 164-1, 164-2, 165-1 and 165-2 were prepared according to method 19 and scheme 19)

Synthesis of Key Intermediates 161
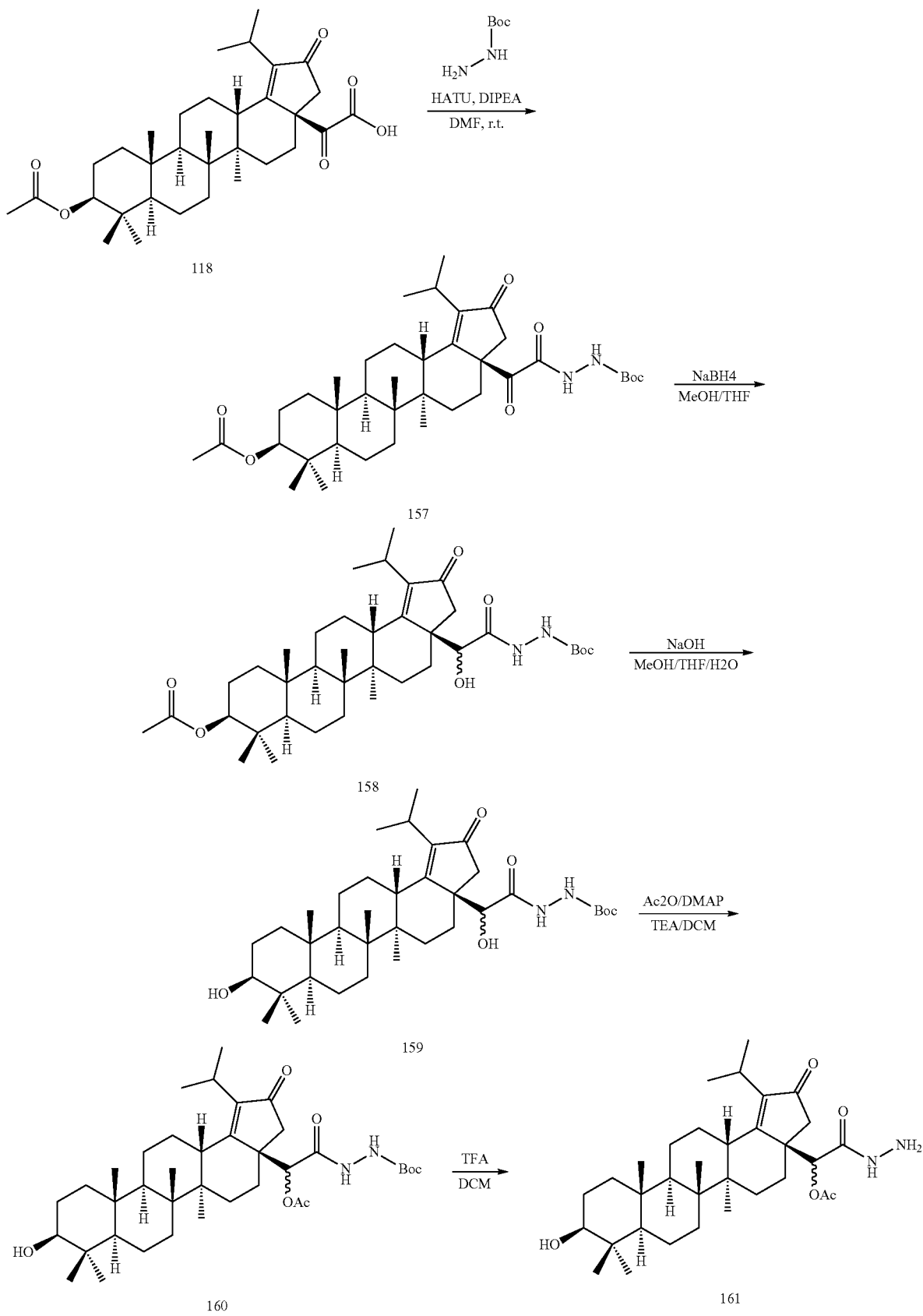

Synthesis of Compound 157

To a solution of tert-butyl hydrazinecarboxylate (73 mg, 0.55 mmol) and ethyldiisopropylamine (109 mg, 0.92 mmol) in N,N-dimethylformamide (5 ml) was added compound 118 (250 mg, 0.46 mmol), and HATU (262 mg, 0.69 mmol). The resulting mixture was stirred at room temperature for overnight, then diluted with dichloromethane (100 ml), washed with water (20 ml×3) and brine, dried over sodium sulfate, filtered and concentrated to afford compound 157 (310 mg, 100%) as a light yellow solid.

Synthesis of Compound 158

To an ice-cooling solution of compound 157 (310 mg, 0.47 mmol) in a mixture solvent of methanol (4 ml) and tetrahydrofuran (1 ml) was added sodium borohydride (53 mg, 1.42 mmol) in small portions. The reaction mixture was stirred at 0° C. for 30 min. The reaction was quenched by the addition of water (20 ml), the mixture was extracted with dichloromethane (30 ml×3). The combined organic phase was washed with brine, dried over sodium sulfate, filtered and concentrated to afford compound 158 (310 mg, 100%) as a light yellow solid.

Synthesis of Compound 159

To a solution of compound 158 (310 mg, 0.47 mmol) in a mixture solvent of methanol (2 ml), tetrahydrofuran (1 ml), water (0.5 ml) was added sodium hydroxide (24 mg, 0.59 mmol). The resulting mixture was stirred overnight at room temperature. The reaction was diluted with dichloromethane (100 ml), washed with water (20 ml×3) and brine, dried over sodium sulfate, filtered and concentrated to afford compound 159 (235 mg, 81%) as a light yellow solid.

Synthesis of Compound 160

To an ice-cooling solution of compound 159 (235 mg, 0.38 mmol), triethylamine (42 mg, 0.42 mmol) and a catalytic amount of 4-dimethylaminopyridine in dichloromethane (10 ml) was added a solution of acetic anhydride in dichloromethane (10 mg/ml) (3.1 ml, 0.31 mmol). The reaction mixture was stirred at 0 for 1 h, then diluted with dichloromethane (50 ml), washed with water (10 ml×3) and brine, dried over sodium sulfate, filtered and concentrated. The residue was purified by chromatography on silica gel (ethyl acetate/petroleum ether=1:10~1:5 to afford compound 160 (250 mg, 99.6%) as an off-white solid.

Synthesis of Compound 161

To a solution of compound 160 (250 mg, 0.38 mmol) in dichloromethane (5 ml) was added trifluoroacetic acid (1 ml), the reaction mixture was stirred at room temperature for 3 h, then diluted with water (20 ml), extracted with dichloromethane (20 ml×3). The combined organic phase was washed with brine, dried over sodium sulfate, filtered and concentrated to afford compound 161 (210 mg, 99%) as an off-white solid.

m/z: [M+H]$^+$ 557.5

Synthesis of Compound 162

To a solution of compound 161 (300 mg, 0.54 mmol) and compound 112 (195 mg, 0.59 mmol) in dichloromethane (10 ml) was added silver benzoate (380 mg, 1.62 mmol) and acetic acid (97 mg, 1.62 mmol). The resulting mixture was stirred at room temperature for 48 h, concentrated. The residues was purified by chromatography on silica gel (methanol/dichloromethane=1:50~1:20) to afford compound 162 (150 mg, 34%) as an off-white solid.

m/z: [M+H]$^+$ 891.4

Synthesis of Compound 163-1 and 163-2

A solution of compound 162 (150 mg, 0.18 mmol), 4-tert-butoxy-3,3-dimethyl-4-oxobutanoic acid 20 (111 mg, 0.55 mmol), 4-dimethylaminopyridine (67 mg, 0.55 mmol) and EDCl (350 mg, 1.8 mmol) in dichloromethane (5 ml) was stirred overnight at room temperature, then diluted with dichloromethane (100 ml), washed with saturated solution of ammonium chloride (10 ml×2) and brine, dried over sodium sulfate, filtered and concentrated. The residue was purified by preparative TLC to afford compound 163-1 (58 mg, 31%) and compound 163-2 (63 mg, 34%) as off-white solids.

Synthesis of Compound 164-1

To a solution of compound 163-1 (58 mg, 0.057 mmol) in dioxane (5 ml) was added concentrated hydrochloric acid (1 ml), the reaction mixture was stirred at 40° C. for overnight, then diluted with water (20 ml), adjusted pH=7 with saturated solution of sodium bicarbonate, extracted with dichloromethane (contained 5% methanol) (10 ml×5). The combined organic phase was washed with brine, dried over sodium sulfate, filtered and concentrated. The residue was purified by preparative TLC to afford compound 164-1 (25 mg, 54%) as a white solid.

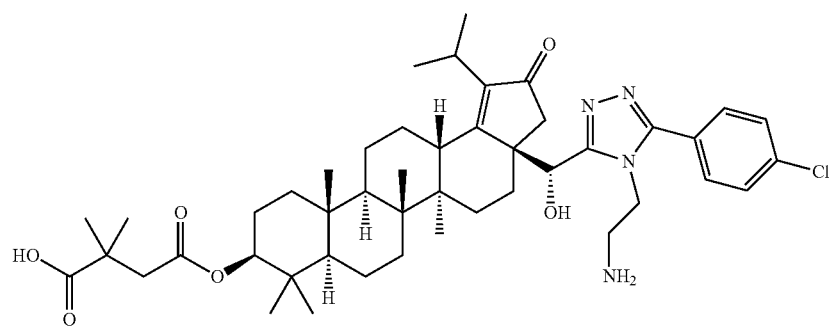

164-1 m/z: [M+H]$^+$ 805.5

Compound 164-2 was prepared according to method 19 and scheme 19, as a white solid.

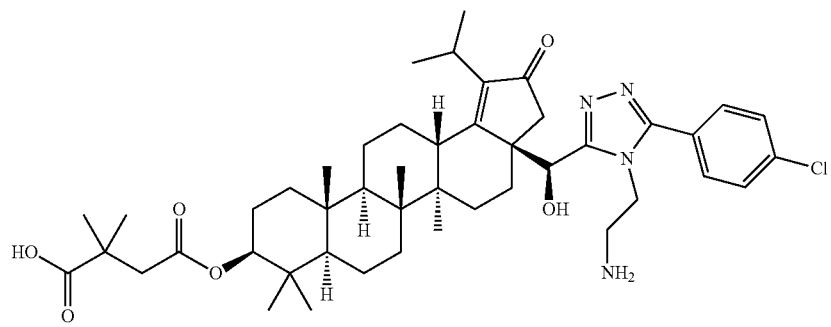

164-2 m/z: [M+H]⁺ 805.5
Synthesis of Compound 165-1

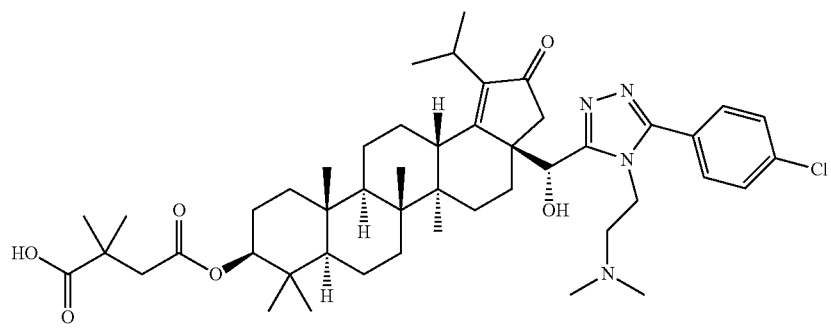

165-1

To a solution of compound 164-1 (15 mg, 0.019 mmol) in methanol (2 ml) was added catalytic amount of zinc chloride, and a drop of aqueous formaldehyde (37%), the reaction mixture was stirred at room temperature for 30 min, then added sodium cyanogroupborohydride (6 mg, 0.095 mmol). The mixture was stirred for overnight and purified directly by preparative TLC (methanol/dichloromethane=1:12) to afford compound 165-1 (5 mg, 32%) as an off-white solid.

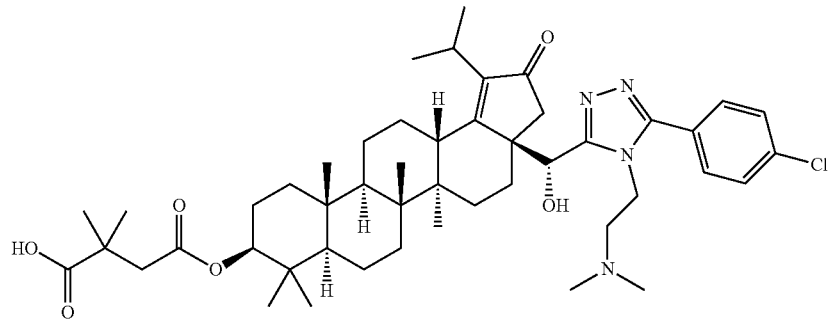

165-1 m/z: [M+H]⁺ 833.5

Compound 165-2 was prepared according to method 19 and scheme 19, as an off white solid.

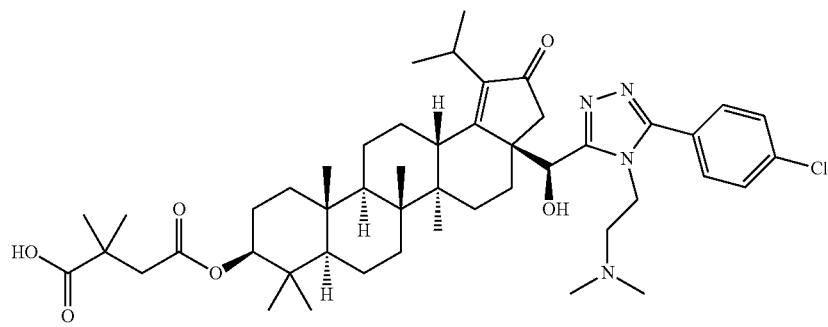

165-2 m/z: [M+H]$^+$ 833.5

Biological Assay

The antiviral activity of the compounds of the present invention was determined in a HIV-1 full replication assay.

In this assay, MT-2 cells that are infected with HIV-1$_{IIIB}$ were co-cultured with different concentration of the tested compounds for 3 days and then supernatant is transferred into new 384-well plates containing TZM-bl cells (also called JC53-bl). TZM-bl cells that could be infected by various kinds of HIV-1 strains stably express a great amount of HIV-1 receptor, co-receptor CD4 molecular, and co-receptor CXCR4 and CCR5. TZM-bl cells harbor LTR-luciferase and β-gal two report genes. The expression of luciferase and β-gal reporter directed by HIV-1 LTR can be activated by Tat protein generated after HIV infection, and the quantity of expression is proportional to the quantity of HIV-1. Compounds that interfere with virus replication in MT-2 cells, maturation of the virus, or post-entry steps in the HIV lifecycle decrease the luciferase signal or β-gal signal. In this experiment, BVM (Bevirimat, PA-457) is used as a positive control drug.

Method for Inhibiting HIV-1 Replication Assay:

1. Cell Culture

The MT-2 cells are infected at a Multiciplicity (MOI) of 0.01 TCID50, and then the MT-2 cells suspension was diluted to a needed concentration. 90 µl of the MT-2 cells suspension from above was added into 384-well plates containing 10 µl of the tested compounds.

2. Compound Preparation

Compounds were dissolved in DMSO and tested as 11 points 3-fold serial dilutions. After addition of cells to compound plates, plates were placed to humidified 5% CO$_2$ 37 incubator for 3 days. 10 µl of cells culture supernatant from the incubated plates was transferred into new black 384-well plates.

3. Method for Compounds' Cytotoxicity Assay:

The MT-2 cells are diluted to a needed concentration. 90 µl of the MT-2 cells suspension was added into 384-well plates containing 10 µl of the tested compounds. Compounds were dissolved in DMSO and tested as 11 points 3-fold serial dilutions. After addition of cells to compound plates, plates were placed to humidified 5% CO2 37 incubator for 3 days. The Luciferase activity was measured by CellTiter-Glo® Luminescent Cell Viability Assay kit (Promega Corp., WI, USA).

4. Method for Compounds' Antiviral Activity Detection

Adjusted the TZMb1 cells concentration and 40 µl of TZMb1 cells was added into each well in the black 384-well plates. After addition of the TZMb1 cells to the black plates, black plates were placed to humidified 5% CO$_2$ 37 incubator for 24 h, then β-Gal activity was measured.

Result Processing:

The anti viral activity %=(measured number-lowest mean number)/(highest mean number-lowest mean number)×100. The IC$_{50}$ values were calculated by Median Equation and the IC curve was generated by Graphpad Prism V 5.03.

TC$_{50}$ is referred to the toxicity in MT-2 cells by the compounds tested at 50% concentration; IC$_{50}$ is referred to the inhibiting HIV-1$_{IIIB}$ replication in MT-2 cells by the compounds tested at 50% concentration; Therapeutic Index (TI)=TC$_{50}$/IC$_{50}$.

The IC$_{50}$ values of the example compounds tested in accordance with the HIV replication in MT-2 cell (HIV-1$_{IIIB}$) assay are represented in table 1.

TABLE 1

| No. | Compound | TC$_{50}$ (PM) | SD | IC$_{50}$ (PM) | SD | TI |
|---|---|---|---|---|---|---|
| 1 | 22-1 | 46 | 1.5 | 0.0033 | 0 | 13939 |
| 2 | 22-2 | 28 | 0.61 | 0.0017 | 0 | 16470 |
| 3 | 22-3 | 36 | 3.60 | 0.0016 | 0 | 22500 |
| 4 | 22-9 | 33 | 11.1 | 0.0043 | 0.0003 | 7674 |
| 5 | 22-12 | 31 | 4.73 | 0.0004 | 0.0002 | 77500 |
| 6 | 22-13 | 35 | 13.6 | 0.0017 | 0.001 | 20588 |
| 7 | 22-14 | 200 | 0 | 0.00017 | 0 | 1176470 |
| 8 | 22-15 | 34 | 1.95 | 0.0021 | 0.0006 | 16191 |
| 9 | 22-16 | 39 | 11.42 | 0.00048 | 0.0001 | 81250 |
| 10 | 22-17 | 200 | 0 | 0.0028 | 0.0007 | 71429 |
| 11 | 22-18 | 48 | 9.4 | 0.0017 | 0.0009 | 28235 |
| 12 | 27-1 | 50 | 8.5 | 0.0033 | 0 | 15151 |
| 13 | 27-2 | 100 | 0 | 0.0020 | 0.00022 | 50000 |
| 14 | 27-3 | 36 | 2.49 | 0.0015 | 0.00062 | 24000 |
| 15 | 27-9 | 200 | 0 | 0.0088 | 0.00075 | 22727 |
| 16 | 27-11 | 23 | 1.9 | 0.025 | 0.023 | 920 |
| 17 | 27-13 | 200 | 0 | 0.017 | 0.011 | 11765 |
| 18 | 27-14 | 46 | 18 | 0.0049 | 0.0016 | 9388 |
| 19 | 33 | 18 | 0.94 | 0.0016 | 0 | 11250 |
| 20 | 38 | 100 | 0 | 0.0016 | 0 | 62500 |
| 21 | 65 | 17.68 | 2.64 | 0.058 | 0.009 | 305 |
| 22 | 77 | 200 | 0 | 0.159 | 0.05 | 1258 |
| 23 | 89-2 | 37 | 2.39 | 0.0584 | 0.007 | 633 |
| 24 | 91-1 | 41 | 0.44 | 0.0047 | 0.00003 | 8723 |
| 25 | 91-5 | 160 | 56 | 2.11 | 0.29 | 76 |
| 26 | 91-6 | 48 | 9.78 | 0.002 | 0.0002 | 24000 |
| 27 | 91-7 | 68 | 2.4 | 0.0007 | 0.0002 | 97143 |
| 28 | 91-8 | 48 | 11.93 | 0.0033 | 0.001 | 14546 |
| 29 | 91-9 | 26 | 0.816 | 0.00017 | 0 | 152941 |
| 30 | 91'-1 | 22 | 0.64 | 0.059 | 0.013 | 373 |
| 31 | 96-1 | 17 | 1.54 | 0.033 | 0.007 | 525 |
| 32 | 98-1 | 24 | 1.83 | 0.0016 | 0 | 14117 |
| 33 | 98-2 | 44 | 4.93 | 0.003 | 0.002 | 14667 |
| 34 | 98-3 | 42 | 9.16 | 0.00046 | 0.00022 | 91304 |
| 35 | 98-4 | 36 | 4.8 | 0.00081 | 0.0005 | 44444 |
| 36 | 98-5 | 13 | 3.62 | 0.00017 | 0 | 76471 |
| 37 | 98-6 | 13 | 1.72 | 0.00017 | 0 | 76471 |
| 38 | 98-7 | 200 | 0 | 0.00017 | 0 | 1176471 |
| 39 | 98'-1 | 62 | 0.097 | 0.00017 | 0 | 364706 |
| 40 | 98'-2 | 56 | 5.53 | 0.00037 | 0.0002 | 151351 |
| 41 | 102 | 9.93 | 1.49 | 0.175 | 0.047 | 56.7 |

TABLE 1-continued

| No. | Compound | TC$_{50}$ (PM) | SD | IC$_{50}$ (PM) | SD | TI |
|---|---|---|---|---|---|---|
| 42 | 108-2 | 26 | 13.2 | 0.16 | 0.04 | 163 |
| 43 | 116-1 | 35 | 13.56 | 0.00017 | 0 | 205882 |
| 44 | 116-2 | 27 | 8.1 | 0.0048 | 0.0002 | 5625 |
| 45 | 116-3 | 33 | 9.73 | 0.00055 | 0.0003 | 60000 |
| 46 | 116-4 | 33 | 14.2 | 0.0025 | 0.0026 | 13200 |
| 47 | 127-1 | 200 | 0 | 0.0016 | 0.0003 | 125000 |
| 48 | 127-2 | 45 | 3.14 | 0.025 | 0.003 | 1800 |
| 49 | 127-3 | 33 | 11.8 | 0.0006 | 0.0002 | 55000 |
| 50 | 127-4 | 200 | 0 | 0.038 | 0.006 | 5263 |
| 51 | 127-5 | 38 | 6.2 | 0.001 | 0.0002 | 38000 |
| 52 | 133-1 | 21 | 5.1 | 0.01 | 0.004 | 2100 |
| 53 | 133-2 | 47 | 5.3 | 0.00017 | 0 | 276471 |
| 54 | 141-1 | 26 | 12.5 | 0.0055 | 0.0007 | 4727 |
| 55 | 141-2 | 24 | 10.2 | 0.00026 | 0.00013 | 92307 |
| 56 | 141-3 | 22 | 4.99 | 0.0017 | 0.0005 | 12941 |
| 57 | 155-1 | 78 | 2.08 | 0.0016 | 0.0004 | 48750 |
| 58 | 156-1 | 19 | 2.08 | 0.00017 | 0 | 111765 |
| 59 | BVM | 64 | 1.40 | 0.005 | 0.00022 | 12800 |

Besides the data given for the compounds in table 1, the IC$_{50}$ values measured for all compounds 91-4, 98-8, 155-2, 156-2, 164-1 and 165-1 are <0.002 uM, the IC$_{50}$ measured for compound 89-3 is <0.005 uM, and the IC$_{50}$ values measured for all other remaining compounds are in the range of 0.5 uM~0.001 uM.

The invention claimed is:

1. A compound of formula (I), or a pharmaceutically acceptable salt thereof,

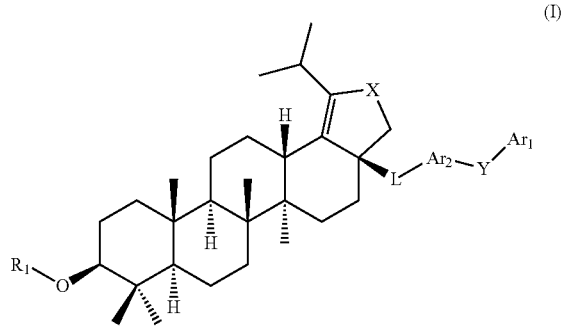

(I)

wherein:
R$_1$ is independently H,

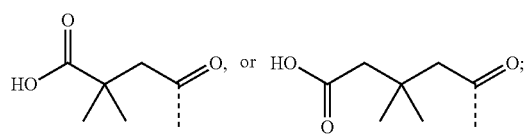

X is independently methylene, or carbonyl;
L is independently a direct bond, —NR$_4$—, —(CH$_2$)r-,

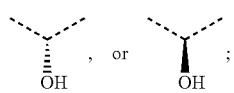

Y is independently a direct bond, —NR$_4$—, —NR$_4$CH$_2$—,

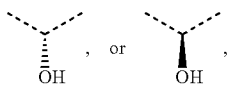

—CH$_2$—, —C(=O)—, —CH(CH$_3$)—, or —C(CH$_3$)$_2$—;

Ar$_1$ is independently substituted or unsubstituted aryl, or substituted or unsubstituted heteroaryl; when substituted, the substituents are one, two or three groups independently selected from the group consisting of: halo, alkyl, alkoxy, haloalkyl, haloalkoxy, amino, aminoalkyl, hydroxyalkyl, thioalkyl, —NHC(O)NH$_2$, —NHC(O)NH(R$_3$), —OH, —NO$_2$, —SH, —CN, —C(O)OH, —R$_3$C(O)OH, HOOC—R$_3$—C(O)—, —C(O)O—R$_3$, —C(O)NH$_2$, —C(O)NH(R$_3$), —C(O)N(R$_3$)$_2$, —(CH$_2$)rCONH$_2$, —(CH$_2$)rCONHR$_3$, and —(CH$_2$)rCON(R$_3$)$_2$;

Ar$_2$ is independently substituted or unsubstituted heteroaryl; when substituted, the substituents are one, two or three groups independently selected from the group consisting of: halo, haloalkyl, haloalkoxy, amino, —OH, —NO$_2$, —SH, —(CH$_2$)rS(=O)CH$_3$, —(CH$_2$)rS(=O)$_2$CH$_3$, —CN, —C(O)OH, —C(O)O—R$_3$, —C(O)NH$_2$, —C(O)NH(R$_3$), —C(O)N(R$_3$)$_2$, —(CH$_2$)rCONH$_2$, —(CH$_2$)rCONHR$_3$, —(CH$_2$)rCON(R$_3$)$_2$, aminoalkyl, hydroxyalkyl, alkyl, alkynyl, alkoxy, cycloalkylalkyl, and heterocycloalkylalkyl;

R$_3$ is independently alkyl, or two R$_3$ groups together with the nitrogen atom to which they are attached, form a 3- to 7-membered heterocycloalkyl ring;

R$_4$ is independently hydrogen, alkyl, cycloalkylalkyl, heterocycloalkylalkyl, aminoalkyl, hydroxyalkyl, —(CH$_2$)rS(=O)CH$_3$, —(CH$_2$)rS(=O)$_2$CH$_3$, —C(O)O—R$_3$, —C(O)NH$_2$, —C(O)NH(R$_3$), —C(O)N(R$_3$)$_2$, —(CH$_2$)rCONH$_2$, —(CH$_2$)rCONHR$_3$, or —(CH$_2$)rCON(R$_3$)$_2$; and r is an integer from 1 to 8.

2. The compound according to claim 1, or a pharmaceutically acceptable salt thereof, in which the compound has the following formula (II),

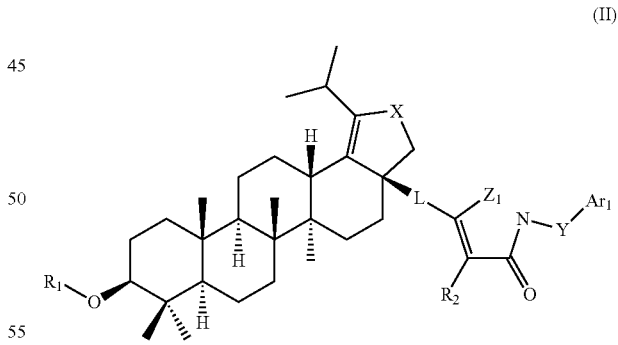

(II)

wherein:
R$_1$ is independently H,

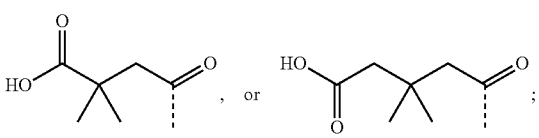

X is independently methylene, or carbonyl;

L is independently a direct bond, —(CH$_2$)r-,

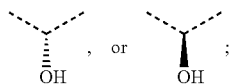

Y is independently a direct bond, —CH$_2$—, —C(=O)—, —CH(CH$_3$)—, or —C(CH$_3$)$_2$—;

R$_2$ is independently hydrogen, halo, —OH, —NO$_2$, amino, alkyl, haloalkyl, hydroxyalkyl, or aminoalkyl;

Ar$_1$ is independently substituted or unsubstituted aryl, or substituted or unsubstituted heteroaryl; when substituted, the substituents are one, two or three groups independently selected from the group consisting of: halo, alkyl, alkoxy, haloalkyl, haloalkoxy, amino, aminoalkyl, hydroxyalkyl, thioalkyl, —NHC(O)NH$_2$, —NHC(O)NH(R$_3$), —OH, —NO$_2$, —SH, —CN, —C(O)OH, —R$_3$C(O)OH, HOOC—R$_3$—C(O)—, —C(O)O—R$_3$, —C(O)NH$_2$, —C(O)NH(R$_3$), —C(O)N(R$_3$)$_2$, —(CH$_2$)rCONH$_2$, —(CH$_2$)rCONHR$_3$, and —(CH$_2$)rCON(R$_3$)$_2$;

R$_3$ is independently alkyl, or two R$_3$ groups together with the nitrogen atom to which they are attached, form a 3- to 7-membered heterocycloalkyl ring;

Z$_1$ is independently O, S, or NR$_4$;

R$_4$ is independently hydrogen, alkyl, cycloalkylalkyl, heterocycloalkylalkyl, aminoalkyl, hydroxyalkyl, —(CH$_2$)rS(=O)CH$_3$, —(CH$_2$)rS(=O)$_2$CH$_3$, —C(O)O—R$_3$, —C(O)NH$_2$, —C(O)NH(R$_3$), —C(O)N(R$_3$)$_2$, —(CH$_2$)rCONH$_2$, —(CH$_2$)rCONHR$_3$, or —(CH$_2$)rCON(R$_3$)$_2$; and r is an integer from 1 to 8.

3. The compound according to claim 2, or a pharmaceutically acceptable salt thereof, wherein:

R$_1$ is independently

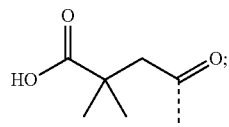

R$_2$ is independently H, Cl, or CH$_3$;

X is independently methylene, or carbonyl;

L is independently a direct bond, or —CH$_2$—;

Z$_1$ is independently NR$_4$;

R$_4$ is independently —CH$_3$, —C$_2$H$_5$, —CH$_2$CH$_2$NH$_2$, or —CH$_2$CH$_2$N(CH$_3$)$_2$;

Y is independently a direct bond, or —CH$_2$—;

Ar$_1$ is independently (R$_5$)n-phenyl-, (R$_5$)n-pyridyl-, or (R$_5$)n-pyrimidyl;

R$_5$ is independently methyl, methoxy, F, Cl, CN, or CF$_3$; and n is independently 0, 1, or 2.

4. The compound according to claim 1, or a pharmaceutically acceptable salt thereof, in which the compound has the following formula (III), (III)

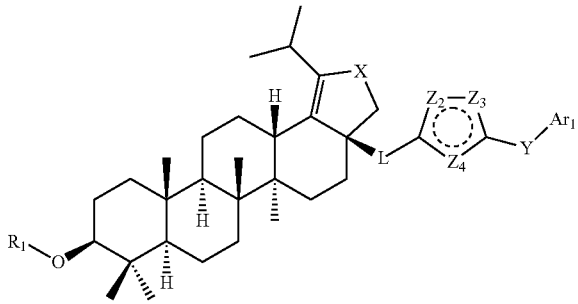

wherein:

R$_1$ is independently H,

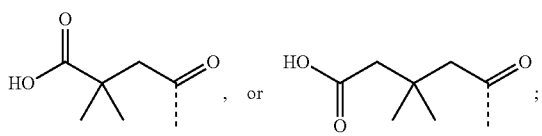

X is independently methylene, or carbonyl;

L is a direct bond, —NR$_4$—, —(CH$_2$)r-,

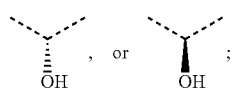

Y is a direct bond, —NR$_4$—, —NR$_4$CH$_2$—, —CH$_2$—, —C(=O)—, —CH(CH$_3$)—, or —C(CH$_3$)$_2$—;

Z$_2$, and Z$_3$ are independently O, N, or CH; Z$_4$ is independently O, S, N, or NR$_4$;

Ar$_1$ is independently substituted or unsubstituted aryl, or substituted or unsubstituted heteroaryl; when substituted, the substituents are one, two or three groups independently selected from the group consisting of: halo, alkyl, alkoxy, haloalkyl, haloalkoxy, amino, aminoalkyl, hydroxyalkyl, thioalkyl, —NHC(O)NH$_2$, —NHC(O)NH(R$_3$), —OH, —NO$_2$, —SH, —CN, —C(O)OH, —R$_3$C(O)OH, HOOC—R$_3$—C(O)—, —C(O)O—R$_3$, —C(O)NH$_2$, —C(O)NH(R$_3$), —C(O)N(R$_3$)$_2$, —(CH$_2$)rCONH$_2$, —(CH$_2$)rCONHR$_3$, and —(CH$_2$)rCON(R$_3$)$_2$;

R$_3$ is independently alkyl, or two R$_3$ groups together with the nitrogen atom to which they are attached, form a 3- to 7-membered heterocycloalkyl ring;

R$_4$ is independently hydrogen, alkyl, cycloalkyl, cycloalkylalkyl, aryl, arylalkyl, heterocycloalkyl, heterocycloalkylalkyl, heteroaryl, heteroarylalkyl, aminoalkyl, hydroxyalkyl, —(CH$_2$)rS(=O)CH$_3$, —(CH$_2$)rS(=O)$_2$CH$_3$, —C(O)O—R$_3$, —C(O)NH$_2$, —C(O)NH(R$_3$), —C(O)N(R$_3$)$_2$, —(CH$_2$)rCONH$_2$, —(CH$_2$)rCONHR$_3$, or —(CH$_2$)rCON(R$_3$)$_2$; and r is an integer from 1 to 8.

5. The compound according to claim 4, or a pharmaceutically acceptable salt thereof, wherein:

$R_1$ is independently

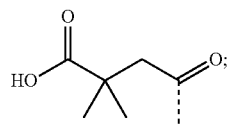

X is independently methylene, or carbonyl;
L is independently a direct bond, —$NR_4$—,

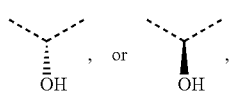

or —$CH_2$—;
Y is independently a direct bond, —$NR_4$—, —$NR_4CH_2$—, or —$CH_2$—;
$Z_2$, and $Z_3$ are independently N, $Z_4$ is O or S;
$Ar_1$ is independently ($R_5$)n-phenyl-, ($R_5$)n-pyridyl-, or ($R_5$)n-pyrimidyl;
$R_5$ is independently methyl, methoxy, F, Cl, Br, CN, or $CF_3$; and
n is independently 0, 1, or 2.

6. The compound according to claim 4, or a pharmaceutically acceptable salt thereof, wherein:

$R_1$ is independently

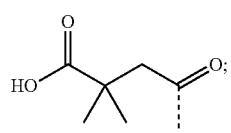

X is independently methylene, or carbonyl;
L is independently a direct bond,

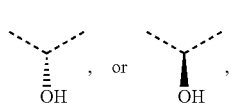

or —$CH_2$—;
Y is independently a direct bond;
$Z_2$, and $Z_3$ are independently N, $Z_4$ is $NR_4$;

$R_4$ is independently methyl, —$CH_2CH_2NH_2$, —$CH_2CH_2NHCH_3$, or —$CH_2CH_2N(CH_3)_2$;
$Ar_1$ is independently ($R_5$)n-phenyl-;
$R_5$ is independently Cl; and
n=1.

7. The compound according to claim 4, or a pharmaceutically acceptable salt thereof, wherein:

$R_1$ is independently

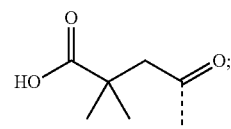

X is independently methylene, or carbonyl;
L is independently a direct bond;
Y is independently a direct bond;
$Z_2$ is N, $Z_3$ is CH, and $Z_4$ is O; or $Z_2$ is CH, $Z_3$ is N, and $Z_4$ is O;
$Ar_1$ is independently ($R_5$)n-phenyl-;
$R_5$ is independently Cl; and
n=1.

8. The compound according to claim 4, or a pharmaceutically acceptable salt thereof, wherein:

$R_1$ is

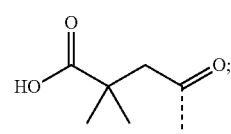

X is independently methylene, or carbonyl;
L is independently a direct bond or —$CH_2$—;
Y is independently a direct bond;
$Z_2$ is O, $Z_3$ and $Z_4$ are independently N; or $Z_3$ is O, $Z_2$, and $Z_4$ are independently N;
$Ar_1$ is independently ($R_5$)n-phenyl-;
$R_5$ is independently Cl; and
n=1.

9. The compound according to claim 1, or a pharmaceutically acceptable salt thereof, which is selected from the following compounds:

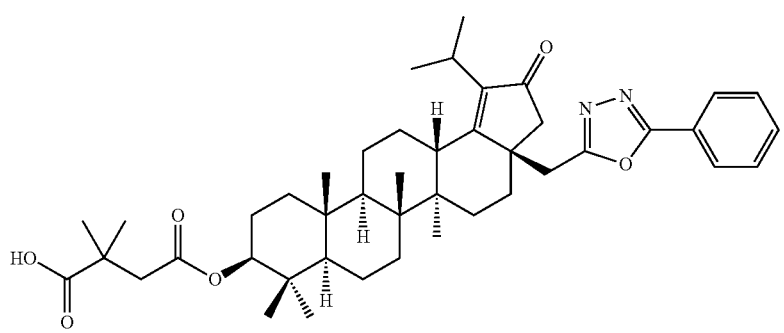

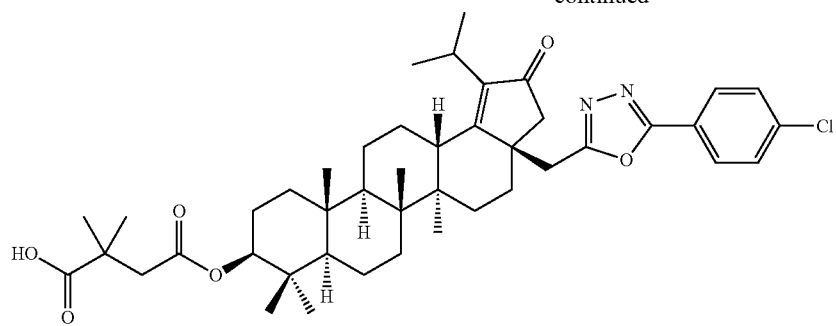
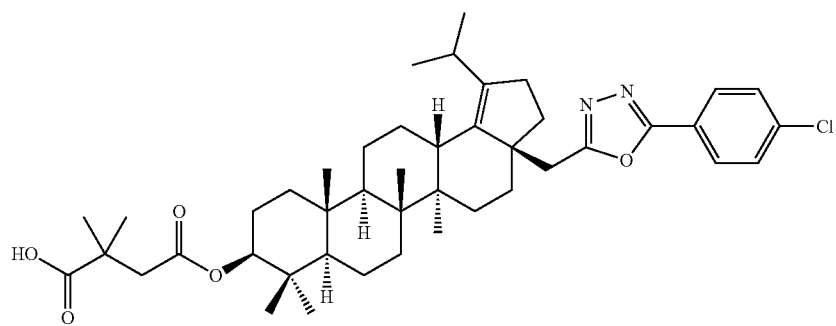
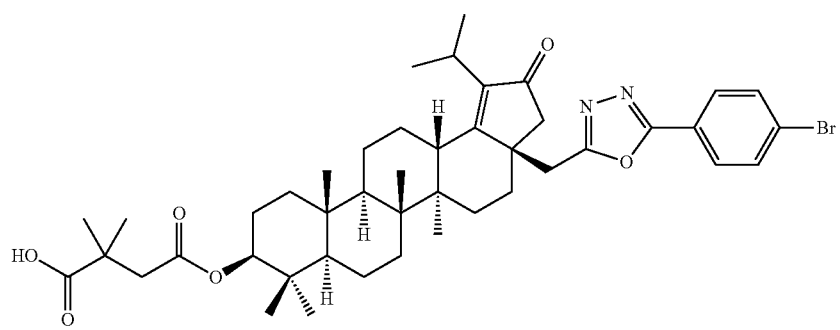
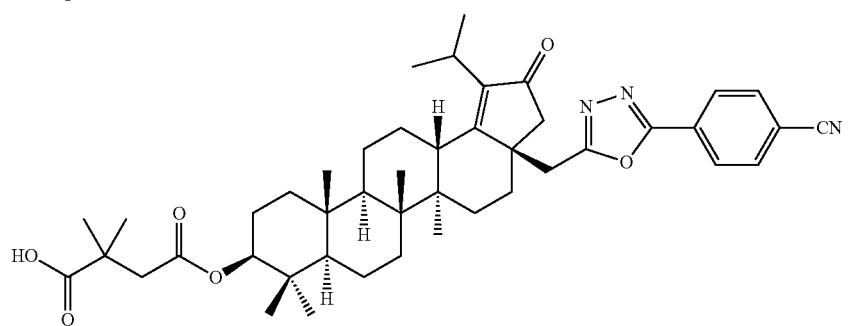
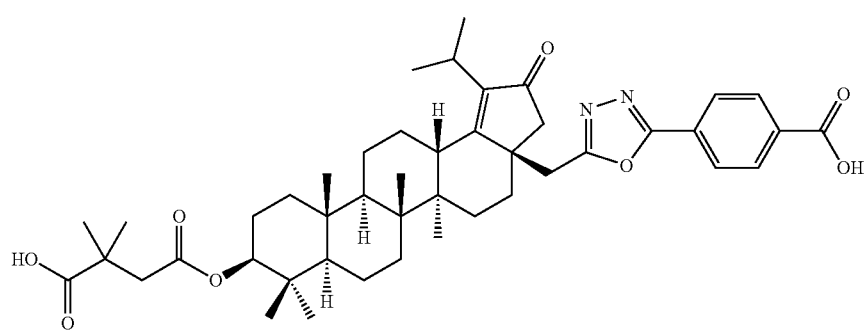

-continued
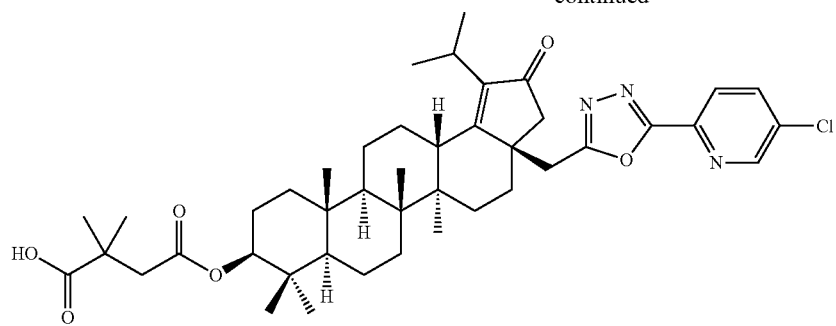
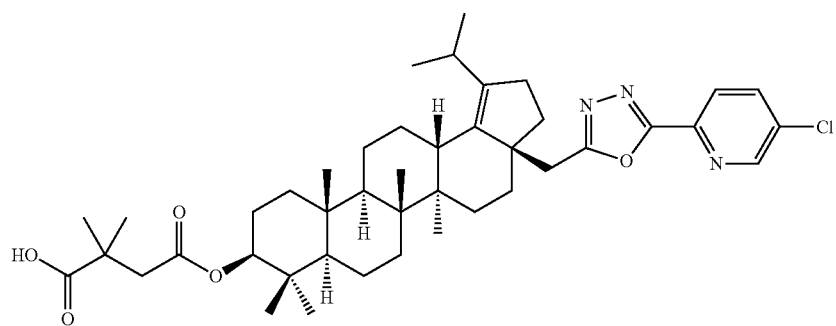
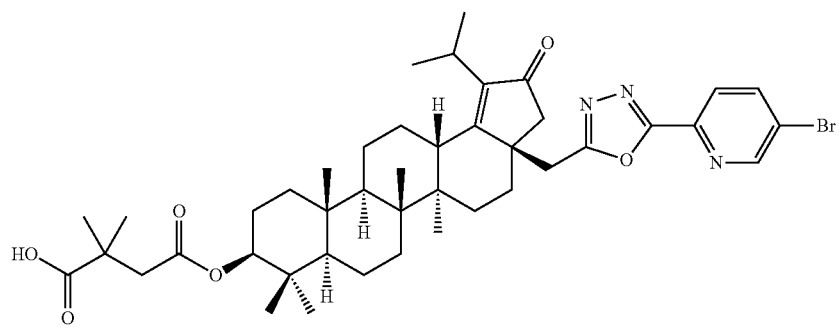
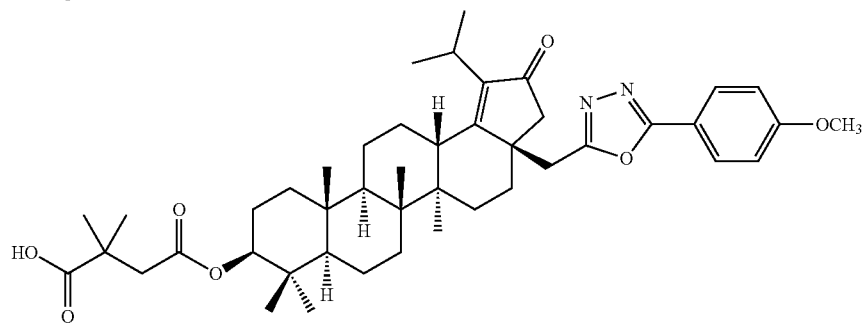
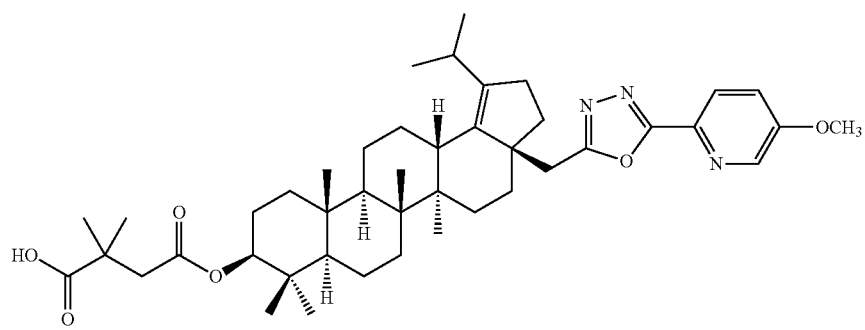

-continued
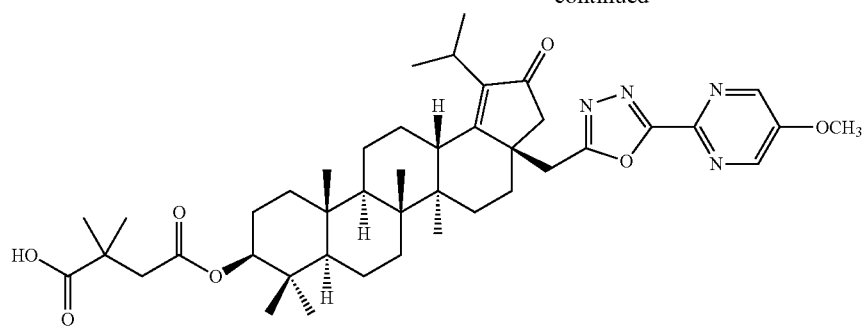
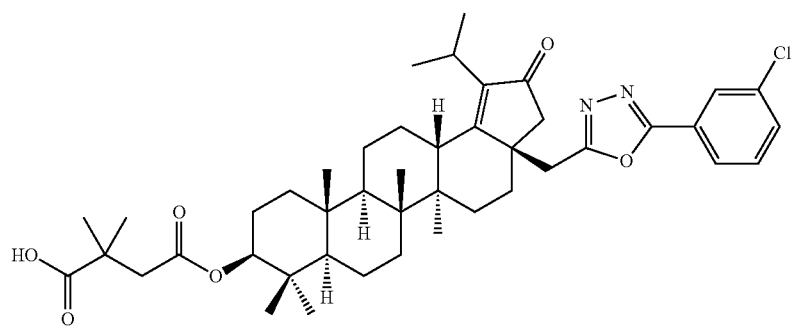
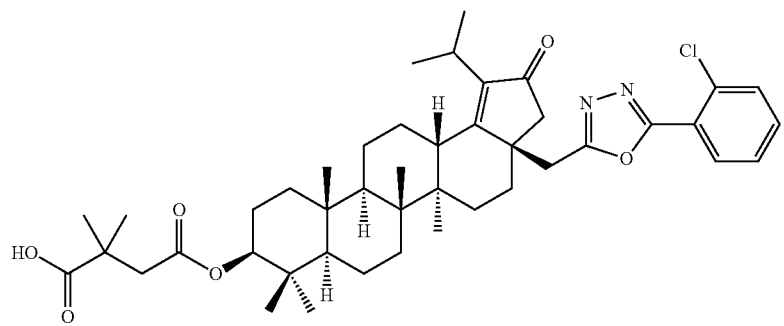
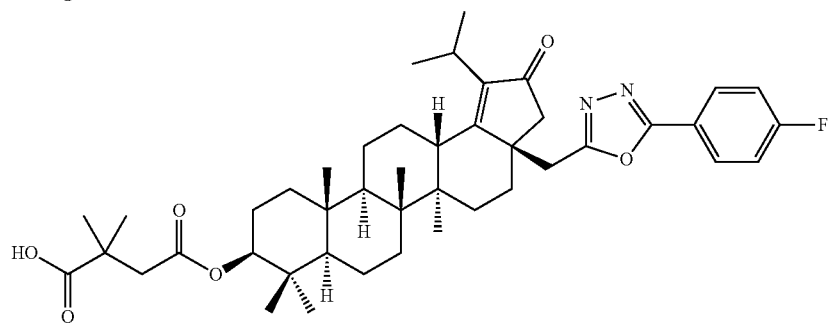
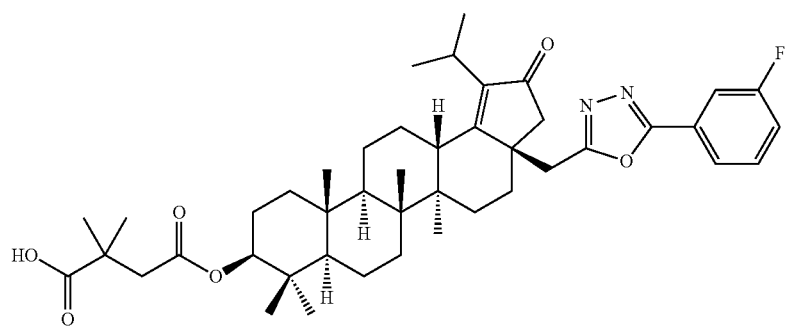

-continued
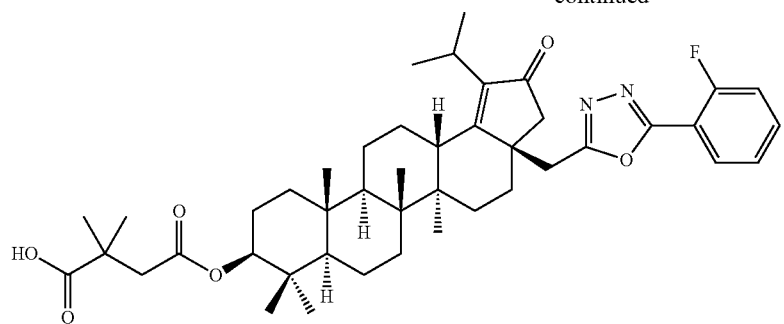
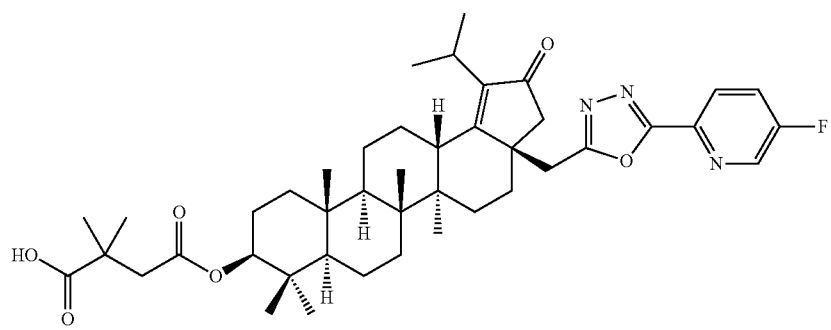
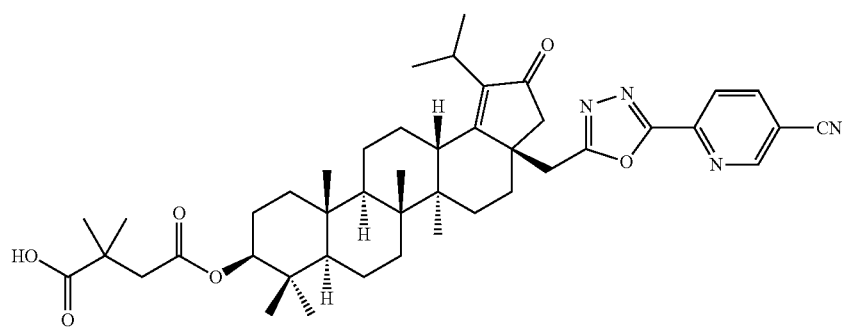
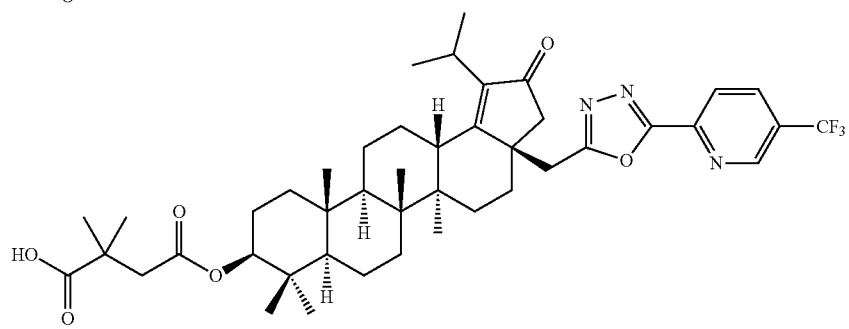
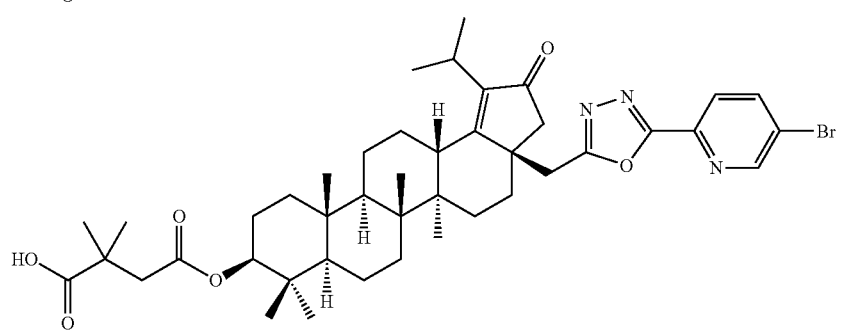

-continued
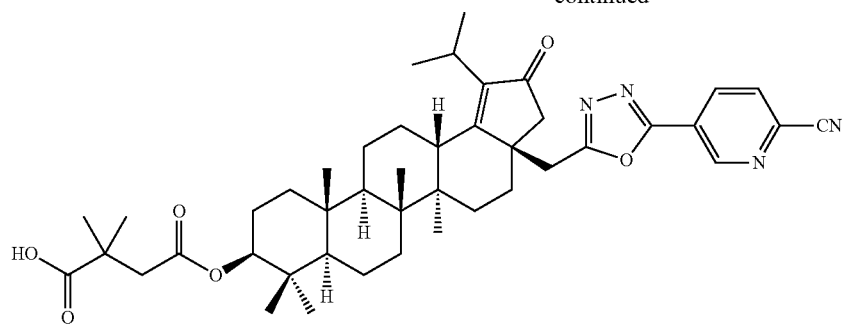
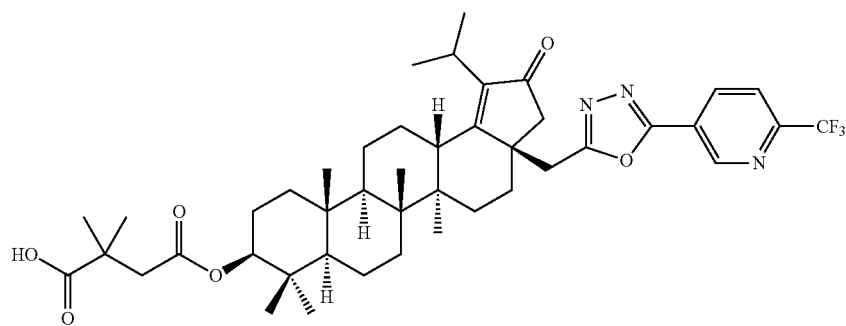
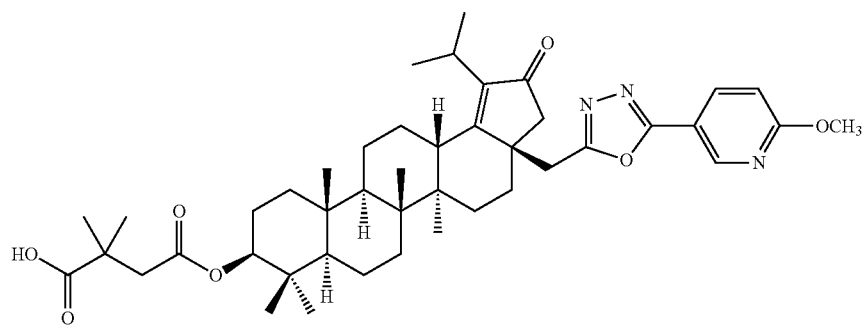
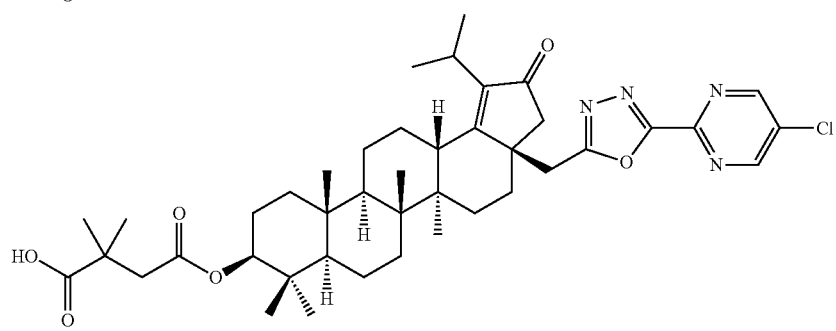
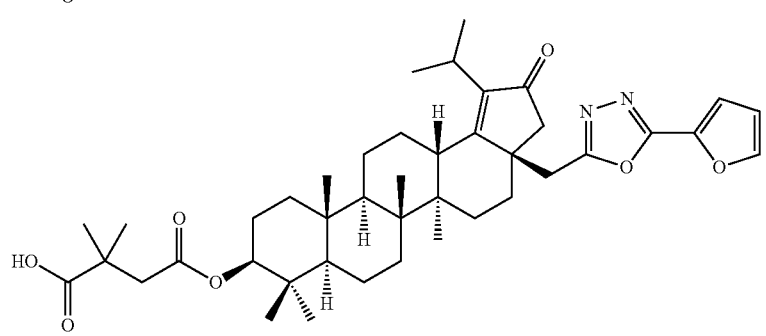

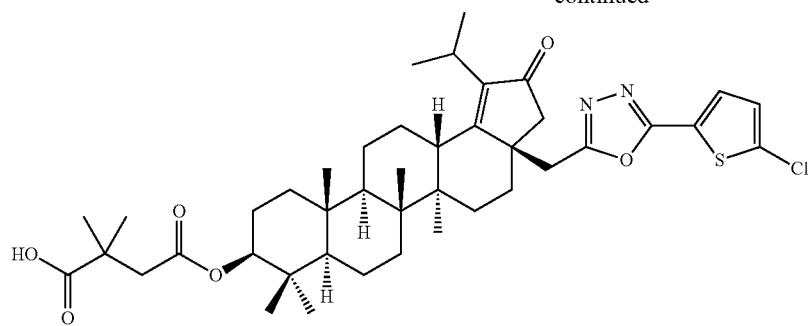
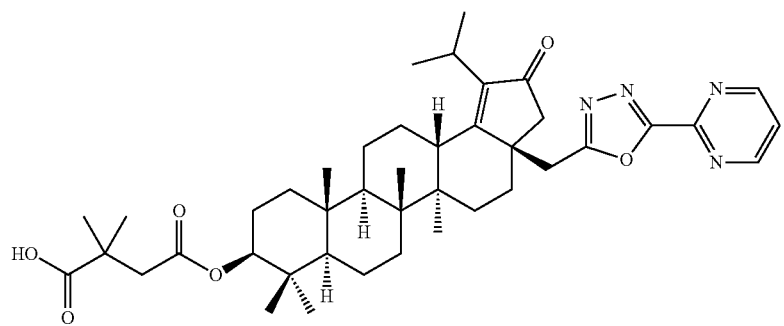
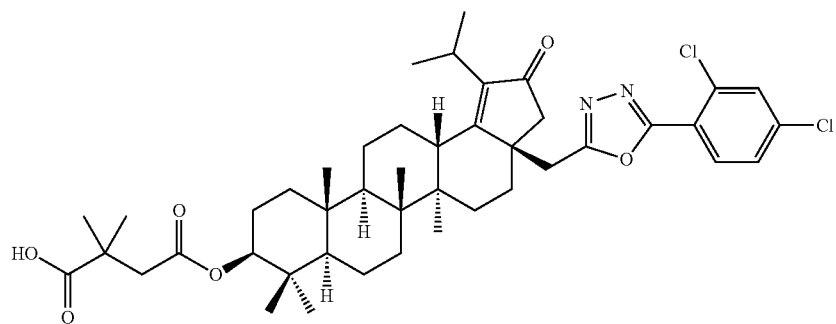
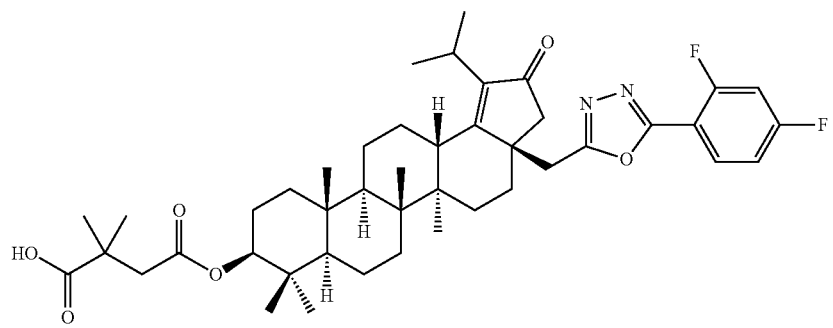
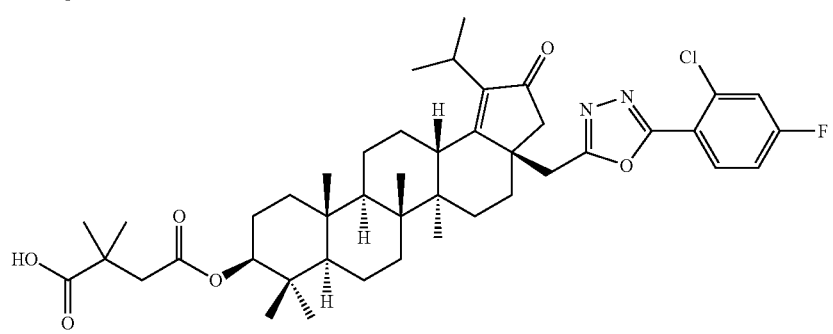

-continued
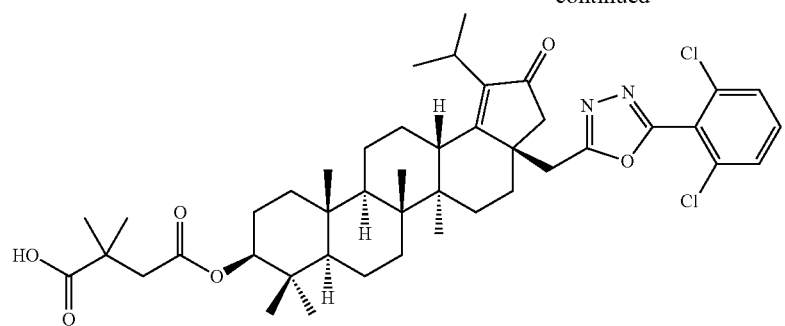
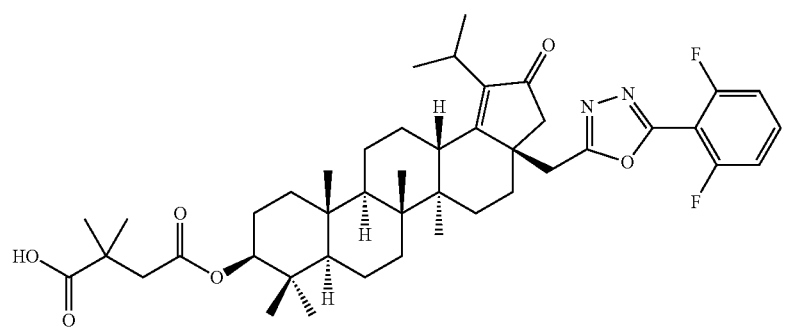
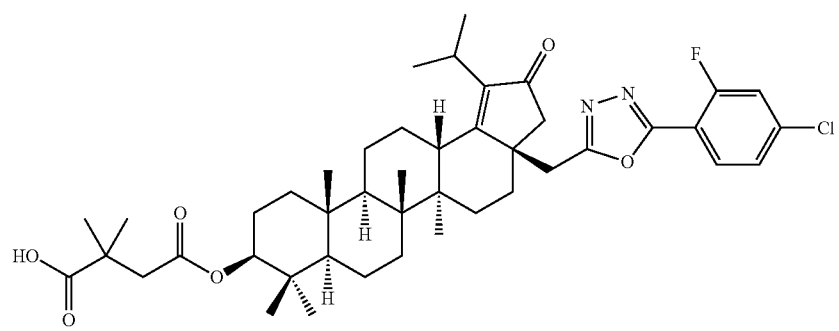
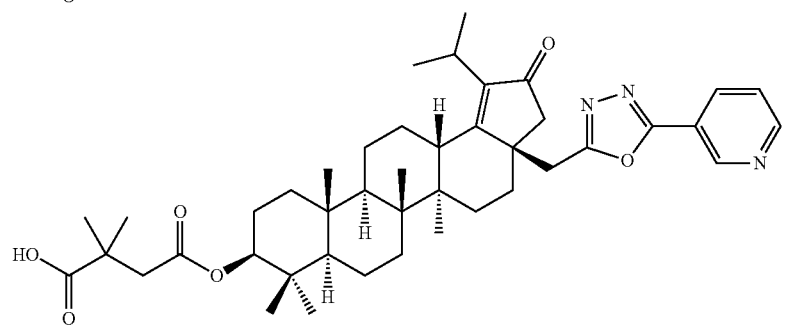
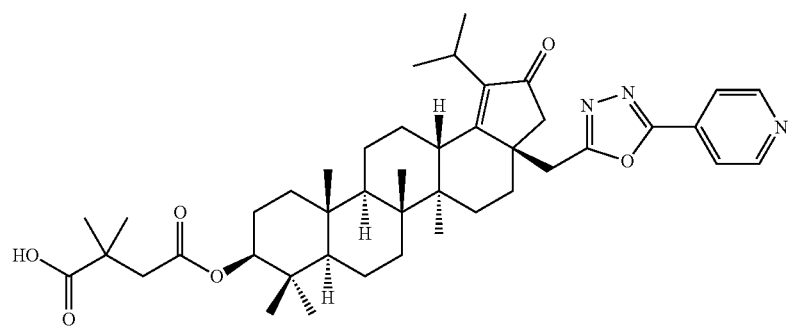

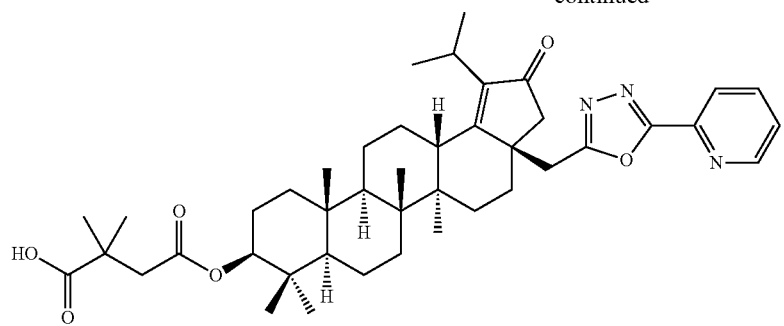
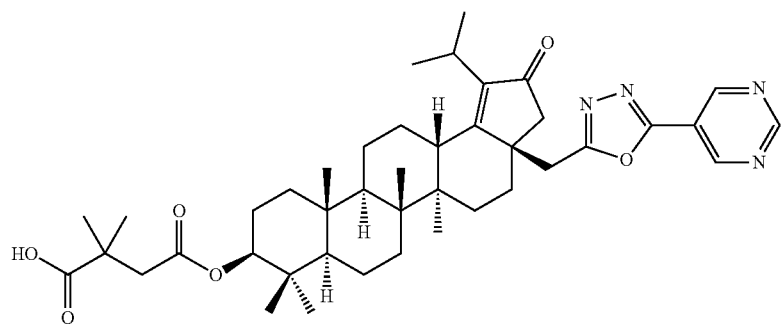
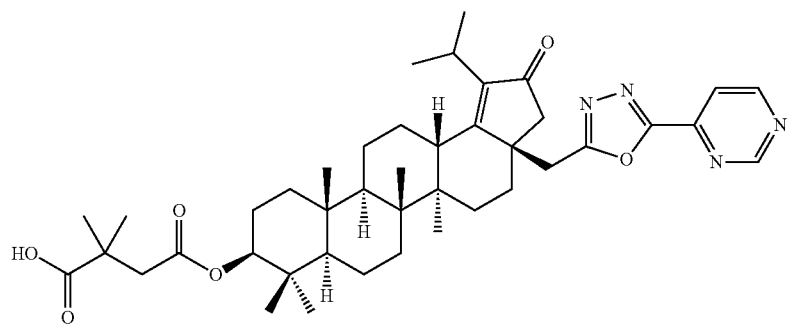
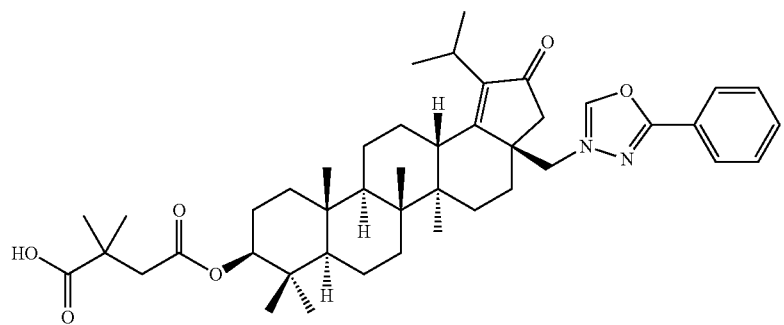
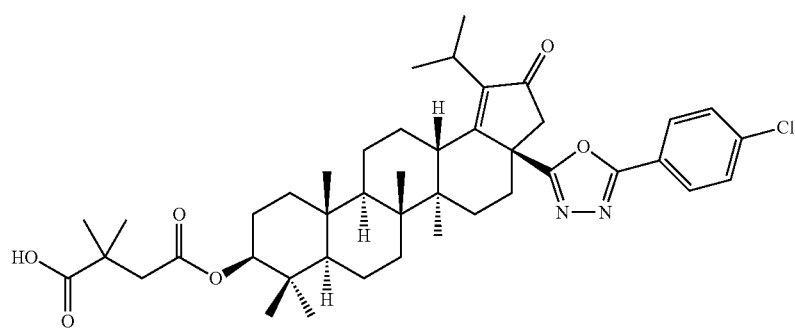

-continued
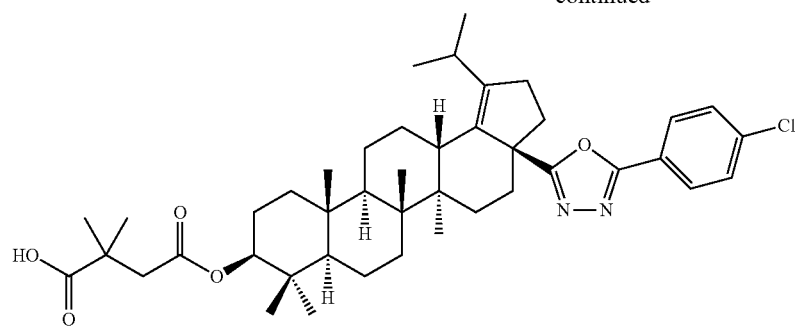
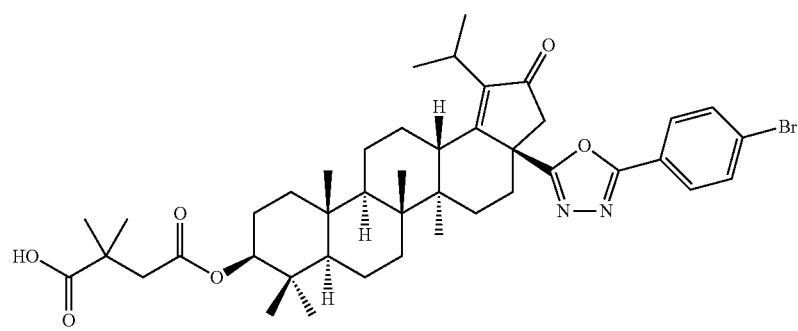
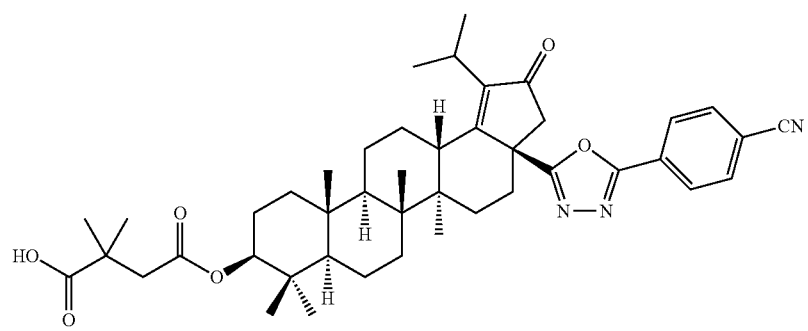
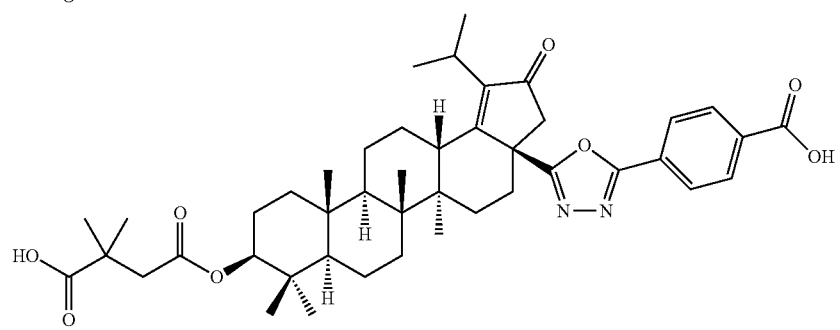
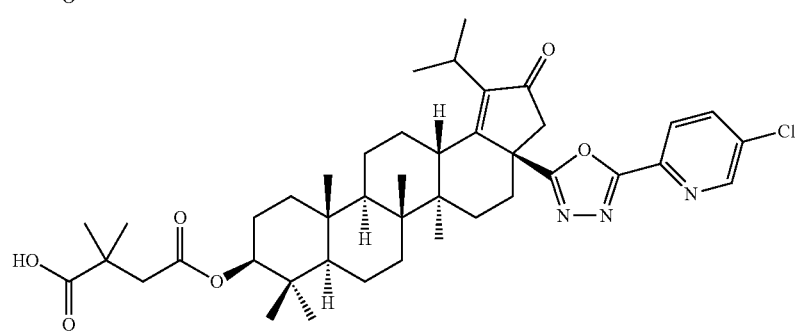

381
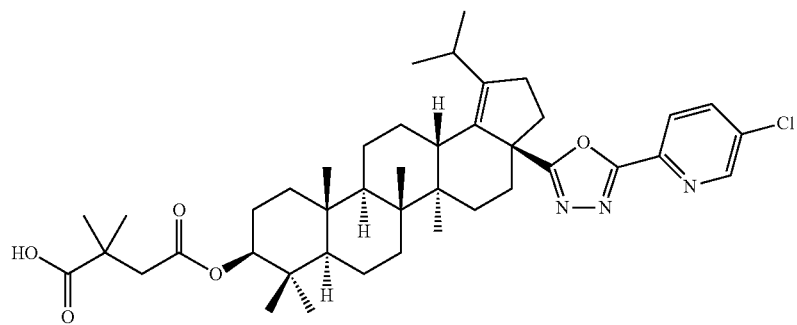
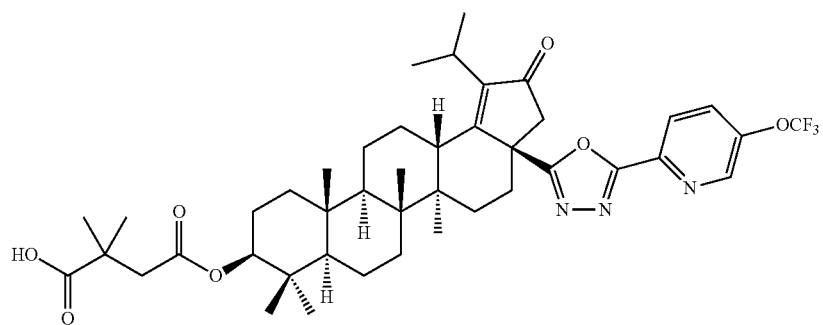
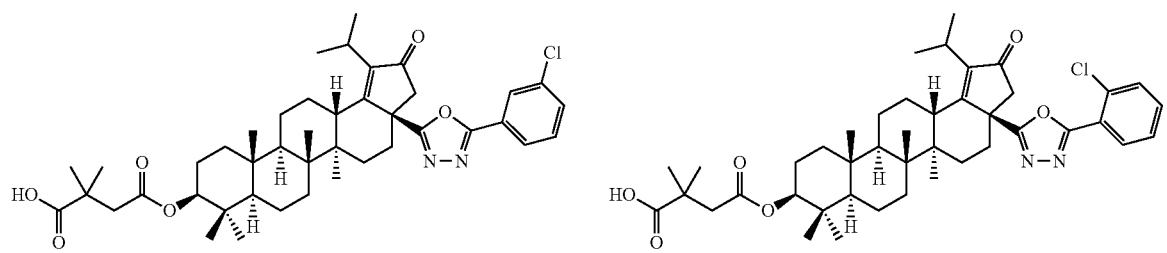
382
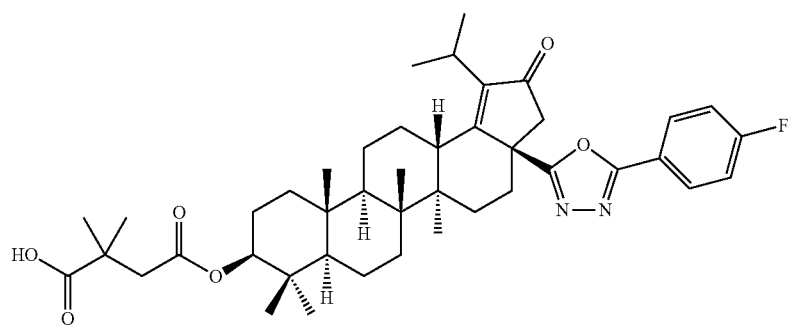
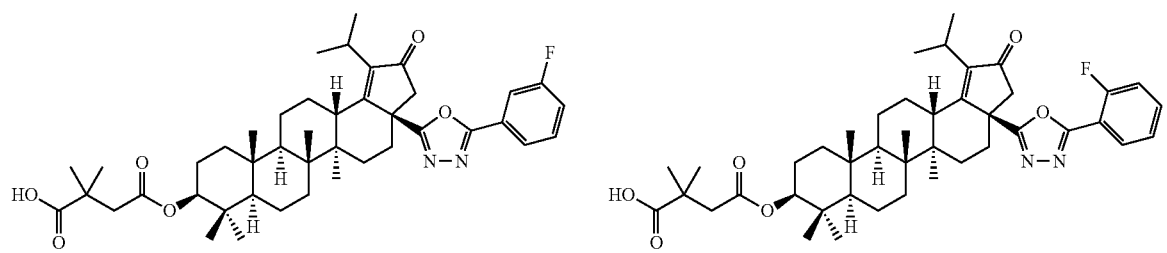

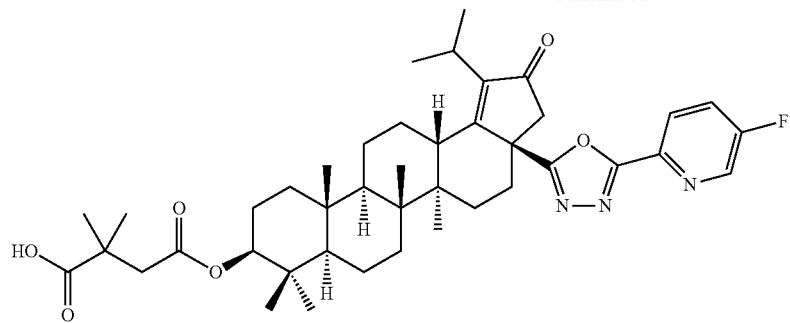
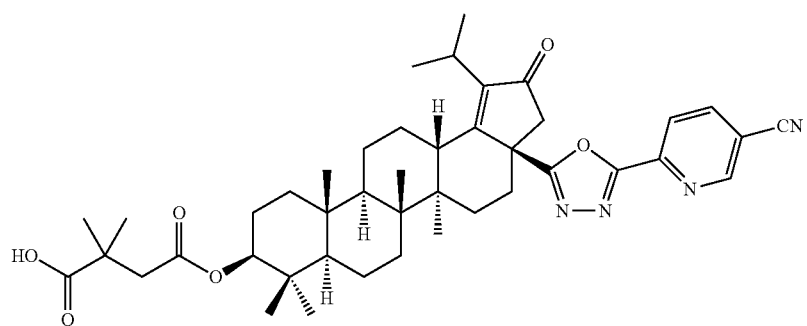
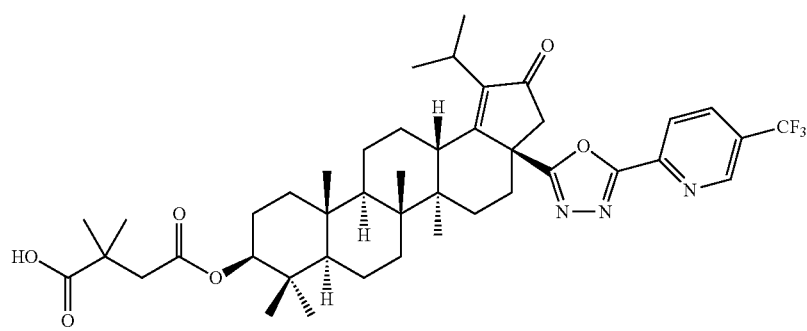
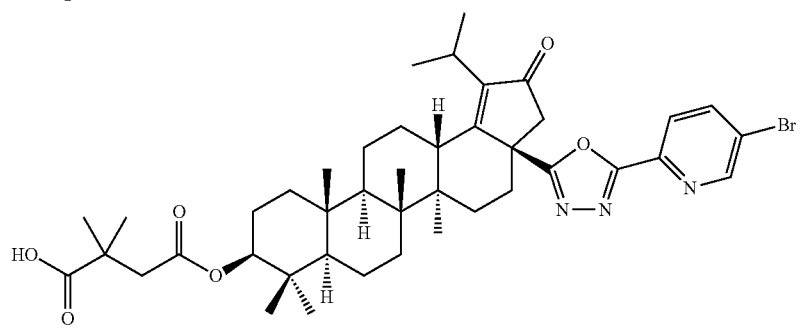
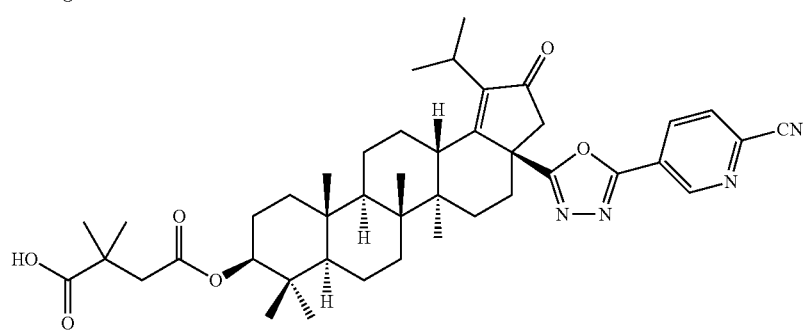

-continued
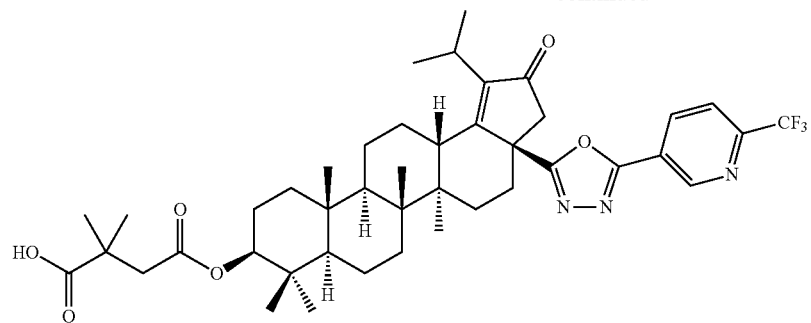
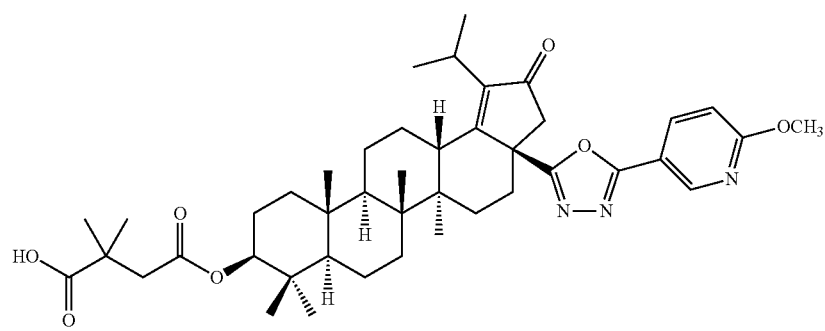
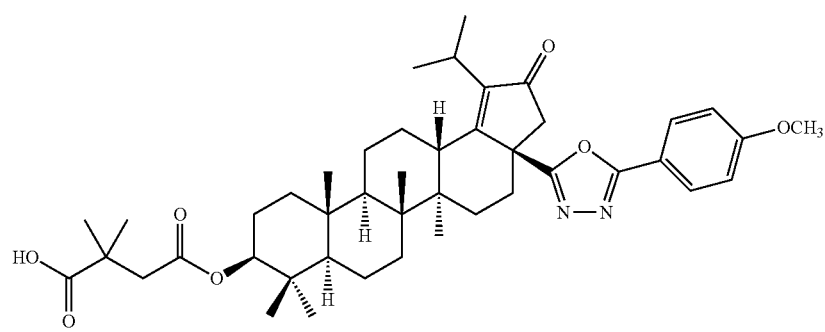
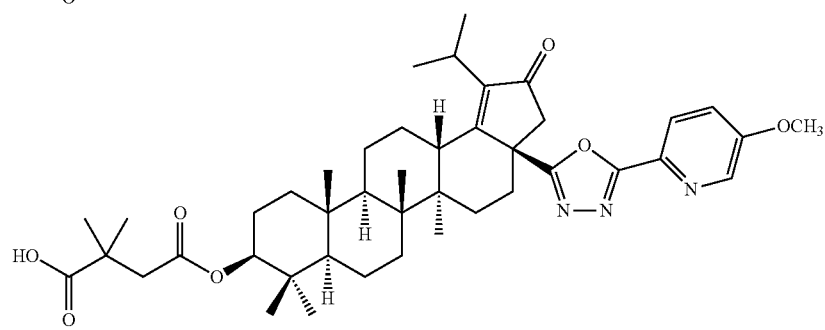
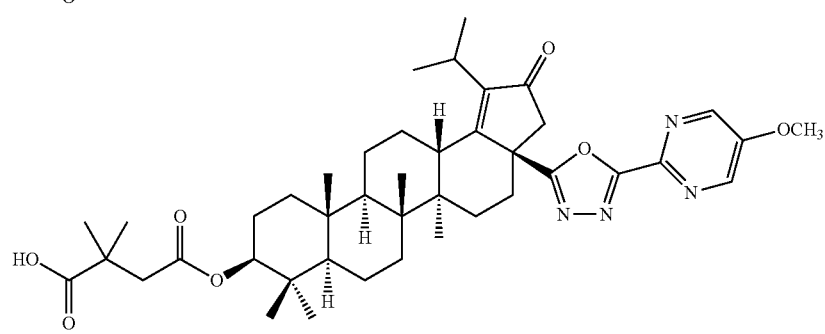

-continued
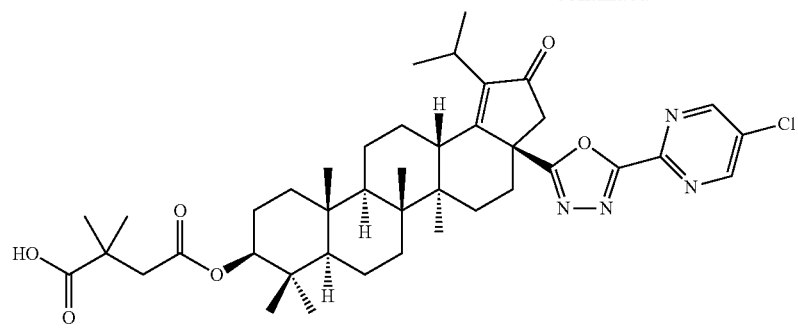
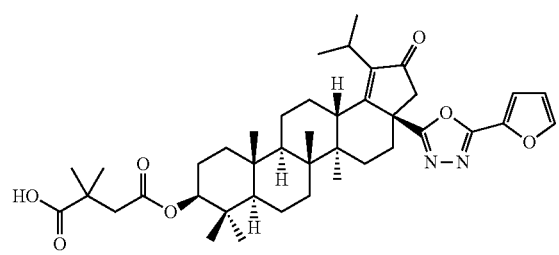
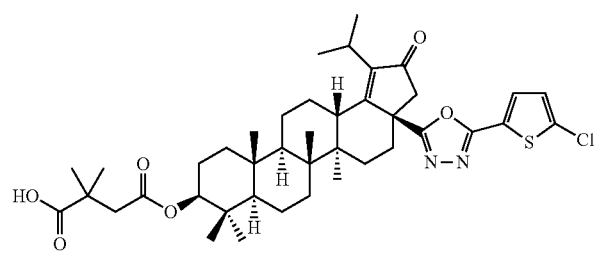
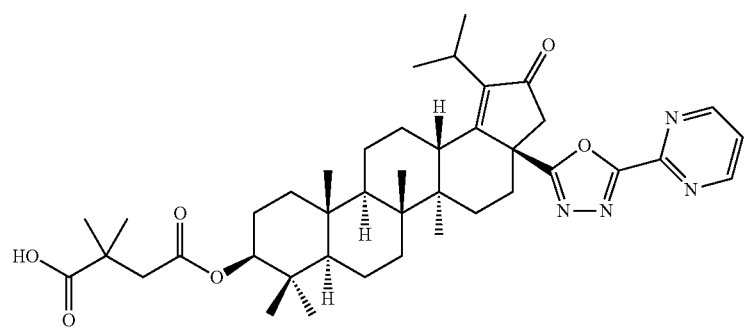
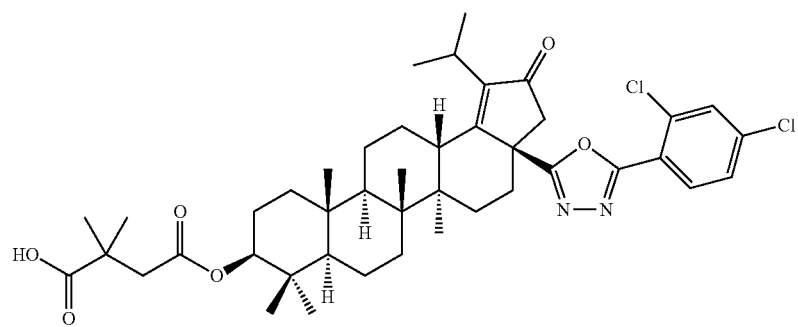
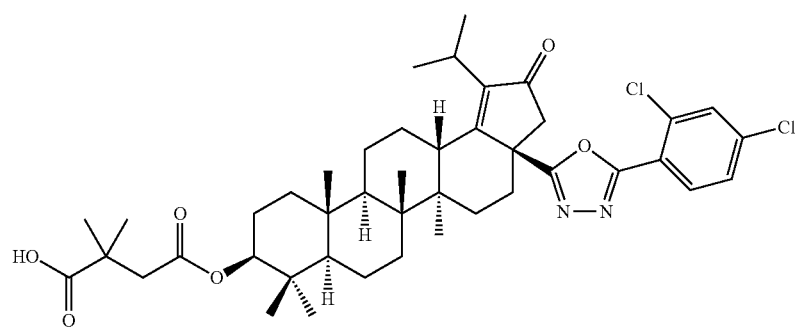

-continued
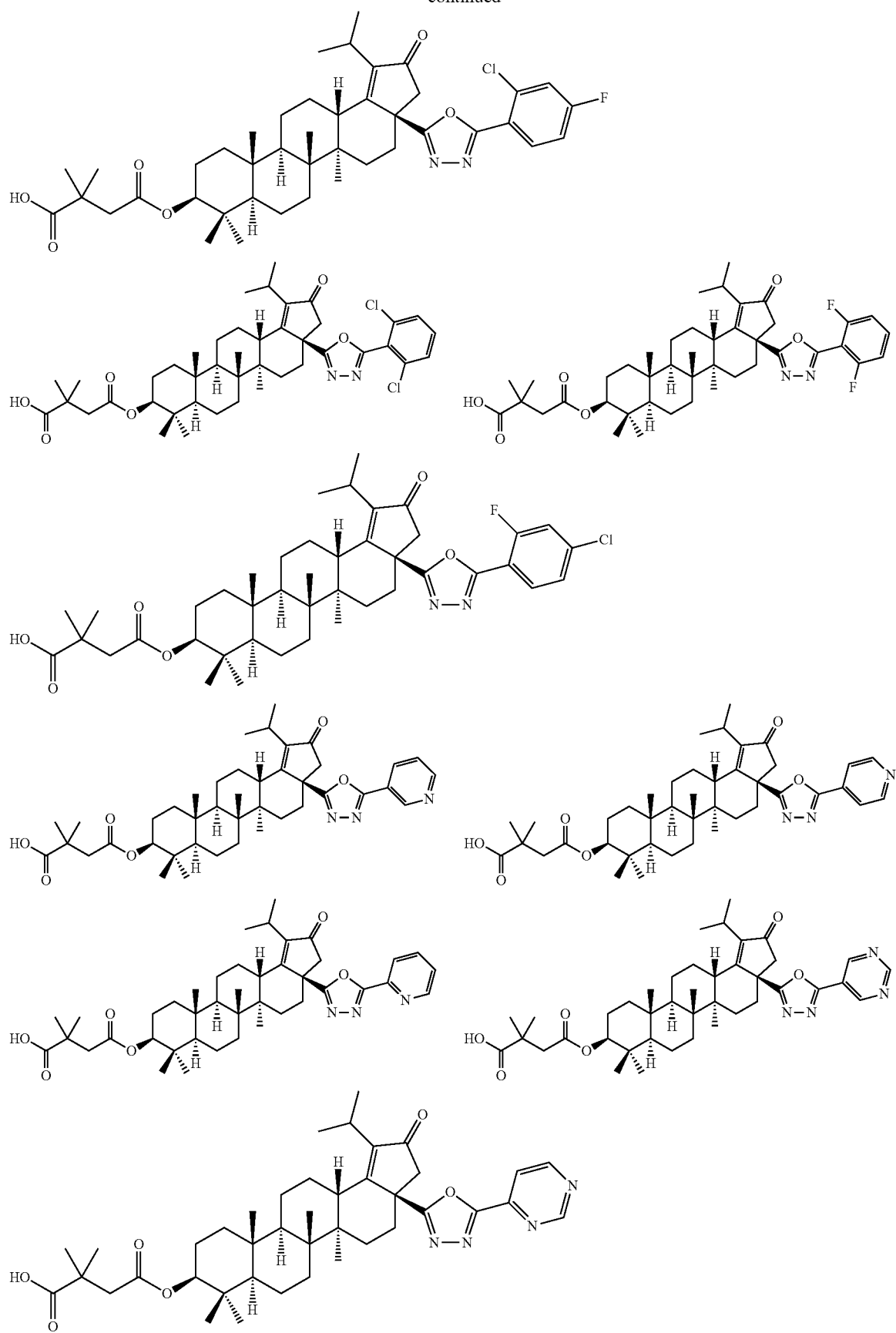

-continued
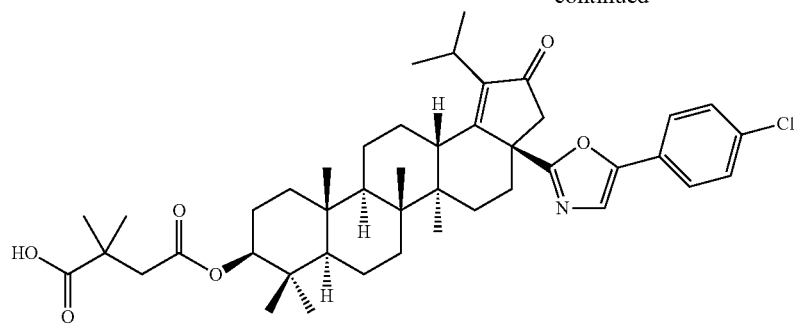
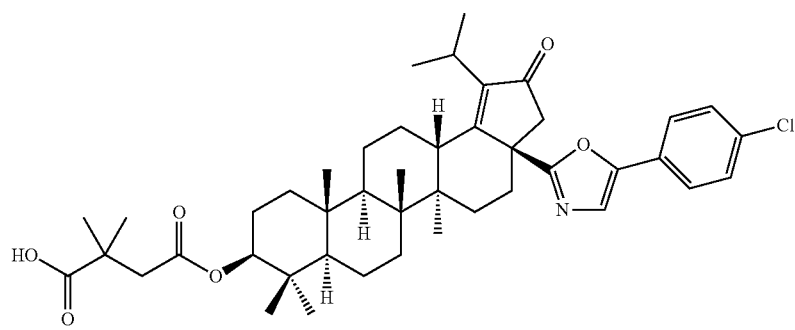
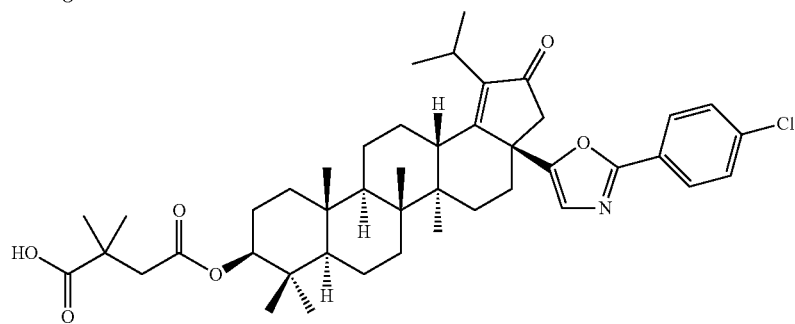
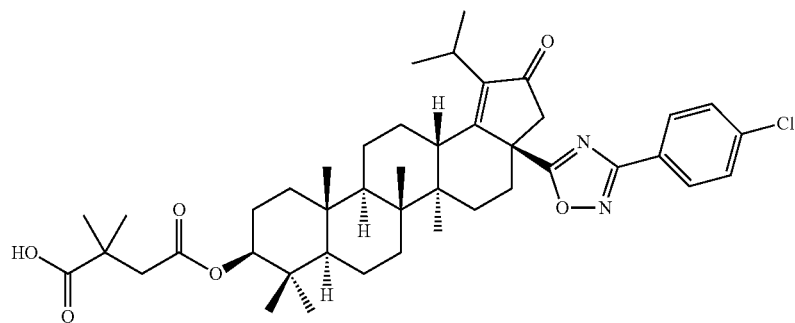
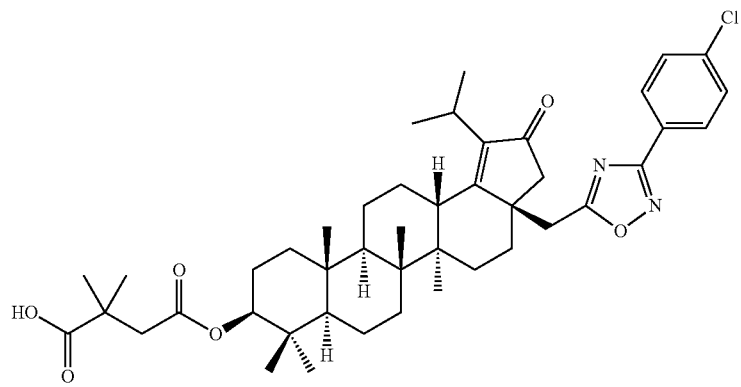

-continued
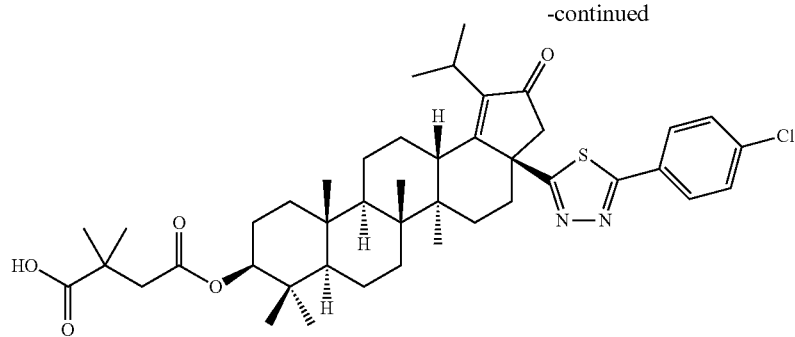
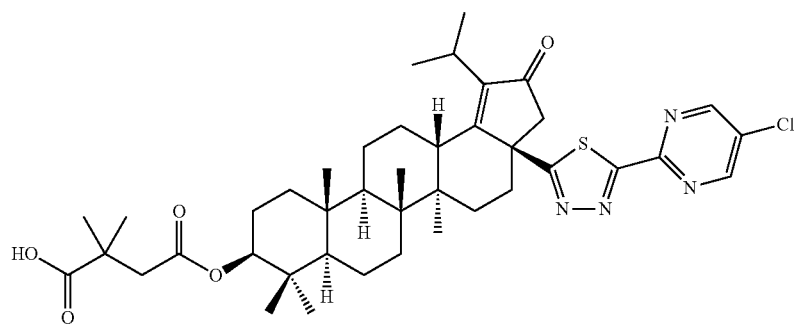
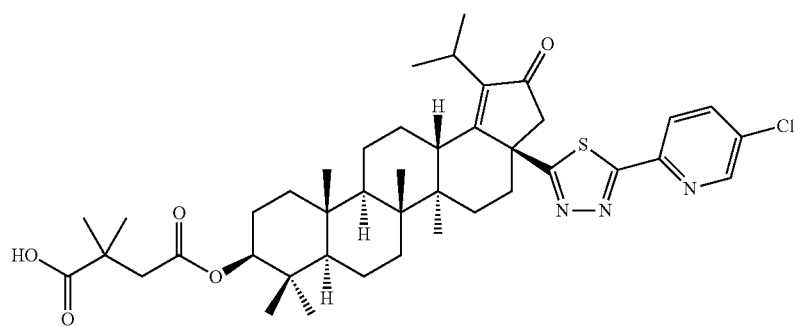
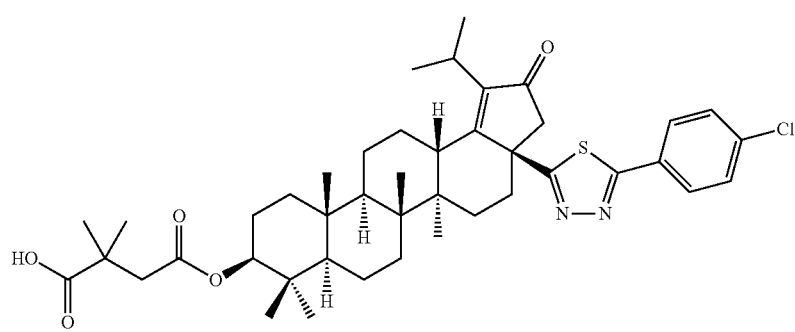
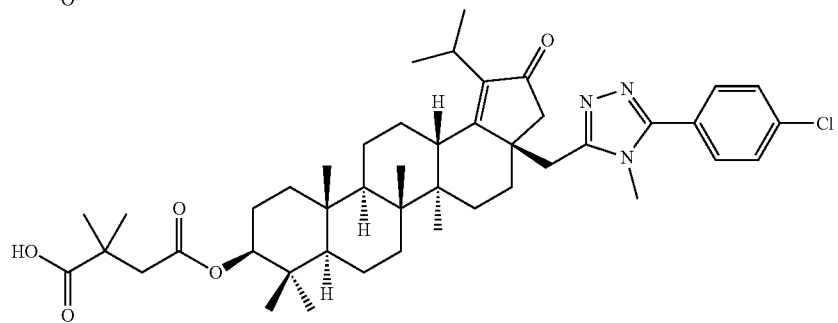

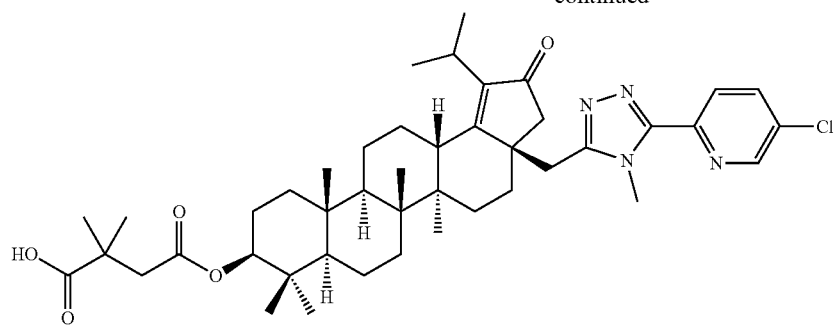
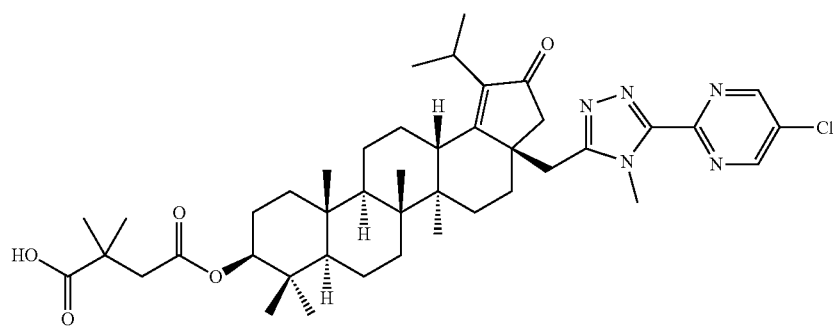
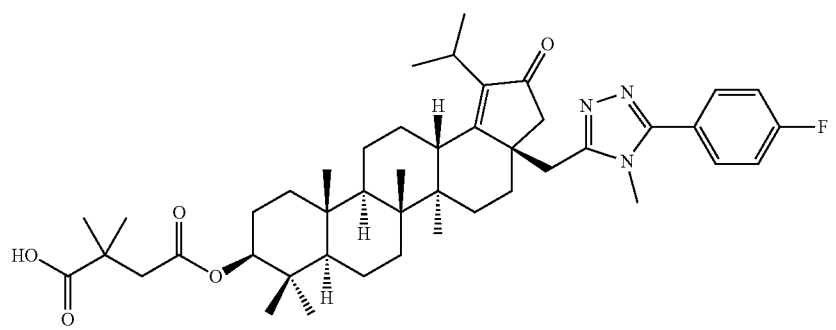
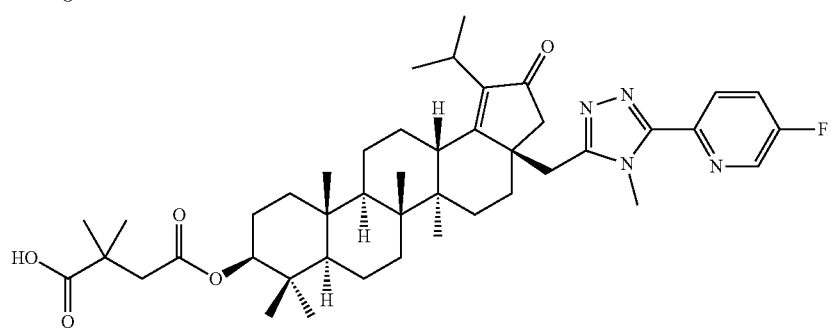
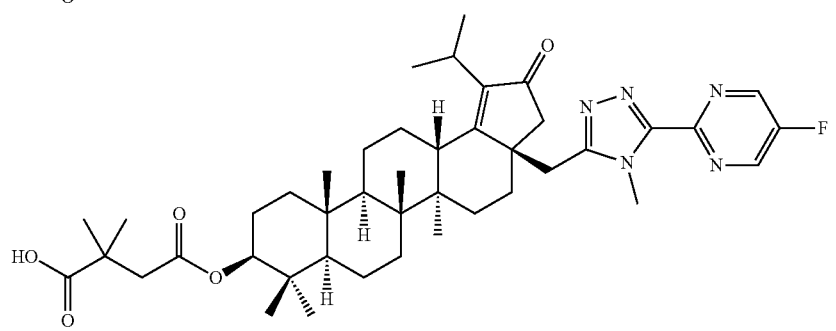

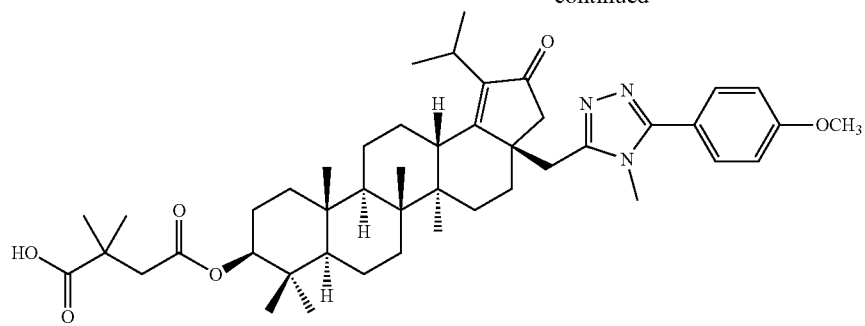
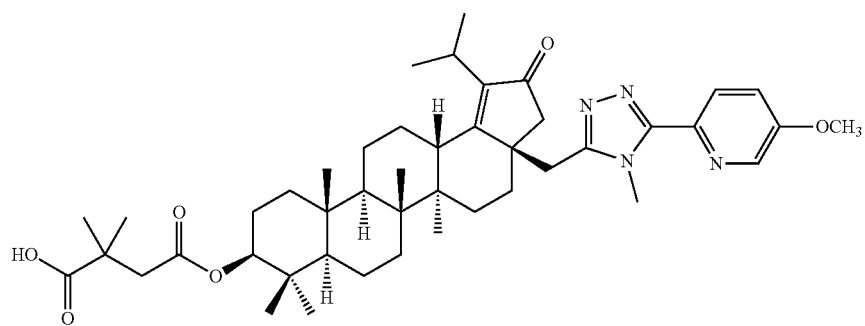
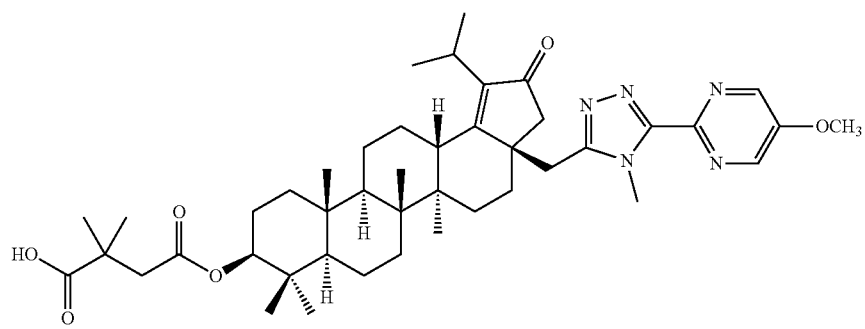
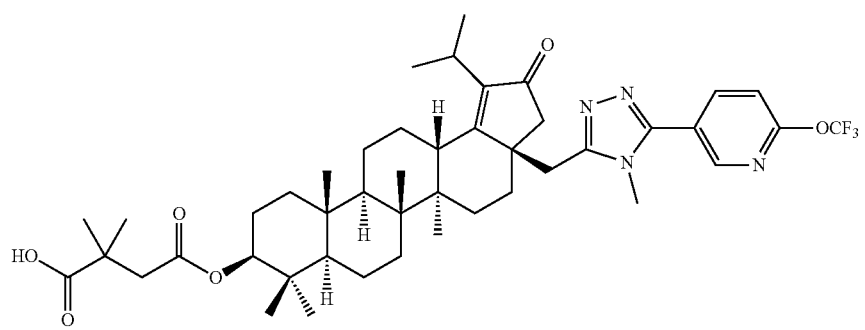
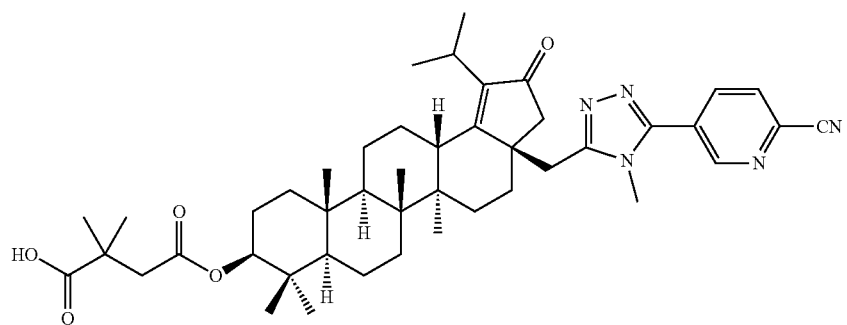

-continued
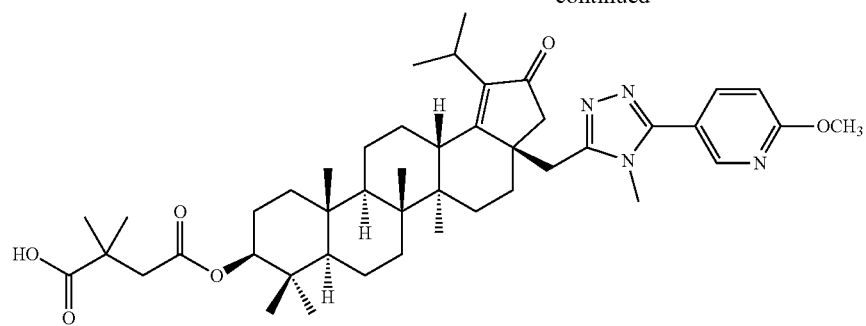
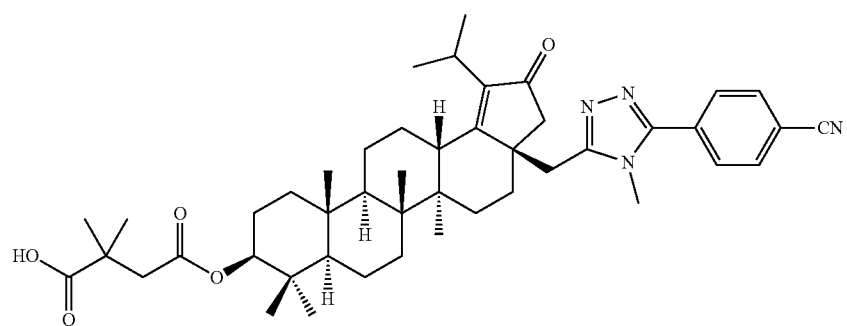
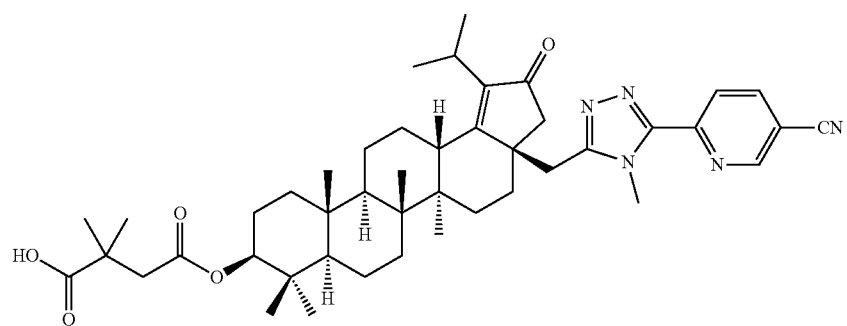
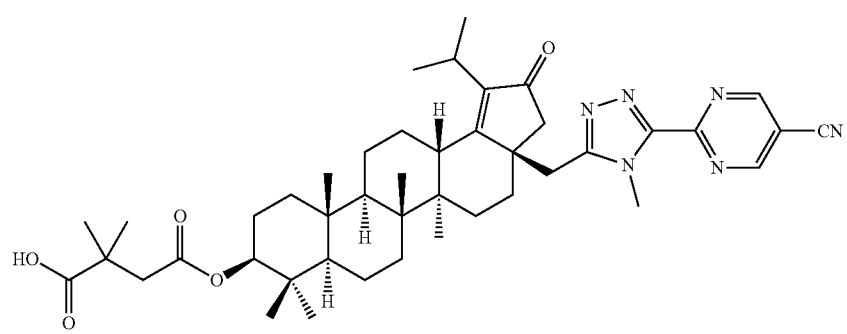
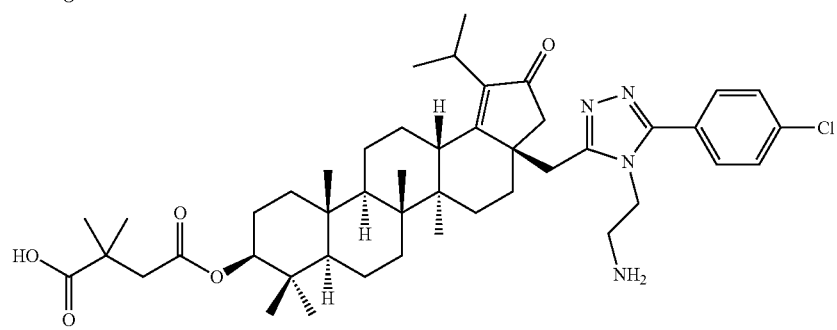

-continued
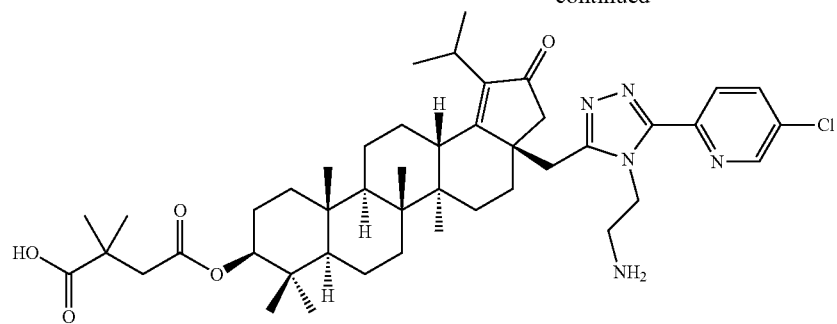
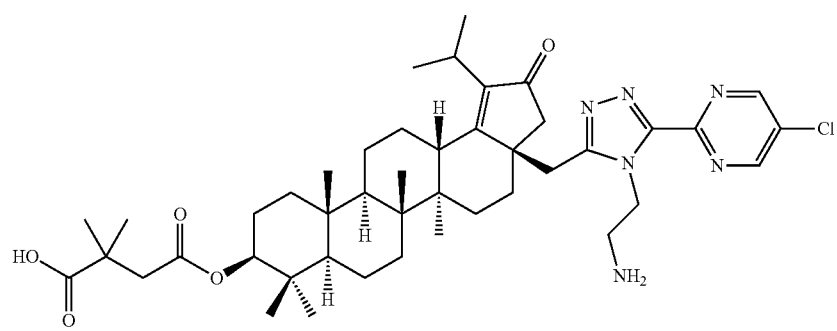
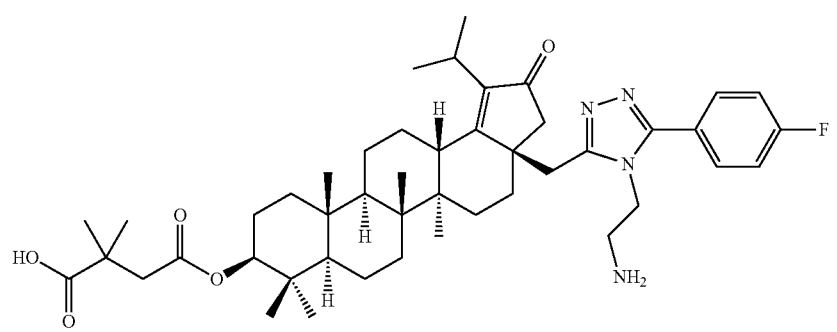
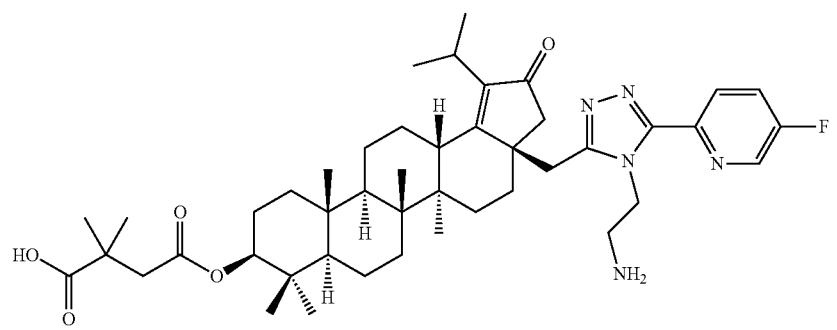
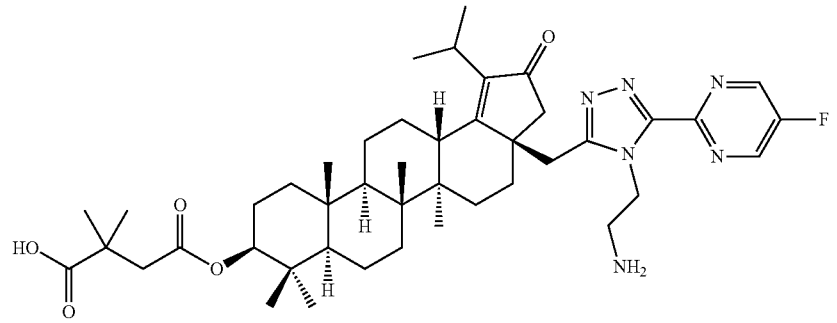

-continued
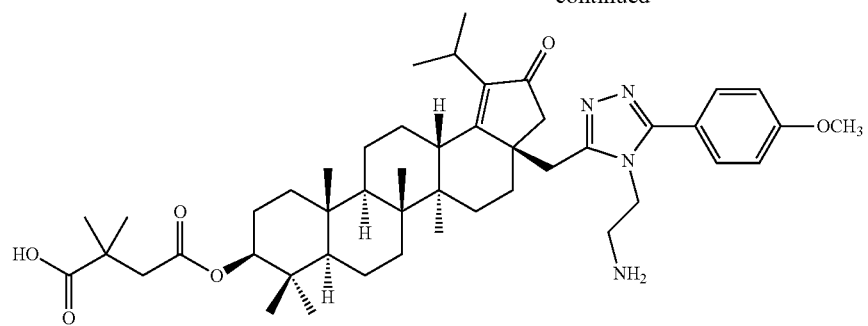
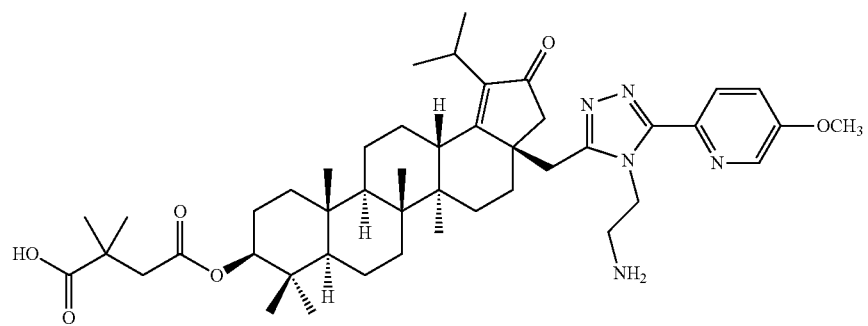
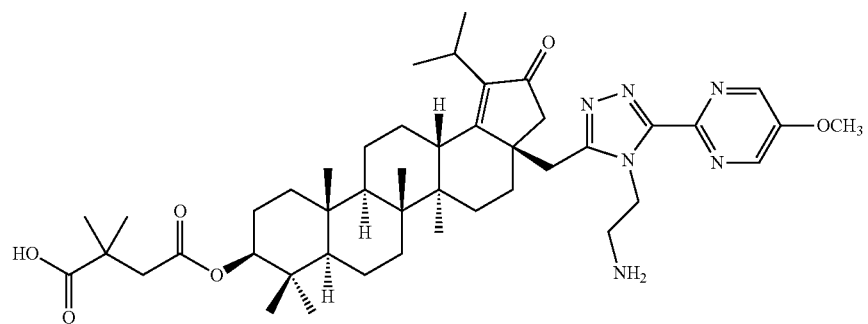
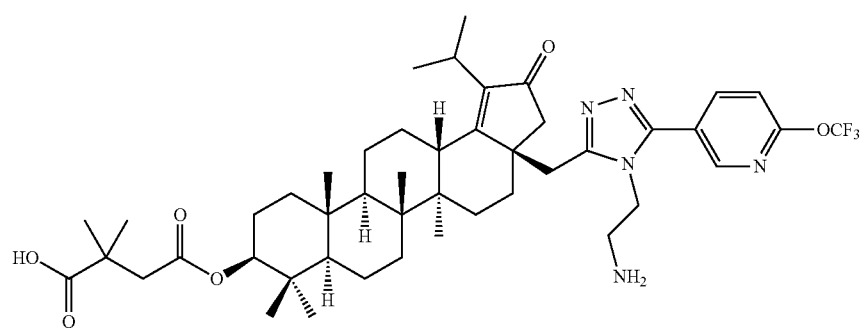
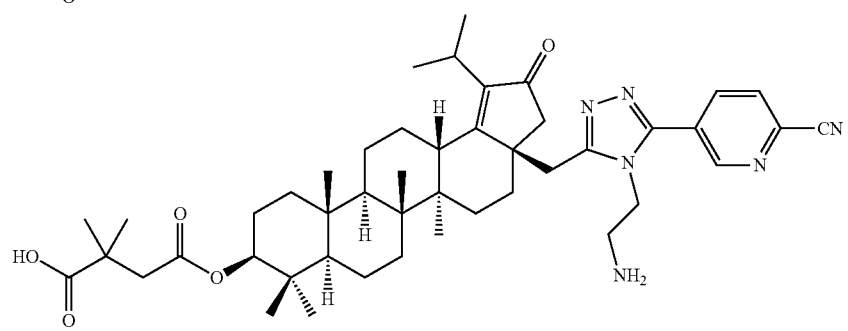

-continued
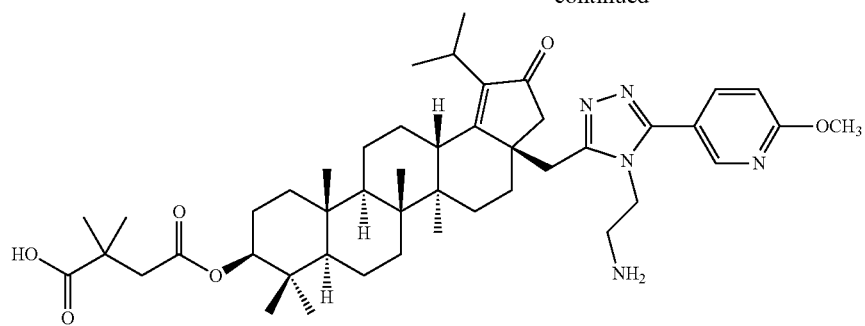
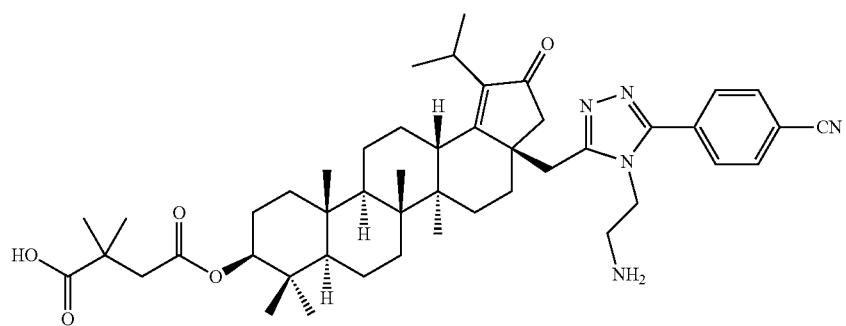
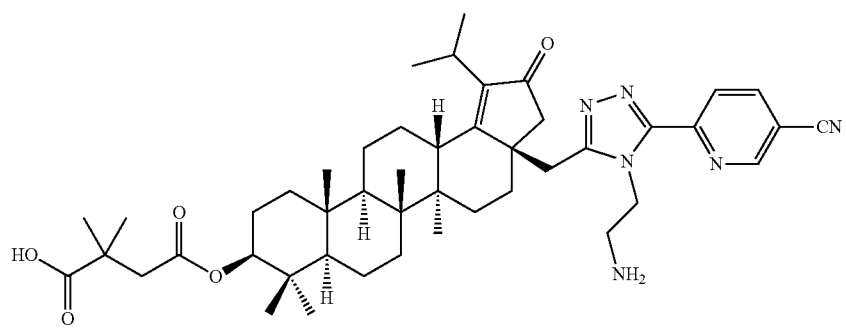
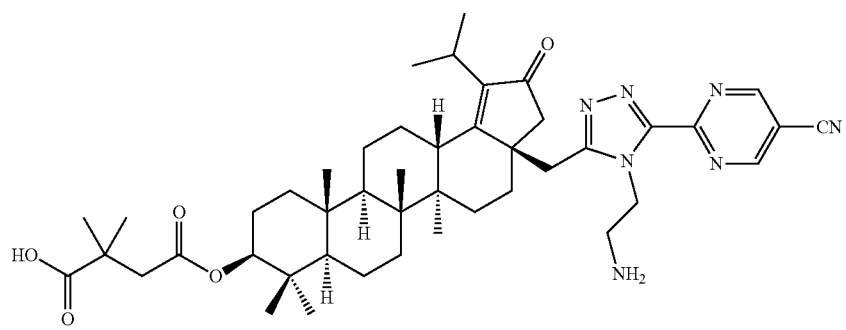
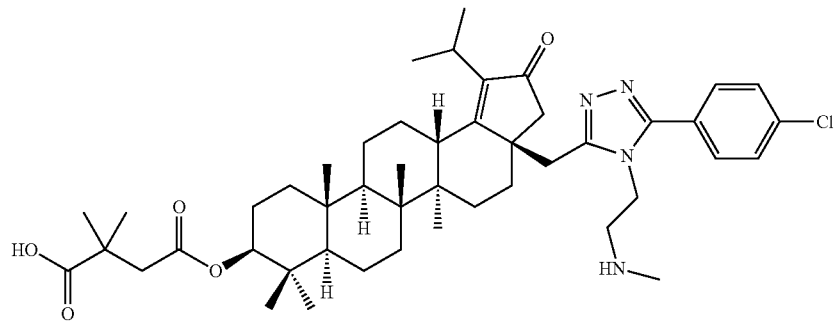

-continued
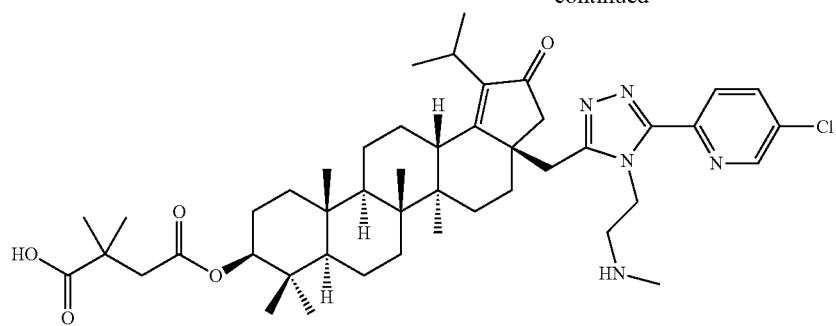
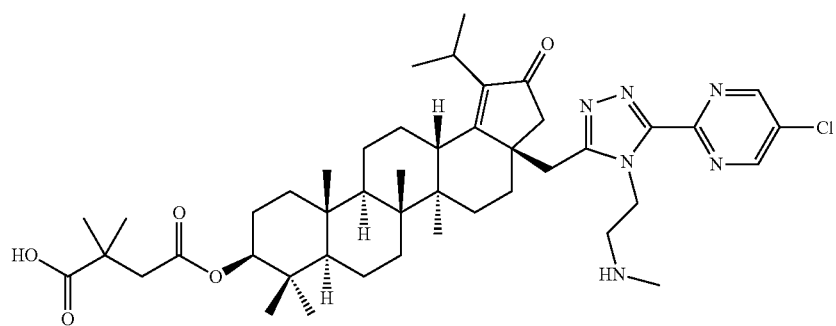
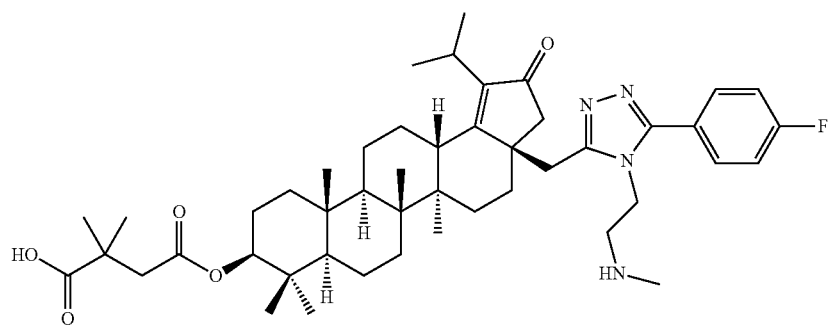
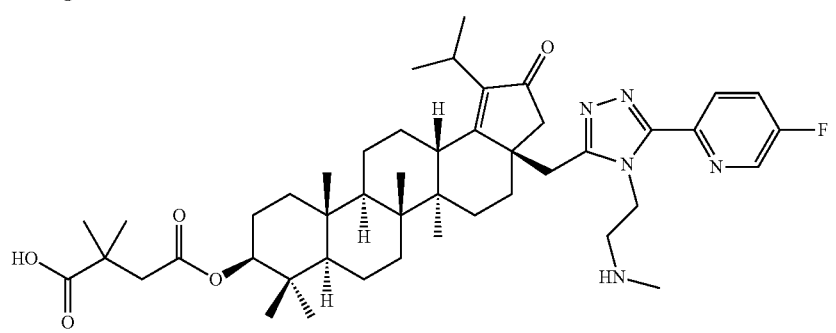
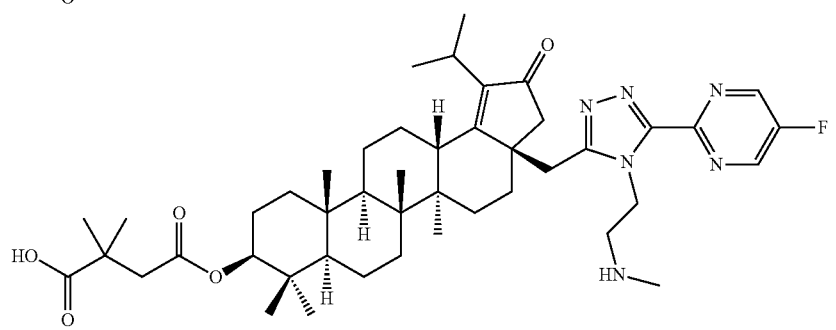

-continued
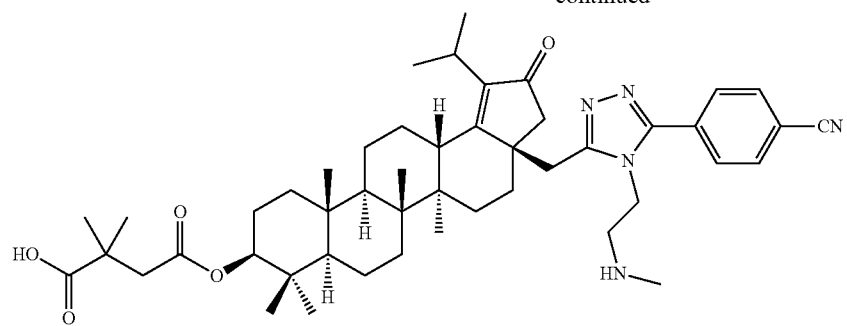
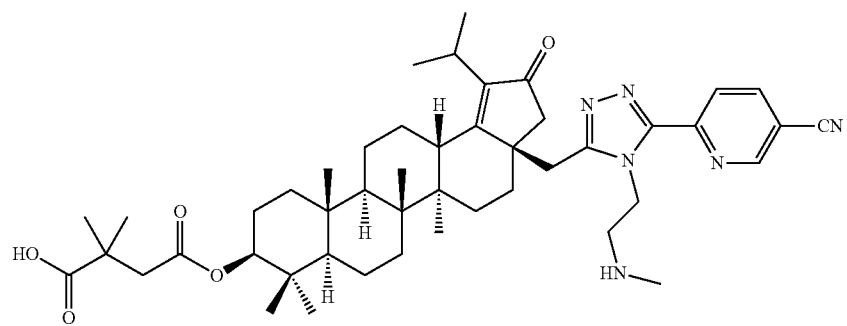
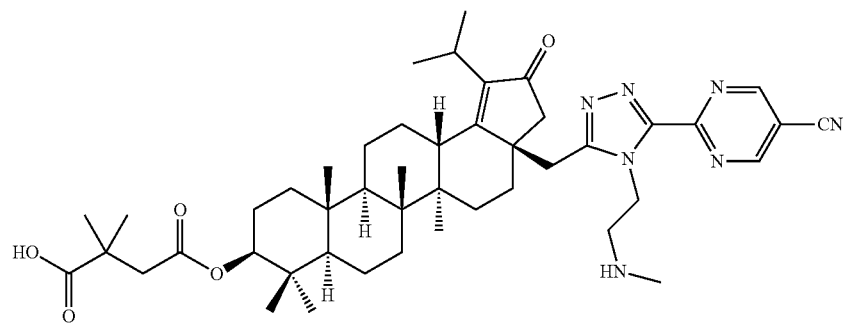
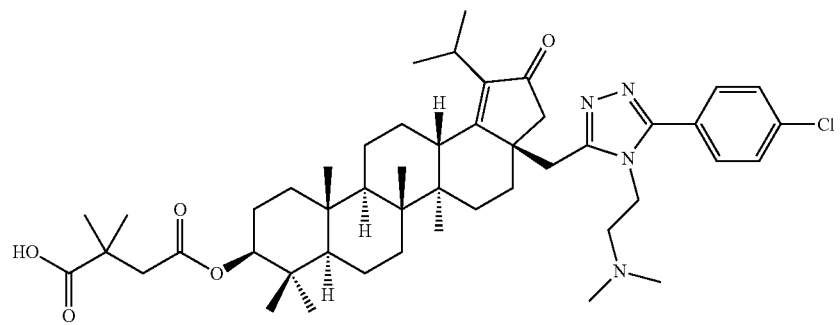
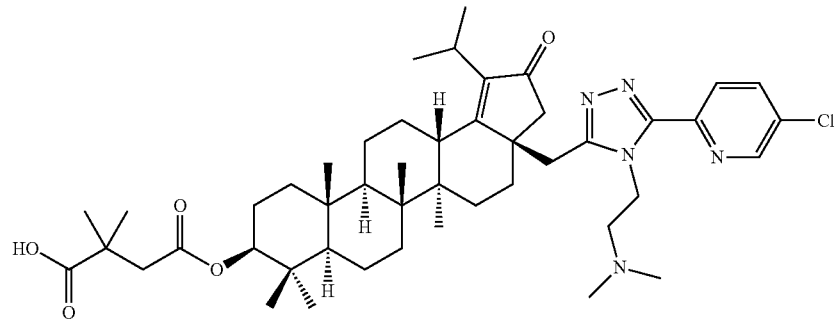

-continued
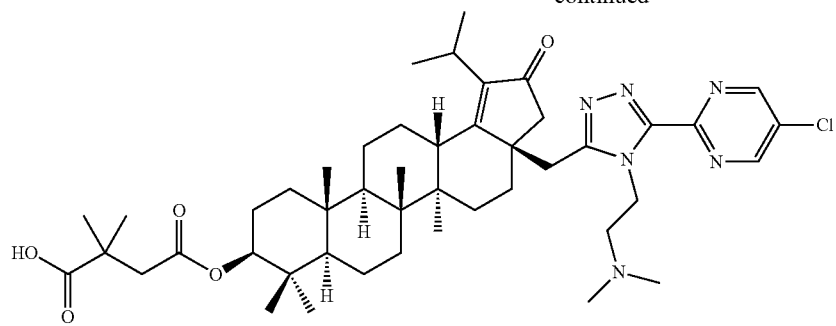
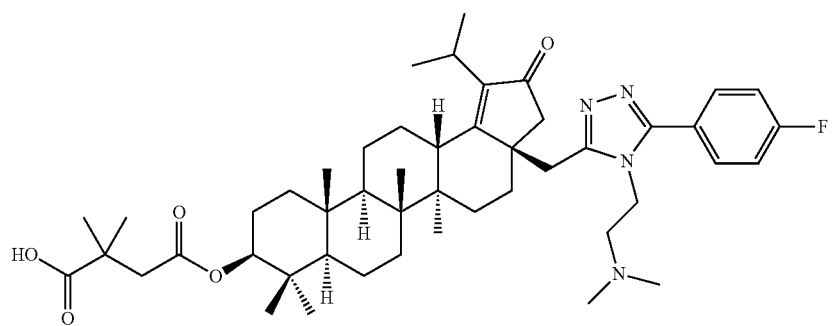
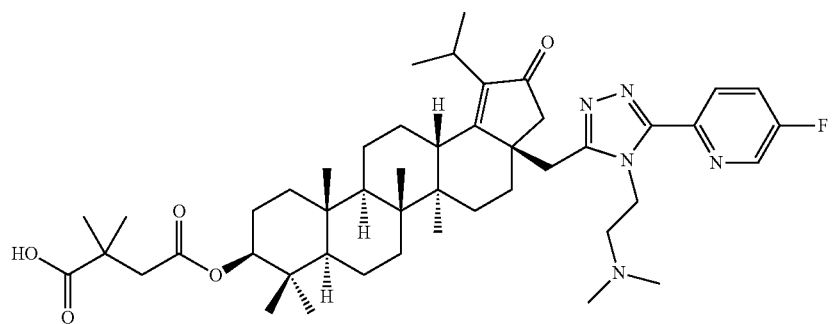
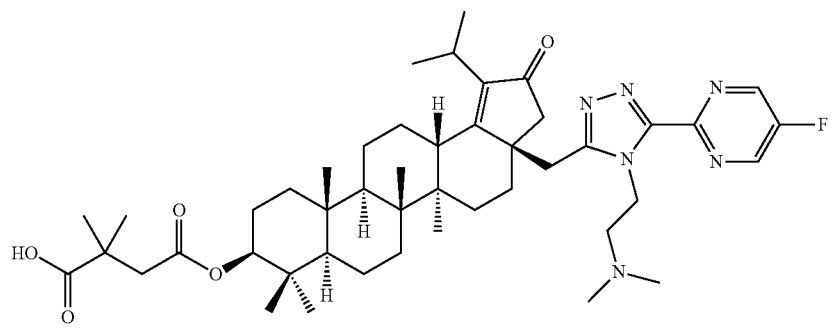
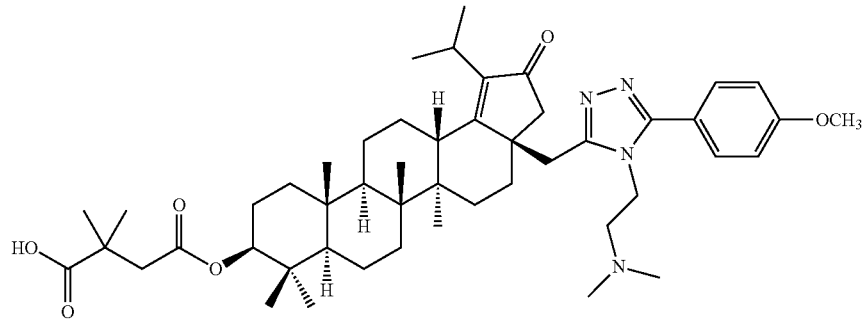

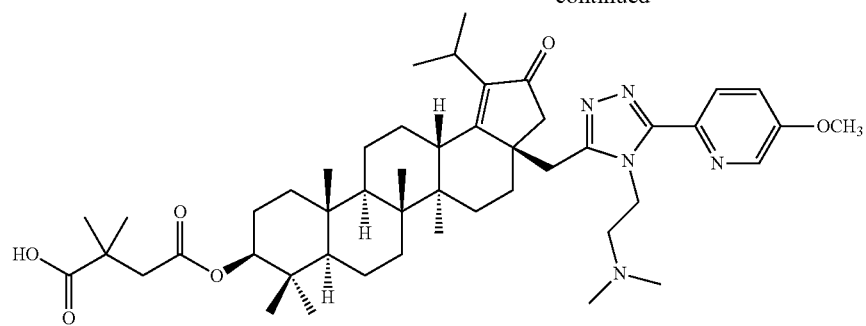
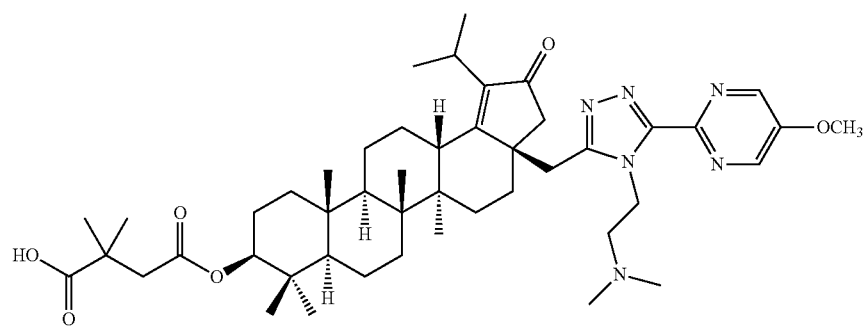
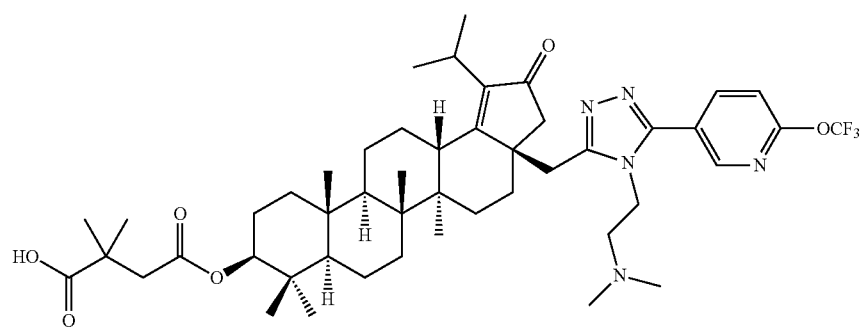
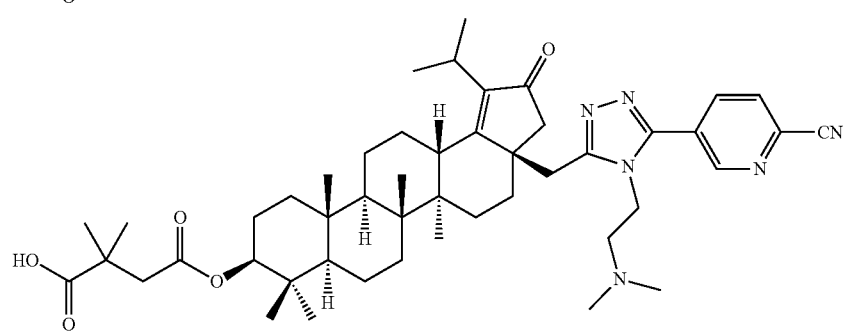
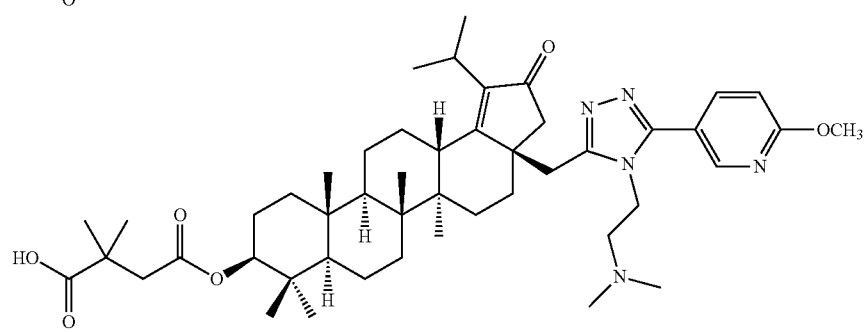

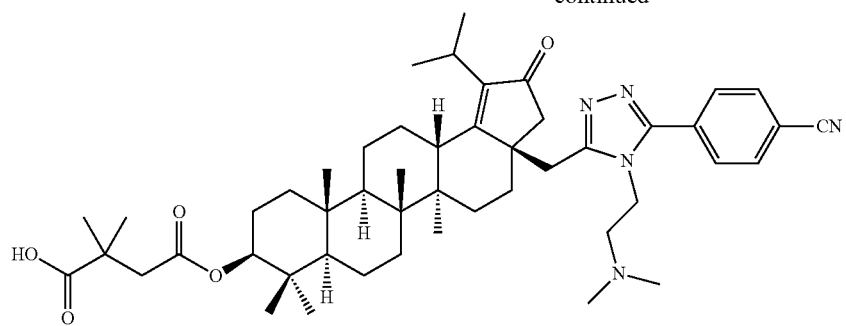
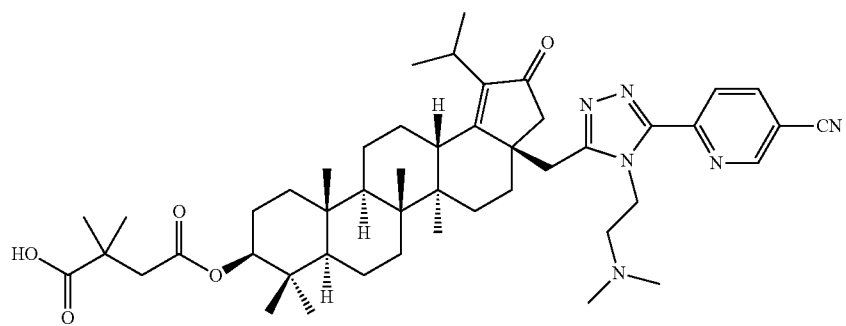
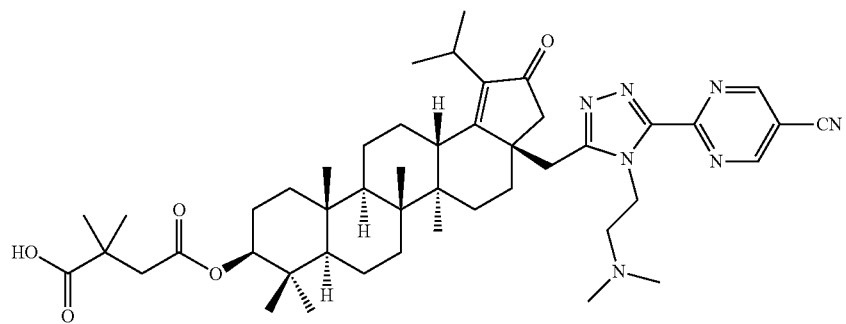
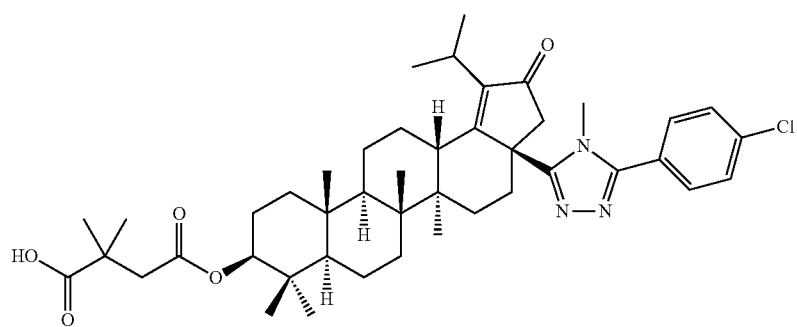
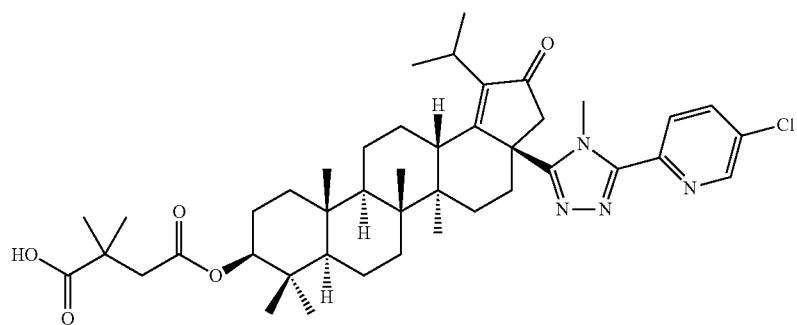

-continued
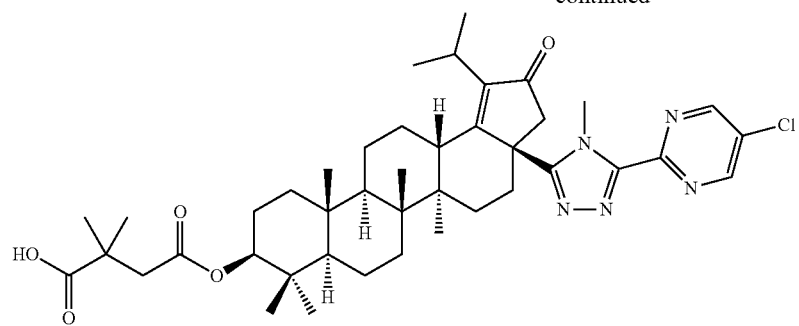
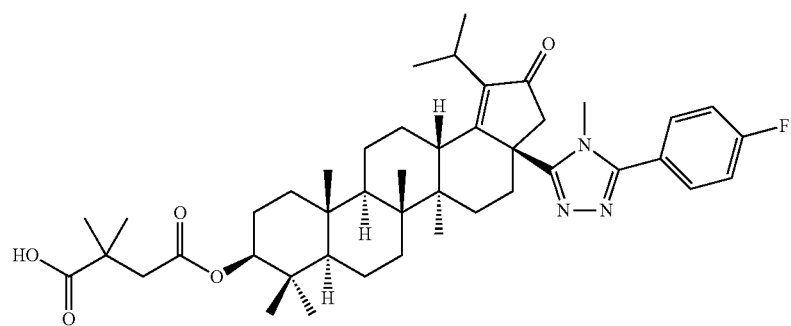
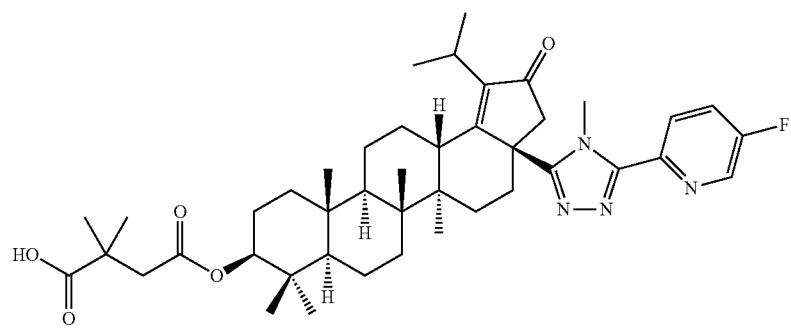
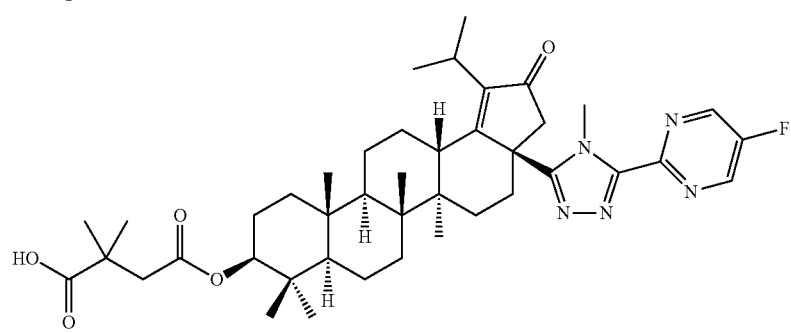
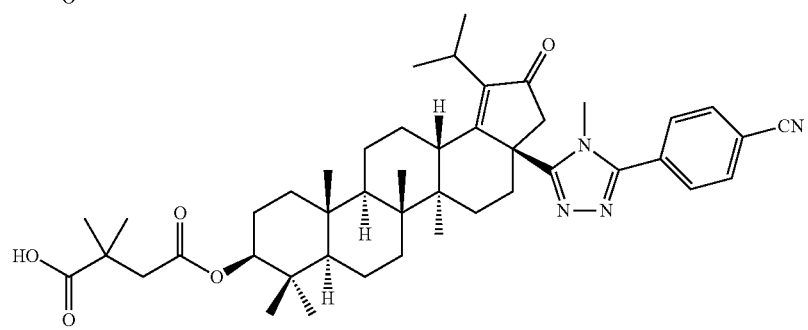

-continued
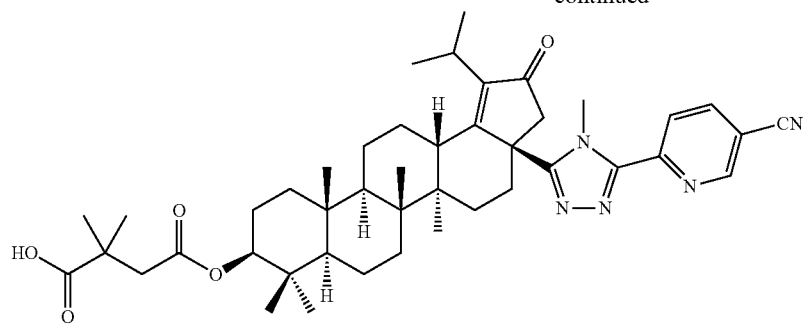
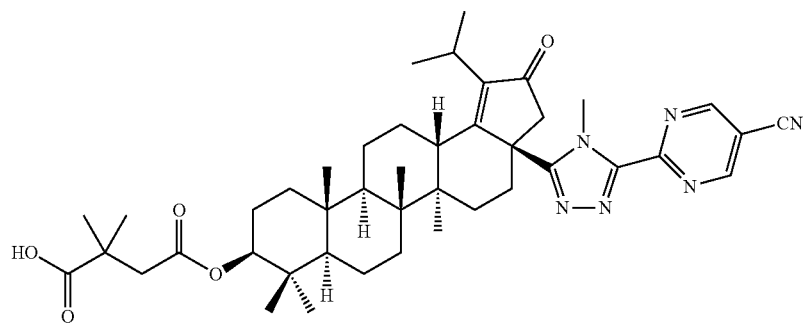
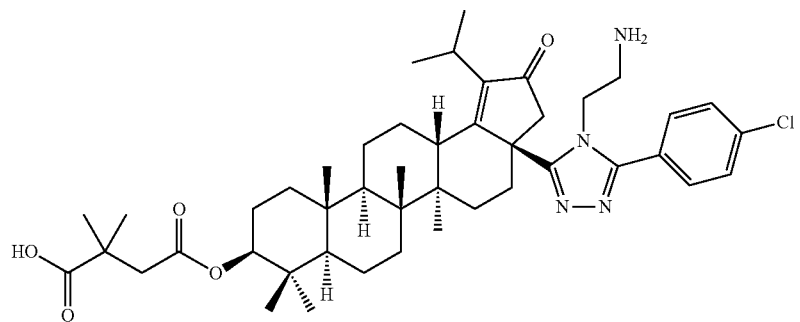
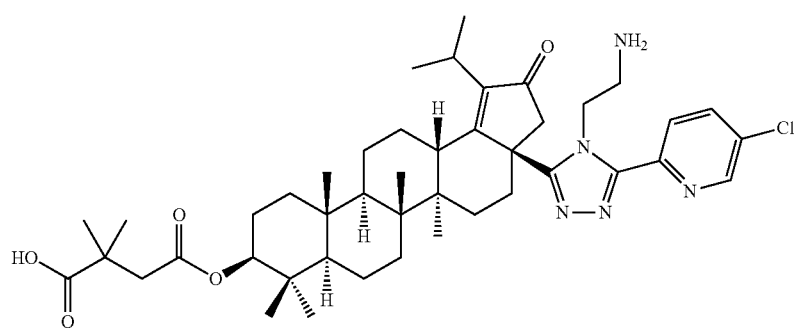
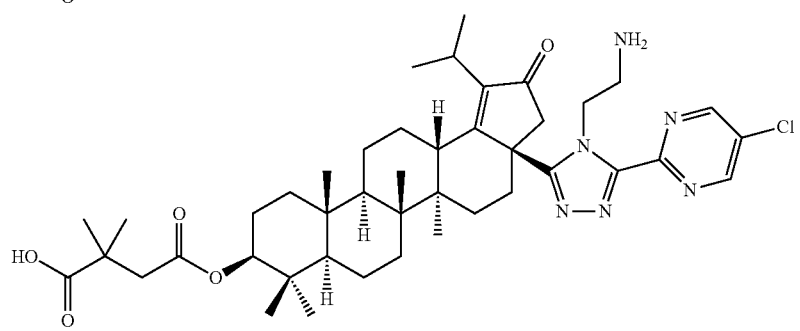

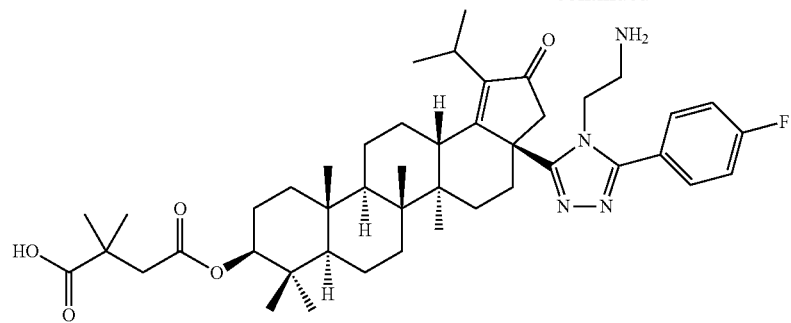
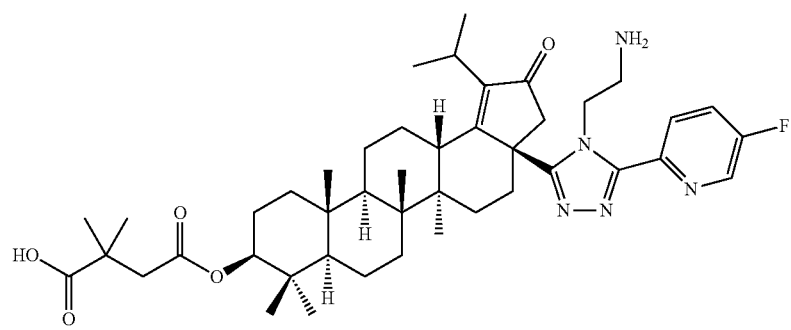
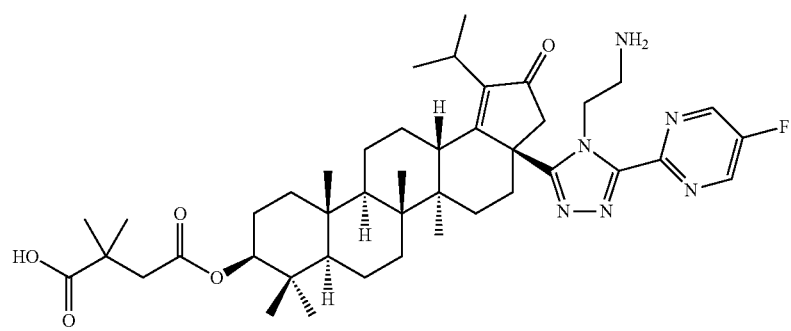
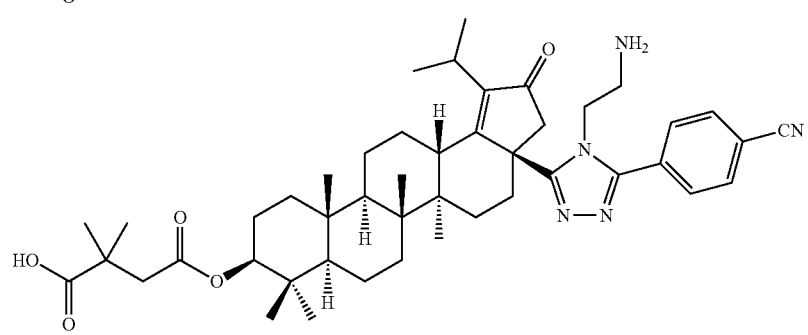
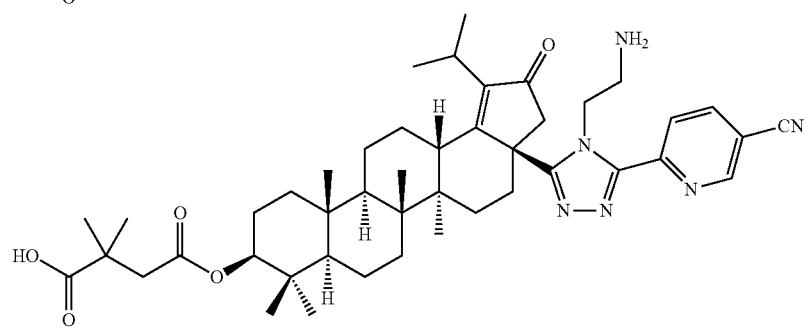

-continued
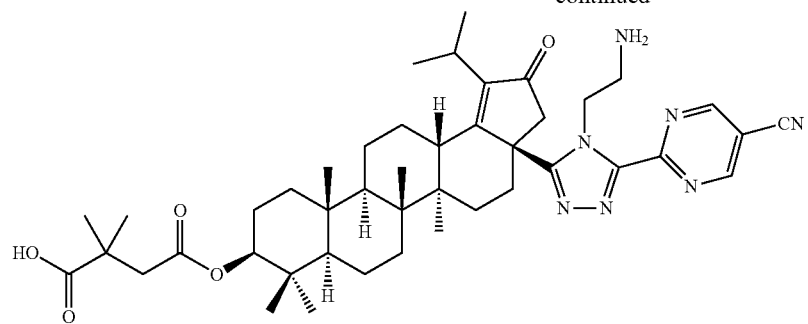
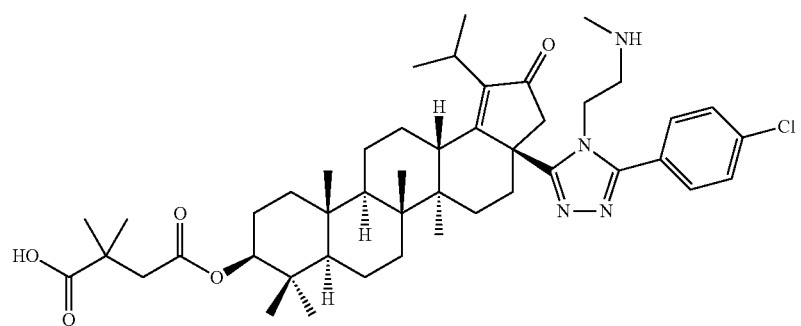
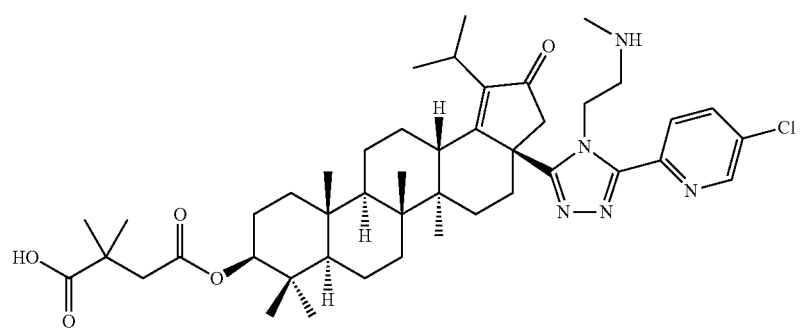
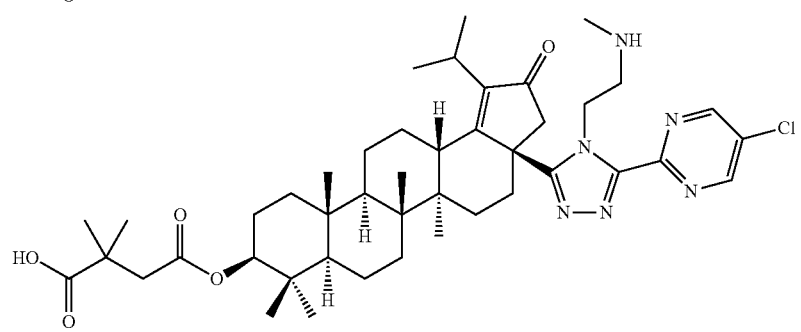
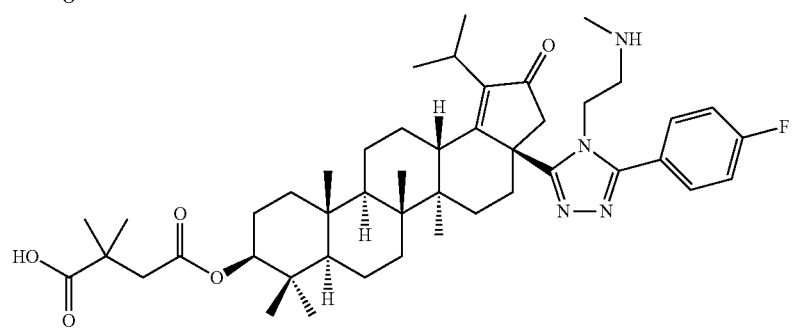

-continued
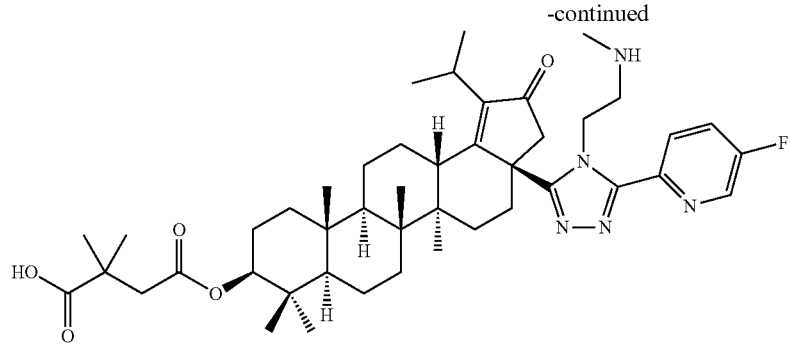
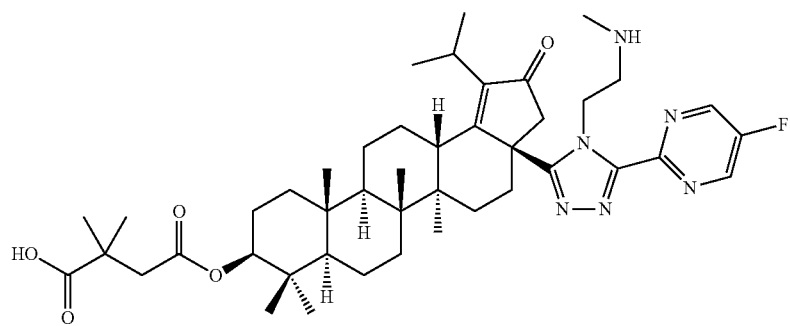
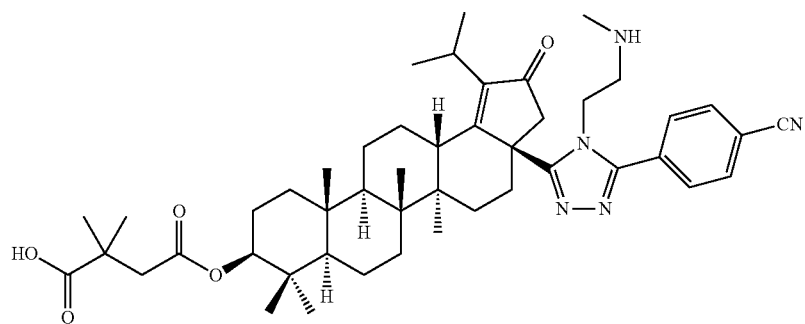
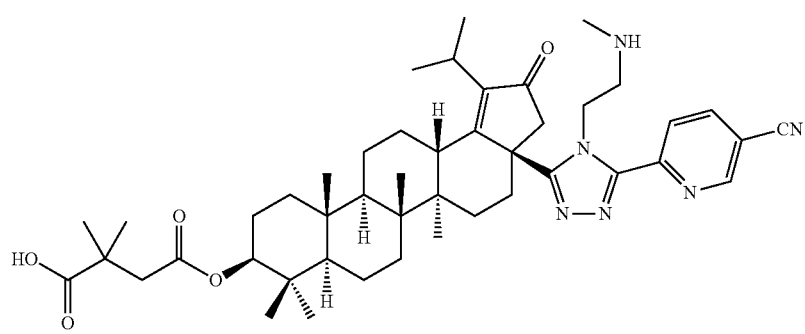
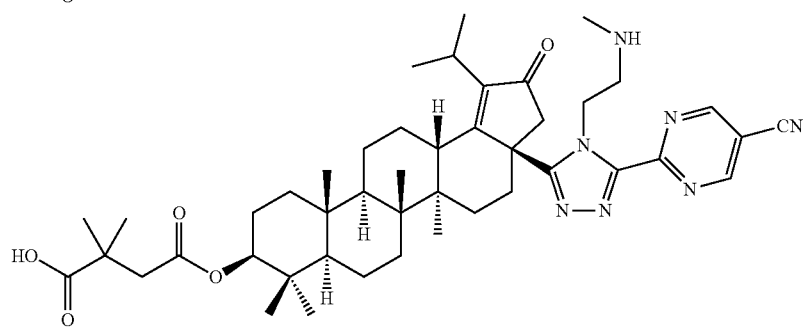

-continued
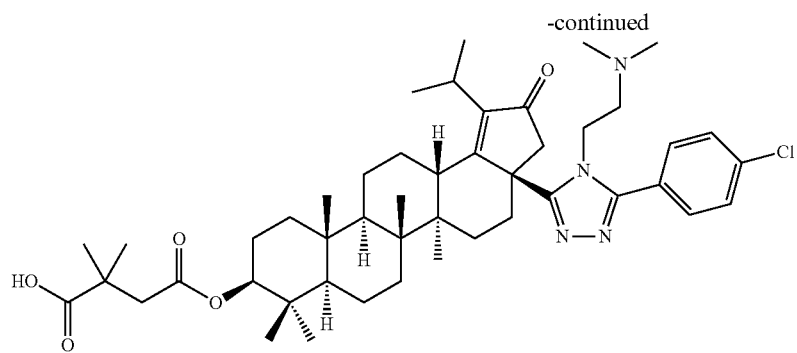
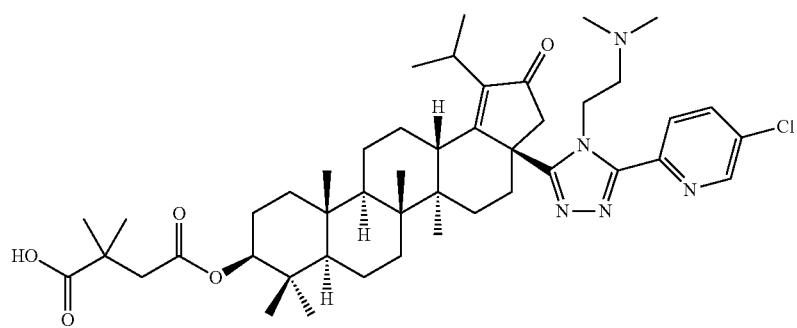
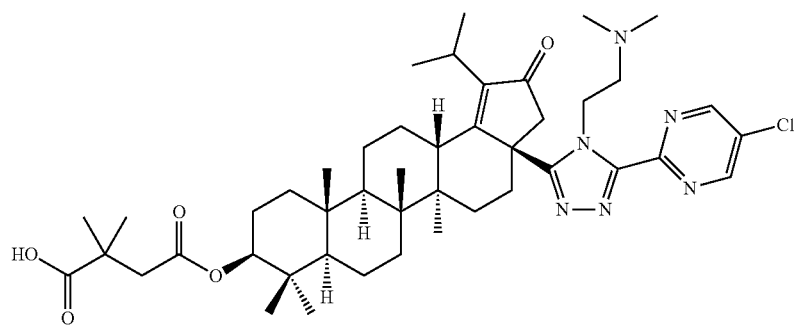
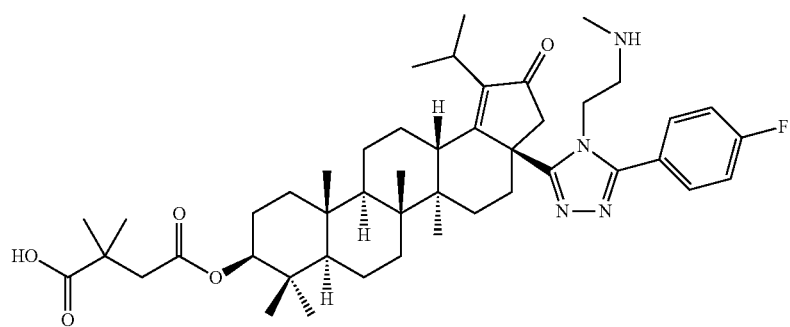
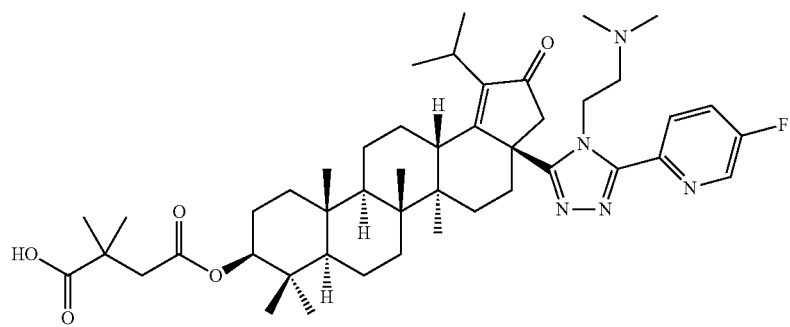

-continued
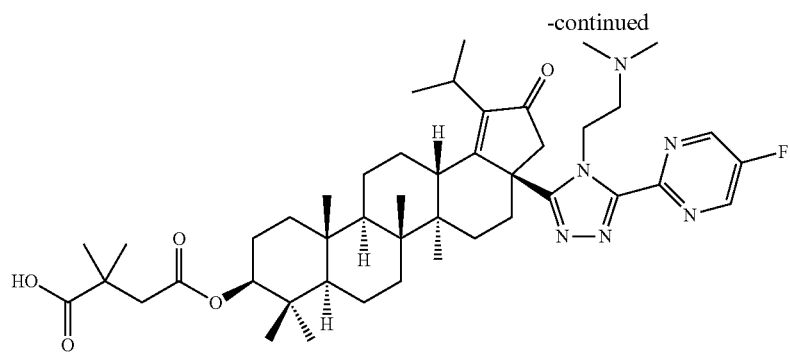
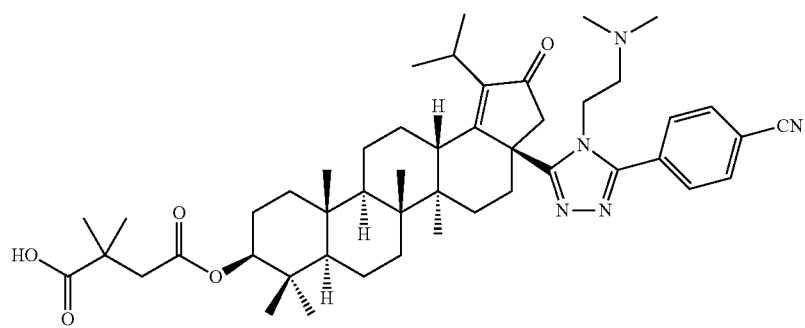
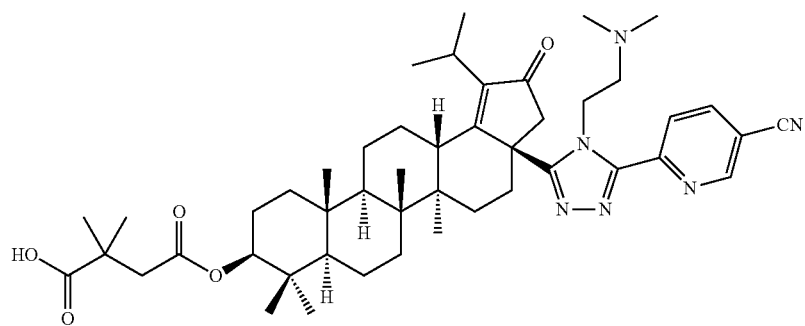
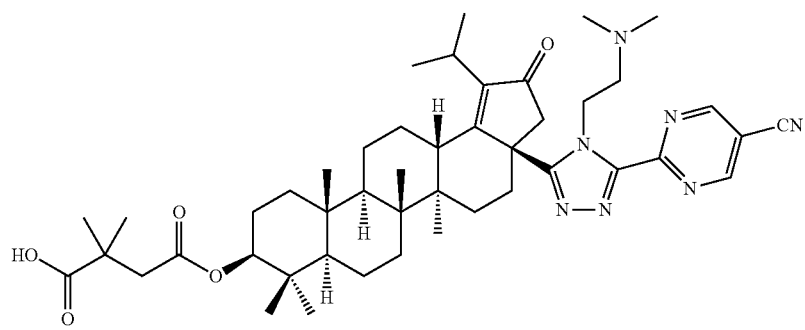
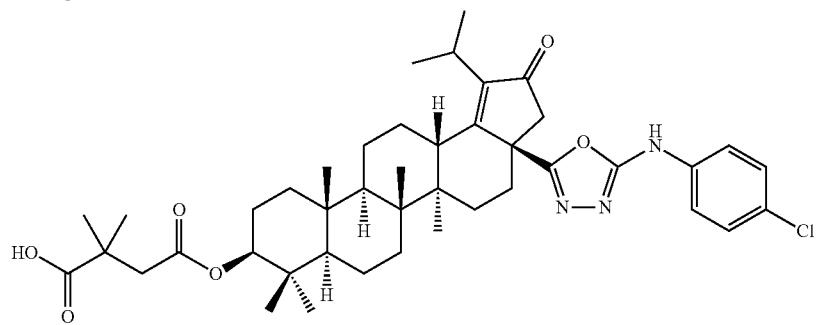

-continued
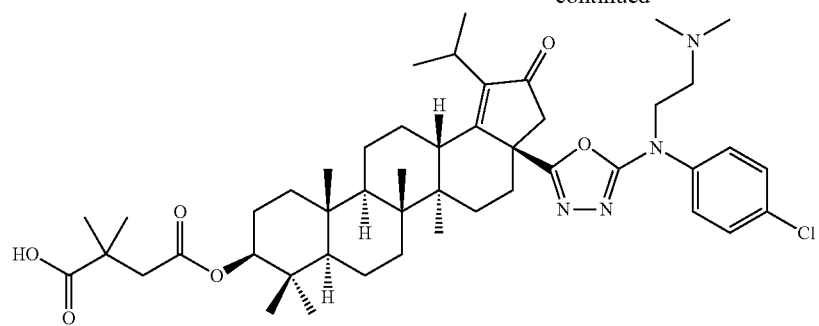
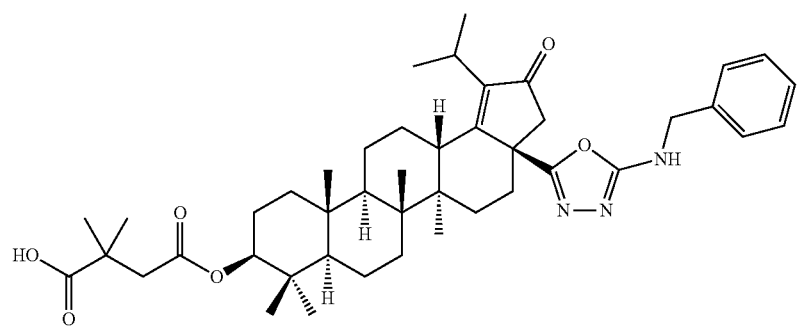
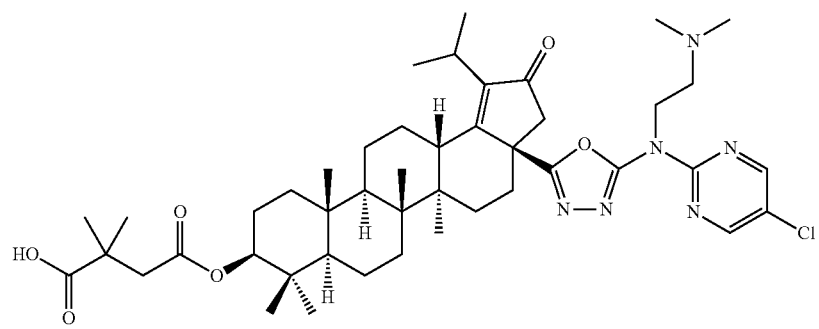
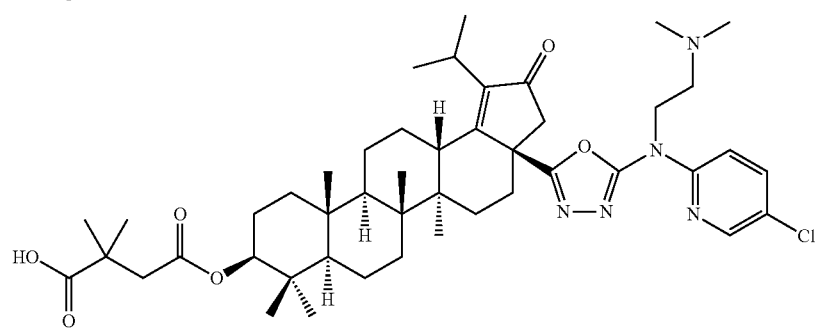
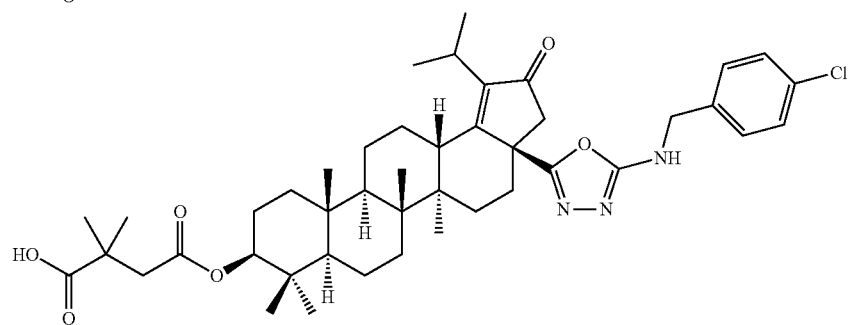

-continued
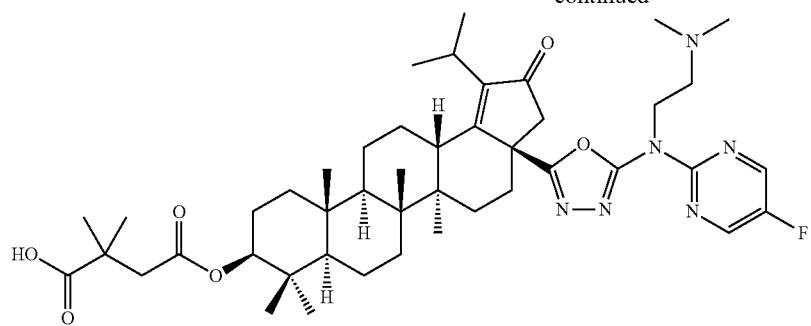
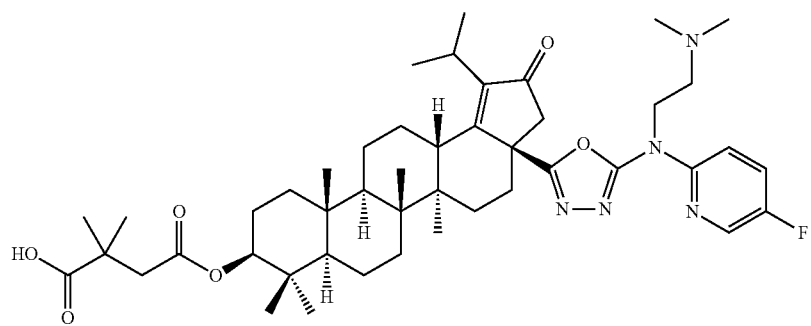
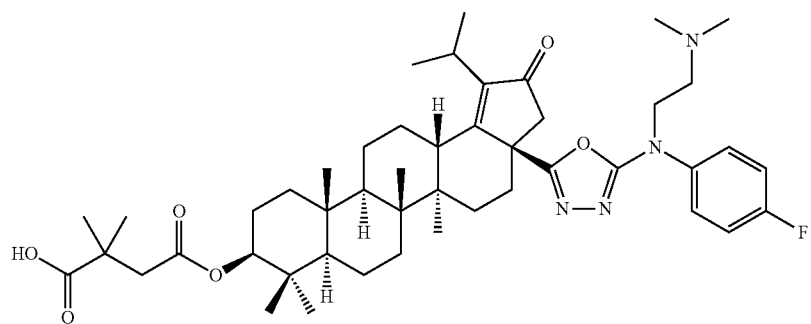
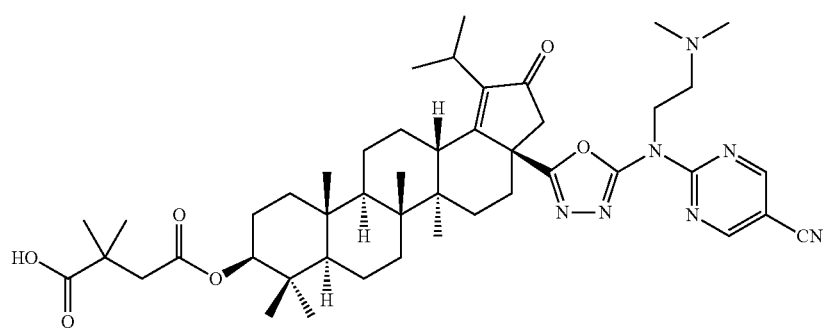
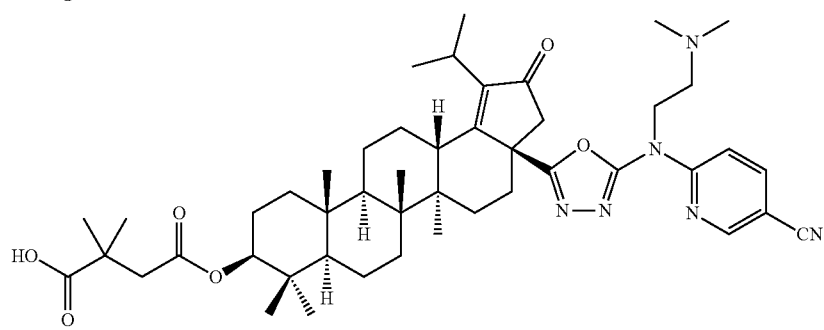

-continued
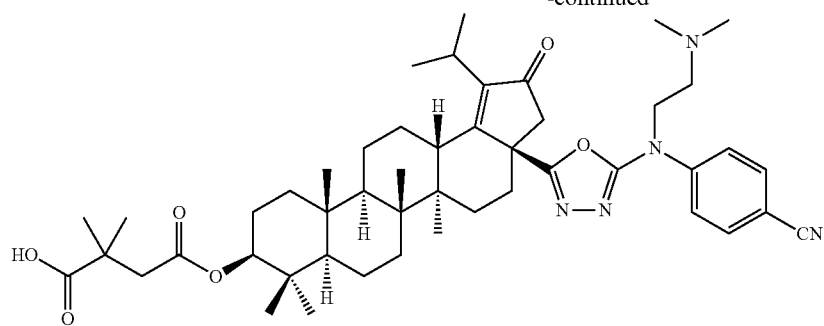
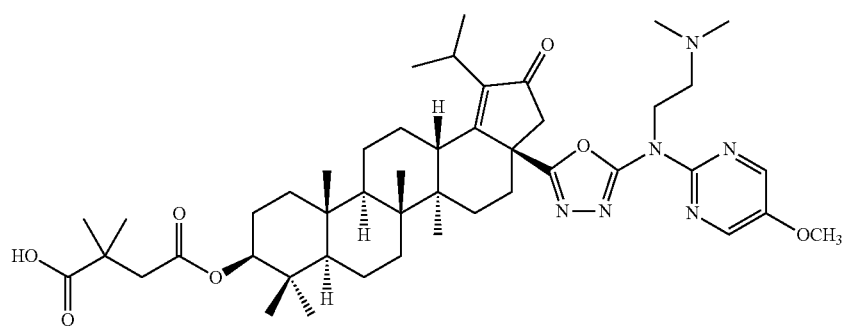
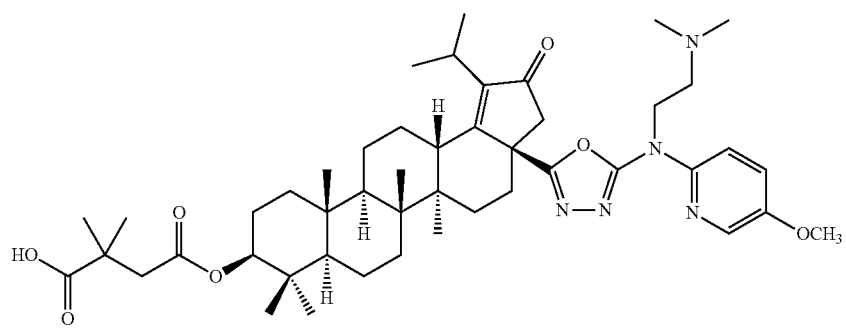
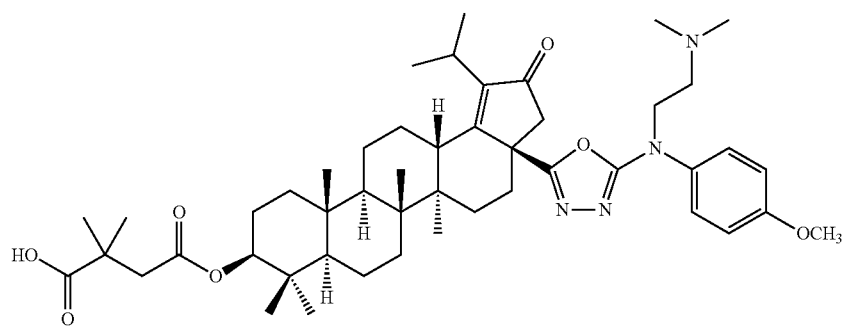
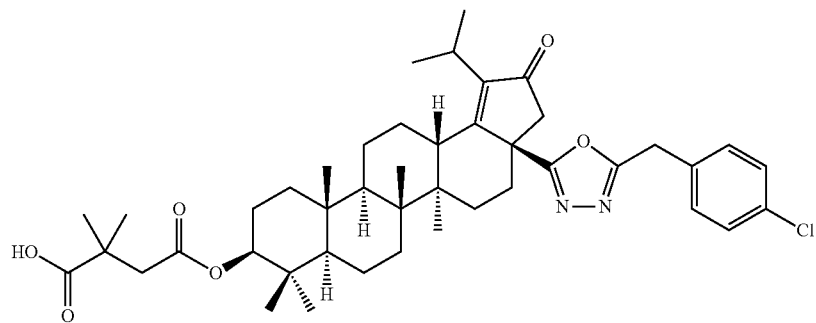

-continued
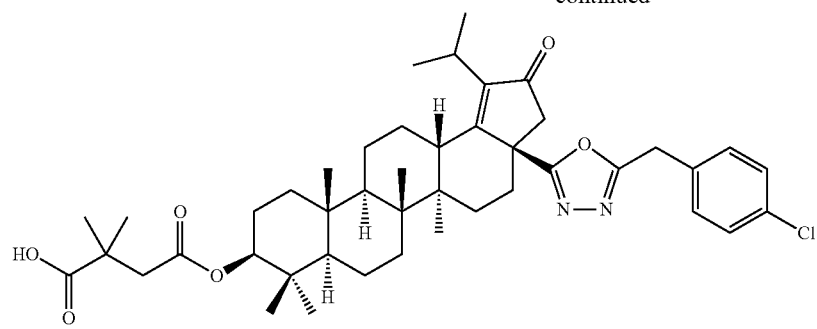
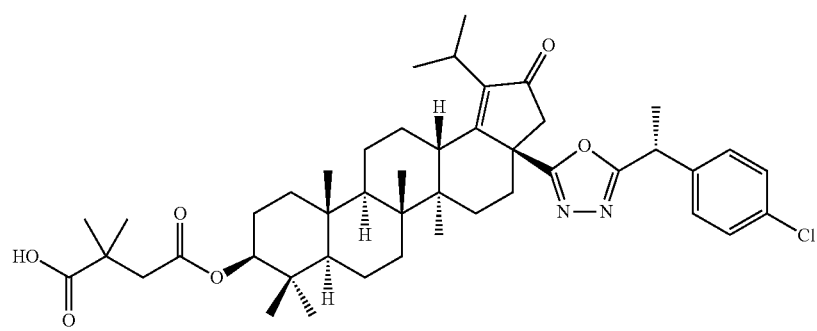
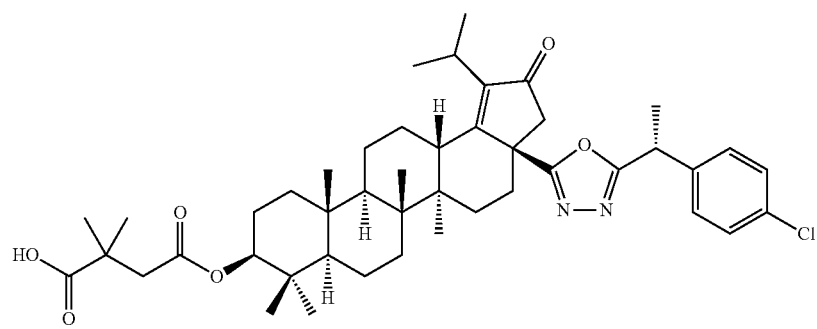
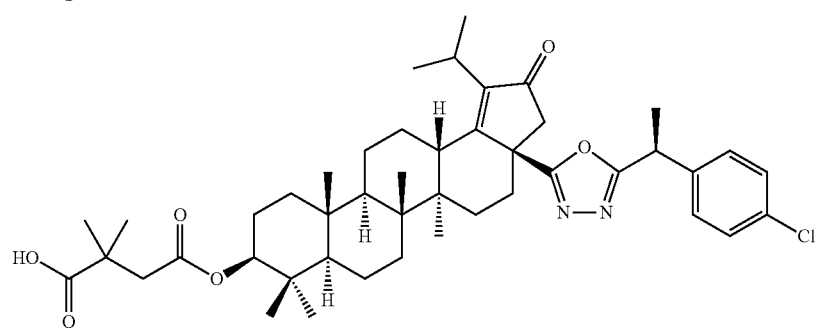
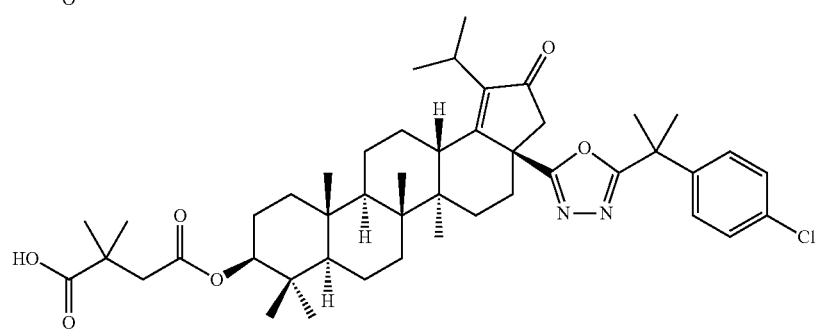

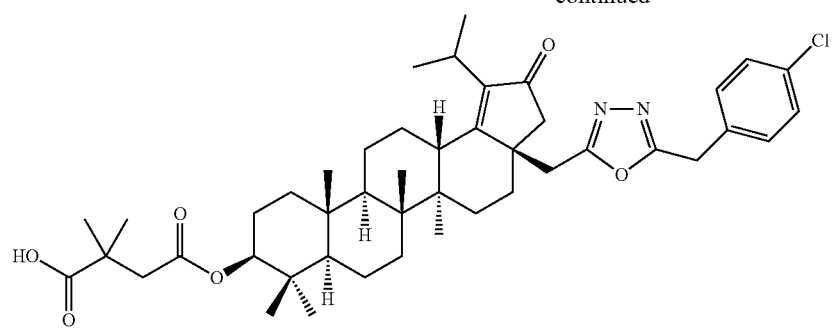
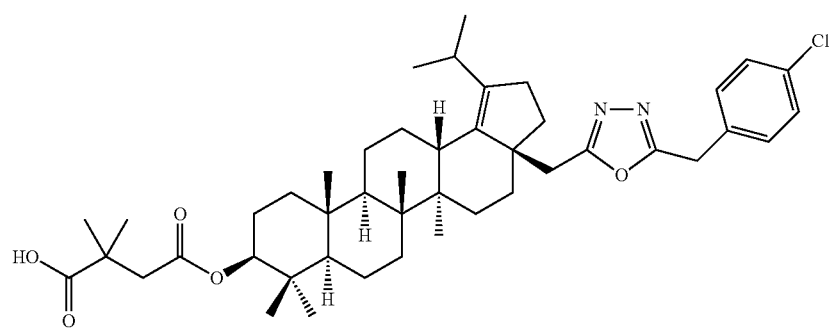
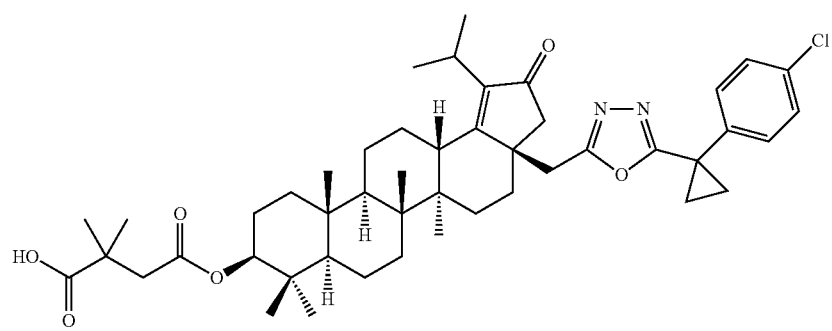
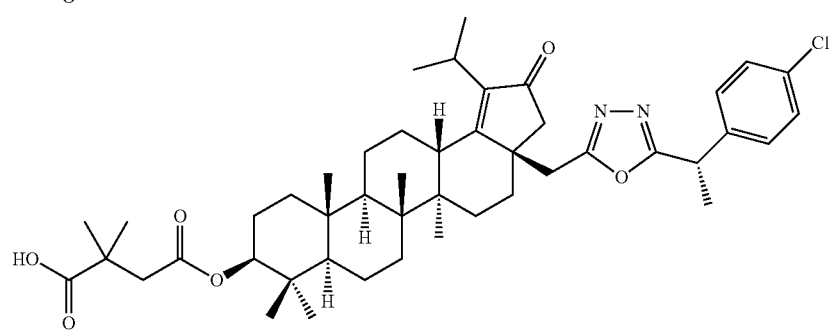
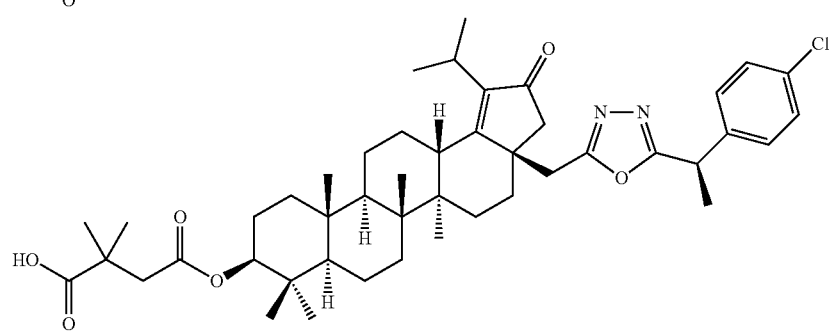

-continued
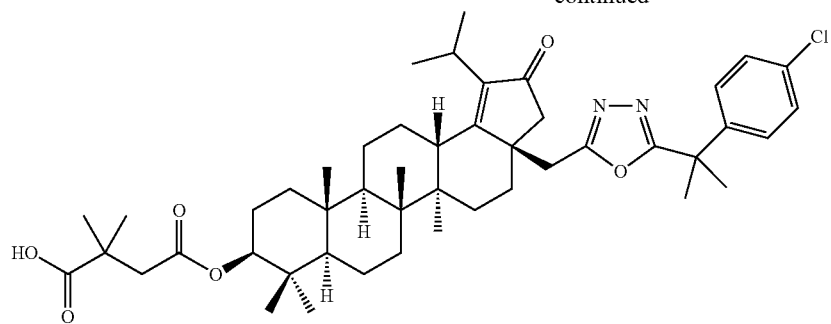
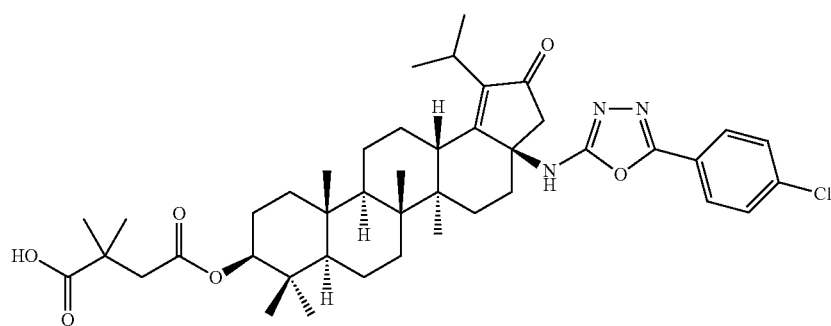
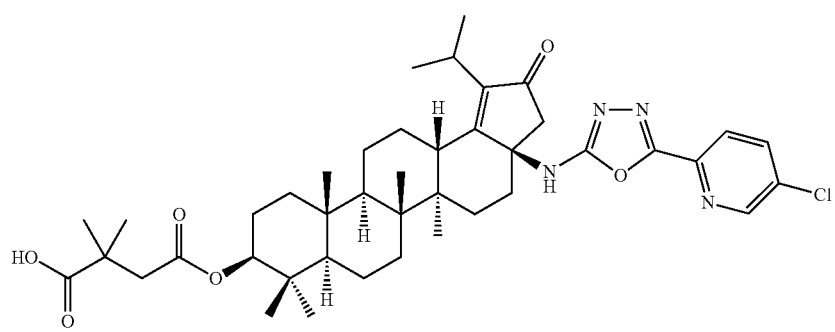
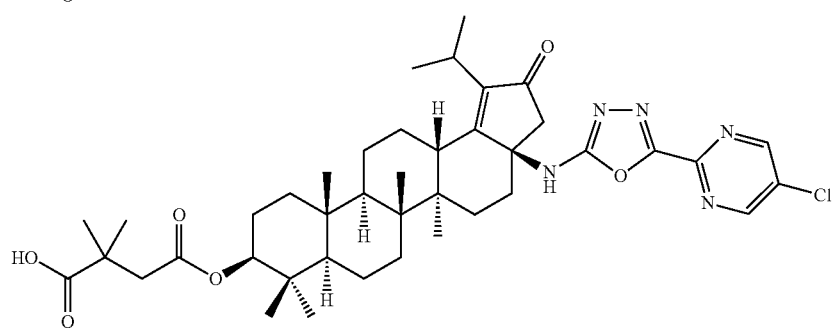
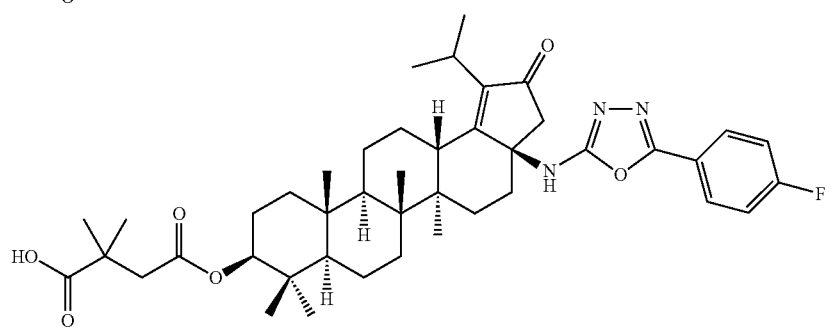

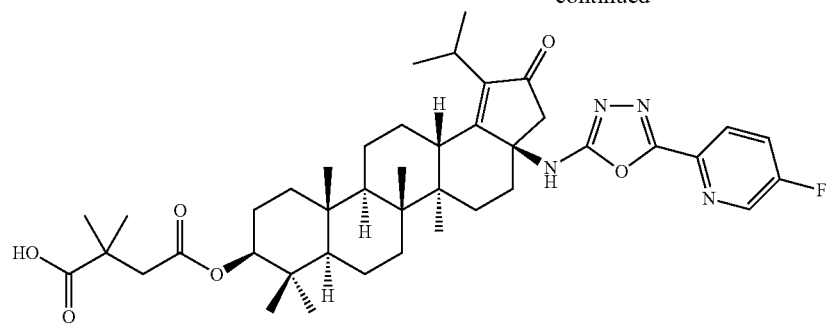
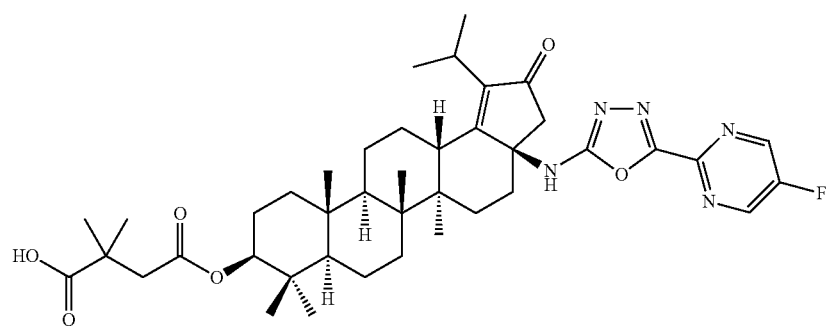
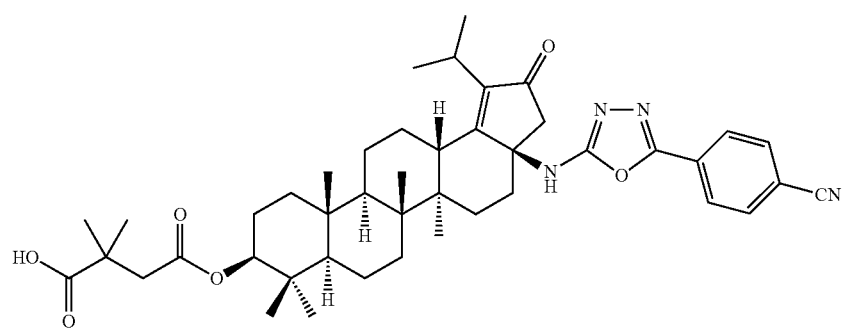
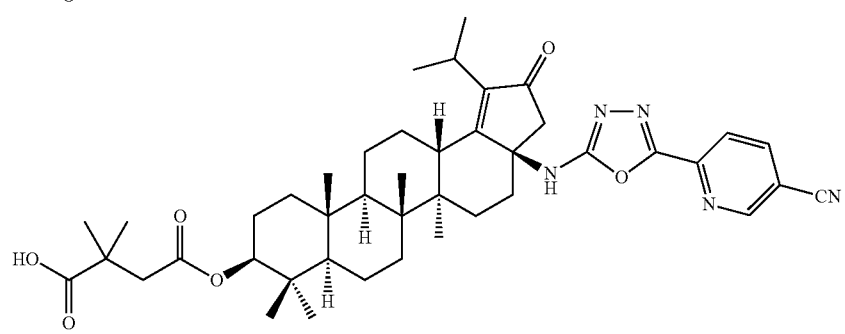
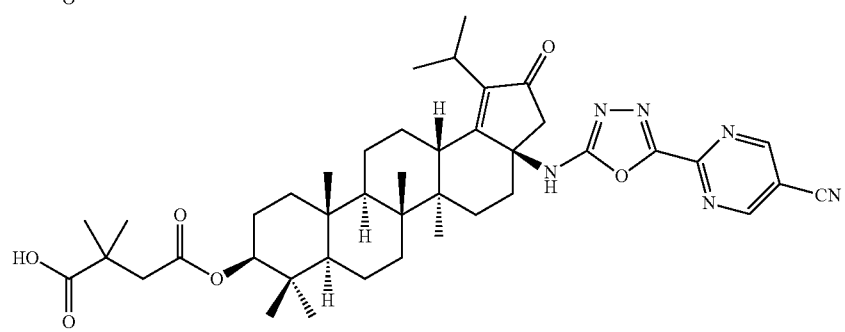

-continued
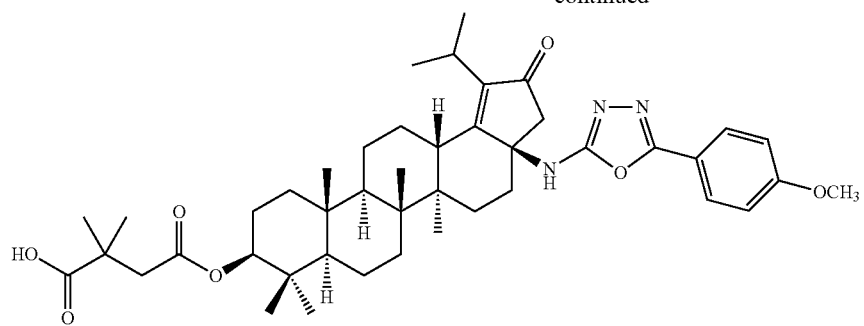
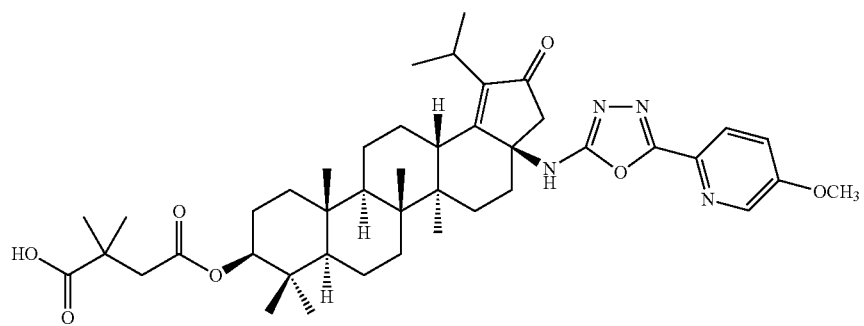
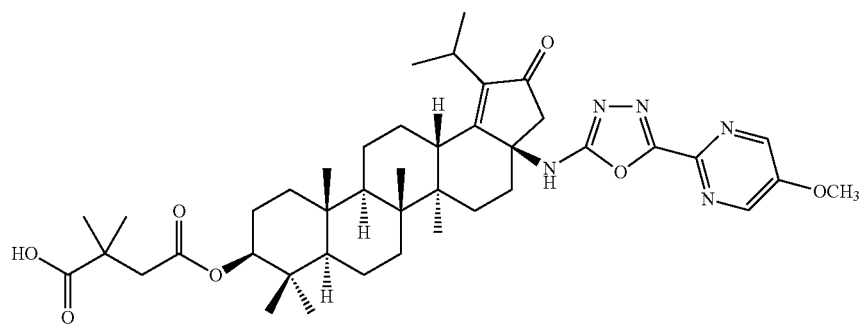
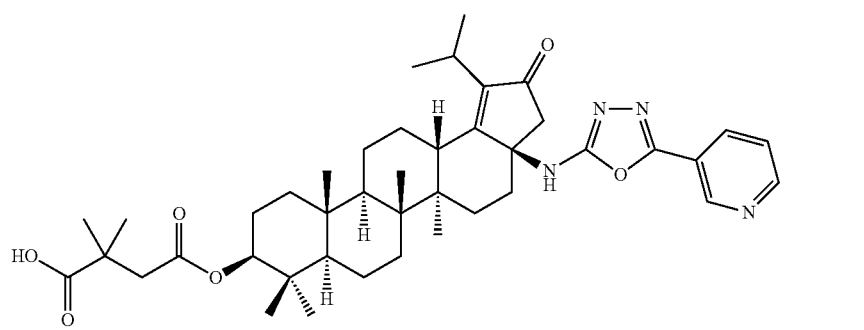
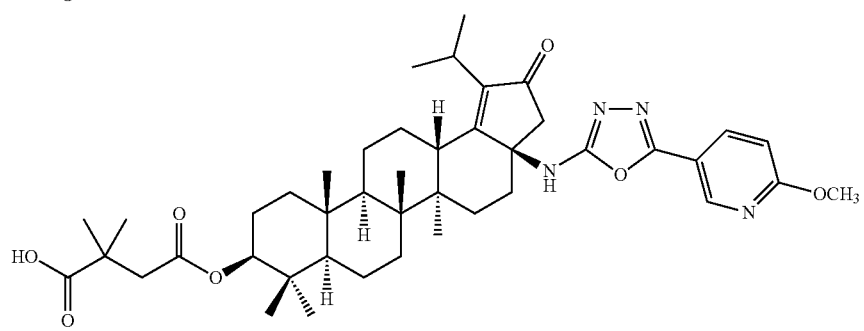

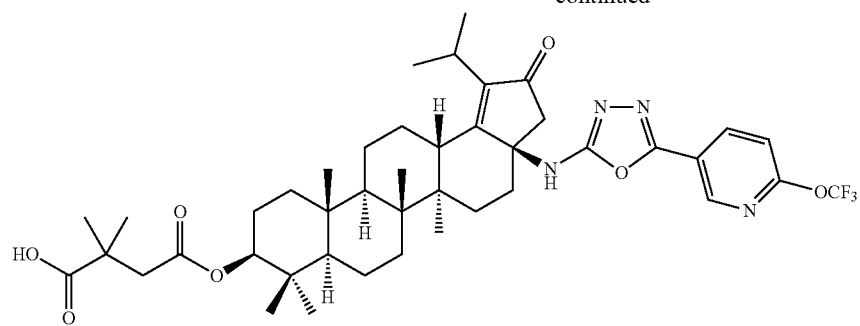
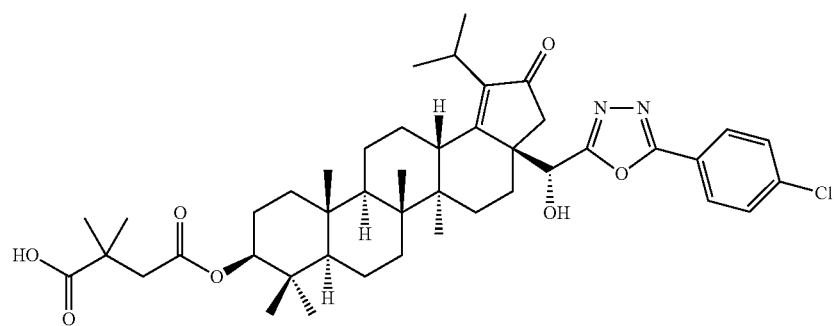
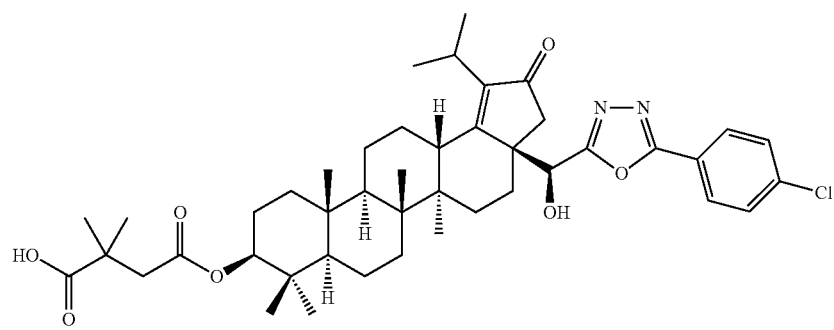
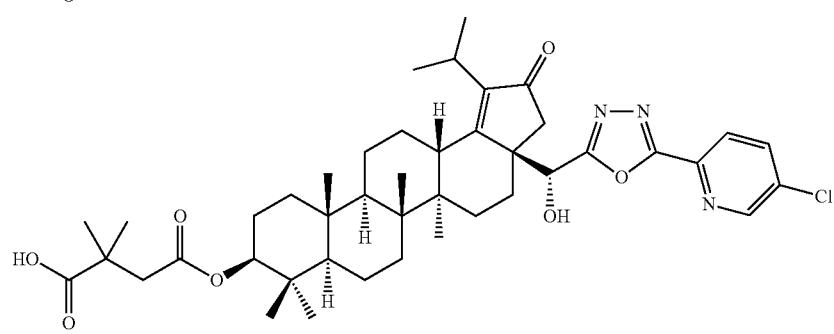
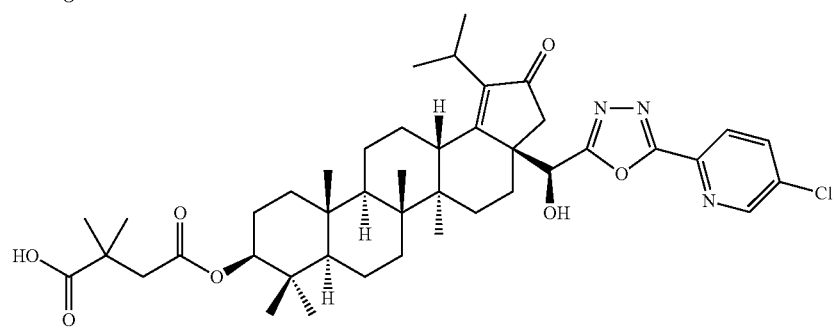

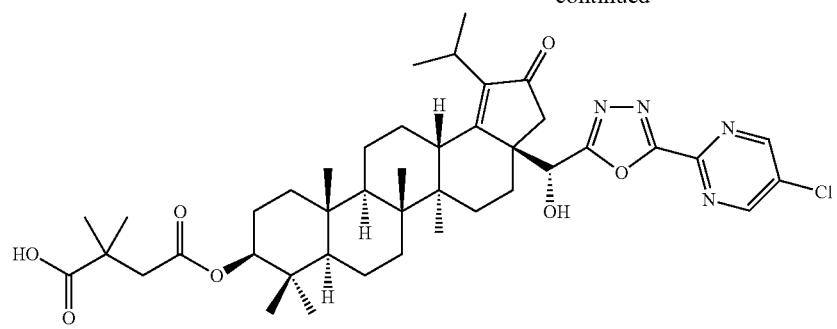
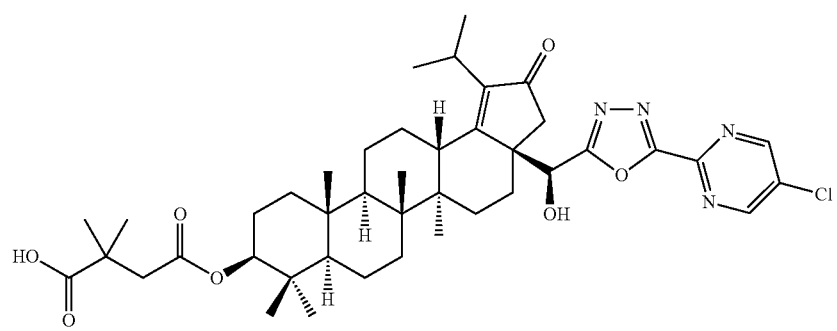
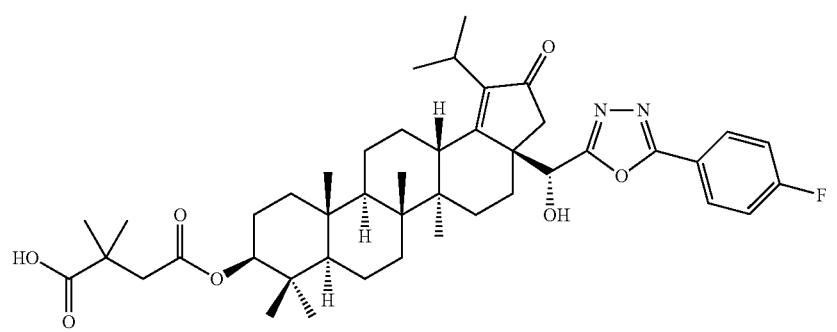
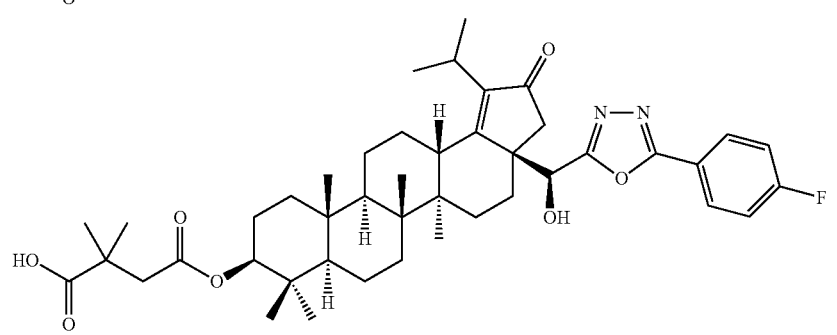
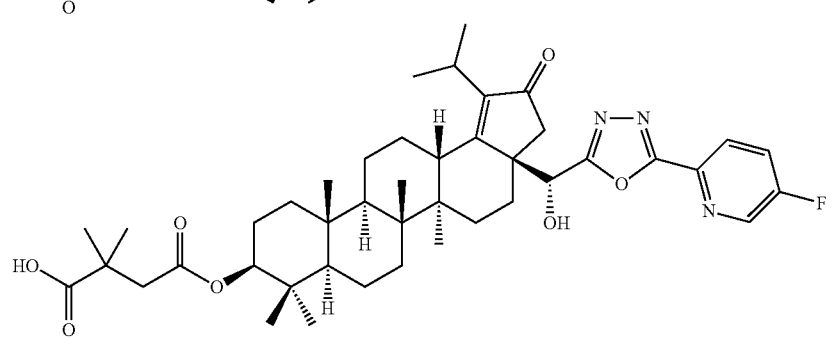

-continued
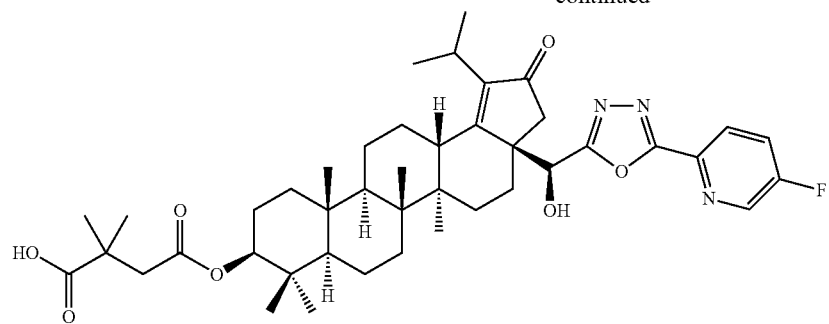
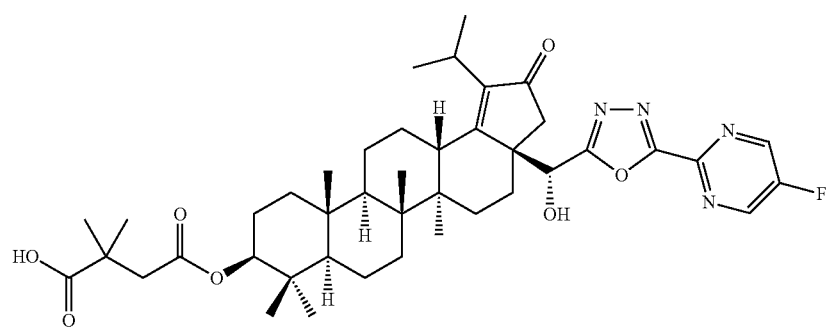
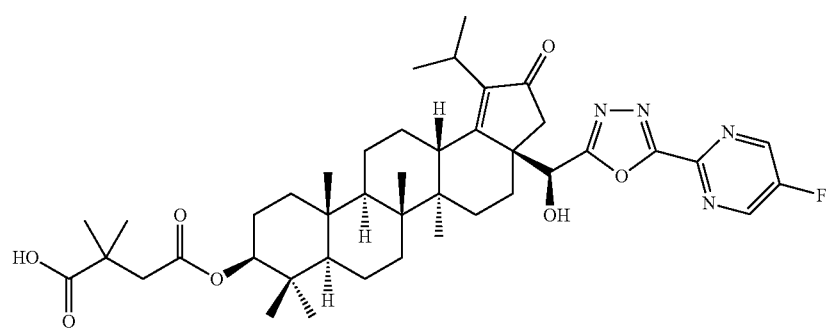
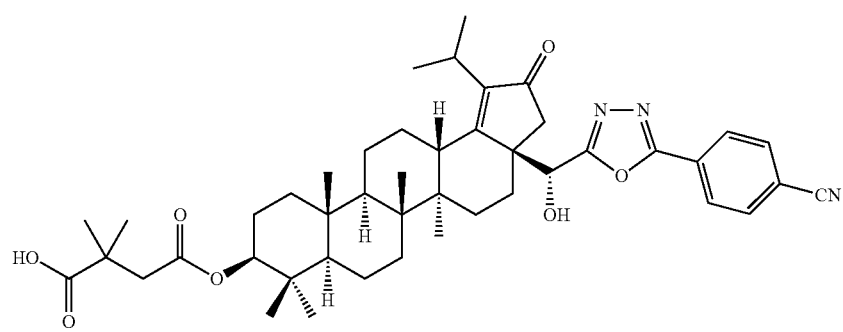
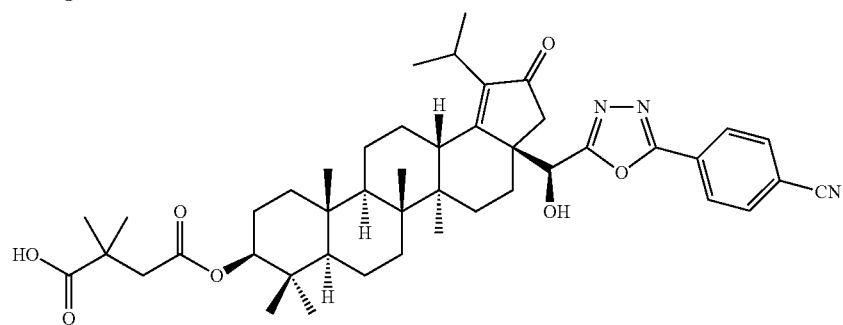

-continued
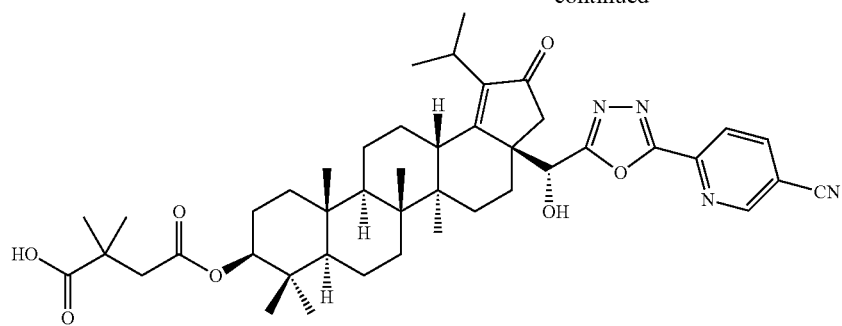
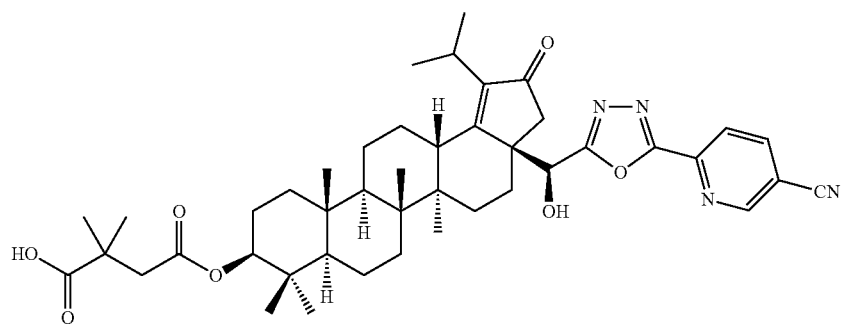
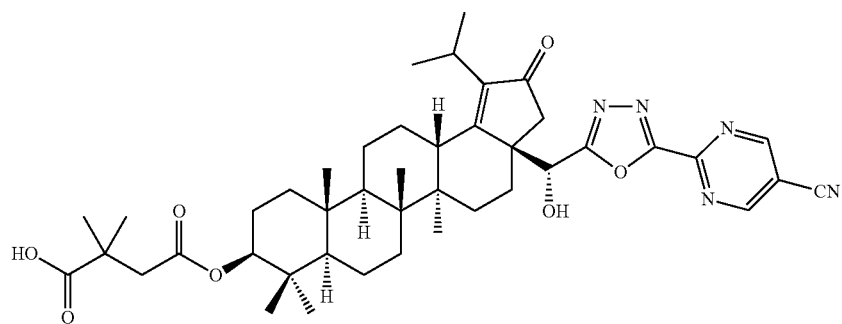
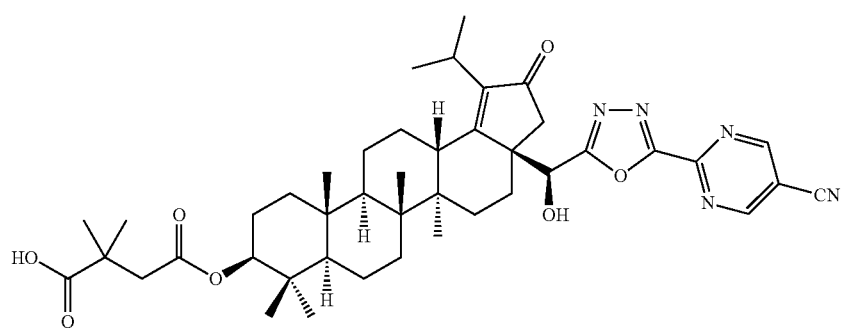
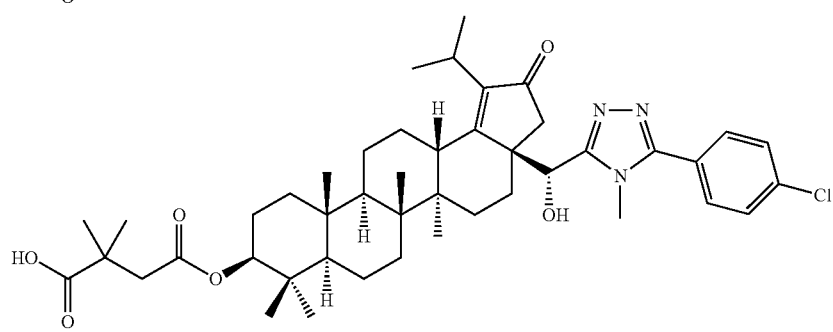

-continued
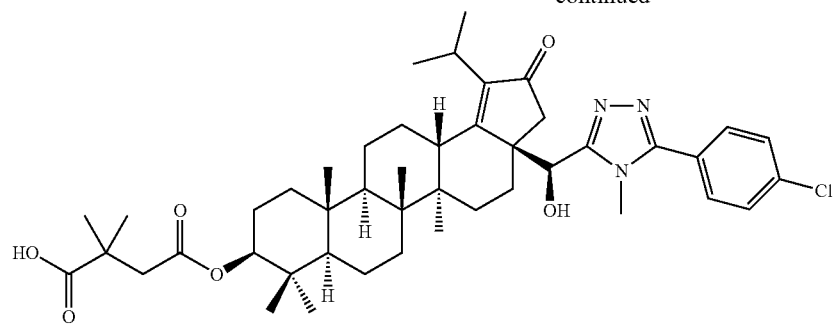
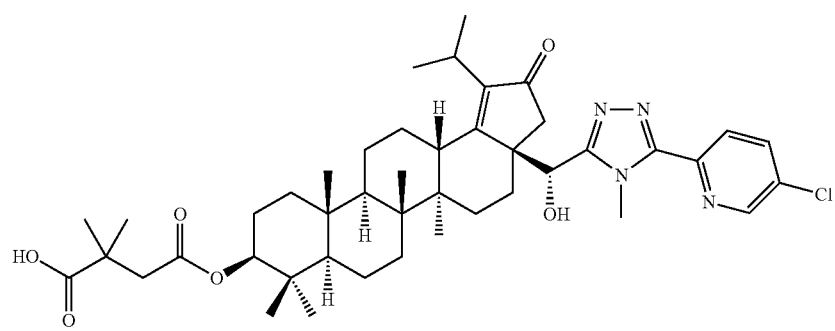
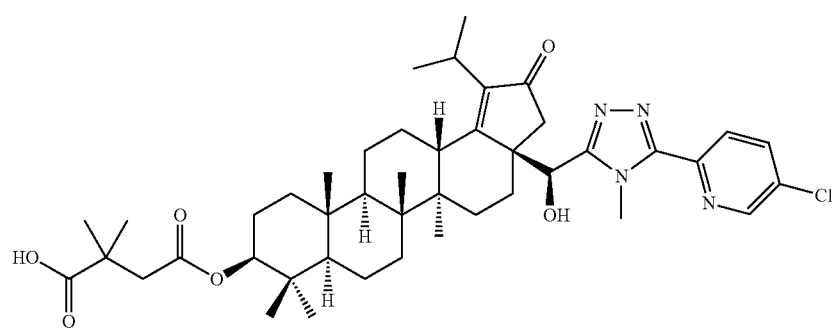
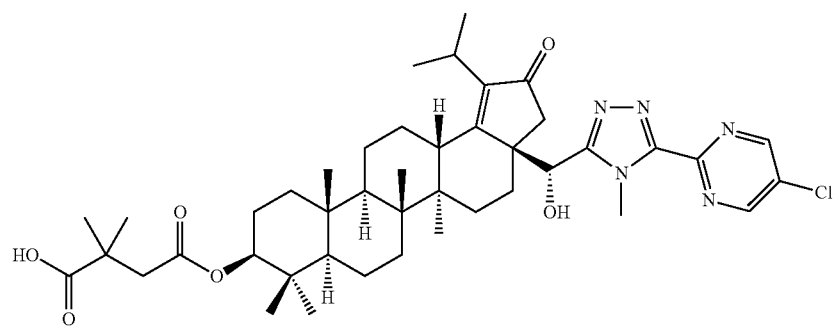
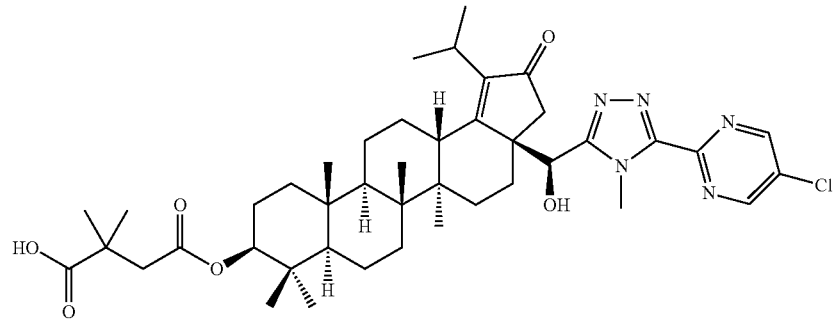

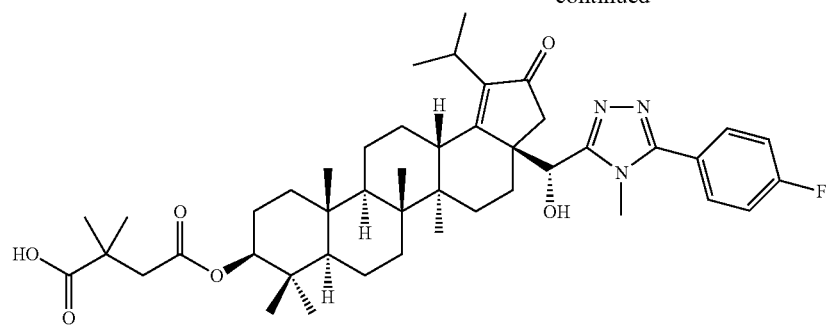
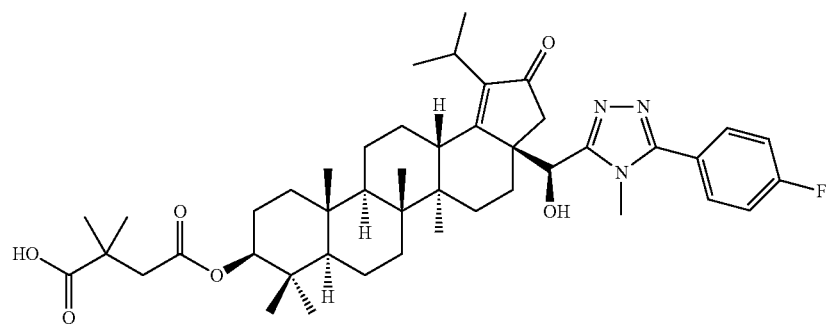
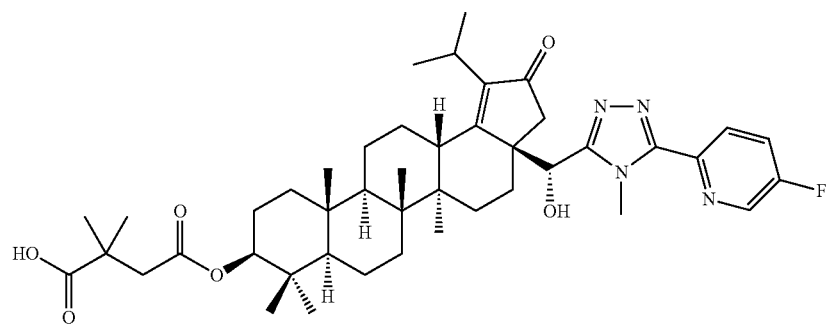
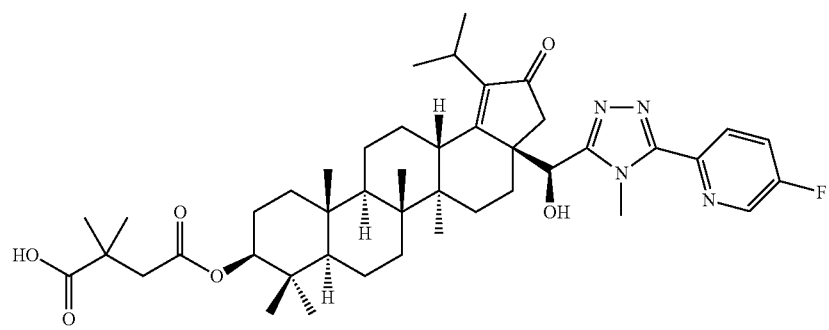
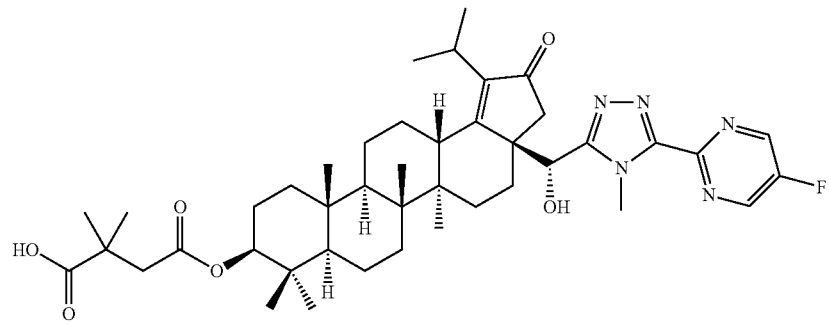

-continued
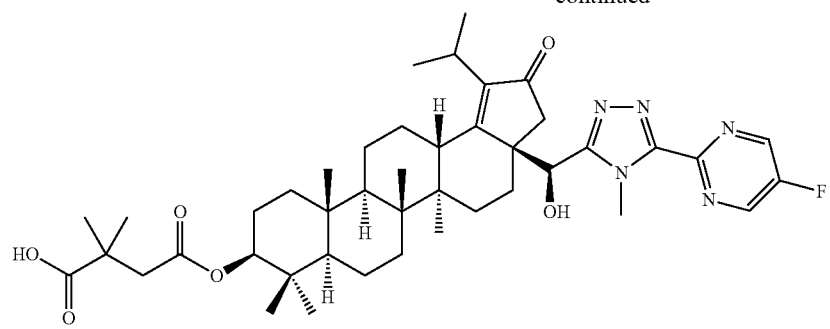
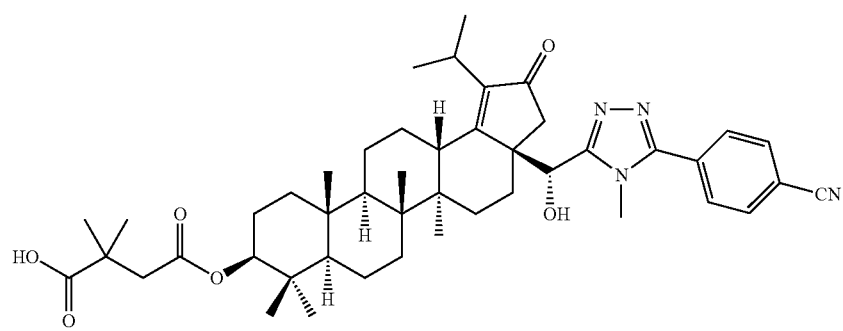
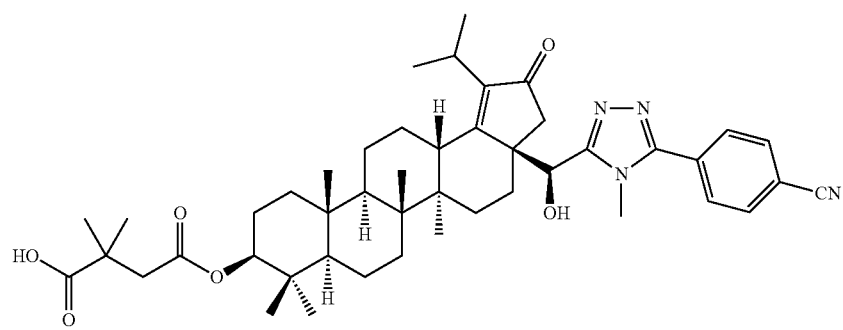
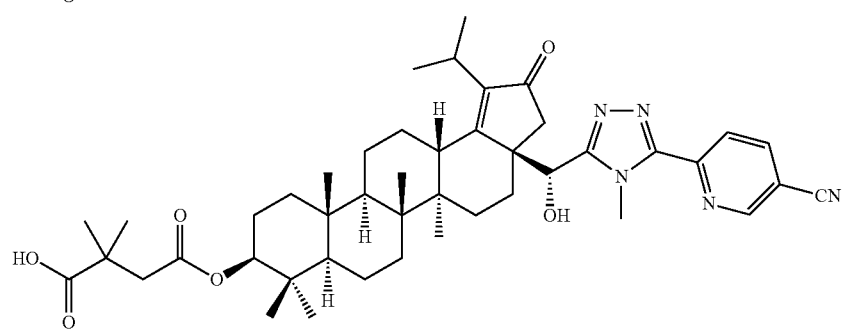
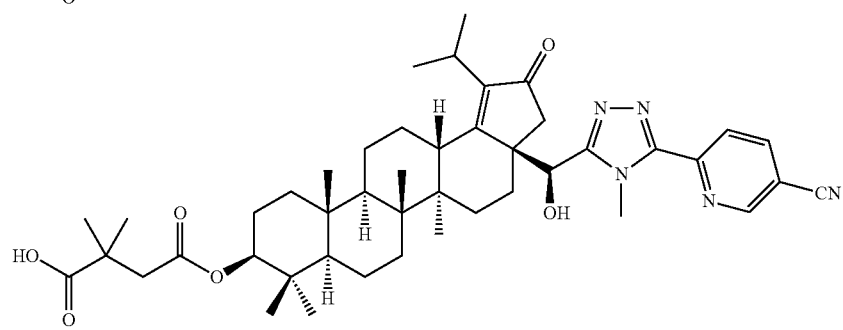

-continued
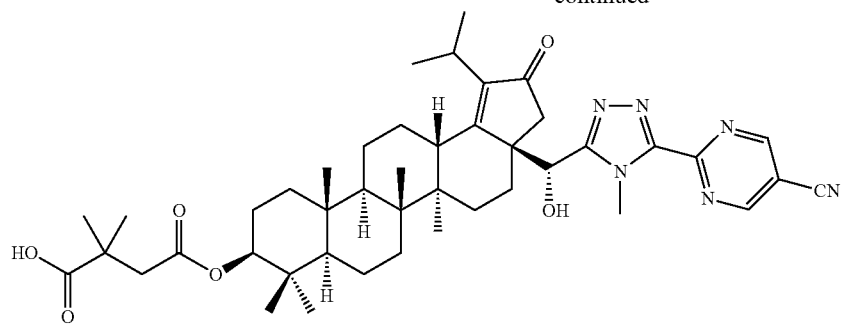
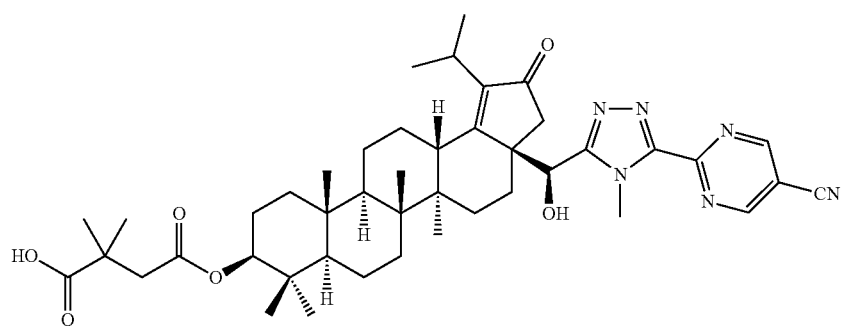
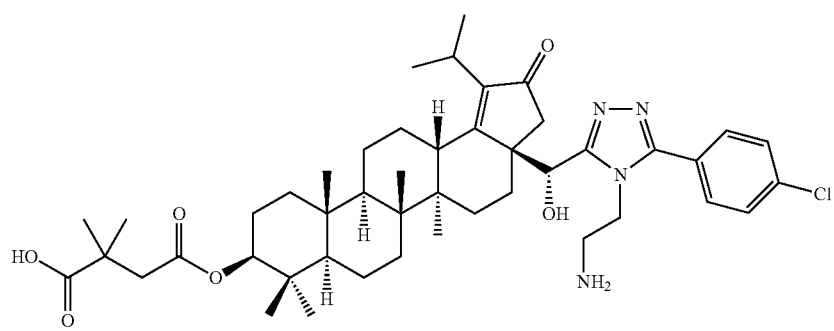
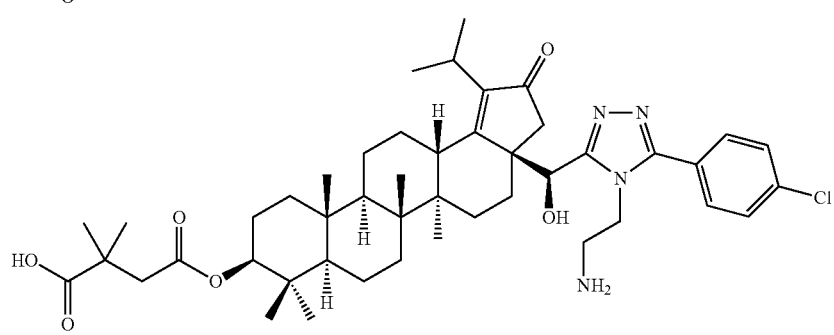
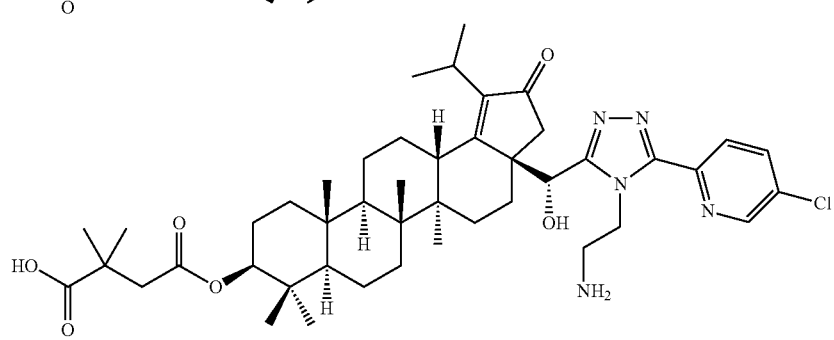

-continued
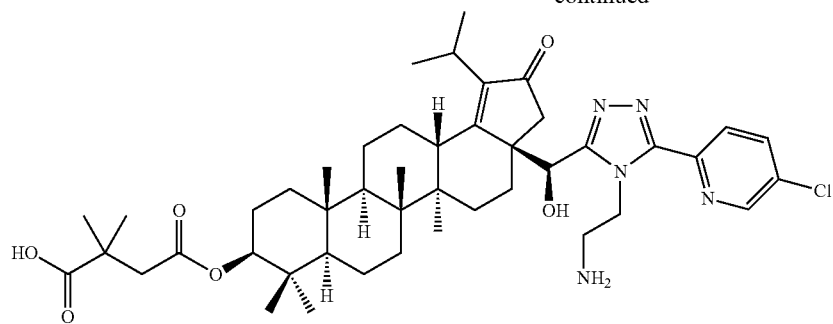
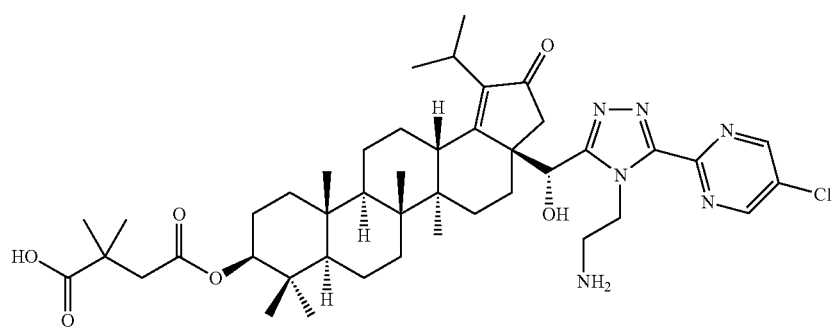
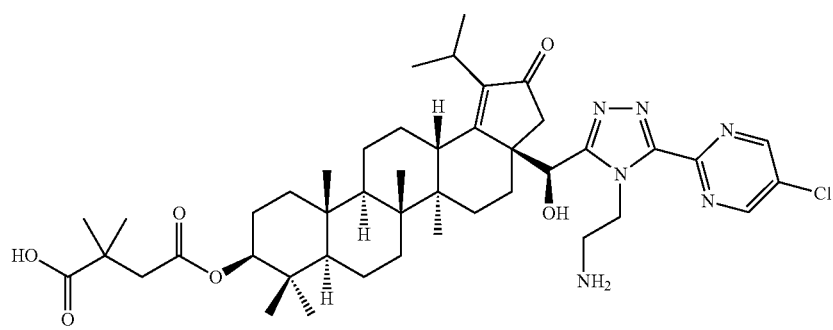
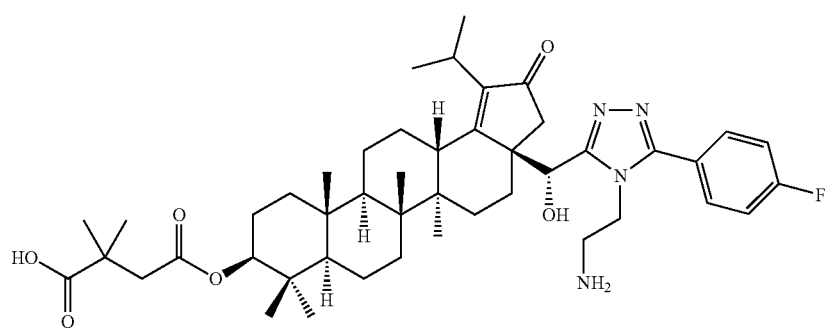
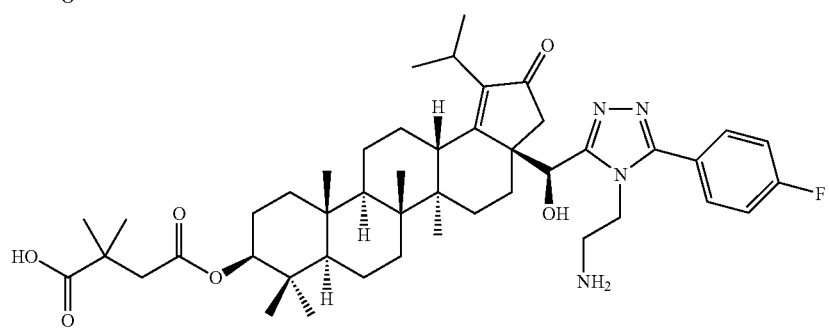

-continued
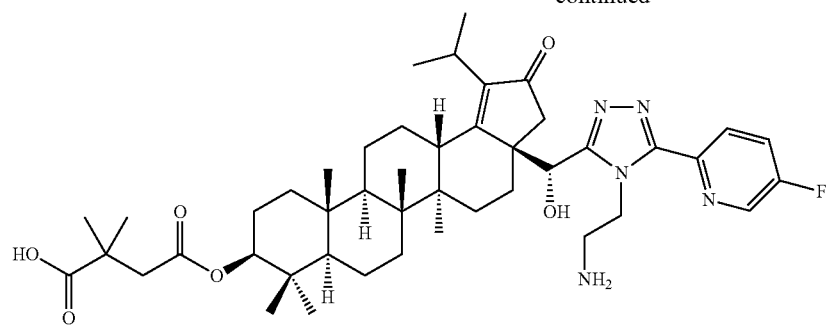
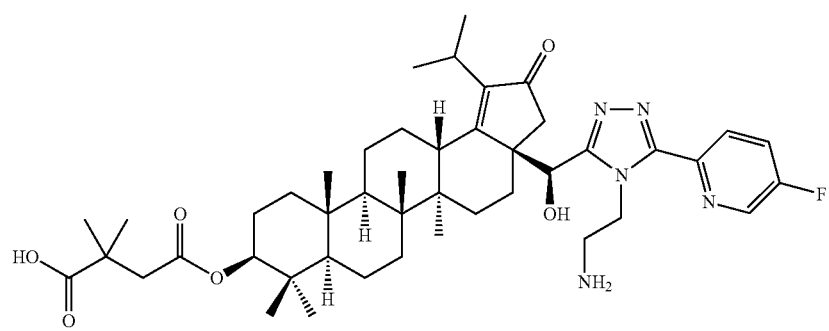
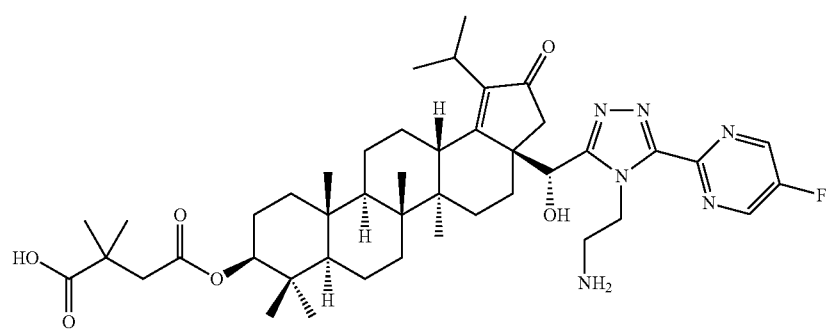
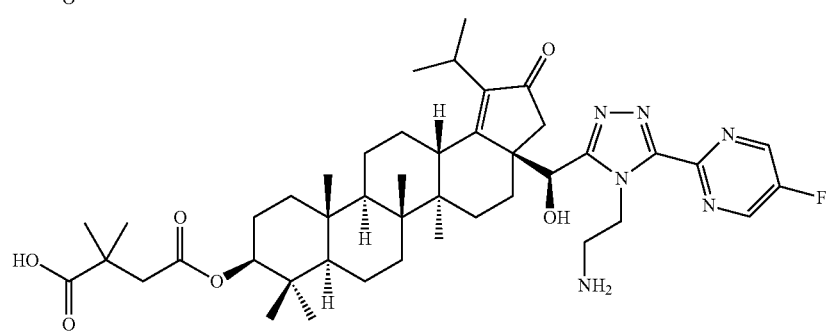
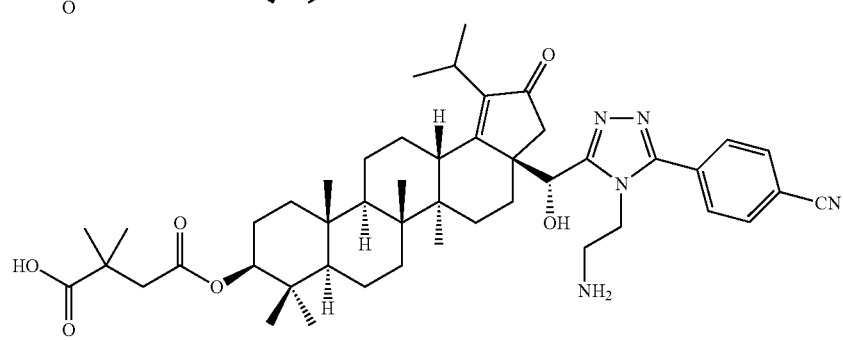

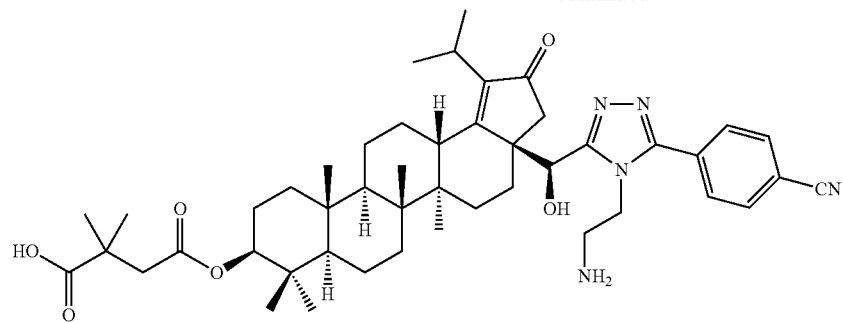
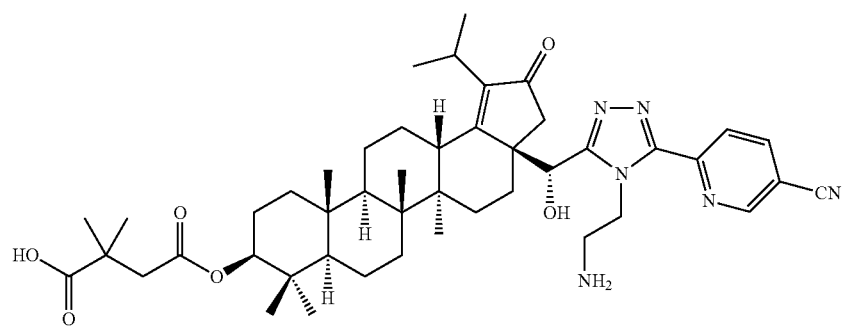
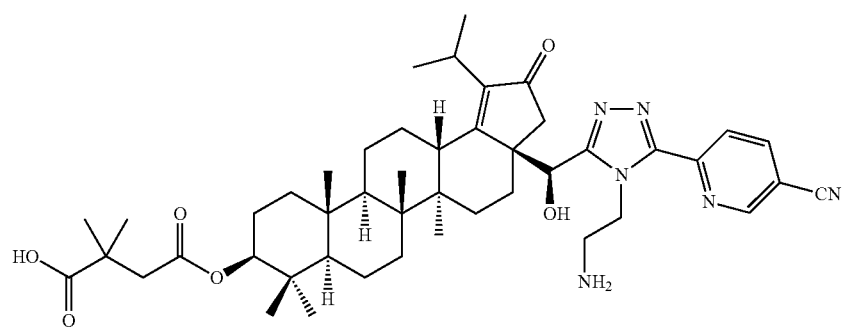
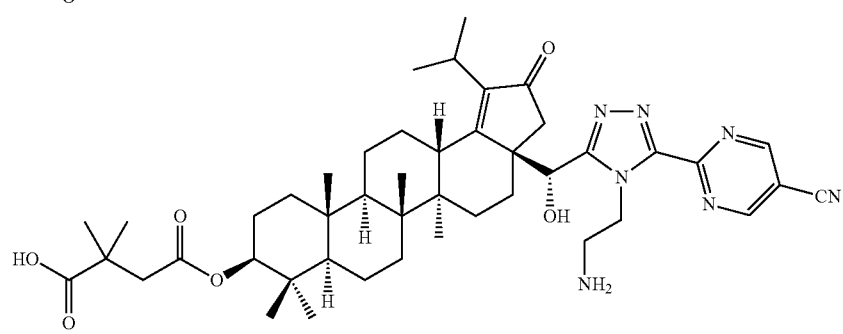
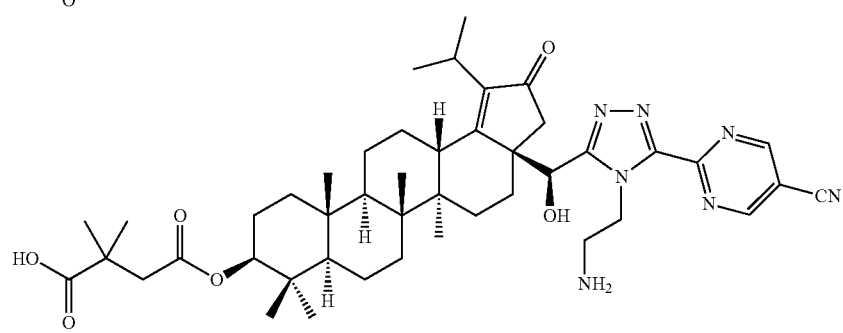

-continued
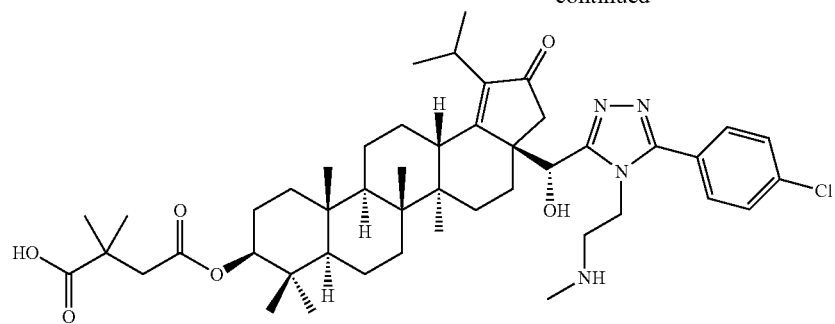
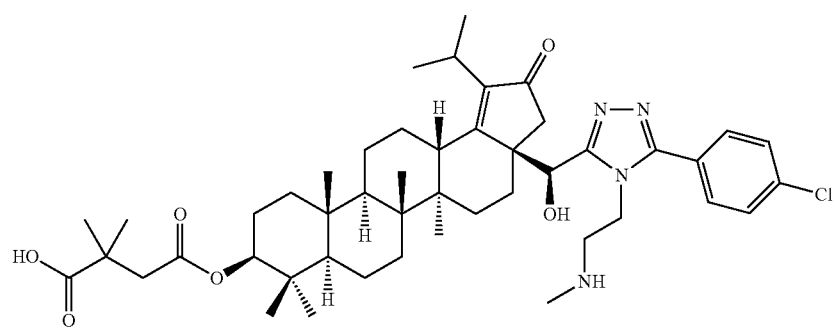
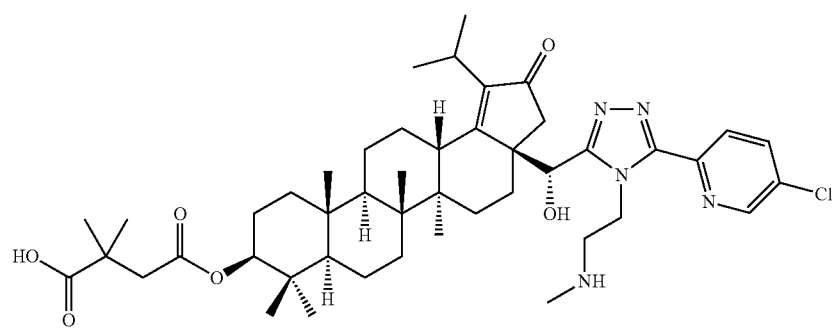
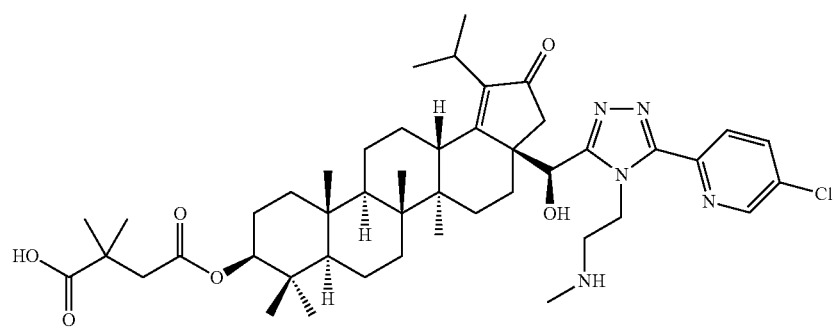
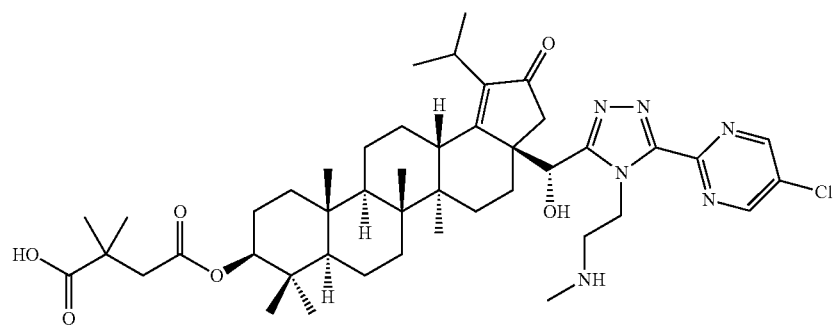

-continued
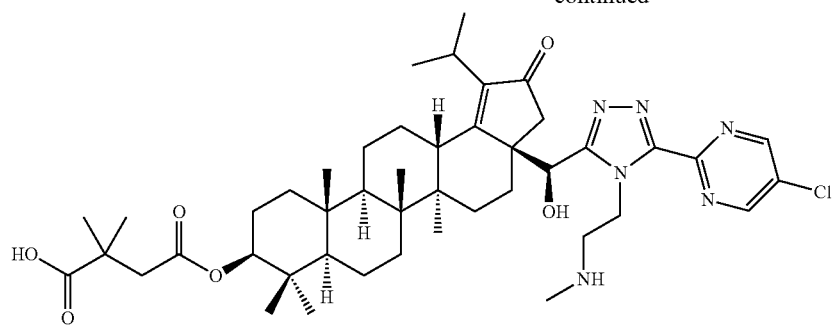
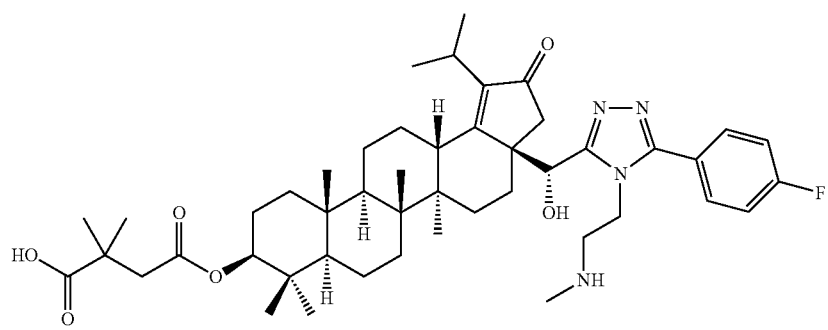
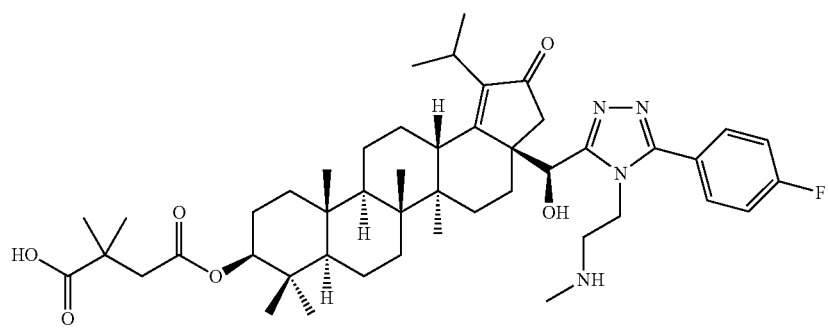
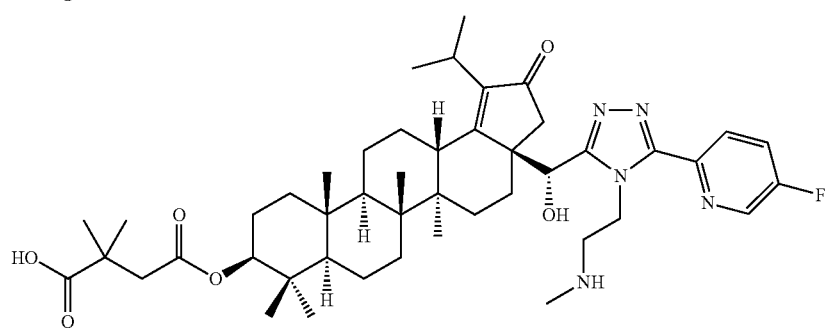
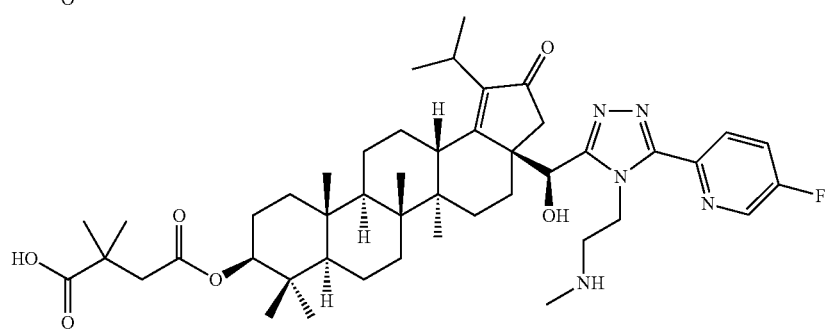

-continued
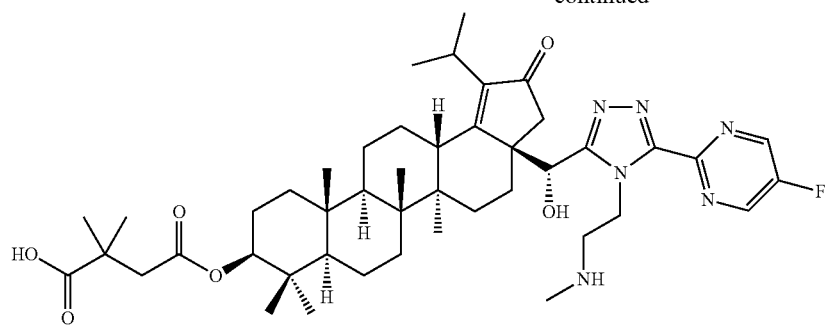
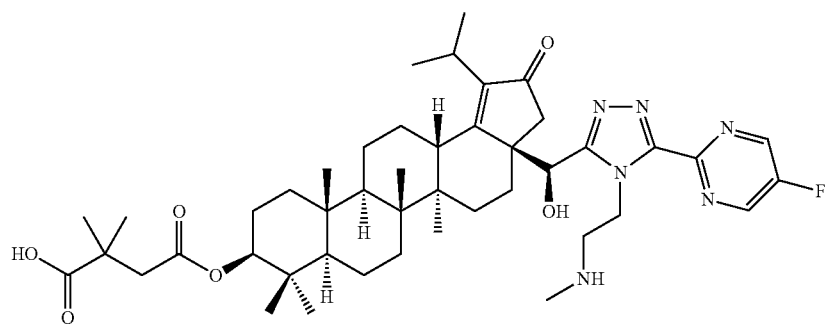
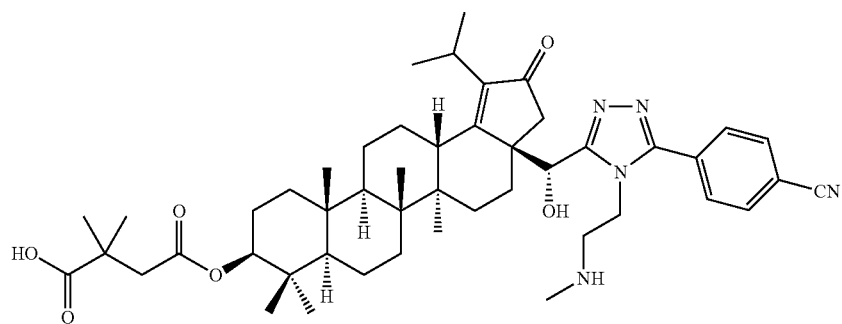
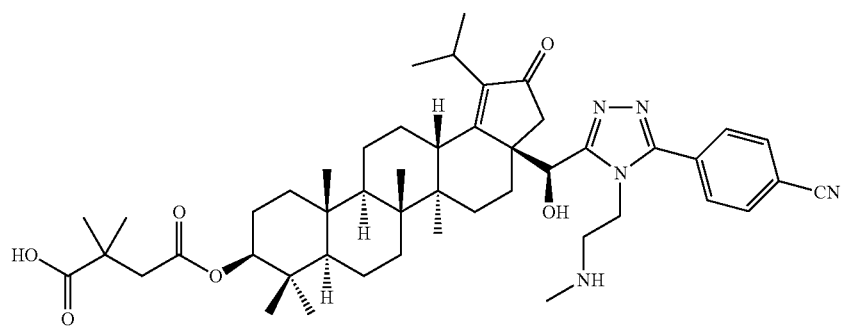
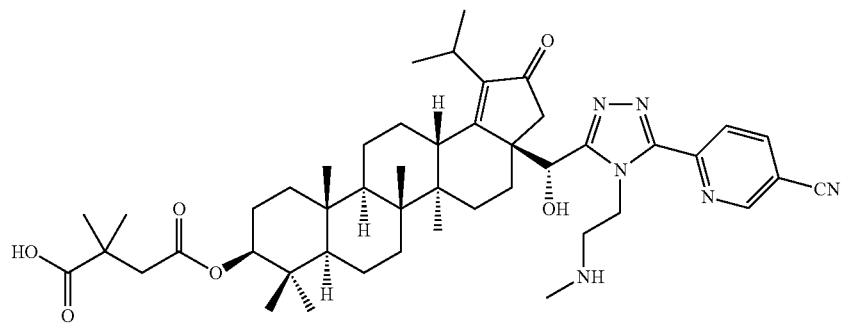

-continued
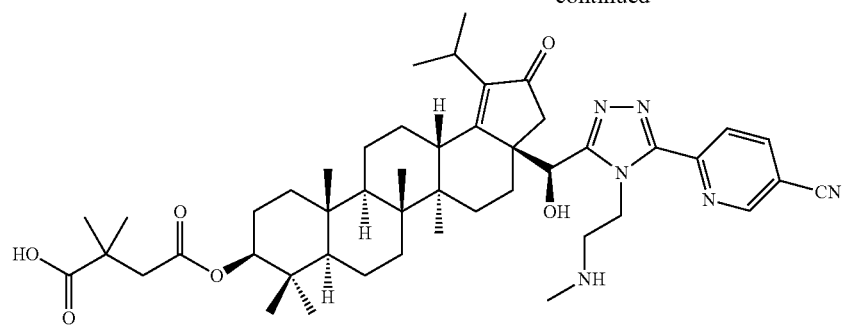
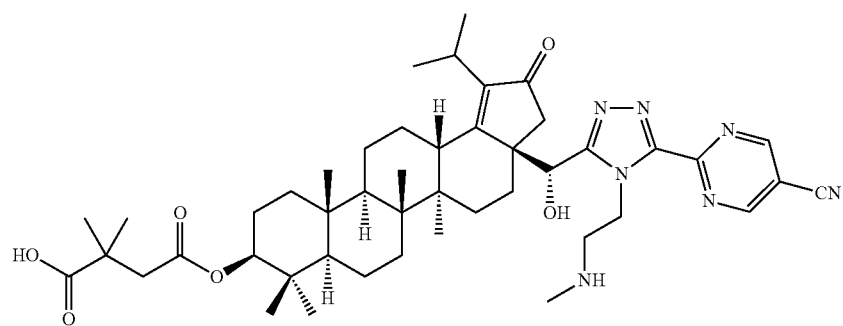
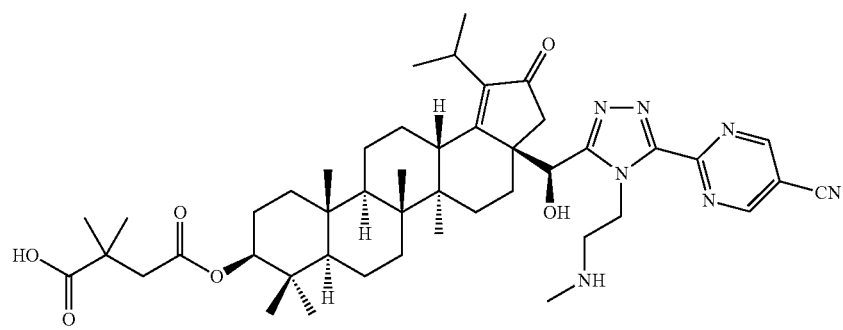
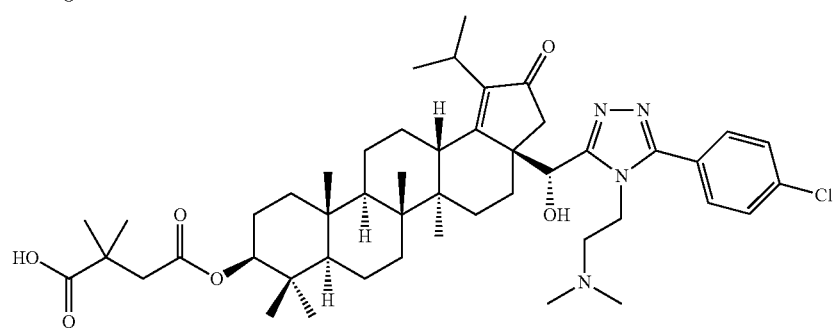
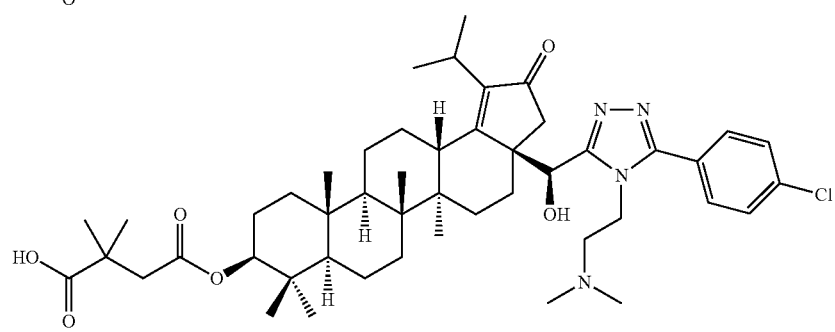

-continued
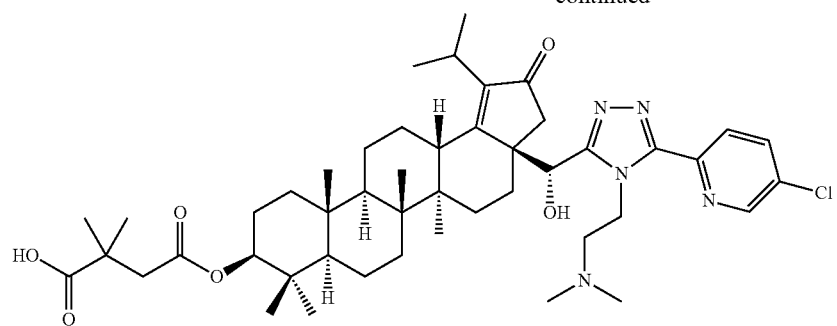
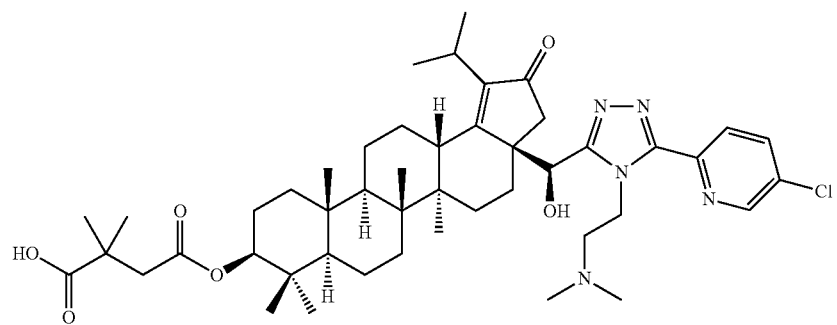
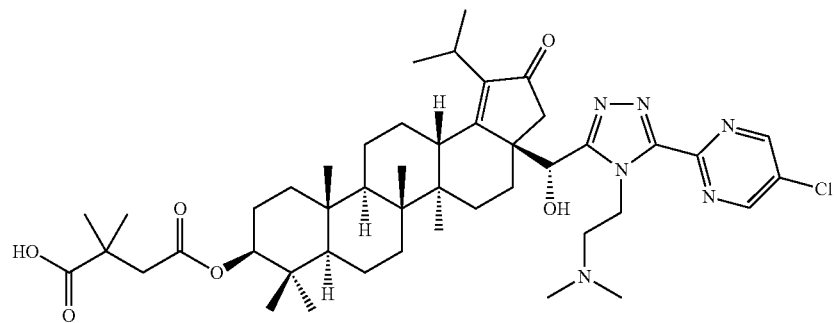
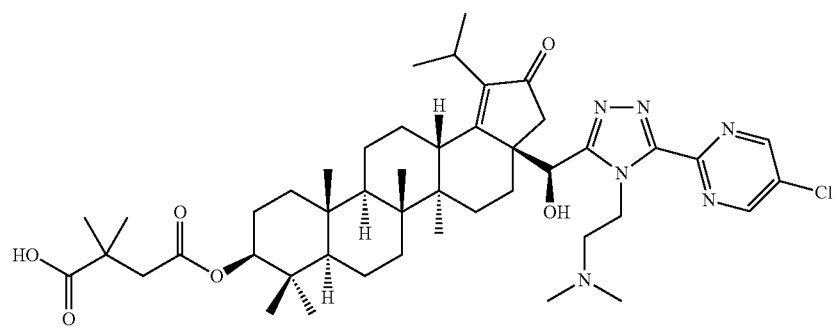
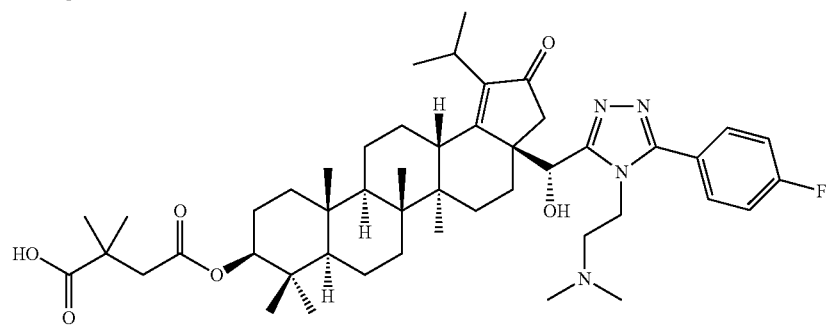

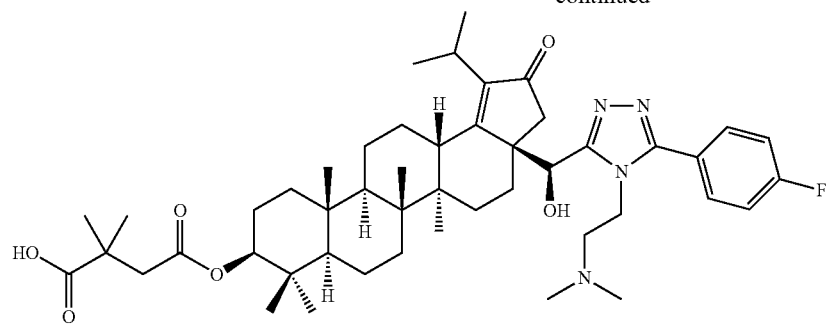
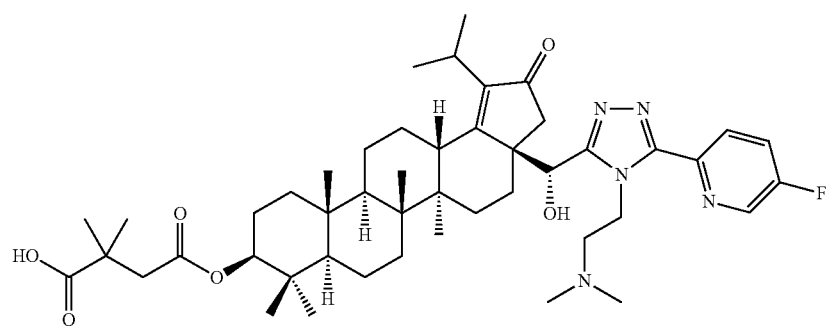
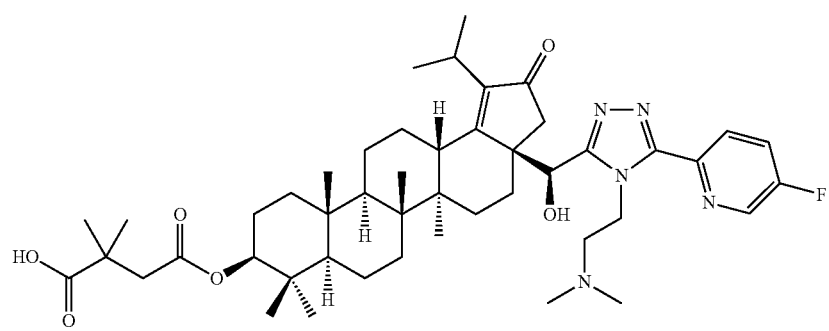
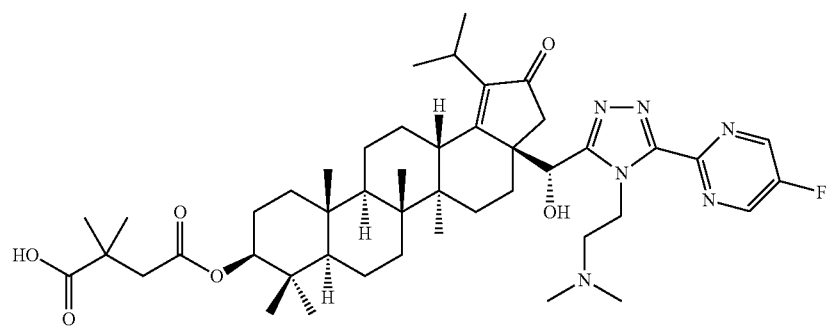
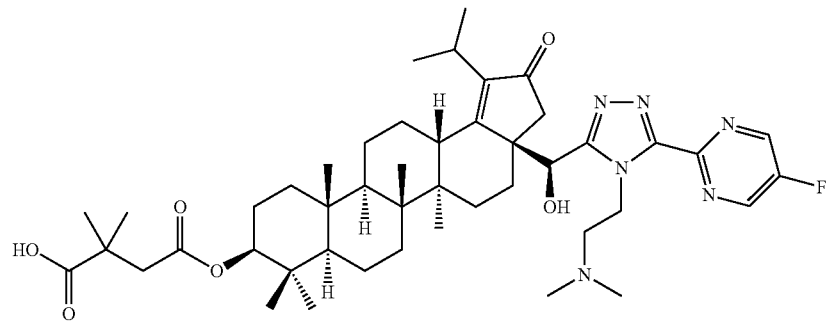

-continued
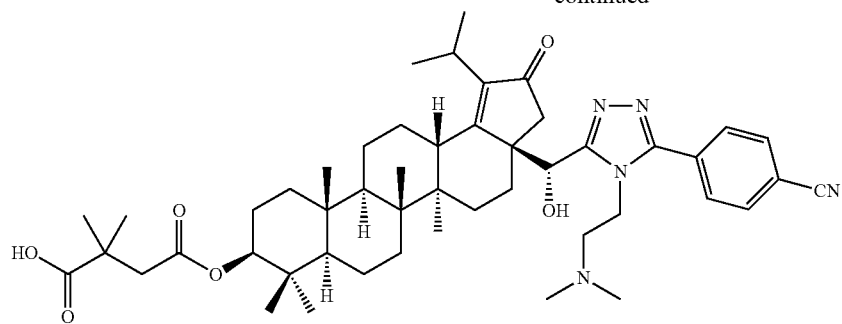
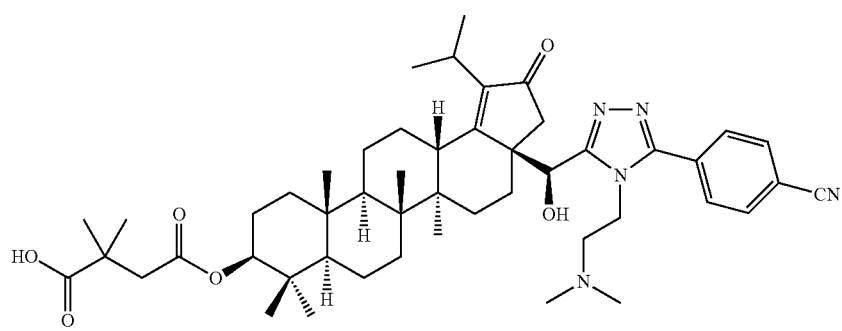
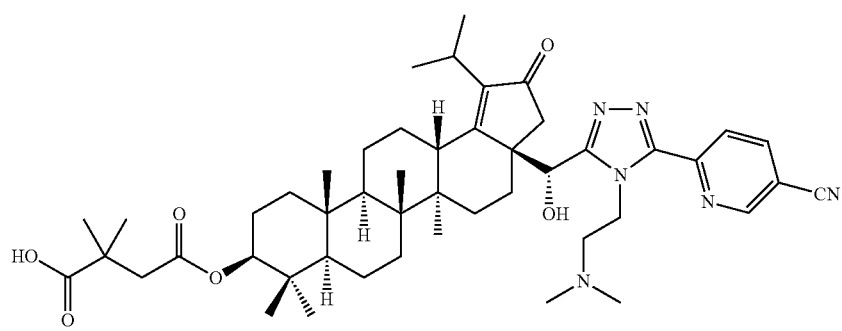
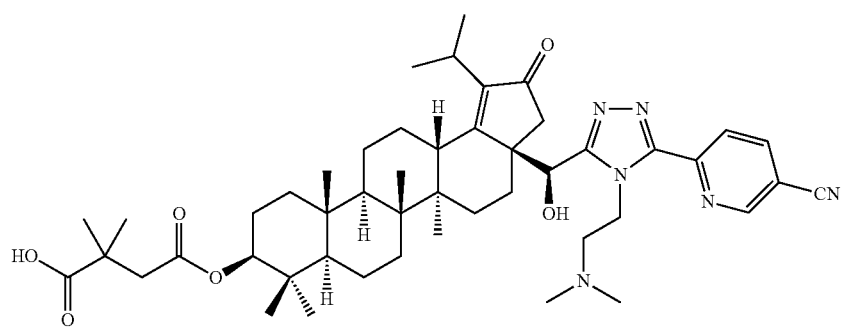
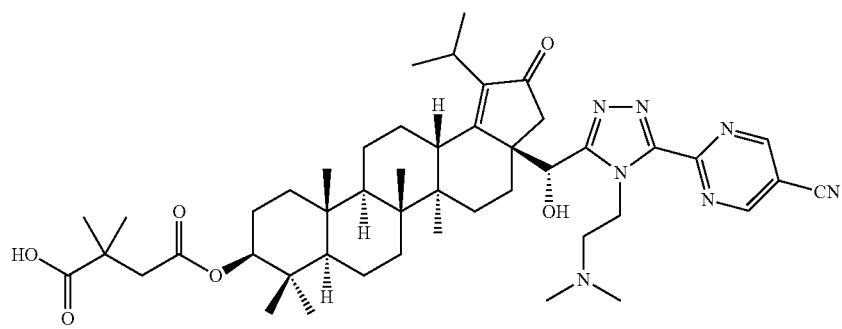

-continued
| 483 | 484 |
|---|---|
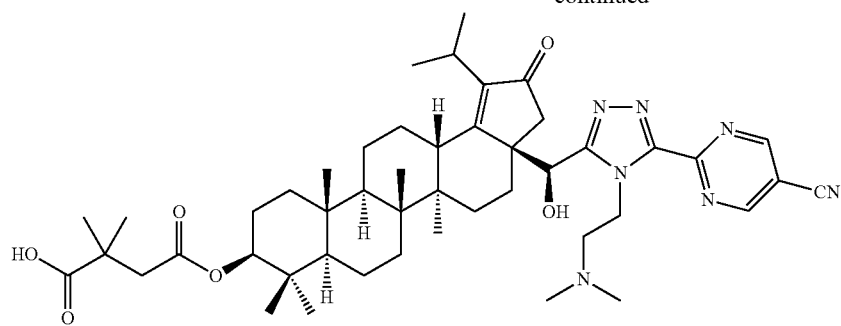
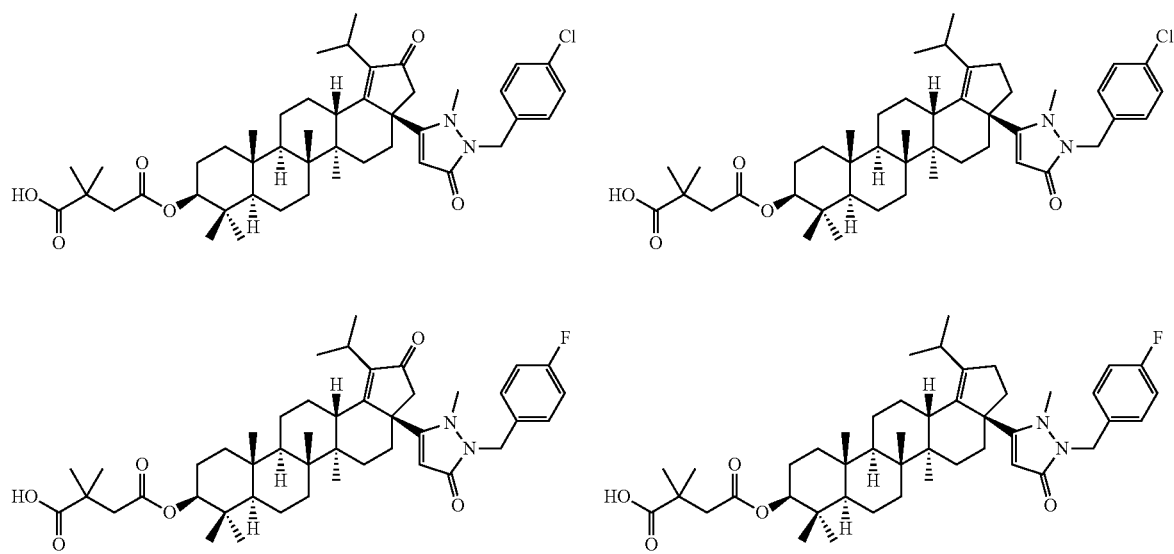
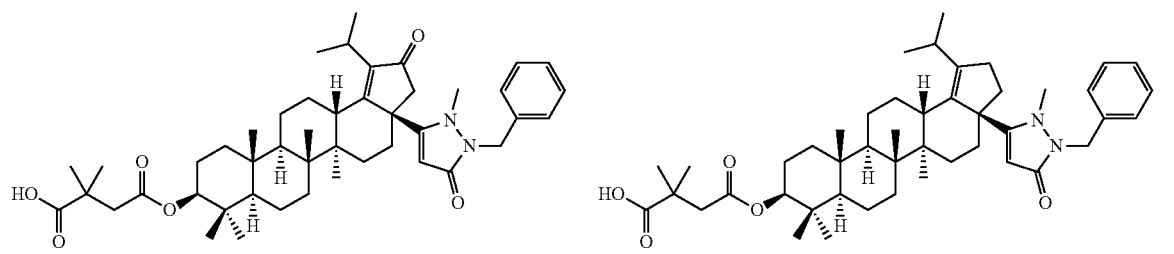
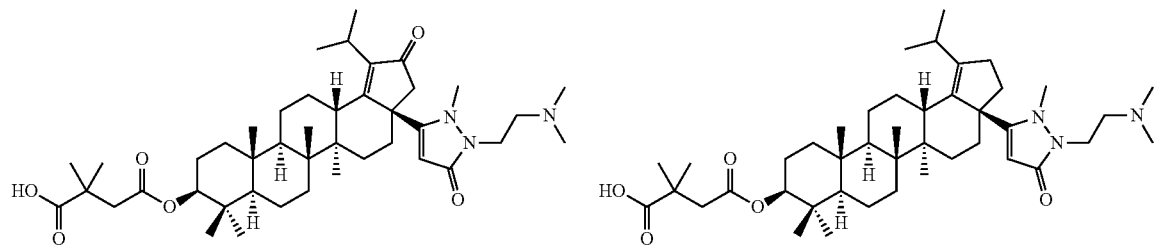
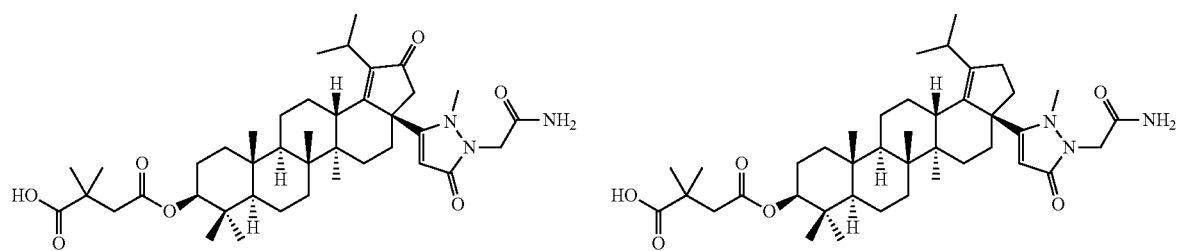

485     486
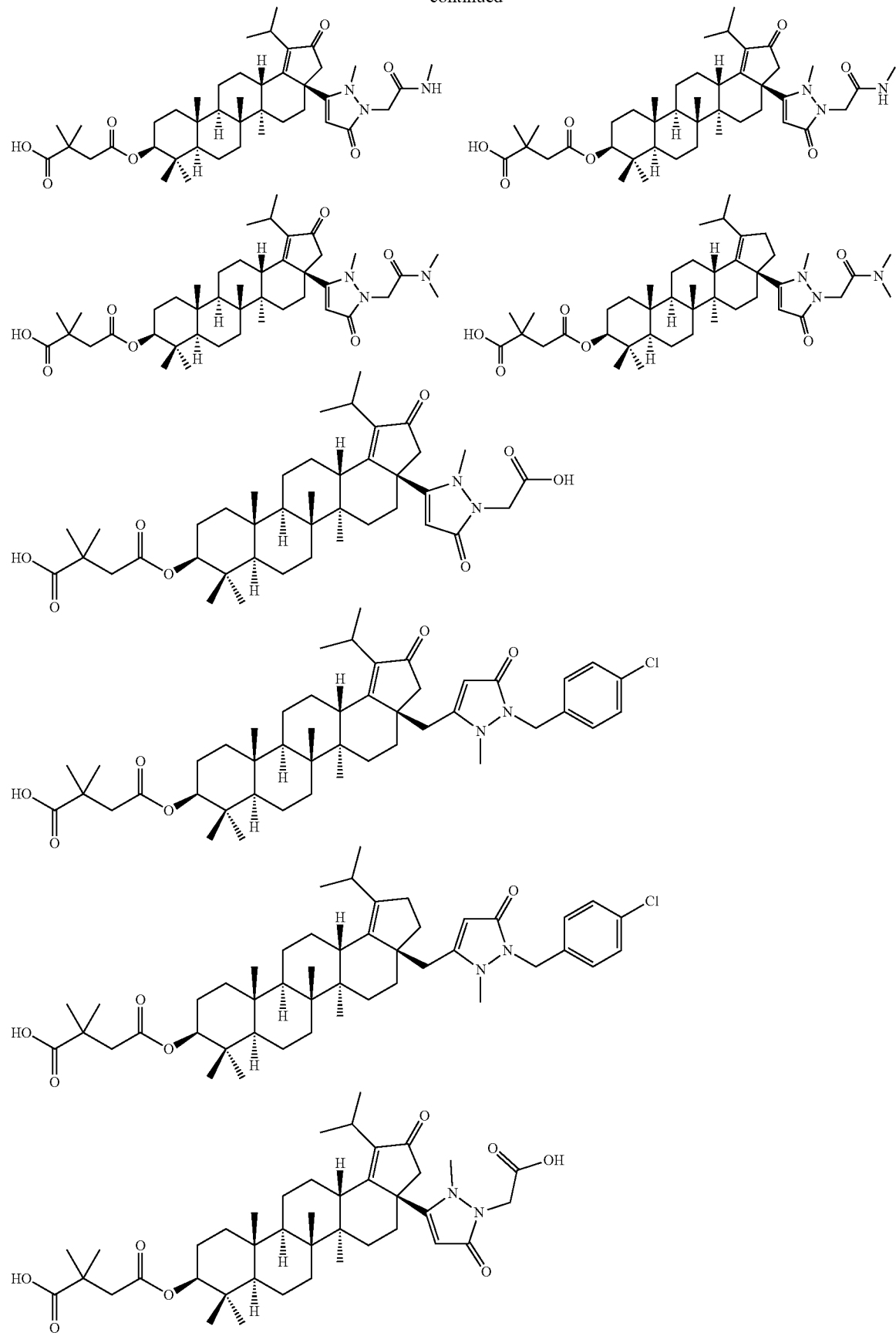
-continued

-continued
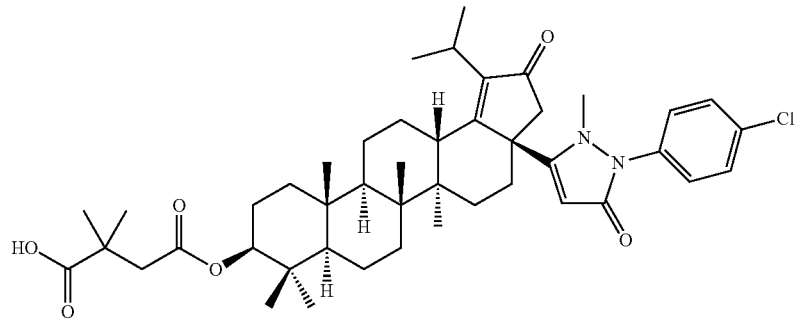
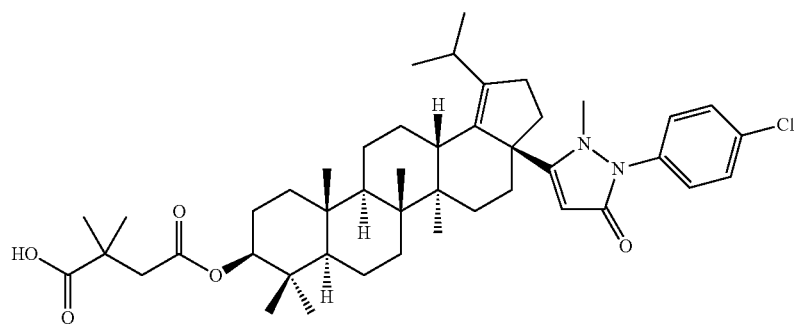
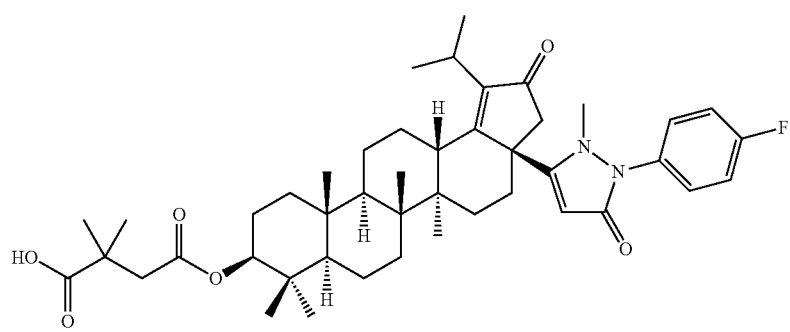
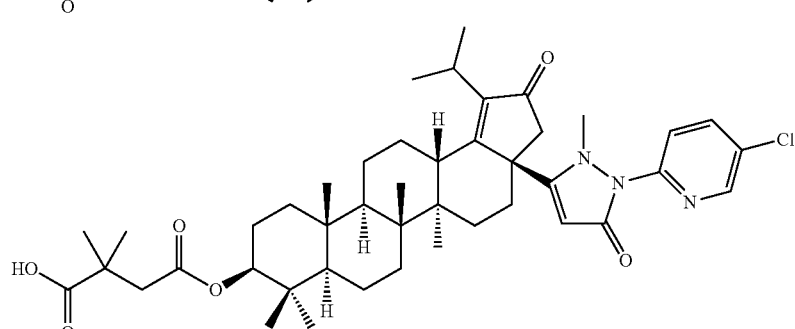
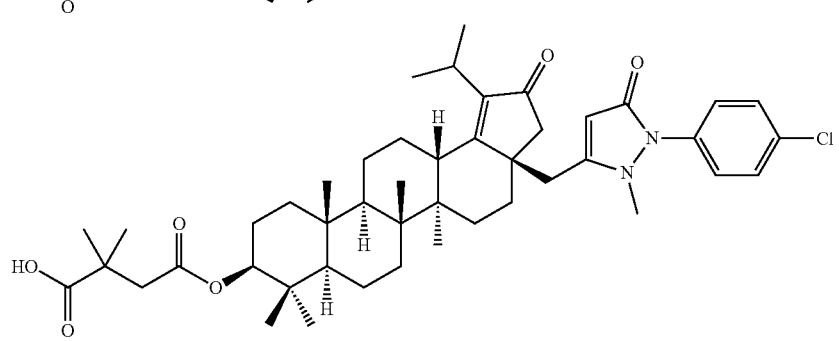

-continued
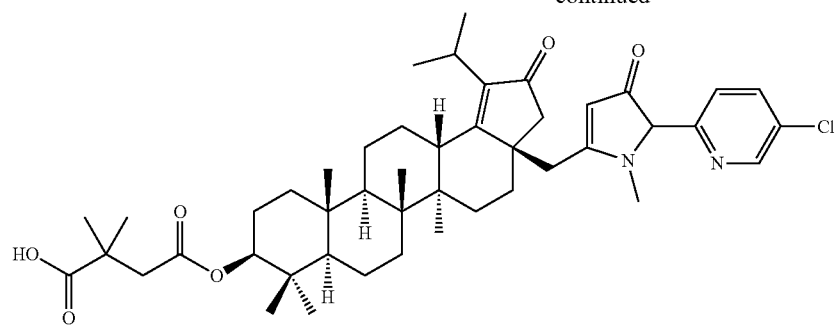
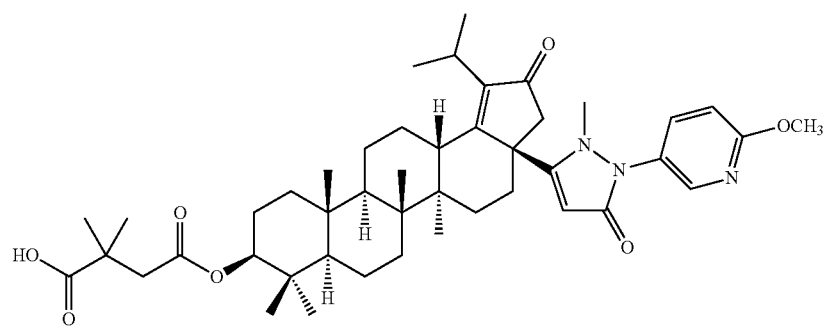
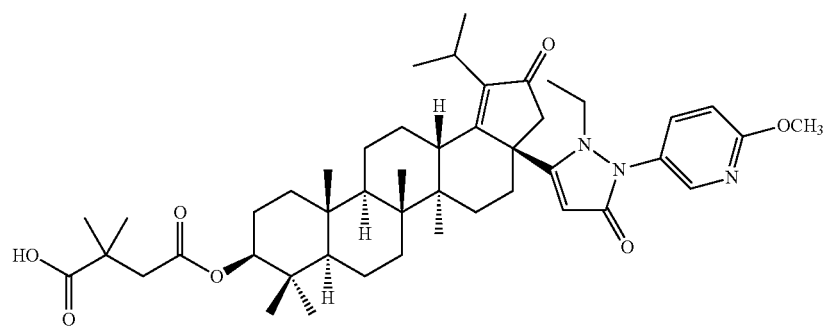
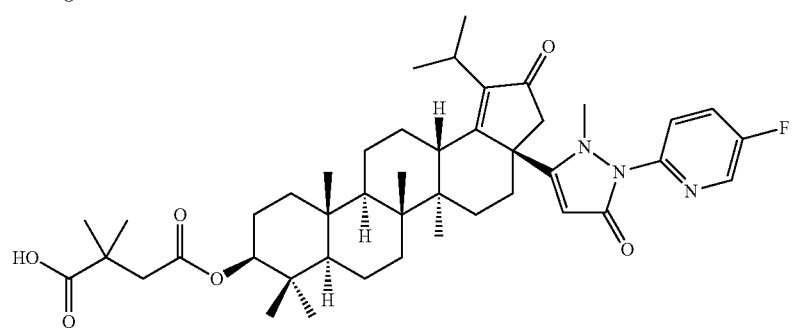
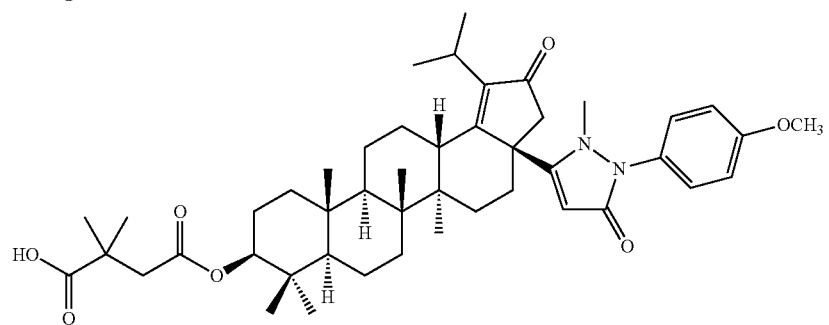

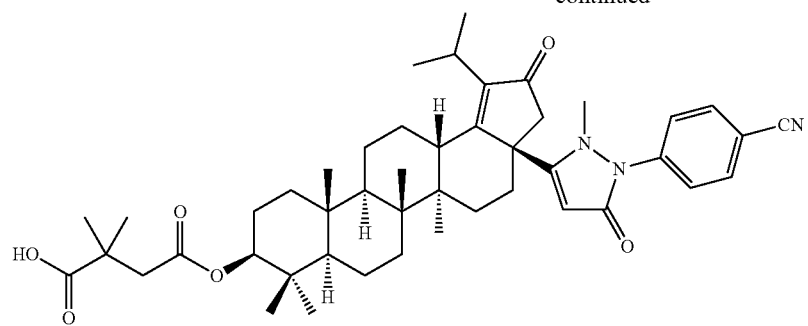
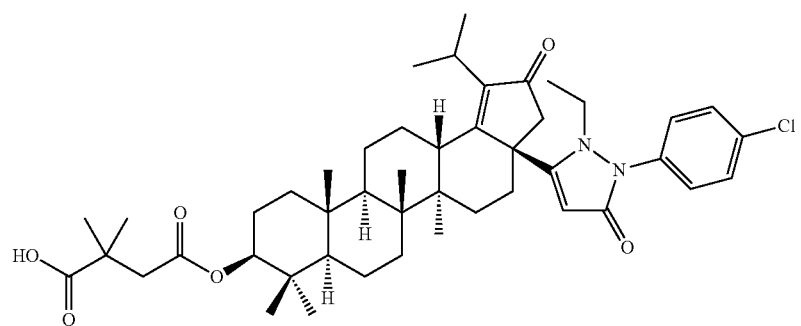
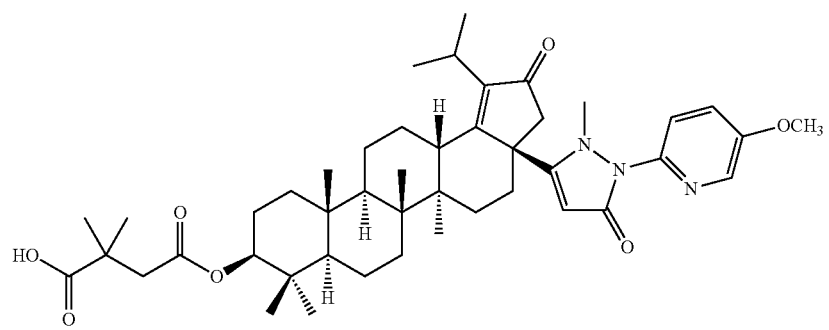
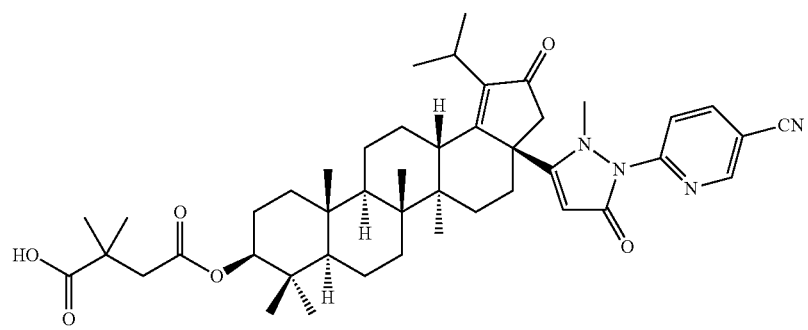
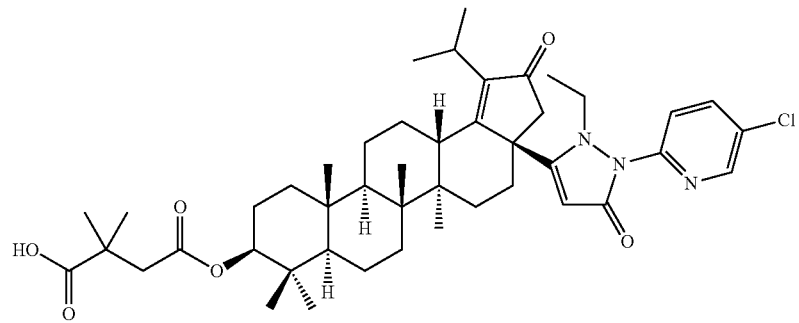

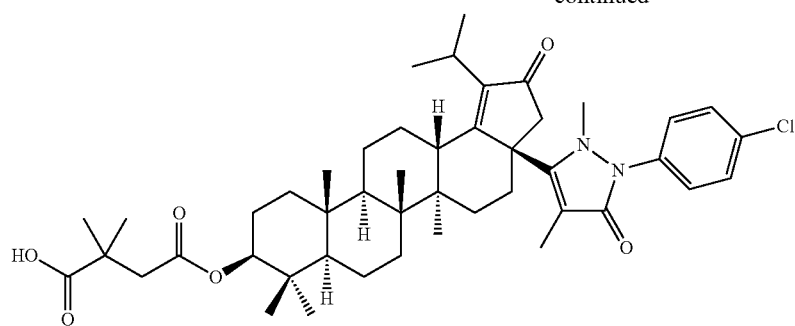
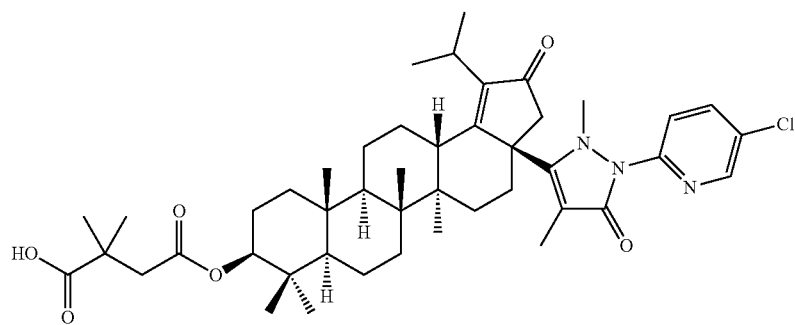
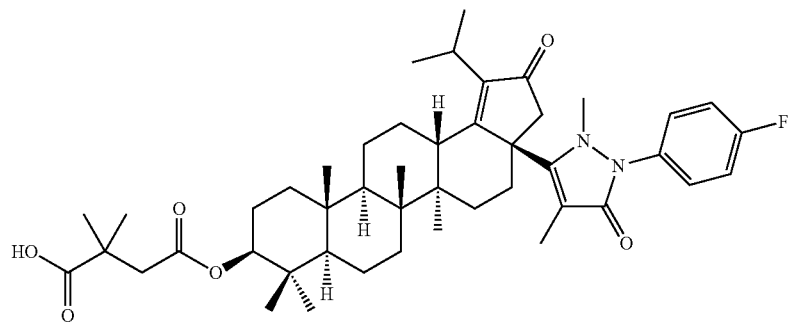
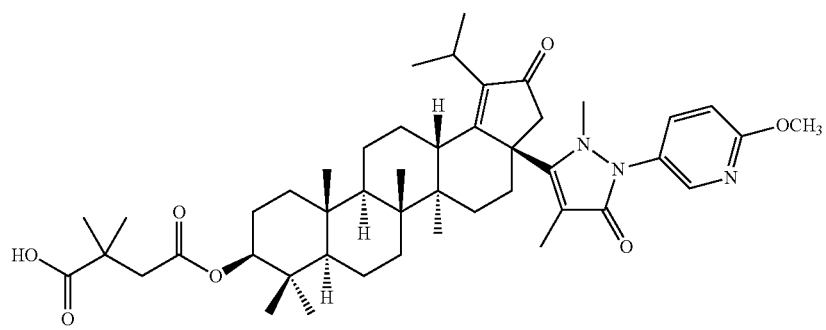
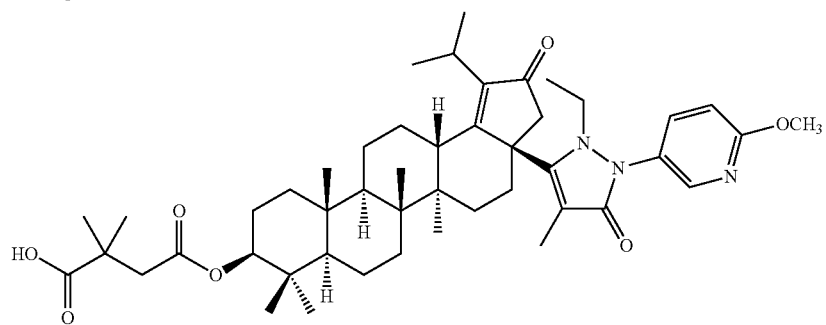

-continued
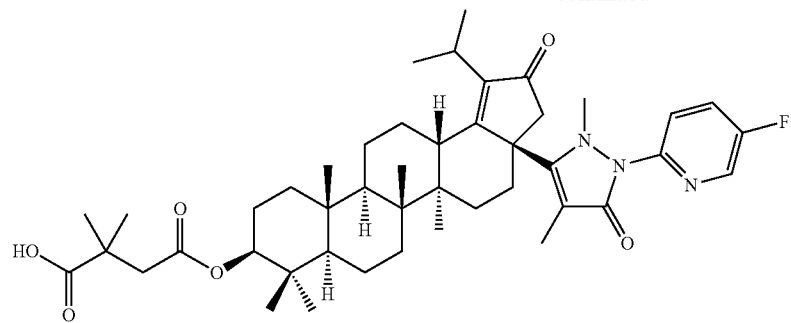
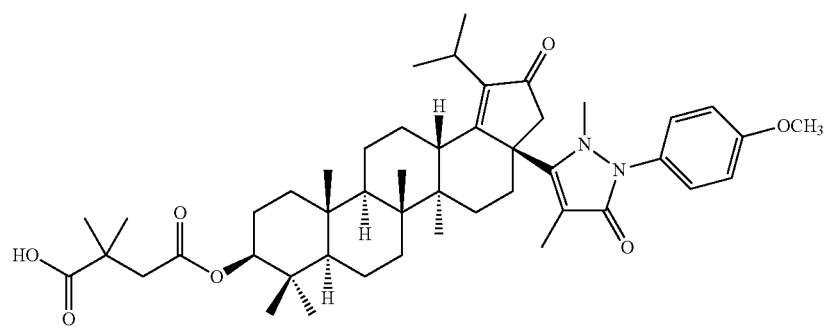
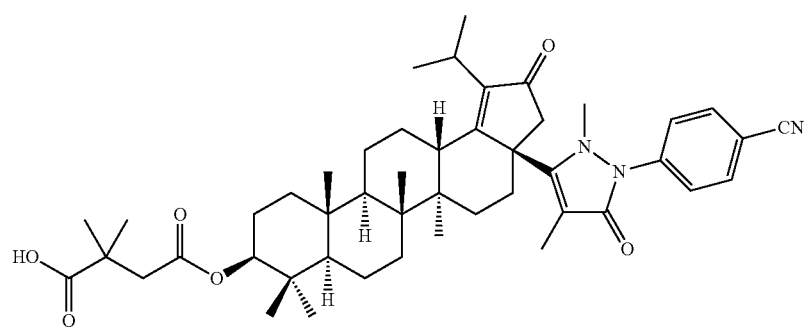
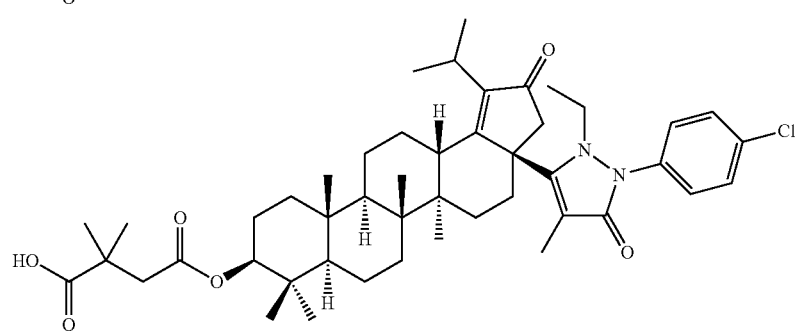
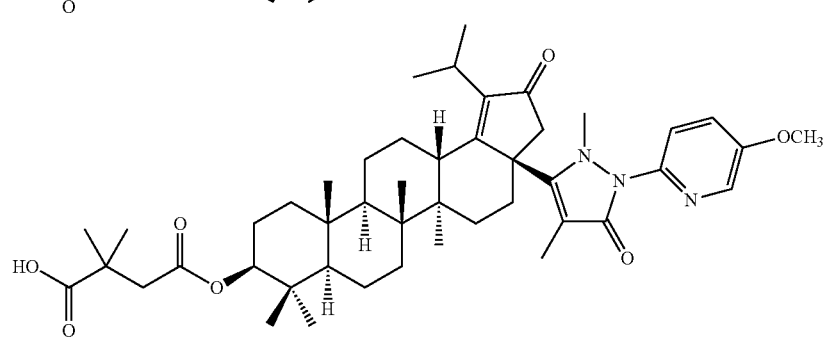

-continued
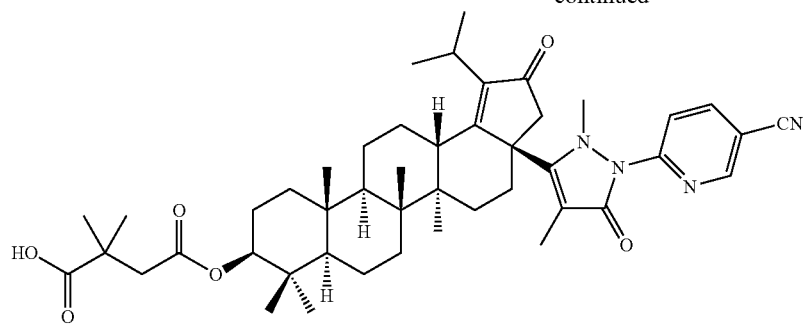
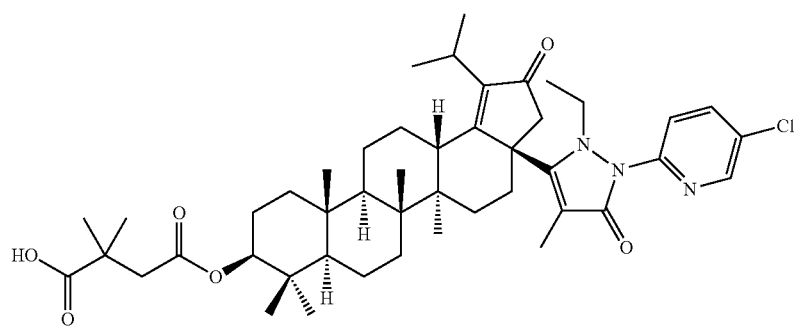
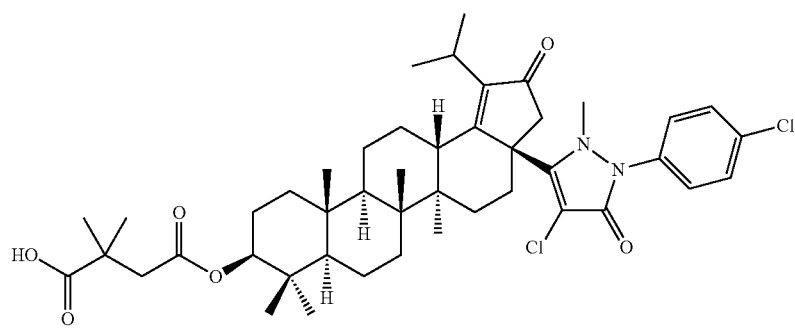
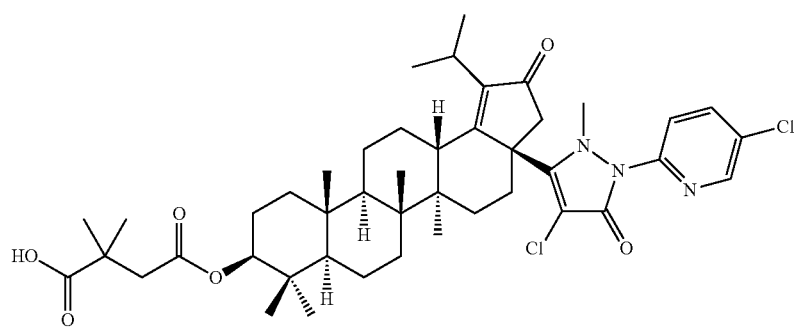
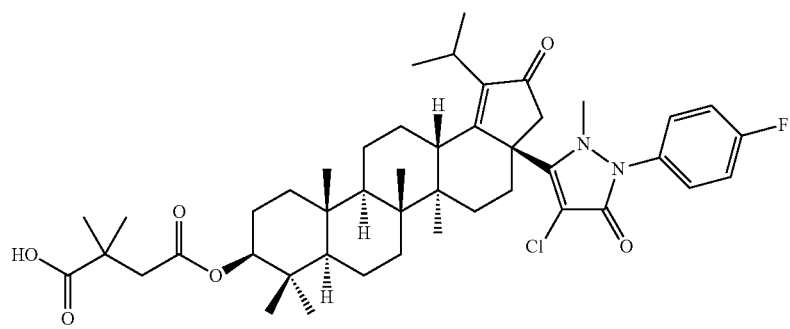

-continued
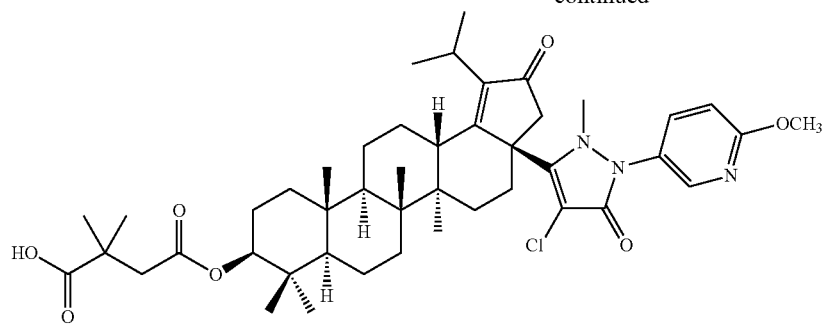
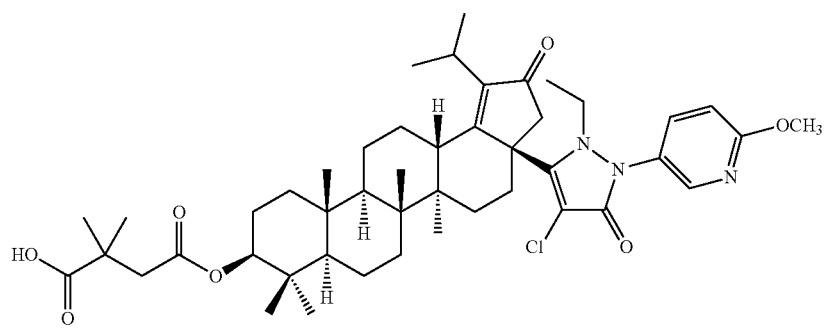
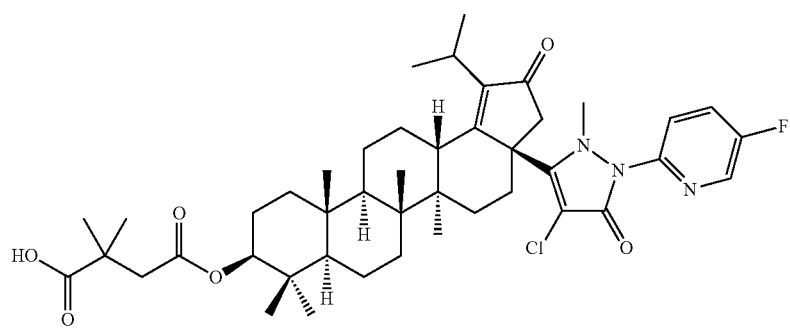
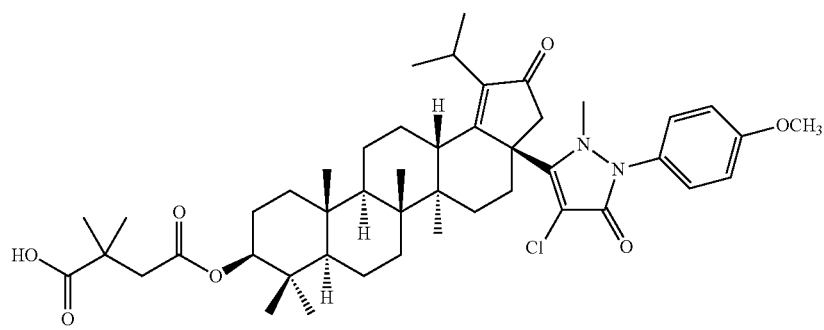
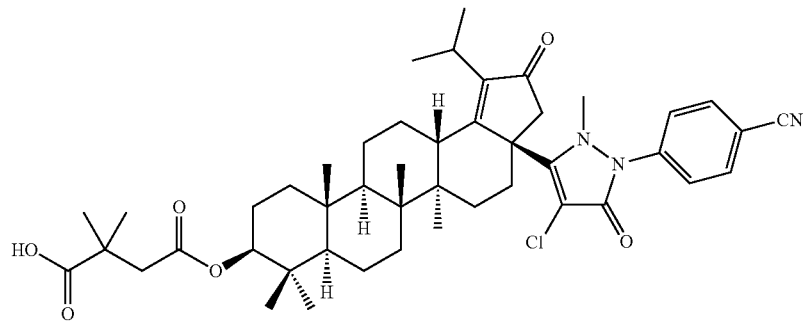

-continued
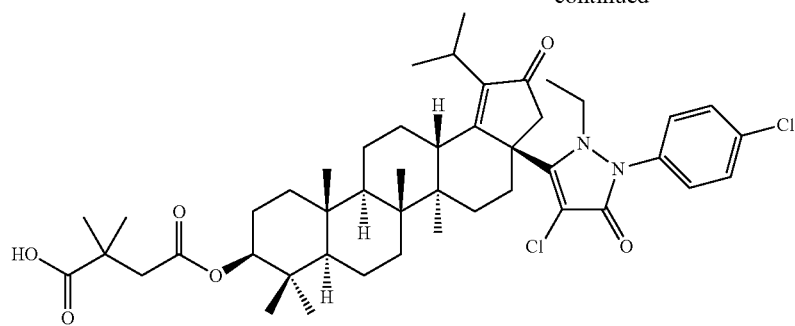
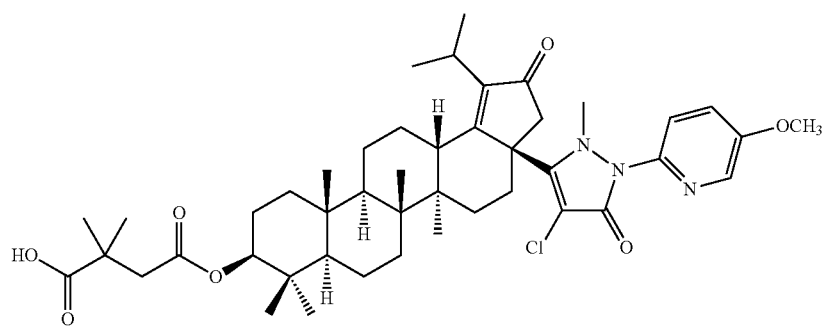
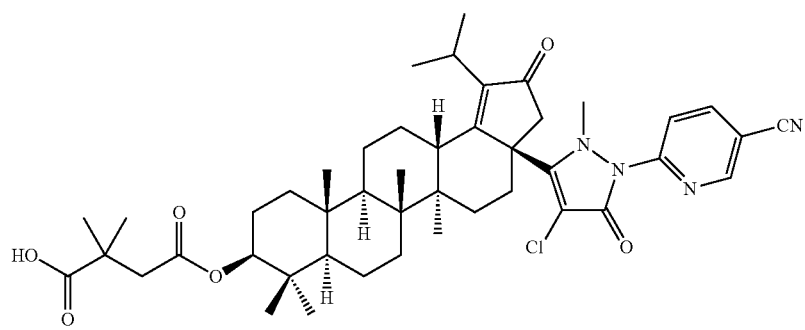
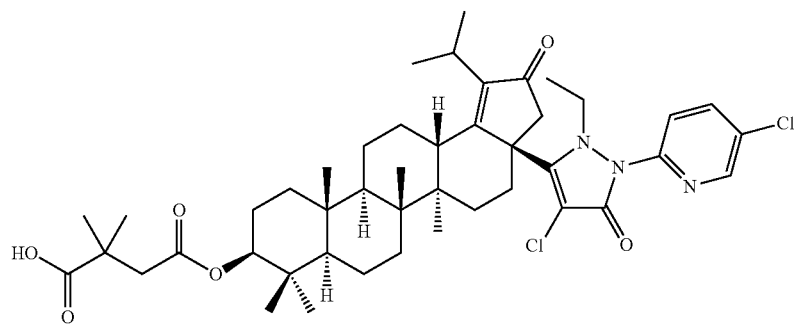
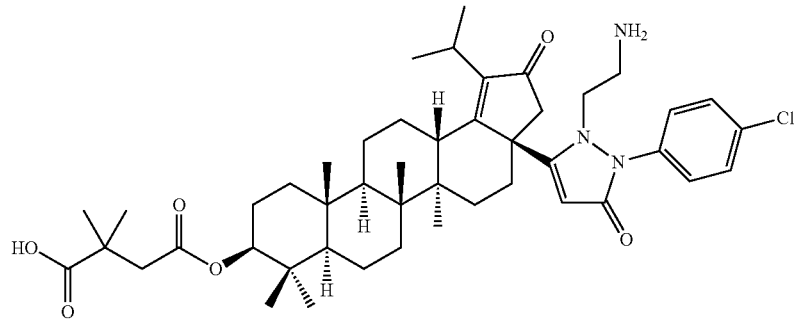

-continued
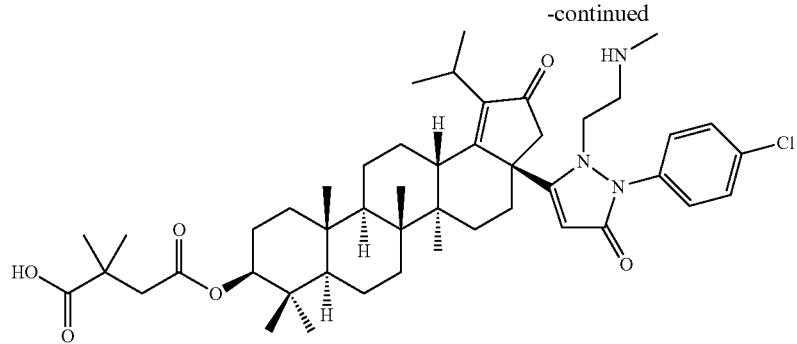
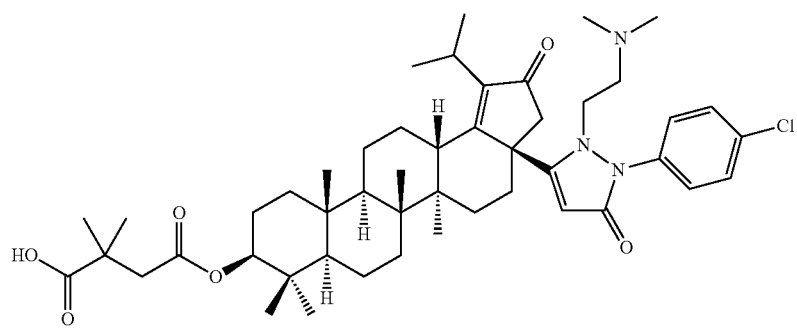
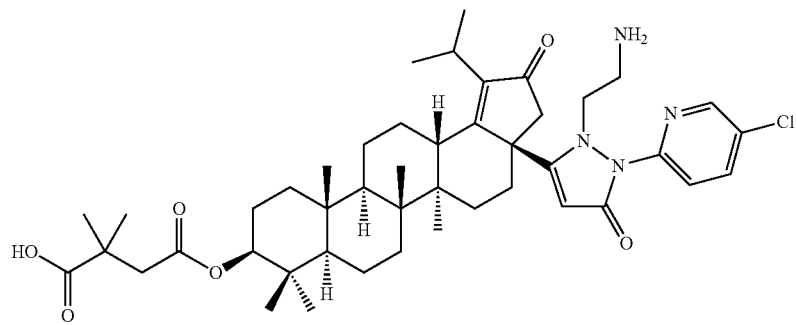
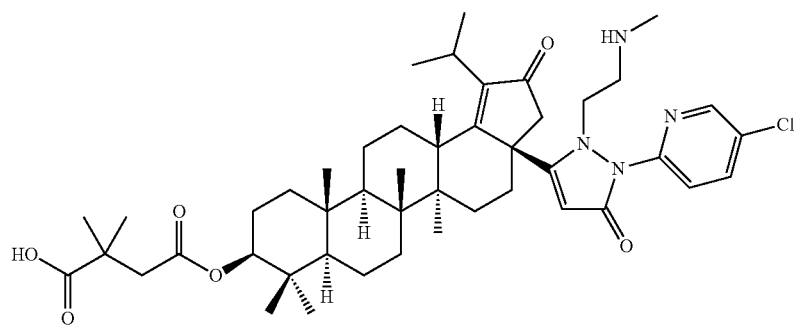
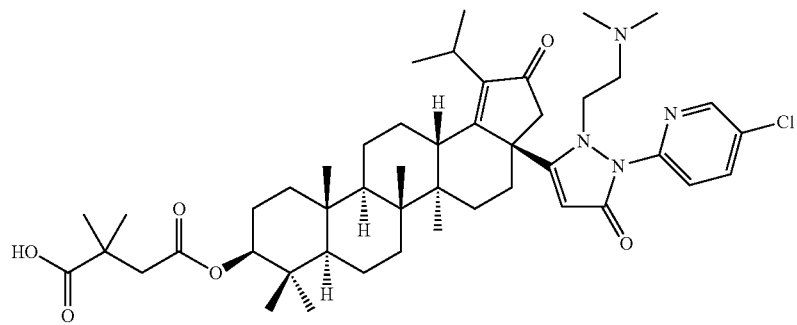

-continued
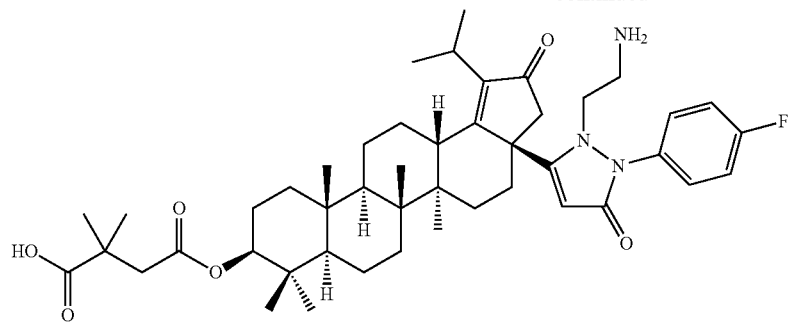
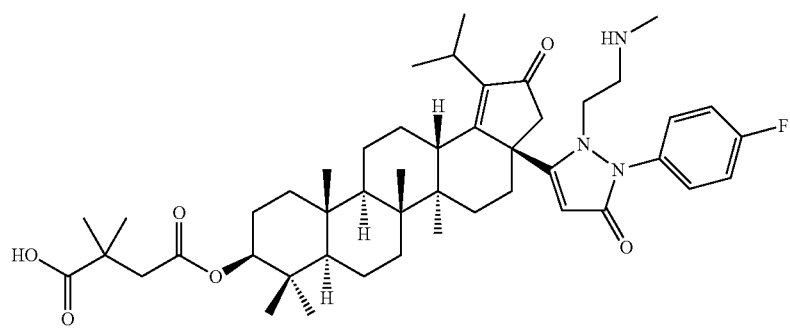
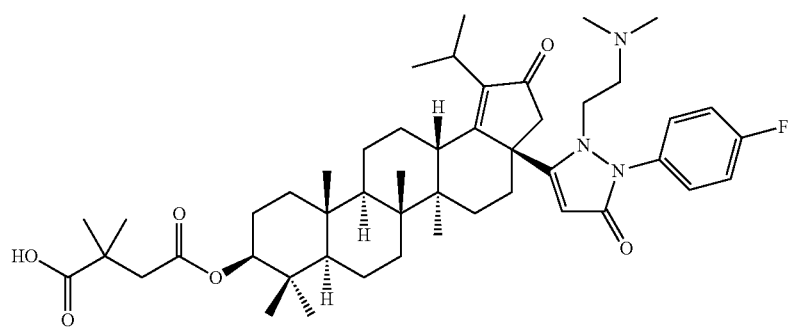
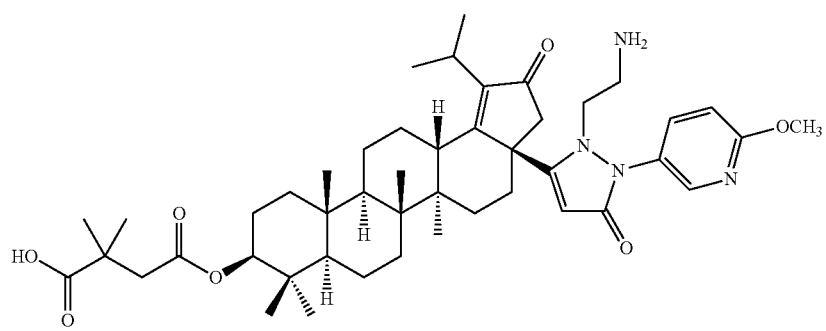
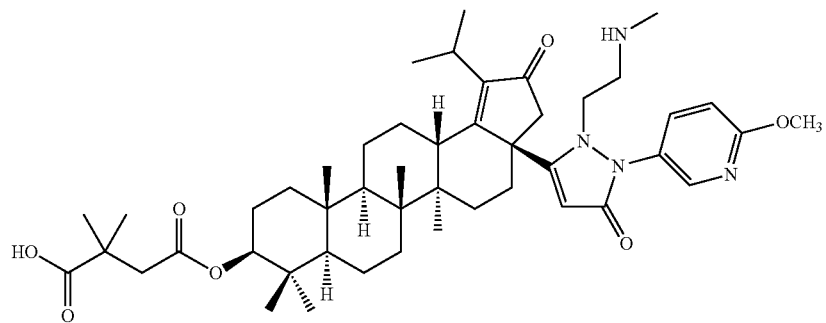

-continued
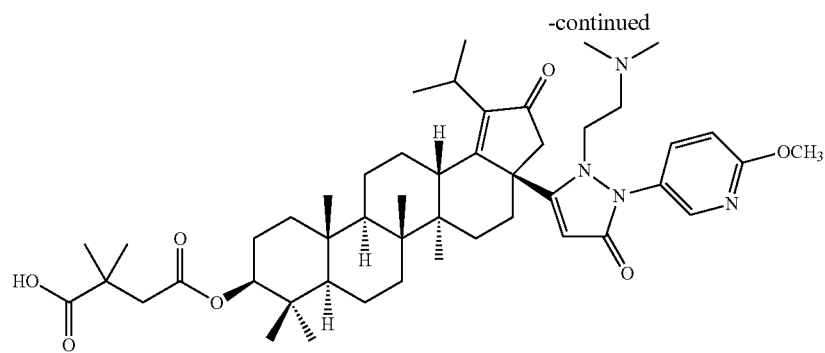
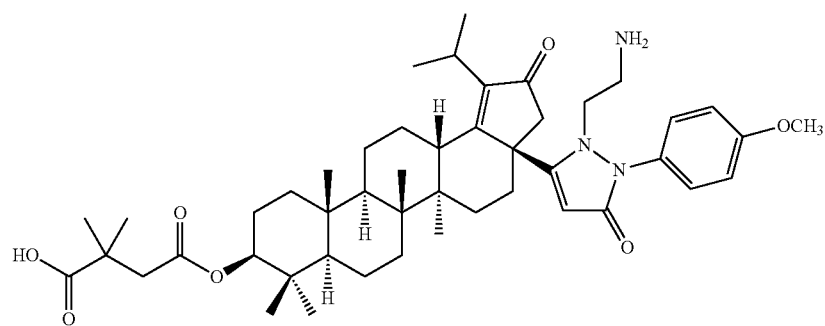
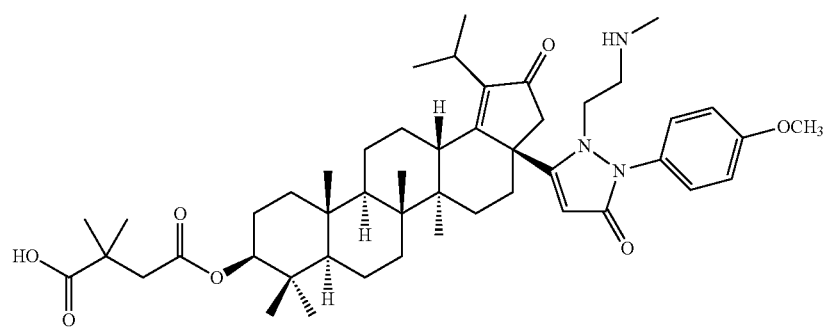
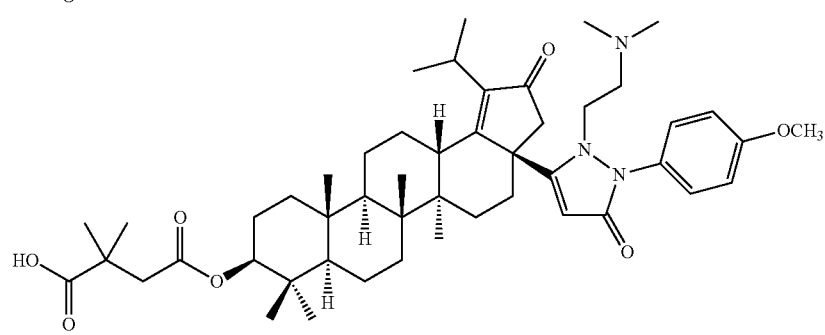
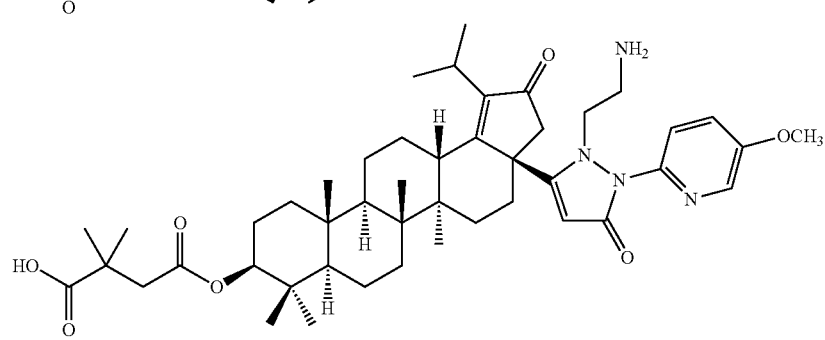

-continued
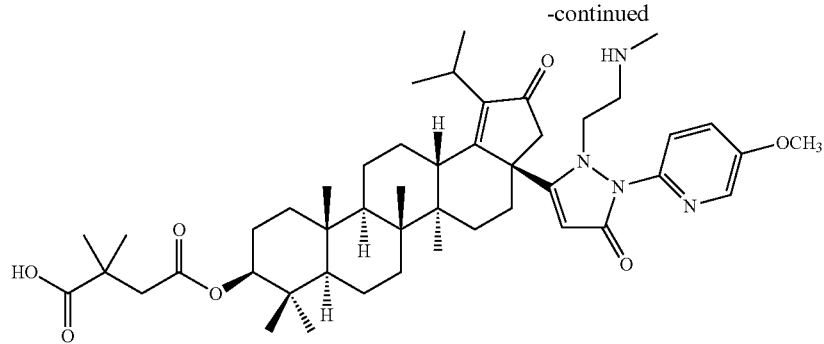
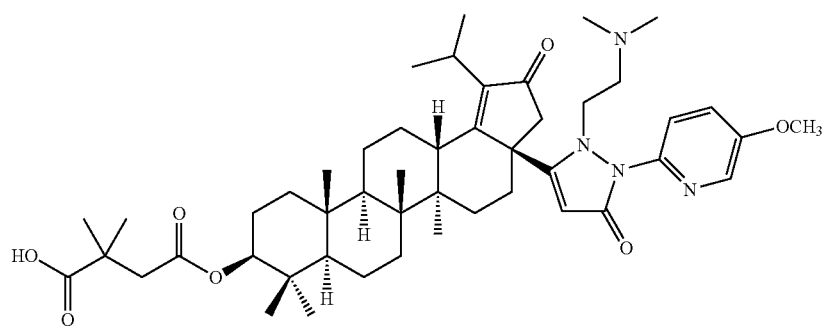
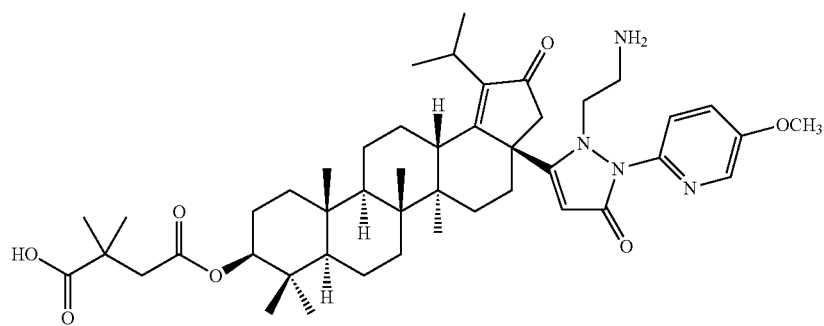
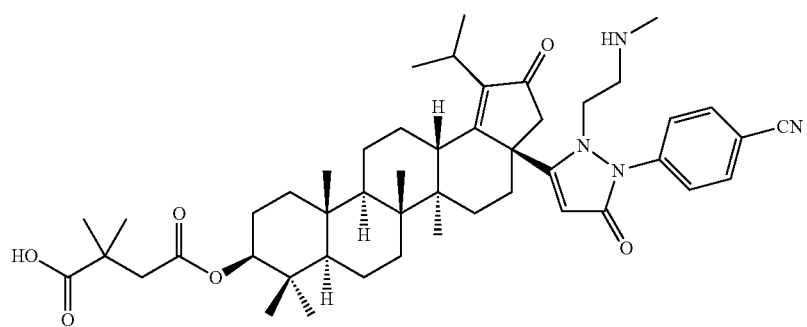
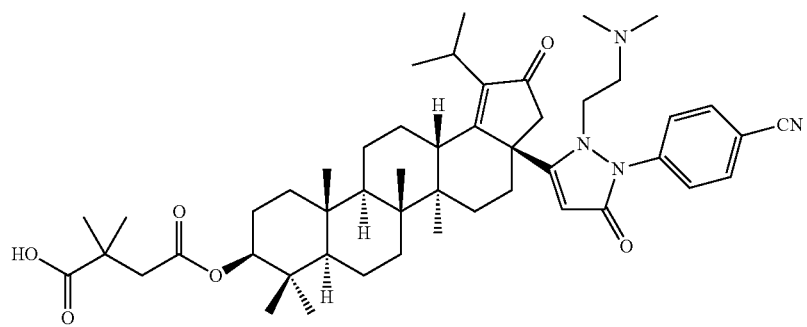

-continued
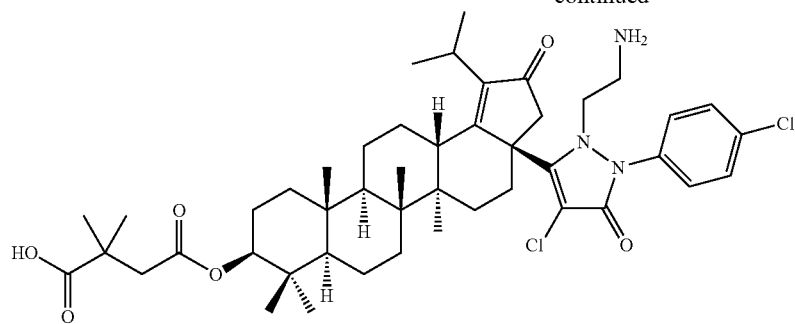
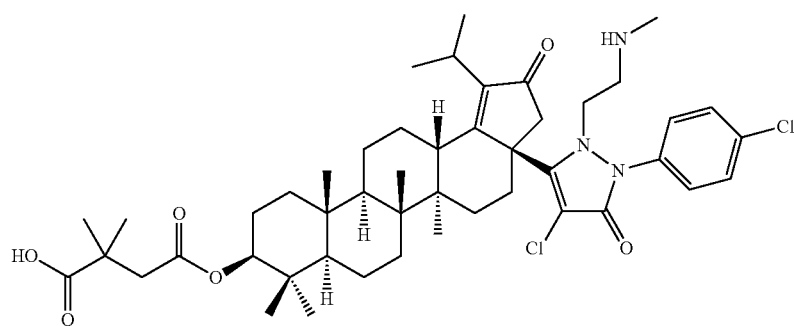
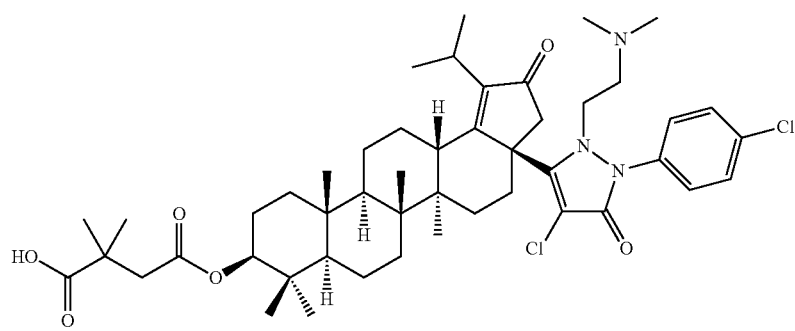
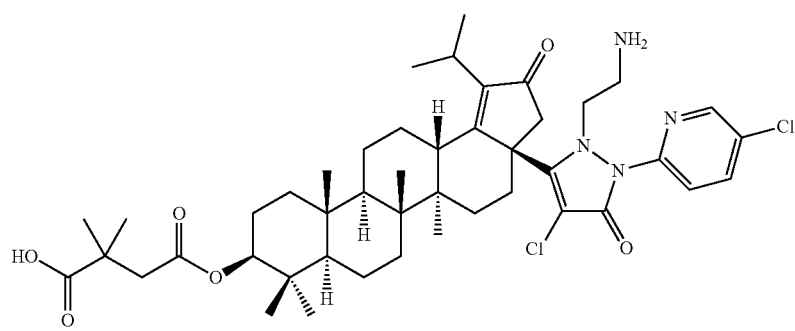
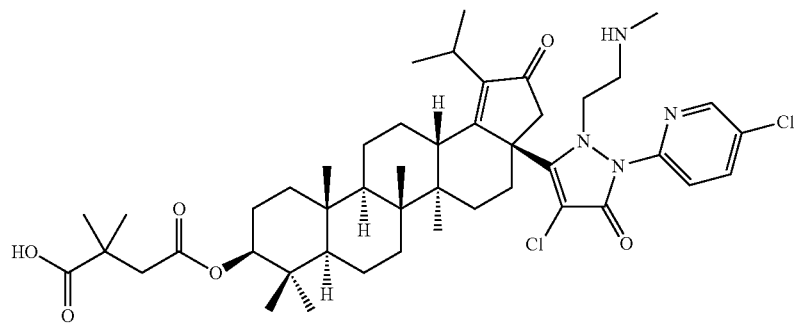

-continued
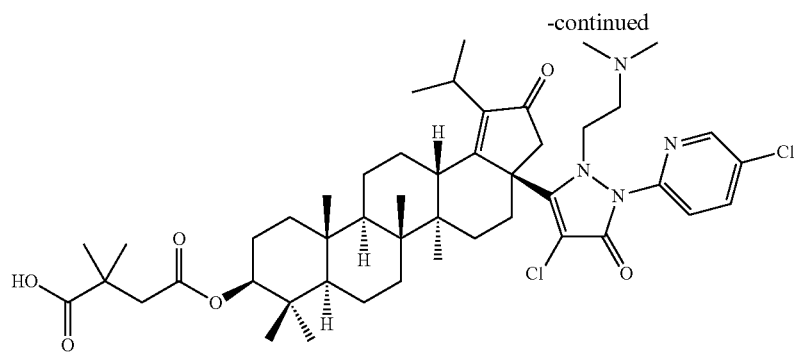
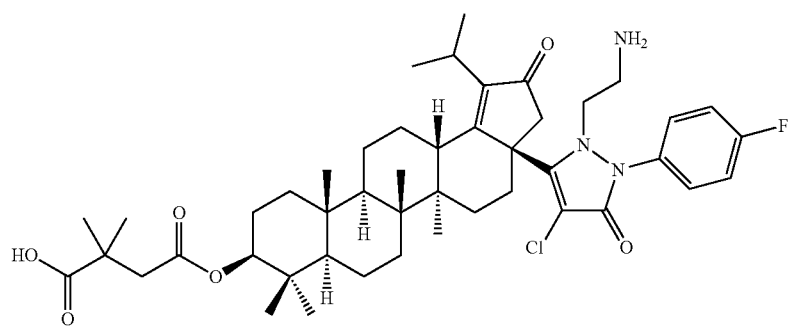
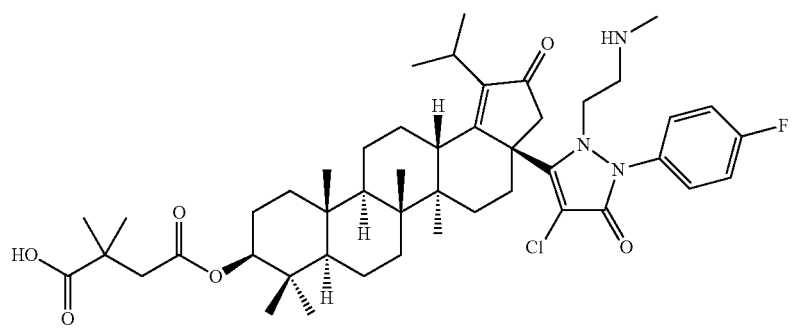
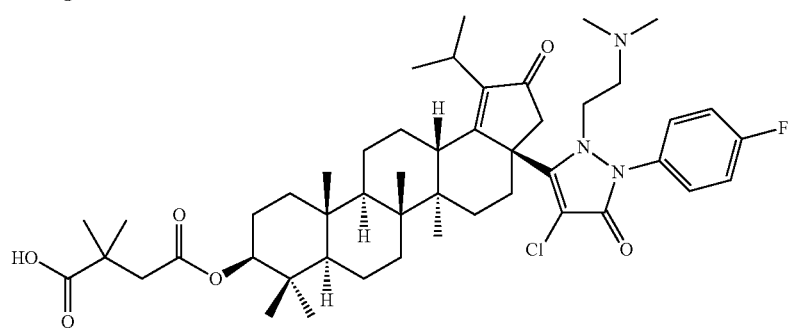
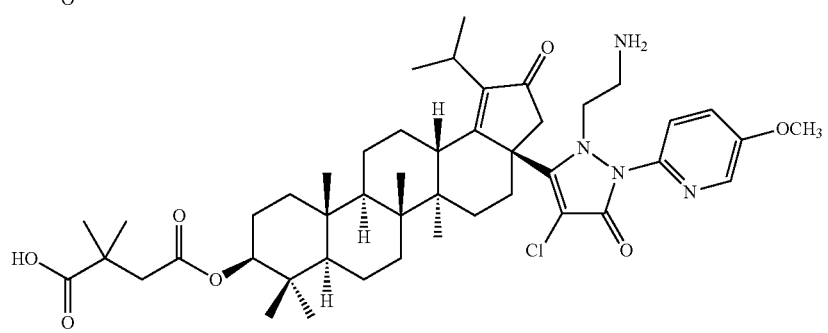

-continued
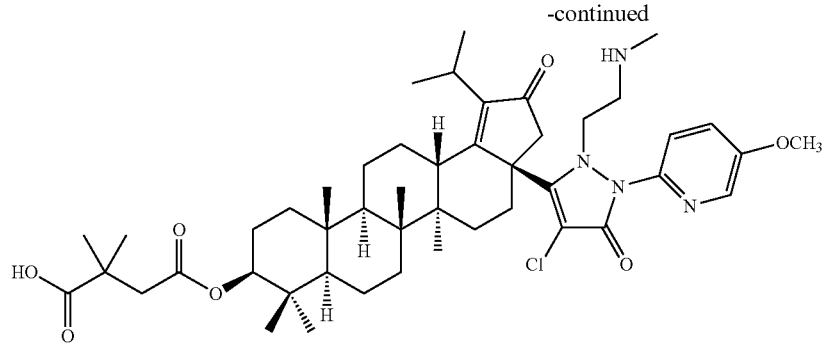
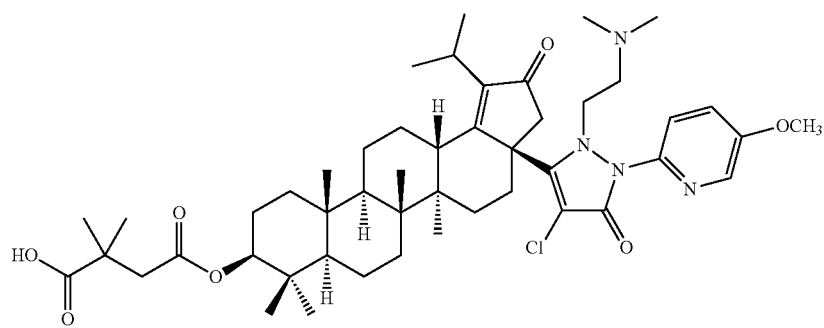
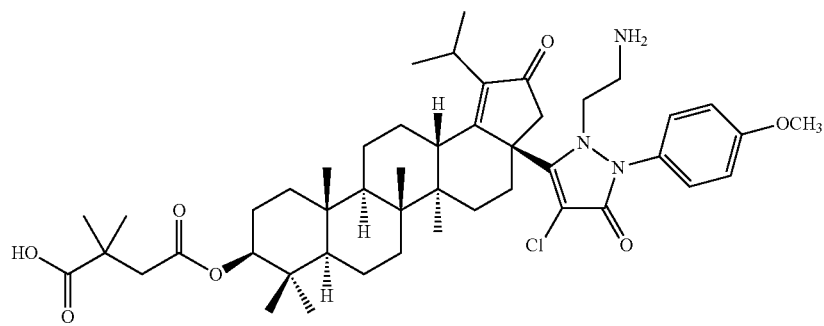
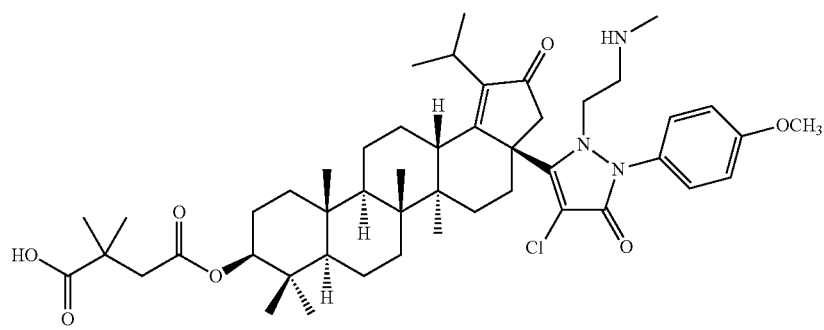
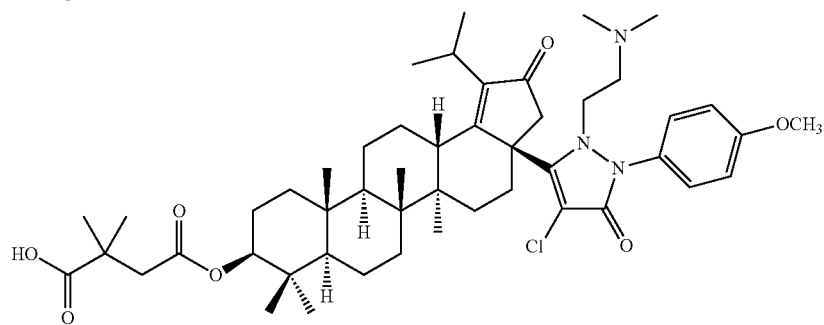

-continued
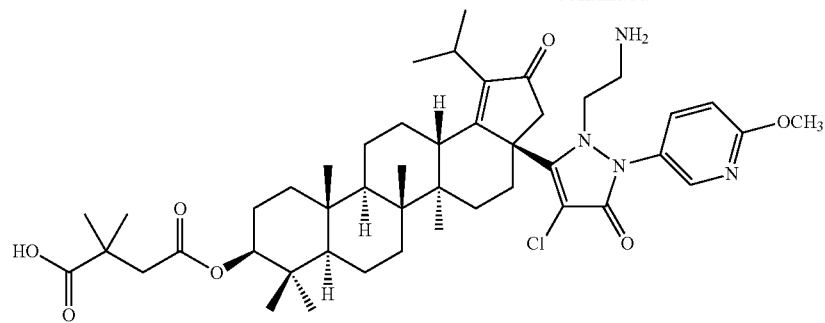
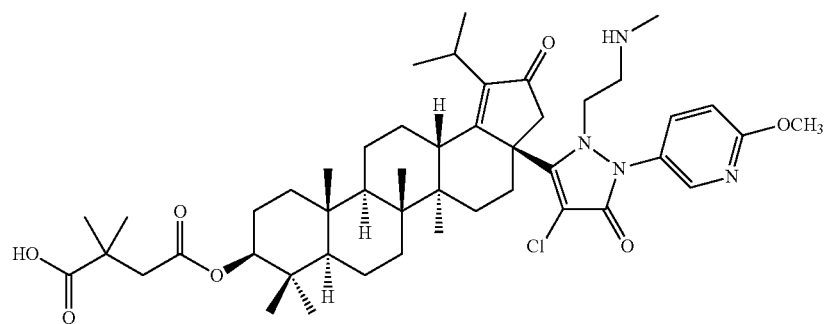
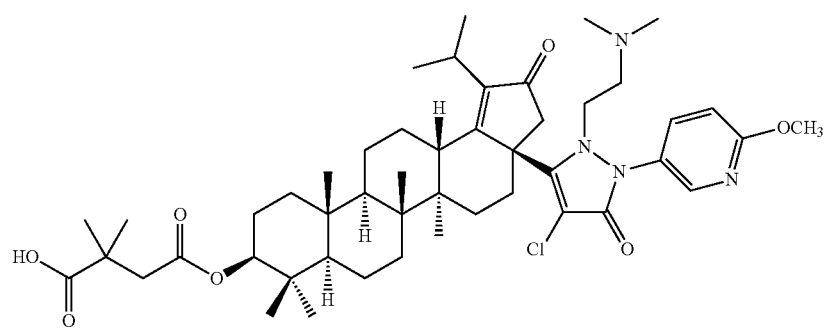
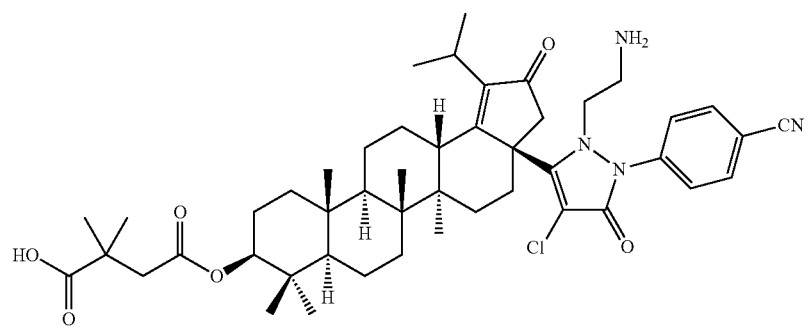
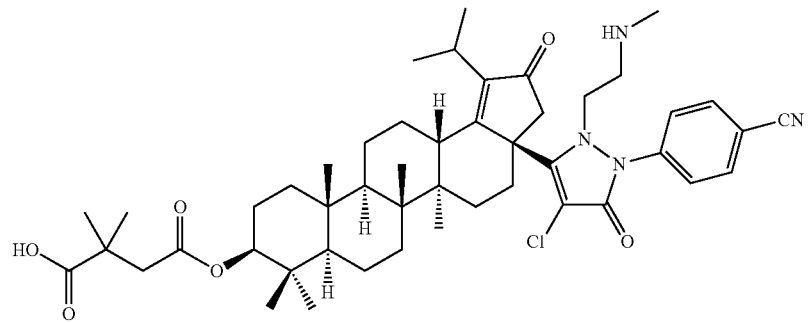

-continued
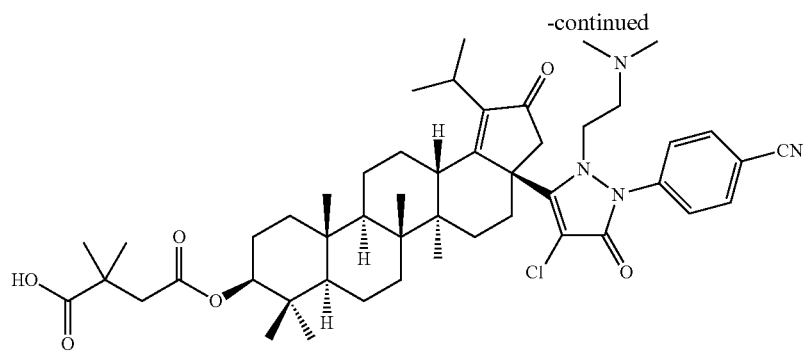
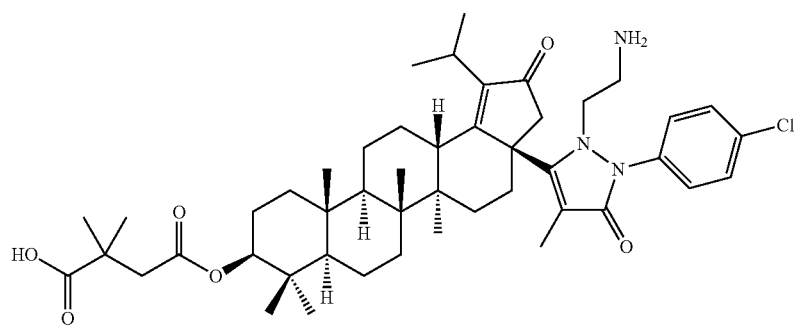
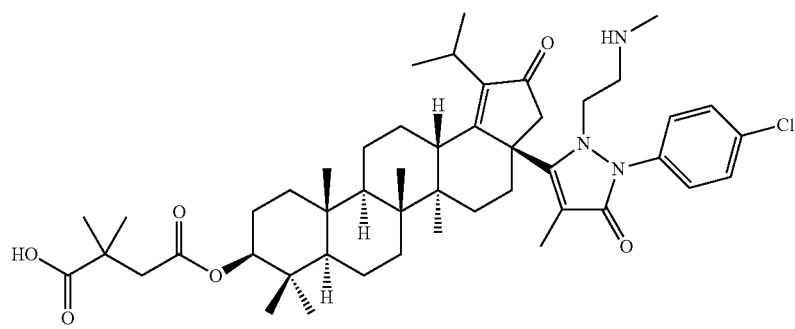
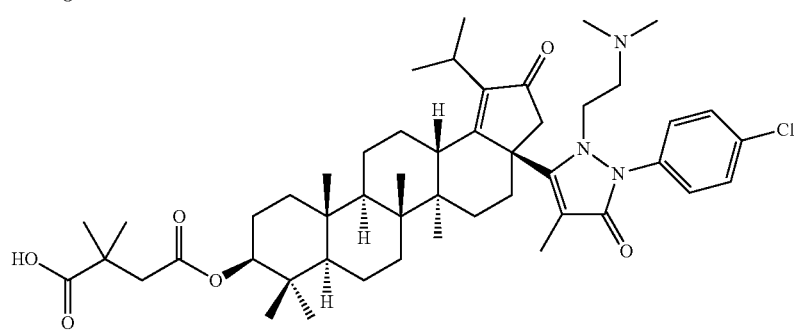
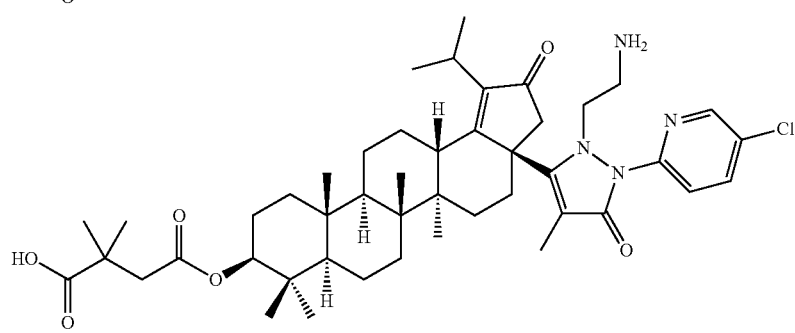

-continued
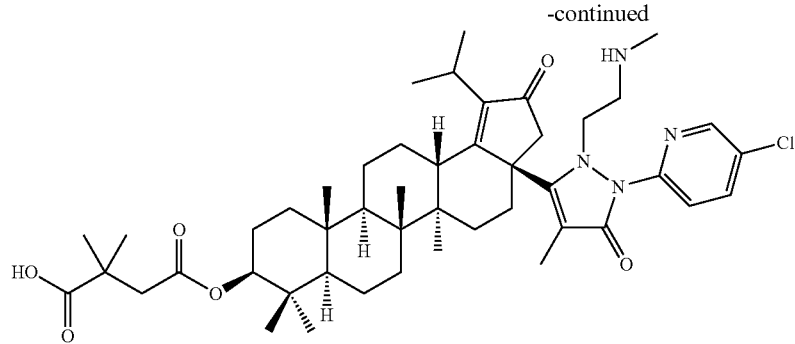
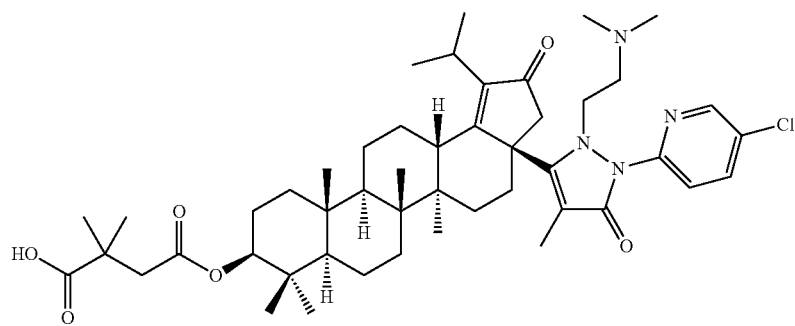
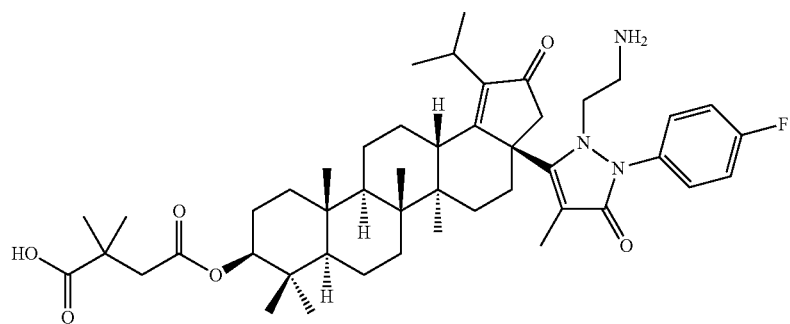
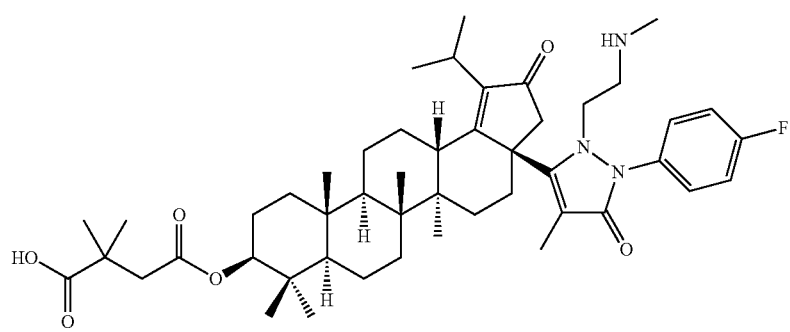
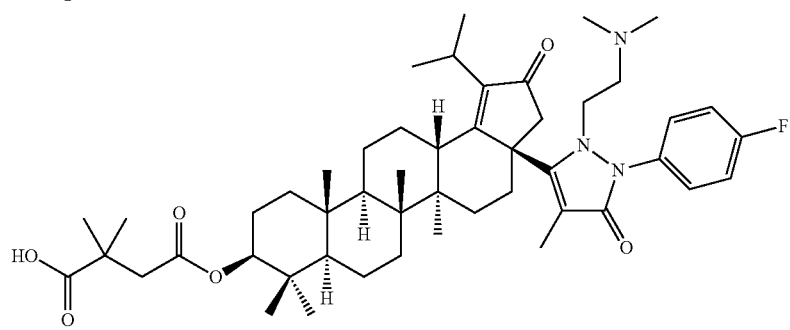

-continued
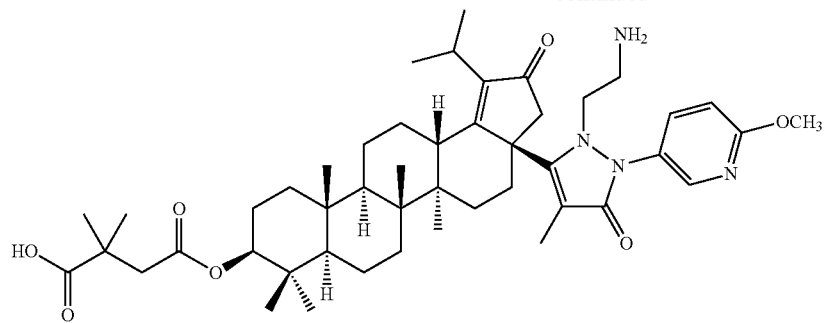
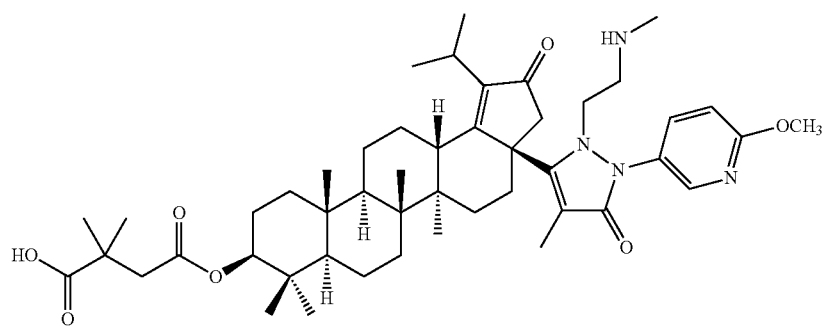
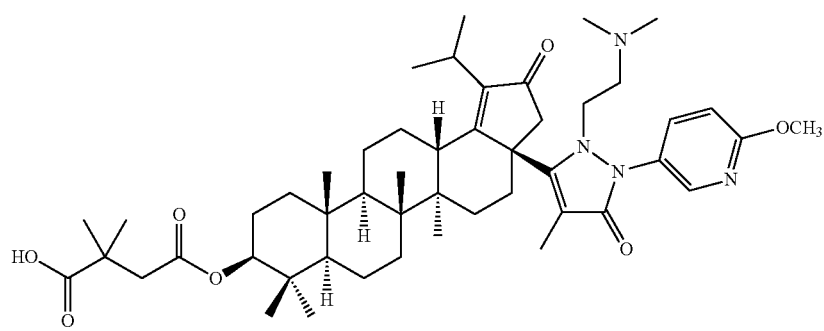
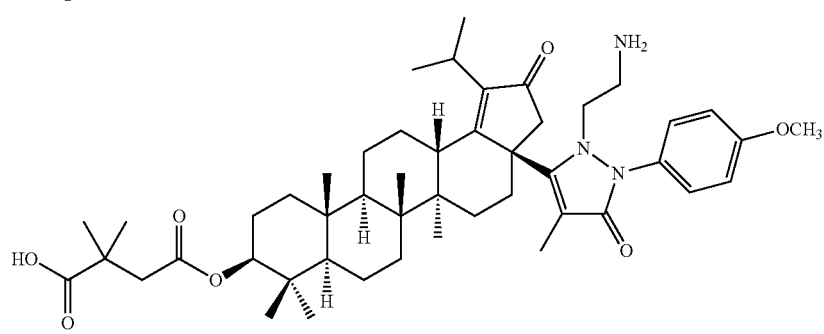
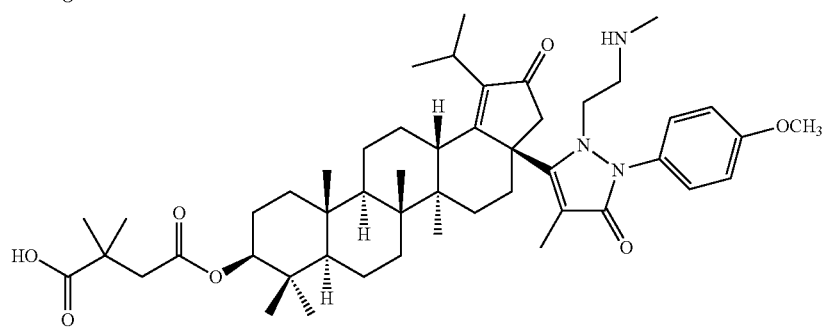

-continued
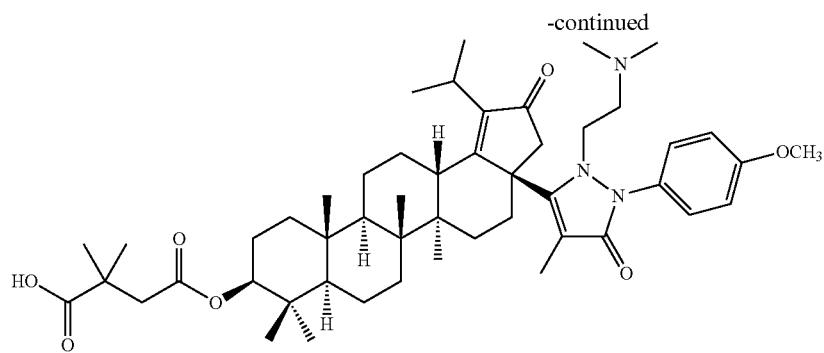
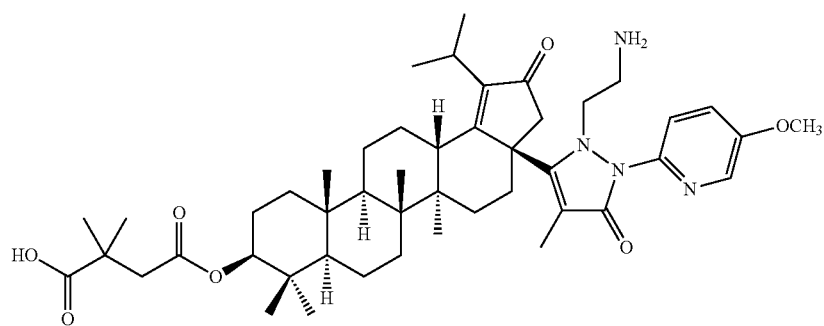
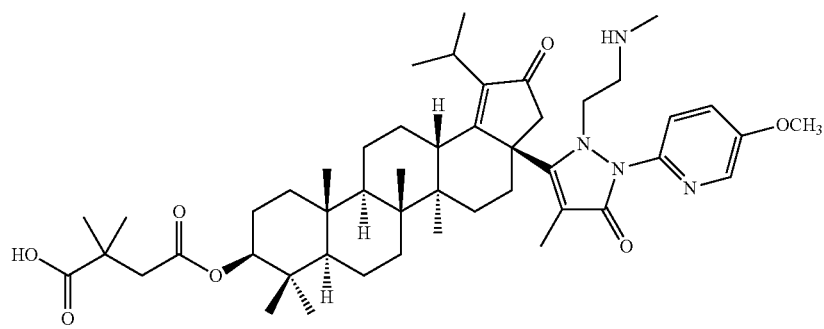
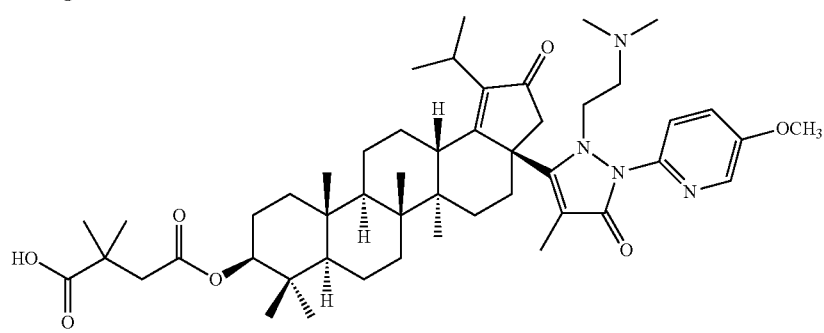
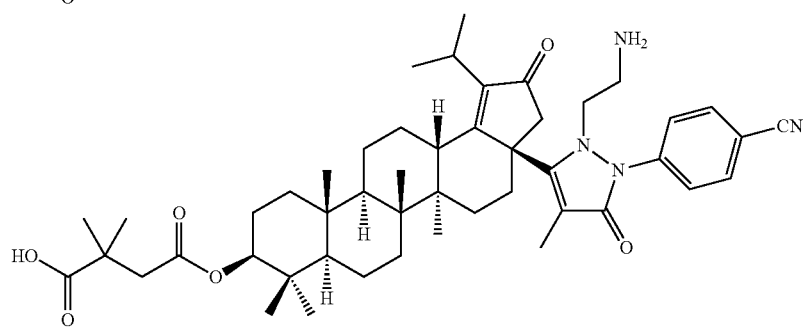

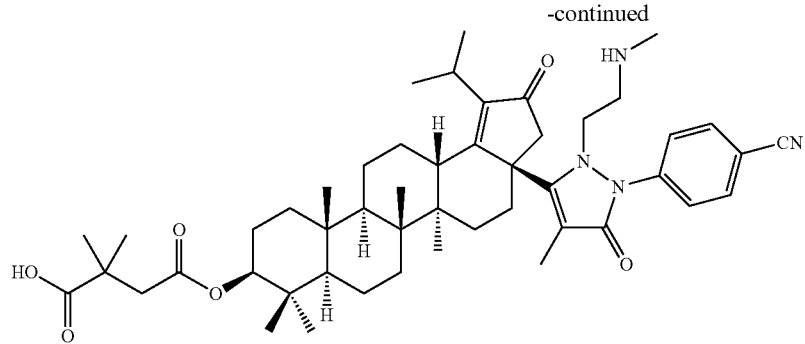
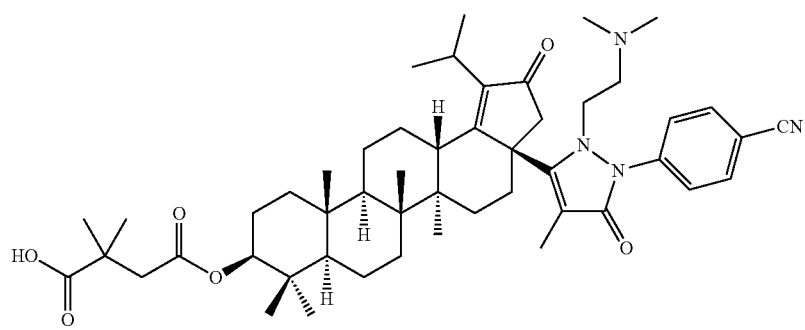
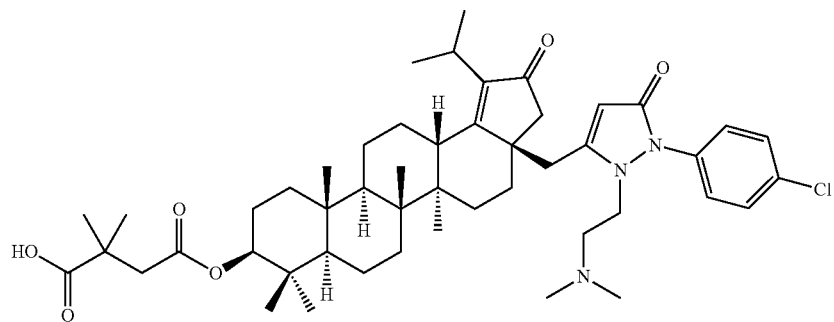
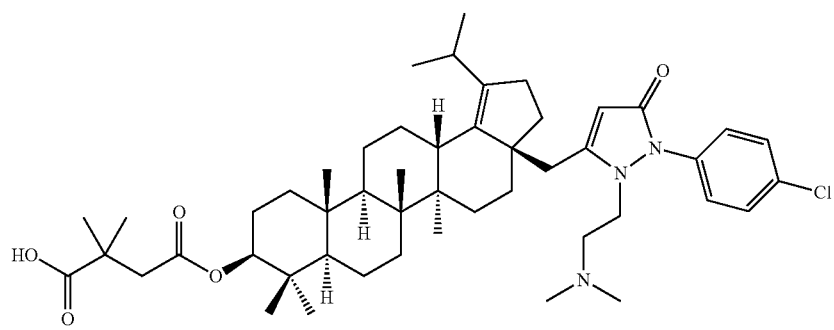
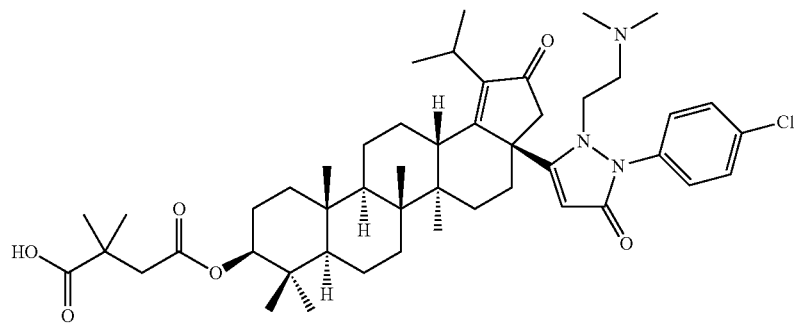

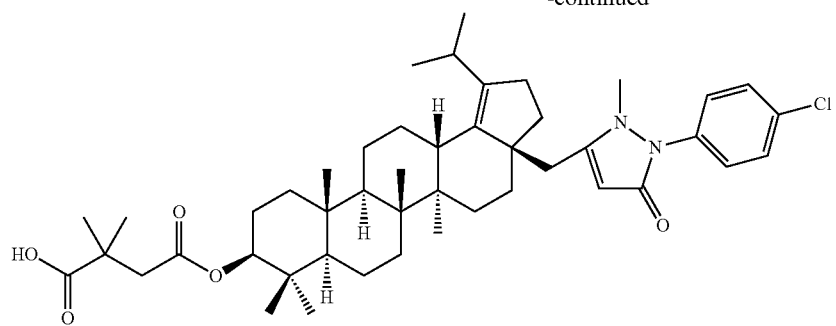
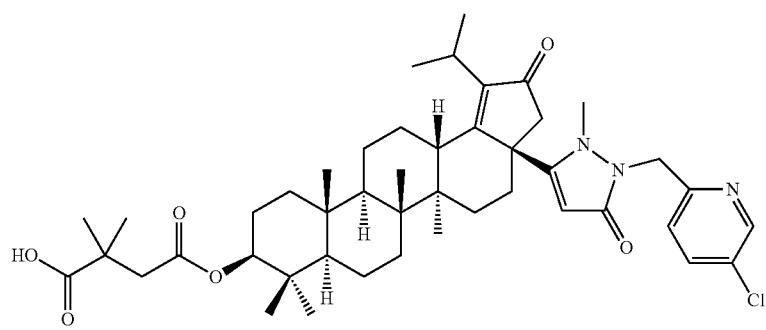
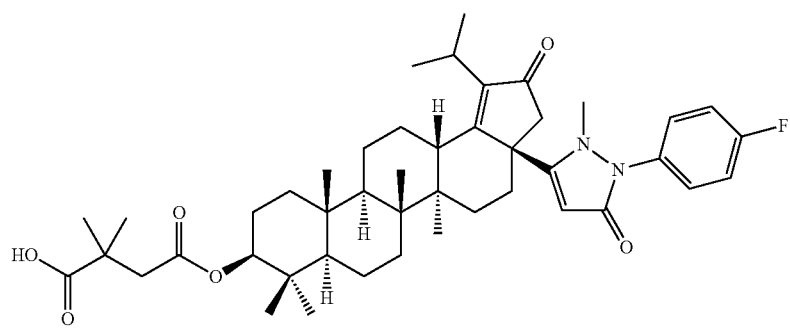
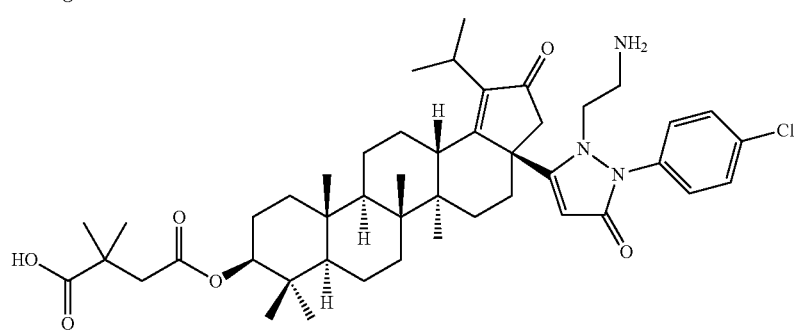
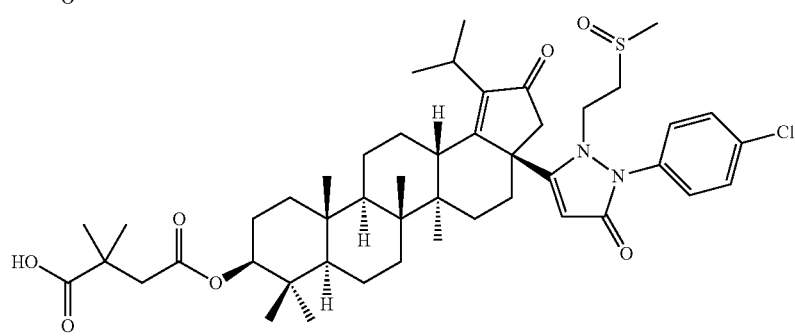

-continued

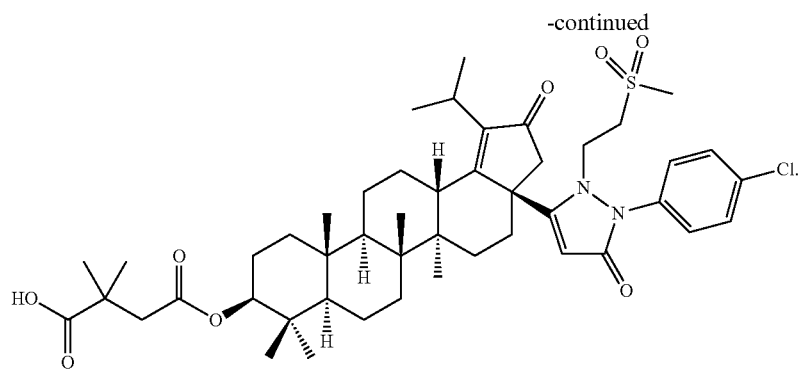

10. A pharmaceutical composition comprising a compound of formula (I) as defined in claim 1, or a pharmaceutically acceptable salt thereof in a therapeutically-effective dose, as well as a pharmaceutical acceptable carrier, adjuvant, excipient, or vehicle.

11. A pharmaceutical composition comprising a compound of formula (II) as defined in claim 2, or a pharmaceutically acceptable salt thereof in a therapeutically-effective dose, as well as a pharmaceutical acceptable carrier, adjuvant, excipient, or vehicle.

12. A pharmaceutical composition comprising a compound of formula (III) as defined in claim 4, or a pharmaceutically acceptable salt thereof in a therapeutically-effective dose, as well as a pharmaceutical acceptable carrier, adjuvant, excipient, or vehicle.

13. A method for treating HIV-1 infections in a subject, comprising administering to said subject a therapeutically-effective amount of a compound of formula (I) or a pharmaceutically acceptable salt thereof as defined in claim 1.

14. A combination preparation for use in anti-HIV combination therapies, wherein said combination preparation comprising a compound of formula (I) as defined in claim 1, or a pharmaceutically acceptable salt thereof, and along with at least one further therapeutic agent.

15. The combination preparation according to claim 14, wherein said another therapeutic agent is at least one selected from the group consisting of: nucleoside/nucleotide reverse transcriptase inhibitor, non-nucleoside reverse transcriptase inhibitors, protease inhibitors, fusion inhibitor, entry inhibitor, and integrase inhibitors.

16. A combination preparation for use in anti-HIV combination therapies, wherein said combination preparation comprising a compound of formula (II) as defined in claim 2, or a pharmaceutically acceptable salt thereof, and along with at least one further therapeutic agent.

17. The combination preparation according to claim 16, wherein said another therapeutic agent is at least one selected from the group consisting of: nucleoside/nucleotide reverse transcriptase inhibitor, non-nucleoside reverse transcriptase inhibitors, protease inhibitors, fusion inhibitor, entry inhibitor, and integrase inhibitors.

18. A combination preparation for use in anti-HIV combination therapies, wherein said combination preparation comprising a compound of formula (III) as defined in claim 4, or a pharmaceutically acceptable salt thereof, and along with at least one further therapeutic agent.

19. The combination preparation according to claim 18, wherein said another therapeutic agent is at least one selected from the group consisting of: nucleoside/nucleotide reverse transcriptase inhibitor, non-nucleoside reverse transcriptase inhibitors, protease inhibitors, fusion inhibitor, entry inhibitor, and integrase inhibitors.

* * * * *